US011819524B2

(12) United States Patent
Toledo et al.

(10) Patent No.: US 11,819,524 B2
(45) Date of Patent: Nov. 21, 2023

(54) METHODS AND COMPOSITIONS FOR TREATING MUSCULOSKELETAL DISEASES

(71) Applicant: Solarea Bio, Inc., Cambridge, MA (US)

(72) Inventors: Gerardo V. Toledo, Hopkinton, MA (US); Eric Michael Schott, Charlestown, MA (US); Maria Juliana Soto-Giron, Cambridge, MA (US); Jinwoo Kim, Acton, MA (US); Julie E. Button, Lincoln, MA (US)

(73) Assignee: Solarea Bio, Inc., Cambridge, MA (US)

( * ) Notice: Subject to any disclaimer, the term of this patent is extended or adjusted under 35 U.S.C. 154(b) by 0 days.

(21) Appl. No.: 16/694,876

(22) Filed: Nov. 25, 2019

(65) Prior Publication Data

US 2020/0164002 A1 May 28, 2020

Related U.S. Application Data

(63) Continuation of application No. PCT/US2019/049823, filed on Sep. 5, 2019.
(Continued)

(51) Int. Cl.

| | |
|---|---|
| ***A61K 35/741*** | (2015.01) |
| ***A23L 33/14*** | (2016.01) |
| ***A23L 33/125*** | (2016.01) |
| ***A23L 33/135*** | (2016.01) |
| ***A61P 19/08*** | (2006.01) |

(Continued)

(52) U.S. Cl.
CPC .......... *A61K 35/741* (2013.01); *A23L 33/125* (2016.08); *A23L 33/135* (2016.08); *A23L 33/14* (2016.08); *A61K 31/702* (2013.01); *A61K 35/744* (2013.01); *A61K 36/062* (2013.01); *A61P 19/08* (2018.01); *A61P 19/10* (2018.01); *A23V 2002/00* (2013.01);
(Continued)

(58) Field of Classification Search
None
See application file for complete search history.

(56) References Cited

U.S. PATENT DOCUMENTS

| | | | |
|---|---|---|---|
| 3,048,526 | A | 8/1962 | Bloswell |
| 3,108,046 | A | 10/1963 | Harbit |

(Continued)

FOREIGN PATENT DOCUMENTS

| | | | |
|---|---|---|---|
| AU | 2008231930 | A1 | 10/2008 |
| CA | 2334877 | A1 | 10/2000 |

(Continued)

OTHER PUBLICATIONS

Williams et al., ISRN Biotechnol. 2013: 1-7 (article ID 137835).*

(Continued)

*Primary Examiner* — Erin M. Bowers
(74) *Attorney, Agent, or Firm* — Goodwin Procter LLP

(57) ABSTRACT

Described herein are methods and compositions for using microbial agents (probiotics) and agents that promote growth of certain microbes (prebiotics) for management (including prevention and treatment) of musculoskeletal disorders, including osteoporosis, osteopenia, Paget's disease, stunting, osteoarthritis, osteomyelitis, and delayed or non-union fractures.

16 Claims, 45 Drawing Sheets

Specification includes a Sequence Listing.

Related U.S. Application Data

(60) Provisional application No. 62/863,722, filed on Jun. 19, 2019, provisional application No. 62/728,018, filed on Sep. 6, 2018, provisional application No. 62/728,020, filed on Sep. 6, 2018, provisional application No. 62/728,019, filed on Sep. 6, 2018, provisional application No. 62/727,503, filed on Sep. 5, 2018.

(51) Int. Cl.

| | |
|---|---|
| ***A61P 19/10*** | (2006.01) |
| ***A61K 31/702*** | (2006.01) |
| ***A61K 35/744*** | (2015.01) |
| ***A61K 36/062*** | (2006.01) |

(52) U.S. Cl.
CPC ....... *A23Y 2220/71* (2013.01); *A23Y 2260/35* (2013.01); *A23Y 2280/55* (2013.01)

(56) References Cited

U.S. PATENT DOCUMENTS

| | | | |
|---|---|---|---|
| 3,536,809 | A | 10/1970 | Applezweig |
| 3,598,123 | A | 8/1971 | Zaffaroni |
| 3,845,770 | A | 11/1974 | Theeuwes et al. |
| 3,916,899 | A | 11/1975 | Theeuwes et al. |
| 4,008,719 | A | 2/1977 | Theeuwes et al. |
| 4,478,822 | A | 10/1984 | Haslam et al. |
| 4,532,126 | A | 7/1985 | Ebert et al. |
| 4,625,494 | A | 12/1986 | Iwatschenko |
| 4,671,953 | A | 6/1987 | Stanley et al. |
| 4,786,505 | A | 11/1988 | Lovgren et al. |
| 4,800,083 | A | 1/1989 | Hom et al. |
| 4,904,479 | A | 2/1990 | Illum |
| 4,919,939 | A | 4/1990 | Baker |
| 4,935,243 | A | 6/1990 | Borkan et al. |
| 4,950,484 | A | 8/1990 | Olthoff et al. |
| 5,013,726 | A | 5/1991 | Ivy et al. |
| 5,059,595 | A | 10/1991 | Grazie |
| 5,073,543 | A | 12/1991 | Marshall et al. |
| 5,120,548 | A | 6/1992 | McClelland et al. |
| 5,225,202 | A | 7/1993 | Hodges et al. |
| 5,354,556 | A | 10/1994 | Sparks et al. |
| 5,591,767 | A | 1/1997 | Mohr et al. |
| 5,610,184 | A | 3/1997 | Shahinian et al. |
| 5,639,476 | A | 6/1997 | Oshlack et al. |
| 5,674,533 | A | 10/1997 | Santus et al. |
| 5,733,556 | A | 3/1998 | Schrier et al. |
| 5,733,575 | A | 3/1998 | Mehra et al. |
| 5,837,284 | A | 11/1998 | Mehta |
| 5,871,776 | A | 2/1999 | Mehta |
| 5,902,632 | A | 5/1999 | Mehta |
| 6,139,875 | A | 10/2000 | Adams et al. |
| 6,258,380 | B1 | 7/2001 | Overholt |
| 6,420,473 | B1 | 7/2002 | Chittamuru et al. |
| 6,455,052 | B1 | 9/2002 | Marcussen et al. |
| 6,482,435 | B1 | 11/2002 | Stratton et al. |
| 6,544,510 | B2 | 4/2003 | Olshenitsk et al. |
| 6,569,457 | B2 | 5/2003 | Ullah et al. |
| 6,572,871 | B1 | 6/2003 | Church et al. |
| 6,750,331 | B1 | 6/2004 | Takaichi et al. |
| 7,214,370 | B2 | 5/2007 | Naidu et al. |
| 8,318,151 | B2 | 11/2012 | Darimont-Nicolau et al. |
| 8,460,726 | B2 | 6/2013 | Harel et al. |
| 8,802,158 | B2 | 8/2014 | Boileau et al. |
| 8,871,266 | B2 | 10/2014 | Sanguansri et al. |
| 8,877,178 | B2 | 11/2014 | Boileau et al. |
| 9,040,101 | B2 | 5/2015 | Heiman et al. |
| 9,095,604 | B2 | 8/2015 | Ikegami et al. |
| 9,173,910 | B2 | 11/2015 | Kaplan et al. |
| 9,301,983 | B2 | 4/2016 | Huang et al. |
| 9,371,510 | B2 | 6/2016 | Moore |
| 9,386,793 | B2 | 7/2016 | Blaser et al. |
| 9,487,764 | B2 | 11/2016 | Falb et al. |
| 9,549,955 | B2 | 1/2017 | Rittmann et al. |
| 9,636,367 | B2 | 5/2017 | Garcia-Rodenas et al. |
| 9,937,211 | B2 | 4/2018 | Kelly et al. |
| 10,064,895 | B2 | 9/2018 | Vincent |
| 2004/0213828 | A1 | 10/2004 | Smith |
| 2005/0147710 | A1 | 7/2005 | Teckoe et al. |
| 2010/0172874 | A1 | 7/2010 | Turnbaugh et al. |
| 2011/0111094 | A1 | 5/2011 | Lavermicocca et al. |
| 2011/0177567 | A1* | 7/2011 | Bakker .................... C12N 1/22 435/110 |
| 2011/0177976 | A1 | 7/2011 | Gordon et al. |
| 2012/0015075 | A1 | 1/2012 | Davis et al. |
| 2014/0065209 | A1 | 3/2014 | Putaala et al. |
| 2014/0179726 | A1 | 6/2014 | Bajaj et al. |
| 2014/0314719 | A1 | 10/2014 | Smith et al. |
| 2015/0259728 | A1 | 9/2015 | Cutcliffe et al. |
| 2015/0366941 | A1 | 12/2015 | Menear et al. |
| 2016/0067289 | A1 | 3/2016 | Berggren et al. |
| 2016/0081309 | A1 | 3/2016 | Newton et al. |
| 2016/0143961 | A1 | 5/2016 | Berry et al. |
| 2016/0199424 | A1 | 7/2016 | Berry et al. |
| 2016/0206666 | A1 | 7/2016 | Falb et al. |
| 2016/0235792 | A1 | 8/2016 | Berry et al. |
| 2016/0263166 | A1 | 9/2016 | Elinav et al. |
| 2016/0271189 | A1 | 9/2016 | Cutcliffe et al. |
| 2016/0302464 | A1 | 10/2016 | Egli et al. |
| 2016/0354417 | A1 | 12/2016 | Smittle et al. |
| 2017/0326190 | A1 | 11/2017 | Ansell et al. |

FOREIGN PATENT DOCUMENTS

| | | | |
|---|---|---|---|
| EP | 1495109 | A1 | 1/2005 |
| EP | 1794283 | A1 | 6/2007 |
| WO | 2004/080200 | A1 | 9/2004 |
| WO | 2010/099617 | A1 | 9/2010 |
| WO | 2012/098254 | A1 | 7/2012 |
| WO | 2012/170047 | A2 | 12/2012 |
| WO | 2013/067146 | A1 | 5/2013 |
| WO | 2013/176774 | A1 | 11/2013 |
| WO | 2014/068338 | A1 | 5/2014 |
| WO | 2015/177246 | A2 | 11/2015 |
| WO | 2016/065075 | A1 | 4/2016 |
| WO | 2016/086205 | A2 | 6/2016 |
| WO | 2016/086210 | A1 | 6/2016 |
| WO | 2016/124940 | A1 | 8/2016 |
| WO | 2017/160711 | A1 | 9/2017 |
| WO | 2020/257722 | A2 | 12/2020 |

OTHER PUBLICATIONS

Gunnarsson et al., Industrial Crops and Products 56: 231-240 (2014).*
Yang et al., Biotechnology Reports 5: 77-88 (2015).*
Morishita et al., J. Dairy Sci. 82(9): 1897-1903 (1999).*
Wikipedia, https://en.wikipedia.org/wiki/Pyruvate_dehydrogenase_complex, accessed Dec. 3, 2021.*
Wagner et al., Appl. Environ. Microbiol. 71(9): 4966-4971 (2005).*
Abuajah, et al., "Functional components and medicinal properties of food: a review", J Food Sci Technol, 2015, vol. 52, No. 5: pp. 2522-2529.
Abubucker, et al., "Metabolic Reconstruction for Metagenomic Data and Its Application to the Human Microbiome", PLoS Computational Biology, Jun. 2012, vol. 8, No. 6: pp. 1-17.
Akamatsu, et al., "Conversion of antigen-specific effector/memory T cells Into Foxp3-expressing Treg cells by Inhibition of CDK8/19", Science Immunology, Oct. 25, 2019, vol. 4: pp. 1-16.
Alcock, et al., "Is eating behavior manipulated by the gastrointestinal microbiota? Evolutionary pressures and potential mechanisms", Bioessays 2014, vol. 36: pp. 940-949.
Allgeier, et al., "A colorimetric method for the determination of butyric acid", J Bacteriol, 1929, vol. 17, No. 2: pp. 79-87.
Ananthakrishnan, et al., "Gut Microbiome Function Predicts Response to Anti-integrin Biologic Therapy in Inflammatory Bowel Diseases", Cell Host & Microbe, May 10, 2017, vol. 21: pp. 603-610.
Anastasilakis, et al., "Head-to-head comparison of risedronate vs. teriparatideon bone turnover markers in women with postmenopausal osteoporosis: a randomised trial", Int J Clin Pract, Jun. 2008, vol. 62, No. 6: pp. 919-924.

(56) References Cited

OTHER PUBLICATIONS

Arjmandi, et al., "Bone-Protective Effects of Dried Plum in Postmenopausal Women: Efficacy and Possible Mechanisms", Nutrients, 2019, vol. 9, No. 496: pp. 1-19.
Aron-Wisnewsky, et al., "The importance of the gut microbiota after bariatric surgery", Nature, 2012, vol. 9, No. 10: pp. 590-598.
Arumugam, et al., "Enterotypes of the human gut microbiome", Nature, 2011, vol. 473, No. 7346: pp. 174-180.
Atarashi, et al., "Induction of Colonic Regulatory T Cells by Indigenous *Clostridium* Species", Science, Jan. 21, 2011, vol. 331: pp. 337-341.
Atarashi, et al., "Treg induction by a rationally selected mixture of Clostridia strains from the human microbiota", Nature, Aug. 8, 2013, vol. 500: pp. 232-236.
Backhed, et al., "The gut microbiota as an environmental factor that regulates fat storage", PNAS, 2004, vol. 101, No. 44: pp. 15718-15723.
Backhed et al., "Mechanisms underlying the resistance to diet-induced obesity in germ-free mice", PNAS, 2007, vol. 104, No. 3: pp. 979-984.
Bahr, et al., "Risperidone-induced weight gain is mediated through shifts in the gut microbiome and suppression of energy expenditure", EBioMedicine, 2015, vol. 2: pp. 1725-1734.
Bai, et al., "Response of gut microbiota and inflammatory status to bitter melon (*Momordica charantia* L.) in high fat diet induced obese rats", J Ethnopharmacol, 2016, vol. 194: pp. 717-726.
Baker, et al., "Estrogen-gut microbiome axis: Physiological and clinical implications", Maturitas, 2017, vol. 103: pp. 45-53.
Bakker-Zierikzee, et al., "Effects of infant formula containing a mixture of galacto- and fructo-oligosaccharides or viable Bifidobacterium animalis on the intestinal microflora during the first 4 months of life", Br J Nutr, 2005, vol. 94: pp. 783-790.
Basu, et al., "Blueberries decrease cardiovascular risk factors in obese men and women with metabolic syndrome", J Nutr, 2010, vol. 140, No. 9: pp. 1582-1587.
Berg, et al., "The Edible plant microbiome: importance and health issues", In: Lugtenberg B. (eds) Principles of plant-microbe interactions. Springer, Cham, 2015.
Bernini, et al., "Beneficial effects of Bifidobacterium lactis on lipid profile and cytokines in patients with metabolic syndrome", Nutrition, 2016, vol. 32: pp. 716-719.
Black, et al., "Postmenopausal Osteoporosis", The New England Journal of Medicine, Jan. 21, 2016, vol. 374, No. 3: pp. 254-262.
Bleau, et al., "Crosstalk between intestinal microbiota, adipose tissue and skeletal muscle as an early event in systemic low-grade inflammation and the development of obesity and diabetes", Diabetes Metab Res Rev, 2015, vol. 31, No. 6: pp. 545-561.
Boden, et al., "Obesity, Insulin Resistance and Free Fatty Acids", Curr Opin Endocrinol Diabetes Obes, 2011, vol. 18, No. 2: pp. 139-143.
Body, et al., "A Randomized Double-Blind Trial to Compare the Efficacy of Teriparatide [Recombinant Human Parathyroid Hormone (1-34)] with Alendronate in Postmenopausal Women with Osteoporosis", The Journal of Clinical Endocrinology & Metabolism, Oct. 2002, vol. 87, No. 10: pp. 4528-4535.
Bouxsein, et al., "Ovariectomy-Induced Bone Loss Varies Among Inbred Strains of Mice", Journal of Bone and Mineral Research, Mar. 7, 2005, vol. 20, No. 7: pp. 1085-1092.
Bouxsein, et al., "Considerations for Development of Surrogate Endpoints for Antifracture Efficacy of New Treatments in Osteoporosis: A Perspective", Journal of Bone and Mineral Research, Mar. 3, 2008, vol. 23, No. 8: pp. 1155-1167.
Brahe, et al., "Is butyrate the link between diet, intestinal microbiota and obesity-related metabolic diseases?", Obes Rev, 2013, vol. 14: pp. 950-959.
Britton, et al., "Probiotic L. reuteri Treatment Prevents Bone Loss in a Menopausal Ovariectomized Mouse Model", Journal of Cellular Physiology, 2014, vol. 229: pp. 1822-1830.
Bron, et al., "Emerging molecular insights into the interaction between probiotics and the host intestinal mucosa", Nat Rev Microbiol, 2012, vol. 10: pp. 66-78.
Brown, et al., "Comparison of the Effect of Denosumab and Alendronate on BMD and Biochemical Markers of Bone Turnover in Postmenopausal Women With Low Bone Mass: A Randomized, Blinded, Phase 3 Trial*", Journal of Bone and Mineral Research, 2009, vol. 24: pp. 153-161.
Brown, et al., "Gut Microbiota Regulation of T Cells During Inflammation and Autoimmunity", Annual Review of Immunology, 2019, vol. 37: pp. 599-624.
Brunkwall, et al., "The gut microbiome as a target for prevention and treatment of hyperglycaemia in type 2 diabetes: from current human evidence to future possibilities", Diabetalogia, 2017, vol. 60: pp. 943-951.
Calise, et el., "Immune Response-Dependent Assembly of IMP Dehydrogenase Filaments", Frontiers in Immunology, Nov. 29, 2018, vol. 9, Article 2789: pp. 1-15.
Camacho, et al., "Metformin in breast cancer—an evolving mystery", Breast Cancer Res, 2015, vol. 17, No. 88: pp. 1-4.
Campbell, et al., "The China Study: The most comprehensive study of nutrition ever conducted and startling implications for diet, weight loss, and long term health," Benbella, 2006, 425 pages.
Cani, et al., "Improvement of glucose tolerance and hepatic insulin sensitivity by oligofructose requires a functional glucagon-like peptide 1 receptor", Diabetes, 2006, vol. 55: pp. 1484-1490.
Cani, et al., "Metabolic endotoxemia initiates obesity and insulin resistance", Diabetes, 2007, vol. 56: pp. 1761-1772.
Cani, et al., "Selective increases of bifidobacteria in gut microflora improve high-fat-diet-induced diabetes in mice through a mechanism associated with endotoxaemia", Diabetologica, 2007, vol. 50: pp. 2374-2383.
Cani, et al., "Changes in gut microbiota control metabolic endotoxemia-induced inflammation in high-fat diet-induced obesity and diabetes in mice", Diabetes, 2008, vol. 57: pp. 1470-1481.
Carbonero, et al., "Microbial pathways in colonic sulfur metabolism and links with health and disease", Frontiers in Immunology, Nov. 28, 2012, vol. 3, Article 448: pp. 1-11.
Chambers, et al., "Effects of targeted delivery of propionate to the human colon on appetite regulation, body weight maintenance and adiposity in overweight adults", Gut, 2015, vol. 64: pp. 1744-1754.
Chanclud, et al., "Plant hormones: key players in gut microbiota and human diseases?", Trends Plant Sci, 2017, vol. 22, No. 9: 754-758.
Charbonneau, et al., "Sialylated Milk Oligosaccharides Promote Microbiota-Dependent Growth in Models of Infant Undernutrition", Cell, Feb. 25, 2016, vol. 164, pp. 859-871.
Chaudhury, et al., "Clinical Review of Antidiabetic Drugs: Implications for Type 2 Diabetes Mellitus Management", Front Endocrinol, 2017, vol. 8, No. 6: pp. 1-12.
Chelliah, et al., "Evaluation of antimicrobial activity and probiotic properties of wild-strain Pichia kudriavzevii isolated from frozen idli batter", Yeast, 2016, vol. 33, pp. 385-401.
Chen, et al., "Metabolism of Fructooligosaccharides in Lactobacillus plantarum ST-III via Differential Gene Transcription and Alteration of Cell Membrane Fluidity", Appl Environ Microbiol, 2015, vol. 81, No. 22: pp. 7697-7707.
Chen, et al., "Estrogen and Microbiota Crosstalk: Should We Pay Attention?", Trends in Endocrinology & Metabolism, Nov. 2016, vol. 27, No. 11, pp. 752-755.
Chiang, et al., "Antiosteoporotic Effects of Lactobacillus-Fermented Soy Skim Milk on Bone Mineral Density and the Microstructure of Femoral Bone in Ovariectomized Mice", Journal of Agricultural and Food Chemistry, 2011, vol. 59: pp. 7734-7742.
Cockburn, et al., "Polysaccharide Degradation by the Intestinal Microbiota and Its Influence on Human Health and Disease", J Mol Biol, 2016, vol. 428, pp. 3230-3252.
Codella, et al., "Exercise has the guts: how physical activity may positively modulate gut microbiota in chronic and immune-based diseases", Digest Liv Dis, 2018, vol. 50: pp. 331-341.
Collins, et al., "Beneficial effects of Lactobacillus reuteri 6475 on bone density in male mice is dependent on lymphocytes", Scientific Reports, 2019, vol. 9: pp. 1-17.

(56) References Cited

OTHER PUBLICATIONS

Correa, et al., "Regulation of immune cell function by short-chain fatty acids", Clinical & Translational Immunology, 2016, vol. 5, pp. 1-8.
Cosman, et al., "Clinician's Guide to Prevention and Treatment of Osteoporosis", 2014, vol. 25, pp. 2359-2381.
Cowardin, et al., "Mechanisms by which sialylated milk oligosaccharides impact bone biology in a gnotobiotic mouse model of infant undernutrition", PNAS, Jun. 11, 2019, vol. 116, No. 24: pp. 11988-11996.
Cowardin, et al., "Supplementary Information for: Mechanisms by which sialylated milk oligosaccharides impact bone biology in a gnotobiotic mouse model of infant undernutrition", PNAS, www.pnas.org/cgi/doi/10.1073/pnas.1821770116.
Cox, et al., "SolexaQA: At-a-glance quality assessment of Illumina second-generation sequencing data", BMC Bioinformatics, 2010, vol. 11, No. 485: pp. 1-6.
Coyle, et al., "Metformin as an adjuvant treatment for cancer: a systematic review and meta analysis", Ann Onc, 2016, vol. 27, pp. 2184-2195.
Dalby, et al., "Dietary Uncoupling of Gut Microbiota and Energy Harvesting from Obesity and Glucose Tolerance in Mice", Cell Reports, 2017, vol. 21 pp. 1521-1533.
Dane, et al., "Effect of risedronate on biochemical marker of bone resorption in postmenopausal women with osteoporosis or osteopenia", Gynecological Endocrinology, 2008, vol. 24, No. 4: pp. 207-213.
Dar, et al., "Bacillus clausii inhibits bone loss by skewing Treg-Th17 cell equilibrium in postmenopausal osteoporotic mice model", Nutrition, 2018, vol. 54, pp. 118-128.
Das, et al., "Prevention of Diabetes—A Historical Note", IJHS, 2013, vol. 48, No. 4, pp. 625-642.
David, et al., "Diet rapidly and reproducibly alters the human gut microbiome", Nature, 2014, vol. 505, pp. 559-563.
Davies, et al., "Effect of Oral Semaglutide Compared With Placebo and Subcutaneous Semaglutide on Glycemic Control in Patients With Type 2 Diabetes", JAMA, 2017, vol. 318, No. 15: pp. 1460-1470.
Deehan, et al., "Precision Microbiome Modulation with Discrete Dietary Fiber Structures Directs Short-Chain Fatty Acid Production", Cell Host & Microbe, Mar. 11, 2020, vol. 27: pp. 1-16.
De Jesus Raposo, et al., "Emergent Sources of prebiotics: seaweed and microalgae", Mar. Drugs, 2016, vol. 14, No. 2: doi: 10.3390/md14020027.
De La Cuesta-Zuluaga, et al., "Metformin Is Associated With Higher Relative Abundance of Mucin-Degrading Akkermansia muciniphila and Several Short-Chain Fatty Acid-Producig Microbiota in the Gut", Diabetes Care, 2017, vol. 40: pp. 54-62.
De Vadder, et al., "Microbiota-Produced Succinate Improves Glucose Homeostasis via Intestinal Gluconeogenesis", Cell Metab, 2016, vol. 24: pp. 151-157.
Delzenne, et al., "Gut microorganisms as promising targets for the management of type 2 diabetes", Diabetalogia, 2015, vol. 58: pp. 2206-2217.
Derrien, et al., "Fate, activity, and impact of ingested bacteria within the human gut microbiota", Trends in Microbiol, 2015, vol. 23, No. 6: pp. 354-366.
Devaraj, et al., "The Human Gut Microbiome and Body Metabolism: Implications for Obesity and Diabetes", Clin Chem, 2013, vol. 59, No. 4: pp. 617-628.
Di Francesco, et al., "A time to fast", Science, 2018, vol. 362: pp. 770-775.
Ding, et al., "The regulation of immune cells by Lactobacilli: a potential therapeutic target for anti-atherosclerosis therapy", Oncotarget, 2017, vol. 8, No. 35: pp. 59915-59928.
Drew, et al., "Reseeding the gut", Nature, 2016, 540:s109-s112.
Duong-Ly, et al., "T cell activation triggers reversible inosine-5'-monophosphate dehydrogenase assembly", Journal of Cell Science, 2018, vol. 131: pp. 1-8.
Duncan, et al., "Contribution of acetate to butyrate formation by human faecal bacteria", Br J Nutr, 2004, vol. 91: pp. 915-923.
Eastell, et al., "Use of bone turnover markers in postmenopausal osteoporosis", Lancet Diabetes Endocrinol 2017, vol. 5: pp. 908-923.
Elzinga, et al., "The Use of Defined Microbial Communities to Model Host-Microbe Interactions in the Human Gut", Microbiology and Molecular Biology Reviews, Jun. 2019, vol. 83, No. 2: pp. 1-40.
Engelke, et al., "Clinical Use of Quantitative Computed Tomography and Peripheral Quantitative Computed Tomography in the Management of Osteoporosis in Adults: The 2007 ISCD Official Positions", Journal of Clinical Densitometry, 2008, vol. 11, No. 1: pp. 123-162.
Engelke, et al., "Regional distribution of spine and hip QCT BMD responses after one year of once-monthly ibandronate in postmenopausal osteoporosis", Bone, 2010, vol. 46: pp. 1626-1632.
Engelke, et al., "Clinical Use of Quantitative Computed Tomography (QCT) of the Hip in the Management of Osteoporosis in Adults: the 2015 ISCD Official Positions—Part I", Journal of Clinical Densitometry: Assessment & Management of Musculoskeletal Health, 2015, vol. 18, No. 3: pp. 338-358.
Ericsson, et al., "Variable Colonization after Reciprocal Fecal Microbiota Transfer between Mice with Low and High Richness Microbiota", Front Microbiol, 2017, vol. 8, No. 196: pp. 1-13.
Everard, et al., "Cross-talk between Akkermansia muciniphila and intestinal epithelium controls diet-induced obesity", PNAS, 2013, vol. 11, No. 22: pp. 9066-9071.
Everard, et al., "Microbiome of prebiotic-treated mice reveals novel targets involved in host response during obesity", ISME, 2014, vol. 8: pp. 2116-2130.
Everard, et al., "Diabetes, obesity and gut microbiota", Best Pract Res Clin Gastroenterol, 2013, vol. 27: pp. 73-83.
Fairbanks, et al., "Importance of Ribonucleotide Availability to ProliferatingT-lymphocytes from Healthy Humans", The Journal of Biological Chemistry, 1995, vol. 270, No. 50; pp. 29682-29689.
Famouri, et al., "Effects of Probiotics on Nonalcoholic Fatty Liver Disease in Obese Children and Adolescents", JPGN, 2017, vol. 64, No. 3: pp. 413-417.
Fang, et al., "Intestinal FXR agonism promotes adipose tissue browning and reduces obesity and insulin resistance", Nature, 2015, vol. 21, No. 2: pp. 159-167.
Fletcher, et al., "Shifts in the Gut Metabolome and Clostridium difficile Transcriptome throughout Colonization and Infection in a Mouse Model", mSphere, Mar. 2018, vol. 3, No. 2: pp. 1-18.
Forslund, et al., "Corrigendum: Disentangling type 2 diabetes and metformin treatment signatures in the human gut microbiota", Nature, 2015, vol. 528, No. 7581: pp. 262-266.
Franzosa, et al., "Species-level functional profiling of metagenomes and metatranscriptomes", Nature Methods, Nov. 2018, vol. 15, pp. 962-968.
Frost, et al., "The short-chain fatty acid acetate reduces appetite via a central homeostatic mechanism", Nat Commun, 2014, vol. 5, No. 3611: pp. 1-11.
Gad, et al., "Anti-aging effects of L-arginine", Journal of Advanced Research, 2010, vol. 1: pp. 169-177.
Gagnon, et al., "Bone Health After Bariatric Surgery", JBMR Plus, 2017, vol. 2: pp. 1-13.
Garidou, et al., "The Gut Microbiota Regulates Intestinal CD4 T Cells Expressing RORgt and Controls Metabolic Disease", Cell Metab, 2015, vol. 22: pp. 100-112.
Gehrig, et al., "Effects of microbiota-directed foods in gnotobiotic animals and undernourished children", Science, Jul. 12, 2019, vol. 365, No. 139: pp. 1-12.
Gehrig, et al., "Supplementary Material for: Effects of microbiota-directed foods in gnotobiotic animals and undernourished children", Science, Jul. 12, 2019, vol. 365, No. 139: pp. 1-42.
Gentile, et al., "The gut microbiota at the intersection of diet and human health", Science, 2018, vol. 362: pp. 776-780.
Geva-Zatorsky, et al., "Mining the Human Gut for Immunomodulatory Organisms", Cell, Feb. 23, 2017, vol. 168: pp. 928-943.
Ahlborg, et al., "Bone Loss and Bone Size after Menopause", The New England Journal of Medicine, Jul. 24, 2003, vol. 349, No. 4: pp. 327-334.

(56) References Cited

OTHER PUBLICATIONS

Li et al., "Pro- and anti-inflammatory effects of short chain fatty acids on immune and endothelial cells." European journal of pharmacology 831 (2018): 52-59.
Lambert, et al., "Combined bioavailable isoflavones and probiotics improve bone status and estrogen metabolism in postmenopausal osteopenic women: a randomized controlled trial", Am J Clin Nutr, 2017, vol. 106: pp. 909-920.
Lang, et al., "The microbes we eat: abundance and taxonomy of microbes consumed in a day's worth of meals for three diet types", PeerJ, 2014, 2:e659; doi 10.7717/peerj.659.
Langmead, at al., "Fast gapped-read alignment with Bowtie 2", Nat Methods, 2012, vol. 9, No. 4: pp. 357-359.
Lee, et al., "Gut microbiota-generated metabolites in animal health and disease", Nat Chem Biol, 2014, vol. 10: pp. 416-424.
Lee, et al., "Effect of Metformin on Metabolic Improvement and Gut Microbiota", Appl Environ Microbiol, 2014, vol. 80, No. 19: p. 59355943.
Lee, et al., "Blueberry Supplementation Influences the Gut Microbiota, Inflammation, and Insulin Resistance in High-Fat-Diet-Fed Rats", J Nutr, 2018, vol. 148, No. 2: pp. 209-219.
Lewiecki, et al., "Once-Monthly Oral Ibandronate Improves Biomechanical Determinants of Bone Strength in Women with Postmenopausal Osteoporosis", J Clin Endocrinol Metab, Jan. 2009, vol. 94, No. 1: pp. 171-180.
Ley, et al., "Obesity alters gut microbial ecology", PNAS, 2005, vol. 102, No. 31: pp. 11070-11075.
Li, et al., "Metabolic Surgery Profoundly Influences Gut Microbial-Host Metabolic Crosstalk", Gut, 2011, vol. 60, No. 9: pp. 1214-1223.
Li, et al., "Butyrate reduces appetite and activates brown adipose tissue via the gut-brain neural circuit", Gut, 2017: pp. 1-11.
Li, et al., "Intermittent Fasting Promotes White Adipose Browning and Decreases Obesity by Shaping the Gut Microbiota", Cell Metab, 2017, vol. 26: pp. 672-685.
Li, et al., "Sex steroid deficiency-associated bone loss is microbiota dependent and prevented by probiotics", The Journal of Clinical Investigation, Jun. 2016, vol. 126, No. 6: pp. 2049-2063.
Li, et al., "Microbial osteoporosis: The interplay between the gut microbiota and bones via host metabolism and immunity", MicrobiologyOpen, 2019: pp. 1-15.
Lin, et al., "Butyrate and propionate protect against diet-induced obesity and regulate gut hormones via free fatty acid receptor 3-independent mechanisms", PLoS ONE, 2012, vol. 7, No. 4: pp. 1-9.
Liu, et al., "VFDB 2019: a comparative pathogenomic platform with an interactive web interface", Nucleic Acids Res, 2019, vol. 47: D687-D692.
Louis, et al., "Formation of propionate and butyrate by the human colonic microbiota", Environ Microbiol, 2017, vol. 19, No. 1: pp. 29-41.
Lu, et al., "Short Chain Fatty Acids Prevent High-fat-diet-induced Obesity in Mice by Regulating G Protein-coupled Receptors and Gut Microbiota", Sci Rep, 2016, vol. 6, No. 37589: pp. 1-13.
Lucas, et al., "Short-chain fatty acids regulate systemic bone mass and protect from pathological bone loss", Nature Communications, 2018, vol. 9, No. 55: pp. 1-10.
Lyu, et al., "Balancing Herbal Medicine and Functional Food for Prevention and Treatment of Cardiometabolic Diseases through Modulating Gut Microbiota", Front Microbiol, 2017, vol. 8, No. 2146: pp. 1-21.
Madiraju, et al., "Metformin suppresses gluconeogenesis by inhibiting mitochondrial glycerophosphate dehydrogenase", Nature, 2014, vol. 510: pp. 542-546.
Maier, et al., Extensive impact of non-antibiotic drugs on human gut bacteria, Nature, 2018: pp. 1-6.
Martinez-Lopez, et al., "System-wide Benefits of Intermeal Fasting by Autophagy", Cell Metab, 2017, vol. 26: pp. 856-871.
McCabe, et al., "Exercise prevents high fat diet induced bone loss, marrow adiposity and dysbiosis in male mice", Bone, 2018: https://doi.org/10.1016/j.bone.2018.03.024.
McCabe, et al., "Prebiotic and Probiotic Regulation of Bone Health: Role of the Intestine and its Microbiome", Curr Osteoporosis Rep., Dec. 2015, vol. 13, No. 6: pp. 636-371.
Meng, et al., "Anti-inflammatory effects of *Bifidobacterium longum* subsp *infantis* secretions on fetal human enterocytes are mediated by TLR-4 receptors", Am J Physiol Gastrointest Liver Physiol, 2016, vol. 311:G744-G753.
Milani, et al., "Bifidobacteria exhibit social behavior through carbohydrate resource sharing in the gut", Sci Rep, 2015, vol. 5, No. 15782: pp. 1-14.
Montandon, et al., "Effects of Antidiabetic Drugs on Gut Microbiota Composition", Genes, 2017, vol. 8, No. 250: pp. 1-12.
Moriwake, et al., "Delphinidin, One of the Major Anthocyanidins, Prevents Bone Loss through the Inhibition of Excessive Osteoclastogenesis in Osteoporosis Model Mice", PLoS ONE, May 2014, vol. 9, No. 5: pp. 1-11.
Morrison, et al., "Formation of short chain fatty acids by the gut microbiota and their impact on human metabolism", Gut Microbes, 2016, vol. 7, No. 3: pp. 189-200.
Moslehi-Jenabian, et al., "Beneficial Effects of Probiotic and Food Borne Yeasts on Human Health", Nutrients, 2010, vol. 2: pp. 449-473.
Muller, et al., "The Plant Microbiota: Systems-Level Insights and Perspectives", The Annual Review of Genetics, 2016, vol. 50: pp. 211-234.
Munder, et al., "Arginase: an emerging key player in the mammalian immune system", British Journal of Pharmacology, 2009, vol. 158: pp. 638-651.
Myneni, et al., "Regulation of bone remodeling by vitamin K2", Oral Diseases, 2017, vol. 23 pp. 1021-1028.
Napolitano, et al., "Novel Gut-Based Pharmacology of Metformin in Patients with Type 2 Diabetes Mellitus", PLoS ONE, 2014, vol. 9, No. 7: e100778.
Naylor, et al., "Response of bone turnover markers to three oral bisphosphonatetherapies in postmenopausal osteoporosis: the TRIO study", Osteoporos Int, 2016, vol. 27: pp. 21-31.
Ni, et al., "A Molecular-Level Landscape of Diet-Gut Microbiome Interactions: Toward Dietary Interventions Targeting Bacterial Genes", mBio, 2015, vol. 6, No. 6: e01263-15.
Nilsson, et al., "Lactobacillus reuteri reduces bone loss in older women with low bone mineral density: a randomized, placebo-controlled, double-blind, clinical trial", The Journal of Internal Medicine, 2018, vol. 284: pp. 307-317.
Ohlsson, et al., "Probiotics Protect Mice from Ovariectomy-Induced Cortical Bone Loss", PLOS ONE, Mar. 2014, vol. 9, No. 3: pp. 1-8.
Okeke, et al., "The Role of the Gut Microbiome in the Pathogenesis and Treatment of Obesity", GAHMJ, 2014, vol. 3, No. 3: pp. 44-57.
Olar, et al., "Prospects for new antimicrobials based on N,N-dimethylbiguanide complexes as effective agents on both planktonic and adhered strains", Eur J Med Chem, 2010, vol. 45: pp. 2868-2875.
Olson, et al., "Obesity and the tumor microenvironment", Science, 2017, vol. 358, No. 6367: pp. 1130-1131.
Ozaki, et al., "The L-type amino acid transporter LAT1 inhibits osteoclastogenesis and maintains bone homeostasis through the mTORC1 pathway", Science Signaling, Jul. 9, 2019, vol. 12: pp. 1-14.
Ozcan, et al., "A Human Gut Commensal Ferments Cranberry Carbohydrates to Produce Formate", Appl Environ Microbiol, 2017, vol. 83, No. 17, pp. 1-16.
Pacifici, et al., "T cells: Critical bone regulators in health and disease", Bone, 2010, vol. 47, pp. 461-471.
Pacifici, et al., "Bone Remodeling and the Microbiome", Cold Spring Harb Perspect Med, 2018, vol. 8, pp. 1-20.
Palacios, et al., "The effect of a novel probiotic on metabolic biomarkers in adults with prediabetes and recently diagnosed type 2 diabetes mellitus: study protocol for a randomized controlled trial", Trials, 2017, vol. 18, No. 7: pp. 1-8.

(56) References Cited

OTHER PUBLICATIONS

Pan, et al., "A single bacterium restores the microbiome dysbiosis to protect bones from destruction in a rat model of rheumatoid arthritis", Microbiome, 2019, vol. 7, No. 107: pp. 1-11.
Pandiyan, et al., "Microbiome Dependent Regulation of Treg and Th17 Cells in Mucosa", Frontiers in Immunology, Mar. 8, 2019, vol. 10, Article 426: pp. 1-17.
Parekh, et al., "The role and influence of gut microbiota in pathogenesis and management of obesity and metabolic syndrome", Front Endocrinol, 2014, vol. 5, No. 47: pp. 1-7.
Patnode, et al., "Interspecies Competition Impacts Targeted Manipulation of Human Gut Bacteria by Fiber-Derived Glycans", Cell, Sep. 19, 2019, vol. 159: pp. 59-73.
Perry, et al., "Acetate mediates a microbiome-brain-b-cell axis to promote metabolic syndrome", Nature, 2016, vol. 534: pp. 213-217.
Plovier, et al., "A purified membrane protein from Akkermansia muciniphila or the pasteurized bacterium improves metabolism in obese and diabetic mice", Nat. Med., 2017, vol. 23, No. 1: pp. 107-113.
Postler, et al., "Understanding the Holobiont: How Microbial Metabolites Affect Human Health and Shape the Immune System", Cell, 2017, vol. 26: pp. 110-130.
Psichas, et al., "The short chain fatty acid propionate stimulates GLP-1 and PYY secretion via free fatty acid receptor 2 in rodents", Int J Obes, 2015, vol. 39: pp. 424-429.
Puertollano, et al., "Biological significance of short-chain fatty acid metabolism by the intestinal microbiome", Curr Opin Clin Nutr Metab Care, 2014, vol. 17, No. 2: pp. 139-144.
Pyra, et al., "Prebiotic Fiber Increases Hepatic Acetyl CoA Carboxylase Phosphorylation and Suppresses Glucose-Dependent Insulinotropic Polypeptide Secretion More Effectively When Used with Metformin in Obese Rats", J Nutr, 2012, vol. 142, No. 2: pp. 213-220.
Qin, et al., "A human gut microbial gene catalogue established by metagenomic sequencing", Nature, 2010, vol. 464: pp. 59-65.
Quach, et al., "Characterizing how probiotic Lactobacillus reuteri 6475 and lactobacillic acid mediate suppression of osteoclast differentiation", Bone Reports, 2019, vol. 11, pp. 1-14.
Raisz, et al., "Short-Term Risedronate Treatment in Postmenopausal Women: Effects on Biochemical Markers of Bone Turnover", Osteoporosis International, 2000, vol. 11: pp. 615-620.
Ramirez-Puebla, et al., "Gut and Root Microbiota Commonalities", App Environ Microbiol, 2013, vol. 79, No. 1: pp. 2-9.
Rastall, et al., "Recent developments in prebiotics to selectively impact beneficial microbes and promote intestinal health", Curr Opin Biotechnol, 2015, vol. 32, pp. 42-46.
Rastogi, et al., "Leaf microbiota in an agroecosystem: spatiotemporal variation in bacterial community composition on field-grown lettuce", ISME J, 2012, vol. 6: pp. 1812-1822.
Ravussin, et al., "Responses of Gut Microbiota to Diet Composition and Weight Loss in Lean and Obese Mice", Obesity, 2012, vol. 20, No. 4: pp. 738-747.
Reichardt, et al., "Phylogenetic distribution of three pathways for propionate production within the human gut microbiota", ISME J, 2014, vol. 8: pp. 1323-1335.
Reichold, et al., "Bifidobacterium adolescentis protects from the development of nonalcoholic steatohepatitis in a mouse model", J Nutr Biochem, 2014, vol. 25: pp. 118-125.
Rendina, et al., "Dried Plum's Unique Capacity to Reverse Bone Loss and Alter Bone Metabolism in Postmenopausal Osteoporosis Model", PLoS ONE, Mar. 2013, vol. 8, No. 3: pp. 1-10.
Rios-Covain, et al., "Enhanced butyrate formation by cross-feeding between Faecalibacterium prausnitzii and Bifidobacterium adolescentis", FEMS Microbiol Lett, 2015, vol. 362, No. 21: pp. 1-7.
Rodriguez-R, et al, "The enveomics collection: a toolbox for specialized analyses of microbial genomes and metagenomes", PeerJ Preprints, 2016, vol. 4: e1900v1.
Rosario, et al., "Understanding the Representative Gut Microbiota Dysbiosis in Metformin-Treated Type 2 Diabetes Patients Using Genome-Scale Metabolic Modeling", Front Physiol, 2018, vol. 9: p. 775.
Rosen, et al., "Treatment With Once-Weekly Alendronate 70 mg Compared With Once-Weekly Risedronate 35 mg in Women With Postmenopausal Osteoporosis: A Randomized Double-Blind Study", Journal of Bone and Mineral Research, 2005, vol. 20, No. 1: pp. 141-151.
Rosenbaum, et al., "The gut microbiota in human energy homeostasis and obesity", Trends Endocrinol Metab, 2015, vol. 26, No. 9: pp. 493-501.
Rosenberg, et al., "Interaction between the Microbiome and Diet: The Hologenome Concept", J Nutr Food Sci, 2016, vol. 6, No. 5: p. 1000545.
Rosenblatt, et al., "Is It Ethical to Conduct Placebo-Controlled Clinical Trials in the Development of New Agents for Osteoporosis? An Industry Perspective", Journal of Bone and Mineral Research, 2003, vol. 18, No. 6: pp. 1142-1145.
Rothschild, et al., "Environment dominates over host genetics in shaping human gut microbiota", Nature, 2018: pp. 1-6.
Round, et al., "The gut microbiota shapes intestinal immune responses during health and disease", Nat Rev Immunol, 2009, vol. 9: pp. 313-324.
Saltiel, et al., "New therapeutic approaches for the treatment of obesity", Sci Transl Med, 2016, vol. 8, No. 323: p. 1-12.
Saltiel, et al., "Inflammatory mechanisms linking obesity and metabolic disease", J Clin Invest, 2017, vol. 127, No. 1: pp. 1-4.
Sam, et al., "The Fungal Mycobiome and Its Interaction with Gut Bacteria in the Host", Int J Mol Sci, 2017, vol. 18, No. 330: pp. 1-11.
Samah, et al., "Probiotics for the management of type 2 diabetes mellitus: A systematic review and meta-analysis", Diabetes Res Clin Pract, 2016, vol. 118: pp. 172-182.
Samuel, et al., "A humanized gnotobiotic mouse model of host-archaeal-bacteria mutualism", PNAS, 2006, vol. 103, No. 26: pp. 10011-10016.
Samuel, et al., "Effects of the gut microbiota on host adiposity are modulated by the short-chain fatty acid binding G protein-coupled receptor, Gpr41", PNAS, 2008, vol. 105, No. 43: pp. 16767-16772.
Sarioglu, et al., "Comparison of the effects of alendronate and risedronate on bone mineral density and bone turnover markers in postmenopausal osteoporosis", Rheumatol Int, 2006, vol. 26: pp. 195-200.
Sawin, et al., "Glycomacropeptide is a prebiotic that reduces Desulfovibrio bacteria, increases cecal short-chain fatty acids, and is anti-inflammatory in mice", Am J Physiol Gastrointest Liver Physiol, 2015, vol. 309: G590-G601.
Schirmer, et al., "Linking the Human Gut Microbiome to Inflammatory Cytokine Production Capacity", Cell, 2016, vol. 167, No. 4: pp. 1125-1136.
Schoch, C.L. et al., "Nuclear ribosomal internal transcribed spacer (ITS) region as a universal DNA barcode marker for Fungi," Proceedings of the National Academy of Sciences, 2012, vol. 109, No. 16, pp. 6241-6246.
Schroeder, et al., "Signals from the gut microbiota to distant organs in physiology and disease", Nat Med, 2016, vol. 22, No. 10: pp. 1079-1089.
Schroeder, et al., "Bifidobacteria or Fiber Protects against Diet-Induced Microbiota-Mediated Colonic Mucus Deterioration", Cell Host & Microbe, 2018, vol. 23: pp. 27-40.
Schwarzer, et al., "Lactobacillus plantarum strain maintains growth of infant mice during chronic undernutrition", Science, Feb. 19, 2016, vol. 351, No. 6275: pp. 854-857.
Scott, et al., "Manipulating the gut microbiota to maintain health and treat disease", Micro Ecol Health Dis, 2015, vol. 26, No. 25877: pp. 1-10.
Seeman, et al., "Age- and Menopause-Related Bone Loss Compromise Cortical and Trabecular Microstructure", J Gerontol A Biol Sci Med Sci, Oct. 2013, vol. 10: pp. 1218-1225.
Serino, et al., "Metabolic adaptation to a high-fat diet is associated with a change in the gut microbiota", Gut, 2012, vol. 61: pp. 543-553.
Sheikhi, et al., "Probiotic Yogurt Culture *Bifidobacterium animalis* Subsp *lactis* BB-12 and Lactobacillus Acidophilus LA-5 Modulate the Cytokine Secretion by Peripheral Blood Mononuclear Cells from Patients with Ulcerative Colitis", Drug Res, 2016, vol. 66: pp. 300-305.

(56) References Cited

OTHER PUBLICATIONS

Sheth, et al., "Spatial metagenomic characterization of microbial biogeography in the gut", Nature Biotechnology, Aug. 2019, vol. 37, pp. 877-883.
Shin, et al., "An increase in the *Akkermansia* spp population induced by metformin treatment improves glucose homeostasis in diet-induced obese mice", Gut, 2014, vol. 63: pp. 727-735.
Shoaie, et al., "Quantifying Diet-Induced Metabolic Changes of the Human Gut Microbiome", Cell Metab, 2015, vol. 22: pp. 320-331.
Simpson, et al., "Review article: dietary fibre-microbiota interactions", Aliment Pharmacol Ther, 2015, vol. 42: pp. 158-179.
Singer, et al., "The initiation of metabolic inflammation in childhood obesity", J Clin Invest, 2017, vol. 127, No. 1: pp. 65-73.
Singh, et al., "Dysregulated Microbial Fermentation of Soluble Fiber Induces Cholestatic Liver Cancer", Cell, 2018, vol. 175: pp. 679-694.
Sjogren, et al., "The Gut Microbiota Regulates Bone Mass in Mice", Journal of Bone and Mineral Research, Jun. 2012, vol. 27, No. 6: pp. 1357-1367.
Magnusdottir, et al., "Generation of genome-scale metabolic reconstructions for 773 members of the human gut microbiota", Nature Biotechnology, Jan. 2017, vol. 35, No. 1: pp. 81-89.
Woo, et al., "Metformin Ameliorates Hepatic Steatosis and Inflammation without Altering Adipose Phenotype in Diet-Induced Obesity", PLoS ONE, 2014, vol. 9, No. 3: e91111.
Wu, et al., "Metformin alters the gut microbiome of individuals with treatment-naïve type 2 diabetes, contributing to the therapeutic effects of the drug", Nat Med, 2017, vol. 23, No. 7: pp. 850-858.
Wu, et al., "Supplement: Metformin alters the gut microbiome of individuals with treatment-naïve type 2 diabetes, contributing to the therapeutic effects of the drug", Nat Med, 2017, vol. 23, No. 7.
Wu, et al., "Arginine metabolism and nutrition in growth, health and disease", Amino Acids, May 2009, vol. 31, No. 1: pp. 153-168.
Xu, et al., "Intestinal microbiota: a potential target for the treatment of postmenopausal osteoporosis", Bone Research, 2017, vol. 5: pp. 1-18.
Yan, et al., "Gut microbiota induce IGF-1 and promote bone formation and growth", PNAS, Nov. 7, 2016: pp. 1-10.
Yang, et al., "Potent Anti-Inflammatory and Antiadipogenic Properties of Bamboo (*Sasa coreana* Nakai) Leaves Extract and Its Major Constituent Flavonoids", J Agric Food Chem, 2017, vol. 65: pp. 6665-6673.
Yassour, et al., "Natural history of the infant gut microbiome and impact of antibiotic treatment on bacterial strain diversity and stability", Sci Transl Med, 2016, vol. 8, No. 343: pp. 1-12.
Yousef, et al., "Metformin: A Unique Herbal Origin Medication", GJMR-B: Pharma, Drug Discovery, Toxicology, and Medicine, 2017, vol. 17, No. 3: pp. 31-37.
Zaiss, et al., "Treg Cells Suppress Osteoclast Formation", Arthritis & Rheumatism, Dec. 2017, vol. 56, No. 12: pp. 4104-4112.
Zaiss, et al., "Increased Bone Density and Resistance to Ovariectomy-Induced Bone Loss in FoxP3-Transgenic Mice Based on Impaired Osteoclast Differentiation", Arthritis & Rheumatism, Aug. 2010, vol. 62, No. 8: pp. 2328-2338.
Zhang, et al., "Human gut microbiota in obesity and after gastric bypass", PNAS, 2009, vol. 106, No. 7: pp. 2365-2370.
Zhang, et al., "Effect of probiotics on glucose metabolism in patients with type 2 diabetes mellitus: a meta-analysis of randomized controlled trials", Medicina, 2016, vol. 52: pp. 28-34.
Zhang, et al., "Structural Changes of Gut Microbiota during Berberine-Mediated Prevention of Obesity and Insulin Resistance in High-Fat Diet-Fed Rats", PLoS ONE, 2012, vol. 7, No. 8: e42529.
Zhang, et al., "Modulation of gut microbiota by berberine and metformin during the treatment of high-fat diet-induced obesity in rats", Sci Rep, 2015, vol. 5, No. 14405: pp. 1-10.
Zhang, et al., "Effects of Acarbose on the Gut Microbiota of Prediabetic Patients: A Randomized, Double-blind, Controlled Crossover Trial", 2017, vol. 8: pp. 293-307.
Zhao, et al., "Gut bacteria selectively promoted by dietary fibers alleviate type 2 diabetes", Science, 2018, vol. 359: pp. 1151-1156.
Zheng, et al., "Prebiotic mannan-oligosaccharides augment the hypoglycemic effects of metformin in correlation with modulating gut microbiota", J Agric Food Chem, 2018, vol. 66, No. 23: pp. 5821-5831.
Zhou, et al., "Age-dependent variations of cancellous bone in response to ovariectomy in C57BL/6J mice", Experimental and Therapeutic Medicine, 2018, vol. 15: pp. 3623-3632.
Zmora, et al., "Personalized Gut Mucosal Colonization Resistance to Empiric Probiotics Is Associated with Unique Host and Microbiome Features", Cell, 2018, vol. 174: pp. 1388-1405.
Forslund et al (2015) Disentangling type 2 diabetes and metformin treatment signatures in the human gut microbiota. Nature 528(7581): 262-266.
Edgar, "Updating the 97% identity threshold for 16S ribosomal RNA OTUs." Bioinformatics 34, No. 14 (2018): 2371-2375.
Nguyen et al., "A perspective on 16S rRNA operational taxonomic unit clustering using sequence similarity." NPJ biofilms and microbiomes 2, No. 1 (2016): 1-8.
Gibson, et al., "Dietary modulation of the human colonic microbiota: introducing the concept of prebiotics", J Nutr, 1995, vol. 125, No. 6: pp. 1401-1412.
Gilbert, et al., "Current understanding of the human microbiome", Nature Medicine, Apr. 2018, vol. 24, No. 4: pp. 392-400.
Gonzalez-Garcia, et al., "Microbial propionic acid production", Fermentation, 2017, vol. 3, No. 21: pp. 1-20.
Gosalbes, et al., "Metabolic adaptation in the human gut microbiota during pregnancy and the first year of life", EBioMedicine, 2019, vol. 39: pp. 497-509.
Graessler, et al., "Metagenomic sequencing of the human gut microbiome before and after bariatric surgery in obese patients with type 2 diabetes: correlation with inflammatory and metabolic parameters", Pharmacogenetics J, 2013, vol. 13: pp. 514-522.
Greenblatt, et al., "Bone Turnover Markers in the Diagnosis and Monitoring of Metabolic Bone Disease", Clinical Chemistry, 2017, vol. 63, No. 2: pp. 464-474.
Greenspan, et al., "Early Changes in Biochemical Markers of Bone Turnover Predict the Long-Term Response to Alendronate Therapy in Representative Elderly Women: A Randomized Clinical Trial", Journal of Bone and Mineral Research, 1998, vol. 13, No. 9: pp. 1431-1438.
Grey, et al., "Duration of Antiresorptive Effects of Low-Dose Zoledronate in Osteopenic Postmenopausal Women: A Randomized, Placebo-Controlled Trial", Journal of Bone and Mineral Research, Jan. 2014, vol. 29, No. 1: pp. 166-172.
Gu, et al., "Analyses of gut microbiota and plasma bile acids enable stratification of patients for antidiabetic treatment", Nature Commun, 2017, vol. 8: p. 1785.
Guo, et al., "Secretions of Bifidobacterium infantis and Lactobacillus acidophilus Protect Intestinal Epithelial Barrier Function", JPGN, 2017, vol. 64, No. 3: pp. 404-412.
Hacquard, et al., "Microbiota and Host Nutrition across Plant and Animal Kingdoms", Cell Host & Microbe, 2015, vol. 17: pp. 603-616.
Harley, et al., "Obesity and the gut microbiome: Striving for causality", Mol Metab, 2012, vol. 1: pp. 21-31.
Heaney, et al., "Dairy and Bone Health", Journal of the American College of Nutrition, 2009, vol. 28, No. 1: pp. 82S-90S.
Hehemann, et al., "Transfer of carbohydrate-active enzymes from marine bacteria to Japanese gut microbiota", Nature, 2010, vol. 464: pp. 908-914.
Heineken, et al., "Systems-level characterization of a host-microbe metabolic symbiosis in the mammalian gut", Gut microbes, 2013, vol. 4, No. 1: pp. 28-40.
Henao-Mejia, et al., "Inflammasome-mediated dysbiosis regulates progression of NAFLD and obesity", Nature, 2012, vol. 482, No. 7384: p. 179-185.
Hess, et al., "Dairy Foods: Current Evidence of their Effects on Bone, Cardiometabolic, Cognitive, and Digestive Health", Comprehensive Reviews in Food Science and Food Safety, 2016, vol. 15: pp. 251-268.
Hildebrandt, et al., "High Fat Diet Determines the Composition of the Murine Gut Microbiome Independently of Obesity", Gastroenterology, 2009, vol. 137, No. 5: p. 1716.

(56) References Cited

OTHER PUBLICATIONS

Holmes, et al., "Diet-Microbiome Interactions in Health Are Controlled by Intestinal Nitrogen Source Constraints", Cell Metab, 2017, vol. 25: pp. 140-151.

Hooper, et al., "Interactions Between the Microbiota and the Immune System", Science, 2012, vol. 336, No. 6086: pp. 1268-1273.

Hugenholtz, et al., "Mouse models for human intestinal microbiota research: a critical evaluation", Cellular and Molecular Life Sciences, 2018, vol. 75: pp. 149-160.

Ibanez, et al., "Gut microbiome and bone", Joint Bone Spine, 2019, vol. 86: pp. 43-47.

Ilhan, et al., (2017) "Distinctive microbiomes and metabolites linked with weight loss after gastric bypass, but not gastric banding", ISME J 11(9): 2047-2058.

Imaoka, et al., "Anti-inflammatory activity of probiotic Bifidobacterium: enhancement of IL-10 production in peripheral blood mononuclear cells from ulcerative colitis patients and inhibition of IL-8 secretion in HT-29 cells", World J Gastroenterol, 2008, vol. 14, No. 16: pp. 2511-2516.

Imlay, et al., "Diagnosing oxidative stress in bacteria: not as easy as you might think", Current Opinion in Microbiology, 2015, vol. 24: pp. 124-131.

Iwami, et al., "Effects of Short Chain Fatty Acid, Sodium Butyrate, on Osteoblastic Cells and Osteoclastic Cells", Int. J. Biochem., 1993, vol. 25, No. 11: pp. 1631-1635.

Jackson, et al., "Culture dependent and independent analysis of bacterial communities associated with commercial salad leaf vegetables", BMC Microbiol, 2013, vol. 13, No. 274: pp. 1-12.

Jackson, et al., "Emerging Perspectives on the Natural Microbiome of Fresh Produce Vegetables", Agriculture, 2015, vol. 5: pp. 170-187.

Jafarnejad, et al., "Effects of a Multispecies Probiotic Supplement on Bone Health in Osteopenic Postmenopausal Women: A Randomized, Double-blind, Controlled Trial", Journal of the American College of Nutrition, 2017, vol. 36, No. 7: pp. 497-506.

Jahangir, et al., "Type 2 Diabetes Current and Future Medications: A Short Review", Int J Pharm Pharmacol, 2017, vol. 1, No. 1: p. 101.

Jain, et al., "High throughput ANI analysis of 90K prokaryotic genomes reveals clear species boundaries", Nature Communications, 2018, vol. 9, No. 5114: pp. 1-8.

Jain, et al., "Nanopore sequencing and assembly of a human genome with ultra-long reads", Nature Biotechnology, 2018, vol. 36, No. 4: p. 338.

Jansson, et al., "Probiotic treatment using a mix of three Lactobacillus strains for lumbar spine bone loss in postmenopausal women: a randomised, double-blind, placebo-controlled, multicentre trial", Lancet Rheumatol, Nov. 2019, vol. 1: e154-62.

Jarvis, et al., "Microbiomes Associated With Foods From Plant and Animal Sources", Front Microbiol, 2018, vol. 9: p. 2540.

Jennings, et al., "Amino Acid Intakes Are Associated With Bone Mineral Density and Prevalence of Low Bone Mass in Women: Evidence From Discordant Monozygotic Twins", Journal of Bone and Mineral Research, Feb. 2016, vol. 31, No. 2: pp. 326-335.

Jia, et al., "CARD 2017: expansion and model-centric curation of the comprehensive antibiotic resistance database", Nucleic Acids Res, 2017, No. 45: p. D566-D573.

Kaluzna-Czaplinska, et al., "Is there a relationship between intestinal microbiota, dietary compounds, and obesity?", Trends Food Sci Technol, 2017, vol. 70: p. 105-113.

Kapitza, et al., "Effects of semaglutide on beta cell function and glycaemic control in participants with type 2 diabetes: a randomized, double-blind, placebo-controlled trial", Diabetalogia, 2017, vol. 60: pp. 1390-1399.

Kaplan, et al., "Fermentation of Fructooligosaccharides by Lactic Acid Bacteria and Bifidobacterial", Appl Environ Microbiol, 2000, vol. 66, No. 6: pp. 2682-2684.

Kasubuchi, et al., "Dietary Gut Microbial Metabolites, Short-chain Fatty Acids, and Host Metabolic Regulation", Nutrients, 2015, vol. 7: pp. 2839-2849.

Kau, et al., "Human nutrition, the gut microbiome and the immune system", Nature, 2011, vol. 474: pp. 327-336.

Kim, et al., "Impact of L-Arginine Metabolism on Immune Response and Anticancer Immunotherapy", Frontiers in Oncology, Mar. 2018, vol. 8, No. 67: pp. 1-5.

Kim, et al., "Immune regulation by microbiome metabolites", Immunology, 2018, vol. 154, pp. 220-229.

Kimura, et al., "The gut microbiota suppresses insulin-mediated fat accumulation via the short-chain fatty acid receptor GPR43", Nat Commun, 2013, vol. 4, No. 1829: pp. 1-12.

King, et al., "Regulation of de novo purine synthesis inhuman bone marrow mononuclear cells by hypoxanthine.", The Journal of Clinical Investigation, 1983;72(3):965-970.

Kishida, et al., "Effect of miglitol on the suppression of nonalcoholic steatohepatitis development and improvement of thegut environment in a rodent model", J Gastroenterol, 2017, vol. 52, No. 11: pp. 1180-1191.

Koh, et al., "From Dietary Fiber to Host Physiology: Short Chain Fatty Acids as Key Bacterial Metabolites", Cell, 2016, vol. 165: pp. 1332-1345.

König, et al., "Specific Collagen Peptides Improve Bone Mineral Density and Bone Markers in Postmenopausal Women—A Randomized Controlled Study", Nutrients, 2018, vol. 10. No. 97: pp. 1-11.

Kreznar, et al., "Host Genotype and Gut Microbiome Modulate Insulin Secretion and Diet-Induced Metabolic Phenotypes", Cell Rep, 2017, vol. 18: pp. 1739-1750.

Kuo, et al., "Bone biomarker for the clinical assessment of osteoporosis: recent developments and future perspectives", Biomarker Research, 2017, vol. 5, No. 18: pp. 1-9.

PCT/US2019/049823—International Search Report and Written Opinion, dated Feb. 20, 2020, 12 pages.

GenBank KC111446.1. Hanseniaspora opuntiae strain JEY269 18S ribosomal RNA gene, partial sequence; internal transcribed spacer 1, 5.8S ribosomal RNA gene, and internal transcribed spacer 2, complete sequence; and 28S ribosomal RNA gene, partial sequence. Jul. 24, 2013 [online]. [Retrieved Dec. 10, 2019]. Retrieved from the Internet: <URL: https:/twww.ncbi.nlm.nih.gov/nuccore/KC111446.1/ >. Especially p. 1.

PCT/US2019/049823—Invitation to Pay Additional Fees, dated Dec. 10, 2019, 2 pages.

PCT/US2020/038830—Invitation to Pay Additional Fees, dated Oct. 29, 2020, 24 pages.

Xu et al., "Paenibacillus panacisoli enhances growth of *Lactobacillus* spp. by producing xylooligosaccharides in corn stover ensilages." Carbohydrate polymers 184 (2018): 435-444.

Rosales-Bravo et al., "Novel consortium of Klebsiella variicola and *Lactobacillus* species enhances the functional potential of fermented dairy products by increasing the availability of branched-chain amino acids and the amount of distinctive volatiles." Journal of applied microbiology 123, No. 5 (2017): 1237-1250.

PCT/US2020/038830—International Search Report and Written Opinion, dated Dec. 16, 2020, 23 pages.

Biaggini et al., "The pathogenic potential of Pseudomonas fluorescens MFN1032 on enterocytes can be modulated by serotonin, substance P and epinephrine." Archives of microbiology 197, No. 8 (2015): 983-990.

Slavin, et al., "Fiber and Prebiotics: Mechanisms and Health Benefits", Nutrients, 2013, vol. 5: pp. 1417-1435.

Smith, et al., "Yeast Modulation of Human Dendritic Cell Cytokine Secretion: An In Vitro Study", PLoS ONE, 2014, vol. 9, No. 5: pp. 1-14.

Sonnenburg, et al., "Diet-microbiota interactions as moderators of human metabolism", Nature, 2016, vol. 535: pp. 56-64.

Strorelli, et al., "Metformin, Microbes, and Aging", Cell Metab, 2013, vol. 17: pp. 809-811.

Stuible, et al., "Mechanism and Function of Monoclonal Antibodies Targeting Siglec-15 for Therapeutic Inhibition of Osteoclastic Bone Resorption*", The Journal of Biological Chemistry, vol. 289, No. 10: pp. 6498-6512.

Stull, et al., "Blueberries' Impact on Insulin Resistance and Glucose Intolerance", Antioxidants, 2016, vol. 5, No. 44: pp. 1-11.

(56) References Cited

OTHER PUBLICATIONS

Stull, et al., "Bioactives in Blueberries Improve Insulin Sensitivity in Obese, Insulin-Resistant Men and Women", J Nutr, 2010, vol. 140, No. 10: pp. 1764-1768.
Suez, et al., "Post-Antibiotic Gut Mucosal Microbiome Reconstitution Is Impaired by Probiotics and Improved by Autologous FMT", Cell, 2018, vol. 174: pp. 1406-1423.
Sun, et al., "Gut mirobiota and intestinal FXR mediate the clinical benefits of metformin", Nat Med, 2018, vol. 24: pp. 1919-1929.
Suzek, et al., "UniRef clusters: a comprehensive and scalable alternative for improving sequence similarity searches", Bioinformatics, 2015, vol. 31, No. 6: pp. 926-932.
Sweeney, et al., "Metabolic surgery: action via hormonal milieu changes, changes in bile acids or gut microbiota? A summary of the literature", Best Pract Res Clin Gastroenterol, 2014, vol. 28: pp. 727-740.
Takimoto, et al., "Effect of Bacillus subtilis C-3102 on bone mineral density in healthy postmenopausal Japanese women: a randomized, placebo-controlled, double-blind clinical trial", Bioscience of Microbiota, Food and Health, 2018, vol. 37, No. 4: pp. 87-96.
Tan, et al., "The Role of Short-Chain Fatty Acids in Health and Disease", Advances in Immunology, 2014, vol. 121: pp. 91-119.
Terrapon, et al., "How do gut microbes break down dietary fiber?", Trends Biochem Sci, 2014, vol. 39, No. 4: pp. 156-158.
Tilg, et al., "The intestinal microbiota fuelling metabolic inflammation", Nature Reviews, Aug. 6, 2019: pp. 1-15.
Tohidi, et al., "Omentin-1, visfatin and adiponectin levels in relation to bone mineral density in Iranian postmenopausal women", Bone, 2012, vol. 51: pp. 876-881.
Tolhurst, et al., "Short-Chain Fatty Acids Stimulate Glucagon-Like Peptide-1 Secretion via the G-Protein-Coupled Receptor FFAR2", Diabetes, 2012, vol. 61: pp. 364-371.
Truong, et al., "MetaPhlAn2 for enhanced metagenomic taxonomic profiling", Nature Methods, Oct. 2015, vol. 12, No. 10: pp. 902-904.
Tuohy, et al., "Up-regulating the Human Intestinal Microbiome Using Whole Plant Foods, Polyphenols, and/or Fiber", J Agric Food Chem, 2012, vol. 60: pp. 8776-8782.
Turnbaugh, et al., "A core gut microbiome in obese and lean twins", Nature, 2009, vol. 457, No. 7228: pp. 480-484.
Turnbaugh, et al., "An obesity-associated gut microbiome with increased capacity for energy harvest", Nature, 2006, vol. 444: pp. 1027-1031.
Turnbaugh, et al., "Diet-Induced Obesity is Linked to Marked but Reversible Alterations in the Mouse Distal Gut Microbiome", Cell Host Microbe, 2008, vol. 3: pp. 213-223.
Turnbaugh, et al., "Supplementary Materials for : The Effect of Diet on the Human Gut Microbiome: A Metagenomic Analysis in Humanized Gnotobiotic Mice", Sci Transl Med, 2009: pp. 1-23.
Turnbaugh, et al., "The Effect of Diet on the Human Gut Microbiome: A Metagenomic Analysis in Humanized Gnotobiotic Mice", Sci Transl Med, 2009: pp. 1-23.
Tyagi, et al., "The Microbial Metabolite Butyrate Stimulates Bone Formation via T Regulatory Cell-Mediated Regulation of WNT10B Expression", Immunity, 2018, vol. 49: pp. 1116-1131.
U.S. Appl. No. 16/235,858, Notice of Allowance, dated Jan. 23, 2020.
U.S. Appl. No. 16/235,858, Office Action, dated Aug. 6, 2019.
Van Der Beek, et al., "Streptococcal dTDP-L-rhamnose biosynthesis enzymes: functional characterization and lead compound identification", Molecular Microbiology, Jan. 1, 2019, vol. 111, No. 4: pp. 1-32.
Van Hul, et al., "Reduced obesity, diabetes and steatosis upon cinnamon and grape pomace are associated with changes in gut microbiota and markers of gut barrier", Am J Physiol Endocrinol Metab, 2017, vol. 314, No. 4: E3340E352.G.
Van Wyk, et al., "Current perspectives on the families of glycoside hydrolases of *Mycobacterium tuberculosis*: their importance and prospects for assigning function to unknowns", Glycobiology, 2017, vol. 27, No. 2: pp. 112-122.
Vatanen, et al., "Variation in Microbiome LPS Immunogenicity Contributes to Autoimmunity in Humans", Cell, 2016, vol. 165: pp. 842-853.
Verma, et al. "Cell surface polysaccharides of Bifidobacterium bifidum induce the generation of Foxp3+ regulatory T cells", Sci Immunol. 3, Oct. 19, 2018: pp. 1-14.
Vital, et al., "A gene-targeted approach to investigate the intestinal butyrate-producing bacterial community", Microbiome, 2013, vol. 1, No. 8: pp. 1-14.
Vogt, et al., "L-Rhamnose increases serum propionate in humans1-3", Am J Clin Nutr, 2004, vol. 80: pp. 89-94.
Voreades, et al., "Diet and the development of the human intestinal microbiome", Front Microbiol, 2014, vol. 5, No. 494: 1-9.
Vorholt, et al., "Microbial life in the phyllosphere", Institute of Microbiology, Dec. 2012, vol. 10: pp. 828-840.
Wagner, et al., "The Pentose Phosphate Pathway in Regenerating Skeletal Muscle", Biochem. 1978, vol. 170: pp. 17-22.
Wahlstrom, et al., "Intestinal Crosstalk between Bile Acids and Microbiota and Its Impact on Host Metabolism", Cell Metab, 2016, vol. 24: pp. 41-50.
Wallace, et al., "Use and Abuse of HOMA Modeling", Diabetes Care, 2004, vol. 27, No. 6: pp. 1487-1495.
Wang, et al., "Modulation of gut microbiota during probiotic-mediated attenuation of metabolic syndrome in high fat diet-fed mice", ISME J, 2015, vol. 9: pp. 1-15.
Wassermann, et al., "Harnessing the microbiomes of *Brassica* vegetables for health issues", Sci Rep, 2017, vol. 7: p. 17649.
Wasserman, et al., "An Apple a Day: Which Bacteria Do We Eat With Organic and Conventional Apples", Frontiers in Microbiology, Jul. 24, 2019, vol. 10, Article 1629: pp. 1-13.
Weitkunat, et al., "Short-chain fatty acids and inulin, but not guar gum, prevent diet-induced obesity and insulin resistance through differential mechanisms in mice", Sci Rep, 2017, vol. 7, No. 6109: pp. 1-13.
Weitzmann, et al., "Estrogen deficiency and bone loss: an inflammatory tale", The Journal of Clinical Investigation, May 2006, vol. 116, No. 5: pp. 1186-1194.
Welch, et al., "The Effects of Flavonoids on Bone", Curr Osteoporos Rep., 2014, vol. 12: pp. 205-210.
White, et al., "A Brief History of the Development of Diabetes Medications", Diabetes Spectr, 2015, vol. 27, No. 2: pp. 82-86.
Whisner, et al., "Prebiotics, Bone and Mineral Metabolism", Calcif Tissue Int, 2018, vol. 102: pp. 443-479.
Winer, et al., "The Intestinal Immune System in Obesity and Insulin Resistance", Cell Metab, 2016, vol. 23: pp. 413-426.
Winer, et al., "Immunologic impact of the intestine in metabolic disease", J Clin Invest, 2017, vol. 127, No. 1: pp. 33-42.
Wolfert, et al., "Adaptive immune activation: glycosylation does matter", Nat Chem Biol, Dec. 2013, vol. 9, No. 12: pp. 776-784.

* cited by examiner

| Name | Readcount (% of classified reads) |
|---|---|
| Neosartorya fischeri | 17656 (22.68%) |
| Aureimonas sp. Leaf427 | 7331 (9.42%) |
| Elizabethkingia anophelis | 6310 (8.1%) |
| Periglandula ipomoeae | 6185 (7.94%) |
| Bacillus sp. LL01 | 3385 (4.35%) |
| Candidatus Burkholderia verschuerenii | 2917 (3.75%) |
| Streptomyces olindensis | 2208 (2.84%) |
| Candidatus Burkholderia calva | 1880 (2.41%) |
| Penicillium paneum | 1444 (1.85%) |
| Pseudoalteromonas luteoviolacea | 1290 (1.66%) |

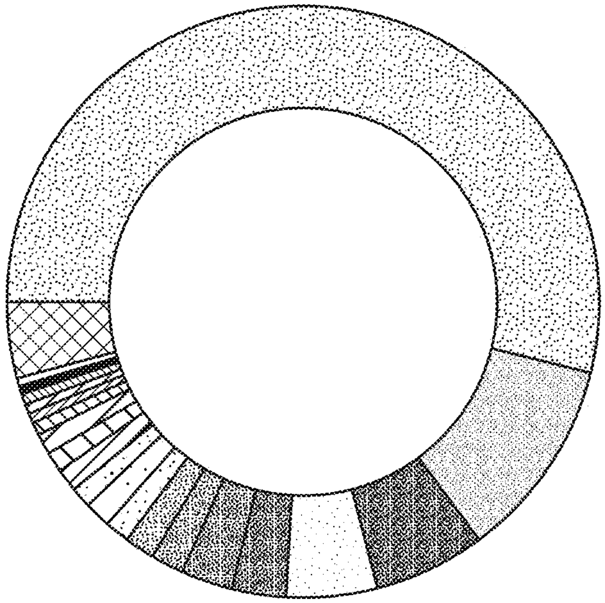

| Name | Estimated Abundance |
|---|---|
| Pseudomonas fluorescens | 53.94% |
| Pseudomonas sp. DSM 29167 | 10.99% |
| Propionibacterium acnes | 6.10% |
| Acinetobacter soli | 4.97% |
| Aureobasidium pullulans | 2.96% |
| Pseudomonas syringae | 2.76% |
| Pseudomonas sp. Leaf15 | 1.84% |
| Acinetobacter baumannii | 1.58% |
| Pantoea sp. SL1_M5 | 1.43% |
| Raoultella ornithinolytica | 1.32% |
| Sphingomonas sp. Ant20 | 1.27% |
| Comamonas testosteroni | 1.18% |
| Rahnella sp. WP5 | 1.18% |
| Enterobacter sp. 940_PEND | 1.06% |
| Pseudomonas sp. FH1 | 0.73% |
| Rothia dentocariosa | 0.54% |
| Pectobacterium carotovorum | 0.54% |
| Enhydrobacter aerosaccus | 0.54% |
| Bacillus sp. LL01 | 0.42% |
| Pseudomonas trivialis | 0.39% |

FIG. 2B

| Name | Estimated Abundance |
|---|---|
| Lactobacillus acetotolerans | 60.98% |
| Lactobacillus buchneri | 12.34% |
| Pediococcus ethanolidurans | 5.47% |
| Lactobacillus parafarraginis | 4.32% |
| Lactobacillus rapi | 2.91% |
| Lactobacillus plantarum | 1.52% |
| Lactobacillus kefiranofaciens | 1.40% |
| Lactobacillus futsaii | 1.38% |
| Lactobacillus brevis | 1.25% |
| Lactobacillus panis | 1.16% |
| (Remaining) | 7.26% |

Blackberries

Squash gourd

SBD111 baseline vs 6 weeks

SBD111 vs OVX

SEQUENCE LISTING

<160> NUMBER OF SEQ ID NOS: 165

<210> SEQ ID NO 1
<211> LENGTH: 1490
<212> TYPE: DNA
<213> ORGANISM: Unknown
<220> FEATURE:
<223> OTHER INFORMATION: Description of Unknown:
      DP1 16S rRNA sequence

<400> SEQUENCE: 1
agtcagacat gcaagtcgag cggtagagag aagcttgctt ctcttgagag cggcggacgg 60
gtgagtaaag cctaggaatc tgcctggtag tgggggataa cgttcggaaa cggacgctaa 120
taccgcatac gtcctacggg agaaagcagg ggaccttcgg gccttgcgct atcagatgag 180
cctaggtcgg attagctagt tggtgaggta atggctcacc aaggcgacga tccgtaactg 240
gtctgagagg atgatcagtc acactggaac tgagacacgg tccagactcc tacgggaggc 300
agcagtgggg aatattggac aatgggcgaa agcctgatcc agccatgccg cgtgtgtgaa 360
gaaggtcttc ggattgtaaa gcactttaag ttgggaggaa gggcattaac ctaatacgtt 420
agtgttttga cgttaccgac agaataagca ccggctaact ctgtgccagc agccgcggta 480
atacagaggg tgcaagcgtt aatcggaatt actgggcgta aagcgcgcgt aggtggtttg 540
ttaagttgga tgtgaaatcc ccgggctcaa cctgggaact gcattcaaaa ctgactgact 600
agagtatggt agagggtggt ggaatttcct gtgtagcggt gaaatgcgta gatataggaa 660
ggaacaccag tggcgaaggc gaccacctgg actaatactg acactgaggt gcgaaagcgt 720

-continued

```
ggggagcaaa caggattaga taccctggta gtccacgccg taaacgatgt caactagccg    780

ttgggagcct tgagctctta gtggcgcagc taacgcatta agttgaccgc ctggggagta    840

cggccgcaag gttaaaactc aaatgaattg acgggggccc gcacaagcgg tggagcatgt    900

ggtttaattc gaagcaacgc gaagaacctt accaggcctt gacatccaat gaactttcta    960

gagatagatt ggtgccttcg ggaacattga gacaggtgct gcatggctgt cgtcagctcg   1020

tgtcgtgaga tgttgggtta agtcccgtaa cgagcgcaac ccttgtcctt agttaccagc   1080

acgtaatggt gggcactcta aggagactgc cggtgacaaa ccggaggaag gtggggatga   1140

cgtcaagtca tcatggccct tacggcctgg gctacacacg tgctacaatg gtcggtacag   1200

agggttgcca agccgcgagg tggagctaat cccataaaac cgatcgtagt ccggatcgca   1260

gtctgcaact cgactgcgtg aagtcggaat cgctagtaat cgcgaatcag aatgtcgcgg   1320

tgaatacgtt cccgggcctt gtacacaccg cccgtcacac catgggagtg ggttgcacca   1380

gaagtagcta gtctaacctt cgggaggacg gttaccacgg tgtgattcat gactggggtg   1440

aagtcgtaac aaggtagccg taggggaacc tgcggctgga tcacctcctt              1490
```

<210> SEQ ID NO 2
<211> LENGTH: 1017
<212> TYPE: DNA
<213> ORGANISM: Unknown
<220> FEATURE:
<223> OTHER INFORMATION: Description of Unknown:
      DP2 ITS sequence
<220> FEATURE:
<221> NAME/KEY: modified_base
<222> LOCATION: (59)..(59)
<223> OTHER INFORMATION: a, c, t, g, unknown or other
<220> FEATURE:
<221> NAME/KEY: modified_base
<222> LOCATION: (61)..(61)
<223> OTHER INFORMATION: a, c, t, g, unknown or other
<220> FEATURE:
<221> NAME/KEY: modified_base
<222> LOCATION: (533)..(533)
<223> OTHER INFORMATION: a, c, t, g, unknown or other
<220> FEATURE:
<221> NAME/KEY: modified_base
<222> LOCATION: (866)..(866)
<223> OTHER INFORMATION: a, c, t, g, unknown or other
<220> FEATURE:
<221> NAME/KEY: modified_base
<222> LOCATION: (876)..(877)
<223> OTHER INFORMATION: a, c, t, g, unknown or other
<220> FEATURE:
<221> NAME/KEY: modified_base
<222> LOCATION: (898)..(899)
<223> OTHER INFORMATION: a, c, t, g, unknown or other
<220> FEATURE:
<221> NAME/KEY: modified_base
<222> LOCATION: (908)..(908)
<223> OTHER INFORMATION: a, c, t, g, unknown or other
<220> FEATURE:
<221> NAME/KEY: modified_base
<222> LOCATION: (922)..(922)
<223> OTHER INFORMATION: a, c, t, g, unknown or other
<220> FEATURE:
<221> NAME/KEY: modified_base
<222> LOCATION: (941)..(942)
<223> OTHER INFORMATION: a, c, t, g, unknown or other
<220> FEATURE:
<221> NAME/KEY: modified_base
<222> LOCATION: (947)..(947)
<223> OTHER INFORMATION: a, c, t, g, unknown or other
<220> FEATURE:
<221> NAME/KEY: modified_base
<222> LOCATION: (949)..(949)
<223> OTHER INFORMATION: a, c, t, g, unknown or other
<220> FEATURE:

<221> NAME/KEY: modified_base
<222> LOCATION: (974)..(974)
<223> OTHER INFORMATION: a, c, t, g, unknown or other
<220> FEATURE:
<221> NAME/KEY: modified_base
<222> LOCATION: (976)..(976)
<223> OTHER INFORMATION: a, c, t, g, unknown or other
<220> FEATURE:
<221> NAME/KEY: modified_base
<222> LOCATION: (978)..(978)
<223> OTHER INFORMATION: a, c, t, g, unknown or other
<220> FEATURE:
<221> NAME/KEY: modified_base
<222> LOCATION: (988)..(988)
<223> OTHER INFORMATION: a, c, t, g, unknown or other
<220> FEATURE:
<221> NAME/KEY: modified_base
<222> LOCATION: (996)..(996)
<223> OTHER INFORMATION: a, c, t, g, unknown or other
<220> FEATURE:
<221> NAME/KEY: modified_base
<222> LOCATION: (1002)..(1002)
<223> OTHER INFORMATION: a, c, t, g, unknown or other
<220> FEATURE:
<221> NAME/KEY: modified_base
<222> LOCATION: (1013)..(1013)
<223> OTHER INFORMATION: a, c, t, g, unknown or other

<400> SEQUENCE: 2
ttgttgctcg agttcttgtt tagatctttt acaataatgt gtatctttaa tgaagatgng 60
ngcttaattg cgctgcttta ttagagtgtc gcagtagaag tagtcttgct tgaatctcag 120
tcaacgttta cacacattgg agttttttta ctttaattta attctttctg ctttgaatcg 180
aaaggttcaa ggcaaaaaac aaacacaaac aattttattt tattataatt ttttaaacta 240
aaccaaaatt cctaacggaa attttaaaat aatttaaaac tttcaacaac ggatctcttg 300
gttctcgcat cgatgaaaaa cgtaccgaat tgcgataagt aatgtgaatt gcaaatactc 360
gtgaatcatt gaatttttga acgcacattg cgcccttgag cattctcaag ggcatgcctg 420
tttgagcgtc atttccttct caaaaaataa tttttttattt tttggttgtg ggcgatactc 480
agggttagct tgaaattgga gactgtttca gtctttttta attcaacact tancttcttt 540
ggagacgctg ttctcgctgt gatgtattta tggatttatt cgttttactt tacaagggaa 600
atggtaatgt accttaggca aagggttgct tttaatattc atcaagtttg acctcaaatc 660
aggtaggatt acccgctgaa cttaagcata tcaataagcg gaggaaaaga aaccaactgg 720
gattacctta gtaacggcga gtgaagcggt aaaagctcaa atttgaaatc tggtactttc 780
agtgcccgag ttgtaatttg tagaatttgt ctttgattag gtccttgtct atgttccttg 840
gaacaggacg tcatagaggg tgagantccc gtttgnngag gatacctttt ctctgtanna 900
ctttttcnaa gagtcgagtt gnttgggaat gcagctcaaa nngggtngna aattccatct 960
aaagctaaat attngncnag agaccganag cgacantaca gngatggaaa gangaaa 1017

<210> SEQ ID NO 3
<211> LENGTH: 1548
<212> TYPE: DNA
<213> ORGANISM: Unknown
<220> FEATURE:
<223> OTHER INFORMATION: Description of Unknown:
DP3 16S rRNA sequence

<400> SEQUENCE: 3
attgagagtt tgatcctggc tcaggatgaa cgctggcggc gtgcctaata catgcaagtc 60
gaacgcacag cgaaaggtgc ttgcaccttt caagtgagtg gcgaacgggt gagtaacacg 120

```
tggacaacct gcctcaaggc tggggataac atttggaaac agatgctaat accgaataaa    180

actcagtgtc gcatgacaca aagttaaaag gcgctttggc gtcacctaga gatggatccg    240

cggtgcatta gttagttggt ggggtaaagg cctaccaaga caatgatgca tagccgagtt    300

gagagactga tcggccacat tgggactgag acacggccca aactcctacg ggaggctgca    360

gtagggaatc ttccacaatg ggcgaaagcc tgatggagca acgccgcgtg tgtgatgaag    420

gctttcgggt cgtaaagcac tgttgtacgg gaagaacagc tagaataggg aatgatttta    480

gtttgacggt accataccag aaagggacgg ctaaatacgt gccagcagcc gcggtaatac    540

gtatgtcccg agcgttatcc ggatttattg ggcgtaaagc gagcgcagac ggttgattaa    600

gtctgatgtg aaagcccgga gctcaactcc ggaatggcat tggaaactgg ttaacttgag    660

tgcagtagag gtaagtggaa ctccatgtgt agcggtggaa tgcgtagata tatggaagaa    720

caccagtggc gaaggcggct tactggactg taactgacgt tgaggctcga aagtgtgggt    780

agcaaacagg attagatacc ctggtagtcc acaccgtaaa cgatgaacac taggtgttag    840

gaggtttccg cctcttagtg ccgaagctaa cgcattaagt gttccgcctg gggagtacga    900

ccgcaaggtt gaaactcaaa ggaattgacg ggacccgca caagcggtgg agcatgtggt     960

ttaattcgaa gcaacgcgaa gaaccttacc aggtcttgac atcctttgaa gcttttagag   1020

atagaagtgt tctcttcgga gacaaagtga caggtggtgc atggtcgtcg tcagctcgtg   1080

tcgtgagatg ttgggttaag tcccgcaacg agcgcaaccc ttattgttag ttgccagcat   1140

tcagatgggc actctagcga gactgccggt gacaaaccgg aggaaggcgg ggacgacgtc   1200

agatcatcat gccccttatg acctgggcta cacacgtgct acaatggcgt atacaacgag   1260

ttgccaaccc gcgagggtga gctaatctct taaagtacgt ctcagttcgg attgtagtct   1320

gcaactcgac tacatgaagt cggaatcgct agtaatcgcg gatcagcacg ccgcggtgaa   1380

tacgttcccg ggtcttgtac acaccgcccg tcacaccatg ggagtttgta atgcccaaag   1440

ccggtggcct aacctttag gaaggagccg tctaaggcag gacagatgac tggggtgaag    1500

tcgtaacaag gtagccgtag gagaacctgc ggctggatca cctccttt                1548


<210> SEQ ID NO 4
<211> LENGTH: 1538
<212> TYPE: DNA
<213> ORGANISM: Unknown
<220> FEATURE:
<223> OTHER INFORMATION: Description of Unknown:
      DP4 16S rRNA sequence

<400> SEQUENCE: 4

ttgaagagtt tgatcatggc tcagattgaa cgctggcggc aggcctaaca catgcaagtc     60

gagcggcagc ggaaagtagc ttgctacttt gccggcgagc ggcggacggg tgagtaatgt    120

ctgggaaact gcctgatgga gggggataac tactggaaac ggtagctaat accgcatgac    180

ctcgaaagag caaagtgggg gatcttcgga cctcacgcca tcggatgtgc ccagatggga    240

ttagctagta ggtgaggtaa tggctcacct aggcgacgat ccctagctgg tctgagagga    300

tgaccagcca cactggaact gagacacggt ccagactcct acgggaggca gcagtgggga    360

atattgcaca atgggcgcaa gcctgatgca gccatgccgc gtgtgtgaag aaggccttag    420

ggttgtaaag cactttcagc gaggaggaag gcatcatact taatacgtgt ggtgattgac    480

gttactcgca gaagaagcac cggctaactc cgtgccagca gccgcggtaa tacggagggt    540

gcaagcgtta atcggaatta ctgggcgtaa agcgcacgca ggcggtttgt taagtcagat    600
```

gtgaaatccc cgcgcttaac gtgggaactg catttgaaac tggcaagcta gagtcttgta 660 gagggggta gaattccagg tgtagcggtg aaatgcgtag agatctggag gaataccggt 720
ggcgaaggcg gccccctgga caaagactga cgctcaggtg cgaaagcgtg gggagcaaac 780
aggattagat accctggtag tccacgccgt aaacgatgtc gacttggagg ttgttccctt 840
gaggagtggc ttccggagct aacgcgttaa gtcgaccgcc tggggagtac ggccgcaagg 900
ttaaaactca aatgaattga cgggggcccg cacaagcggt ggagcatgtg gtttaattcg 960
atgcaacgcg aagaacctta cctactcttg acatccacgg aatttggcag agatgcctta 1020
gtgccttcgg gaaccgtgag acaggtgctg catggctgtc gtcagctcgt gttgtgaaat 1080
gttgggttaa gtcccgcaac gagcgcaacc cttatccttt gttgccagcg attcggtcgg 1140
gaactcaaag gagactgccg gtgataaacc ggaggaaggt ggggatgacg tcaagtcatc 1200
atggccctta cgagtagggc tacacacgtg ctacaatggc gcatacaaag agaagcgacc 1260
tcgcgagagc aagcggacct cacaaagtgc gtcgtagtcc ggatcggagt ctgcaactcg 1320
actccgtgaa gtcggaatcg ctagtaatcg tggatcagaa tgccacggtg aatacgttcc 1380
cgggccttgt acacaccgcc cgtcacacca tgggagtggg ttgcaaaaga agtaggtagc 1440
ttaaccttcg ggagggcgct taccactttg tgattcatga ctggggtgaa gtcgtaacaa 1500
ggtaaccgta ggggaacctg cggttggatc acctcctt 1538

<210> SEQ ID NO 5
<211> LENGTH: 1042
<212> TYPE: DNA
<213> ORGANISM: Unknown
<220> FEATURE:
<223> OTHER INFORMATION: Description of Unknown:
DP5 ITS sequence
<220> FEATURE:
<221> NAME/KEY: modified_base
<222> LOCATION: (53)..(54)
<223> OTHER INFORMATION: a, c, t, g, unknown or other
<220> FEATURE:
<221> NAME/KEY: modified_base
<222> LOCATION: (1024)..(1024)
<223> OTHER INFORMATION: a, c, t, g, unknown or other

<400> SEQUENCE: 5
gcgcttattg cgcggcgaaa aaaccttaca cacagtgttt tttgttatta cannaacttt 60
tgctttggtc tggactagaa atagtttggg ccagaggtta ctaaactaaa cttcaatatt 120
tatattgaat tgttatttat ttaattgtca atttgttgat taaattcaaa aaatcttcaa 180
aactttcaac aacggatctc ttggttctcg catcgatgaa gaacgcagcg aaatgcgata 240
agtaatatga attgcagatt ttcgtgaatc atcgaatctt tgaacgcaca ttgcgccctc 300
tggtattcca gagggcatgc ctgtttgagc gtcatttctc tctcaaacct tcgggtttgg 360
tattgagtga tactcttagt cgaactaggc gtttgcttga aatgtattgg catgagtggt 420
actggatagt gctatatgac tttcaatgta ttaggtttat ccaactcgtt gaatagttta 480
atggtatatt tctcggtatt ctaggctcgg ccttacaata taacaaacaa gtttgacctc 540
aaatcaggta ggattacccg ctgaacttaa gcatatcaat aagcggagga aaagaaacca 600
acagggattg ccttagtaac ggcgagtgaa gcggcaaaag ctcaaatttg aaatctggca 660
ccttcggtgt ccgagttgta atttgaagaa ggtaactttg gagttggctc ttgtctatgt 720
tccttggaac aggacgtcac agagggtgag aatcccgtgc gatgagatgc ccaattctat 780
gtaaagtgct ttcgaagagt cgagttgttt gggaatgcag ctctaagtgg gtggtaaatt 840
ccatctaaag ctaaatattg gcgagagacc gatagcgaac aagtacagtg atggaaagat 900
gaaaagaact ttgaaaagag agtgaaaaag tacgtgaaat tgttgaaagg gaaagggctt 960
gagatcagac ttggtatttt gcgatccttt ccttcttggt tgggttcctc gcagcttact 1020
gggncagcat cggtttggat gg 1042

<210> SEQ ID NO 6
<211> LENGTH: 1165
<212> TYPE: DNA
<213> ORGANISM: Unknown
<220> FEATURE:
<223> OTHER INFORMATION: Description of Unknown:
DP6 16S rRNA sequence

<400> SEQUENCE: 6
gaaaggcggc ttcggctgtc acttatggat ggacccgcgt cgcattagct agttggtgag 60
gtaacggctc accaaggcaa cgatgcgtag ccgacctgag agggtgatcg gccacactgg 120
gactgagaca cggcccagac tcctacggga ggcagcagta gggaatcttc cgcaatggac 180
gaaagtctga cggagcaacg ccgcgtgagt gatgaaggct ttcgggtcgt aaaactctgt 240
tgttagggaa gaacaagtgc tagttgaata agctgcacct tgacggtacc taaccagaaa 300
gccacggcta actacgtgcc agcagccgcg gtaatacgta ggtggcaagc gttatccgga 360
attattgggc gtaaagcgcg cgcaggtggt ttcttaagtc tgatgtgaaa gcccacggct 420
caaccgtgga gggtcattgg aaactgggag acttgagtgc agaagaggaa agtggaattc 480
catgtgtagc ggtgaaatgc gtagagatat ggaggaacac cagtggcgaa ggcgactttc 540
tggtctgtaa ctgacactga ggcgcgaaag cgtggggagc aaacaggatt agataccctg 600
gtagtccacg ccgtaaacga tgagtgctaa gtgttagagg gtttccgccc tttagtgctg 660
aagttaacgc attaagcact ccgcctgggg agtacggccg caaggctgaa actcaaagga 720
attgacgggg gcccgcacaa gcggtggagc atgtggttta attcgaagca acgcgaagaa 780
ccttaccagg tcttgacatc ctctgaaaac cctagagata gggcttctcc ttcgggagca 840
gagtgacagg tggtgcatgg ttgtcgtcag ctcgtgtcgt gagatgttgg gttaagtccc 900
gcaacgagcg caacccttga tcttagttgc catcattaag ttgggcactc taaggtgact 960
gccggtgaca aaccggagga aggtggggat gacgtcaaat catcatgccc cttatgacct 1020
gggctacaca cgtgctacaa tggacggtac aaagagctgc aagaccgcga ggtggagcta 1080
atctcataaa accgttctca gttcggattg taggctgcaa ctcgcctaca tgaagctgga 1140
atcgctagta atcgcggatc agcat 1165

<210> SEQ ID NO 7
<211> LENGTH: 871
<212> TYPE: DNA
<213> ORGANISM: Unknown
<220> FEATURE:
<223> OTHER INFORMATION: Description of Unknown:
DP7 ITS sequence
<220> FEATURE:
<221> NAME/KEY: modified_base
<222> LOCATION: (5)..(5)
<223> OTHER INFORMATION: a, c, t, g, unknown or other

<400> SEQUENCE: 7
ccacnctgcg tgggcgacac gaaacaccga aaccgaacgc acgccgtcaa gcaagaaatc 60
cacaaaactt tcaacaacgg atctcttggt tctcgcatcg atgaagagcg cagcgaaatg 120
cgatacctag tgtgaattgc agccatcgtg aatcatcgag ttcttgaacg cacattgcgc 180

```
ccgctggtat tccggcgggc atgcctgtct gagcgtcgtt tccttcttgg agcggagctt    240

cagacctggc gggctgtctt tcgggacggc gcgcccaaag cgaggggcct tctgcgcgaa    300

ctagactgtg cgcgcggggc ggccggcgaa cttataccaa gctcgacctc agatcaggca    360

ggagtacccg ctgaacttaa gcatatcaat aagcggagga aaagaaacca acagggattg    420

ccccagtagc ggcgagtgaa gcggcaaaag ctcagatttg gaatcgcttc ggcgagttgt    480

gaattgcagg ttggcgcctc tgcggcggcg gcggtccaag tcccttggaa cagggcgcca    540

ttgagggtga gagccccgtg ggaccgtttg cctatgctct gaggcccttc tgacgagtcg    600

agttgtttgg gaatgcagct ctaagcgggt ggtaaattcc atctaaggct aaatactggc    660

gagagaccga tagcgaacaa gtactgtgaa ggaaagatga aaagcacttt gaaaagagag    720

tgaaacagca cgtgaaattg ttgaaaggga agggtattgc gcccgacatg gagcgtgcgc    780

accgctgccc ctcgtgggcg gcgctctggg cgtgctctgg gccagcatcg gtttttgccg    840

cgggagaagg gcggcgggca tgtagctctt c                                   871


<210> SEQ ID NO 8
<211> LENGTH: 942
<212> TYPE: DNA
<213> ORGANISM: Unknown
<220> FEATURE:
<223> OTHER INFORMATION: Description of Unknown:
      DP8 ITS sequence
<220> FEATURE:
<221> NAME/KEY: modified_base
<222> LOCATION: (31)..(31)
<223> OTHER INFORMATION: a, c, t, g, unknown or other
<220> FEATURE:
<221> NAME/KEY: modified_base
<222> LOCATION: (531)..(531)
<223> OTHER INFORMATION: a, c, t, g, unknown or other
<220> FEATURE:
<221> NAME/KEY: modified_base
<222> LOCATION: (780)..(781)
<223> OTHER INFORMATION: a, c, t, g, unknown or other
<220> FEATURE:
<221> NAME/KEY: modified_base
<222> LOCATION: (841)..(841)
<223> OTHER INFORMATION: a, c, t, g, unknown or other
<220> FEATURE:
<221> NAME/KEY: modified_base
<222> LOCATION: (854)..(854)
<223> OTHER INFORMATION: a, c, t, g, unknown or other
<220> FEATURE:
<221> NAME/KEY: modified_base
<222> LOCATION: (862)..(862)
<223> OTHER INFORMATION: a, c, t, g, unknown or other
<220> FEATURE:
<221> NAME/KEY: modified_base
<222> LOCATION: (867)..(867)
<223> OTHER INFORMATION: a, c, t, g, unknown or other
<220> FEATURE:
<221> NAME/KEY: modified_base
<222> LOCATION: (876)..(876)
<223> OTHER INFORMATION: a, c, t, g, unknown or other
<220> FEATURE:
<221> NAME/KEY: modified_base
<222> LOCATION: (879)..(879)
<223> OTHER INFORMATION: a, c, t, g, unknown or other
<220> FEATURE:
<221> NAME/KEY: modified_base
<222> LOCATION: (894)..(894)
<223> OTHER INFORMATION: a, c, t, g, unknown or other
<220> FEATURE:
<221> NAME/KEY: modified_base
<222> LOCATION: (903)..(903)
<223> OTHER INFORMATION: a, c, t, g, unknown or other
<220> FEATURE:
<221> NAME/KEY: modified_base
```

<222> LOCATION: (905)..(905)
<223> OTHER INFORMATION: a, c, t, g, unknown or other
<220> FEATURE:
<221> NAME/KEY: modified_base
<222> LOCATION: (919)..(919)
<223> OTHER INFORMATION: a, c, t, g, unknown or other
<220> FEATURE:
<221> NAME/KEY: modified_base
<222> LOCATION: (931)..(931)
<223> OTHER INFORMATION: a, c, t, g, unknown or other
<220> FEATURE:
<221> NAME/KEY: modified_base
<222> LOCATION: (940)..(940)
<223> OTHER INFORMATION: a, c, t, g, unknown or other

<400> SEQUENCE: 8

```
gttgctcgag ttcttgttta gatcttttac nataatgtgt atctttaatg aagatgtgcg      60
cttaattgcg ctgctttatt agagtgtcgc agtagaagta gtcttgcttg aatctcagtc     120
aacgtttaca cacattggag tttttttact ttaatttaat tctttctgct ttgaatcgaa     180
aggttcaagg caaaaaacaa acacaaacaa ttttatttta ttataatttt ttaaactaaa     240
ccaaaattcc taacggaaat tttaaaataa tttaaaactt tcaacaacgg atctcttggt     300
tctcgcatcg atgaaaaacg tagcgaattg cgataagtaa tgtgaattgc aaatactcgt     360
gaatcattga atttttgaac gcacattgcg cccttgagca ttctcaaggg catgcctgtt     420
tgagcgtcat ttccttctca aaagataatt ttttattttt tggttgtggg cgatactcag     480
ggttagcttg aaattggaga ctgtttcagt ctttttttaat tcaacactta ncttctttgg     540
agacgctgtt ctcgctgtga tgtatttatg gatttattcg ttttacttta caagggaaat     600
ggtaatgtac cttaggcaaa gggttgcttt taatattcat caagtttgac ctcaaatcag     660
gtaggattac ccgctgaact taagcatatc aataagcgga ggaaaagaaa ccaactggga     720
ttaccttagt aacggcgagt gaagcggtaa aagctcaaat ttgaaatctg gtactttcan     780
ngcccgagtt gtaatttgta gaatttgtct ttgattaggt ccttgtctat gttccttgga     840
ncaggacgtc atanagggtg antcccnttt ggcgangana ccttttctct gtanactttt     900
tcnanagtcg agttgtttng gatgcagctc naagtggggn gg                        942
```

<210> SEQ ID NO 9
<211> LENGTH: 1572
<212> TYPE: DNA
<213> ORGANISM: Unknown
<220> FEATURE:
<223> OTHER INFORMATION: Description of Unknown:
DP9 16S rRNA sequence

<400> SEQUENCE: 9

```
atgagagttt gatcttggct caggatgaac gctggcggcg tgcctaatac atgcaagtcg      60
aacgaacttc cgttaattga ttatgacgta cttgtactga ttgagatttt aacacgaagt     120
gagtggcgaa cgggtgagta acacgtgggt aacctgccca gaagtagggg ataacacctg     180
gaaacagatg ctaataccgt ataacagaga aaaccgcatg gttttctttt aaaagatggc     240
tctgctatca cttctggatg gacccgcggc gtattagcta gttggtgagg caaaggctca     300
ccaaggcagt gatacgtagc cgacctgaga gggtaatcgg ccacattggg actgagacac     360
ggcccagact cctacgggag gcagcagtag ggaatcttcc acaatggacg caagtctgat     420
ggagcaacgc cgcgtgagtg aagaagggtt tcggctcgta aagctctgtt gttaaagaag     480
aacgtgggta agagtaactg tttacccagt gacggtattt aaccagaaag ccacggctaa     540
ctacgtgcca gcagccgcgg taatacgtag gtggcaagcg ttatccggat ttattgggcg     600
```

taaagcgagc gcaggcggtc ttttaagtct aatgtgaaag ccttcggctc aaccgaagaa 660
gtgcattgga aactgggaga cttgagtgca gaagaggaca gtggaactcc atgtgtagcg 720
gtgaaatgcg tagatatatg gaagaacacc agtggcgaag gcggctgtct ggtctgcaac 780
tgacgctgag gctcgaaagc atgggtagcg aacaggatta gataccctgg tagtccatgc 840
cgtaaacgat gattactaag tgttggaggg tttccgccct tcagtgctgc agctaacgca 900
ttaagtaatc cgcctgggga gtacgaccgc aaggttgaaa ctcaaaagaa ttgacggggg 960
cccgcacaag cggtggagca tgtggtttaa ttcgaagcta cgcgaagaac cttaccaggt 1020
cttgacatct tctgacagtc taagagatta gaggttccct tcggggacag aatgacaggt 1080
ggtgcatggt tgtcgtcagc tcgtgtcgtg agatgttggg ttaagtcccg caacgagcgc 1140
aacccttatt actagttgcc agcattaagt tgggcactct agtgagactg ccggtgacaa 1200
accggaggaa ggtggggacg acgtcaaatc atcatgcccc ttatgacctg ggctacacac 1260
gtgctacaat ggatggtaca acgagtcgcg agaccgcgag gttaagctaa tctcttaaaa 1320
ccattctcag ttcggactgt aggctgcaac tcgcctacac gaagtcggaa tcgctagtaa 1380
tcgcggatca gcatgccgcg gtgaatacgt tcccgggcct tgtacacacc gcccgtcaca 1440
ccatgagagt ttgtaacacc caaagccggt ggggtaacct tttaggagct agccgtctaa 1500
ggtgggacag atgattaggg tgaagtcgta acaaggtagc cgtaggagaa cctgcggctg 1560
gatcacctcc tt 1572

<210> SEQ ID NO 10
<211> LENGTH: 1300
<212> TYPE: DNA
<213> ORGANISM: Unknown
<220> FEATURE:
<223> OTHER INFORMATION: Description of Unknown:
DP10 16S rRNA sequence

<400> SEQUENCE: 10
cagatagttg gtgaggtaac ggctcaccaa ggcaacgatg cgtagccgac ctgagagggt 60
gatcggccac actgggactg agacacggcc cagactccta cgggaggcag cagtagggaa 120
tcttccgcaa tggacgaaag tctgacggag caacgccgcg tgagtgatga aggttttcgg 180
atcgtaaagc tctgttgtta gggaagaaca agtgccgttc aaatagggcg gcaccttgac 240
ggtacctaac cagaaagcca cggctaacta cgtgccagca gccgcggtaa tacgtaggtg 300
gcaagcgttg tccggaatta ttgggcgtaa agggctcgca ggcggtttct taagtctgat 360
gtgaaagccc ccggctcaac cggggagggt cattggaaac tggggaactt gagtgcagaa 420
gaggagagtg gaattccacg tgtagcggtg aaatgcgtag agatgtggag gaacaccagt 480
ggcgaaggcg actctctggt ctgtaactga cgctgaggag cgaaagcgtg gggagcgaac 540
aggattagat accctggtag tccacgccgt aaacgatgag tgctaagtgt tagggggttt 600
ccgcccctta gtgctgcagc taacgcatta agcactccgc ctggggagta cggtcgcaag 660
actgaaactc aaaggaattg acgggggccc gcacaagcgg tggagcatgt ggtttaattc 720
gaagcaacgc gaagaacctt accaggtctt gacatcctct gacaatccta gagataggac 780
gtccccttcg gggcagagt gacaggtggt gcatggttgt cgtcagctcg tgtcgtgaga 840
tgttgggtta agtcccgcaa cgagcgcaac ccttgatctt agttgccagc attcagttgg 900
gcactctaag gtgactgccg gtgacaaacc ggaggaaggt ggggatgacg tcaaatcatc 960
atgcccctta tgacctgggc tacacacgtg ctacaatgga cagaacaaag ggcagcgaaa 1020

```
ccgcgaggtt aagccaatcc cacaaatctg ttctcagttc ggatcgcagt ctgcaactcg   1080

actgcgtgaa gctggaatcg ctagtaatcg cggatcagca tgccgcggtg aatacgttcc   1140

cgggccttgt acacaccgcc cgtcacacca cgagagtttg taacacccga agtcggtgag   1200

gtaacctttt aggagccagc cgccgaaggt gggacagatg attggggtga agtcgtaaca   1260

aggtagccgt atcggaaggt gcggctggat cacctccttt                         1300
```

<210> SEQ ID NO 11
<211> LENGTH: 1419
<212> TYPE: DNA
<213> ORGANISM: Unknown
<220> FEATURE:
<223> OTHER INFORMATION: Description of Unknown:
DP11 16S rRNA sequence

<400> SEQUENCE: 11

```
tgaagagttt gatcatggct cagattgaac gctggcggca ggcctaacac atgcaagtcg     60

agcggtagag agaagcttgc ttctcttgag agcggcggac gggtgagtaa tgcctaggaa    120

tctgcctggt agtgggggat aacgttcgga aacggacgct aataccgcat acgtcctacg    180

ggagaaagca ggggaccttc gggccttgcg ctatcagatg agcctaggtc ggattagcta    240

gttggtgagg taatggctca ccaaggcgac gatccgtaac tggtctgaga ggatgatcag    300

tcacactgga actgagacac ggtccagact cctacgggag gcagcagtgg ggaatattgg    360

acaatgggcg aaagcctgat ccagccatgc cgcgtgtgtg aagaaggtct tcggattgta    420

aagcacttta agttgggagg aagggttgta gattaatact ctgcaatttt gacgttaccg    480

acagaataag caccggctaa ctctgtgcca gcagccgcgg taatacagag ggtgcaagcg    540

ttaatcggaa ttactgggcg taaagcgcgc gtaggtggtt cgttaagttg gatgtgaaag    600

ccccgggctc aacctgggaa ctgcattcaa aactgacgag ctagagtatg gtagagggtg    660

gtggaatttc ctgtgtagcg gtgaaatgcg tagatatagg aaggaacacc agtggcgaag    720

gcgaccacct ggactgatac tgacactgag gtgcgaaagc gtggggagca aacaggatta    780

gataccctgg tagtccacgc cgtaaacgat gtcaactagc cgttggaatc cttgagattt    840

tagtggcgca gctaacgcat taagttgacc gcctggggag tacggccgca aggttaaaac    900

tcaaatgaat tgacgggggc ccgcacaagc ggtggagcat gtggtttaat tcgaagcaac    960

gcgaagaacc ttaccaggcc ttgacatcca atgaactttc cagagatgga tgggtgcctt   1020

cgggaacatt gagacaggtg ctgcatggct gtcgtcagct cgtgtcgtga gatgttgggt   1080

taagtcccgt aacgagcgca acccttgtcc ttagttacca gcacgttatg gtgggcactc   1140

taaggagact gccggtgaca aaccggagga aggtggggat gacgtcaagt catcatggcc   1200

cttacggcct gggctacaca cgtgctacaa tggtcggtac aaagggttgc caagccgcga   1260

ggtggagcta atcccataaa accgatcgta gtccggatcg cagtctgcaa ctcgactgcg   1320

tgaagtcgga atcgctagta atcgcgaatc agaatgtcgc ggtgaatacg ttcccgggcc   1380

ttgtacacac cgcccgtcac atcccacacg aattgcttg                          1419
```

<210> SEQ ID NO 12
<211> LENGTH: 1520
<212> TYPE: DNA
<213> ORGANISM: Unknown
<220> FEATURE:
<223> OTHER INFORMATION: Description of Unknown:
DP12 16S rRNA sequence

<400> SEQUENCE: 12

```
tacggagagt ttgatcctgg ctcaggatga acgctggcgg cgtgcttaac acatgcaagt      60
cgaacggtga agccaagctt gcttggtgga tcagtggcga acgggtgagt aacacgtgag     120
caacctgccc tggactctgg gataagcgct ggaaacggcg tctaatactg gatatgagcc     180
ttcatcgcat ggtgggggtt ggaaagattt tttggtctgg gatgggctcg cggcctatca     240
gcttgttggt gaggtaatgg ctcaccaagg cgtcgacggg tagccggcct gagagggtga     300
ccggccacac tgggactgag acacggccca gactcctacg ggaggcagca gtggggaata     360
ttgcacaatg ggcgaaagcc tgatgcagca acgccgcgtg agggatgacg gccttcgggt     420
tgtaaacctc ttttagcagg gaagaagcga aagtgacggt acctgcagaa aaagcgccgg     480
ctaactacgt gccagcagcc gcggtaatac gtagggcgca agcgttatcc ggaattattg     540
ggcgtaaaga gctcgtaggc ggtttgtcgc gtctgctgtg aaatcccgag gctcaacctc     600
gggcctgcag tgggtacggg cagactagag tgcggtaggg gagattggaa ttcctggtgt     660
agcggtggaa tgcgcagata tcaggaggaa caccgatggc gaaggcagat ctctgggccg     720
taactgacgc tgaggagcga aagggtgggg agcaaacagg cttagatacc ctggtagtcc     780
accccgtaaa cgttgggaac tagttgtggg gaccattcca cggtttccgt gacgcagcta     840
acgcattaag ttccccgcct ggggagtacg gccgcaaggc taaaactcaa aggaattgac     900
ggggacccgc acaagcggcg gagcatgcgg attaattcga tgcaacgcga agaaccttac     960
caaggcttga catacaccag aacgggccag aaatggtcaa ctctttggac actggtgaac    1020
aggtggtgca tggttgtcgt cagctcgtgt cgtgagatgt tgggttaagt cccgcaacga    1080
gcgcaaccct cgttctatgt tgccagcacg taatggtggg aactcatggg atactgccgg    1140
ggtcaactcg gaggaaggtg gggatgacgt caaatcatca tgccccttat gtcttgggct    1200
tcacgcatgc tacaatggcc ggtacaaagg gctgcaatac cgtgaggtgg agcgaatccc    1260
aaaaagccgg tcccagttcg gattgaggtc tgcaactcga cctcatgaag tcggagtcgc    1320
tagtaatcgc agatcagcaa cgctgcggtg aatacgttcc cgggtcttgt acacaccgcc    1380
cgtcaagtca tgaaagtcgg taacacctga agccggtggc ccaacccttg tggagggagc    1440
cgtcgaaggt gggatcggta attaggacta agtcgtaaca aggtagccgt accggaaggt    1500
gcggctggat cacctccttt                                                1520
```

<210> SEQ ID NO 13
<211> LENGTH: 1457
<212> TYPE: DNA
<213> ORGANISM: Unknown
<220> FEATURE:
<223> OTHER INFORMATION: Description of Unknown:
DP13 16S rRNA sequence

<400> SEQUENCE: 13

```
agttagcggc ggacgggtga gtaacacgtg ggtaacctgc ctataagact gggataactc      60
cgggaaaccg gggctaatac cggataacat tttgcaccgc atggtgcgaa attgaaaggc     120
ggcttcggct gtcacttata gatggacctg cggcgcatta gctagttggt gaggtaacgg     180
ctcaccaagg cgacgatgcg tagccgacct gagagggtga tcggccacac tgggactgag     240
acacggccca gactcctacg ggaggcagca gtagggaatc ttccgcaatg gacgaaagtc     300
tgacggagca acgccgcgtg aacgatgaag gctttcgggt cgtaaagttc tgttgttagg     360
gaagaacaag tgctagttga ataagctggc accttgacgg tacctaacca gaaagccacg     420
```

-continued

```
gctaactacg tgccagcagc cgcggtaata cgtaggtggc aagcgttatc cggaattatt    480

gggcgtaaag cgcgcgcagg tggtttctta agtctgatgt gaaagcccac ggctcaaccg    540

tggagggtca ttggaaactg ggagacttga gtgcagaaga ggaaagtgga attccatgtg    600

tagcggtgaa atgcgtagag atatggagga acaccagtgg cgaaggcgac tttctggtct    660

gcaactgaca ctgaggcgcg aaagcgtggg gagcaaacag gattagatac cctggtagtc    720

cacgccgtaa acgatgagtg ctaagtgtta gagggtttcc gccctttagt gctgaagtta    780

acgcattaag cactccgcct ggggagtacg gccgcaaggc tgaaactcaa aggaattgac    840

gggggcccgc acaagcggtg gagcatgtgg tttaattcga agcaacgcga agaaccttac    900

caggtcttga catcctctga aaaccctaga gatagggctt ccccttcggg ggcagagtga    960

caggtggtgc atggttgtcg tcagctcgtg tcgtgagatg ttgggttaag tcccgcaacg   1020

agcgcaaccc ttgatcttag ttgccatcat taagttgggc actctaaggt gactgccggt   1080

gacaaaccgg aggaaggtgg ggatgacgtc aaatcatcat gccccttatg acctgggcta   1140

cacacgtgct acaatggacg gtacaaagag tcgcaagacc gcgaggtgga gctaatctca   1200

taaaaccgtt ctcagttcgg attgtaggct gcaactcgcc tacatgaagc tggaatcgct   1260

agtaatcgcg gatcagcatg ccgcggtgaa tacgttcccg ggccttgtac acaccgcccg   1320

tcacaccacg agagtttgta acacccgaag tcggtggggt aaccttttgg agccagccgc   1380

ctaaggtggg acagatgatt ggggtgaagt cgtaacaagg tagccgtatc ggaaggtgcg   1440

gctggatcac ctccttt                                                  1457
```

<210> SEQ ID NO 14
<211> LENGTH: 1526
<212> TYPE: DNA
<213> ORGANISM: Unknown
<220> FEATURE:
<223> OTHER INFORMATION: Description of Unknown:
DP1416S rRNA sequence

<400> SEQUENCE: 14

```
tacggagagt ttgatcctgg ctcaggatga acgctggcgg cgtgcttaac acatgcaagt     60

cgaacgatga cttctgtgct tgcacagaat gattagtggc gaacgggtga gtaacacgtg    120

agtaacctgc ccttaacttc gggataagcc tgggaaaccg ggtctaatac cggatacgac    180

ctcctggcgc atgccatggt ggtggaaagc tttagcggtt ttggatggac tcgcggccta    240

tcagcttgtt ggttggggta atggcccacc aaggcgacga cgggtagccg gcctgagagg    300

gtgaccggcc acactgggac tgagacacgg cccagactcc tacgggaggc agcagtgggg    360

aatattgcac aatgggcgaa agcctgatgc agcgacgccg cgtgagggat gacggccttc    420

gggttgtaaa cctctttcag cagggaagaa gcgaaagtga cggtacctgc agaagaagcg    480

ccggctaact acgtgccagc agccgcggta atacgtaggg cgcaagcgtt atccggaatt    540

attgggcgta aagagctcgt aggcggtttg tcgcgtctgc tgtgaaagcc cggggctcaa    600

ccccgggtct gcagtgggta cgggcagact agagtgcagt aggggagact ggaattcctg    660

gtgtagcggt gaaatgcgca gatatcagga ggaacaccga tggcgaaggc aggtctctgg    720

gctgtaactg acgctgagga gcgaaagcat ggggagcgaa caggattaga taccctggta    780

gtccatgccg taaacgttgg gcactaggtg tgggggacat tccacgtttt ccgcgccgta    840

gctaacgcat taagtgcccc gcctggggag tacggccgca aggctaaaac tcaaaggaat    900

tgacgggggc ccgcacaagc ggcggagcat gcggattaat tcgatgcaac gcgaagaacc    960
```

-continued

```
ttaccaaggc ttgacatgaa ccggtaagac ctggaaacag gtcccccact tgtggccggt   1020

ttacaggtgg tgcatggttg tcgtcagctc gtgtcgtgag atgttgggtt aagtcccgca   1080

acgagcgcaa ccctcgttct atgttgccag cgggttatgc cggggactca taggagactg   1140

ccggggtcaa ctcggaggaa ggtggggacg acgtcaaatc atcatgcccc ttatgtcttg   1200

ggcttcacgc atgctacaat ggccggtaca aagggttgcg atactgtgag gtggagctaa   1260

tcccaaaaag ccggtctcag ttcggattga ggtctgcaac tcgacctcat gaagttggag   1320

tcgctagtaa tcgcagatca gcaacgctgc ggtgaatacg ttcccgggcc ttgtacacac   1380

cgcccgtcaa gtcacgaaag ttggtaacac ccgaagccgg tggcctaacc ccttgtggga   1440

gggagccgtc gaaggtggga ccggcgattg ggactaagtc gtaacaaggt agccgtaccg   1500

gaaggtgcgg ctggatcacc tccttt                                         1526


<210> SEQ ID NO 15
<211> LENGTH: 1520
<212> TYPE: DNA
<213> ORGANISM: Unknown
<220> FEATURE:
<223> OTHER INFORMATION: Description of Unknown:
      DP15 16S rRNA sequence

<400> SEQUENCE: 15

tacggagagt ttgatcctgg ctcaggacga acgctggcgg cgtgcttaac acatgcaagt     60

cgaacgatga tcaggagctt gctcctgtga ttagtggcga acgggtgagt aacacgtgag    120

taacctgccc ctgactctgg gataagcgtt ggaaacgacg tctaatactg gatatgatca    180

ctggccgcat ggtctggtgg tggaaagatt ttttggttgg ggatggactc gcggcctatc    240

agcttgttgg tgaggtaatg gctcaccaag gcgacgacgg gtagccggcc tgagagggtg    300

accggccaca ctgggactga gacacggccc agactcctac gggaggcagc agtggggaat    360

attgcacaat gggcgaaagc ctgatgcagc aacgccgcgt gagggatgac ggccttcggg    420

ttgtaaacct cttttagtag ggaagaagcg aaagtgacgg tacctgcaga aaaagcaccg    480

gctaactacg tgccagcagc cgcggtaata cgtagggtgc aagcgttgtc cggaattatt    540

gggcgtaaag agctcgtagg cggtttgtcg cgtctgctgt gaaatcccga ggctcaacct    600

cgggcttgca gtgggtacgg gcagactaga gtgcggtagg ggagattgga attcctggtg    660

tagcggtgga atgcgcagat atcaggagga acaccgatgg cgaaggcaga tctctgggcc    720

gtaactgacg ctgaggagcg aaagcgtggg gagcgaacag gattagatac cctggtagtc    780

cacgccgtaa acgttgggcg ctagatgtag ggacctttcc acggtttctg tgtcgtagct    840

aacgcattaa gcgccccgcc tggggagtac ggccgcaagg ctaaaactca aaggaattga    900

cgggggcccg cacaagcggc ggagcatgcg gattaattcg atgcaacgcg aagaacctta    960

ccaaggcttg acatacaccg gaaacggcca gagatggtcg ccccccttgtg gtcggtgtac  1020

aggtggtgca tggttgtcgt cagctcgtgt cgtgagatgt tgggttaagt cccgcaacga   1080

gcgcaaccct cgttctatgt tgccagcgcg ttatggcggg gactcatagg agactgccgg   1140

ggtcaactcg gaggaaggtg gggatgacgt caaatcatca tgccccttat gtcttgggct   1200

tcacgcatgc tacaatggcc ggtacaaagg gctgcgatac cgtaaggtgg agcgaatccc   1260

aaaaagccgg tctcagttcg gattgaggtc tgcaactcga cctcatgaag tcggagtcgc   1320

tagtaatcgc agatcagcaa cgctgcggtg aatacgttcc cgggccttgt acacaccgcc   1380

cgtcaagtca tgaaagtcgg taacacccga agccggtggc ctaacccttg tggaaggagc   1440
```

cgtcgaaggt gggatcggtg attaggacta agtcgtaaca aggtagccgt accggaaggt 1500
gcggctggat cacctccttt 1520

<210> SEQ ID NO 16
<211> LENGTH: 1368
<212> TYPE: DNA
<213> ORGANISM: Unknown
<220> FEATURE:
<223> OTHER INFORMATION: Description of Unknown:
DP16 16S rRNA sequence

<400> SEQUENCE: 16
gcacttcatc gtggtgcacc gtgaagggtc tttgggcgtt ttacacatgc aagcaagtgt 60
tctataattt aggttatgga acagccaaat ggtcagtaca gctcagtcct aggcgatgga 120
ctccgtaaaa cggggacaga ctatccttta ataattaata ggtttattat ttcaataata 180
atctctagga agggatatac atatatcctt attagtctaa aggttaataa accgccttag 240
tcaggactga gttctcaaca gctacgggtt aaaccccagg caacgacgag taggggatag 300
tgatagctac aaccccgaca ctggccgcaa gccagggtac ttaagtacgc agcagtgaag 360
aatcctcggc aatgcatcgc aattaccggt gacccaatat aaaataatat cagggaggta 420
gtaggtgtga ccgggtgacc caaagacgag tagtgacata agttattatt cgcgtatgtc 480
gaacatgata gtgacgtgtt caacatcaag ccccgtccaa cctctgtgcc agcagtcgcg 540
gtaaaacagg aggggcagct cttatggtca tgaatgggcg tatagggcac gcagccagtt 600
agtaaaagct tgaatattta ttttttaaa aagaatgttt gagaggctat gagtttttat 660
aaagtgtacc cacgacacca gacttagggc tgagatccta tgaagtctgg gggcggtcct 720
ttagggtgca ttgtaaaaac tgacggtaag gtgcgacagc tgggataccg aagcggagta 780
gagcccgcct agccccagcc gtaaacgata ggggccgttg ttgactacgg ttttcaataa 840
ggctaacgcc tgagcccctc gcctgtaggg tatagccgca aggccgacat attaacgatg 900
agaccgctgg tgagcaaacg ggtgcggggc atgctgttca atcagacagt acgctgacaa 960
ccttaccact ccttgaatct tttagattat atttctaaaa tgacaggtgc tgcatggccg 1020
tcgtcagttc gtggtcgtga gtcgtccggt tgagtccatg aacgaacgca gacccgtctg 1080
tatactcagt gaaaagaaat ttagctgaac tatacagttg tacttctata aaaggtacct 1140
gtacgggatt atgacaggtc gtcatggcct ttatggagtg ggctacaggc gtgccacacg 1200
agccgtttta acgagttcct catttttatg aataaggtct cttaatcacg gctagtatac 1260
ggatcgtagg ctgtaactcg cctacgtgaa gtcggagtcc cgagtaatcg ccgatcatca 1320
cgcggcggtg aatctacact ctcactgggg tactaaccgc tcgtcacg 1368

<210> SEQ ID NO 17
<211> LENGTH: 898
<212> TYPE: DNA
<213> ORGANISM: Unknown
<220> FEATURE:
<223> OTHER INFORMATION: Description of Unknown:
DP17 16S rRNA sequence

<400> SEQUENCE: 17
gtgattgacg ttactcgcag aagaagcacc ggctaactcc gtgccagcag ccgcggtaat 60
acggagggtg caagcgttaa tcggaattac tgggcgtaaa gcgcacgcag gcggtttgtt 120
aagtcagatg tgaaatcccc gcgcttaacg tgggaactgc atttgaaact ggcaagctag 180
agtcttgtag aggggggtag aattccaggt gtagcggtga aatgcgtaga gatctggagg 240
aataccggtg gcgaaggcgg ccccctggac aaagactgac gctcaggtgc gaaagcgtgg 300
ggagcaaaca ggattagata ccctggtagt ccacgctgta aacgatgtcg acttggaggt 360
tgtgcccttg aggcgtggct tccggagcta acgcgttaag tcgaccgcct ggggagtacg 420
gccgcaaggt taaaactcaa atgaattgac gggggcccgc acaagcggtg gagcatgtgg 480
tttaattcga tgcaacgcga agaaccttac ctactcttga catccacgga attcgccaga 540
gatggcttag tgccttcggg aaccgtgaga caggtgctgc atggctgtcg tcagctcgtg 600
ttgtgaaatg ttgggttaag tcccgcaacg agcgcaaccc ttatcctttg ttgccagcac 660
gtaatggtgg gaactcaaag gagactgccg gtgataaacc ggaggaaggt ggggatgacg 720
tcaagtcatc atggccctta cgagtagggc tacacacgtg ctacaatggc atatacaaag 780
agaagcgaac tcgcgagagc aagcggacct cataaagtat gtcgtagtcc ggattggagt 840
ctgcaactcg actccatgaa gtcggaatcg ctagtaatcg tagatcagaa tgctacgg 898

<210> SEQ ID NO 18
<211> LENGTH: 1532
<212> TYPE: DNA
<213> ORGANISM: Unknown
<220> FEATURE:
<223> OTHER INFORMATION: Description of Unknown:
DP18 16S rRNA sequence

<400> SEQUENCE: 18
tgaagagttt gatcatggct cagattgaac gctggcggca ggcctaacac atgcaagtcg 60
agcggatgaa aggagcttgc tcctggattc agcggcggac gggtgagtaa tgcctaggaa 120
tctgcctggt agtgggggac aacgtttcga aaggaacgct aataccgcat acgtcctacg 180
ggagaaagca ggggaccttc gggccttgcg ctatcagatg agcctaggtc ggattagcta 240
gttggtgagg taatggctca ccaaggcgac gatccgtaac tggtctgaga ggatgatcag 300
tcacactgga actgagacac ggtccagact cctacgggag gcagcagtgg ggaatattgg 360
acaatgggcg aaagcctgat ccagccatgc cgcgtgtgtg aagaaggtct tcggattgta 420
aagcacttta agttgggagg aagggcagta aattaatact ttgctgtttt gacgttaccg 480
acagaataag caccggctaa ctctgtgcca gcagccgcgg taatacagag ggtgcaagcg 540
ttaatcggaa ttactgggcg taaagcgcgc gtaggtggtt tgttaagttg aatgtgaaat 600
ccccgggctc aacctgggaa ctgcatccaa aactggcaag ctagagtatg gtagagggtg 660
gtggaatttc ctgtgtagcg gtgaaatgcg tagatatagg aaggaacacc agtggcgaag 720
gcgaccacct ggactgatac tgacactgag gtgcgaaagc gtggggagca aacaggatta 780
gataccctgg tagtccacgc cgtaaacgat gtcaactagc cgttgggagc cttgagctct 840
tagtggcgca gctaacgcat taagttgacc gcctggggag tacggccgca aggttaaaac 900
tcaaatgaat tgacgggggc ccgcacaagc ggtggagcat gtggtttaat tcgaagcaac 960
gcgaagaacc ttaccaggcc ttgacatcca atgaactttc cagagatgga ttggtgcctt 1020
cgggaacatt gagacaggtg ctgcatggct gtcgtcagct cgtgtcgtga gatgttgggt 1080
taagtcccgt aacgagcgca acccttgtcc ttagttacca gcacgttatg gtgggcactc 1140
taaggagact gccggtgaca aaccggagga aggtggggat gacgtcaagt catcatggcc 1200
cttacggcct gggctacaca cgtgctacaa tggtcggtac aaagggttgc caagccgcga 1260
ggtggagcta atcccataaa accgatcgta gtccggatcg cagtctgcaa ctcgactgcg 1320
tgaagtcgga atcgctagta atcgcgaatc agaatgtcgc ggtgaatacg ttcccgggcc 1380

```
ttgtacacac cgcccgtcac accatgggag tgggttgcac cagaagtagc tagtctaacc   1440

ttcgggagga cggttaccac ggtgtgattc atgactgggg tgaagtcgta acaaggtagc   1500

cgtaggggaa cctgcggctg gatcacctcc tt                                 1532


<210> SEQ ID NO 19
<211> LENGTH: 1520
<212> TYPE: DNA
<213> ORGANISM: Unknown
<220> FEATURE:
<223> OTHER INFORMATION: Description of Unknown:
      DP19 16S rRNA sequence

<400> SEQUENCE: 19

tacggagagt ttgatcctgg ctcaggacga acgctggcgg cgtgcttaac acatgcaagt     60

cgaacgatga tgcccagctt gctgggtgga ttagtggcga acgggtgagt aacacgtgag    120

taacctgccc ctgactctgg gataagcgtt ggaaacgacg tctaatactg gatacgactg    180

ccggccgcat ggtctggtgg tggaaagatt ttttggttgg ggatggactc gcggcctatc    240

agcttgttgg tgaggtaatg gctcaccaag gcgacgacgg gtagccggcc tgagagggtg    300

accggccaca ctgggactga gacacggccc agactcctac gggaggcagc agtggggaat    360

attgcacaat gggcgaaagc ctgatgcagc aacgccgcgt gagggatgac ggccttcggg    420

ttgtaaacct cttttagtag ggaagaagcg aaagtgacgg tacctgcaga aaaagcaccg    480

gctaactacg tgccagcagc cgcggtaata cgtagggtgc aagcgttgtc cggaattatt    540

gggcgtaaag agctcgtagg cggtttgtcg cgtctgctgt gaaatcccga ggctcaacct    600

cgggcttgca gtgggtacgg gcagactaga gtgcggtagg ggagattgga attcctggtg    660

tagcggtgga atgcgcagat atcaggagga acaccgatgg cgaaggcaga tctctgggcc    720

gtaactgacg ctgaggagcg aaagcgtggg gagcgaacag gattagatac cctggtagtc    780

cacgccgtaa acgttgggcg ctagatgtag ggacctttcc acggtttctg tgtcgtagct    840

aacgcattaa gcgccccgcc tggggagtac ggccgcaagg ctaaaactca aaggaattga    900

cgggggcccg cacaagcggc ggagcatgcg gattaattcg atgcaacgcg aagaacctta    960

ccaaggcttg acatacaccg gaaacggcca gagatggtcg ccccccttgtg gtcggtgtac   1020

aggtggtgca tggttgtcgt cagctcgtgt cgtgagatgt tgggttaagt cccgcaacga   1080

gcgcaaccct cgttctatgt tgccagcgcg ttatggcggg gactcatagg agactgccgg   1140

ggtcaactcg gaggaaggtg gggatgacgt caaatcatca tgccccttat gtcttgggct   1200

tcacgcatgc tacaatggcc ggtacaaagg gctgcgatac cgtaaggtgg agcgaatccc   1260

aaaaagccgg tctcagttcg gattgaggtc tgcaactcga cctcatgaag tcggagtcgc   1320

tagtaatcgc agatcagcaa cgctgcggtg aatacgttcc cgggccttgt acacaccgcc   1380

cgtcaagtca tgaaagtcgg taacacccga agccggtggc ctaacccttg tggaaggagc   1440

cgtcgaaggt gggatcggtg attaggacta agtcgtaaca aggtagccgt accggaaggt   1500

gcggctggat cacctccttt                                                1520


<210> SEQ ID NO 20
<211> LENGTH: 1543
<212> TYPE: DNA
<213> ORGANISM: Unknown
<220> FEATURE:
<223> OTHER INFORMATION: Description of Unknown:
      DP20 16S rRNA sequence
```

-continued

<400> SEQUENCE: 20
tgaagagttt gatcctggct cagagtgaac gctggcggta ggcctaacac atgcaagtcg 60
aacggcagca cagtaagagc ttgctcttat gggtggcgag tggcggacgg gtgaggaata 120
catcggaatc taccttttcg tgggggataa cgtagggaaa cttacgctaa taccgcatac 180
gaccttcggg tgaaagcagg ggaccttcgg gccttgcgcg gatagatgag ccgatgtcgg 240
attagctagt tggcggggta aaggcccacc aaggcgacga tccgtagctg gtctgagagg 300
atgatcagcc acactggaac tgagacacgg tccagactcc tacgggaggc agcagtgggg 360
aatattggac aatgggcgca agcctgatcc agccataccg cgtgggtgaa gaaggccttc 420
gggttgtaaa gcccttttgt tgggaaagaa aagcagtcgg ctaatacccg gttgttctga 480
cggtacccaa agaataagca ccggctaact tcgtgccagc agccgcggta atacgaaggg 540
tgcaagcgtt actcggaatt actgggcgta aagcgtgcgt aggtggttgt ttaagtctgt 600
tgtgaaagcc ctgggctcaa cctgggaatt gcagtggata ctgggcgact agagtgtggt 660
agagggtagt ggaattcccg gtgtagcagt gaaatgcgta gagatcggga ggaacatcca 720
tggcgaaggc agctacctgg accaacactg acactgaggc acgaaagcgt ggggagcaaa 780
caggattaga taccctggta gtccacgccc taaacgatgc gaactggatg ttgggtgcaa 840
tttggcacgc agtatcgaag ctaacgcgtt aagttcgccg cctggggagt acggtcgcaa 900
gactgaaact caaaggaatt gacgggggcc cgcacaagcg gtggagtatg tggtttaatt 960
cgatgcaacg cgaagaacct tacctggtct tgacatgtcg agaactttcc agagatggat 1020
tggtgccttc gggaactcga acacaggtgc tgcatggctg tcgtcagctc gtgtcgtgag 1080
atgttgggtt aagtcccgca acgagcgcaa cccttgtcct tagttgccag cacgtaatgg 1140
tgggaactct aaggagaccg ccggtgacaa accggaggaa ggtggggatg acgtcaagtc 1200
atcatggccc ttacgaccag ggctacacac gtactacaat ggtagggaca gagggctgca 1260
aacccgcgag ggcaagccaa tcccagaaac cctatctcag tccggattgg agtctgcaac 1320
tcgactccat gaagtcggaa tcgctagtaa tcgcagatca gcattgctgc ggtgaatacg 1380
ttcccgggcc ttgtacacac cgcccgtcac accatgggag tttgttgcac cagaagcagg 1440
tagcttaacc ttcgggaggg cgcttgccac ggtgtggccg atgactgggg tgaagtcgta 1500
acaaggtagc cgtatcggaa ggtgcggctg gatcacctcc ttt 1543

<210> SEQ ID NO 21

<400> SEQUENCE: 21

000

<210> SEQ ID NO 22
<211> LENGTH: 1539
<212> TYPE: DNA
<213> ORGANISM: Unknown
<220> FEATURE:
<223> OTHER INFORMATION: Description of Unknown:
DP22 16S rRNA sequence

<400> SEQUENCE: 22
ttgaagagtt tgatcatggc tcagattgaa cgctggcggc aggcctaaca catgcaagtc 60
gagcggcagc gggaagtagc ttgctacttt gccggcgagc ggcggacggg tgagtaatgt 120
ctgggaaact gcctgatgga gggggataac tactggaaac ggtagctaat accgcatgac 180
ctcgcaagag caaagtgggg gaccttcggg cctcacgcca tcggatgtgc ccagatggga 240
ttagctagta ggtgaggtaa tggctcacct aggcgacgat ccctagctgg tctgagagga 300
tgaccagcca cactggaact gagacacggt ccagactcct acgggaggca gcagtgggga 360
atattgcaca atgggcgcaa gcctgatgca gccatgccgc gtgtgtgaag aaggccttag 420
ggttgtaaag cactttcagc gaggaggaag ggttcagtgt taatagcact gaacattgac 480
gttactcgca gaagaagcac cggctaactc cgtgccagca gccgcggtaa tacggagggt 540
gcaagcgtta atcggaatta ctgggcgtaa agcgcacgca ggcggtttgt taagtcagat 600
gtgaaatccc cgagcttaac ttgggaactg catttgaaac tggcaagcta gagtcttgta 660
gaggggggta gaattccagg tgtagcggtg aaatgcgtag agatctggag gaataccggt 720
ggcgaaggcg gccccctgga caaagactga cgctcaggtg cgaaagcgtg gggagcaaac 780
aggattagat accctggtag tccacgctgt aaacgatgtc gacttggagg ttgtgccctt 840
gaggcgtggc ttccggagct aacgcgttaa gtcgaccgcc tggggagtac ggccgcaagg 900
ttaaaactca aatgaattga cgggggcccg cacaagcggt ggagcatgtg gtttaattcg 960
atgcaacgcg aagaacctta cctactcttg acatccagag aattcgctag agatagctta 1020
gtgccttcgg gaactctgag acaggtgctg catggctgtc gtcagctcgt gttgtgaaat 1080
gttgggttaa gtcccgcaac gagcgcaacc cttatccttt gttgccagcg agtaatgtcg 1140
ggaactcaaa ggagactgcc ggtgataaac cggaggaagg tggggatgac gtcaagtcat 1200
catggccctt acgagtaggg ctacacacgt gctacaatgg catatacaaa gagaagcaaa 1260
ctcgcgagag caagcggacc tcataaagta tgtcgtagtc cggattggag tctgcaactc 1320
gactccatga agtcggaatc gctagtaatc gtagatcaga atgctacggt gaatacgttc 1380
ccgggccttg tacacaccgc ccgtcacacc atgggagtgg gttgcaaaag aagtaggtag 1440
cttaaccttc gggagggcgc ttaccacttt gtgattcatg actggggtga agtcgtaaca 1500
aggtaaccgt aggggaacct gcggttggat cacctcctt 1539

<210> SEQ ID NO 23
<211> LENGTH: 1536
<212> TYPE: DNA
<213> ORGANISM: Unknown
<220> FEATURE:
<223> OTHER INFORMATION: Description of Unknown:
DP23 16S rRNA sequence

<400> SEQUENCE: 23
ttgaagagtt tgatcatggc tcagattgaa cgctggcggc aggcctaaca catgcaagtc 60
gaacggtagc acagagagct tgctcttggg tgacgagtgg cggacgggtg agtaatgtct 120
gggaaactgc ccgatggagg gggataacta ctggaaacgg tagctaatac cgcataacgt 180
cttcggacca aagtggggga ccttcgggcc tcacaccatc ggatgtgccc agatgggatt 240
agctagtagg tggggtaatg gctcacctag gcgacgatcc ctagctggtc tgagaggatg 300
accagccaca ctggaactga gacacggtcc agactcctac gggaggcagc agtggggaat 360
attgcacaat gggcgcaagc ctgatgcagc catgccgcgt gtatgaagaa ggccttcggg 420
ttgtaaagta ctttcagcgg ggaggaaggc gatacggtta ataaccgtgt cgattgacgt 480
tacccgcaga agaagcaccg gctaactccg tgccagcagc cgcggtaata cggagggtgc 540
aagcgttaat cggaattact gggcgtaaag cgcacgcagg cggtctgtca agtcagatgt 600
gaaatccccg ggcttaacct gggaactgca tttgaaactg gcaggcttga gtctcgtaga 660
ggggggtaga attccaggtg tagcggtgaa atgcgtagag atctggagga ataccggtgg 720

-continued cgaaggcggc cccctggacg aagactgacg ctcaggtgcg aaagcgtggg gagcaaacag 780
gattagatac cctggtagtc cacgctgtaa acgatgtcga cttggaggtt gtgcccttga 840
ggcgtggctt ccggagctaa cgcgttaagt cgaccgcctg gggagtacgg ccgcaaggtt 900
aaaactcaaa tgaattgacg ggggcccgca caagcggtgg agcatgtggt ttaattcgat 960
gcaacgcgaa gaaccttacc tggccttgac atccacagaa ttcggcagag atgccttagt 1020
gccttcggga actgtgagac aggtgctgca tggctgtcgt cagctcgtgt tgtgaaatgt 1080
tgggttaagt cccgcaacga gcgcaaccct tatcctttgt tgccagcgat tcggtcggga 1140
actcaaagga gactgccggt gataaaccgg aggaaggtgg ggatgacgtc aagtcatcat 1200
ggcccttacg gccagggcta cacacgtgct acaatggcgc atacaaagag aagcgacctc 1260
gcgagagcaa gcggacctca taaagtgcgt cgtagtccgg atcggagtct gcaactcgac 1320
tccgtgaagt cggaatcgct agtaatcgta gatcagaatg ctacggtgaa tacgttcccg 1380
ggccttgtac acaccgcccg tcacaccatg ggagtgggtt gcaaaagaag taggtagctt 1440
aaccttcggg agggcgctta ccactttgtg attcatgact ggggtgaagt cgtaacaagg 1500
taaccgtagg ggaacctgcg gttggatcac ctcctt 1536

<210> SEQ ID NO 24
<211> LENGTH: 1316
<212> TYPE: DNA
<213> ORGANISM: Unknown
<220> FEATURE:
<223> OTHER INFORMATION: Description of Unknown:
DP24 16S rRNA sequence

<400> SEQUENCE: 24
agcatttgat tatggtgctt actgattgct atctaggggt ttaacacatg ctagtcaatg 60
atcttttaga ttatggcgta cgggctagga atacttagaa tgataactct atgatcgcag 120
taatagcgta aaaggtataa taccgcatag aggttcgctt cgtatctcaa taggtagttg 180
gtgaggtaaa gctcaacaag ccgatgatga gtaatattgg atgaaagtct taaatatagc 240
agtggaaatg aaaaagtcca ccgttattta ttaacgcagc agtggagaat cgtcgtaatg 300
tgcagtattc atttatggat aagcatgaac gcgctaccta gattcggata ggagatagca 360
tcttctaccg ataaaagaac ttagaataat gatctagttc tcattagtgg gtgacaatcg 420
ccgtgccagc atcagcggta aaacggcttc cgcaagcaat agtaatttaa attggtgtaa 480
agggtacgta gccggcctta ttaggctaga gttagatacg ggtaagtaca atacttggag 540
tagggctgat atcttatgat cccaagggga gtgctaaagg cgaaggcaac ttactggtaa 600
taactgacgg tgaggtacga aggtcagggc atggaaagag attagatacc tcattactcc 660
tgacagtaaa cgatgtagat taaagattgg aataattctg tcttaacgct aacgcattaa 720
atctaccacc tgtagagtat agtcgcaagg ccgaaataca aataattaga cggctctaga 780
gcaaacggag tgaagcatgt tatttaatac gataacccgc gtaaaatctt accagttctt 840
gaatcttaga caggtgttgc atggttgtcg tcagctcgtg ctaatggtgt ctggttaatt 900
ccaaataacg agcgcaatcc ttacttctag ttttctagga gtctccattt gacatacgtg 960
tcaatggttt aaggaatatg acaaaccctc atggccctta tggactgggc aatagacgtg 1020
ccacaagaat ctagacaaaa tgacgcgaaa tggtaacaat gagctaatca tcaaagaaga 1080
ttaatgtacg aattatgggc tggaactcgc ccatatgaag taggaattcc gagtaatcgc 1140
gtatcagaac gacgcggtga acatcatctc tggagtgtac taactgctcg tcacgggacg 1200
aaagggagtg tattatgaag tggggctaat tggttaactc cggtgagtgt cacgaataat 1260
ccttcccgat tgttctgaag tcgaaacaag gtaaccgtaa gggaacttgc ggttga 1316

<210> SEQ ID NO 25
<211> LENGTH: 1520
<212> TYPE: DNA
<213> ORGANISM: Unknown
<220> FEATURE:
<223> OTHER INFORMATION: Description of Unknown:
DP25 16S rRNA sequence

<400> SEQUENCE: 25
tacggagagt ttgatcctgg ctcaggatga acgctggcgg cgtgcttaac acatgcaagt 60
cgaacggtga agccaagctt gcttggtgga tcagtggcga acgggtgagt aacacgtgag 120
caacctgccc tggactctgg gataagcgct ggaaacggcg tctaatactg gatatgagct 180
ccttccgcat ggtgggggtt ggaaagattt ttcggtctgg gatgggctcg cggcctatca 240
gcttgttggt gaggtaatgg ctcaccaagg cgtcgacggg tagccggcct gagagggtga 300
ccggccacac tgggactgag acacggccca gactcctacg ggaggcagca gtggggaata 360
ttgcacaatg ggcggaagcc tgatgcagca acgccgcgtg agggatgacg gccttcgggt 420
tgtaaacctc ttttagcagg gaagaagcga aagtgacggt acctgcagaa aaagcgccgg 480
ctaactacgt gccagcagcc gcggtaatac gtagggcgca agcgttatcc ggaattattg 540
ggcgtaaaga gctcgtaggc ggtttgtcgc gtctgctgtg aaatcccgag gctcaacctc 600
gggcctgcag tgggtacggg cagactagag tgcggtaggg gagattggaa ttcctggtgt 660
agcggtggaa tgcgcagata tcaggaggaa caccgatggc gaaggcagat ctctgggccg 720
taactgacgc tgaggagcga aagggtgggg agcaaacagg cttagatacc ctggtagtcc 780
accccgtaaa cgttgggaac tagttgtggg gaccattcca cggtttccgt gacgcagcta 840
acgcattaag ttccccgcct ggggagtacg gccgcaaggc taaaactcaa aggaattgac 900
ggggacccgc acaagcggcg gagcatgcgg attaattcga tgcaacgcga agaaccttac 960
caaggcttga catatacgag aacgggccag aaatggtcaa ctctttggac actcgtaaac 1020
aggtggtgca tggttgtcgt cagctcgtgt cgtgagatgt tgggttaagt cccgcaacga 1080
gcgcaaccct cgttctatgt tgccagcacg taatggtggg aactcatggg atactgccgg 1140
ggtcaactcg gaggaaggtg gggatgacgt caaatcatca tgccccttat gtcttgggct 1200
tcacgcatgc tacaatggcc ggtacaaagg gctgcaatac cgtaaggtgg agcgaatccc 1260
aaaaagccgg tcccagttcg gattgaggtc tgcaactcga cctcatgaag tcggagtcgc 1320
tagtaatcgc agatcagcaa cgctgcggtg aatacgttcc cgggtcttgt acacaccgcc 1380
cgtcaagtca tgaaagtcgg taacacctga agccggtggc ccaacccttg tggagggagc 1440
cgtcgaaggt gggatcggta attaggacta agtcgtaaca aggtagccgt accggaaggt 1500
gcggctggat cacctccttt 1520

<210> SEQ ID NO 26
<211> LENGTH: 1482
<212> TYPE: DNA
<213> ORGANISM: Unknown
<220> FEATURE:
<223> OTHER INFORMATION: Description of Unknown:
DP26 16S rRNA sequence

<400> SEQUENCE: 26

```
cttgagagtt tgatcctggc tcagagcgaa cgctggcggc aggcttaaca catgcaagtc     60

gagcgggcat cttcggatgt cagcggcaga cgggtgagta acacgtggga acgtaccctt    120

cggttcggaa taacgctggg aaactagcgc taataccgga tacgcccttt tggggaaagg    180

tttactgccg aaggatcggc ccgcgtctga ttagctagtt ggtggggtaa cggcctacca    240

aggcgacgat cagtagctgg tctgagagga tgatcagcca cactgggact gagacacggc    300

ccagactcct acgggaggca gcagtgggga atattggaca atgggcgcaa gcctgatcca    360

gccatgccgc gtgagtgatg aaggccttag ggttgtaaag ctcttttgtc cgggacgata    420

atgacggtac cggaagaata agccccggct aacttcgtgc cagcagccgc ggtaatacga    480

agggggctag cgttgctcgg aatcactggg cgtaaagggc gcgtaggcgg ccattcaagt    540

cgggggtgaa agcctgtggc tcaaccacag aattgccttc gatactgttt ggcttgagta    600

tggtagaggt tggtggaact gcgagtgtag aggtgaaatt cgtagatatt cgcaagaaca    660

ccggtggcga aggcggccaa ctggaccatt actgacgctg aggcgcgaaa gcgtggggag    720

caaacaggat tagataccct ggtagtccac gccgtaaacg atgaatgcca gctgttgggg    780

tgcttgcacc tcagtagcgc agctaacgct ttaagcattc cgcctgggga gtacggtcgc    840

aagattaaaa ctcaaaggaa ttgacggggg cccgcacaag cggtggagca tgtggtttaa    900

ttcgaagcaa cgcgcagaac cttaccatcc cttgacatgg catgttaccc ggagagattc    960

ggggtccact tcggtggcgt gcacacaggt gctgcatggc tgtcgtcagc tcgtgtcgtg   1020

agatgttggg ttaagtcccg caacgagcgc aacccacgtc cttagttgcc atcattcagt   1080

tgggcactct agggagactg ccggtgataa gccgcgagga aggtgtggat gacgtcaagt   1140

cctcatggcc cttacgggat gggctacaca cgtgctacaa tggcggtgac agtgggacgc   1200

gaaggagcga tctggagcaa atccccaaaa accgtctcag ttcagattgc actctgcaac   1260

tcgagtgcat gaaggcggaa tcgctagtaa tcgtggatca gcatgccacg gtgaatacgt   1320

tcccgggcct tgtacacacc gcccgtcaca ccatgggagt tggtcttacc cgacggcgct   1380

gcgccaaccg caaggaggca ggcgaccacg gtagggtcag cgactggggt gaagtcgtaa   1440

caaggtagcc gtaggggaac ctgcggctgg atcacctcct tt                      1482


<210> SEQ ID NO 27
<211> LENGTH: 935
<212> TYPE: DNA
<213> ORGANISM: Unknown
<220> FEATURE:
<223> OTHER INFORMATION: Description of Unknown:
      DP27 16S rRNA sequence

<400> SEQUENCE: 27

cttgagagtt tgatcctggc tcagaacgaa cgctggcggc atgcctaaca catgcaagtc     60

gaacgatgct ttcgggcata gtggcgcacg ggtgcgtaac gcgtgggaat ctgccctcag    120

gttcggaata acagctggaa acggctgcta ataccggatg atatcgcaag atcaaagatt    180

tatcgcctga ggatgagccc gcgttggatt aggtagttgg tggggtaaag gcctaccaag    240

ccgacgatcc atagctggtc tgagaggatg atcagccaca ctgggactga gacacggccc    300

agactcctac gggaggcagc agtggggaat attggacaat gggcgcaagc ctgatccagc    360

aatgccgcgt gagtgatgaa ggccctaggg ttgtaaagct cttttacccg ggaagataat    420

gactgtaccg ggagaataag ccccggctaa ctccgtgcca gcagccgcgg taatacggag    480

ggggctagcg ttgttcggaa ttactgggcg taaagcgcac gtaggcggct ttgtaagtca    540
```

gaggtgaaag cctggagctc aactccagaa ctgcctttga gactgcatcg cttgaatcca 600
ggagaggtca gtggaattcc gagtgtagag gtgaaattcg tagatattcg gaagaacacc 660
agtggcgaag gcggctgact ggactggtat tgacgctgag gtgcgaaagc gtggggagca 720
aacaggatta gataccctgg tagtccacgc cgtaaacgat gataactagc tgtccgggca 780
cttggtgctt gggtggcgca gctaacgcat taagttatcc gcctggggag tacggccgca 840
aggttaaaac tcaaaggaat tgacgggggc ctgcacaagc ggtggagcat gtggtttaat 900
tcgaagcaac gcgcagaacc ttaccagcgt ttgac 935

<210> SEQ ID NO 28
<211> LENGTH: 931
<212> TYPE: DNA
<213> ORGANISM: Unknown
<220> FEATURE:
<223> OTHER INFORMATION: Description of Unknown:
DP28 16S rRNA sequence

<400> SEQUENCE: 28
atagtcgggg gcatcagtat tcaattgtca gaggtgaaat tcttggattt attgaagact 60
aactactgcg aaagcatttg ccaaggatgt tttcattaat cagtgaacga aagttagggg 120
atcgaagacg atcagatacc gtcgtagtct taaccataaa ctatgccgac tagggatcgg 180
gcgatgttat cattttgact cgctcggcac cttacgagaa atcaaagtct ttgggttctg 240
gggggagtat ggtcgcaagg ctgaaactta aagaaattga cggaagggca ccaccaggcg 300
tggagcctgc ggcttaattt gactcaacac ggggaaactc accaggtcca gacacaataa 360
ggattgacag attgagagct ctttcttgat tttgtgggtg gtggtgcatg gccgttctta 420
gttggtggag tgatttgtct gcttaattgc gataacgaac gagaccttaa cctgctaaat 480
agcccggccc gctttggcgg gtcgccggct tcttagaggg actatcggct caagccgatg 540
gaagtttgag gcaataacag gtctgtgatg cccttagatg ttctgggccg cacgcgcgct 600
acactgacag agccaacgag ttcatttcct tgcccggaag ggttgggtaa tcttgttaaa 660
ctctgtcgtg ctggggatag agcattgcaa ttattgctct tcaacgagga atgcctagta 720
agcgtacgtc atcagcgtgc gttgattacg tccctgccct ttgtacacac cgcccgtcgc 780
tactaccgat tgaatggctg agtgaggcct tcggactggc ccagggaggt cggcaacgac 840
cacccagggc cggaaagttg gtcaaactcc gtcatttaga ggaagtaaaa gtcgtaacaa 900
ggtttccgta ggtgaacctg cggaaggatc a 931

<210> SEQ ID NO 29
<211> LENGTH: 1002
<212> TYPE: DNA
<213> ORGANISM: Unknown
<220> FEATURE:
<223> OTHER INFORMATION: Description of Unknown:
DP29 16S rRNA sequence

<400> SEQUENCE: 29
tacggagagt ttgatcctgg ctcaggacga acgctggcgg cgtgcttaac acatgcaagt 60
cgaacgatga agcccagctt gctgggttga ttagtggcga acgggtgagt aacacgtgag 120
caacgtgccc ataactctgg gataacctcc ggaaacggtg gctaatactg gatatctaac 180
acgatcgcat ggtctgtgtt tggaaagatt ttttggttat ggatcggctc acggcctatc 240
agcttgttgg tgaggtaatg gctcaccaag gcgacgacgg gtagccggcc tgagagggtg 300
accggccaca ctgggactga gacacggccc agactcctac gggaggcagc agtggggaat 360
attgcacaat gggcgaaagc ctgatgcagc aacgccgcgt gagggatgac ggcattcggg 420
ttgtaaacct cttttagtag ggaagaagcg aaagtgacgg tacctgcaga aaaagcaccg 480
gctaactacg tgccagcagc cgctgtaata cgtagggtgc aagcgttgtc cggaattatt 540
gggcgtaaag agctcgtagg cggtttgtcg cgtctgctgt gaaatcccga ggctcaacct 600
cgggtctgca gtgggtacgg gcagactaga gtgtggtagg ggagattgga attcctggtg 660
tagcggtgga atgcgcagat atcaggagga acaccgatgg cgaaggcaga tctctgggcc 720
attactgacg ctgaggagcg aaagcatggg gagcgaacag gattagatac cctggtagtc 780
catgccgtaa acgttgggcg ctagatgtgg ggaccattcc acggtttccg tgtcgtagct 840
aacgcattaa gcgccccgcc tggggagtac ggccgcaagg ctaaaactca aaggaattga 900
cgggggcccg cacaagcggc ggagcatgcg gattaattcg atgcaacgcg aagaacctta 960
ccaaggcttg acatataccg gaaacgttca gaaatgttcg cc 1002

<210> SEQ ID NO 30
<211> LENGTH: 1520
<212> TYPE: DNA
<213> ORGANISM: Unknown
<220> FEATURE:
<223> OTHER INFORMATION: Description of Unknown:
DP30 16S rRNA sequence

<400> SEQUENCE: 30
tacggagagt ttgatcctgg ctcaggatga acgctggcgg cgtgcttaac acatgcaagt 60
cgaacggtga agccaagctt gcttggtgga tcagtggcga acgggtgagt aacacgtgag 120
caacctgccc tggactctgg gataagcgct ggaaacggcg tctaatactg gatatgagac 180
gtgatcgcat ggtcgtgttt ggaaagattt ttcggtctgg gatgggctcg cggcctatca 240
gcttgttggt gaggtaatgg ctcaccaagg cgtcgacggg tagccggcct gagagggtga 300
ccggccacac tgggactgag acacggccca gactcctacg ggaggcagca gtggggaata 360
ttgcacaatg ggcgaaagcc tgatgcagca acgccgcgtg agggatgacg gccttcgggt 420
tgtaaacctc ttttagcagg gaagaagcga aagtgacggt acctgcagaa aaagcgccgg 480
ctaactacgt gccagcagcc gcggtaatac gtagggcgca agcgttatcc ggaattattg 540
ggcgtaaaga gctcgtaggc ggtttgtcgc gtctgctgtg aaatcccgag gctcaacctc 600
gggcctgcag tgggtacggg cagactagag tgcggtaggg gagattggaa ttcctggtgt 660
agcggtggaa tgcgcagata tcaggaggaa caccgatggc gaaggcagat ctctgggccg 720
taactgacgc tgaggagcga aagggtgggg agcaaacagg cttagatacc ctggtagtcc 780
accccgtaaa cgttgggaac tagttgtggg gaccattcca cggtttccgt gacgcagcta 840
acgcattaag ttccccgcct ggggagtacg gccgcaaggc taaaactcaa aggaattgac 900
ggggacccgc acaagcggcg gagcatgcgg attaattcga tgcaacgcga agaaccttac 960
caaggcttga catatacgag aacgggccag aaatggtcaa ctctttggac actcgtaaac 1020
aggtggtgca tggttgtcgt cagctcgtgt cgtgagatgt tgggttaagt cccgcaacga 1080
gcgcaaccct cgttctatgt tgccagcacg taatggtggg aactcatggg atactgccgg 1140
ggtcaactcg gaggaaggtg gggatgacgt caaatcatca tgccccttat gtcttgggct 1200
tcacgcatgc tacaatggcc ggtacaaagg gctgcaatac cgtgaggtgg agcgaatccc 1260
aaaaagccgg tcccagttcg gattgaggtc tgcaactcga cctcatgaag tcggagtcgc 1320
tagtaatcgc agatcagcaa cgctgcggtg aatacgttcc cgggtcttgt acacaccgcc 1380
cgtcaagtca tgaaagtcgg taacacctga agccggtggc ccaacccttg tggagggagc 1440
cgtcgaaggt gggatcggta attaggacta agtcgtaaca aggtagccgt accggaaggt 1500
gcggctggat cacctccttt 1520

<210> SEQ ID NO 31
<211> LENGTH: 941
<212> TYPE: DNA
<213> ORGANISM: Unknown
<220> FEATURE:
<223> OTHER INFORMATION: Description of Unknown:
DP31 16S rRNA sequence

<400> SEQUENCE: 31
cagccggggg cattagtatt tgcacgctag aggtgaaatt cttggattgt gcaaagactt 60
cctactgcga aagcatttgc caagaatgtt ttcattaatc aagaacgaag gttagggtat 120
cgaaaacgat tagataccgt tgtagtctta acagtaaact atgccgactc cgaatcggtc 180
gatgctcatt tcactggctc gatcggcgcg gtacgagaaa tcaaagtttt tgggttctgg 240
ggggagtatg gtcgcaaggc tgaaacttaa agaaattgac ggaagggcac caccaggagt 300
ggagcctgcg gcttaatttg actcaacacg ggaaaactca ccgggtccgg acatagtaag 360
gattgacaga ttgatggcgc tttcatgatt ctatgggtgg tggtgcatgg ccgttcttag 420
ttggtggagt gatttgtctg gttaattccg ataacgaacg agaccttgac ctgctaaata 480
gacgggttga cattttgttg gccccttatg tcttcttaga gggacaatcg accgtctagg 540
tgatggaggc aaaaggcaat aacaggtctg tgatgccctt agatgttccg ggctgcacgc 600
gcgctacact gacagagaca acgagtgggg ccccttgtcc gaaatgactg ggtaaacttg 660
tgaaactttg tcgtgctggg gatggagctt tgtaattttt gctcttcaac gaggaattcc 720
tagtaagcgc aagtcatcag cttgcgttga ctacgtccct gccctttgta cacaccgccc 780
gtcgctacta ccgattgaat ggcttagtga ggacttggga gagtacatcg ggagccagc 840 aatggcaccc tgacggctca aactcttaca aacttggtca tttagaggaa gtaaaagtcg 900
taacaaggta tctgtaggtg aacctgcaga tggatcattt c 941

<210> SEQ ID NO 32
<211> LENGTH: 1072
<212> TYPE: DNA
<213> ORGANISM: Unknown
<220> FEATURE:
<223> OTHER INFORMATION: Description of Unknown:
DP32 16S rRNA sequence

<400> SEQUENCE: 32
actgagcatt gacgttactc gcagaagaag caccggctaa ctccgtgcca gcagccgcgg 60
taatacggag ggtgcaagcg ttaatcggaa ttactgggcg taaagcgcac gcaggcggtt 120
tgttaagtca gatgtgaaat ccccgagctt aacttgggaa ctgcatttga aactggcaag 180
ctagagtctt gtagaggggg gtagaattcc aggtgtagcg gtgaaatgcg tagagatctg 240
gaggaatacc ggtggcgaag gcggcccct ggacaaagac tgacgctcag gtgcgaaagc 300
gtggggagca aacaggatta gataccctgg tagtccacgc tgtaaacgat gtcgacttgg 360
aggttgtgcc cttgaggcgt ggcttccgga gctaacgcgt taagtcgacc gcctggggag 420
tacggccgca aggttaaaac tcaaatgaat tgacgggggc ccgcacaagc ggtggagcat 480
gtggtttaat tcgatgcaac gcgaagaacc ttacctactc ttgacatcca gagaattcgc 540

-continued

```
tagagatagc ttagtgcctt cgggaactct gagacaggtg ctgcatggct gtcgtcagct    600

cgtgttgtga aatgttgggt taagtcccgc aacgagcgca acccttatcc tttgttgcca    660

gcgagtaatg tcgggaactc aaaggagact gccggtgata aaccggagga aggtggggat    720

gacgtcaagt catcatggcc cttacgagta gggctacaca cgtgctacaa tggcatatac    780

aaagagaagc gaactcgcga gagcaagcgg acctcataaa gtatgtcgta gtccggattg    840

gagtctgcaa ctcgactcca tgaagtcgga atcgctagta atcgtagatc agaatgctac    900

ggtgaatacg ttcccgggcc ttgtacacac cgcccgtcac accatgggag tgggttgcaa    960

aagaagtagg tagcttaacc ttcgggaggg cgcttaccac tttgtgattc atgactgggg   1020

tgaagtcgta acaaggtaac cgtaggggaa cctgcggttg gatcacctcc tt           1072
```

<210> SEQ ID NO 33
<211> LENGTH: 853
<212> TYPE: DNA
<213> ORGANISM: Unknown
<220> FEATURE:
<223> OTHER INFORMATION: Description of Unknown:
DP33 16S rRNA sequence

<400> SEQUENCE: 33

```
ggaggaaggc gtagagatct ggaggaatac cggtggcgaa ggcggccccc tggacaaaga     60

ctgacgctca ggtgcgaaag cgtggggagc aaacaggatt agataccctg gtagtccacg    120

ccgtaaacga tgtcgacttg gaggttgtgc ccttgaggcg tggcttccgg agctaacgcg    180

ttaagtcgac cgcctgggga gtacggccgc aaggttaaaa ctcaaatgaa ttgacggggg    240

cccgcacaag cggtggagca tgtggtttaa ttcgatgcaa cgcgaagaac cttacctggc    300

cttgacatcc acggaattcg gcagagatgc cttagtgcct tcgggaaccg tgagacaggt    360

gctgcatggc tgtcgtcagc tcgtgttgtg aaatgttggg ttaagtcccg caacgagcgc    420

aacccttatc ctttgttgcc agcacgtaat ggtgggaact caaaggagac tgccggtgat    480

aaaccggagg aaggtgggga tgacgtcaag tcatcatggc ccttacggcc agggctacac    540

acgtgctaca atggcgcata caaagagaag cgacctcgcg agagcaagcg gacctcataa    600

agtgcgtcgt agtccggatc ggagtctgca actcgactcc gtgaagtcgg aatcgctagt    660

aatcgtagat cagaatgcta cggtgaatac gttcccgggc cttgtacaca ccgcccgtca    720

caccatggga gtgggttgca aaagaagtag gtagcttaac cttcgggagg gcgcttacca    780

ctttgtgatt catgactggg gtgaagtcgt aacaaggtaa ccgtagggga acctgcggtt    840

ggatcacctc ctt                                                       853
```

<210> SEQ ID NO 34
<211> LENGTH: 1519
<212> TYPE: DNA
<213> ORGANISM: Unknown
<220> FEATURE:
<223> OTHER INFORMATION: Description of Unknown:
DP34 16S rRNA sequence

<400> SEQUENCE: 34

```
tacggagagt ttgatcctgg ctcaggacga acgctggcgg cgtgcttaac acatgcaagt     60

cgaacgatga agcccagctt gctgggtgga ttagtggcga acgggtgagt aacacgtgag    120

taacctgccc ttgactctgg gataagcgtt ggaaacgacg tctaataccg gatacgagct    180

tccaccgcat ggtgagttgc tggaaagaat tttggtcaag gatggactcg cggcctatca    240

gcttgttggt gaggtaatgg ctcaccaagg cgacgacggg tagccggcct gagagggtga    300
```

```
ccggccacac tgggactgag acacggccca gactcctacg ggaggcagca gtggggaata    360

ttgcacaatg ggcgaaagcc tgatgcagca acgccgcgtg agggacgacg gccttcgggt    420

tgtaaacctc ttttagcagg gaagaagcga aagtgacggt acctgcagaa aaagcaccgg    480

ctaactacgt gccagcagcc gcggtaatac gtagggtgca agcgttgtcc ggaattattg    540

ggcgtaaaga gctcgtaggc ggtttgtcgc gtctgctgtg aaatcccgag gctcaacctc    600

gggtctgcag tgggtacggg cagactagag tgcggtaggg gagattggaa ttcctggtgt    660

agcggtggaa tgcgcagata tcaggaggaa caccgatggc gaaggcagat ctctgggccg    720

ctactgacgc tgaggagcga aagggtgggg agcaaacagg cttagatacc ctggtagtcc    780

accccgtaaa cgttgggcgc tagatgtggg gaccattcca cggtttccgt gtcgtagcta    840

acgcattaag cgccccgcct ggggagtacg gccgcaaggc taaaactcaa aggaattgac    900

gggggcccgc acaagcggcg gagcatgcgg attaattcga tgcaacgcga agaaccttac    960

caaggcttga catatacgag aacgggccag aaatggtcaa ctctttggac actcgtaaac   1020

aggtggtgca tggttgtcgt cagctcgtgt cgtgagatgt tgggttaagt cccgcaacga   1080

gcgcaaccct cgttctatgt tgccagcacg taatggtggg aactcatggg atactgccgg   1140

ggtcaactcg gaggaaggtg gggacgacgt caaatcatca tgccccttat gtcttgggct   1200

tcacgcatgc tacaatggcc agtacaaagg gctgcaatac cgtaaggtgg agcgaatccc   1260

aaaaagctgg tcccagttcg gattgaggtc tgcaactcga cctcatgaag tcggagtcgc   1320

tagtaatcgc agatcagcaa cgctgcggtg aatacgttcc cgggccttgt acacaccgcc   1380

cgtcaagtca tgaaagtcgg taacacccga agccagtggc ctaaccgcaa ggatggagct   1440

gtctaaggtg ggatcggtaa ttaggactaa gtcgtaacaa ggtagccgta ccggaaggtg   1500

cggctggatc acctccttt                                                1519
```

```
<210> SEQ ID NO 35
<211> LENGTH: 1536
<212> TYPE: DNA
<213> ORGANISM: Unknown
<220> FEATURE:
<223> OTHER INFORMATION: Description of Unknown:
      DP35 16S rRNA sequence

<400> SEQUENCE: 35

ttgaagagtt tgatcatggc tcagattgaa cgctggcggc aggcctaaca catgcaagtc     60

ggacggtagc acagagagct tgctcttggg tgacgagtgg cggacgggtg agtaatgtct    120

ggggatctgc ccgatagagg gggataacca ctggaaacgg tggctaatac cgcataacgt    180

cgcaagacca aagaggggga ccttcgggcc tctcactatc ggatgaaccc agatgggatt    240

agctagtagg cggggtaatg gcccacctag gcgacgatcc ctagctggtc tgagaggatg    300

accagccaca ctggaactga gacacggtcc agactcctac gggaggcagc agtggggaat    360

attgcacaat gggcgcaagc ctgatgcagc catgccgcgt gtatgaagaa ggccttcggg    420

ttgtaaagta ctttcagcgg ggaggaaggc gatgaggtta ataaccgcgt cgattgacgt    480

tacccgcaga agaagcaccg gctaactccg tgccagcagc cgcggtaata cggagggtgc    540

aagcgttaat cggaattact gggcgtaaag cgcacgcagg cggtctgtta agtcagatgt    600

gaaatccccg ggcttaacct gggaactgca tttgaaactg gcaggcttga gtcttgtaga    660

ggggggtaga attccaggtg tagcggtgaa atgcgtagag atctggagga ataccggtgg    720

cgaaggcggc cccctggaca aagactgacg ctcaggtgcg aaagcgtggg gagcaaacag    780
```

gattagatac cctggtagtc cacgccgtaa acgatgtcga cttggaggtt gttcccttga 840
ggagtggctt ccggagctaa cgcgttaagt cgaccgcctg gggagtacgg ccgcaaggtt 900
aaaactcaaa tgaattgacg gggcccgca caagcggtgg agcatgtggt ttaattcgat 960
gcaacgcgaa gaaccttacc tactcttgac atccagcgaa cttagcagag atgctttggt 1020
gccttcggga acgctgagac aggtgctgca tggctgtcgt cagctcgtgt tgtgaaatgt 1080
tgggttaagt cccgcaacga gcgcaaccct tatcctttgt tgccagcgat tcggtcggga 1140
actcaaagga gactgccggt gataaaccgg aggaaggtgg ggatgacgtc aagtcatcat 1200
ggcccttacg agtagggcta cacacgtgct acaatggcgc atacaaagag aagcgacctc 1260
gcgagagcaa gcggacctca caaagtgcgt cgtagtccgg atcggagtct gcaactcgac 1320
tccgtgaagt cggaatcgct agtaatcgtg gatcagaatg ccacggtgaa tacgttcccg 1380
ggccttgtac acaccgcccg tcacaccatg ggagtgggtt gcaaaagaag taggtagctt 1440
aaccttcggg agggcgctta ccactttgtg attcattact ggggtgaagt cgtaacaagg 1500
taaccgtagg ggaacctgcg gttggatcac ctcctt 1536

<210> SEQ ID NO 36
<211> LENGTH: 993
<212> TYPE: DNA
<213> ORGANISM: Unknown
<220> FEATURE:
<223> OTHER INFORMATION: Description of Unknown:
DP36 16S rRNA sequence

<400> SEQUENCE: 36
ttgaagagtt tgatcatggc tcagattgaa cgctggcggc aggcctaaca catgcaagtc 60
ggacggtagc acagagagct tgctcttggg tgacgagtgg cggacgggtg agtaatgtct 120
ggggatctgc ccgatagagg gggataacca ctggaaacgg tggctaatac cgcataacgt 180
cgcaagacca aagaggggga ccttcgggcc tctcactatc ggatgaaccc agatgggatt 240
agctagtagg cggggtaatg gcccacctag gcgacgatcc ctagctggtc tgagaggatg 300
accagccaca ctggaactga gacacggtcc agactcctac gggaggcagc agtggggaat 360
attgcacaat gggcgcaagc ctgatgcagc catgccgcgt gtatgaagaa ggccttcggg 420
ttgtaaagta ctttcagcgg ggaggaaggc gatgcggtta ataaccgcgt cgattgacgt 480
tacccgcaga agaagcaccg gctaactccg tgccagcagc cgcggtaata cggagggtgc 540
aagcgttaat cggaattact gggcgtaaag cgcacgcagg cggtctgtta agtcagatgt 600
gaaatccccg ggcttaacct gggaactgca tttgaaactg gcaggcttga gtcttgtaga 660
ggggggtaga attccaggtg tagcggtgaa atgcgtagag atctggagga ataccggtgg 720
cgaaggcggc cccctggaca aagactgacg ctcaggtgcg aaagcgtggg gagcaaacag 780
gattagatac cctggtagtc cacgccgtaa acgatgtcga cttggaggtt gttcccttga 840
ggagtggctt ccggagctaa cgcgttaagt cgaccgcctg gggagtacgg ccgcaaggtt 900
aaaactcaaa tgaattgacg gggcccgca caagcggtgg agcatgtggt ttaattcgat 960
gcaacgcgaa gaaccttacc tactcttgac atc 993

<210> SEQ ID NO 37
<211> LENGTH: 1532
<212> TYPE: DNA
<213> ORGANISM: Unknown
<220> FEATURE:
<223> OTHER INFORMATION: Description of Unknown:

-continued

DP37 16S rRNA sequence

<400> SEQUENCE: 37
tgaagagttt gatcatggct cagattgaac gctggcggca ggcctaacac atgcaagtcg 60
agcggtagag agaagcttgc ttctcttgag agcggcggac gggtgagtaa tgcctaggaa 120
tctgcctggt agtgggggat aacgttcgga aacgaacgct aataccgcat acgtcctacg 180
ggagaaagca ggggaccttc gggccttgcg ctatcagatg agcctaggtc ggattagcta 240
gttggtgggg taatggctca ccaaggcgac gatccgtaac tggtctgaga ggatgatcag 300
tcacactgga actgagacac ggtccagact cctacgggag gcagcagtgg ggaatattgg 360
acaatgggcg aaagcctgat ccagccatgc cgcgtgtgtg aagaaggtct tcggattgta 420
aagcacttta agttgggagg aagggccatt acctaatacg tgatggtttt gacgttaccg 480
acagaataag caccggctaa ctctgtgcca gcagccgcgg taatacagag ggtgcaagcg 540
ttaatcggaa ttactgggcg taaagcgcgc gtaggtggtt tgttaagttg gatgtgaaat 600
ccccgggctc aacctgggaa ctgcattcaa aactgactga ctagagtatg gtagagggtg 660
gtggaatttc ctgtgtagcg gtgaaatgcg tagatatagg aaggaacacc agtggcgaag 720
gcgaccacct ggactgatac tgacactgag gtgcgaaagc gtggggagca aacaggatta 780
gataccctgg tagtccacgc cgtaaacgat gtcaactagc cgttgggagc cttgagctct 840
tagtggcgca gctaacgcat taagttgacc gcctggggag tacggccgca aggttaaaac 900
tcaaatgaat tgacgggggc ccgcacaagc ggtggagcat gtggtttaat tcgaagcaac 960
gcgaagaacc ttaccaggcc ttgacatcca atgaactttc tagagataga ttggtgcctt 1020
cgggaacatt gagacaggtg ctgcatggct gtcgtcagct cgtgtcgtga gatgttgggt 1080
taagtcccgt aacgagcgca acccttgtcc ttagttacca gcacgtaatg gtgggcactc 1140
taaggagact gccggtgaca aaccggagga aggtggggat gacgtcaagt catcatggcc 1200
cttacggcct gggctacaca cgtgctacaa tggtcggtac agagggttgc caagccgcga 1260
ggtggagcta atcccataaa accgatcgta gtccggatcg cagtctgcaa ctcgactgcg 1320
tgaagtcgga atcgctagta atcgcgaatc agaatgtcgc ggtgaatacg ttcccgggcc 1380
ttgtacacac cgcccgtcac accatgggag tgggttgcac cagaagtagc tagtctaacc 1440
ttcgggggga cggttaccac ggtgtgattc atgactgggg tgaagtcgta acaaggtagc 1500
cgtaggggaa cctgcggctg gatcacctcc tt 1532

<210> SEQ ID NO 38
<211> LENGTH: 1517
<212> TYPE: DNA
<213> ORGANISM: Unknown
<220> FEATURE:
<223> OTHER INFORMATION: Description of Unknown:
DP38 16S rRNA sequence

<400> SEQUENCE: 38
tacggagagt ttgatcctgg ctcaggacga acgctggcgg cgtgcttaac acatgcaagt 60
cgagcggtaa ggcctttcgg ggtacacgag cggcgaacgg gtgagtaaca cgtgggtgat 120
ctgccctgca ctctgggata agcttgggaa actgggtcta ataccggata tgaccacagc 180
atgcatgtgt tgtggtggaa agatttatcg gtgcaggatg ggcccgcggc ctatcagctt 240
gttggtgggg taatggccta ccaaggcgac gacgggtagc cgacctgaga gggtgaccgg 300
ccacactggg actgagacac ggcccagact cctacgggag gcagcagtgg ggaatattgc 360

-continued acaatgggcg gaagcctgat gcagcgacgc cgcgtgaggg atgaaggcct tcgggttgta 420
aacctctttc agcagggacg aagcgtgagt gacggtacct gcagaagaag caccggctaa 480
ctacgtgcca gcagccgcgg taatacgtag ggtgcgagcg ttgtccggaa ttactgggcg 540
taaagagttc gtaggcggtt tgtcgcgtcg tttgtgaaaa cccggggctc aacttcgggc 600
ttgcaggcga tacgggcaga cttgagtgtt tcaggggaga ctggaattcc tggtgtagcg 660
gtgaaatgcg cagatatcag gaggaacacc ggtggcgaag gcgggtctct gggaaacaac 720
tgacgctgag gaacgaaagc gtgggtagca aacaggatta gataccctgg tagtccacgc 780
cgtaaacggt gggcgctagg tgtgggttcc ttccacggga tctgtgccgt agctaacgca 840
ttaagcgccc cgcctgggga gtacggccgc aaggctaaaa ctcaaaggaa ttgacggggg 900
cccgcacaag cggcggagca tgtggattaa ttcgatgcaa cgcgaagaac cttacctggg 960
tttgacatac accggaaaac cgtagagata cggtccccct tgtggtcggt gtacaggtgg 1020
tgcatggctg tcgtcagctc gtgtcgtgag atgttgggtt aagtcccgca acgagcgcaa 1080
cccttgtctt atgttgccag cacgtaatgg tggggactcg taagagactg ccggggtcaa 1140
ctcggaggaa ggtggggacg acgtcaagtc atcatgcccc ttatgtccag ggcttcacac 1200
atgctacaat ggccagtaca gagggctgcg agaccgtgag gtggagcgaa tcccttaaag 1260
ctggtctcag ttcggatcgg ggtctgcaac tcgaccccgt gaagtcggag tcgctagtaa 1320
tcgcagatca gcaacgctgc ggtgaatacg ttcccgggcc ttgtacacac cgcccgtcac 1380
gtcatgaaag tcggtaacac ccgaagccgg tggcctaacc ccttacgggg agggagccgt 1440
cgaaggtggg atcggcgatt gggacgaagt cgtaacaagg tagccgtacc ggaaggtgcg 1500
gctggatcac ctccttt 1517

<210> SEQ ID NO 39
<211> LENGTH: 1482
<212> TYPE: DNA
<213> ORGANISM: Unknown
<220> FEATURE:
<223> OTHER INFORMATION: Description of Unknown:
DP39 16S rRNA sequence

<400> SEQUENCE: 39
cttgagagtt tgatcctggc tcagaacgaa cgctggcggc aggcttaaca catgcaagtc 60
gaacgccccg caaggggagt ggcagacggg tgagtaacgc gtgggaatct accgtgccct 120
gcggaatagc tccgggaaac tggaattaat accgcatacg ccctacgggg gaaagattta 180
tcggggtatg atgagcccgc gttggattag ctagttggtg gggtaaaggc ctaccaaggc 240
gacgatccat agctggtctg agaggatgat cagccacatt gggactgaga cacggcccaa 300
actcctacgg gaggcagcag tggggaatat tggacaatgg gcgcaagcct gatccagcca 360
tgccgcgtga gtgatgaagg ccttagggtt gtaaagctct ttcaccggag aagataatga 420
cggtatccgg agaagaagcc ccggctaact tcgtgccagc agccgcggta atacgaaggg 480
ggctagcgtt gttcggaatt actgggcgta aagcgcacgt aggcggatat ttaagtcagg 540
ggtgaaatcc cagagctcaa ctctggaact gcctttgata ctgggtatct tgagtatgga 600
agaggtaagt ggaattccga gtgtagaggt gaaattcgta gatattcgga ggaacaccag 660
tggcgaaggc ggcttactgg tccattactg acgctgaggt gcgaaagcgt ggggagcaaa 720
caggattaga taccctggta gtccacgccg taaacgatga atgttagccg tcgggcagta 780
tactgttcgg tggcgcagct aacgcattaa acattccgcc tggggagtac ggtcgcaaga 840

-continued ttaaaactca aaggaattga cgggggcccg cacaagcggt ggagcatgtg gtttaattcg 900
aagcaacgcg cagaacctta ccagctcttg acattcgggg tttgggcagt ggagacattg 960
tccttcagtt aggctggccc cagaacaggt gctgcatggc tgtcgtcagc tcgtgtcgtg 1020
agatgttggg ttaagtcccg caacgagcgc aaccctcgcc cttagttgcc agcatttagt 1080
tgggcactct aaggggactg ccggtgataa gccgagagga aggtggggat gacgtcaagt 1140
cctcatggcc cttacgggct gggctacaca cgtgctacaa tggtggtgac agtgggcagc 1200
gagacagcga tgtcgagcta atctccaaaa gccatctcag ttcggattgc actctgcaac 1260
tcgagtgcat gaagttggaa tcgctagtaa tcgcagatca gcatgctgcg gtgaatacgt 1320
tcccgggcct tgtacacacc gcccgtcaca ccatgggagt tggttttacc cgaaggtagt 1380
gcgctaaccg caaggaggca gctaaccacg gtagggtcag cgactggggt gaagtcgtaa 1440
caaggtagcc gtaggggaac ctgcggctgg atcacctcct tt 1482

<210> SEQ ID NO 40
<211> LENGTH: 903
<212> TYPE: DNA
<213> ORGANISM: Unknown
<220> FEATURE:
<223> OTHER INFORMATION: Description of Unknown:
DP40 16S rRNA sequence

<400> SEQUENCE: 40
ttgacgttac ccgcagaaga agcaccggct aactccgtgc cagcagccgc ggtaatacgg 60
agggtgcaag cgttaatcgg aattactggg cgtaaagcgc acgcaggcgg tctgttaagt 120
cagatgtgaa atccccgggc ttaacctggg aactgcattt gaaactggca ggcttgagtc 180
ttgtagaggg gggtagaatt ccaggtgtag cggtgaaatg cgtagagatc tggaggaata 240
ccggtggcga aggcggcccc ctggacaaag actgacgctc aggtgcgaaa gcgtggggag 300
caaacaggat tagataccct ggtagtccac gccgtaaacg atgtcgactt ggaggttgtt 360
cccttgagga gtggcttccg gagctaacgc gttaagtcga ccgcctgggg agtacggccg 420
caaggttaaa actcaaatga attgacgggg gcccgcacaa gcggtggagc atgtggttta 480
attcgatgca acgcgaagaa ccttacctac tcttgacatc cagagaactt tccagagatg 540
gattggtgcc ttcgggaact ctgagacagg tgctgcatgg ctgtcgtcag ctcgtgttgt 600
gaaatgttgg gttaagtccc gcaacgagcg caacccttat cctttgttgc cagcgcgtga 660
tggcgggaac tcaaaggaga ctgccggtga taaaccggag gaaggtgggg atgacgtcaa 720
gtcatcatgg cccttacgag tagggctaca cacgtgctac aatggcgcat acaaagagaa 780
gcgacctcgc gagagcaagc ggacctcaca aagtgcgtcg tagtccggat cggagtctgc 840
aactcgactc cgtgaagtcg gaatcgctag taatcgtgga tcagaatgcc acggtgaata 900
cgt 903

<210> SEQ ID NO 41
<211> LENGTH: 1457
<212> TYPE: DNA
<213> ORGANISM: Unknown
<220> FEATURE:
<223> OTHER INFORMATION: Description of Unknown:
DP41 16S rRNA sequence

<400> SEQUENCE: 41
gtggagagtt tgatcctggc tcaggatgaa cgctggcggc gtgcttaaca catgcaagtc 60
gaacggaaag gcccaagctt gcttgggtac tcgagtggcg aacgggtgag taacacgtgg 120
gtgatctgcc ctgcacttcg ggataagcct gggaaactgg gtctaatacc ggataggacg 180
atggtttgga tgccattgtg gaaagttttt tcggtgtggg atgagctcgc ggcctatcag 240
cttgttggtg gggtaatggc ctaccaaggc gtcgacgggt agccggcctg agagggtgta 300
cggccacatt gggactgaga tacggcccag actcctacgg gaggcagcag tggggaatat 360
tgcacaatgg gcgcaagcct gatgcagcga cgccgcgtgg gggatgacgg ccttcgggtt 420
gtaaactcct ttcgctaggg acgaagcgtt ttgtgacggt acctggagaa gaagcaccgg 480
ctaactacgt gccagcagcc gcggtaatac gtagggtgcg agcgttgtcc ggaattactg 540
ggcgtaaaga gctcgtaggt ggtttgtcgc gtcgtttgtg taagcccgca gcttaactgc 600
gggactgcag gcgatacggg cataacttga gtgctgtagg ggagactgga attcctggtg 660
tagcggtgga atgcgcagat atcaggagga acaccgatgg cgaaggcagg tctctgggca 720
gtaactgacg ctgaggagcg aaagcatggg tagcgaacag gattagatac cctggtagtc 780
catgccgtaa acggtgggcg ctaggtgtga gtcccttcca cggggttcgt gccgtagcta 840
acgcattaag cgccccgcct ggggagtacg gccgcaaggc taaaactcaa aggaattgac 900
gggggcccgc acaagcggcg gagcatgtgg attaattcga tgcaacgcga agaaccttac 960
ctgggcttga catacaccag atcgccgtag agatacggtt tccctttgtg gttggtgtac 1020
aggtggtgca tggttgtcgt cagctcgtgt cgtgagatgt tgggttaagt cccgcaacga 1080
gcgcaaccct tgtcttatgt tgccagcacg tgatggtggg gactcgtgag agactgccgg 1140
ggttaactcg gaggaaggtg gggatgacgt caaatcatca tgccccttat gtccagggct 1200
tcacacatgc tacaatggtc ggtacaacgc gcatgcgagc ctgtgagggt gagcgaatcg 1260
ctgtgaaagc cggtcgtagt tcggattggg gtctgcaact cgaccccatg aagtcggagt 1320
cgctagtaat cgcagatcag caacgctgcg gtgaatacgt tcccgggcct tgtacacacc 1380
gcccgtcaca ccatgggagt gggttgcaaa agaagtaggt agcttaacct tcgggagggc 1440
gcttaccact ttgtgat 1457

<210> SEQ ID NO 42
<211> LENGTH: 1532
<212> TYPE: DNA
<213> ORGANISM: Unknown
<220> FEATURE:
<223> OTHER INFORMATION: Description of Unknown:
DP42 16S rRNA sequence

<400> SEQUENCE: 42
tgaagagttt gatcatggct cagattgaac gctggcggca ggcctaacac atgcaagtcg 60
agcggtagag aggtgcttgc acctcttgag agcggcggac gggtgagtaa tacctaggaa 120
tctgcctgat agtgggggat aacgttcgga aacggacgct aataccgcat acgtcctacg 180
ggagaaagca ggggaccttc gggccttgcg ctatcagatg agcctaggtc ggattagcta 240
gttggtgagg taatggctca ccaaggctac gatccgtaac tggtctgaga ggatgatcag 300
tcacactgga actgagacac ggtccagact cctacgggag gcagcagtgg ggaatattgg 360
acaatgggcg aaagcctgat ccagccatgc cgcgtgtgtg aagaaggtct tcggattgta 420
aagcacttta agttgggagg aagggcatta acctaatacg ttagtgtctt gacgttaccg 480
acagaataag caccggctaa ctctgtgcca gcagccgcgg taatacagag ggtgcaagcg 540
ttaatcggaa ttactgggcg taaagcgcgc gtaggtggtt tgttaagttg aatgtgaaat 600
ccccgggctc aacctgggaa ctgcatccaa aactggcaag ctagagtatg gtagagggta 660
gtggaatttc ctgtgtagcg gtgaaatgcg tagatatagg aaggaacacc agtggcgaag 720
gcgactacct ggactgatac tgacactgag gtgcgaaagc gtggggagca aacaggatta 780
gataccctgg tagtccacgc cgtaaacgat gtcaactagc cgttgggaac cttgagttct 840
tagtggcgca gctaacgcat taagttgacc gcctggggag tacggccgca aggttaaaac 900
tcaaatgaat tgacgggggc ccgcacaagc ggtggagcat gtggtttaat tcgaagcaac 960
gcgaagaacc ttaccaggcc ttgacatcca atgaactttc cagagatgga ttggtgcctt 1020
cgggaacatt gagacaggtg ctgcatggct gtcgtcagct cgtgtcgtga gatgttgggt 1080
taagtcccgt aacgagcgca acccttgtcc ttagttacca gcacgtaatg gtgggcactc 1140
taaggagact gccggtgaca aaccggagga aggtggggat gacgtcaagt catcatggcc 1200
cttacggcct gggctacaca cgtgctacaa tggtcggtac aaagggttgc caagccgcga 1260
ggtggagcta atcccataaa accgatcgta gtccggatcg cagtctgcaa ctcgactgcg 1320
tgaagtcgga atcgctagta atcgtgaatc agaatgtcac ggtgaatacg ttcccgggcc 1380
ttgtacacac cgcccgtcac accatgggag tgggttgcac cagaagtagc tagtctaacc 1440
ctcgggagga cggttaccac ggtgtgattc atgactgggg tgaagtcgta acaaggtagc 1500
cgtaggggaa cctgcggctg gatcacctcc tt 1532

<210> SEQ ID NO 43
<211> LENGTH: 1525
<212> TYPE: DNA
<213> ORGANISM: Unknown
<220> FEATURE:
<223> OTHER INFORMATION: Description of Unknown:
DP43 16S rRNA sequence

<400> SEQUENCE: 43
ctgagtttga tcctggctca gattgaacgc tggcggcatg ccttacacat gcaagtcgaa 60
cggcagcacg gagcttgctc tggtggcgag tggcgaacgg gtgagtaata tatcggaacg 120
taccctggag tgggggataa cgtagcgaaa gttacgctaa taccgcatac gatctaagga 180
tgaaagtggg ggatcgcaag acctcatgct cgtggagcgg ccgatatctg attagctagt 240
tggtagggta aaagcctacc aaggcatcga tcagtagctg gtctgagagg acgaccagcc 300
acactggaac tgagacacgg tccagactcc tacgggaggc agcagtgggg aattttggac 360
aatgggcgaa agcctgatcc agcaatgccg cgtgagtgaa gaaggccttc gggttgtaaa 420
gctcttttgt cagggaagaa acggtgagag ctaatatctc ttgctaatga cggtacctga 480
agaataagca ccggctaact acgtgccagc agccgcggta atacgtaggg tgcaagcgtt 540
aatcggaatt actgggcgta aagcgtgcgc aggcggtttt gtaagtctga tgtgaaatcc 600
ccgggctcaa cctgggaatt gcattggaga ctgcaaggct agaatctggc agaggggggt 660
agaattccac gtgtagcagt gaaatgcgta gatatgtgga ggaacaccga tggcgaaggc 720
agccccctgg gtcaagattg acgctcatgc acgaaagcgt ggggagcaaa caggattaga 780
taccctggta gtccacgccc taaacgatgt ctactagttg tcgggtctta attgacttgg 840
taacgcagct aacgcgtgaa gtagaccgcc tggggagtac ggtcgcaaga ttaaaactca 900
aaggaattga cggggacccg cacaagcggt ggatgatgtg gattaattcg atgcaacgcg 960
aaaaacctta cctacccttg acatggctgg aatccttgag agatcaggga gtgctcgaaa 1020
gagaaccagt acacaggtgc tgcatggctg tcgtcagctc gtgtcgtgag atgttgggtt 1080
aagtcccgca acgagcgcaa cccttgtcat tagttgctac gaaagggcac tctaatgaga 1140
ctgccggtga caaaccggag gaaggtgggg atgacgtcaa gtcctcatgg cccttatggg 1200
tagggcttca cacgtcatac aatggtacat acagagcgcc gccaacccgc gagggggagc 1260
taatcgcaga aagtgtatcg tagtccggat tgtagtctgc aactcgactg catgaagttg 1320
gaatcgctag taatcgcgga tcagcatgtc gcggtgaata cgttcccggg tcttgtacac 1380
accgcccgtc acaccatggg agcgggtttt accagaagta ggtagcttaa ccgtaaggag 1440
ggcgcttacc acggtaggat tcgtgactgg ggtgaagtcg taacaaggta gccgtatcgg 1500
aaggtgcggc tggatcacct ccttt 1525

<210> SEQ ID NO 44
<211> LENGTH: 1497
<212> TYPE: DNA
<213> ORGANISM: Unknown
<220> FEATURE:
<223> OTHER INFORMATION: Description of Unknown:
DP44 16S rRNA sequence

<400> SEQUENCE: 44
tggcggcatg ccttacacat gcaagtcgaa cggcagcata ggagcttgct cctgatggcg 60
agtggcgaac gggtgagtaa tatatcggaa cgtgccctag agtgggggat aactagtcga 120
aagactagct aataccgcat acgatctacg gatgaaagtg ggggatcgca agacctcatg 180
ctcctggagc ggccgatatc tgattagcta gttggtgggg taaaagctca ccaaggcgac 240
gatcagtagc tggtctgaga ggacgaccag ccacactggg actgagacac ggcccagact 300
cctacgggag gcagcagtgg ggaattttgg acaatggggg caaccctgat ccagcaatgc 360
cgcgtgagtg aagaaggcct tcgggttgta aagctctttt gtcagggaag aaacggttct 420
ggataatacc taggactaat gacggtacct gaagaataag caccggctaa ctacgtgcca 480
gcagccgcgg taatacgtag ggtgcaagcg ttaatcggaa ttactgggcg taaagcgtgc 540
gcaggcggtt gtgtaagtca gatgtgaaat ccccgggctc aacctgggaa ttgcatttga 600
gactgcacgg ctagagtgtg tcagaggggg gtagaattcc acgtgtagca gtgaaatgcg 660
tagatatgtg gaggaatacc gatggcgaag gcagcccccct gggataacac tgacgctcat 720
gcacgaaagc gtggggagca aacaggatta gataccctgg tagtccacgc cctaaacgat 780
gtctactagt tgtcgggtct taattgactt ggtaacgcag ctaacgcgtg aagtagaccg 840
cctggggagt acggtcgcaa gattaaaact caaaggaatt gacggggacc cgcacaagcg 900
gtggatgatg tggattaatt cgatgcaacg cgaaaaacct tacctaccct tgacatggat 960
ggaatcccga agagatttgg gagtgctcga aagagaacca tcacacaggt gctgcatggc 1020
tgtcgtcagc tcgtgtcgtg agatgttggg ttaagtcccg caacgagcgc aacccttgtc 1080
attagttgct acgaaagggc actctaatga gactgccggt gacaaaccgg aggaaggtgg 1140
ggatgacgtc aagtcctcat ggcccttatg ggtagggctt cacacgtcat acaatggtac 1200
atacagaggg ccgccaaccc gcgagggggga gctaatccca gaaagtgtat cgtagtccgg 1260
attggagtct gcaactcgac tccatgaagt tggaatcgct agtaatcgcg gatcagcatg 1320
tcgcggtgaa tacgttcccg ggtcttgtac acaccgcccg tcacaccatg ggagcgggtt 1380
ttaccagaag tgggtagcct aaccgcaagg agggcgctca ccacggtagg attcgtgact 1440
ggggtgaagt cgtaacaagg tagccgtatc ggaaggtgcg gctggatcac ctccttt 1497

<210> SEQ ID NO 45
<211> LENGTH: 1522

<212> TYPE: DNA
<213> ORGANISM: Unknown
<220> FEATURE:
<223> OTHER INFORMATION: Description of Unknown:
DP45 16S rRNA sequence

<400> SEQUENCE: 45
tacggagagt ttgatcctgg ctcaggacga acgctggcgg cgtgcttaac acatgcaagt 60
cgaacggtga cgctagagct tgctctggtt gatcagtggc gaacgggtga gtaacacgtg 120
agtaacctgc ccttgactct gggataactc cgggaaaccg gggctaatac cggatacgag 180
acgcgaccgc atggtcggcg tctggaaagt ttttcggtca aggatggact cgcggcctat 240
cagcttgttg gtgaggtaat ggctcaccaa ggcgtcgacg ggtagccggc ctgagagggc 300
gaccggccac actgggactg agacacggcc cagactccta cgggaggcag cagtggggaa 360
tattgcacaa tgggcgaaag cctgatgcag cgacgccgcg tgagggatga aggccttcgg 420
gttgtaaacc tctttcagta gggaagaagc gaaagtgacg gtacctgcag aagaagcgcc 480
ggctaactac gtgccagcag ccgcggtaat acgtagggcg caagcgttgt ccggaattat 540
tgggcgtaaa gagctcgtag gcggtttgtc gcgtctggtg tgaaaactca aggctcaacc 600
ttgagcttgc atcgggtacg ggcagactag agtgtggtag gggtgactgg aattcctggt 660
gtagcggtgg aatgcgcaga tatcaggagg aacaccgatg gcgaaggcag gtcactgggc 720
cactactgac gctgaggagc gaaagcatgg ggagcgaaca ggattagata ccctggtagt 780
ccatgccgta aacgttgggc actaggtgtg ggctcattc cacgagttcc gcgccgcagc 840
taacgcatta agtgccccgc ctggggagta cggccgcaag gctaaaactc aaaggaattg 900
acgggggccc gcacaagcgg cggagcatgc ggattaattc gatgcaacgc gaagaacctt 960
accaaggctt gacatacacc ggaatcatgc agagatgtgt gcgtcttcgg actggtgtac 1020
aggtggtgca tggttgtcgt cagctcgtgt cgtgagatgt tgggttaagt cccgcaacga 1080
gcgcaaccct cgtcctatgt tgccagcacg ttatggtggg gactcatagg agactgccgg 1140
ggtcaactcg gaggaaggtg gggatgacgt caaatcatca tgccccttat gtcttgggct 1200
tcacgcatgc tacaatggcc ggtacaaagg gctgcgatac cgcgaggtgg agcgaatccc 1260
aaaaagccgg tctcagttcg gattggggtc tgcaactcga ccccatgaag tcggagtcgc 1320
tagtaatcgc agatcagcaa cgctgcggtg aatacgttcc cgggccttgt acacaccgcc 1380
cgtcaagtca cgaaagtcgg taacacccga agccggtggc ctaacccctt gtgggatgga 1440
gccgtcgaag gtgggattgg cgattgggac taagtcgtaa caaggtagcc gtaccggaag 1500
gtgcggctgg atcacctcct tt 1522

<210> SEQ ID NO 46
<211> LENGTH: 831
<212> TYPE: DNA
<213> ORGANISM: Unknown
<220> FEATURE:
<223> OTHER INFORMATION: Description of Unknown:
DP46 16S rRNA sequence

<400> SEQUENCE: 46
ttgaagagtt tgatcatggc tcagattgaa cgctggcggc aggcctaaca catgcaagtc 60
ggacggtagc acagaggagc ttgctccttg ggtgacgagt ggcggacggg tgagtaatgt 120
ctggggatct gcccgataga gggggataac cactggaaac ggtggctaat accgcataac 180
gtcgcaagac caaagagggg gaccttcggg cctctcacta tcggatgaac ccagatggga 240
ttagctagta ggcggggtaa tggcccacct aggcgacgat ccctagctgg tctgagagga 300
tgaccagcca cactggaact gagacacggt ccagactcct acgggaggca gcagtgggga 360
atattgcaca atgggcgcaa gcctgatgca gccatgccgc gtgtatgaag aaggccttcg 420
ggttgtaaag tactttcagc ggggaggaag gcgacagggt taataaccct gtcgattgac 480
gttacccgca gaagaagcac cggctaactc cgtgccagca gccgcggtaa tacggagggt 540
gcaagcgtta atcggaatta ctgggcgtaa agcgcacgca ggcggtctgt taagtcagat 600
gtgaaatccc cgggcttaac ctgggaactg catttgaaac tggcaggctt tagtcttgta 660
gagtggggta gaattccagg tgtagcggtg aaatgcgtag agatgtggag gaacaccagt 720
ggcgaaggcg gctttttggt ctgtaactga cgctgaggcg cgaaagcgtg gggagcaaac 780
aggattagat accctggtag tccacgccgt aaacgatgag tgctaagtgt t 831

<210> SEQ ID NO 47
<211> LENGTH: 960
<212> TYPE: DNA
<213> ORGANISM: Unknown
<220> FEATURE:
<223> OTHER INFORMATION: Description of Unknown:
DP47 16S rRNA sequence

<400> SEQUENCE: 47
agggtgcaag cgttaatcgg aattactggg cgtaaagcgc gcgtaggtgg tttgttaagt 60
tgaatgtgaa atccccgggc tcaacctggg aactgcattt gaaactggca agctagagtc 120
tcgtagaggg gggtagaatt ccaggtgtag cggtgaaatg cgtagagatc tggaggaata 180
ccggtggcga aggcggcccc ctggacgaag actgacgctc aggtgcgaaa gcgtggggag 240
caaacaggat tagataccct ggtagtccac gccgtaaacg atgtcaacta gccgttggaa 300
gccttgagct tttagtggcg cagctaacgc attaagttga ccgcctgggg agtacggccg 360
caaggttaaa actcaaatga attgacgggg gcccgcacaa gcggtggagc atgtggttta 420
attcgaagca acgcgaagaa ccttaccagg ccttgacatc caatgaactt tctagagata 480
gattggtgcc ttcgggaaca ttgagacagg tgctgcatgg ctgtcgtcag ctcgtgtcgt 540
gagatgttgg gttaagtccc gcaacgagcg caacccttgt cctgtgttgc cagcgcgtaa 600
tggcggggac tcgcaggaga ctgccggggt caactcggag gaaggtgggg atgacgtcaa 660
atcatcatgc cccttatgtc ttgggcttca cgcatgctac aatggccggt acaaagggct 720
gcaataccgt gaggtggagc gaatcccaaa aagccggtcc cagttcggat tgaggtctgc 780
aactcgacct catgaagtcg gagtcgctag taatcgcaga tcagcaacgc tgcggtgaat 840
acgttcccgg gtcttgtaca caccgcccgt caagtcatga aagtcggtaa cacctgaagc 900
cggtggccca acccttgtgg agggagccgt cgaaggtggg atcggtaatt aggactaagt 960

<210> SEQ ID NO 48
<211> LENGTH: 1548
<212> TYPE: DNA
<213> ORGANISM: Unknown
<220> FEATURE:
<223> OTHER INFORMATION: Description of Unknown:
DP48 16S rRNA sequence

<400> SEQUENCE: 48
catggagagt ttgatcctgg ctcaggacga acgctggcgg cgtgcctaat acatgcaagt 60
cgagcggaca gatgggagct tgctccctga tgttagcggc ggacgggtga gtaacacgtg 120
ggtaacctgc ctgtaagact gggataactc cgggaaaccg gggctaatac cggatgcttg 180

```
attgaaccgc atggttcaat tataaaaggt ggcttttagc taccacttac agatggaccc    240

gcggcgcatt agctagttgg tgaggtaacg gctcaccaag gcaacgatgc gtagccgacc    300

tgagagggtg atcggccaca ctgggactga gacacggccc agactcctac gggaggcagc    360

agtagggaat cttccgcaat ggacgaaagt ctgacggagc aacgccgcgt gagtgatgaa    420

ggttttcgga tcgtaaaact ctgttgttag ggaagaacaa gtaccgttcg aatagggcgg    480

taccttgacg gtacctaacc agaaagccac ggctaactac gtgccagcag ccgcggtaat    540

acgtaggtgg caagcgttgt ccggaattat tgggcgtaaa gcgcgcgcag gcggtttctt    600

aagtctgatg tgaaagcccc cggctcaacc ggggagggtc attggaaact ggggaacttg    660

agtgcagaag aggagagtgg aattccacgt gtagcggtga aatgcgtaga gatgtggagg    720

aacaccagtg gcgaaggcga ctctctggtc tgtaactgac gctgaggcgc gaaagcgtgg    780

ggagcgaaca ggattagata ccctggtagt ccacgccgta aacgatgagt gctaagtgtt    840

agagggtttc cgccctttag tgctgcagca aacgcattaa gcactccgcc tggggagtac    900

ggtcgcaaga ctgaaactca aaggaattga cgggggcccg cacaagcggt ggagcatgtg    960

gtttaattcg aagcaacgcg aagaacctta ccaggtcttg acatcctctg acaaccctag   1020

agatagggct tccccttcgg gggcagagtg acaggtggtg catggttgtc gtcagctcgt   1080

gtcgtgagat gttgggttaa gtcccgcaac gagcgcaacc cttgatctta gttgccagca   1140

ttcagttggg cactctaagg tgactgccgg tgacaaaccg gaggaaggtg gggatgacgt   1200

caaatcatca tgccccttat gacctgggct acacacgtgc tacaatgggc agaacaaagg   1260

gcagcgaagc cgcgaggcta agccaatccc acaaatctgt tctcagttcg gatcgcagtc   1320

tgcaactcga ctgcgtgaag ctggaatcgc tagtaatcgc ggatcagcat gccgcggtga   1380

atacgttccc gggccttgta cacaccgccc gtcacaccac gagagtttgt aacacccgaa   1440

gtcggtgagg taacctttgg gagccagccg ccgaaggtgg gacagatgat tggggtgaag   1500

tcgtaacaag gtagccgtat cggaaggtgc ggctggatca cctccttt                1548


<210> SEQ ID NO 49
<211> LENGTH: 1551
<212> TYPE: DNA
<213> ORGANISM: Unknown
<220> FEATURE:
<223> OTHER INFORMATION: Description of Unknown:
      DP49 16S rRNA sequence

<400> SEQUENCE: 49

tatggagagt ttgatcctgg ctcaggacga acgctggcgg cgtgcctaat acatgcaagt     60

cgagcggacg tttttgaagc ttgcttcaaa aacgttagcg gcggacgggt gagtaacacg    120

tgggcaacct gccttatcga ctgggataac tccgggaaac cggggctaat accggataat    180

atctagcacc tcctggtgca agattaaaag agggccttcg ggctctcacg gtgagatggg    240

cccgcggcgc attagctagt tggagaggta atggctcccc aaggcgacga tgcgtagccg    300

acctgagagg gtgatcggcc acactgggac tgagacacgg cccagactcc tacgggaggc    360

agcagtaggg aatcttccgc aatggacgaa agtctgacgg agcaacgccg cgtgagtgat    420

gaagggtttc ggctcgtaaa gctctgttat gagggaagaa cacgtaccgt tcgaataggg    480

cggtaccttg acggtacctc atcagaaagc cacggctaac tacgtgccag cagccgcggt    540

aatacgtagg tggcaagcgt tgtccggaat tattgggcgt aaagcgcgcg caggcggcct    600

tttaagtctg atgtgaaatc ttgcggctca accgcaagcg gtcattggaa actgggaggc    660
```

```
ttgagtacag aagaggagag tggaattcca cgtgtagcgg tgaaatgcgt agatatgtgg    720

aggaacacca gtggcgaagg cgactctctg gtctgtaact gacgctgagg cgcgaaagcg    780

tggggagcaa acaggattag ataccctggt agtccacgcc gtaaacgatg agtgctaggt    840

gttaggggtt tcgatgcccg tagtgccgaa gttaacacat taagcactcc gcctggggag    900

tacggccgca aggctgaaac tcaaaggaat tgacgggggc ccgcacaagc agtggagcat    960

gtggtttaat tcgaagcaac gcgaagaacc ttaccaggtc ttgacatcct ttgaccactc   1020

tggagacaga gcttcccctt cggggggcaaa gtgacaggtg gtgcatggtt gtcgtcagct   1080

cgtgtcgtga gatgttgggt taagtcccgc aacgagcgca acccttgacc ttagttgcca   1140

gcatttagtt gggcactcta aggtgactgc cggtgacaaa ccggaggaag gtggggatga   1200

cgtcaaatca tcatgcccct tatgacctgg gctacacacg tgctacaatg gatggtacaa   1260

agggttgcga agccgcgagg tgaagccaat cccataaagc cattctcagt tcggattgta   1320

ggctgcaact cgcctgcatg aagctggaat tgctagtaat cgcggatcag catgccgcgg   1380

tgaatacgtt cccgggcctt gtacacaccg cccgtcacac cacgagagtt tgtaacaccc   1440

gaagtcggtg aggtaacctt ttggagccag ccgccgaagg tgggacagat gattggggtg   1500

aagtcgtaac aaggtagccg tatcggaagg tgcggctgga tcacctcctt t            1551
```

<210> SEQ ID NO 50
<211> LENGTH: 1536
<212> TYPE: DNA
<213> ORGANISM: Unknown
<220> FEATURE:
<223> OTHER INFORMATION: Description of Unknown:
DP50 16S rRNA sequence

<400> SEQUENCE: 50

```
ttgaagagtt tgatcatggc tcagattgaa cgctggcggc aggcctaaca catgcaagtc     60

gaacggtagc acagagagct tgctcttggg tgacgagtgg cggacgggtg agtaatgtct    120

gggaaactgc ccgatggagg gggataacta ctggaaacgg tagctaatac cgcataacgt    180

cgcaagacca aagtggggga ccttcgggcc tcacaccatc ggatgtgccc agatgggatt    240

agctagtagg tggggtaatg gctcacctag gcgacgatcc ctagctggtc tgagaggatg    300

accagccaca ctggaactga gacacggtcc agactcctac gggaggcagc agtggggaat    360

attgcacaat gggcgcaagc ctgatgcagc catgccgcgt gtatgaagaa ggccttcggg    420

ttgtaaagta ctttcagcga ggaggaaggc attgtggtta ataaccgcag tgattgacgt    480

tactcgcaga agaagcaccg gctaactccg tgccagcagc cgcggtaata cggagggtgc    540

aagcgttaat cggaattact gggcgtaaag cgcacgcagg cggtctgtca agtcggatgt    600

gaaatccccg ggctcaacct gggaactgca ttcgaaactg gcaggctaga gtcttgtaga    660

ggggggtaga attccaggtg tagcggtgaa atgcgtagag atctggagga ataccggtgg    720

cgaaggcggc cccctggaca aagactgacg ctcaggtgcg aaagcgtggg gagcaaacag    780

gattagatac cctggtagtc cacgccgtaa acgatgtcga cttggaggtt gtgcccttga    840

ggcgtggctt ccggagctaa cgcgttaagt cgaccgcctg gggagtacgg ccgcaaggtt    900

aaaactcaaa tgaattgacg gggggcccgca caagcggtgg agcatgtggt ttaattcgat    960

gcaacgcgaa gaaccttacc tactcttgac atccacggaa tttagcagag atgctttagt   1020

gccttcggga accgtgagac aggtgctgca tggctgtcgt cagctcgtgt tgtgaaatgt   1080

tgggttaagt cccgcaacga gcgcaaccct tatcctttgt tgccagcggt tcggccggga   1140
```

```
actcaaagga gactgccagt gataaactgg aggaaggtgg ggatgacgtc aagtcatcat   1200

ggcccttacg agtagggcta cacacgtgct acaatggcat atacaaagag aagcgacctc   1260

gcgagagcaa gcggacctca taaagtatgt cgtagtccgg atcggagtct gcaactcgac   1320

tccgtgaagt cggaatcgct agtaatcgta gatcagaatg ctacggtgaa tacgttcccg   1380

ggccttgtac acaccgcccg tcacaccatg ggagtgggtt gcaaaagaag taggtagctt   1440

aaccttcggg agggcgctta ccactttgtg attcatgact ggggtgaagt cgtaacaagg   1500

taaccgtagg ggaacctgcg gttggatcac ctcctt                             1536


<210> SEQ ID NO 51
<211> LENGTH: 1537
<212> TYPE: DNA
<213> ORGANISM: Unknown
<220> FEATURE:
<223> OTHER INFORMATION: Description of Unknown:
      DP51 16S rRNA sequence

<400> SEQUENCE: 51

ttgaagagtt tgatcatggc tcagattgaa cgctggcggc aggcctaaca catgcaagtc     60

gagcggtagc acagggagct tgctcctggg tgacgagcgg cggacgggtg agtaatgtct    120

gggaaactgc ctgatggagg gggataacta ctggaaacgg tagctaatac cgcataacgt    180

cgcaagacca aagaggggga ccttcgggcc tcttgccatc agatgtgccc agatgggatt    240

agctagtagg tgaggtaatg gctcacctag gcgacgatcc ctagctggtc tgagaggatg    300

accagccaca ctggaactga gacacggtcc agactcctac gggaggcagc agtggggaat    360

attgcacaat gggcgcaagc ctgatgcagc catgccgcgt gtatgaagaa ggccttcggg    420

ttgtaaagta ctttcagcga ggaggaaggc attaaggtta ataaccttgg tgattgacgt    480

tactcgcaga agaagcaccg gctaactccg tgccagcagc cgcggtaata cgggggggtgc    540

aagcgttaat cggaattact gggcgtaaag cgcacgcagg cggtttgtca agtcggatgt    600

gaaatccccg ggctcaacct gggaactgca ttcgaaacgg gcaagctaga gtcttgtaga    660

gggggtaga attccaggtg tagcggtgaa atgcgtagag atctggagga ataccggtgg    720

cgaaggcggc cccctggaca aagactgacg ctcaggtgcg aaagcgtggg gagcaaacag    780

gattagatac cctggtagtc cacgccgtaa acgatgtcga cttggaggtt gtgcccttga    840

ggcgtggctt ccggagctaa cgcgttaagt cgaccgcctg gggagtacgg ccgcaaggtt    900

aaaactcaaa tgaattgacg ggggcccgca caagcggtgg agcatgtggt ttaattcgat    960

gcaacgcgaa gaaccttacc tactcttgac atccagagaa ctttccagag atggattggt   1020

gccttcggga actctgagac aggtgctgca tggctgtcgt cagctcgtgt tgtgaaatgt   1080

tgggttaagt cccgcaacga gcgcaaccct tatcctttgt tgccagcgag taatgtcggg   1140

aactcaaagg agactgccag tgacaaactg gaggaaggtg gggatgacgt caagtcatca   1200

tggcccttac gagtagggct acacacgtgc tacaatggca tatacaaaga gaagcgacct   1260

cgcgagagca agcggacctc acaaagtatg tcgtagtccg gatcggagtc tgcaactcga   1320

ctccgtgaag tcggaatcgc tagtaatcgt agatcagaat gctacggtga atacgttccc   1380

gggccttgta cacaccgccc gtcacaccat gggagtgggt tgcaaaagaa gtaggtagct   1440

taaccttcgg gagggcgctt accactttgt gattcatgac tggggtgaag tcgtaacaag   1500

gtaaccgtag gggaacctgc ggttggatca cctcctt                            1537
```

<210> SEQ ID NO 52
<211> LENGTH: 1517
<212> TYPE: DNA
<213> ORGANISM: Unknown
<220> FEATURE:
<223> OTHER INFORMATION: Description of Unknown:
DP52 16S rRNA sequence

<400> SEQUENCE: 52
acggagagtt tgatcctggc tcaggatgaa cgctggcggc gtgcttaaca catgcaagtc 60
gaacgatgat cccagcttgc tgggggatta gtggcgaacg ggtgagtaac acgtgagtaa 120
cctgcccttg actctgggat aagcctggga aactgggtct aataccggat atgactgtct 180
gacgcatgtc aggtggtgga aagcttttgt ggttttggat ggactcgcgg cctatcagct 240
tgttggtggg gtaatggcct accaaggcga cgacgggtag ccggcctgag agggtgaccg 300
gccacactgg gactgagaca cggcccagac tcctacggga ggcagcagtg gggaatattg 360
cacaatgggc gcaagcctga tgcagcgacg ccgcgtgagg gatgacggcc ttcgggttgt 420
aaacctcttt cagtagggaa gaagcgaaag tgacggtacc tgcagaagaa gcgccggcta 480
actacgtgcc agcagccgcg gtaatacgta gggcgcaagc gttatccgga attattgggc 540
gtaaagagct cgtaggcggt ttgtcgcgtc tgctgtgaaa gaccggggct caactccggt 600
tctgcagtgg gtacgggcag actagagtgc agtaggggag actggaattc ctggtgtagc 660
ggtgaaatgc gcagatatca ggaggaacac cgatggcgaa ggcaggtctc tgggctgtaa 720
ctgacgctga ggagcgaaag catggggagc gaacaggatt agataccctg gtagtccatg 780
ccgtaaacgt tgggcactag gtgtggggga cattccacgt tttccgcgcc gtagctaacg 840
cattaagtgc cccgcctggg gagtacggcc gcaaggctaa aactcaaagg aattgacggg 900
ggcccgcaca agcggcggag catgcggatt aattcgatgc aacgcgaaga accttaccaa 960
ggcttgacat gaaccggtaa tacctggaaa caggtgcccc gcttgcggtc ggtttacagg 1020
tggtgcatgg ttgtcgtcag ctcgtgtcgt gagatgttgg gttaagtccc gcaacgagcg 1080
caaccctcgt tctatgttgc cagcgcgtta tggcggggac tcataggaga ctgccggggt 1140
caactcggag gaaggtgggg acgacgtcaa atcatcatgc cccttatgtc ttgggcttca 1200
cgcatgctac aatggccggt acaaagggtt gcgatactgt gaggtggagc taatcccaaa 1260
aagccggtct cagttcggat tggggtctgc aactcgaccc catgaagtcg gagtcgctag 1320
taatcgcaga tcagcaacgc tgcggtgaat acgttcccgg gccttgtaca caccgcccgt 1380
caagtcacga aagttggtaa cacccgaagc cggtggccta acccttgtgg ggggagccgt 1440
cgaaggtggg accggcgatt gggactaagt cgtaacaagg tagccgtacc ggaaggtgcg 1500
gctggatcac ctccttt 1517

<210> SEQ ID NO 53
<211> LENGTH: 1406
<212> TYPE: DNA
<213> ORGANISM: Unknown
<220> FEATURE:
<223> OTHER INFORMATION: Description of Unknown:
DP53 16S rRNA sequence

<400> SEQUENCE: 53
tgaagagttt gatcatggct cagattgaac gctggcggca ggcctaacac atgcaagtcg 60
agcggtagag agaagcttgc ttctcttgag agcggcggac gggtgagtaa tacctaggaa 120
tctgcctgat agtgggggat aacgttcgga aacggacgct aataccgcat acgtcctacg 180

-continued ggagaaagca ggggaccttc gggccttgcg ctatcagatg agcctaggtc ggattagcta 240
gttggtgagg taatggctca ccaaggctac gatccgtaac tggtctgaga ggatgatcag 300
tcacactgga actgagacac ggtccagact cctacgggag gcagcagtgg ggaatattgg 360
acaatgggcg aaagcctgat ccagccatgc cgcgtgtgtg aagaaggtct tcggattgta 420
aagcacttta agttgggagg aagggcagtt acctaatacg tgattgtctt gacgttaccg 480
acagaataag caccggctaa ctctgtgcca gcagccgcgg taatacagag ggtgcaagcg 540
ttaatcggaa ttactgggcg taaagcgcgc gtaggtggtt tgttaagttg aatgtgaaat 600
ccccgggctc aacctgggaa ctgcatccaa aactggcaag ctagagtatg gtagagggta 660
gtggaatttc ctgtgtagcg gtgaaatgcg tagatatagg aaggaacacc agtggcgaag 720
gcgactacct ggactgatac tgacactgag gtgcgaaagc gtggggagca aacaggatta 780
gataccctgg tagtccacgc cgtaaacgat gtcaactagc cgttgggagt cttgaactct 840
tagtggcgca gctaacgcat taagttgacc gcctggggag tacggccgca aggttaaaac 900
tcaaatgaat tgacgggggc ccgcacaagc ggtggagcat gtggtttaat tcgaagcaac 960
gcgaagaacc ttaccaggcc ttgacatcca atgaactttc tagagataga ttggtgcctt 1020
cgggaacatt gagacaggtg ctgcatggct gtcgtcagct cgtgtcgtga gatgttgggt 1080
taagtcccgt aacgagcgca acccttgtcc ttagttacca gcacgtaatg gtgggcactc 1140
taaggagact gccggtgaca aaccggagga aggtggggat gacgtcaagt catcatggcc 1200
cttacggcct gggctacaca cgtgctacaa tggtcggtac aaagggttgc caagccgcga 1260
ggtggagcta atcccataaa accgatcgta gtccggatcg cagtctgcaa ctcgactgcg 1320
tgaagtcgga atcgctagta atcgtgaatc agaatgtcac ggtgaatacg ttcccgggcc 1380
ttgtacacac cgcccgtcac accatg 1406

<210> SEQ ID NO 54
<211> LENGTH: 1136
<212> TYPE: DNA
<213> ORGANISM: Unknown
<220> FEATURE:
<223> OTHER INFORMATION: Description of Unknown:
DP54 16S rRNA sequence

<400> SEQUENCE: 54
cttgagagtt tgatcctggc tcagagcgaa cgctggcggc aggcttaaca catgcaagtc 60
gagcgggcac cttcgggtgt cagcggcaga cgggtgagta acacgtggga acgtaccctt 120
cggttcggaa taacgctggg aaactagcgc taataccgga tacgcccttt tggggaaagg 180
tttactgccg aaggatcggc ccgcgtctga ttagctagtt ggtggggtaa cggcctacca 240
aggcgacgat cagtagctgg tctgagagga tgatcagcca cactgggact gagacacggc 300
ccagactcct acgggaggca gcagtgggga atattggaca atgggcgcaa gcctgatcca 360
gccatgccgc gtgagtgatg aaggccttag ggttgtaaag ctcttttgtc cgggacgata 420
atgacggtac cggaagaata agccccggct aacttcgtgc cagcagccgc ggtaatacga 480
agggggctag cgttgctcgg aatcactggg cgtaaagggc gcgtaggcgg ccattcaagt 540
cgggggtgaa agcctgtggc tcaaccacag aattgccttc gatactgttt ggcttgagtt 600
tggtagaggt tggtggaact gcgagtgtag aggtgaaatt cgtagatatt cgcaagaaca 660
ccagtggcga aggcggccaa ctggaccaat actgacgctg aggcgcgaaa gcgtggggag 720
caaacaggat tagataccct ggtagtccac gccgtaaacg atgaatgcta gctgttgggg 780

-continued tgcttgcacc tcagtagcgc agctaacgct ttaagcattc cgcctgggga gtacggtcgc 840
aagattaaaa ctcaaaggaa ttgacggggg cccgcacaag cggtggagca tgtggtttaa 900
ttcgaagcaa cgcgcagaac cttaccatcc cttgacatgt cgtgccatcc ggagagatcc 960
ggggttccct tcggggacgc gaacacaggt gctgcatggc tgtcgtcagc tcgtgtcgtg 1020
agatgttggg ttaagtcccg caacgagcgc aacccacgtc cttagttgcc atcatttagt 1080
tgggcactct agggagactg ccggtgataa gccgcgagga aggtgtggat gacgtc 1136

<210> SEQ ID NO 55
<211> LENGTH: 1374
<212> TYPE: DNA
<213> ORGANISM: Unknown
<220> FEATURE:
<223> OTHER INFORMATION: Description of Unknown:
DP55 16S rRNA sequence

<400> SEQUENCE: 55
tcggagagtt tgatcctggc tcaggatgaa cgctggcggc gtgcctaata catgcaagtc 60
gagcgaactg attagaagct tgcttctatg acgttagcgg cggacgggtg agtaacacgt 120
gggcaacctg cctgtaagac tggataact tcgggaaacc gaagctaata ccggatagga 180
tcttctcctt catgggagat gattgaaaga tggtttcggc tatcacttac agatgggccc 240
gcggtgcatt agctagttgg tgaggtaacg gctcaccaag gcaacgatgc atagccgacc 300
tgagagggtg atcggccaca ctgggactga gacacggccc agactcctac gggaggcagc 360
agtagggaat cttccgcaat ggacgaaagt ctgacggagc aacgccgcgt gagtgatgaa 420
ggctttcggg tcgtaaaact ctgttgttag ggaagaacaa gtacaagagt aactgcttgt 480
accttgacgg tacctaacca gaaagccacg gctaactacg tgccagcagc cgcggtaata 540
cgtaggtggc aagcgttatc cggaattatt gggcgtaaag cgcgcgcagg cggtttctta 600
agtctgatgt gaaagcccac ggctcaaccg tggagggtca ttggaaactg gggaacttga 660
gtgcagaaga gaaaagcgga attccacgtg tagcggtgaa atgcgtagag atgtggagga 720
acaccagtgg cgaaggcggc tttttggtct gtaactgacg ctgaggcgcg aaagcgtggg 780
gagcaaacag gattagatac cctggtagtc cacgccgtaa acgatgagtg ctaagtgtta 840
gagggtttcc gccctttagt gctgcagcta acgcattaag cactccgcct ggggagtacg 900
gtcgcaagac tgaaactcaa aggaattgac gggggcccgc acaagcggtg gagcatgtgg 960
tttaattcga agcaacgcga agaaccttac caggtcttga catcctctga caactctaga 1020
gatagagcgt tccccttcgg gggacagagt gacaggtggt gcatggttgt cgtcagctcg 1080
tgtcgtgaga tgttgggtta agtcccgcaa cgagcgcaac ccttgatctt agttgccagc 1140
atttagttgg gcactctaag gtgactgccg gtgacaaacc ggaggaaggt ggggatgacg 1200
tcaaatcatc atgcccctta tgacctgggc tacacacgtg ctacaatgga tggtacaaag 1260
ggctgcaaga ccgcgaggtc aagccaatcc cataaaacca ttctcagttc ggattgtagg 1320
ctgcaactcg cctacatgaa gctggaatcg ctagtaatcg cggatcagca tgct 1374

<210> SEQ ID NO 56
<211> LENGTH: 1554
<212> TYPE: DNA
<213> ORGANISM: Unknown
<220> FEATURE:
<223> OTHER INFORMATION: Description of Unknown:
DP56 16S rRNA sequence

<400> SEQUENCE: 56

```
attggagagt ttgatcctgg ctcaggacga acgctggcgg cgtgcctaat acatgcaagt     60
cgagcggacc tgatggagtg cttgcactcc tgatggttag cggcggacgg gtgagtaaca    120
cgtaggcaac ctgccctcaa gactgggata actaccggaa acggtagcta ataccggata    180
atttatttca cagcattgtg gaataatgaa agacggagca atctgtcact tggggatggg    240
cctgcggcgc attagctagt tggtggggta acggctcacc aaggcgacga tgcgtagccg    300
acctgagagg gtgaacggcc acactgggac tgagacacgg cccagactcc tacgggaggc    360
agcagtaggg aatcttccgc aatgggcgaa agcctgacgg agcaacgccg cgtgagtgat    420
gaaggttttc ggatcgtaaa gctctgttgc caaggaagaa cgtcttctag agtaactgct    480
aggagagtga cggtacttga gaagaaagcc ccggctaact acgtgccagc agccgcggta    540
atacgtaggg ggcaagcgtt gtccggaatt attgggcgta aagcgcgcgc aggcggttct    600
ttaagtctgg tgtttaaacc cgaggctcaa cttcgggtcg cactggaaac tggggaactt    660
gagtgcagaa gaggagagtg gaattccacg tgtagcggtg aaatgcgtag atatgtggag    720
gaacaccagt ggcgaaggcg actctctggg ctgtaactga cgctgaggcg cgaaagcgtg    780
gggagcaaac aggattagat accctggtag tccacgccgt aaacgatgaa tgctaggtgt    840
taggggtttc gatacccttg gtgccgaagt taacacatta agcattccgc ctggggagta    900
cggtcgcaag actgaaactc aaaggaattg acggggaccc gcacaagcag tggagtatgt    960
ggtttaattc gaagcaacgc gaagaacctt accaagtctt gacatccctc tgaatcctct   1020
agagatagag gcggccttcg ggacagaggt gacaggtggt gcatggttgt cgtcagctcg   1080
tgtcgtgaga tgttgggtta agtcccgcaa cgagcgcaac ccttgatttt agttgccagc   1140
acatcatggt gggcactcta gaatgactgc cggtgacaaa ccggaggaag gcggggatga   1200
cgtcaaatca tcatgcccct tatgacttgg gctacacacg tactacaatg gctggtacaa   1260
cgggaagcga agccgcgagg tggagccaat cctataaaag ccagtctcag ttcggattgc   1320
aggctgcaac tcgcctgcat gaagtcggaa ttgctagtaa tcgcggatca gcatgccgcg   1380
gtgaatacgt tcccgggtct tgtacacacc gcccgtcaca ccacgagagt ttacaacacc   1440
cgaagtcggt ggggtaaccc gcaagggagc cagccgccga aggtggggta gatgattggg   1500
gtgaagtcgt aacaaggtag ccgtatcgga aggtgcggct ggatcacctc cttt          1554
```

<210> SEQ ID NO 57
<211> LENGTH: 1550
<212> TYPE: DNA
<213> ORGANISM: Unknown
<220> FEATURE:
<223> OTHER INFORMATION: Description of Unknown:
DP57 16S rRNA sequence

<400> SEQUENCE: 57

```
attggagagt ttgatcctgg ctcaggatga acgctggcgg cgtgcctaat acatgcaagt     60
cgagcgaatg gattaagagc ttgctcttat gaagttagcg gcggacgggt gagtaacacg    120
tgggtaacct gcccataaga ctgggataac tccgggaaac cggggctaat accggataac    180
attttgcacc gcatggtgcg aaattcaaag gcggcttcgg ctgtcactta tggatggacc    240
cgcgtcgcat tagctagttg gtgaggtaac ggctcaccaa ggcaacgatg cgtagccgac    300
ctgagagggt gatcggccac actgggactg agacacggcc cagactccta cgggaggcag    360
cagtagggaa tcttccgcaa tggacgaaag tctgacggag caacgccgcg tgagtgatga    420
aggctttcgg gtcgtaaaac tctgttgtta gggaagaaca agtgctagtt gaataagctg    480
```

-continued

```
gcaccttgac ggtacctaac cagaaagcca cggctaacta cgtgccagca gccgcggtaa    540

tacgtaggtg gcaagcgtta tccggaatta ttgggcgtaa agcgcgcgca ggtggtttct    600

taagtctgat gtgaaagccc acggctcaac cgtggagggt cattggaaac tgggagactt    660

gagtgcagaa gaggaaagtg gaattccatg tgtagcggtg aaatgcgtag agatatggag    720

gaacaccagt ggcgaaggcg actttctggt ctgtaactga cactgaggcg cgaaagcgtg    780

gggagcaaac aggattagat accctggtag tccacgccgt aaacgatgag tgctaagtgt    840

tagagggttt ccgcccttta gtgctgaagt taacgcatta agcactccgc ctggggagta    900

cggccgcaag gctgaaactc aaaggaattg acgggggccc gcacaagcgg tggagcatgt    960

ggtttaattc gaagcaacgc gaagaacctt accaggtctt gacatcctct gacaacccta   1020

gagatagggc ttccccttcg gggcagagt  gacaggtggt gcatggttgt cgtcagctcg   1080

tgtcgtgaga tgttgggtta agtcccgcaa cgagcgcaac ccttgatctt agttgccatc   1140

attaagttgg gcactctaag gtgactgccg gtgacaaacc ggaggaaggt ggggatgacg   1200

tcaaatcatc atgcccctta tgacctgggc tacacacgtg ctacaatgga cggtacaaag   1260

agctgcaaga ccgcgaggtg gagctaatct cataaaaccg ttctcagttc ggattgtagg   1320

ctgcaactcg cctacatgaa gctggaatcg ctagtaatcg cggatcagca tgccgcggtg   1380

aatacgttcc cgggccttgt acacaccgcc cgtcacacca cgagagtttg taacacccga   1440

agtcggtggg gtaacctttt tggagccagc cgcctaaggt gggacagatg attggggtga   1500

agtcgtaaca aggtagccgt atcggaaggt gcggctggat cacctccttt              1550
```

<210> SEQ ID NO 58
<211> LENGTH: 1060
<212> TYPE: DNA
<213> ORGANISM: Unknown
<220> FEATURE:
<223> OTHER INFORMATION: Description of Unknown:
DP58 16S rRNA sequence

<400> SEQUENCE: 58

```
aatgacggta cctgaagaat aagcaccggc taactacgtg ccagcagccg cggtaatacg     60

tagggtgcaa gcgttaatcg gaattactgg gcgtaaagcg tgcgcaggcg gttttgtaag    120

tctgatgtga aatccccggg ctcaacctgg gaattgcatt ggagactgca aggctagaat    180

ctggcagagg ggggtagaat tccacgtgta gcagtgaaat gcgtagatat gtggaggaac    240

accgatggcg aaggcagccc cctgggtcaa gattgacgct catgcacgaa agcgtgggga    300

gcaaacagga ttagataccc tggtagtcca cgccctaaac gatgtctact agttgtcggg    360

tcttaattga cttggtaacg cagctaacgc gtgaagtaga ccgcctgggg agtacggtcg    420

caagattaaa actcaaagga attgacgggg acccgcacaa gcggtggatg atgtggatta    480

attcgatgca acgcgaaaaa ccttacctac ccttgacatg gctggaatcc tcgagagatt    540

ggggagtgct cgaaagagaa ccagtacaca ggtgctgcat ggctgtcgtc agctcgtgtc    600

gtgagatgtt gggttaagtc ccgcaacgag cgcaaccctt gtcattagtt gctacgaaag    660

ggcactctaa tgagactgcc ggtgacaaac cggaggaagg tggggatgac gtcaagtcct    720

catggccctt atgggtaggg cttcacacgt catacaatgg tacatacaga gcgccgccaa    780

cccgcgaggg ggagctaatc gcagaaagtg tatcgtagtc cggattgtag tctgcaactc    840

gactgcatga agttggaatc gctagtaatc gcggatcagc atgtcgcggt gaatacgttc    900

ccgggtcttg tacacaccgc ccgtcacacc atgggagcgg gttttaccag aagtaggtag    960
```

-continued cttaaccgta aggagggcgc ttaccacggt aggattcgtg actggggtga agtcgtaaca 1020
aggtagccgt atcggaaggt gcggctggat cacctccttt 1060

<210> SEQ ID NO 59
<211> LENGTH: 1538
<212> TYPE: DNA
<213> ORGANISM: Unknown
<220> FEATURE:
<223> OTHER INFORMATION: Description of Unknown:
DP59 16S rRNA sequence

<400> SEQUENCE: 59
ttgaagagtt tgatcatggc tcagattgaa cgctggcggc aggcctaaca catgcaagtc 60
gaacggtaac aggaagcagc ttgctgcttt gctgacgagt ggcggacggg tgagtaatgt 120
ctgggaaact gcctgatgga gggggataac tactggaaac ggtagctaat accgcataac 180
gtcgcaagac caaagagggg gaccttcggg cctcttgcca tcagatgtgc ccagatggga 240
ttagctagta ggtggggtaa cggctcacct aggcgacgat ccctagctgg tctgagagga 300
tgaccagcca cactggaact gagacacggt ccagactcct acgggaggca gcagtgggga 360
atattgcaca atgggcgcaa gcctgatgca gccatgccgc gtgtatgaag aaggccttcg 420
ggttgtaaag tactttcagc ggggaggaag gcgatgcggt taataaccgc gtcgattgac 480
gttacccgca gaagaagcac cggctaactc cgtgccagca gccgcggtaa tacggagggt 540
gcaagcgtta atcggaatta ctgggcgtaa agcgcacgca ggcggtctgt caagtcggat 600
gtgaaatccc cgggctcaac ctgggaactg catccgaaac tggcaggctt gagtctcgta 660
gaggggggta gaattccagg tgtagcggtg aaatgcgtag agatctggag gaataccggt 720
ggcgaaggcg gccccctgga cgaagactga cgctcaggtg cgaaagcgtg gggagcaaac 780
aggattagat accctggtag tccacgccgt aaacgatgtc gacttggagg ttgtgccctt 840
gaggcgtggc ttccggagct aacgcgttaa gtcgaccgcc tggggagtac ggccgcaagg 900
ttaaaactca aatgaattga cgggggcccg cacaagcggt ggagcatgtg gtttaattcg 960
atgcaacgcg aagaacctta cctggtcttg acatccacag aacttggcag agatgccttg 1020
gtgccttcgg gaactgtgag acaggtgctg catggctgtc gtcagctcgt gttgtgaaat 1080
gttgggttaa gtcccgcaac gagcgcaacc cttatccttt gttgccagcg gttaggccgg 1140
gaactcaaag gagactgcca gtgataaact ggaggaaggt ggggatgacg tcaagtcatc 1200
atggccctta cgaccagggc tacacacgtg ctacaatggc gcatacaaag agaagcgatc 1260
tcgcgagagc cagcggacct cataaagtgc gtcgtagtcc ggattggagt ctgcaactcg 1320
actccatgaa gtcggaatcg ctagtaatcg tgaatcagaa tgtcacggtg aatacgttcc 1380
cgggccttgt acacaccgcc cgtcacacca tgggagtggg ttgcaaaaga agtaggtagc 1440
ttaaccttcg ggagggcgct taccactttg tgattcatga ctggggtgaa gtcgtaacaa 1500
ggtaaccgta ggggaacctg cggttggatc acctcctt 1538

<210> SEQ ID NO 60
<211> LENGTH: 1547
<212> TYPE: DNA
<213> ORGANISM: Unknown
<220> FEATURE:
<223> OTHER INFORMATION: Description of Unknown:
DP60 16S rRNA sequence

<400> SEQUENCE: 60

-continued

```
tcggagagtt tgatcctggc tcaggacgaa cgctggcggc gtgcctaata catgcaagtc     60

gagcgaatcg atgggagctt gctccctgag attagcggcg gacgggtgag taacacgtgg    120

gcaacctgcc tataagactg ggataacttc gggaaaccgg agctaatacc ggatacgttc    180

ttttctcgca tgagagaaga tggaaagacg gttttgctgt cacttataga tgggcccgcg    240

gcgcattagc tagttggtga ggtaatggct caccaaggcg acgatgcgta gccgacctga    300

gagggtgatc ggccacactg ggactgagac acggcccaga ctcctacggg aggcagcagt    360

agggaatctt ccgcaatgga cgaaagtctg acggagcaac gccgcgtgaa cgaagaaggc    420

cttcgggtcg taaagttctg ttgttaggga agaacaagta ccagagtaac tgctggtacc    480

ttgacggtac ctaaccagaa agccacggct aactacgtgc cagcagccgc ggtaatacgt    540

aggtggcaag cgttgtccgg aattattggg cgtaaagcgc gcgcaggtgg ttccttaagt    600

ctgatgtgaa agcccacggc tcaaccgtgg agggtcattg gaaactgggg aacttgagtg    660

cagaagagga aagtggaatt ccaagtgtag cggtgaaatg cgtagagatt tggaggaaca    720

ccagtggcga aggcgacttt ctggtctgta actgacactg aggcgcgaaa gcgtggggag    780

caaacaggat tagataccct ggtagtccac gccgtaaacg atgagtgcta agtgttagag    840

ggtttccgcc ctttagtgct gcagctaacg cattaagcac tccgcctggg gagtacggcc    900

gcaaggctga aactcaaagg aattgacggg ggcccgcaca agcggtggag catgtggttt    960

aattcgaagc aacgcgaaga accttaccag gtcttgacat cctctgacaa ccctagagat   1020

agggcgttcc ccttcggggg acagagtgac aggtggtgca tggttgtcgt cagctcgtgt   1080

cgtgagatgt tgggttaagt cccgcaacga gcgcaaccct tgatcttagt tgccagcatt   1140

cagttgggca ctctaaggtg actgccggtg acaaaccgga ggaaggtggg gatgacgtca   1200

aatcatcatg ccccttatga cctgggctac acacgtgcta caatggatgg tacaaagggc   1260

tgcaaacctg cgaaggtaag cgaatcccat aaagccattc tcagttcgga ttgtaggctg   1320

caactcgcct acatgaagcc ggaatcgcta gtaatcgcgg atcagcatgc cgcggtgaat   1380

acgttcccgg gccttgtaca caccgcccgt cacaccacga gagtttgtaa cacccgaagt   1440

cggtgaggta acctttatgg agccagccgc ctaaggtggg acagatgatt ggggtgaagt   1500

cgtaacaagg tagccgtatc ggaaggtgcg gctggatcac ctccttt                  1547
```

<210> SEQ ID NO 61
<211> LENGTH: 962
<212> TYPE: DNA
<213> ORGANISM: Unknown
<220> FEATURE:
<223> OTHER INFORMATION: Description of Unknown:
DP61 16S rRNA sequence

<400> SEQUENCE: 61

```
ggaaggcggt ctgtcaagtc ggatgtgaaa tccccgggct caacctggga actgcattcg     60

aaactggcag gctagagtct tgtagagggg ggtagaattc caggtgtagc ggtgaaatgc    120

gtagagatct ggaggaatac cggtggcgaa ggcggccccc tggacaaaga ctgacgctca    180

ggtgcgaaag cgtggggagc aaacaggatt agataccctg gtagtccacg ccgtaaacga    240

tgtcgacttg gaggttgttc ccttgaggag tggcttccgg agctaacgcg ttaagtcgac    300

cgcctgggga gtacggccgc aaggttaaaa ctcaaatgaa ttgacggggg cccgcacaag    360

cggtggagca tgtggtttaa ttcgatgcaa cgcgaagaac cttacctact cttgacatcc    420

acggaattta gcagagatgc tttagtgcct tcgggaaccg tgagacaggt gctgcatggc    480
```

-continued

```
tgtcgtcagc tcgtgttgtg aaatgttggg ttaagtcccg caacgagcgc aacccttatc    540

ctttgttgcc agcggtccgg ccgggaactc aaaggagact gccagtgata aactggagga    600

aggtggggat gacgtcaagt catcatggcc cttacgagta gggctacaca cgtgctacaa    660

tggcgcatac aaagagaagc gacctcgcga gagcaagcgg acctcataaa gtgcgtcgta    720

gtccggatcg gagtctgcaa ctcgactccg tgaagtcgga atcgctagta atcgtagatc    780

agaatgctac ggtgaatacg ttcccgggcc ttgtacacac cgcccgtcac accatgggag    840

tgggttgcaa aagaagtagg tagcttaacc ttcgggaggg cgcttaccac tttgtgattc    900

atgactgggg tgaagtcgta acaaggtaac cgtaggggaa cctgcggttg gatcacctcc    960

tt                                                                   962
```

<210> SEQ ID NO 62
<211> LENGTH: 876
<212> TYPE: DNA
<213> ORGANISM: Unknown
<220> FEATURE:
<223> OTHER INFORMATION: Description of Unknown:
DP62 16S rRNA sequence

<400> SEQUENCE: 62

```
tggctcagat tgaacgctgg cggcaggcct aacacatgca agtcgaacgg tagcacagag     60

gagcttgctc cttgggtgac gagtggcgga cgggtgagta atgtctggga aactgcccga    120

tggaggggga taactactgg aaacggtagc taataccgca taacgtcttc ggaccaaagt    180

gggggacctt cgggcctcac accatcggat gtgcccagat gggattagct agtaggtggg    240

gtaatggctc acctaggcga cgatccctag ctggtctgag aggatgacca gccacactgg    300

aactgagaca cggtccagac tcctacggga ggcagcagtg gggaatattg cacaatgggc    360

gcaagcctga tgcagccatg ccgcgtgtat gaagaaggcc ttcgggttgt aaagtacttt    420

cagtggggag gaaggcgtta aggttaataa ccttggcgat tgacgttacc cgcagaagaa    480

gcaccggcta actccgtgcc agcagccgcg gtaatacgga gggtgcaagc gttaatcgga    540

attactgggc gtaaagcgca cgcaggcggt ctgtcaagtc ggatgtgaaa tccccgggct    600

caacctggga actgcattcg aaactggcag gctagagtct tgtagagggg ggtagaattc    660

caggtgtagc ggtgaaatgc gtagagatct ggaggaatac cggtggcgaa ggcggccccc    720

tggacaaaga ctgacgctca ggtgcgaaag cgtggggagc aaacaggatt agataccctg    780

gtagtccacg ccgtaaacga tgtcgacttg gaggttgttc ccttgaggag tggcttccgg    840

agctaacgcg ttaagtcgac cgcctgggga gtacgg                              876
```

<210> SEQ ID NO 63
<211> LENGTH: 1532
<212> TYPE: DNA
<213> ORGANISM: Unknown
<220> FEATURE:
<223> OTHER INFORMATION: Description of Unknown:
DP63 16S rRNA sequence

<400> SEQUENCE: 63

```
tgaagagttt gatcatggct cagattgaac gctggcggca ggcctaacac atgcaagtcg     60

agcggtagag agaagcttgc ttctcttgag agcggcggac gggtgagtaa tgcctaggaa    120

tctgcctggt agtgggggat aacgttcgga aacggacgct aataccgcat acgtcctacg    180

ggagaaagca ggggaccttc gggccttgcg ctatcagatg agcctaggtc ggattagcta    240

gttggtgagg taatggctca ccaaggcgac gatccgtaac tggtctgaga ggatgatcag    300
```

-continued

```
tcacactgga actgagacac ggtccagact cctacgggag gcagcagtgg ggaatattgg    360

acaatgggcg aaagcctgat ccagccatgc cgcgtgtgtg aagaaggtct tcggattgta    420

aagcacttta agttgggagg aagggttgta gattaatact ctgcaatttt gacgttaccg    480

acagaataag caccggctaa ctctgtgcca gcagccgcgg taatacagag ggtgcaagcg    540

ttaatcggaa ttactgggcg taaagcgcgc gtaggtggtt tgttaagttg gatgtgaaat    600

ccccgggctc aacctgggaa ctgcattcaa aactgactga ctagagtatg gtagagggtg    660

gtggaatttc ctgtgtagcg gtgaaatgcg tagatatagg aaggaacacc agtggcgaag    720

gcgaccacct ggactaatac tgacactgag gtgcgaaagc gtggggagca aacaggatta    780

gataccctgg tagtccacgc cgtaaacgat gtcaactagc cgttggaagc cttgagcttt    840

tagtggcgca gctaacgcat taagttgacc gcctggggag tacggccgca aggttaaaac    900

tcaaatgaat tgacgggggc ccgcacaagc ggtggagcat gtggtttaat tcgaagcaac    960

gcgaagaacc ttaccaggcc ttgacatcca atgaactttc tagagataga ttggtgcctt   1020

cgggaacatt gagacaggtg ctgcatggct gtcgtcagct cgtgtcgtga gatgttgggt   1080

taagtcccgt aacgagcgca acccttgttc ttagttacca gcacgttatg gtgggcactc   1140

taaggagact gccggtgaca aaccggagga aggtggggat gacgtcaagt catcatggcc   1200

cttacggcct gggctacaca cgtgctacaa tggtcggtac agagggttgc caagccgcga   1260

ggtggagcta atcccataaa accgatcgta gtccggatcg cagtctgcaa ctcgactgcg   1320

tgaagtcgga atcgctagta atcgcgaatc agaatgtcgc ggtgaatacg ttcccgggcc   1380

ttgtacacac cgcccgtcac accatgggag tgggttgcac cagaagtagc tagtctaacc   1440

ttcgggagga cggttaccac ggtgtgattc atgactgggg tgaagtcgta acaaggtagc   1500

cgtaggggaa cctgcggctg gatcacctcc tt                                 1532
```

```
<210> SEQ ID NO 64
<211> LENGTH: 1649
<212> TYPE: DNA
<213> ORGANISM: Unknown
<220> FEATURE:
<223> OTHER INFORMATION: Description of Unknown:
      DP64 ITS sequence

<400> SEQUENCE: 64

tccgtaggtg aacctgcgga aggatcatta aataatcaat aattttggct tgtccattat     60

tatctattta ctgtgaactg tattattact tgacgcttga gggatgctcc actgctataa    120

ggataggcgg tggggatgtt aaccgagtca tagtcaagct taggcttggt atcctattat    180

tatttaccaa aagaattcag aattaatatt gtaacataga cctaaaaaat ctataaaaca    240

acttttaaca acggatctct tggttctcgc atcgatgaag aacgtagcaa agtgcgataa    300

ctagtgtgaa ttgcatattc agtgaatcat cgagtctttg aacgcaactt gcgctcattg    360

gtattccaat gagcacgcct gtttcagtat caaaacaaac cctctattca atatttttgt    420

tgaataggaa tactgagagt ctcttgatct tttctgatct cgaacctctt gaaatgtaca    480

aaggcctgat cttgtttgaa tgcctgaact ttttttaat ataaagagaa gctcttgcgg     540

taaactgtgc tggggcctcc caaataatac tctttttaaa tttgatctga aatcaggcgg    600

gattacccgc tgaacttaag catatcaata agcggaggaa aagaaaataa caatgatttc    660

cctagtaacg gcgagtgaag aggaaagagc tcaaagttgg aaactgtttg gcttagctaa    720

accgtattgt aaactgtaga aacattttcc tggcacgccg gattaataag tcctttggaa    780
```

-continued

```
caaggcatca tggagggtga gaatcccgtc tttgatccga gtagttgtct tttgtgatat    840

gttttcaaag agtcaggttg tttgggaatg cagcctaaat tgggtggtaa atctcaccta    900

aagctaaata tttgcgagag accgatagcg aacaagtacc gtgagggaaa gatgaaaaga    960

actttgaaaa gagagttaaa cagtatgtga aattgttaaa agggaaccgt ttggagccag   1020

actggtttga ctgtaatcaa cctagaattc gttctgggtg cacttgcagt ctatacctgc   1080

caacaacagt ttgatttgga ggaaaaaatt agtaggaatg tagcctctcg aggtgttata   1140

gcctactatc atactctgga ttggactgag gaacgcagcg aatgccatta ggcgagattg   1200

ctgggtgctt tcgctaataa atgttagaat ttctgcttcg ggtggtgcta atgtttaaag   1260

gaggaacaca tctagtatat tttttattcg cttaggttgt tggcttaatg actctaaatg   1320

acccgtcttg aaacacggac caaggagtcc accataagtg caagtatttg agtgacaaac   1380

tcatatgcgt aaggaaactg attgatacga aatcttttga tggcagtatc acccggcgtt   1440

gacgttttat actgaactga ccgaggtaaa gcacttatga tgggacccga aagatggtga   1500

actatgcctg aatagggtga agccagagga aactctggtg gaggctcgta gcgattctga   1560

cgtgcaaatc gatcgtcaaa tttgggtata ggggcgaaag actaatcgaa ccatctagta   1620

gctggttcct gccgaagttt ccctcagga                                     1649
```

<210> SEQ ID NO 65
<211> LENGTH: 1498
<212> TYPE: DNA
<213> ORGANISM: Unknown
<220> FEATURE:
<223> OTHER INFORMATION: Description of Unknown:
DP65 ITS sequence

<400> SEQUENCE: 65

```
tccgtaggtg aacctgcgga aggatcatta ttgaaaacaa gggtgtccaa tttaacttgg     60

aacccgaact tctcaattct aactttgtgc atctgtatta tggcgagcag tcttcggatt    120

gtgagccttc acttataaac actagtctat gaatgtaaaa tttttataac aaataaaaac    180

tttcaacaac ggatctcttg gctctcgcat cgatgaagaa cgcagcgaaa tgcgatacgt    240

aatgtgaatt gcagaattca gtgaatcatc gaatctttga acgcatcttg cgctctctgg    300

tattccggag agcatgtctg tttgagtgtc atgaattctt caacccaatc ttttcttgta    360

atcgattggt gtttggattt tgagcgctgc tggcttcggc ctagctcgtt cgtaatacat    420

tagcatccct aatacaagtt tggattgact tggcgtaata gactattcgc taaggattcg    480

gtggaaacat cgagccaact tcattaagga agctcctaat ttaaaagtct accttttgat    540

tagatctcaa atcaggcagg attacccgct gaacttaagc atatcaataa gcggaggaaa    600

agaaactaac aaggattccc ctagtagcgg cgagcgaagc gggaaaagct caaatttgta    660

atctggcgtc ttcgacgtcc gagttgtaat ctcgagaagt gttttccgtg atagaccgca    720

tacaagtctc ttggaacaga gcgtcatagt ggtgagaacc cagtacacga tgcggatgcc    780

tattactttg tgatacactt tcgaagagtc gagttgtttg ggaatgcagc tcaaattggg    840

tggtaaattc catctaaagc taaatattgg cgagagaccg atagcgaaca agtaccgtaa    900

gggaaagatg aaaagcactt tggaaagaga gttaacagta cgtgaaattg ttggaaggga    960

aacacatgca gtgatacttg ctattcgggg caactcgatt ggcaggcccg catcagtttt   1020

tcggggcgga aaagcgtaga gagaaggtag caatttcggt tgtgttatag ctctttactg   1080

gattcgccct gggggactga ggaacgcagc gtgcttttag caattccttc gggaattcca   1140
```

cgcttaggat gcgggtttat ggctgtatat gacccgtctt gaaacacgga ccaaggagtc 1200
taacatgctt gcgagtattt gggtgtcaaa cccggatgcg caatgaaagt gaatggaggt 1260
gggaagcgca agctgcacca tcgaccgatc tggatttttt aagatggatt tgagtaagag 1320
caagtatgtt gggacccgaa agatggtgaa ctatgcctga atagggcgaa gccagaggaa 1380
actctggtgg aggctcgtag cggttctgac gtgcaaatcg atcgtcaaat ttgggtatag 1440
gggcgaaaga ctaatcgaac catctagtag ctggttcctg ccgaagtttc cctcagga 1498

<210> SEQ ID NO 66
<211> LENGTH: 1340
<212> TYPE: DNA
<213> ORGANISM: Unknown
<220> FEATURE:
<223> OTHER INFORMATION: Description of Unknown:
DP66 ITS sequence

<400> SEQUENCE: 66
tccgtaggtg aacctgcgga aggatcatta ctgtgattta tccaccacac tgcgtgggcg 60
acacgaaaca ccgaaaccga acgcacgccg tcaagcaaga aatccacaaa actttcaaca 120
acggatctct tggttctcgc atcgatgaag agcgcagcga aatgcgatac ctagtgtgaa 180
ttgcagccat cgtgaatcat cgagttcttg aacgcacatt gcgcccgctg gtattccggc 240
gggcatgcct gtctgagcgt cgtttccttc ttggagcgga gcttcagacc tggcgggctg 300
tctttcggga cggcgcgccc aaagcgaggg gccttctgcg cgaactagac tgtgcgcgcg 360
gggcggccgg cgaacttata ccaagctcga cctcagatca ggcaggagta cccgctgaac 420
ttaagcatat caataagcgg aggaaaagaa accaacaggg attgccccag tagcggcgag 480
tgaagcggca aaagctcaga tttggaatcg cttcggcgag ttgtgaattg caggttggcg 540
cctctgcggc ggcggcggtc caagtccctt ggaacagggc gccattgagg gtgagagccc 600
cgtgggaccg tttgcctatg ctctgaggcc cttctgacga gtcgagttgt ttgggaatgc 660
agctctaagc gggtggtaaa ttccatctaa ggctaaatac tggcgagaga ccgatagcga 720
acaagtactg tgaaggaaag atgaaaagca ctttgaaaag agagtgaaac agcacgtgaa 780
attgttgaaa gggaagggta ttgcgcccga catggagcgt gcgcaccgct gcccctcgtg 840
ggcggcgctc tgggcgtgct ctgggccagc atcggttttt gccgcgggag aagggcggcg 900
ggcatgtagc tcttcggagt gttatagcct gccgccggcg ccgcgagcgg ggaccgagga 960
ctgcgacttt tgtctcggat gctggcacaa cggcgcaaca ccgcccgtct tgaaacatgg 1020
accaaggagt ctaacgtcta tgcgagtgtt tgggtgtgaa accccgggcg cgtaatgaaa 1080
gtgaacgtag gtcggaccgc tcctctcggg gggcgggcac gatcgaccga tcctgatgtc 1140
ttcggatgga tttgagtaag agcatagctg ttgggacccg aaagatggtg aactatgcct 1200
gaatagggtg aagccagagg aaactctggt ggaggctcgt agcggttctg acgtgcaaat 1260
cgatcgtcga atttgggtat aggggcgaaa gactaatcga accatctagt agctggttcc 1320
tgccgaagtt tccctcagga 1340

<210> SEQ ID NO 67
<211> LENGTH: 1698
<212> TYPE: DNA
<213> ORGANISM: Unknown
<220> FEATURE:
<223> OTHER INFORMATION: Description of Unknown:
DP53 Glutamine--tRNA ligase sequence

<400> SEQUENCE: 67

```
atgagcaagc ccactgtcga ccccactctg aatccaaagg ctggccctgc tgtcccggct     60
aacttcctgc gtccaatcgt tcaggcggac ctagactcgg gtaaatacac acagatcgtg    120
acccgctttc cgccggagcc aaacggctat ctgcacatcg gtcatgccaa atccatttgt    180
gtgaactttg ggctggctca agagtttggc ggcgtgacgc atttgcgttt tgacgacacc    240
aacccggcaa aagaagacca ggaatacatc gacgccatcg aaagcgacgt caagtggctg    300
ggcttcgagt gggccggtga agtgcgttac gcgtcgcaat acttcgatca actgcacgag    360
tgggcgattt acctgatcaa agaaggcaag gcctacgtct gcgacctgac gcccgagcaa    420
gccaaggaat accgtggcag cctgaccgag cccggcaaga acagcccgtt ccgcgaccgt    480
agcgttgaag agaacctgga tctgttcgcc cgcatgaccg ccggtgagtt tgaagacggc    540
aagcgtgtgc tgcgcgccaa gatcgacatg acctcgccga acatgaacct gcgcgacccg    600
atcatgtacc gcatccgtca tgcccatcac caccagaccg gtgacaagtg gtgcatctac    660
cccaactatg acttcaccca cggtcagtcg gatgccattg aaggcatcac ccattcgatc    720
tgcaccctgg agttcgaaag ccatcgtccg ctgtacgaat ggttcctgga cagcctgcca    780
gtaccggcgc gcccgcgtca gtacgagttc agccgtctga acctcaacta caccatcacc    840
agcaagcgca agctcaagca gctggtcgat gaaaagcacg tcaacggctg ggatgacccg    900
cgcatgtcga cgctgtcggg tttccgccgt cgcggttaca cgcctaaatc gattcgtaat    960
ttctgtgaca tggtcggcac caaccgttct gacggtgttg ttgacttcgg catgctggaa   1020
ttcagcattc gtgacgattt ggaccacagc gcgccgcgcg ccatgtgcgt gctgcgtcca   1080
ttgaaggtga ttattaccaa ctacccggaa ggtcaggtcg aaaacctcga gctgccttgc   1140
cacccgaaag aagacatggg tgtgcgggtg ttgccgtttg cccgtgaaat ctacatcgac   1200
cgtgaagact tcatggaaga gccgccaaaa ggctacaagc gtcttgagcc tgcgggcgaa   1260
gtgcgtttgc gcggcagcta tgtgatccgt gccgacgaag cgatcaagga tgccgatggc   1320
aacatcgttg aactgcattg ctcgtacgat ccgctgaccc tgggtaaaaa ccctgaaggt   1380
cgcaaggtca agggtgttgt gcactgggtg ccggcggcgg ccagcgtcga atgcgaagtg   1440
cgtttgtatg atcgtctgtt ccgctcgccg aaccctgaaa aggccgaaga cggcgcgggc   1500
ttcctggaaa acatcaaccc tgactcgctg caggtactga ccggttgtcg tgctgaaccc   1560
tcgctgggca atgcacagcc ggaagaccgt ttccagttcg agcgcgaagg ctacttctgc   1620
gcagatatca aggactcgaa acccggtcac ccggtattca accgtaccgt gaccctgcgt   1680
gattcgtggg gccagtga                                                 1698
```

<210> SEQ ID NO 68
<211> LENGTH: 2418
<212> TYPE: DNA
<213> ORGANISM: Unknown
<220> FEATURE:
<223> OTHER INFORMATION: Description of Unknown:
DP53 DNA gyrase subunit B sequence

<400> SEQUENCE: 68

```
ttgagcgaag aaaacacgta cgactcaacg agcattaaag tgctgaaagg ccttgatgcc     60
gtacgcaaac gtcccggtat gtacattggt gatactgacg atggcagcgg tctgcaccac    120
atggtgttcg aagtagtcga caactccatc gacgaagcgc tggctggcca ttgcgacgac    180
atcaccatca cgatccaccc ggacgagtcc atcaccgtgc gcgataacgg ccgcggtatt    240
```

-continued

```
ccggttgacg tgcataaaga agaaggcgta tctgcagccg aggtcatcat gaccgtgctg    300
cacgccggcg gtaagttcga tgacaactcc tacaaagtat ccggcggctt gcacggtgta    360
ggtgtttcgg tggtaaacgc cctgtccgaa ctgctggtct tgactgtacg ccgcagcggc    420
aagatctggg aacagaccta cgtccacggt gttcctcagg cgcctatggc tattgtgggt    480
gaaagcgaaa ccacgggtac gcagatccac ttcaagcctt cggctgaaac cttcaagaat    540
atccacttta gctgggacat cctggccaag cggattcgtg aactgtcctt cctgaactcc    600
ggtgtgggta tcgtcctcaa ggacgagcgc agcggcaagg aggagctgtt caagtacgaa    660
ggtggcctgc gtgcattcgt tgattacctg aacaccaaca agaacgctgt gaaccaggtg    720
ttccacttca atgttcagcg tgaagacggc atcggcgtag aaatcgccct gcagtggaac    780
gacagcttca acgagaacct gttgtgcttc accaacaaca ttccacagcg cgatggtggc    840
acgcacttgg tgggcttccg ctctgccctg acgcgtaacc tcaacacgta catcgaagct    900
gaaggcctgg ccaagaagca caaggtcgcc accaccggtg atgacgcccg tgaaggcttg    960
accgcgatca tctcggtgaa agtgccggat ccaaagttca gctcgcagac taaagacaag   1020
ctggtgtctt ccgaagtgaa gaccgctgtt gaacaggaaa tgggcaagtt cttctccgac   1080
ttcctgctgg aacacccgaa cgaagccaag ttgattgtcg gcaagatgat cgacgcagcc   1140
cgtgctcgtg aagctgcacg taaagcccgt gagatgaccc gtcgtaaagg cgcgttggac   1200
atcgcgggct tgccgggcaa gctggctgac tgccaggaaa aagaccctgc tctgtccgaa   1260
ctgtacctgg tggaaggtga ctctgctggc ggctccgcca agcagggtcg caaccgtcgt   1320
acccaagcca tcctgccgtt gaaaggtaaa atcctcaacg tcgagaaagc ccgttttgac   1380
aagatgatct cttcgcaaga agtcggcacc ttgatcactg cgctgggctg tggcatcggc   1440
cgcgaagagt acaacatcga caaactgcgc tatcacaaca tcatcatcat gaccgatgct   1500
gacgttgacg gttcgcacat ccgtaccctg ctgctgacct tcttcttccg tcagttgccg   1560
gagctgatcg agcgtggcta catctacatc gcccagccac cgttgtacaa agtgaaaaag   1620
ggcaagcaag agcagtacat caaagacgac gaggccatgg aagagtacat gacccagtcg   1680
gctcttgaag atgccagcct gcacttgaac gaagatgccc ctggcatctc cggtgaggca   1740
ctggagcgtc tggtgtacga cttccgcatg gtgatgaaga ccctcaagcg tttgtcgcgc   1800
ctgtaccctc aggagctgac cgagcacttc atctacctgc cggctgtaag ccttgagcag   1860
ttgggtgacc acgctgccat gcaggactgg atggccaagt ttgaagagcg tctgcgtctg   1920
gttgagaaat cgggcctggt ctacaaagcc agcctgcgtg aagaccgtga gcgtaatgtc   1980
tggttgccag aggtcgaact gatctcccac ggccactcga cgttcatcac cttcaaccgc   2040
gacttcttcg gcagcaacga ttacaaaacc gttgtgaccc tgggcgctca actgagcacc   2100
ctgctggatg aaggcgccta tatccagcgt ggcgaacgtc gcaagcaagt gaccgagttc   2160
aaagaagcac tggactggtt gatggctgaa agcaccaagc gtcacaccat ccagcgctac   2220
aaaggactgg gtgaaatgaa cccggatcag ctctgggaaa ccacgatgga cccaagcgtg   2280
cgtcgcatgc tgaaagtcac catcgaagac gcgatcggcg ccgatcagat cttcaacacc   2340
ttgatgggcg atgctgtaga accacgtcgt gaattcatcg agagcaacgc actggcagtg   2400
tccaacctgg atttctga                                                 2418
```

<210> SEQ ID NO 69
<211> LENGTH: 2832
<212> TYPE: DNA
<213> ORGANISM: Unknown

```
<220> FEATURE:
<223> OTHER INFORMATION: Description of Unknown:
      DP53 Isoleucine--tRNA ligase sequence

<400> SEQUENCE: 69

atgaccgact acaaagccac gctaaacctc ccggacaccg ccttcccaat gaaggccggc     60

ctgccacagc gcgaaccgca aattttgcag cgctgggaca gcattggcct gtacgggaag    120

ttgcgcgaga ttggcaagga tcgtccgaag ttcgtacttc acgacggtcc tccgtacgcc    180

aacggcacta tccatatcgg tcatgcgctg aacaagattc tgaaagacat gatcatccgc    240

tccaagaccc tgtcgggttt tgacgcgccg tatgtgccgg gctgggattg ccatggtttg    300

ccgattgaac acaaggtcga agtgacccac ggtaaaaacc tgagcgcgga taaaacccgc    360

gagctgtgcc gtgcctacgc caccgagcag atcgaggggc agaagtccga gttcatccgt    420

ctgggtgtgc tgggtgattt cgccaacccg tacaagacca tggacttcaa aaacgaagcc    480

ggtgaaatcc gtgctttggc tgagatcgtc aagggcggtt ttgtgttcaa gggcctcaag    540

ccggtgaact ggtgcttcga ttgcggttcg gccctggctg aagctgaagt tgaataccag    600

gacaagaagt ctgcggccat cgacgttgcc ttcccggttg ccgacgaggc caagctggcc    660

gaggcctttg gtctggcggc actgagcaaa cctgcttcga tcgtgatctg gaccaccacc    720

ccgtggacca ttccggccaa ccaggcgctt aacgtacacc cggaattcac ctacgcgctg    780

gtcgacgtgg gcgacaagtt gctggtactg gctgaagaac tggtcgaatc gagtctggcg    840

cgttacaacc tgcagggttc ggtcatcgcc accaccactg gctcagcgct tgaactaatc    900

aacttccgtc acccgttcta tgaccgtctg tcgcctgttt atctggccga ctacgttgag    960

ctgggtgctg gcactggtgt ggttcactcg gctccagcct acggcgtaga cgacttcgtg   1020

acctgcaaag cctatggcat ggtcaacgac gacatcatca acccggtgca aagcaatggc   1080

gtttacgtgc cgtcgctgga gttcttcggt ggccagttca tctggaaggc caaccagaac   1140

atcatcgaca agctgatcga agtcggttcg ctgatgttca ccgagaccat cagccacagc   1200

tatatgcact gctggcgcca caagacgccg ctgatctacc gtgccaccgc ccagtggttt   1260

atcggtatgg acaagcagcc gactgatggc gataccttgc gcacccgtgc gctgcaagcg   1320

atcgaagaca cccagttcgt tccggcctgg ggtcaggcgc gcctgcactc gatgatcgcc   1380

aaccgcccgg actggtgcat ctcgcgtcaa cgcaactggg gcgtgccgat cccgtttttc   1440

ctgaacaagg aaagcggcga gctgcacccg cgcaccgtcg aaatgatgga agaagtggcc   1500

aagcgcgttg aagtcgaagg catcgaggcg tggttcaagc tggatgctgc cgagctgctg   1560

ggcgacgaag cgccgctgta cgacaagatc agcgataccc tcgacgtctg gttcgattcg   1620

ggcaccacgc actggcatgt ccttcgcggt tcgcacccga tgggtcatga aaccggccca   1680

cgcgctgatc tctaccttga aggctccgac cagcaccgtg gctggttcca ctcgtcgttg   1740

ctgaccggtt gcgccatcga caaccacgcg ccgtaccgcg agctgctgac ccacggtttt   1800

accgtggacg aagcgggccg caagatgtcc aagtcgctgg gcaacgtgat tgcaccgcaa   1860

aaggtcaacg acaccctggg cgccgacatc atgcgtctgt gggttgcttc gaccgactac   1920

tcgggcgaaa tcgcggtttc cgaccagatc ctgcagcgca gtgcggacgc ctaccgacgt   1980

atccgcaata ccgcacgctt cctgctgtcg aacctgaccg gtttcaatcc agccaccgac   2040

atcctgcctg ccgaagaaat gctggcactg gaccgctggg cggtggatcg tgcgttgctg   2100

ctgcaacgtg agctggagct gcattacggc gaataccgtt tctggaacgt gtactccaag   2160

gtgcacaact tctgcgttca ggagctgggc ggtttctatc tcgacatcat caaggaccgc   2220
```

```
cagtacacca ccggcgccaa cagcaaggct cgccgttcgt gccagaccgc gctgttccac   2280

atctctgaag cgctggtgcg ctggatcgct ccgatcctgg cgttcaccgc tgatgagttg   2340

tggcagtacc tgccgggcga gcgcaacgaa tcggtcatgc tcaacacctg gtacgaaggc   2400

ctgactgaac tgccggaagg caccgaactg gatcgcgcct actgggagcg aatcatggcg   2460

gtcaaggttg cggtcaacaa ggaaatggaa aacttgcgcg cagccaaggc cattggcggt   2520

aacttgcaag cagaagtgac cttgttcgcc gaagatcagc tggctgctga tttgtccaag   2580

ttgagcaacg aactgcgttt cgtgttgatc acctccactg ccagcgttgc gccttttgcg   2640

caggctccag cagatgccgt ggttaccgaa gtggctggcc tcaaactcaa ggtggtcaag   2700

tcggcccatg ccaagtgcgc ccgttgctgg cactgccgtg aagacgtcgg cgttaacccc   2760

gagcaccctg aaatctgcgg tcgttgtgta gacaatatca gcggcgctgg tgaggtacgt   2820

cactatgcct aa                                                       2832
```

<210> SEQ ID NO 70
<211> LENGTH: 1785
<212> TYPE: DNA
<213> ORGANISM: Unknown
<220> FEATURE:
<223> OTHER INFORMATION: Description of Unknown:
DP53 NADH-quinone oxidoreductase subunit C/D sequence

<400> SEQUENCE: 70

```
atgactgcag gctccgctct gtacatcccg ccttacaagg ctgacgacca agatgtggtt     60

gtcgaactca atacccgttt tggccctgag gcgttcaccg cccaggccac gcgcaccggc    120

atgccggtgc tttgggttag ccgcgcaaaa ctggtcgaag tactgacctt cctgcgcaac    180

ctgccaaaac cctacgtcat gctctatgac ctgcacggtg tggacgaacg tctgcgtacc    240

aagcgtcagg gcctgccatc gggtgcagac ttcaccgtct tctaccacct gatgtcgctg    300

gaacgtaaca gcgacgtcat gatcaaggtg gccctgtctg aaaaagacct gagtgtccct    360

accgtgaccg gtatctggcc gaacgccaac tggtacgagc gtgaagtctg ggacatgttc    420

ggcatcgatt tcaaaggcca cccgcacctg tcgcgcatca tgatgccgcc gacctgggaa    480

ggtcacccgc tgcgcaagga cttcccggcc cgtgccacag agttcgatcc gtacagcctg    540

accctggcca aggtgcagct ggaagaggaa gccgcgcgct tccgcccgga agactggggc    600

atgaaacgct ccggtgaaaa cgaggactac atgttcctca acctgggccc taaccaccct    660

tcggctcacg gtgccttccg catcatcctg cagctggacg gtgaagagat cgtcgactgc    720

gtgcctgacg tcggttacca ccaccgtggc gccgagaaaa tggccgaacg ccagtcctgg    780

cacagtttca tcccgtacac cgaccggatc gattacctcg gcggagtgat gaacaacctg    840

ccgtacgtgc tctcggtcga gaagctggcc ggtatcaaag tgccggatcg ggtcgacacc    900

atccgcatca tgatggccga attcttccgt atcaccagcc acctgctgtt cctgggtacc    960

tatatccagg acgtgggcgc catgaccccg gtgttcttca cgttcaccga ccgtcagcgc   1020

gcttacaagg tgatcgaggc catcaccggt ttccgtctgc acccggcctg gtaccgcatc   1080

ggcggcgttg cccacgacct gccgaacggc tgggatcgcc tggtcaagga attcatcgac   1140

tggatgccca agcgtctgga cgagtaccag aaagccgctc tggacaacag catcctgcgt   1200

ggtcgtacca tcggcgttgc cgcctacaac accaaagagg ccctggaatg gggcgtcacc   1260

ggtgccggcc tgcgctccac cggttgtgac ttcgatatcc gcaaggcgcg cccgtattcc   1320

ggctacgaga acttcgaatt cgaagtcccg ctggcagcca acggcgatgc ctacgatcgt   1380
```

-continued

```
tgcatcgtgc gcgtcgaaga aatgcgccag agcctgaaaa tcatcgagca gtgcatgcgc   1440

aacatgccgg ccggcccgta caaggcggat cacccgctga ccacgccgcc gcctaaagaa   1500

cgcacgctgc agcatatcga gaccttgatc acgcacttcc tgcaagtttc gtggggcccg   1560

gtgatgccgg ccaacgaatc cttccagatg atcgaagcga ccaagggcat caacagttat   1620

tacctgacga gcgatggcgg caccatgagc taccgcaccc ggattcgcac cccaagcttc   1680

ccgcacctgc aacagatccc ttcggtgatc aaaggtgaaa tggtcgcgga cttgattgcg   1740

tacctgggta gtatcgattt cgttatggcc gacgtggacc gctaa                   1785
```

<210> SEQ ID NO 71
<211> LENGTH: 1119
<212> TYPE: DNA
<213> ORGANISM: Unknown
<220> FEATURE:
<223> OTHER INFORMATION: Description of Unknown:
DP53 Protein RecA sequence

<400> SEQUENCE: 71

```
atggacgaca acaagaagaa agccttggct gcggccctgg gtcagatcga acgtcaattc     60

ggcaagggtg ccgtgatgct gatgggcgac caggagcgtc aggcagtccc ggcgatctcc    120

accggctccc tgggtctgga catcgcactg ggcattggcg gtctgccaaa aggccgtatt    180

gttgaaatct acggccctga gtcgtcgggt aaaaccacac tgaccctgtc cgtgattgcc    240

caggcgcaaa aggccggtgc tacctgcgcc ttcgtcgatg ccgagcacgc ccttgatcct    300

gagtacgctg ccaaactggg cgtaaacgtt gatgacctgc tggtttcaca gcctgacacc    360

ggcgaacagg cactggaaat caccgatatg ctggtgcgtt ccaatgcggt tgacgtgatc    420

atcatcgact ccgttgctgc actgacgcca aaagctgaaa tcgaaggcga catgggcgat    480

acccacgttg gcctgcaagc ccgtctgatg tcgcaagcgc tgcgtaaaat caccggtaac    540

atcaagaacg ccaactgcct ggttatcttc atcaaccaga tccgcatgaa aatcggcgtg    600

atgttcggca gccctgaaac caccaccggt ggtaacgcac tgaagttcta cgcttcggta    660

cgtctggata tccgccgcac cggcgccgta aaagaaggcg atgtggtggt gggtagcgaa    720

acccgcgtga aagtggtcaa gaacaaggtg gcaccaccgt tccgtcaggc tgaattccag    780

atcctgtacg gcaagggtat ctacctgaac ggtgaaatga ttgacctggg cgtactgcat    840

ggctttgttg aaaaagctgg cgcctggtac agctacaacg gcagcaaaat cggtcagggc    900

aaggccaact ccgccaagtt cctggacgat aacccggaca tcaaggatgc gctggagaag    960

cagctgcgtg agaagttgct cgggccaaaa accgatgccg aactggcagc gacggactgc   1020

aatggacctg ctcgcgcgac gcgagcacgg tcgagtcgag ctgacgcgca agttgcgtca   1080

gcgcggcgct tgccccgaca tgatcgacgc tgcccttga                          1119
```

<210> SEQ ID NO 72
<211> LENGTH: 1848
<212> TYPE: DNA
<213> ORGANISM: Unknown
<220> FEATURE:
<223> OTHER INFORMATION: Description of Unknown:
DP53 RNA polymerase sigma factor RpoD sequence

<400> SEQUENCE: 72

```
atgtccggaa aagcgcaaca gcagtctcgt atcaaagagt tgatcaccct cggccgtgag     60

cagaagtatc tgacttacgc agaggtcaac gaccacctgc ccgaagatat ttcagatccg    120
```

-continued gagcaagtgg aagacatcat ccgcatgatt aatgacatgg ggatccccgt acacgagagt 180
gctccggatg cggacgccct tatgttggcc gatgccgaca ccgacgaagc agcagctgaa 240
gaagcggctg cagcgttggc ggcagtagag accgacattg gtcgtactac cgaccctgtg 300
cgcatgtata tgcgtgaaat gggcacggta gaactgctga cacgtgaagg cgaaatcgaa 360
atcgccaagc gtatcgaaga aggcatccgt gaagtgatgg gcgcaatcgc gcacttccct 420
ggcacggttg accatattct ctccgagtac actcgcgtca ccaccgaagg tggccgcctg 480
tccgacgttc tgagcggtta tatcgacccg gacgacggta ttgcgccgcc cgcagccgaa 540
gtacctcctc ctgtcgacac caaggtgaaa gccgaaggtg atgacgaaga ggacgacaag 600
gaagattccg gcgaagacga ggaagaggtc gaaagcggcc ctgatccgat catcgcggcc 660
cagcgctttg gcgctgtttt cgatcagatg gaaatcgctc gcaaggccct gaaaaagcac 720
ggtcgcggca gcaagcaggc aattgccgag ctggttgcac tggctgagct gttcatgccg 780
atcaaactgg ttccgaagca attcgaaggc ctggttgagc gtgttcgcag cgccctggag 840
cgtctgcgtg cacaagagcg cgcaatcatg cagctgtgtg tacgtgatgc acgcatgccg 900
cgcaccgatt tcctgcgtct gttcccgggc aacgaagtcg acgaaagctg gagcgatgcg 960
ctggccaaag gcaaaagcaa atatgctgaa gccattggtc gcctgcaacc ggacatcatc 1020
cgttgccagc aaaagctctc tgctctggaa gcagaaaccg gcttgaagat tgccgagatc 1080
aaggacatca accgtcgcat gtcgatcggc gaggccaagg cccgccgcgc gaagaaagaa 1140
atggttgaag ccaacttgcg tctggtgatc tccatcgcca agaagtacac caaccgtggc 1200
ctgcagttcc tcgatctgat ccaggaaggc aacatcggct tgatgaaagc ggtagacaag 1260
tttgaatacc gccgcggcta caaattctcg acttatgcca cctggtggat ccgtcaggcg 1320
atcactcgct cgatcgccga ccaggcccgc accatccgta ttccggtgca catgatcgag 1380
acgatcaaca agctcaaccg tatttcccgt cagatgttgc aggaaatggg ccgtgaaccg 1440
accccggaag agctgggcga acgcatggaa atgcctgagg ataaaatccg caaggtattg 1500
aagatcgcta aagagccgat ctccatggaa accccgatcg gtgatgacga agactcccat 1560
ctgggtgact tcatcgaaga ctcgaccatg cagtcgccaa tcgatgttgc taccgttgag 1620
agccttaaag aagcgacacg cgacgtactc ggcggcctca cagcccgtga agccaaggta 1680
ctgcgcatgc gtttcggtat cgacatgaat accgaccaca cccttgagga ggttggtaaa 1740
cagttcgacg ttacccgtga gcggattcgt cagatcgaag ccaaggcgct gcgcaagctg 1800
cgccacccga cgagaagcga gcatttgcgc tccttcctcg acgagtga 1848

<210> SEQ ID NO 73
<211> LENGTH: 4073
<212> TYPE: DNA
<213> ORGANISM: Unknown
<220> FEATURE:
<223> OTHER INFORMATION: Description of Unknown:
DP53 DNA-directed RNA polymerase subunit beta sequence

<400> SEQUENCE: 73
atggcttact catatactga gaaaaaacgt atccgcaagg actttagcaa gttgccggac 60
gtcatggatg tgccgtatct cttggcaatc cagctggatt cgtatcgtga attcttgcag 120
gcgggagcga ctaaagatca gttccgcgac gtgggcctgc atgcggcctt caaatccgtt 180
ttcccgatca tcagctactc cggcaatgct gcgctggagt acgtcggtta tcgcttgggc 240
gaaccggcat ttgatgtcaa agaatgcgtg ttgcgtggcg taacgtacgc cgtacctttg 300

-continued

```
cgggtaaaag ttcgtttgat cattttcgac aaagaatcgt cgaacaaagc gatcaaggac    360
atcaaagagc aagaagtcta catgggtgaa atccccctga tgactgaaaa cggtaccttc    420
gtaatcaacg gtaccgagcg tgtaattgtt tcccagctgc accgttcccc gggcgtgttc    480
tttgccacga ccgcggcaag acgcacagct ccggtaagct gctttattcc gcgcgtatca    540
ttccttaccg tggttcgtgg ctcgacttcg agttcgaccc gaaagactgc gtgttcgtgc    600
gtattgaccg tcgtcgcaag ctgcctgcat cggtattgct gcgcgcgctg ggttatacca    660
ctgagcaagt gctggacgcg ttctacacca ccaacgtgtt ccacgttcag ggtgagagca    720
tcagcctgga gctggttcca cagcgtctgc gcggtgaaat cgcggccatc gacattaccg    780
atgacaaagg caaggtgatt gttgagcagg gtcgtcgtat cactgctcgt catatcaacc    840
agctggaaaa agccggtgtc aaagagctcg ttatgcctct ggactatgtc ctgggtcgca    900
caacggccaa ggctatcgtg catccggcta ctggcgaaat cattgctgag tgcaacaccg    960
agctgaccac tgaaatcctg gcaaaagttg ccaagggcca ggttgttcgc atcgaaacgt   1020
tgtacaccaa cgatatcgac tgcggtccgt tcgtctccga cacgctgaag atcgactcca   1080
ccagcaacca actggaagcg ctggtcgaaa tctatcgcat gatgcgtcca ggcgagccgc   1140
caaccaaaga cgctgccgag actctgttca acaacctgtt cttcagccct gagcgctatg   1200
acctgtctgc ggtcggccgg atgaagttca accgtcgtat cggtcgtacc gagatcgaag   1260
gttcgggcgt gttgtgcaaa gaagacatcg ttgccgtgct gaagaccctg gtcgacatcc   1320
gtaacggtaa aggcatcgtc gatgacatcg accacctggg taaccgtcgt gttcgctgtg   1380
taggcgaaat ggccgagaac cagttccgcg ttggcctggt acgtgttgag cgtgcggtca   1440
aagagcgtct gtcgatggct gaaagcgaag gcctgatgcc gcaagacctg atcaacgcca   1500
agcctgtggc tgcggcggtg aaagagttct tcggttccag ccagctgtcc cagttcatgg   1560
accagaacaa ccctctgtcc gagatcaccc acaagcgccg tgtttctgca ctgggcccgg   1620
gcggtctgac gcgtgagcgt gcgggctttg aagttcgtga cgtacacccg actcactacg   1680
gccgtgtttg ccctattgag acgccggaag gtccgaacat cggtctgatc aactccctgg   1740
ctgcctatgc gcgcaccaac cagtacggct tcctcgagag cccgtaccgt gtagtgaaag   1800
acgcactggt aactgacgag atcgttttcc tgtccgccat cgaagaagct gatcacgtga   1860
tcgctcaggc ctcggccacg atgaacgaca agaaagtgct gatcgacgag ctggttgctg   1920
ttcgtcactt gaacgaattc accgtcaagg cgccggaaga cgtcaccttg atggacgttt   1980
cgccgaagca ggttgtttcg gttgcagcgt cgctgatccc gttcctggaa cacgatgacg   2040
ccaaccgtgc gttgatgggt tccaacatgc agcgtcaagc tgtaccaacc ctgcgcgctg   2100
acaagccgct ggtaggtacc ggcatggagc gtaacgtagc tcgtgactcc ggcgtttgcg   2160
tcgtggctcg tcgtggcggc gtgatcgact ctgttgatgc cagccgtatc gtggttcgtg   2220
ttgctgatga cgaagttgaa actggcgaag ccggtgtcga catctacaac ctgaccaaat   2280
acacccgttc caaccagaac acttgcatca accagcgtcc gctggtgcgc aagggtgacc   2340
gtgtacagcg tagcgacatc atggctgacg gcccgtccac cgatatgggt gaactggcgc   2400
tgggtcaaaa catgcgcatc gcgttcatgg cctggaacgg ttacaacttc gaagactcca   2460
tctgcttgtc ggaacgagtt gttcaagaag accgctttac cacgatccac attcaggaac   2520
tgacctgtgt ggcacgtgac accaagcttg ggcctgaaga gatcactgca gacatcccta   2580
acgtgggtga agctgcactg aacaaactgg acgaagccgg tatcgtttac gtaggtgctg   2640
aagttggcgc cggcgacatt ctggtaggta aggtcactcc gaaaggcgag acccagctga   2700
```

ctccggaaga gaagctgttg cgtgccatct tcggtgaaaa agccagcgac gttaaagaca 2760
cctccctgcg cgtacctacc ggtaccaaag gtactgttat cgacgtgcag gtcttcaccc 2820
gtgacggcgt tgagcgtgat gctcgtgcac tgtcgatcga gaagacccag ctggacgaga 2880
tccgcaagga tctgaacgaa gagttccgta tcgttgaagg cgctaccttc gaacgtctgc 2940
gctctgctct ggttggccgc attgccgaag gtggtgccgg tctgaagaaa ggtcaggaaa 3000
tcaccaatga aatcctggac ggtcttgagc atggtcagtg gttcaaactg cgcatggctg 3060
aagatgctct gaacgagcag cttgaaaagg ctcaggctta catcatcgat cgccgtcgtc 3120
tgctggacga caagttcgaa gacaagaagc gcaaactgca gcagggcgat gacctggctc 3180
caggcgtgct gaaaatcgtc aaggtttacc tggcaatccg ccgtcgcatc cagccgggtg 3240
acaagatggc cggtcgtcac ggtaacaagg gtgtggtctc cgtgatcatg ccggttgaag 3300
acatgccgta cgatgccaat ggcaccccgg ttgatgtggt cctcaacccg ttgggcgtac 3360
cttcgcgtat gaacgttggt cagattctcg aaactcacct gggcctcgcg gccaaaggtc 3420
tgggcgagaa gatcaacctc atgattgaag aacaacgcaa ggtcgctgac ctgcgtaagt 3480
tcctgcatga gatctacaac gaaattggcg gtcgtcaaga aagcctggat gacttctccg 3540
atcaggaaat cctggatctg gcgaagaacc ttcgcggcgg tgtgccaatg gctaccccgg 3600
tgttcgacgg tgccaaggaa agcgaaatca aggcaatgct tcgtttggca gacctgccag 3660
acagcggcca gatggtgctg actgatggtc gtaccggcaa caagttcgag cgtccggtta 3720
ccgttggcta catgtacatg ctgaagctga accacttggt agacgacaag atgcacgctc 3780
gttctaccgg ttcttacagc ctggttaccc agcagccgct gggtggtaag gcgcagttcg 3840
gtggtcagcg tttcggggag atggaggtct gggcgctgga agcctacggc gcggcataca 3900
ctctgcaaga aatgctcaca gtgaagtcgg acgatgtgaa cggccgtacc aagatgtaca 3960
aaaacatcgt ggacggcgat caccgtatgg agccgggcat gcccgagtcc ttcaacgtgt 4020
tgatcaaaga aattcgttcc ctcggcatcg atatcgatct ggaaaccgaa taa 4073

<210> SEQ ID NO 74
<211> LENGTH: 2073
<212> TYPE: DNA
<213> ORGANISM: Unknown
<220> FEATURE:
<223> OTHER INFORMATION: Description of Unknown:
DP9 Glycine--tRNA ligase beta subunit sequence

<400> SEQUENCE: 74
atggcacata attatttact agaaattgga ttggaagaaa ttccggccca tgttgtaact 60
ccaagtatca aacagttagt acaaaaagta acagccttct taaaagaaaa tcgcttaaca 120
tacgactcaa ttgatcattt ttcaactcct cgtcgtttgg caattcgaat caatgggtta 180
ggcgaccaac aacctgatat tgaagaagat gctaaaggcc ctgctcgtaa aattgctcaa 240
gatgctgatg gaaattggac taaggctgca attggcttta cacgtggaca aggtcttacg 300
gttgacgata ttacttttaa aacaatcaaa ggtacggact atgtgtacgt ccataagtta 360
atcaaaggaa agatgactaa ggaaatcctt acggggataa aagaagttgt tgaatcaatt 420
aatttcccaa caatgatgaa gtgggctaac tttgatttta aatatgtacg cccaattcgt 480
tggctggttt ctattctaga tgaagaagtc cttcctttta gtatcttaga cgtaactgcg 540
ggacgccgaa cagaaggaca tcgtttctta ggtgaagctg tcgaactggc taatgctgaa 600
gaatatgaag caaaattaca cgatcaattt gtgattgttg atgccgacga gcgtaaacaa 660

-continued

```
ttaatttcaa accaaattaa agcaattgct gaaagcaatc gttggaacgt taccccctaac    720

ccaggtcttt tagaagaggt taacaatttg gttgagtggc caaccgcttt taatggggga    780

tttgatgaaa agtatttagc tattccagaa gaggtattga taacatcaat gcgtgaccac    840

caacgcttct tctttgtccg cgaccaagct ggaaagctat tgccaaactt catctccgta    900

cgaaatggga atgaagaatt tattgaaaat gttgttcgtg gaaatgaaaa agttttaact    960

gcacgtttag aagacgctgc tttcttctac gaagaagatc aaaaacatga tattaattat   1020

tatgttgacc gacttaaaaa ggttagtttc catgataaga ttggttcaat gtacgaaaaa   1080

atgcaacgag ttaattctat tgctaaagtt attggaaaca ccttaaatct taatcaaacg   1140

gaacttgatg atatcgatcg cgctacaatg atttataaat ttgatttggt aactggtatg   1200

gttggtgagt tctcagaatt acaaggagta atgggtgaaa aatatgctca acttaatggt   1260

gaaaaccaag cagtagccca agccattcgc gaacattaca tgccaaatag cgcagaaggt   1320

gatttgcctg aaagtgtaac gggcgcggta gtcgcattag ctgataagtt tgataacatc   1380

tttagttttt tctcagctgg tatgattcca agtggttcaa acgatccata tgcattacgc   1440

cgacatgcat atggaattgt tagaatctta aatagccgtg attggcaatt agatttaaat   1500

caattcaaat cacaatttaa gactgaatta gcggagaatg gcacagcgtt tggtgtggat   1560

gtcgatcaaa actttgacca agtacttaac ttctttaatg accgtattaa acaattgctt   1620

gatcatcaaa agattagtca tgatatcgtt gaaacggtgc ttacaggtaa taatcatgat   1680

gttacggaaa ttatcgaagc tgcccaagta ctagcagatg ctaaagcgag ctctacattt   1740

aaagatgata ttgaagcttt aacacgagtt caaagaattg ctacaaagaa tgaagaaagt   1800

ggagaactta atgtagatcc acaattattt aataatgctt ctgaaggcga actttttgat   1860

caaattatta aaattgaagc tgcaaataat ttgacaatga gccaactatt tgctaaatta   1920

tgcgagttga ctcctgcgat tagcaagtac tttgacgcaa cgatggtcat ggacaaagac   1980

gaaaatatta agtgtaatcg tttgaatatg atgagtcggt tagctaattt aattctaaaa   2040

attggggatc taactaacgt acttgtaaaa taa                                2073
```

<210> SEQ ID NO 75
<211> LENGTH: 1341
<212> TYPE: DNA
<213> ORGANISM: Unknown
<220> FEATURE:
<223> OTHER INFORMATION: Description of Unknown:
DP9 Glutamine synthetase sequence

<400> SEQUENCE: 75

```
atggcaaaga aaaattattc gcaagcagat attcgtcaga tggcaaagga tgaaaatgta     60

cgttttctcc gattaatgtt tacagatctt tttggaataa ttaagaacgt tgaagtacca    120

attagtcaat tggacaaact attagataat aaattgatgt ttgatggttc ctcaattgac    180

gggtttgttc ggattgaaga aagtgacatg tatttatacc cagatctttc tacttggatg    240

gttttcccat ggggaagcga acatggcaag gtggctcgca ttatttgtga agtatactca    300

aatgatcgta aaccattcgt gggtgatcca cgtaacaatt taattcgagt actccaagag    360

atgaaggatg caggatttac tgattttaat atcggacctg aacctgagtt tttcttgttg    420

aaattagatg aaaatggtaa accaaccact aatttaaatg ataaaggtag ttactttgat    480

ttagctcctg ttgatttagg tgaaaactgc cgtcgtgata ttgttttgga acttgaaaat    540

atgggctttg atgttgaagc ttctcatcat gaagttgctc caggacaaca cgaaattgac    600
```

```
tttaaatacg ccgatgcttt gaccgctgcc gataacattc aaacctttaa gttggttgtt     660

aagacagttg cccgtaaata taacctgcat gctacattta tgcctaaacc tatggatgga     720

atcaatggtt cagggatgca tttaaacatg tcacttttca ataaggaagg caatgctttc     780

tatgacgaaa agggtgactt acaactttct caaaatgctt actggttcct tggtggacta     840

ttgaagcatg ctcgtagtta tacggccgta tgtaacccaa ttgttaactc gtacaaacgt     900

ttagttcctg gatatgaagc tccagtatac gttgcttggt caggttcaaa tcgttcacca     960

cttattcgcg ttccttcaag taagggactc tcaactcgtt ttgaagttcg aagcgtcgat    1020

ccagctgcta acccatactt agcaattgca tcagtattgg aagcaggctt agatggcatt    1080

agaaacaaga ttgaaccaga agattccgtt gatcgtaata tctatcgaat gaacattcaa    1140

gaacgtaatg aagagcatat tacagatcta ccttcaacat tacacaatgc tttgaaggaa    1200

ttccaaaatg atgatgtaat gcgtaaggca ttaggagatc acattttcca aagcttcctc    1260

gaagctaaga agttagaatg ggcttcttac cgtcaagaag tgacacaatg ggaacgtgat    1320

caatatctcg aaatgttcta g                                              1341


<210> SEQ ID NO 76
<211> LENGTH: 1947
<212> TYPE: DNA
<213> ORGANISM: Unknown
<220> FEATURE:
<223> OTHER INFORMATION: Description of Unknown:
      DP9 DNA gyrase subunit B sequence

<400> SEQUENCE: 76

ttggcagacg aaaaagaaac gaaagcagaa ttagccagag aatatgatgc gagtcaaatt      60

caggttttag aggggctcga agcagttcgt aaacgcccag gaatgtatat tgggtcgact     120

agttctcaag gactacacca tttggtttgg gaaattattg ataatggtat tgatgaagct     180

cttgcaggat ttgcagacaa aattgatgtg atcgttgaaa aagacaatag tattaccgtc     240

actgataatg gacgtgggat tccggttgat atccaaaaga aaactggaaa accagcttta     300

gaaacagtct ttacggtcct acatgccgga ggtaaattcg gcggtggcgg ttataaagtt     360

tctggaggat tgcatggtgt gggcgcatcc gttgtaaatg cgttatcaac ggaattagat     420

gcgcgcgtca tgaaggacgg taaaatctat tacattgatt ttgcgctagg aaaagtaaaa     480

acaccgatga aaacgattgg tgatactgaa catcctgacg atcatggaac tattgttcat     540

ttcgttccag atccagatat tttccaagaa actaccacat acgacattaa tatcttaaaa     600

acacgaattc gtgaattagc ctttttgaac aaaggtctac ggattacttt gaaggatatg     660

cgtcctgaaa agccaactga agacgacttc ttgtatgaag gtgggattcg ccactacgtt     720

gaatatctaa acgaaggcaa agaagtaatt ttccctgaac ctatctatgt tgaaggggtt     780

acaaaaggta tcactgttga agtagctatg caatatatcg aaggttatca aagtaaattg     840

ttaactttta ctaacaatat tcatacttac gaaggcggta cccacgaaga aggtttcaaa     900

cgtgctttaa cacgagttat taacgattac gctaaaaaca acaatatttt aaaagaaaat     960

gatgataaat tgtctggtga tgatgttcga gaaggtttga cggcagtagt cagcgttaag    1020

catcctgatc ctcaattcga aggacaaacg aaaacaaaat tgggtaactc agatgctcgg    1080

acagctgtta acgaagtgtt tgctgaaact ttcaataaat tcttattgga aaatcctaag    1140

gttgcacgtc aaattgttga taagggaatc ttggcagcaa aagcaagagt cgccgctaaa    1200

cgagctcgtg aagttacgcg taagaagagt ggcctagaac tcaataatct tcctggtaaa    1260
```

ttagctgata atacttctaa ggatccttca attagtgaat tattcattgt cgagggtgat 1320
tctgccggtg gtagtgctaa gtcgggacgt tcgcgtctca cacaagctat tttgccaatt 1380
cgtgggaaga ttttgaacgt tgaaaaagcc actttggatc gggttttggc caatgaagaa 1440
attcgttcac tctttacagc gctcggaact ggatttggtg aggactttga tgtaagtaaa 1500
gccaactatc ataaattgat tatcatgacc gatgccgatg tcgatggtgc tcatattcgg 1560
acactattat tgacgctgtt ctatcgttac atgcgtccaa tgattgatgc aggatttgtt 1620
tacattgctc aaccaccgct ctaccaagta cgtcaaggta agatgattca atatatcgat 1680
tctgatgaag aattagaaac agtacttgga caattgtcac catcaccaaa acctgtaatt 1740
caacgttata aaggtcttgg tgaaatggat gctgagcaac tttgggaaac aaccatgaat 1800
ccagaaaatc gacgcttgtt acgagtttca gccgaagatg ctgatgctgc aagtggtgat 1860
tttgaaatgt tgatgggtga caaggttgaa ccacgtcgta aattcattga agagaacgct 1920
gtgtttgtta aaaacttgga tatctaa 1947

<210> SEQ ID NO 77
<211> LENGTH: 2418
<212> TYPE: DNA
<213> ORGANISM: Unknown
<220> FEATURE:
<223> OTHER INFORMATION: Description of Unknown:
DP9 Leucine--tRNA ligase sequence

<400> SEQUENCE: 77
atggcttata atcataaaga tatcgaacag aagtggcagc aattctggag cgacaatgag 60
acttttaaga cggtcgaaga tgcagacaaa cccaaatatt atgcattaga catgttccct 120
tatccatcag gtcaaggact ccatgtgggc catcctgaag gatatacagc aacagatatt 180
atgtcacgaa tgaaacggat gcaaggttac aaagtacttc atccaatggg atgggatgct 240
tttggtcttc cagcagaaca atatgcgatg aagacgggta acaatccgcg tgattttaca 300
gctaagaata ttcaaaactt taagcgtcaa atccaatcac ttggtttttc ttatgactgg 360
tcgcgagaag ttaatacaac tgatccagct tactacaagt ggactcaatg gatttttgag 420
caactctaca agaagggctt agcttatgaa aaagaaacgc tggtaaactg ggctcctgat 480
ttaatgggtg gaacggtagt tgctaacgaa gaagttgtgg atggtaagac agaacgtggt 540
gggttccccg tttatcgtaa accaatgaaa caatggattc ttaaaattac agcttacgcc 600
gaccgtttga ttgacgattt ggacctggta gattggcccg atagtattaa agaaatgcaa 660
aaaaactgga ttggtcgttc agtgggggct agcgtcttct ttaatgttga agatagcgaa 720
aaacaaattg aagtatttac aacgcgtcca gatacattat ttggcgcaac atacttggta 780
atttcaccag aacatgacct cgttgaccaa attacaactc cagaaagtaa agctgccgtt 840
gaagaataca agaaagctgt tgcaactaaa tcagatcttg aacggacgga tttgagtaaa 900
gataagacgg gagtctttac gggagcatac gcggttaacc ctgttaatgg taagaaaatt 960
ccagtttgga ttagtgatta cgtattggct tcatacggaa ctggagcagt gatggctgtt 1020
cctgctcatg atggccgtga ctacgaattt gctaagaaat tcaagataga tatggtgcca 1080
gtttatgaag gtggcaatct tgaagatgga gtattggaca gcgaaggcgg gctaattaac 1140
tctggattcc tagatgggat ggataagcag acggctattg ataccatgat tagctggttg 1200
gaagaacatg gagttggtca taagaaggtt aactatcgtc ttcgtgactg ggtcttctct 1260
cgccaacgct actggggtga accaatccct gtaattcatt gggaagatgg agaaacaact 1320
ttgattcctg aagatgaatt gccattgaga ctcccggctg caactgacat tcgtccttcc 1380
ggtaccggag aaagcccatt agctaaccta gatgattggg taaacgtagt tgatgaaaat 1440
ggtcgtaagg gtcgccggga aactaataca atgccacaat gggcgggtag ttcatggtac 1500
ttcctccgtt acgttgatcc taagaatgat caaaagattg ctgacgaaga tttacttaaa 1560
gaatggttac cagtcgactt atatgttggt ggagctgaac atgcggtact tcatttactt 1620
tatgcacgtt tctggcacaa agttttatat gatctaggag ttgtaccaac taaggaacca 1680
ttccaaaaat tggtcaacca agggatgatt ctcggtagca atcatgagaa gatgtctaag 1740
tcaaaaggga acgtggttaa tccagatgat attgttgagc gctttggagc ggatactttta 1800 cgattatacg aaatgttcat gggacctctg acagaatcag tcgcctggag tgaagatggg 1860
cttaacggaa gtcgtaagtg gattgaccgc gtctggcgct tgatgattga cgacgaaaac 1920
caattgcgtg atcatattgt tactgaaaat gatggcagtt tggatatgat ttataaccaa 1980
actgttaaga aggtaactga tgattatgaa aacatgcgct ttaacacggc tatttcacaa 2040
atgatggtct ttgttaatga agcatacaag gctgataaac ttccagcagt atatatggaa 2100
ggattagtta agatgttagc tccaattatt ccgcacgttg ctgaagaact ttggagtttg 2160
ctaggtcacg aaggtggtat ttcatacgct gaatggccaa catatgatga aagtaagtta 2220
gtagaagcta cagttcaagt cattctacaa gttaatggta aagttcggag taaaattacc 2280
gttgacaagg atatcgccaa agaagaactt gaaaaattag cgttagctga tgctaagatt 2340
caacaatgga cggcagataa gactgttcgt aaggtaattg ttattcctaa caagattgtt 2400
aatatcgtag taggctaa 2418

<210> SEQ ID NO 78
<211> LENGTH: 1350
<212> TYPE: DNA
<213> ORGANISM: Unknown
<220> FEATURE:
<223> OTHER INFORMATION: Description of Unknown:
DP9 Glucose-6-phosphate isomerase sequence

<400> SEQUENCE: 78
atggcacata tttcatttga cagttctaat gttgcagatt ttgtacatga aaacgaactt 60
gcagaaatcc aaccacttgt tacagctgct gatcagattt tacgtgatgg ctctggcgct 120
ggtagtgatt tccgtggatg gatcgattta ccatcaaatt atgataagga cgaatttgcc 180
cgtatcaaga aagccgctga taagatccgc aatgactcag aagtattcgt tgctatcggt 240
attggtggtt catatttggg tgctcgtgca gccattgatt tcttgaacaa cactttctac 300
aatcttctta ctaaagaaca acgtaatggt gctcctcaag taatcttcgc tggtaactca 360
attagttcaa cttaccttgc tgacgtattg aacttaatcg gggaccgtga cttctcaatt 420
aacgtaattt ctaagtcagg tacaactaca gaaccagcta ttgcattccg tgttcttaaa 480
gaaaaactaa tcaagaagta cggtgaagaa gaagctaaga aacgtatcta tgcaacaact 540
gaccgtgcta aaggcgccct aaagacagaa gctgatgcag aaaactatga agaattcgta 600
gttcctgatg acattggtgg tcgtttctct gttctttcag ctgttggttt attaccaatc 660
gcggttgccg gtggcgatat tgaccaattg atgaagggtg ctgaagatgc aagcaacgaa 720
tacaaggatg ctgatgttac aaagaacgaa gcatacaagt acgctgcttt acgtaacatc 780
ctttatcgta agggctacac aacagaactt cttgaaaact acgaaccaac acttcaatac 840
ttcggcgaat ggtggaagca attgatgggt gaatcagaag gtaaagatca aaagggtatc 900
tacccatctt ctgctaactt ctcaactgac ttacattcac taggacaata catccaagaa 960
ggtcgtcgca atttaatgga aacagttatc aatgttgaaa agcctaacca tgacatcgac 1020
attcctaagg ctgaccaaga ccttgatgga ttacgttatc tcgaaggtcg cacaatggac 1080
gaagttaaca agaaagctta ccaaggtgta actcttgctc ataacgacgg tggtgttcca 1140
gttatgacgg ttaacattcc tgatcaaaca gcttacacat taggctatat gatttacttc 1200
ttcgaagcag ctgttgctgt atctggttac ttgaacggaa ttaatccatt caaccaacca 1260
ggtgttgaag catacaagtc aaatatgttt gcattacttg gtaaaccagg ttatgaagat 1320
aagacagctg aattaaacgc tcgtctataa 1350

<210> SEQ ID NO 79
<211> LENGTH: 1725
<212> TYPE: DNA
<213> ORGANISM: Unknown
<220> FEATURE:
<223> OTHER INFORMATION: Description of Unknown:
DP9 Phosphoglucomutase sequence

<400> SEQUENCE: 79
atgagttggg aagattctgt caaagaatgg caagattatg cagatttaga ttttaattta 60
aaaaaagaat tagcaacttt agctgaagat aaagatgctt taaaagaagc cttttatgct 120
ccaatggaat ttggtacagc aggaatgcgt ggcgtaatgg gccctggtat caaccggatg 180
aatatctata cggttcgtca agcaacagaa ggtttagcta attttatgga taccttagat 240
tttactgata agaaacgggg agtggcgatc agttttgatt cccgctatca ctcacaagag 300
tttgctttag cagcagctgg tgttttaggt aagcatggta ttccaagttt tgtttttgat 360
agtatgcgtc ccactccaga attatcatat acagtacgtg agttaaacac ttatgctgga 420
atcatgatta ctgctagtca taatcctaaa caatataatg gatataagat ttatggtcct 480
gatggcggac aaatgccacc aatggaatct gataagatta cagaatatat tcgccaagta 540
actgacatct ttggtgttga agctcttact caaagtgaat taagagctaa gggcttaatg 600
accattattg gtgaagacat tgacctcaag tatcttgagg aagttaagac ggtatcaatt 660
aatcatgaac taatccagcg ctttggtgca gacatgaagt tgatctactc accattacat 720
ggtactggaa aagtagttgg tggacgtgcg ttagaaaatg ctggttttaa ggattacact 780
atggtccctg aacaagcaat tgctgaccca gaatttatta caacgccatt ccctaaccca 840
gaattcccac aaacttttga tttggctatt gaattaggta aaaagcaaga tgctgacctt 900
ttgattgcca ctgatccgga tgccgatcgt ttgggagctg ccgttcgttt accaaatggt 960
gactacaaat tattgacagg gaaccaaatt gcagccttga tgttagaata catcttaact 1020
gcgcatgatg cagcaggtga cttgccaggt aacgcagctg ccgttaagtc aattgtttct 1080
agtgaactag caaccagaat tgccgaagcc catcatgtag aaatgattaa cgttctaact 1140
gggtttaagt acattgctga ccaaattaaa cattacgaag aaaatggcga ccataccttt 1200
atgtttggtt tcgaagaaag ttatggctat cttgttcggc catttgttcg cgataaagat 1260
gccatccaag gaattgtcct attggctgaa attgctgctt attatcgtag taaggggcaa 1320
accttatatg acggtcttca aaacttattt actacttacg gatatcatga agaaaagacc 1380
atttcaaaag atttccctgg agttgacggt aaagaaaaaa tggctgccat tatggaaaag 1440
gttcgtgaag aacgcccaag tcaatttgat cagtacaagg tattagaaac tgaagacttc 1500
ttagctcaaa ctaagtatga agcagatgga tctacccaag ctatcaaatt accaaaagcg 1560
gatgttttga aatttacatt agatgatggt acttggattg caattcgtcc ttctggaaca 1620
gaaccaaaaa ttaaattcta tattggtaca gttggcgaag atgaaaaaga tgctttgaat 1680
aagattgatg tttttgaaac agctattaat gaacttataa aataa 1725

<210> SEQ ID NO 80
<211> LENGTH: 3426
<212> TYPE: DNA
<213> ORGANISM: Unknown
<220> FEATURE:
<223> OTHER INFORMATION: Description of Unknown:
DP9 2-oxoglutarate carboxylase small subunit sequence

<400> SEQUENCE: 80
atgcaccgta ttttaattgc caaccgaggc gaaattgcga cccgaattat tcgggcaacg 60
catgaactcg gaaaaacagc tgtagcaatt tatgctaaag cggatgaatt ttctatgcat 120
cgttttaaag cagatgaagc ttaccaagtt ggtgaagata gtgatccaat tggagcatat 180
ttaaatattg atgacattat tcgtattgca aaagaaaata atattgatgc aattcacccc 240
ggctatggat tttgtcgga aaatgctgta tttgcgcgag cagttgaagc agctgggatt 300
aagttcattg gacctcgacc cgaattacta gaaatgtttg gtgataaatt acaagctaaa 360
aatgcagcca ttaaggccgg tgtaccaact attccgggaa cggaaaaacc agttaaagat 420
gtcgatgacg cgctaaattt tgcagagcaa tttggctatc ctatatttgt taagtcagcg 480
gcaggtggcg gcggaaaagg gatgcggatt gtacatcatc aacaagagat gcgcgaagca 540
tttaagatgg ctcagtcaga agcttcttcg tcttttggtg acgatgaaat ttacttagaa 600
cgttacttag ttgatccaat ccatattgag gttcaagtag ttgcggatga acacggtgag 660
atggttcatt tgtatgaacg aaattcatcg attcagcgac gccatcaaaa aatcattgaa 720
tttgctccag cagtgggaat ttctgccacc gtccgtgatc aaataagaaa agctgcttta 780
aaattattga agtcggtcaa ttatagtaac gctgcaacca ttgagttttt ggtagaaggt 840
aatcaatttt actttatgga agtgaatcca cgaattcagg ttgaacatac agttaccgaa 900
gaagtcacgg gaatcgatat tgtgcaaacc caaattaagg ttgctgaagg tcaaagatta 960
cacgaagaaa tcggtgttcc tcaacaagcc caaattgaag ctgtgggagt ggcaattcaa 1020
gcccgaatta ccactgaaga tccaatgaat aactttattc cagatgtcgg tagaatccag 1080
acgtatcgtt cacctggtgg aacaggtgtg agattggatg ctggaaatgc ctttgctgga 1140
gccattgtaa ctccgcatta tgattcactt ctgaccaagg caattgtcca tgcgccaacc 1200
tttgacgaag ccttggtaaa gatggatcga gtgctcaatg aatttgtaat tgctggggtt 1260
aaaactaata ttccattttt aaagaaatta attcatcatc ctatttttag atcggaatta 1320
gctccgacaa cctttgtgga tgagacacca gaactctttg atttaaaagc tgaaactccg 1380
gtagttactc aacttttgag ttacattgct aatactacta tcaatggtta tccaggctta 1440
gaaaagcaga atccagtagt gttaactcgg ccagtccgtc cacattttga agcacaagta 1500
ccgcatgaaa atgcgaaaca gatcttggat agtaagggac ctgatgccat gatcaattgg 1560
ctgttaaaac aaaagcaggt cttgctaacc gatacgacca tgcgggatgc ccatcaatca 1620
ttatttgcta cgcgaatgcg gaccaaagac atggtagaaa ttgccgatca agtccagaaa 1680
ggtctgccta acctattttc agctgaagtt tggggcggtg cgacctttga tgttgcttat 1740
cggttcctag gtgaggatcc atgggaaaga ctccaacaat tgcgggctaa aatgccaaat 1800
acgatgctcc aaatgctttt acgtgggtca aatgcagtag ggtatcaaaa ttatccagac 1860

```
aacgccattg acgaatttat tcgattggct gccaaaaatg gaattgatgt tttccgaatc   1920
tttgattctc ttaattgggt gccacagctt gaagaatcta tccaacgggt gcgtgataat   1980
ggaaaagtgg ctgaagcagc catggcatat actggcgata ttttagatac taatcgtact   2040
aaatataatt tgaaatatta tgtggatttg gctcaagaac tccaagcagc aggtgctcat   2100
attattggaa tcaaagatat gtcaggaatt ttaaaaccac aagctgctta tgcattaatt   2160
tcagagttaa aaaatcatct ggatgtgcca attcatttgc atacgcacga tactacaggc   2220
aacggcattt tcttatattc tgaagcaata cgagctggag ttgatgtggt cgacgttgcc   2280
acttctgcgc tagcgggaac gacttctcag ccttcaatgc agtctcttta ctatgcgttg   2340
tctaataacc agcgccaacc agatttagat attcaaaaag cagaaaaact agatgaatat   2400
tggggcggaa ttcgaccata ttacgaagga tttggcaccc aattaaatgg accacaaact   2460
gaaatttatc gaattgaaat gcctggtgga cagtatacca accttcgcca gcaagctaac   2520
gcagtccatt tgggtaagcg ttgggatgag attaaggaaa tgtacgcaac cgtcaatcaa   2580
atgtttggcg atattccaaa ggttacgcct tcttctaaag tagttggcga tatggcacta   2640
ttcatggtcc aaaatgattt gacgcctgaa atggtaatga acgataaggg acaattaagt   2700
tttcccgaat cagtggtaaa ctttttccgt ggtgatttag gacaaccggc gggtggtttt   2760
ccaaaacagc tccaaaaggt gattctaaaa gagcaagccc cattgacagt acgaccagga   2820
gctttagccg atccagttga ttttgatcaa gttcgtaaac aggcaactaa ggttttaggt   2880
caccaagcaa gtgatgaaga agttatgtcg tttattatgt atccagatgt gatgaccgaa   2940
tacattcaac gtcaaaatga atatggtcca gtaccattat tagatactcc aatctttttc   3000
caaggcatgc atattggcca acgcattgat ttacaattgg gacgcggaaa atcggtcatt   3060
attgtccttc gagaaattag tgaagcagat gaggcgggcc aaaggtcact tttctttgat   3120
ataaatggac aaagtgaaga agtgattgtt tatgatgtta atgcgcaggt aacgaaagta   3180
aagaagatta aagctgatcc gactaaagcc gaacagattg gcgctactat ggcgggctcg   3240
gtcattgaag tccaagtaga agcgggccaa aaggtccagc gaggtgataa cttaattgtc   3300
actgaggcga tgaaaatgga gaccgcgtta agagcacctt tcgacgcaac cattaagaag   3360
atttatgcta cccctgaaat gcaaatcgag acgggggatt tattgattga actagaaaag   3420
gagtaa                                                              3426
```

<210> SEQ ID NO 81
<211> LENGTH: 2058
<212> TYPE: DNA
<213> ORGANISM: Unknown
<220> FEATURE:
<223> OTHER INFORMATION: Description of Unknown:
      DP3 Glycine--tRNA ligase beta subunit sequence

<400> SEQUENCE: 81

```
atgtcaacat ttttattaga aattggactt gaagaaatac cagctcattt ggtaaccagt     60
tcagagaatc agttaattga aagaactaaa aagttcttat cagagcatcg tttaacagta    120
ggtgatatta aaccatattc aacaccgcga cgtctggctg tcgttttgac agatgttgct    180
gaaacatcag aaagtttaag cgaagaaaag cgtggaccat ctgttgaccg tgcacaagac    240
gaaaacggta attggacaaa ggcagcatta ggttttgcac gtggtcaagg tgctaatcct    300
gaagcatttg aaattaaaga tggatatgtt tggctaacaa aacgtactgc tggtgtagcc    360
gcgaatgaaa ttttagctaa aattggtgat gaagttgtcg cccaaatgaa attttcaact    420
```

-continued tatatgaagt gggctaatca cagctttttg tatgttcgac ctattcgttg gctcgtagca 480
cttcttgata gtgaagtcat ttctttcaac gtgttagata ttaccacaga tcgtttcaca 540
cgtggtcatc gttttttgtc ttcagaacat gttgaaatat cttctgcaga taattatgta 600
acgactttgc agggtgctaa cgtggttgtt gatgctacag tgcgcaaaaa tgaaattcga 660
tcgcagttga atgcaattgc tgaagctaat ggttgggttc tgcaacttga gaccgatgcg 720
gcgcaagatt tgttggaaga agttaataac attgttgagt ggccaacagc gtttgctggc 780
agtttcgatg agaaatattt agaaatacca gatgaagttt tgattacatc aatgcgcgaa 840
catcagcgtt tcttctttgt gacgaatgaa aaaggacaat tattgccaca ctttttgtca 900
ataagaaatg gtaaccgtga gcatctaaac aacgttattg ctggaaatga aaaagtattg 960
gtagcaaggt tagaagatgc cgaattcttc tatcatgaag accaaaccaa atcaatttct 1020
gattacatga ctaaagttaa aaagttagtc ttccatgaaa aaattggtac ggtgtatgaa 1080
cacatgcaac gcactggtgc tttggcttca gcaatggcgg tggttttgaa gtttgatgaa 1140
gtacaacagg ctgatttgac ccgtgcatca gaaatttata aatttgattt gatgaccggt 1200
atggttggtg aatttgatga acttcaaggc attatgggtg agcattatgc caagcttttt 1260
ggcgaagatg atgcggttgc aacagccatt cgagagcatt atatgccaac ttcagctaat 1320
ggtgaggttg cgcaatctga aattggtgct ttgttggccg ttgcggataa acttgatagc 1380
attgtgacgt tttttgctgc tggattaata ccaagtggtt ctaatgatcc ttatggctta 1440
cgacgtgcag ctactggcat cgtgcgtaca ttggtggata aaaaatggca tattgatttg 1500
cggcctttgc tagctgattt tgtgcaacag caaggtaagg taactgacac cgatttaacg 1560
acatttgttg atttcatgtt ggatcgtgtt cgtaaattat cgttggatgc tggaatacgt 1620
caagatattg tcattgctgg attaggcaac gttgatagag ctgatatcgt atatattagt 1680
cagcgagtcg aagttttgtc ccaacatagt ggtgatggca atttccgaga tgtaattgag 1740
gcactgactc gtgtggatcg cttagccgta aagcaagtaa ctaatgcaac ggttgatcct 1800
gctaagtttg aaaatcaatc tgaaaaggac ctatatcaag caacgttaac gcttgattta 1860
aatactttga tgcatgacgg tgcagaaaat ctctacatgg ccttagcaaa tttgcaaaaa 1920
ccaattgcgg cttattttga tgaaaccatg gttaacgctg aagatgaatc tgttaaagat 1980
aatcgatatg cgcagctgaa cgtcatacaa cgactaacca acggattagg agatttgacg 2040
caaatcgtca ttaagtaa 2058

<210> SEQ ID NO 82
<211> LENGTH: 1347
<212> TYPE: DNA
<213> ORGANISM: Unknown
<220> FEATURE:
<223> OTHER INFORMATION: Description of Unknown:
DP3 Glutamine synthetase sequence

<400> SEQUENCE: 82
atggctcgta aaacatttac caaagaagaa attaaacaaa ttgttgttga tgaaaatgta 60
gaattcattc gtgtaacatt cactgatgtc ttaggtgcga ttaaaaacgt tgaagtacca 120
acttctcaat tagataaggt gcttgacaac aatttaatgt ttgacggttc atcaatcgag 180
ggatttgttc gtatcaatga atcagatatg tatctttacc ccgatttatc aacatttatg 240
attttcccat gggcaacgga tggtcatggt ggtaaagtgg cccgcttgat tgccgacatt 300
tatactgctg atcgtgagcc atttgctgga gacccccgtc atgcgttacg ttcggtactc 360
gctgacgcgc gtgaagctgg gtttacggcg tttaatgtcg ggacagaacc tgaatttttc 420
ttgtttaaac ttgatgaaaa aggcaaccca accacagagt taaacgacaa aggtggttat 480
tttgacctag caccattgga tatgggtgaa aatgttcgtc gtgaaattgt tttgactttg 540
gaaaaaatgg gctttgaaat tgaagctgct caccacgaag ttgccgaagg acagcatgaa 600
gtagacttta aatacgcttc agctcttgaa gccgctgaca acattcagac gtttaagttg 660
gttgttaaaa ccatcgcacg caagaatggt tactatgcta cctttatgcc aaagcctgtt 720
gcaggtatta acggatccgg tatgcacaca aacatgtcat tatttacaaa agatggtaac 780
gcatttgttg atacatcgga tgaaatgggc ttgtcaaaaa cagcatataa cttcttgggt 840
ggtattttag aacatgcgac tgcgtttaca gcgcttgcaa acccaacagt taactcatac 900
aagcgcttga caccaggatt cgaagcacct gtttatgttg catggtcagc atcaaatcgt 960
tcaccaatgg ttcgagttcc ggcctcacgt ggtaattcaa cacgtttgga acttcgttca 1020
gttgacccaa cagctaatcc ttatactgca ttggcagcca ttttggcttc aggactggat 1080
gggatcaagc gtgaattaga gcctttggcc tcagttgata aaaatattta tttgatggat 1140
gaggtcgaac gggaaaaggc aggcattaca gacttaccag atactctgtt ggctgcagtt 1200
cgtgagttgg cggctgatga tgttgttcgt tcagctattg gagaacatat tgctgataag 1260
tttattgaag caaagaagat tgaatacaca tcatatcgtc agtttgtttc tgaatgggaa 1320
acagattctt atcttgaaaa ttactaa 1347

<210> SEQ ID NO 83
<211> LENGTH: 2049
<212> TYPE: DNA
<213> ORGANISM: Unknown
<220> FEATURE:
<223> OTHER INFORMATION: Description of Unknown:
DP3 DNA gyrase subunit B sequence

<400> SEQUENCE: 83
gtgttcgcag attatatctg ttcacacgct aataatatgg cagagaatat cgaaaatgaa 60
gcattggaga acattgatgg catcgtaacc gatgataccg aaatccgtca agcaagcacc 120
gttcatgcag cagcaggcgc ttacaatgct gatcagattc aagttttgga aggattggaa 180
gctgtccgca aacgccctgg catgtacatt ggtacgacca cagcgcaagg cttgcaccat 240
ttggtatggg aaattgttga taacgggatt gatgaggcat tagcagggtt tgcgtcacat 300
attacggtca caatcgaaaa ggataactca atcacggtaa ccgatgacgg ccgtggtatt 360
cctgtcgaca ttcaaactaa aacgggtaag ccagctcttg aaactgtctt tacggtatta 420
cacgccggtg gtaaatttgg cggtggcggt tataaagtat ctggtggatt acacggtgtt 480
ggagcttctg ttgtcaatgc cttgtcaacg gatttggacg ttagagttgt tcgtgataat 540
actgtttatt acatggactt caaagtggga cgcgtcaaca caccgatgaa acaattgacg 600
gaaaagccca ctattgagcg tggtacaatt gttcatttta agcccgatgc agatattttc 660
cgtgaaacaa cagtttataa ctacaacaca ttactaacac gtgtgcgcga attggccttt 720
ttgaataaag gtttgcgcat ttcgattaca gataatcgac ctgaagaagc tgtttctgaa 780
agctttcatt ttgaaggtgg gattaaagaa tacgtcagct atttgaataa ggacaagact 840
gctattttcc ctgaacctgt ttacgttgag ggtgaagaaa atggcattgt agtggaagct 900
gccttacagt acactaccga tattaaagac aatctgcgga cgtttactaa caatatcaat 960
acctatgaag gtgggacgca cgaaactggc tttaaaacag ccttaacacg tgtaatcaat 1020
gattacgctc gtaaaaatgg tcagctcaaa gataatgcag aaagtttgac aggggaagat 1080
gtgcgcgaag gcatgactgc tatcgtgtca atcaagcacc cagatccaca atttgaagga 1140
caaaccaaaa ctaaattagg taactccgat gcacgtcaag caacggatcg gatgttctca 1200
gaaacgttca gtcgtttcat gatggaaaat ccagcagttg ccaagcaaat tgttgaaaaa 1260
ggtgtcttag cccaaaaagc acgattggct gccaagcgtg cacgcgaaat gacacgcaaa 1320
caatctggtt tggaaattgg taatttgcca ggtaaattag ctgataatac ctcaaatgat 1380
cctgaaattt cagaattatt tattgttgag ggtgattcag ccggtggttc agctaagcaa 1440
ggacgtaacc gtttgacgca agctattttg ccaattcgag gcaaaatttt aaatgttggg 1500
aaagcctcat tggatcgggt gttagccaac gaagaaattc gatcattgtt tacagcaatg 1560
ggaactggat ttggtgagga ctttaatgtt gaaaaagcca attatcacaa agtcattatt 1620
atgacagatg ccgatgtcga tggcgcccat attcgaacac tattgttaac gctattttat 1680
cgttatatgc gaccacttgt tgacgcaggc tatatttata ttgcgcagcc accgctttac 1740
ggtgttgcct taggcaataa taaatcaatg acgtacattg attctgatga agaacttgaa 1800
gactatttgt cacaattgcc atctaatatt aaaccaaaag ttcaacgtta taagggacta 1860
ggggaaatgg attacgatca actagcagat acaaccatgg atccgcagaa tcgtcgtttg 1920
ctacgtgttg acccaactga tgctgaagaa gccgaagcag ttattgatat gttaatgggt 1980
ggggatgtac caccacgtcg taagtttatt gaagacaatg ctgtctttgt tgagaacttg 2040
gatatttaa 2049

<210> SEQ ID NO 84
<211> LENGTH: 375
<212> TYPE: DNA
<213> ORGANISM: Unknown
<220> FEATURE:
<223> OTHER INFORMATION: Description of Unknown:
DP3 Leucine--tRNA ligase sequence

<400> SEQUENCE: 84
atgattttcg tcaacgaagc ttacaaaacc gatgctgtgc cgaaagcggc ggcggaaaac 60
ttcgtacaga tgctgtcccc actggcaccg catttggcag aagaactgtg ggaacgactt 120
ggtcataccg atacgattac gtatgaacca tggccaacgt acgatgaggc ttggaccata 180
gaatccgaag tggaaatcgt cgtgcaagtg aacggcaaaa tcgtagaacg cacgaaaatt 240
tccaaagacc tggatcaagc agcgatgcaa gaacacagct taagcctgcc gaatgttcag 300
caggctgtgg ctgggaagac gatccgcaaa gtgattgcgg tgccaggcaa gctggtgaat 360
atcgtcgttg gataa 375

<210> SEQ ID NO 85
<211> LENGTH: 1353
<212> TYPE: DNA
<213> ORGANISM: Unknown
<220> FEATURE:
<223> OTHER INFORMATION: Description of Unknown:
DP3 Glucose-6-phosphate isomerase sequence

<400> SEQUENCE: 85
atggcacaca ttacatttga cacaaagaac attgagaatt ttgttgcacc atacgaattg 60
gacgaaatgc aaccattaat tacgatggct gaccaacaat tgcgcaatcg tacgggcgct 120
ggtgcagaat attctgattg gttgactcta cctactgatt acgacaagga agaatttgca 180

-continued cgtattcaaa aggcggcgca acaaattcaa tctgattcaa agattttggt tgtcattggt 240
attggtggtt catatttggg cgcgaagatg gcggttgatt tcttgaatcc aatgtttaat 300
aatgaattgt cggatgacca acgtcaaggt gttaaaattt attttgctgg taactcaact 360
tctgcagctt acttaaatga tttagttcgt gtcattggtg atcaagactt ttctgtcaac 420
gttatctcaa agtctggcac aacaacggaa ccatcaatcg ctttccgtgt gtttaaacaa 480
ttgttagaga aaaagtatgg ttctgatgct gctaagaagc gtatctatgc cacaacagat 540
gccaatcgtg gtgctttgca cgatgaagca gcggcttcag gttatgaaac attcacaatt 600
cctgatggtg tcggtggtcg cttctctgtt ttgacagctg ttggcttgtt gccaattgct 660
gcttcaggcg ctgatatcca aaaattgatg gacggcgctc gtgatgcgca aaacgaatat 720
actgattctg atttgaaaaa gaacgaggca tataaatatg cagccgttcg tcgtattttg 780
tatgataagg gttatacaac agaattgttg attaactggg aaccttcaat gcaatatttg 840
tcagagtggt ggaagcaatt gatgggcgag tctgaaggta aaaatcaaaa gggtatctat 900
ccatcttcag ctaacttctc aaccgacttg cactcacttg gacaatatat tcaagaagga 960
cgccgtgatt tgtttgagac ggtggttaag ttagacaatc ctgtatctaa tttggaccta 1020
ccacatgaag aaggcaacaa tgatggtttg caatatttgg aaggtatcac gatcgatgaa 1080
gtgaacacca aagcatctca aggggttact ttggctcacg ttgatggtgg tgtgcctaac 1140
ttggctgttc acttgccagc acaagatgct tattcactcg gttacatgat ttacttcttt 1200
gaaatggctg ttggggcgtc tggttatacg tttggtatta acccattcaa ccaaccgggt 1260
gtcgaagcct ataagacagc tatgtttgca ctattaggta agcctggcta tgaggaagcg 1320
acaaaagcat tccgtgcccg cttagacaaa taa 1353

<210> SEQ ID NO 86
<211> LENGTH: 672
<212> TYPE: DNA
<213> ORGANISM: Unknown
<220> FEATURE:
<223> OTHER INFORMATION: Description of Unknown:
DP3 Beta-phosphoglucomutase sequence

<400> SEQUENCE: 86
atgactaaat tttcagatat taaaggtttt gcctttgatt tagatggggt tattgctgat 60
acggcgcgtt tccatggtga agcttggcat caaacagctg atgaggttgg cacaacttgg 120
acaccagaat tggctgaagg tttgaagggc attagtcgta tggcttcctt gcaaatgatt 180
ttggatgctg ggatcatgc cgatgatttt tcgcaagcag ataaagaagc attagcagaa 240
aagaaaaatc ataattatca acaacttatt tcaacattga cggaagatga tattttgcct 300
ggcatgaaag attttattca atcagccaag gcagccggct atacaatgtc ggtggcatca 360
gcttctaaaa acgcaccaat gattctagat catttgggat tgaccaagta ttttgtcggc 420
attgttgatc ccgccacttt gacaaaggga aaacctgatc ctgaaatctt cgttcgtgct 480
gcggaagtct tacatttaaa tccagaaaat gttattggat tggaagattc agctgctggt 540
attgtgtcaa tcaatggcgc aggtgagaca tcactagcca ttggtaacgc agatgttttg 600
tcaggagcgg acttgaattt tgcgtctact tcagaagtga ccttagcaaa tattgaagct 660
aaaatgcaat ag 672

<210> SEQ ID NO 87
<211> LENGTH: 1377
<212> TYPE: DNA

<213> ORGANISM: Unknown
<220> FEATURE:
<223> OTHER INFORMATION: Description of Unknown:
      DP3 2-oxoglutarate carboxylase small subunit sequence

<400> SEQUENCE: 87
atgtttaaaa aagtgcttgt tgctaatcgt ggtgaaattg cggttcgcat cattcgaacg 60
ctcaaagaaa tggggattgc ttcagtcgct atttactcga cagccgataa agatagttta 120
cacgtacaaa tcgctgacga agcgattgct gtggggggac cgaaacctaa agattcatac 180
ttaaatatga aaaatatttt aagtgcagcc ctgctgtcgg gagcagaggc aattcatcca 240
ggatatggct ttttagctga aaatacattg tttgctgaaa tggttggcga agttggtatt 300
aaatggattg ggcctaggcc agaaacaatt gagttaatgg gtaacaaagc taacgcacgt 360
gaagaaatgc ggcgtgccgg cgtaccagta attccaggtt cagagggatt tatccgtgat 420
tttcatgaag caaaaacggt tgctgataaa attggctatc ctttgttgct aaaagctgcc 480
gctggtggtg gtggtaaagg catgcgtttt gtttacggtg aggatgagtt atcagataaa 540
tttgatgatg ctcaaaacga agcgcgtgct tcgtttggcg atgatcacat gtatattgaa 600
aaagttatgt cacgtgttcg ccacattgaa atgcaagtgt ttcgtgatga gaatggtcat 660
gttgtttact tgccagaacg aaattgctca ttgcaacgca ataatcaaaa ggtgattgaa 720
gaatcaccag ctacgggtgt aacgcctgaa atgcgtgcgc atcttggcga aattgttact 780
aaagccgcaa aagcattggc gtatgaaaat actggaacca ttgaattttt gcaagatcgc 840
gatggtcatt tctactttat ggaaatgaac acacgtattc aagtagaaca tccagtttct 900
gaaatggtaa cgggattaga tttaattaag ttacaaattc aagttgctgc aggcttagat 960
ttaccggtgg ttcaagatga cgtgatcgtt caaggccact ctatcgaagt acgtttgacg 1020
gctgagcagc cagaaaaaca ctttgcacct agtgctggaa cgattgattt tgttttttg 1080 ccaactggtg gaccgggtgt tcgtattgat tcagccttat ttaatggcga taaaattcaa 1140
ccattttacg attctatgat tggcaaatta attgttaagg ccgatgatcg tgaaacagcc 1200
atgagaaaga ttcaacgtgt ggttgatgaa actgttgtac gtggtgtagc aacgagccgt 1260
aattttcaaa aagctctgtt agctgatcca caggttcaac gtggcgaatt tgacacacgt 1320
tatttggaaa ctgaattttt accgagatgg acacaaacat tgccagataa tcaataa 1377

<210> SEQ ID NO 88
<211> LENGTH: 1701
<212> TYPE: DNA
<213> ORGANISM: Unknown
<220> FEATURE:
<223> OTHER INFORMATION: Description of Unknown:
      DP1 Glutamine--tRNA ligase sequence

<400> SEQUENCE: 88
atgagcaagc ccactgtcga ccctacctcg aattccaagg ccggacctgc cgtcccggtc 60
aatttcctgc gcccgatcat ccaggcggac ctggattcgg gcaagcatac gcagatcgtc 120
acccgcttcc cgccagagcc caacggctac ctgcacatcg gtcatgccaa gtcgatttgt 180
gtgaacttcg gcctggctca ggagttcggt ggcgttacgc acctgcgttt cgacgacacc 240
aacccggcca aggaagacca ggaatacatc gacgccatcg aaagcgacat caagtggctg 300
ggcttcgaat ggtccggtga agtgcgctat gcatccaagt atttcgacca gctgttcgac 360
tgggccgtcg agttgatcaa ggccggcaag gcctacgttg acgacctgac cccgagcaa 420 gccaaggaat accgtggcag cctgaccgag ccgggcaaga acagcccgtt ccgcgaccgt 480
tcggtcgaag agaacctcga ctggttcaac cgcatgcgcg ccggtgagtt cccggacggc 540
gcccgcgtgc tgcgcgccaa gatcgacatg gcctcgccga acatgaacct gcgcgacccg 600
atcatgtacc gcattcgcca tgcccatcac caccagaccg gtgacaagtg gtgcatctac 660
cccaactacg acttcaccca cggtcagtcg gacgccatcg aaggcatcac ccactccatc 720
tgcaccctgg agttcgaaag ccatcgccct ctgtacgaat ggttcctgga cagcctgccg 780
gtgccggcgc acccgcgtca gtacgaattc agccgcctga acctgaacta caccatcacc 840
agcaagcgca agctcaagca actggtcgat gaaaagcacg tgcatggctg ggacgacccg 900
cgcatgtcga cgctctcggg tttccgtcgt cgtggctaca ccccggcgtc gatccgcaat 960
ttctgcgaca tggtcggcac caaccgttct gacggtgtgg tcgattacgg catgcttgag 1020
ttcagcatcc gtcaggatct ggacgcgaac gcgccgcgcg ccatgtgcgt gctgcgtccg 1080
ttgaaagtcg tgatcaccaa ctacccggaa gacaaggtcg accaccttga gctgccgcgt 1140
cacccgcaga aagaagagct gggcgtgcgc aagctgccgt tcgcgcgcga aatctacatc 1200
gaccgtgacg acttcatgga agagccgccg aagggttaca agcgcctgga gccgaacggc 1260
gaagtgcgcc tgcgtggcag ctacgtgatc cgcgccgacg aagcaatcaa ggacgccgaa 1320
ggcaacatcg tcgaactgcg ctgctcgtac gatccggaaa cactcggcaa gaaccctgaa 1380
ggccgtaagg tcaagggcgt gatccactgg gtgccggccg ctgccagcat cgagtgcgaa 1440
gtgcgtctgt acgatcgtct gttccgatcg ccgaacccgg agaaggccga agacagcgcc 1500
agcttcctgg acaacatcaa ccctgactcg ctgcaagtgc ttacaggttg tcgtgctgag 1560
ccatcgcttg gcgacgcaca gccggaagac cgtttccagt tcgagcgcga aggttacttc 1620
tgcgcggata tcaaggactc gaaacccggt gctccggtat tcaaccgtac cgtgaccttg 1680
cgtgattcgt ggggccagtg a 1701

<210> SEQ ID NO 89
<211> LENGTH: 2418
<212> TYPE: DNA
<213> ORGANISM: Unknown
<220> FEATURE:
<223> OTHER INFORMATION: Description of Unknown:
DP1 DNA gyrase subunit B sequence

<400> SEQUENCE: 89
atgagcgaag aaaacacgta cgactcgacc agcattaaag tgctgaaagg tttggatgcc 60
gtacgcaaac gtcccggtat gtacatcggc gacaccgatg atggtagcgg tctgcaccac 120
atggtgttcg aggtggtcga caactccatc gacgaagctt tggccggtca ctgcgacgac 180
atcagcatta tcatccaccc ggatgagtcc atcacggtgc gcgacaacgg tcgcggcatt 240
ccggtcgatg tgcacaaaga agaaggcgtt tcggcggctg aggtcatcat gaccgtgctg 300
cacgccggcg gtaagttcga tgacaactct tataaagtct ccggcggtct gcacggtgta 360
ggtgtgtcgg tagtgaacgc actgtccgaa gagctgatcc tgaccgttcg ccgtagcggc 420
aagatttggg agcagacgta cgtccatggt gtgccacaag agccgatgaa aatcgttggc 480
gacagtgaat ccacgggtac gcagatccac ttcaagccat cggctgaaac cttcaagaac 540
atccacttta gctgggacat cctggccaag cggattcgcg aactgtcctt cctcaactcc 600
ggtgtgggta tcgtcctcaa ggacgagcgc agcggcaagg aagaactgtt caagtacgaa 660
ggcggtctgc gcgcgttcgt tgaatacctg aacaccaata agaccgcggt caaccaggtg 720
ttccacttca acattcagcg tgaagacggc atcggcgtgg aaatcgccct gcagtggaac 780
gacagcttca acgagaactt gttgtgcttc accaacaaca ttccacagcg cgatggcggt 840
actcacttgg tgggtttccg ttccgcactg acgcgtaacc tgaacactta catcgaagcc 900
gaaggcttgg ccaagaagca caaagtcgcc accaccggtg acgatgcgcg tgaaggcctg 960
accgcgatta tctcggtgaa agtgccggat cccaagttca gctcccagac caaagacaag 1020
ctggtttctt ccgaggtgaa gaccgccgtg gaacaggaga tggcaagta cttctccgac 1080 ttcctgctgg agaacccgaa cgaagccaag ctggtcgtcg gcaagatgat cgacgctgca 1140
cgtgctcgcg aagcggcgcg taaagcccgt gagatgaccc gtcgtaaagg cgcgctggat 1200
attgctggct tgcctggcaa gttggctgac tgccaggaga aggacccagc gctctccgag 1260
ctatatcttg tggaaggtga ctctgctggc ggttccgcca agcagggtcg taaccgtcgc 1320
acccaggcga tcctgccgtt gaaaggcaag attctcaacg tagagaaggc ccgcttcgac 1380
aagatgattt cctcccagga agtcggcacc ttgattacgg cgttgggttg cggcattggc 1440
cgcgatgagt acaacatcga caagctgcgc taccacaaca tcatcatcat gaccgatgct 1500
gacgtcgacg gttcgcacat ccgtaccttg ctgctgacct tcttcttccg tcagttgcct 1560
gagctgattg agcgtggcta catctatatc gcgcagccgc cgttgtacaa agtgaaaaag 1620
ggcaagcaag agcagtacat caaagacgac gacgccatgg aagagtacat gacgcagtcg 1680
gccctggaag atgcaagcct gcacttgaac gacgaagcac cgggtatctc cggtgaggcg 1740
ttggagcgtc tggttaacga cttccgtatg gtgatgaaga ccctcaagcg tctatcgcgt 1800
ctgtaccctc aggaactgac cgagcacttc atctacctgc cggccgtcag tctggagcag 1860
ttgggtgatc atgcagcgat gcaagagtgg ctggctcagt acgaagtacg cctgcgcact 1920
gttgagaagt ctggcctggt gtacaaagcc agtctgcgtg aagaccgtga acgtaacgtg 1980
tggctgccgg aggttgagtt gatctcccac ggcctgtcga attacgtcac cttcaaccgc 2040
gacttcttcg gcagtaatga ctacaagacg gtcgtgaccc tcggcgcgca gttgagcacc 2100
ttgctggatg atggtgctta cattcaacgt ggcgagcgta agaaagcggt caaggagttc 2160
aaggaagcct tggactggct gatggcggaa agcaccaagc gtcataccat tcagcgatac 2220
aaaggtctgg gcgagatgaa ccctgatcag ttgtgggaaa ccaccatgga tccagcacag 2280
cgtcgcatgc tgcgcgtgac catcgaagac gccattggcg cagatcagat cttcaacacc 2340
ctgatgggtg atgcggtcga acctcgccgt gacttcatcg agagcaatgc cttggcggtg 2400
tccaacctgg acttctga 2418

<210> SEQ ID NO 90
<211> LENGTH: 1632
<212> TYPE: DNA
<213> ORGANISM: Unknown
<220> FEATURE:
<223> OTHER INFORMATION: Description of Unknown:
DP1 Isoleucine--tRNA ligase sequence

<400> SEQUENCE: 90
atgaccgact ataaagccac gctaaacctt ccggacaccg ccttcccaat gaaggccggc 60
ctgccacagc gcgaaccgca gatcctgcag cgctgggaca gtattggcct gtacggaaag 120
ttgcgcgaaa ttggcaagga tcgtccgaag ttcgtcctgc acgacggccc tccttatgcc 180
aacggcacga ttcacatcgg tcatgcgctg aacaaaattc tcaaggacat gatcctgcgc 240
tcgaaaaccc tgtcgggttt tgacgcgccg tatgtcccgg gctgggactg ccatggcctg 300
ccgatcgaac acaaagtcga agtgacctac ggcaaaaacc tgggcgcgga taaaacccgc 360

-continued gaactgtgcc gtgcctacgc cactgagcag atcgaagggc agaagtccga attcatccgc 420
ctgggcgtgc tgggcgagtg ggacaacccg tacaagacca tgaacttcaa gaacgaggcc 480
ggtgaaatcc gtgccttggc tgaaatcgtc aaaggcggtt ttgtgttcaa gggcctcaag 540
cccgtgaact ggtgcttcga ctgcggttcg gccctggctg aggcggaagt cgaatacgaa 600
gacaagaagt cctcgaccat cgacgtggcc ttcccgatcg ccgacgacgc caagttggcc 660
caggctttcg gcctggcaag cctgagcaag ccggcggcca tcgtgatctg gaccaccacc 720
ccgtggacca tcccggccaa ccaggcgctg aacgtgcacc cggaattcac ctacgccctg 780
gtggacgtcg gtgatcgcct gctggtgctg gccgaggaaa tggtcgaggc ctgtctggcg 840
cgctacgaac tgcaaggttc ggtgatcgcc accaccaccg gctccgcgct ggaactgatc 900
aacttccgtc acccgttcta tgaccgcctg tcgccggttt acctggctga ctacgtcgaa 960
ctgggttcgg gtacgggtgt ggttcactcc gcaccggcct acggcgttga cgacttcgtg 1020
acctgcaaag cctacggtat ggtcaacgat gacatcctca acccggtgca gagcaatggt 1080
gtgtacgcgc catcgctgga gttcttcggc ggccagttca tcttcaaggc taacgagccg 1140
atcatcgaca aactgcgtga agtcggtgcg ctgctgcaca ccgaaaccat caagcacagc 1200
tacatgcact gctggcgcca caaaaccccg ctgatctacc gcgccaccgc gcagtggttt 1260
atcggcatgg acaaagagcc gaccagcggc gacaccctgc gtgtgcgctc gctcaaagcc 1320
atcgaagaca ccaagttcgt cccggcctgg ggccaggcgc gcctgcactc gatgatcgcc 1380
aatcgtccgg actggtgcat ctcccgccag cgtaactggg gcgtaccgat cccgttcttc 1440
ctgaacaagg aaagcggcga gctgcaccca cgcaccgtcg agctgatgga agccgtggcc 1500
ttgcgcgttg aacaggaagg catcgaagcc tggttcaagc tggacgccgc cgagctgctg 1560
ggcgacgaag cgccgctgta cgacaagaag gctcggacca acaccgtggc tggttccact 1620
cgtcgctgct ga 1632

<210> SEQ ID NO 91
<211> LENGTH: 1784
<212> TYPE: DNA
<213> ORGANISM: Unknown
<220> FEATURE:
<223> OTHER INFORMATION: Description of Unknown:
DP1 NADH-quinone oxidoreductase subunit C/D sequence

<400> SEQUENCE: 91
atgactacag gcagtgctct gtacatcccg ccttataagg cagacgacca ggatgtggtt 60
gtcgaactca ataaccgttt tggccctgac gcctttaccg cccaggccac acgtaccggc 120
atgccggtgc tgtgggtggc gcgcgccagg ctcgtcgaag tcctgacctt cctgcgcaac 180
ctgcccaagc cgtacgtcat gctctatgac ctgcatggcg tggacgagcg tctgcggacc 240
aagcgccagg gcctgccgag cggcgccgat ttcaccgtgt tctatcacct gctgtcgatc 300
gaacgtaaca gcgacgtgat gatcaaggtc gccctctccg aaagcgacct gagcgtcccg 360
accgtgaccg gcatctggcc caacgccagt tggtacgagc gtgaagtctg ggacatgttc 420
ggtatcgact tccctggcca cccgcacctg acgcgcatca tgatgccgcc gacctgggaa 480
ggtcacccgc tgcgcaagga cttccctgcg cgcgccaccg aattcgaccc gttcagcctg 540
aacctcgcca agcaacagct tgaagaagag gctgcacgct tccggccgga agactggggc 600
atgaaacgct ccggcaccaa cgaggactac atgttcctca acctgggccc gaaccaccct 660
tcggcgcacg gtgccttccg tatcatcctg caactggacg gcgaagaaat cgtcgactgc 720
gtgccggaca tcggttacca ccaccgtggt gccgagaaga tggccgagcg ccagtcgtgg 780
cacagcttca tcccgtacac cgaccgtatc gactacctcg gcggcgtgat gaacaatctg 840
ccgtacgtgc tctcggtcga gaagctggcc ggtatcaagg tgccggaccg cgtcgacacc 900
atccgcatca tgatggccga gttcttccgg atcaccagcc acctgctgtt cctgggtacc 960
tacatccagg acgtcggcgc catgaccccg gtgttcttca ccttcaccga ccgtcagcgc 1020
gcctacaagg tcatcgaagc catcaccggc ttccgcctgc acccggcctg gtaccgcatc 1080
ggcggtgtcg cgcacgacct gccaaatggc tgggaacgcc tggtcaagga attcatcgac 1140
tggatgccca agcgtctgga cgagtaccag aaagccgccc tggacaacag catcctcaag 1200
ggccggacca ttggggtcgc ggcctacaac accaaagagg ccctggaatg gggcgtcacc 1260
ggtgctggcc tgcgttccac cggttgcgat ttcgacctgc gtaaagcgcg cccgtactcc 1320
ggctacgaga acttcgaatt cgaagtgccg ttggcggcca atggcgatgc ctacgaccgt 1380
tgcatcgtgc gcgtcgaaga aatgcgccag agcctgaaga tcatcgagca atgcatgcgc 1440
aacatccggc aggcccgtac aaggcggacc acccgctgac cacgccgccg ccgaaagagc 1500
gcacgctgca acacatcgaa accctgatca cgcacttcct gcaggtttcg tggggcccgg 1560
tgatgccggc caacgaatcc ttccagatga tcgaagcgac caagggtatc aacagttatt 1620
acctgacgag cgatggcggc accatgagct accgcacccg gattcgcact ccaagcttcc 1680
cgcacctgca gcagatccct tcggtgatca aaggtgaaat ggtcgcggac ttgattgcgt 1740
acctgggtag tatcgatttc gttatggccg acgtggaccg ctaa 1784

<210> SEQ ID NO 92
<211> LENGTH: 1059
<212> TYPE: DNA
<213> ORGANISM: Unknown
<220> FEATURE:
<223> OTHER INFORMATION: Description of Unknown:
DP1 Protein RecA sequence

<400> SEQUENCE: 92
atggacgaca acaagaagaa agccttggct gcggccctgg gtcagatcga acgtcaattc 60
ggcaagggtg ccgtaatgcg tatgggcgat cacgaccgtc aggcgatccc ggctatttcc 120
actggctctc tgggtctgga catcgcactc ggcattggcg gcctgccaaa aggccgtatc 180
gttgaaatct acggccctga atcttccggt aaaaccaccc tgaccctgtc ggtgattgcc 240
caggcgcaaa aaatgggcgc cacttgtgcg ttcgtcgatg ccgagcacgc tcttgaccct 300
gaatacgccg gcaagctggg cgtcaacgtt gacgacctgc tggtttccca accggacacc 360
ggtgagcaag ccttggaaat caccgacatg ctggtgcgct ccaacgccat cgacgtgatc 420
gtggtcgact ccgtggctgc cctggtgccg aaagctgaaa tcgaaggcga aatgggcgac 480
atgcacgtgg gcctgcaagc ccgtctgatg tcccaggcgc tgcgtaaaat caccggtaac 540
atcaagaacg ccaactgcct ggtgatcttc atcaaccaga tccgtatgaa gattggcgtg 600
atgttcggca gcccggaaac caccaccggt ggtaacgcgt tgaagttcta cgcttcggtc 660
cgtctggata tccgccgtac tggcgcggtg aaggaaggcg acgaggtggt gggtagcgaa 720
acccgcgtta aagttgtgaa gaacaaggtg gccccgccat tccgtcaggc tgagttccag 780
attctctacg gcaagggtat ctacctgaac ggcgagatga tcgacctggg cgtactgcac 840
ggtttcgtcg agaagtccgg tgcctggtat gcctacaacg gcagcaagat cggtcagggc 900
aaggccaact cggccaagtt cctggcggac aacccggata tcgctgccac gcttgagaag 960
cagattcgcg acaagctgct gaccccggca ccagacgtga aagctgctgc caaccgcgag 1020
ccggttgaag aagtagaaga agtcgacact gacatctga 1059

<210> SEQ ID NO 93
<211> LENGTH: 1161
<212> TYPE: DNA
<213> ORGANISM: Unknown
<220> FEATURE:
<223> OTHER INFORMATION: Description of Unknown:
DP1 RNA polymerase sigma factor RpoD sequence

<400> SEQUENCE: 93
atggaaatca cccgcaaggc tctgaaaaag cacggtcgcg gcaacaagct ggcaattgcc 60
gagctggtgg ccctggctga gctgttcatg ccaatcaagc tggtgccgaa gcaatttgaa 120
ggcctggttg agcgtgtgcg cagtgctctt gagcgtctgc gtgcccaaga gcgcgcaatc 180
atgcagctct gcgtacgtga tgcacgcatg ccgcgtgccg acttcctgcg ccagttcccg 240
ggcaacgaag tggatgaaag ctggaccgac gcactggcca aaggcaaggc gaagtacgcc 300
gaagccattg gtcgcctgca gccggacatc atccgttgcc agcagaagct gaccgcgctt 360
caaaccgaaa ccggtctgac gattgctgag atcaaggaca tcaaccgtcg catgtcgatc 420
ggtgaggcca aggcccgccg cgcgaagaaa gagatggttg aagcgaactt gcgtctggtg 480
atctccatcg ccaagaagta caccaaccgt ggcctgcaat tcctcgatct gatccaggaa 540
ggcaacatcg gcttgatgaa ggctgtggac aagttcgaat accgtcgcgg ctacaagttc 600
tcgacttatg ccacctggtg gatccgtcag gcgatcactc gctcgatcgc agaccaggcc 660
cgcaccatcc gtattccggt gcacatgatc gagaccatca acaagctcaa ccgtatttcc 720
cggcagatgt tgcaggaaat gggtcgcgaa ccgacgccgg aagagctggg cgaacgcatg 780
gaaatgcctg aggataaaat ccgtaaggta ttgaagatcg ctaaagagcc gatctccatg 840
gaaacgccga ttggtgatga cgaagactcc catctgggtg acttcatcga agactcgacc 900
atgcagtcgc ccatcgatgt ggctaccgtt gagagcctta aagaagcgac tcgcgacgta 960
ctgtccggcc tcactgcccg tgaagccaag gtactgcgca tgcgtttcgg catcgacatg 1020
aataccgacc acacccttga ggaagtcggt aagcagtttg acgtgacccg tgaacggatc 1080
cgtcagatcg aagccaaggc actgcgcaag ttgcgccacc cgacgcgaag cgagcatcta 1140
cgctccttcc tcgacgagtg a 1161

<210> SEQ ID NO 94
<211> LENGTH: 4074
<212> TYPE: DNA
<213> ORGANISM: Unknown
<220> FEATURE:
<223> OTHER INFORMATION: Description of Unknown:
DP1 DNA-directed RNA polymerase subunit beta sequence

<400> SEQUENCE: 94
atggcttact catatactga gaaaaaacgt atccgcaagg actttagcaa gttgccggac 60
gtcatggatg tcccgtacct tctggctatc cagctggatt cgtatcgtga attcttgcaa 120
gcgggagcga ctaaagatca gttccgcgac gtgggcctgc atgcggcctt caaatccgtt 180
ttcccgatca tcagctactc cggcaatgct gcgctggagt acgtgggtta tcgcctgggc 240
gaaccggcat ttgatgtcaa agaatgcgtg ttgcgcggtg ttacgtacgc cgtacctttg 300
cgggtaaaag tccgtctgat cattttcgac aaagaatcgt cgaacaaagc gatcaaggac 360

-continued

```
atcaaagagc aagaagtcta catgggcgaa atcccattga tgactgaaaa cggtaccttc    420
gttatcaacg gtaccgagcg cgttatcgtt tcccagctgc accgttcccc gggcgtgttc    480
ttcgaccacg accgcggcaa gacgcacagc tccggtaagc tcctgtactc cgcgcggatc    540
attccgtacc gcggctcgtg gttggacttc gagttcgacc cgaaagactg cgtgttcgtg    600
cgtatcgacc gtcgtcgtaa gctgccggcc tcggtactgc tgcgcgcgct cggctatacc    660
actgagcaag tgcttgatgc tttctacacc accaacgtat tcagcctgaa ggatgaaacc    720
ctcagcctgg aactgattgc ttcgcgtctg cgtggtgaaa ttgccgtcct ggatatccag    780
gatgaaaacg gcaaggtcat cgttgaagct ggccgccgta ttaccgcgcg ccacatcaac    840
cagatcgaaa aagccggtat caagtcgctg gacgtgccgc tggactacgt cctgggtcgc    900
accactgcca aggtcatcgt tcacccggct acaggcgaaa tcctggctga gtgcaacacc    960
gagctgaaca ccgagatcct ggcaaaaatc gccaaggccc aggttgttcg catcgagacc   1020
ctgtacacca acgacatcga ctgcggtccg ttcatctccg acacgctgaa gatcgactcc   1080
accagcaacc aattggaagc gctggtcgag atctatcgca tgatgcgtcc tggtgagcca   1140
ccgaccaaag acgctgccga gaccctgttc aacaacctgt tcttcagccc tgagcgctat   1200
gacctgtctg cggtcggccg gatgaagttc aaccgtcgta tcggtcgtac cgagatcgaa   1260
ggttcgggcg tgctgtgcaa ggaagacatc gtcgcggtac tgaagacctt ggtcgacatc   1320
cgtaacggta aaggcatcgt cgatgacatc gaccacttgg gtaaccgtcg tgttcgctgc   1380
gtaggcgaaa tggccgagaa ccagttccgc gttggcctgg tacgtgttga gcgtgcggtc   1440
aaagagcgtc tgtcgatggc tgaaagcgaa ggcctgatgc cgcaagatct gatcaacgcc   1500
aagccagtgg ctgcggcggt gaaagagttc ttcggttcca gccagctctc gcagttcatg   1560
gaccagaaca acccgctctc cgagatcacc cacaagcgcc gtgtttccgc actgggcccg   1620
ggcggtctga cccgtgagcg tgcaggcttt gaagttcgtg acgtacaccc aacgcactac   1680
ggtcgtgttt gcccgatcga aacgccggaa ggtccgaaca tcggtctgat caactccctt   1740
gccgcttatg cacgcactaa ccagtacggc ttcctcgaga gcccgtaccg tgtagtgaaa   1800
gatgcactgg tcaccgacga gatcgtgttc ctgtccgcca tcgaagaagc cgatcacgtg   1860
atcgctcagg cttcggccac gatgaacgac aagaaagtcc tgatcgacga gctggtagct   1920
gttcgtcact tgaacgagtt caccgttaag gcgccggaag acgtcacctt gatggacgtt   1980
tcgccgaagc aggtagtttc ggttgcagcg tcgctgatcc cgttcctgga gcacgatgac   2040
gccaaccgtg cgttgatggg ttccaacatg cagcgtcaag ctgtacccac cctgcgtgcc   2100
gacaagccgc tggtaggtac cggcatggag cgtaacgtag cccgtgactc cggcgtttgc   2160
gtcgtggctc gtcgtggcgg cgtgatcgac tctgttgatg ccagccgtat cgtggttcgt   2220
gttgccgatg acgaagttga gactggcgaa gccggtgtcg acatctacaa cctgaccaaa   2280
tacacccgct cgaaccagaa cacctgcatc aaccagcgcc cgctggtgag caagggtgat   2340
cgcgttcagc gtagcgacat catggccgac ggcccgtcca ccgatatggg tgagctggca   2400
ctgggtcaga acatgcgcat cgcgttcatg gcatggaacg gcttcaactt cgaagactcc   2460
atctgcctgt ccgagcgtgt tgttcaagaa gaccgcttca ccacgatcca cattcaggag   2520
ctgacctgtg tggcgcgtga caccaagctt gggccagagg aaatcactgc agacatcccg   2580
aacgtgggtg aagctgcact gaacaaactg gacgaagccg gtatcgttta cgtaggtgct   2640
gaagttggcg caggcgacat cctggttggt aaggtcactc cgaaaggcga gacccaactg   2700
actccggaag agaagctgtt gcgtgccatc ttcggtgaaa aagccagcga cgttaaagac   2760
```

acttccctgc gcgtacctac cggtaccaag ggtactgtca tcgacgtaca ggtcttcacc 2820
cgtgacggcg ttgagcgtga tgctcgtgca ctgtccatcg agaagactca actcgacgag 2880
atccgcaagg acctgaacga agagttccgt atcgttgaag gcgcgacctt cgaacgtctg 2940
cgttccgctc tggtaggcca caaggctgaa ggcggcgcag gtctgaagaa aggtcaggac 3000
atcaccgacg aaatcctcga cggtcttgag cacggccagt ggttcaaact gcgcatggct 3060
gaagacgctc tgaacgagca gctcgagaag gcccaggcct atatcgttga tcgccgccgt 3120
ctgctggacg acaagttcga agacaagaag cgcaaactgc agcagggcga tgacctggct 3180
ccaggcgtgc tgaaaatcgt caaggtttac ctggcaatcc gtcgccgcat tcagccgggc 3240
gacaagatgg ccggtcgtca cggtaacaag ggtgtggtct ccgtgatcat gccggttgaa 3300
gacatgccgc acgatgccaa tggcaccccg gtcgacgtcg tcctcaaccc gttgggcgta 3360
ccttcgcgta tgaacgttgg tcagatcctt gaaacccacc tgggcctcgc ggccaaaggt 3420
ctgggcgaga agatcaaccg tatgatcgaa gagcagcgca aggtcgcaga cctgcgtaag 3480
ttcctgcacg agatctacaa cgagatcggc ggtcgcaacg aagagctgga caccttctcc 3540
gaccaggaaa tcctggatct ggcgaagaac ctgcgcggcg gcgttccaat ggctaccccg 3600
gtattcgacg gtgccaagga aagcgaaatc aaggccatgc tgaaactggc agacctgccg 3660
gaaagtggcc agatgcagct gttcgacggc cgtaccggca acaagtttga gcgcccggtt 3720
actgttggct acatgtacat gctgaagctg aaccacttgg tagacgacaa gatgcacgct 3780
cgttctaccg gttcgtacag cctggttacc cagcagccgc tgggtggtaa ggctcagttc 3840
ggtggtcagc gtttcgggga gatggaggtc tgggcactgg aagcatacgg tgctgcttac 3900
actctgcaag aaatgctcac agtgaagtcg gacgatgtga acggtcggac caagatgtac 3960
aaaaacatcg tggacggcga tcaccgtatg gagccgggca tgcccgagtc cttcaacgtg 4020
ttgatcaaag aaattcgttc cctcggcatc gatatcgatc tggaaaccga ataa 4074

<210> SEQ ID NO 95
<211> LENGTH: 1671
<212> TYPE: DNA
<213> ORGANISM: Unknown
<220> FEATURE:
<223> OTHER INFORMATION: Description of Unknown:
DP22 Glutamine--tRNA ligase sequence

<400> SEQUENCE: 95
atgagtgagg ctgaagcccg cccaacaaat tttatccgtc agattattga tgaagatctg 60
gcgaccggga aacacaatac cgttcatacc cgtttcccgc ctgagccaaa tggctatctg 120
catatcggtc atgcgaaatc tatctgcctg aacttcggca ttgcgcaaga ctatcagggg 180
cagtgcaacc tgcgttttga cgataccaac ccggcaaaag aagacatcga attcgttgag 240
tcgatcaaac acgacgtcca gtggttaggt ttcgactgga gcggtgatat tcactactct 300
tcagactatt ttgatcaact gcacgcttat gcgctggaac tgatcaacaa aggtctggcg 360
tacgttgacg aactgtcacc ggatcagatc cgtgaatacc gcggctcgct gacgtctccg 420
ggcaaaaaca gcccgtaccg tgaccgttca gtggaagaga acatcgcgct gtttgagaaa 480
atgcgtaacg gtgaatttgc cgaaggcgct gcctgtctgc gtgcaaaaat cgatatggcg 540
tcgcctttct tcgtgatgcg cgatccggtt ctgtaccgta ttaagtttgc agaacaccac 600
cagaccggca aaaaatggtg catctatccg atgtacgatt tcacccactg catttccgat 660
gcgctggaag ggatcaccca ttcgctgtgt acgctggaat tccaggacaa ccgccgtctg 720

```
tacgactggg ttctggataa catctccatt ccatgccacc cgcgtcagta cgagttctcc    780

cgtctgaatc tcgagtactc catcatgtct aagcgtaagc tgaaccagct ggtgaccgag    840

aagattgtgg aaggctggga cgacccgcgt atgccgactg tttcaggtct gcgtcgtcgt    900

ggttacaccg ccgcgtctat ccgtgaattc tgccgtcgta tcggcgtcac caagcaagac    960

aacaacgtcg aaatgatggc gctggaatcc tgtatccgtg acgatctgaa cgaaaatgca   1020

ccgcgcgcca tggcggtgat caacccggtt aaagtgatca ttgaaaactt taccggtgat   1080

gacgtgcaga gggtgaaaat gccgaaccac ccgagcaaac cggaaatggg cacccgcgaa   1140

gtgccattta cccgtgagat ttatatcgat caggcagatt tccgcgaaga agcgaacaag   1200

caatacaagc gtctggtgct cggcaaagaa gtgcgtctgc gcaatgcgta tgtgatcaaa   1260

gcagaacgta tcgagaaaga tgcagaaggc aatatcacca cgatcttctg ttcttacgat   1320

atcgatacac tgagcaaaga tcctgccgat ggccgcaagg tgaaaggcgt gatccactgg   1380

gtttcggcgt cagaaggcaa accggcggag ttccgcctgt atgaccgtct gttcagcgtc   1440

gccaacccgg gtcaggcaga agatttcctg accaccatca acccggaatc tctggtgatt   1500

tcccacggtt tcgtggagcc atcactggtg gctgcacagg ctgaaatcag cctgcagttc   1560

gagcgtgaag gttacttctg cgccgacagc cgctactcaa gcgctgaaca tctggtgttt   1620

aaccgtaccg ttggcctgcg cgatacctgg gaaagcaaac ccgtcgtgta a            1671
```

<210> SEQ ID NO 96
<211> LENGTH: 2415
<212> TYPE: DNA
<213> ORGANISM: Unknown
<220> FEATURE:
<223> OTHER INFORMATION: Description of Unknown:
      DP22 DNA gyrase subunit B sequence

<400> SEQUENCE: 96

```
atgtcgaatt cttatgactc ctcaagtatc aaggtattaa aagggctgga cgcggtgcgt     60

aagcgccccg gcatgtatat cggcgatacc gatgacggca ctggtctgca ccacatggta    120

ttcgaggttg tggacaacgc tatcgacgaa gccctcgcgg gccactgtaa agagattcag    180

gtcacgatcc atgcggataa ctctgtgtcc gtacaggatg atggtcgtgg cattccgacc    240

ggtattcatg aagaagaggg cgtttctgct gctcaggtca tcatgaccgt tcttcacgcc    300

ggcggtaaat ttgacgataa ctcgtataaa gtctccggcg gtctgcatgg cgtgggtgtt    360

tccgtcgtta acgccctgtc agaaaaactg gaactggtta tccgccgcga aggcaaagtg    420

cacacccaga cttacgtgca tggcgaacct caggatccgc tgaaagtgat tggcgatact    480

gacgtgaccg gtaccacggt acgtttctgg ccaagcttca acaccttcac caatcacact    540

gaattcgagt atgacattct ggcgaaacgc ctgcgtgaac tgtcattcct gaactccggc    600

gtggcgatcc gcctgctgga taaacgtgat ggtaaaaacg atcacttcca ttatgaaggc    660

ggtatcaaag ctttcgtgga atatctgaac aaaaacaaaa ccccaatcca tccgaccgta    720

ttctatttct ccacggtcaa agatgacatt ggcgttgaag tggcgttgca gtggaacgac    780

ggtttccagg aaaacattta ctgcttcacc aacaacattc cacagcgcga tggcgggact    840

cacttagccg gtttccgttc ggcaatgacc cgtaccctga acgcgtacat ggataaagaa    900

ggctacagca agaaatccaa aatcagcgcc accggtgatg atgcccgtga aggcctgatt    960

gctgtggtgt cggtgaaggt gccggatcct aagttctctt ctcagaccaa agacaaactg   1020

gtgtcttctg aagtgaaaac agcggttgaa acgctgatga acgagaagct ggtggattac   1080
```

ctgatggaaa acccgtcaga cgccaaaatc gttgtcggta aaatcatcga cgcagcgcgt 1140
gcccgtgaag cagcacgtaa agcgcgtgaa atgacccgcc gtaaaggcgc gctggatctg 1200
gctggcttgc caggcaaact ggcggactgt caggaacgcg atccggcaca ttccgaactg 1260
tacttagtgg aaggggactc agcgggcggc tctgcaaaac aaggccgtaa ccgtaagaac 1320
caggcgattc tgccgttgaa aggtaaaatc ctcaacgtgg agaaagcgcg cttcgacaaa 1380
atgctctctt ctcaggaagt ggcaacgctg attacagcac tcggttgcgg cattggccgt 1440
gacgaataca acccggacaa actgcgctat cacagcatca tcatcatgac cgatgccgac 1500
gtcgatggtt cgcacatccg taccctgttg ctgacattct tctaccgtca gatgcctgaa 1560
attgtagaac gtggccacgt gtttatcgcc cagccgccgt tgtacaaagt gaaaaaaggc 1620
aagcaggaac agtacattaa agatgacgaa gcgatggatc agtatcagat ttccattgcg 1680
atggacgggg caacgttaca cgccaacgct catgcgccag ccctggcggg tgaaccgctg 1740
gagaaactgg tcgctgaaca tcacagcgtg cagaaaatga ttggccgcat ggaacgtcgt 1800
tatccgcgtg cgctgctgaa taacctgatc tatcagccga ccctgccggg tgcagatctg 1860
gccgatcagg cgaaagtgca ggcctggatg gaatcgctgg tggcgcgtct caacgagaaa 1920
gagcagcacg gcagttctta cagcgcgatc gtgcgtgaaa accgcgaaca tcagctgttc 1980
gaaccggttc tgcgtatccg cacccacggt gttgataccg attacgatct ggatgccgac 2040
ttcatcaaag gcggcgaata ccgcaaaatc tgtgcgctgg gtgaacagct gcgcggcctg 2100
atcgaagaag atgccttcat cgaacgtggc gaacgccgtc agcccgtcac cagcttcgaa 2160
caggcgctgg aatggctggt gaaagagtcc cgtcgtggtc tgtcgattca gcgatacaaa 2220
ggtctgggtg aaatgaaccc tgaacagctg tgggaaacca ccatggatcc tgagcaacgt 2280
cgcatgttac gtgtgaccgt gaaggatgcc atcgccgctg accagttgtt cacgacgctg 2340
atgggcgatg cggttgaacc gcgccgcgcc tttatcgaag agaacgccct gaaagccgcc 2400
aatatcgata tctga 2415

<210> SEQ ID NO 97
<211> LENGTH: 2733
<212> TYPE: DNA
<213> ORGANISM: Unknown
<220> FEATURE:
<223> OTHER INFORMATION: Description of Unknown:
DP22 Isoleucine--tRNA ligase sequence

<400> SEQUENCE: 97
atgagtgact acaagaacac cctgaatttg ccggaaacag ggttcccgat gcgtggcgat 60
ctggccaagc gtgaacctga catgctgaaa aattggtatg accaggatct gtacgggatt 120
attcgtgctg ccaagaaagg caaaaaaacc tttattttgc atgacggccc tccgtatgcg 180
aacggcagca ttcatattgg tcactcagta aacaaaattc ttaaagacat gattatcaag 240
tccaaaggac ttgcgggctt tgatgcgccg tatgtgccgg gctgggattg tcatggtctg 300
ccgatcgagc tgaaagtcga acaactgatc ggtaagccgg gcgagaaagt tacggcggcg 360
gaattccgtg aagcctgccg taaatatgcc gcagaacagg ttgaaggcca gaagaaagac 420
ttcatccgtc tgggcgtgct gggcgactgg gatcatccgt acctgacgat ggatttcaaa 480
accgaagcca acatcatccg tgcgctgggc aaaatcatcg gtaacggcca cctgcataaa 540
ggcgccaagc cggtgcactg gtgtacagat tgcggttcgt cgctggccga agccgaagtc 600
gaatattacg acaaagcctc gccttctatt gatgtggcgt tcaacgcgac ggatgccgca 660

-continued

```
gccgtggcag cgaaatttgg cgttactgcc tttaatggcc cgatctcgct ggttatctgg    720
accacaacac cgtggactat gcccgctaac cgcgccattt cactgaatcc tgagtttgct    780
tatcagctgg ttcaggtcga aggtcagtgt ctgatcctgg caaccgatct ggttgaaagc    840
gtcatgaaac gtgccggtat tgccggatgg accgttctgg gcgagtgcaa aggcgcagac    900
ctcgaactgc tgcgcttcaa acacccgttc ctcggtttcg acgttccggc gatcctgggc    960
gatcacgtga cgctcgatgc gggtaccggt gccgtgcata ccgcaccagg ccacggccct   1020
gacgactttg ttatcggcca gaaatacggt ctggaagtgg cgaatccggt agggccgaac   1080
ggttgctacc tgccgggcac ttacccgacg ctggacggta aatttgtctt taaagccaac   1140
gacctgatcg ttgagttgct gcgtgaaaaa ggcgcattgc tgcacgttga gaaaatcacg   1200
cacagctatc cttgctgctg gcgccacaaa acgccaatca tcttccgcgc gacgccgcaa   1260
tggttcatca gcatggatca gaagggcctg cgtcagcagt cgctggaaga gatcaaaggc   1320
gtgcagtgga tcccggactg ggtcaggca cgtatcgaaa acatggtcgc taaccgtcct   1380
gactggtgta tctcccgtca gcgtacctgg ggcgtgccga tgtctctgtt cgttcacaaa   1440
gacactgagc agctgcatcc gcgcagcctt gagctgatgg aagaagtggc gaaacgtgtt   1500
gaggtggatg gcattcaggc gtggtgggat ctgaatccgg aagacattct gggtgcagac   1560
gccgcagatt acgtcaaagt accggacacg ctggacgtct ggtttgactc cggttcaacg   1620
cattcttccg ttgtggatgt gcgtcctgag ttcaacgggc attctcctga tctgtatctg   1680
gaaggttctg accagcatcg cggctggttc atgtcttccc tgatgatttc gacggcaatg   1740
aaaggcaaag cgccttacaa acaagtgctg actcacggtt tcaccgtgga tggtcagggc   1800
cgcaaaatgt ctaaatccat cggcaatacc atcgcgccgc aagacgtgat gaacaagctg   1860
ggtggcgaca ttctgcgtct gtgggtcgcg tcgacggatt acaccggcga aatcgccgtg   1920
tccgacgaaa tcctcaaacg tgctgctgat tcttaccgcc gtatccgtaa caccgcgcgc   1980
ttcctgctgg cgaaccttaa cggtttcgat ccggcgctgc acagcgtggc tccggaagac   2040
atggtggtgc tggaccgctg ggcggttggc cgtgcgaaag ccgctcagga agaaatcatt   2100
gctgcgtatg aagcctatga tttccatggc gttgttcagc gtctgatgca gttctgctcg   2160
atcgaaatgg gttccttcta tctggatatc attaaagatc gtcagtacac cgcgaaaagc   2220
gacagcgttg cacgtcgcag ctgtcagacc gcgctgtatc acatcagtga agcgctggtt   2280
cgctggatgg caccgatcat gtcgttcaca gccgatgaaa tctgggcgga actgccggga   2340
agccgtgaga aattcgtctt caccgaagag tggtacgacg gtctgttcgg tctcgcaggc   2400
aacgaatcca tgaacgatgc gttctgggat gaactgctga aagtgcgtgg cgaagtgaac   2460
aaagtgatcg aacaggcgcg tgcggataaa cgtctgggcg gttctctgga agcagcggtt   2520
acgctgtttg ctgatgatgc gctggcaaca gacctgcgtt ctctgggcaa tgaactgcgc   2580
tttgtgctgc tgacgtcagg ggcgaaagtt gccgcactga gtgatgcaga tgacgcggct   2640
cagtcgagtg aattgctgaa aggcctgaag attggtctgg cgaaagcaga aggcgacaag   2700
tgcccgcgct gctggcatta cactaccgat taa                                2733
```

<210> SEQ ID NO 98
<211> LENGTH: 1800
<212> TYPE: DNA
<213> ORGANISM: Unknown
<220> FEATURE:
<223> OTHER INFORMATION: Description of Unknown:
      DP22 NADH-quinone oxidoreductase subunit C/D sequence

<400> SEQUENCE: 98
atgacagatt tgacgacgca agattccgcc ctgccagcat ggcatacccg tgatcatctc 60
gatgatccgg ttatcggcga attgcgtaac cgttttgggc cagaggcctt tactgtccag 120
gcaacccgca ccggaattcc cgtggtgtgg ttcaagcgtg aacagttact ggaagcgatt 180
acctttttac gaaaacagcc aaaaccttac gtcatgcttt tcgatttgca tggctttgat 240
gagcgtttac gtacacaccg cgacggttta ccggctgcgg atttttccgt tttctaccac 300
ctgatctccg tcgagcgtaa ccgcgacatc atgatcaaag tggcgttgtc agaaaacgat 360
cttcatgttc cgacgatcac caaagtgttc ccgaacgcta actggtacga acgcgaaaca 420
tgggaaatgt tcggtattac cttcgacggc catccgcacc tgacgcgcat catgatgccg 480
cagacctggg aagggcatcc gctgcgtaaa gactatccgg cgcgcgccac cgagttcgat 540
ccttatgagc tgactaagca aaaagaagaa ctcgagatgg aatcgctgac cttcaagccg 600
gaagactggg gcatgaagcg cggtaccgat aacgaggact ttatgttcct caacctcggt 660
cctaaccacc cgtcagcgca tggtgcattc cgtattatcc tgcagctgga tggcgaagag 720
attgtcgact gcgtgcctga cgtcggttac caccaccgtg gtgcggagaa aatgggcgaa 780
cgccagtcat ggcacagcta cattccgtat actgaccgta tcgaatatct cggcggttgt 840
gttaacgaaa tgccttacgt gctggctgtt gaaaaactcg ccggtatcgt gacgccggat 900
cgcgttaaca ccatccgtgt gatgctgtct gaactgttcc gtatcaacag ccatctgctg 960
tacatctcta cgtttattca ggacgtgggt gcgatgacgc cggtattctt cgcctttacc 1020
gatcgtcaga aaatttacga tctggtggaa gcgatcaccg gtttccgtat gcacccggcc 1080
tggttccgta tcggtggcgt agcgcatgac ctgccgaaag gctgggaccg cctgctgcgt 1140
gaattccttg actggatgcc agcccgtttg gattcctacg tcaaagcggc gctgagaaac 1200
accattctga ttggccgttc caaaggcgtg gccgcgtata acgccgacga cgcactggcc 1260
tggggcacca ccggtgctgg cctgcgcgca acgggtatcc cgttcgatgt gcgtaaatgg 1320
cgtccgtatt caggttatga aaactttgac tttgaagtgc cgaccggtga tggcgtcagt 1380
gactgctatt cccgcgtgat gctgaaagtg gaagaacttc gtcagagcct gcgcattctg 1440
gaacagtgct acaaaaacat gccggaaggc ccgttcaagg cggatcaccc gctgaccacg 1500
ccgccaccga aagagcgcac gctgcaacac atcgagaccc tgatcacgca cttcctgcaa 1560
gtgtcgtggg ggccggtcat gcctgcacaa gaatctttcc agatggttga agcaaccaaa 1620
gggatcaaca gctactacct gaccagtgac ggcagcacca tgagctaccg cacccgtgtc 1680
cgtacgccga gcttcccgca tttgcagcag atcccgtccg taatccgtgg cagcctggta 1740
tccgacctga tcgtgtatct gggcagtatc gattttgtaa tgtcagatgt ggaccgctaa 1800

<210> SEQ ID NO 99
<211> LENGTH: 1065
<212> TYPE: DNA
<213> ORGANISM: Unknown
<220> FEATURE:
<223> OTHER INFORMATION: Description of Unknown:
DP22 Protein RecA sequence

<400> SEQUENCE: 99
atggctattg atgagaacaa gcaaaaagcg ttagctgcag cactgggcca gattgaaaag 60
caattcggta aaggctccat catgcgtctg ggtgaagatc gctccatgga cgttgaaacg 120
atctctaccg gctctttgtc tctggatatc gcgttaggtg ccggcggttt gccaatgggc 180
cgtatcgttg agatctatgg cccggaatct tccggtaaaa caacgctgac cttgcaagtt 240
atcgcggctg cacagcgtga aggcaaaacc tgtgcgttca tcgatgcaga acacgccctg 300
gacccgatct acgctaaaaa actgggcgtg gatatcgata acctgctgtg ttctcagcca 360
gataccggcg aacaggctct ggaaatctgt gacgcgctga cccgttcagg cgctgttgac 420
gtgatcatcg ttgactccgt tgccgcactg acaccgaaag cggaaatcga aggcgaaatt 480
ggtgactctc acatgggcct cgcggcacgt atgatgagcc aggcgatgcg taagctggcc 540
ggtaacctga aaaacgccaa caccttgctg atcttcatca accagatccg tatgaaaatt 600
ggtgtgatgt tcggtaaccc ggaaaccacc accggcggta acgccctgaa attctacgct 660
tctgtgcgtc tggatatccg ccgtatcggc gcgatcaaag aaggcgatgt ggttgtcggt 720
agcgaaacgc gtgtgaaagt ggtgaagaac aaaatcgctg cgccatttaa acaagctgaa 780
ttccagatca tgtacggcga aggcatcaat atcaacggcg agctgattga tctcggcgtg 840
aagcacaagc tgatcgaaaa agccggtgca tggtatagct acaacggtga gaagattggt 900
cagggtaaag cgaactcctg caacttcctg aaagaaaacc cgaaagtggc tgccgagctg 960
gataaaaaac tgcgtgatat gctgttgagc ggtaccggtg aactgagtgc tgcgaccacg 1020
gctgaagatg ctgacgacaa catggaaacc agcgaagagt tttaa 1065

<210> SEQ ID NO 100
<211> LENGTH: 1839
<212> TYPE: DNA
<213> ORGANISM: Unknown
<220> FEATURE:
<223> OTHER INFORMATION: Description of Unknown:
DP22 RNA polymerase sigma factor RpoD sequence

<400> SEQUENCE: 100
atggagcaaa acccgcagtc acagcttaag ctacttgtca cccgtggtaa ggagcaaggc 60
tatctgacct atgctgaggt caatgaccat ctgccggaag atatcgtcga ttccgaccag 120
atcgaagaca tcatccagat gattaacgac atgggcatcc aggtacttga agaagcaccg 180
gacgccgatg atttgatgct ggccgaaaac cgccctgata ccgatgaaga cgctgcagaa 240
gccgcggcgc aggtgctttc cagcgttgaa tccgaaattg gccgtaccac cgaccctgtg 300
cgtatgtata tgcgcgagat gggtaccgtt gagttgctga cccgtgaagg cgaaatcgac 360
atcgccaaac gtatcgaaga cggtatcaat caggtccagt gctccgttgc tgaatatcct 420
gaagctatca cttatttgtt agagcaatat gaccgtgtgg aagcaggcga agtacgtctg 480
tctgacctga tcaccggttt tgttgacccg aacgccgaag aagaaatcgc accaactgcg 540
actcacgtgg gttctgaact gaccactgaa gagcagaatg atgacgacga agacgaagat 600
gaagacgacg acgctgaaga cgacaacagc atcgatccgg aactggctcg ccagaagttc 660
accgaactgc gtgaacagca tgaagcgacg cgtctggtca tcaagaaaaa cggccgtagt 720
cacaagagcg cagcagaaga aatcctgaag ctgtccgatg tgttcaaaca gttccgtctg 780
gtgccaaaac agttcgattt cctggttaac agcatgcgtt ccatgatgga tcgcgttcgt 840
gctcaggaac gtctgatcat gaaagtgtgc gttgaacagt gcaaaatgcc gaagaaaaac 900
ttcgtcaatc tgttcgccgg taacgaaacc agcgatacct ggtttgatgc cgctctggca 960
atgggtaaac catggtccga gaagctgaaa gaagtcaccg aagacgtgca acgcggcctg 1020
atgaaactgc gtcagatcga agaagaaacc ggcctgacta tcgaacaggt taaagacatc 1080
aaccgtcgca tgtcgatcgg cgaagcgaaa gcccgtcgcg cgaagaaaga gatggttgaa 1140
gcaaacttac gtctggttat ttctatcgcc aagaaataca ccaaccgtgg tctgcagttc 1200
cttgacctga tccaggaagg taacatcggc ctgatgaaag ccgttgataa gtttgaatat 1260
cgccgtggtt ataagttctc aacttatgcg acctggtgga tccgtcaggc tatcacccgc 1320
tccatcgccg accaggcgcg taccatccgt atcccggtac atatgattga gacgatcaac 1380
aaactcaacc gtatctcccg tcagatgctg caagagatgg gccgcgaacc gacaccggaa 1440
gagctggctg agcgtatgtt gatgccggaa gacaaaatcc gcaaagtgct gaaaattgcc 1500
aaagagccaa tctccatgga aacgccaatc ggcgacgatg aagattcgca tctgggcgat 1560
ttcatcgagg ataccaccct cgagctgcca ctggattctg cgacgtctga aagcctgcgt 1620
tctgcaacgc atgacgttct ggctggcctg actgcacgtg aagcgaaagt tctgcgtatg 1680
cgtttcggta tcgatatgaa cactgaccac acgctggaag aagtgggcaa acagttcgac 1740
gtgacccgtg agcgtatccg tcagatcgaa gcgaaagcgt tgcgtaaact gcgccacccg 1800
agccgctccg aagtactgcg cagcttcctg gacgattaa 1839

<210> SEQ ID NO 101
<211> LENGTH: 4221
<212> TYPE: DNA
<213> ORGANISM: Unknown
<220> FEATURE:
<223> OTHER INFORMATION: Description of Unknown:
DP22 DNA-directed RNA polymerase subunit beta' sequence

<400> SEQUENCE: 101
gtgaaagact tactaaagtt tctgaaagcg caaactaaga ccgaagagtt tgatgcgatc 60
aaaattgctc tggcatcgcc agacatgatc cgttcttggt cttttggtga agttaagaag 120
ccagaaacca ttaactaccg tacgttcaaa ccagaacgtg acggcctttt ctgtgcccgt 180
attttcggac cagtaaaaga ctacgaatgc ctgtgcggta agtacaagcg tttaaaacat 240
cgcggcgtga tctgcgagaa gtgcggcgtt gaagtgaccc agactaaagt acgccgtgag 300
cgtatgggcc acatcgaact ggcttccccg actgcacaca tctggttcct gaaatcgctg 360
ccatcgcgca tcggtttgct gctggatatg ccactgcgtg acatcgaacg tgttctgtac 420
ttcgaatcct atgtggttat cgaaggcggc atgactaacc tcgaaaaacg ccagatcctg 480
actgaagagc agtatctgga tgcgttggaa gagtttggtg atgagttcga cgcgaagatg 540
ggtgcggaag ctattcaggc cctgttgaaa aacatggatc tggaagcaga gtgcgagcaa 600
ctgcgtgaag agttgaacga aaccaactcc gaaaccaaac gtaagaagct gaccaagcgt 660
atcaagctgc tggaagcgtt cgttcagtct ggtaacaaac cagagtggat gatcctgact 720
gtgctgccgg tactgccacc agacttgcgt ccattggttc cgttggacgg cggccgtttc 780
gcaacgtcgg atctgaacga tctgtatcgt cgcgtgatca accgtaacaa ccgtctgaaa 840
cgcctgctgg atctggctgc gccagacatc atcgtacgta acgaaaaacg tatgctgcaa 900
gaagcggtag atgctttgct ggataacggc cgtcgcggtc gtgctatcac cggctctaac 960
aagcgtccgc tgaaatctct ggcagacatg attaaaggta aacagggtcg tttccgtcag 1020
aacttgctgg gtaaacgtgt cgactactct ggtcgttccg ttatcaccgt aggtccatac 1080
ctgcgtctgc accagtgtgg tctgccgaag aaaatggcac tggaactgtt caaaccgttc 1140
atctacggca agctggaact gcgtggcctg gccaccacca tcaaagccgc gaagaaaatg 1200
gttgagcgcg aagaagctgt cgtttgggac atcctggacg aagttatccg cgaacacccg 1260
gtactgctga accgtgcacc aaccctgcac cgtttgggta tccaggcgtt tgaaccggtt 1320

-continued ctgatcgaag gtaaagcaat ccagctgcac ccgctggttt gtgcggcata taacgccgac 1380
ttcgatggtg accagatggc tgttcacgta ccgttgacgc tggaagccca gctggaagcg 1440
cgtgcgttga tgatgtctac caacaacatc ctgtcacctg cgaacggcga gccaatcatc 1500
gttccttctc aggacgttgt attgggtctg tactacatga cccgtgactg tgttaacgcc 1560
aaaggcgaag gcatggttct gaccggtcct aaagaagctg agcgtattta ccgcgccggt 1620
ttggcctctc tgcatgcgcg tgtcaaagtg cgtattacag aagagatcaa aaataccgaa 1680
ggcgaagtta cgcacaagac gtcgattatc gacacgacag ttggtcgcgc catcctttgg 1740
atgatcgtac ctaaaggtct gccgttctct atcgtcaacc agcctctggg caaaaaagct 1800
atctccaaaa tgctgaacac ctgttaccgc attttgggcc tgaagccgac cgttattttt 1860
gctgaccaga tcatgtacac cggttttgct tacgctgccc gttcaggcgc gtcagtaggt 1920
atcgatgaca tggtaatccc tgcgaagaaa gcagagatca tcgaagaagc agaaaccgaa 1980
gttgctgaaa tccaggaaca gttccagtct ggtctggtca ctgctggcga acgctataac 2040
aaagtgatcg acatctgggc tgcggccaac gaacgtgttg ctaaggcaat gatggaaaac 2100
ttgtctgttg aagacgtcgt caaccgtgac ggtgttgttg aacagcaggt ttccttcaac 2160
agtatcttta tgatggccga ctccggtgcg cgtggttctg ctgcacagat tcgtcagctg 2220
gccggtatgc gtggcctgat ggcgaaacca gatggttcca tcattgaaac gccaatcacc 2280
gcgaacttcc gtgaaggtct gaacgtactc cagtacttca tctctactca cggtgctcgt 2340
aaaggtttgg cggataccgc acttaaaacg gctaactccg gttatctgac ccgtcgtctg 2400
gttgacgtcg cgcaggatct ggttgtgacc gaagacgact gtgggactca cgaaggcatc 2460
atgatgactc cggtcatcga aggtggcgac gttaaagaac cactgcgtga gcgtgtactg 2520
ggtcgtgtga ctgcagaaga tatcctcaag ccgggtacgg cggatatcct ggttccacgt 2580
aacaccctgc ttcacgagaa gacgtgtgat ctgttagaag agaactcagt cgacagcgtg 2640
aaagtacgtt cagtcgtaag ttgcgaaacc gactttggtg tgtgtgcaaa ctgctacggt 2700
cgcgacctgg cacgtggtca catcatcaac aaaggtgaag cgatcggtgt tattgcagca 2760
cagtccatcg gtgagccggg tacccagctg acgatgcgta cgttccacat cggtggtgcg 2820
gcatctcgtg cggcagcgga atccagcatc caggttaaga acactggtac cattaaactg 2880
agcaaccaca agcacgttag caactctaac ggcaaactgg tgatcacttc ccgtaacact 2940
gagctgaaat tgatcgacga attcggtcgt accaaagaaa gctataaagt gccttacggt 3000
tccgtgatgg gcaaaggcga tggcgcatca gttaacggcg gcgaaaccgt tgctaactgg 3060
gatccgcaca ccatgccagt tatcagtgaa gtgagtggtt tcattcgctt tgccgatatg 3120
gtggatactc agaccatcac acgccagacc gacgacctga ccggtttgtc ttctctggtt 3180
gttctggact ctgcagagcg taccggtagc ggtaaagacc tgcgtccggc actgaaaatc 3240
gttgacgcta aaggcgacga cgtattgatt ccaggtactg atatgcctgc tcaatacttc 3300
ctgccaggta aagcgattgt tcagctggaa gatggtactc agatccactc tggtgacacc 3360
ctggcgcgta ttcctcagga atccggcggt accaaggaca tcaccggtgg tctgccacgc 3420
gttgctgacc tgttcgaagc acgtcgtccg aaagagcctg caatccttgc tgaaatcagc 3480
gggatcatct ccttcggtaa agaaaccaaa ggcaaacgtc gtctggtaat ttctccgtta 3540
gatggcagcg atgcttacga agaaatgatc cctaaatggc gtcagctgaa cgtgttcgaa 3600
ggcgaagttg tggaacgtgg tgacgtcgta tccgacggcc ctgagtctcc gcacgacatc 3660

-continued

```
ttgcgtttac gtggtgttca cgcggttacc cgctacatca ccaacgaagt gcaggaagtt   3720

taccgtctgc aaggcgttaa gattaacgat aagcacatcg aagttatcgt tcgtcagatg   3780

ttgcgtaaag gcaccatcgt tagcgctggt ggcactgact tcctggaagg cgagcaggca   3840

gaaatgtctc gcgttaaaat cgctaaccgt aagctggaag ctgaaggcaa aatcacggca   3900

acattcagcc gtgacctgct cggtatcacc aaggcatccc tggcgaccga atccttcatc   3960

tctgcagcgt cgttccagga aaccacgcgt gttcttaccg aagcggctgt tgccggtaaa   4020

cgtgatgaac tgcgtggcct gaaagagaac gttatcgttg gccgtctgat cccagccggt   4080

accggttacg cttatcatca ggatcgtgca cgccgtaaag cacaaggcga agtgccagtt   4140

gtaccgcaag tcagcgcgga tgaagcaacg gctaacctgg ctgaactgct gaacgcaggt   4200

ttcggtaaca gcgacgatta a                                             4221
```

<210> SEQ ID NO 102
<211> LENGTH: 1668
<212> TYPE: DNA
<213> ORGANISM: Unknown
<220> FEATURE:
<223> OTHER INFORMATION: Description of Unknown:
DP67 Glutamine--tRNA ligase sequence

<400> SEQUENCE: 102

```
atgagtgagg ctgaagcccg cccaactaac tttattcgtc agattatcga cgaagatctg     60

gcgaacggta agcacagttc agtgcacacc cgcttcccgc ctgagccgaa tggctatctg    120

catattggcc atgcgaaatc aatctgcctg aactttggta tcgctcagga ttatcagggg    180

cagtgtaacc tgcgctttga tgacactaac ccggtgaaag aagatctgga gtttgttgaa    240

tcaatcaagc gtgatgtgca gtggctgggc tttaagtgga gtggtgacgt acgctactca    300

tctgactatt tcgagcaact gcacaattat gccgttgagc tgattagtaa agggctggcg    360

tacgttgatg aactgtcacc ggagcagatc cgtgaatacc gtggcagcct gacctcagcg    420

ggtaaaaaca gccccttccg cgatcgcagc gtggacgaaa accttgcgct ctttgcaaaa    480

atgcgcgcgg gcggctttgc cgagggcacc gcgtgtttac gagccaaaat tgatatggct    540

tccaacttta tcgttctgcg cgatccggtg atctaccgca tcaaatttgc cgaacatcat    600

cagaccggca ataagtggtg catctatccg atgtatgact ttacccactg catctctgat    660

gcgctggaag gcattactca ctcactgtgt acgctggaat tccaggataa ccgtcgcctg    720

tacgactggg tgctggataa catcaccatt ccggttcatc cgcgtcagta tgaattctct    780

cgcctgaatc ttgaatatgc catcatgtcc aagcgtaagt tgagtcagtt ggtgaccgag    840

aacgtggtgg aaggttggga tgatccccgt atgctgactg tttcgggttt gcgccgccgt    900

ggctacactg cggaatccat ccgtgaattc tgccgccgca ttggggtgac caagcaggac    960

aatattgttg aaatggccgc tctggaatcc tgtatccgtg acgacctcaa tgagaatgcc   1020

ccgcgtgcca tggcagtgat ggatccggta aaagtggtga tagaaaatct gcctgcgcat   1080

cacgatgagg tgatcaccat gccgaatcat ccgagcaagc cggaaatggg tacccgcgaa   1140

gtcccgttca gtcgtgagat ctacatcgat cgtgctgact tccgtgagga agcaaacaag   1200

cagtacaagc ggctggtgct gggcaaagaa gtgcgtctgc gtaacgctta tgtgatcaaa   1260

gccgagcgcg tggcaaagga cgatgaaggc aacattacct gcctgttctg tacctgtgat   1320

gtggatactc tgagcaagga tccggccgac gggcgtaaag tgaagggcgt tatccactgg   1380

gtgtcagctg ttcatgccct tccggcagag ttccgtctgt acgatcggct gttcagcgta   1440
```

ccgaatccgg gggcggcaga agacttcctg gccagcatca acccggaatc tctggtgatc 1500
cgtcagggct tcgtggagcc cgggatgcag caggcggagg cgtcagcccc gtatcagttt 1560
gagcgtgaag gctacttctg cgctgacagt gtctactcca gtgccagcaa tctggtgttc 1620
aaccgcaccg ttggcctgcg tgacacctgg gcgaaagtcg gcgagtaa 1668

<210> SEQ ID NO 103
<211> LENGTH: 2409
<212> TYPE: DNA
<213> ORGANISM: Unknown
<220> FEATURE:
<223> OTHER INFORMATION: Description of Unknown:
DP67 DNA gyrase subunit B sequence

<400> SEQUENCE: 103
atgtcgaatt cttatgactc ctccagtatc aaagttctga aagggctcga tgctgtacgc 60
aaacgcccgg gtatgtatat cggcgatacg gatgacggta ccggtctgca tcacatggta 120
tttgaggtcg tggataacgc cattgacgaa gcgctcgccg gtcactgttc cgatattctt 180
gtcactattc atgccgataa ctctgtttcc gttgtggatg atggccgtgg tattccgacc 240
ggtattcacg aagaagaagg catctcagcc gctgaagtga tcatgaccgt gctgcacgcc 300
ggcggtaagt tcgacgataa ctcttataaa gtctccggcg gcctgcacgg cgtgggcgtg 360
tcagtggtga acgccctgtc ggaaaaactg gagctgacca ttcgtcgcga agggaaagtt 420
caccagcaga cttacgtcca cggcgtgcca caggccccgt tgagtgtgag cggtgaaact 480
gacctgacgg gaacgcgcgt gcgtttctgg cccagccatc agacgttcac taacgtcgtg 540
gagttcgagt acgaaatttt ggcaaagcgc ctgcgtgagc tgtcgttcct gaactccggt 600
gtatcaatca agctggaaga taagcgcgac ggtaaaagcg accattacca ctatgaaggt 660
ggtatcaagg cgtttgttga gtacctcaac aagaacaaaa ccccgatcca cccgaatgtg 720
ttctatttct caaccgagaa agacggcatt ggtgtggaag tggcgctgca gtggaacgat 780
ggtttccagg aaaatatcta ctgctttacc aacaacatcc cacagcggga tgggggcacg 840
cacctcgttg gtttccgtac cgcgatgacc cgtaccctga atgcctacat ggataaagaa 900
ggctacagca agaaagccaa agtcagcgcc accggtgacg acgcgcgtga aggcctgatt 960
gctgtggtgt cggtgaaagt gccggatccg aaattctctt cacagaccaa agataaactg 1020
gtctcttctg aagtgaaaac cgccgttgag cagcagatga acgagctgct ggcagaatac 1080
ctgctggaaa acccgaccga tgccaaaatc gtcgtcggta aaatcattga tgcggcccgc 1140
gcccgtgaag cggcccgtcg tgcacgtgaa atgacccgcc gtaaaggcgc gctggatctg 1200
gcaggcctgc cgggcaaact ggcggactgc caggagcgtg atccggctct gtccgaaatt 1260
tacctggtgg aaggggactc tgcgggcggc tctgccaagc agggacgtaa ccgtaaaaac 1320
caggccatcc tgccgctgaa gggtaaaatc ctcaacgtcg agaaggcgcg ctttgacaag 1380
atgctcgcgt cgcaggaagt cgctacgctg atcaccgcgc tgggctgtgg tatcggtcgt 1440
gatgagtaca accccgacaa actgcgctat cacagcatca ttatcatgac cgatgccgac 1500
gtggatggct cgcatatccg taccctgctg ctgaccttct tctaccgtca gatgccagaa 1560
atcattgagc gtggtcatgt ctatattgcc cagccaccgc tgtacaaggt gaaaaaaggc 1620
aagcaggagc agtatattaa agacgacgat gcgatggatc agtaccagat cgccatcgcg 1680
ctggacggtg ccacgctgca tgcgaacgcc agcgccccgg cccttggcgg taagccactg 1740
gaagatctgg tgtctgagtt caacagcacg cgcaagatga tcaagcgcat ggagcgccgt 1800
tacccggtgg ccttgctgaa tgcgctggtc tacaacccga ccctgagcga tttgaccgcc 1860
gaagcgccgg tacagagctg gatggatgtg ctggtgaagt atctgaacga caacgaccag 1920
cacggcagca cctacagcgg tctggtacgc gaaaatctgg agctgcatat ctttgagccg 1980
gtactgcgta tcaaaaccca cggcgtggat accgattatc cgctcgacag cgagtttatg 2040
ctcggcggcg aataccgtaa gctctgcgcg ctgggtgaga agctgcgtgg cctgatcgaa 2100
gaagacgcgt tcatcgaacg tggtgagcgg cgtcagccga ttgccagctt tgagcaggcg 2160
atggagtggc tggttaaaga gtcacgccgt ggcctgacgg ttcagcgtta taaaggtctg 2220
ggcgagatga acccggatca gctgtgggaa accaccatgg atccggacag ccgccgtatg 2280
ctgcgcgtga ccatcaaaga tgccgtggcc gccgaccagc tgttcaccac cctgatgggg 2340
gatgcggtag agccccgtcg tgcctttatt gaagagaacg ccctgcgcgc ggcaaacatc 2400
gatatctga 2409

<210> SEQ ID NO 104
<211> LENGTH: 2817
<212> TYPE: DNA
<213> ORGANISM: Unknown
<220> FEATURE:
<223> OTHER INFORMATION: Description of Unknown:
DP67 Isoleucine--tRNA ligase sequence

<400> SEQUENCE: 104
atgagtgact ataaatctac cctgaatttg ccggaaacgg ggttcccgat gcgtggcgat 60
ctggccaaac gcgaaccggg tatgctgcaa cgttggtatg atgacaagct gtacggcatc 120
attcgcgaag ccaagaaagg gaaaaaaacc tttatcctgc acgatggccc tccttacgcc 180
aacggcagca ttcatattgg tcactccgtt aacaagattc tgaaagacat tatcgttaag 240
tcgaaaggca tggcgggcta tgactcgcct tatgtaccgg gttgggactg ccacggtctg 300
cctatcgagc ataaagttga gcagatgatc ggtaagccgg gagagaaagt cagcgccgct 360
gagttccgtg ctgcctgccg caaatacgct gccgagcagg tggaagggca gaaagccgac 420
tttatccgtc tgggtgtgtt gggtgactgg gatcgtccgt atctgacaat gaacttccag 480
accgaagcca atattatccg tgcgctgggt aaaatcatcg gtaacgggca cctgcacaaa 540
ggggccaagc cggtacactg gtgcctggac tgccgttctg ccctggctga ggcggaagtg 600
gagtactacg ataaaacctc tccgtctatc gatgtcatgt tcaatgcgac tgataaagag 660
ggggtacagg ccaaatttgc ggcaacgaat gttgacggcc cgatctcgct ggtgatctgg 720
actaccacgc cgtggaccat gccggctaac cgcgctatct cactgcatcc tgaattcgac 780
taccagctgg tacagattga aggccgtgct ctgatcctcg ccaaagagat ggttgagagc 840
gtgatgcagc gcgttggtgt tgccgcctgg accgtgctgg gcgaagcgaa aggggcagac 900
ctggagctga tgggcttcca gcatccgttc ctcgaccata cctctccggt tgtgctgggt 960
gagcatgtca cgctggaagc cggtaccggt gcggtccata ccgcaccagg ccatggcccg 1020
gacgactatg ttatcggtca gaaatacggt atcgaagtgg ctaacccggt cggcccggat 1080
ggctgctacc tgccgggaac ctacccgacg ctggatggtg tgaacgtctt taaagccaac 1140
gatatgatcg ttgaactgct gcgtgaaaag ggtgctctgc tgcacgttga gaaactgttc 1200
cacagctatc cacactgctg gcgtcataaa acgcccatca tcttccgcgc tacgccacag 1260
tggtttatca gcatggatca gaagggcctg cgtgcgcagt cgctgaaaga gatcaagggc 1320
gtgcagtgga tcccggactg ggtcaggca cgtattgaat cgatggtcgc gaaccgtcct 1380
gactggtgta tttcccgtca gcgtacctgg ggcgtgccga tggcgctgtt cgtccataaa 1440
gacaccgaac agctgcaccc ggattcgctg gagctgatgg agaaagtggc gaagcgggtt 1500
gagcaggacg gcattcaggc atggtgggat cttgatgccc gcgacctgat gggcgccgat 1560
gctgacaact acgttaaagt cccggatacc ctggacgtct ggtttgactc cggttcaacc 1620
agctactcgg tcgtcgatgc ccgccctgaa tttgacggca atgcccctga cctgtatctg 1680
gaaggatcgg atcagcaccg cggctggttt atgtcctcac tgatgatctc gaccgcgatg 1740
aaaggcaaag cgccttaccg tcaggtactg acgcacggct tcaccgtcga tggtcagggc 1800
cgtaagatgt ccaagtcact gggcaatact gtcagcccgc aggatgtgat gaacaaactg 1860
ggcgccgata ttctgcgcct gtgggtcgcc tctacggact actccggtga gatcgccgta 1920
tccgacgaga tccttaaacg ctctgccgac agctatcgcc gcatccgtaa caccgcacgt 1980
ttcctgctgg caaaccttgc cggttttaat ccggaaaccg atagggtgaa accggaagag 2040
atggtggtgg tggatcgctg ggccgttggc cgtgcgctgg cggcacagaa tgatatcgta 2100
gcctcgtatg aagcttatga cttccatgaa gtcgtgcagc gtctgatgca gttctgttcg 2160
gttgagatgg gctccttcta cctggatatc atcaaggatc gtcagtacac cgcgaaggcc 2220
gatggcctgg cgcgtcgcag ctgtcagacg gcgctgtggt atatcgtgga agcgctggtg 2280
cgctggatgg caccgattat gtccttcact gccgatgaaa tctggggtta cctgccgggt 2340
aaacgcagcc agtatgtctt taccgaagag tggtttgacg ggctgttcag cctggaggac 2400
aatcagccga tgaacgacag ttactgggca gaactgctga aagtacgcgg tgaagtcaac 2460
aaggtgatcg agcaggcccg cgctgataag cggattggcg ggtctctgga agccagcgtg 2520
acgctgtatg ctgacgcaga cctggccgcg aagctgacca gcctgggtga ggagctgcgc 2580
tttgtgttgc tgacttccgg ggcgcaggtt gcggattatg cgcaggccac cgctgatgca 2640
cagcaaagcg aaggggtaaa aggtctgaaa attgccctga gcaaagcgga aggcgagaag 2700
tgcccgcgct gctggcatta cactaacgat atcggccaga atgctgaaca cgctgacgtg 2760
tgcggccgtt gtgtcactaa cgtcgcgggc agcggcgaac agcgtaagtt tgcatga 2817

<210> SEQ ID NO 105
<211> LENGTH: 1731
<212> TYPE: DNA
<213> ORGANISM: Unknown
<220> FEATURE:
<223> OTHER INFORMATION: Description of Unknown:
DP67 NADH-quinone oxidoreductase subunit C/D sequence

<400> SEQUENCE: 105
gtgatcggcg agctgcgtaa tcgttttggg cctgatgcct ttacagtaca agcgacccgt 60
accggcgtgc cggtggtctg ggtaaaacgt gagcagttgc ttgagattat tgagttcctg 120
cgcaagctgc ctaaacccta tgtgatgctg tatgacctgc atggcatgga tgagcgcctg 180
cgtactcacc gtgccggttt accggcggcg gatttttccg ttttctatca cttcatctcc 240
attgaacgta accgcgacat catgctcaag gtggcgttgt ctgaaaacga tttgaatgtg 300
cccaccatca ccaaaatttt cccgaatgcc aactggtatg agcgtgaaac ctgggagatg 360
tttggtatca atgttgaagg ccacccgcac ctgacgcgca ttatgatgcc gcagagctgg 420
gaagggcatc cgctgcgcaa agattaccct gcgcgtgcga ccgagttcga tccgtttgaa 480
ctgaccaagc agaaagaaga tctggagatg gaatctctga ccttcaagcc tgaagactgg 540
ggcatgaagc gttcgaccaa caatgaggac ttcatgttcc tcaacctggg cccgaaccac 600

```
ccttctgcgc acggcgcgtt ccgtatcatc ctgcaactgg acggtgaaga gatcgtcgac    660

tgcgtgccgg atatcggata ccaccatcgt ggtgccgaaa aaatgggtga acgccagtcc    720

tggcacagct acattccgta taccgaccgt attgagtatc tcggcggctg cgtaaacgaa    780

atgccgtacg tgctggcggt agaaaagctg gctggtatca aagtccctga gcgcgtggaa    840

gtcattcgcg tgatgctatc agagctgttc cgtataaaca gccacctgct gtacatctct    900

acgtttatcc aggacgtcgg tgctatgtcc ccggtgttct ttgcctttac tgaccgccag    960

aaaatttacg acgtggtaga agccattacc ggcttccgta tgcatccggc ctggttccgc   1020

attggtggcg tggcgcatga tctgcctaaa ggctgggagc gcctgctgcg tgagttcctg   1080

gattggatgc ctaagcgtct gaaagcctat gagcagaccg cactgaaaaa ctccgtgctt   1140

attgcccgtt ccaaaggggt ttctgcctat aacatggaag aagcactggc ctggggcacg   1200

acgggggctg gcctgcgtgg taccggtctg gactttgatg tgcgtaaatg gcgtccatat   1260

tccggttatg aaaacttcga tttcgaagtg ccaatcggag atggcgtaag ctgtgcttac   1320

acccgtgtca tgctgaagat ggaagagatg cgccagagta tgcgcatcct ggaacagtgc   1380

ctgaagaaca tgccagcagg cccgttcaag gctgaccatc cgctgaccac gccgccgccg   1440

aaagagcgca cgctgcagca tatcgaaacc ctgatcactc acttcctgca ggtttcgtgg   1500

ggcccggtaa tgccggcaaa cgaatccttc cagatgattg aagcgaccaa agggatcaac   1560

agttactacc tgaccagtga tggcagcacg atgagctacc gcacccgcgt gcgtacgccg   1620

agcttcccgc atttgcaaca gatcccatcg gtgatcaacg gcagcctggt atccgatctg   1680

atcgtatacc tcggtagtat cgattttgtt atgtcagacg tggaccgcta a            1731
```

```
<210> SEQ ID NO 106
<211> LENGTH: 1062
<212> TYPE: DNA
<213> ORGANISM: Unknown
<220> FEATURE:
<223> OTHER INFORMATION: Description of Unknown:
      DP67 Protein RecA sequence

<400> SEQUENCE: 106
```

```
atggctatcg acgaaaacaa gcaaaaagca ctggcagcag cgctgggcca gattgaaaag     60

cagtttggta aaggctccat catgcgcctg ggtgaagacc gcaccatgga tgtggaaacc    120

atctcaaccg gttctttatc actggatatc gcgctgggtg ccggtggttt accaatgggc    180

cgtatcgttg aaatctatgg cccggagtct tccggtaaaa ccaccctgac gctgcaggtt    240

atcgcttctg cacagcgtaa agggaaaacc tgtgcattta tcgatgccga gcatgctctg    300

gacccggtct acgctaaaaa actgggcgtg gatatcgata acttgctgtg ttctcagccg    360

gataccggtg agcaggcgct ggaaatctgt gatgcgctgg cccgttccgg tgcggttgac    420

gtcatcatcg tcgactccgt agcggcgttg acaccaaaag cagaaatcga aggtgaaatc    480

ggtgactctc atatgggcct tgcggcacgt atgatgagcc aggcgatgcg taagctggcc    540

ggtaacctga agaactccgg tacgctgctg atctttatca accagatccg tatgaaaatt    600

ggcgtgatgt tcggtaaccc ggaaaccact accggtggta acgctctgaa attctacgct    660

tctgtccgtc tggatattcg ccgcatcggc gcgatcaaag agggtgatga agtggtgggt    720

agcgaaaccc gcgttaaagt ggtgaaaaac aaaatcgcag caccgtttaa acaggctgag    780

ttccagatca tgtacggcga aggtatcaac gtttacggtg agctggtcga cctgggcgtg    840

aagcacaagc tgatcgaaaa agccggtgcc tggtacagct ataacggtga caagattggt    900
```

```
cagggtaaag ccaactcagg taacttcctg aaagagaacc cggctatcgc taacgaaatc    960

gaagcaaaac tgcgtgaaat gctgttgaac agcccggacg ataagcctga ttttgttccg   1020

gctccgcatg aagccgatag tgaagttaac gaagatatct aa                      1062
```

<210> SEQ ID NO 107
<211> LENGTH: 1842
<212> TYPE: DNA
<213> ORGANISM: Unknown
<220> FEATURE:
<223> OTHER INFORMATION: Description of Unknown:
RNA polymerase sigma factor RpoD sequence

<400> SEQUENCE: 107

```
atggagcaaa acccgcagtc acagcttaag ctacttgtca cccgtggtaa ggagcaaggc     60

tatctgacct atgccgaggt caatgaccat ctgccggaag atatcgtcga ctccgatcag    120

attgaagaca tcattcagat gatcaacgac atgggcattc aggttgtaga agaagcgcct    180

gatgccgatg atttgatgct gaatgagaac aacaacgaca cggacgaaga cgctgccgaa    240

gcggctgctc aggtattatc cagcgtagaa tctgaaatcg gacgtaccac cgacccggtg    300

cgcatgtaca tgcgcgaaat ggggacggtt gaactgctga cgcgtgaagg cgagatcgat    360

atcgccaaac gcatcgaaga gggtatcaac caggtacagt gttccgttgc tgaatatcct    420

gaagcgatta cttacctgct tgagcaatat gaccgtgttg aagcgggcga agcgcgcctg    480

tcggatctga tcaccggttt tgtcgacccg aatgccgaag cagagatcgc ccctactgcg    540

actcacgtgg gttcagaact ttccgctgaa gagcgtgatg acgaagaaga agacgaagag    600

tctgacgacg acagctcgga tgatgacaac agcatcgatc cggaactggc gcgggaaaaa    660

ttcaacgacc tgcgcgttca gtacgaaacc acccgtaccg ttatcaaagc gaaaagccgc    720

agccacgctg atgccatcgc tgagatccag aatctgtccg acgtgttcaa gcagttccgc    780

ctggtgccga agcagttcga cttcctggtg aacagcatgc gcaccatgat ggatcgcgtc    840

cgtactcagg aacgcctgat cctcaagctg tgcgtagaaa tctgtaagat gccgaagaag    900

aacttcatta ccctgttcac cggtaatgaa accagcgaaa cctggttcaa agcggcactg    960

gcaatgaata agccgtggtc agagaagctg aacgatgtgt cagatgacgt acaccgtagc   1020

ctgatgaagc tgcagcagat cgaaacggaa actggcctga cgattgaaca ggtaaaagac   1080

atcaaccgtc gtatgtcgat cggcgaagcg aaagcgcgcc gtgcgaagaa agagatggtt   1140

gaggctaacc tgcgtctggt tatctctatc gccaagaagt acaccaaccg tggcctgcag   1200

ttcctggatc tgattcagga aggtaacatc ggtctgatga aagcggtgga taagtttgaa   1260

tatcgccgtg gttataagtt ctcgacttat gccacctggt ggatccgtca ggcgatcacc   1320

cgttcaatcg ctgaccaggc gcgtaccatc cgtattccgg tgcacatgat tgagacgatt   1380

aacaagctca accgtatttc ccgccagatg ctgcaagaga tgggccgtga gccgacgccg   1440

gaagagctgg ccgagcgtat gctgatgccg gaagataaga tccgtaaggt gctgaaaatt   1500

gccaaagagc cgatctctat ggagacgccg attggtgatg atgaagattc acatctgggt   1560

gattttatcg aagacaccac gctggagctg ccgctggact ccgcgacgtc agagagcctg   1620

cgttctgcca cgcacgacgt gctggccggt ctgaccgcgc gtgaagccaa agtactgcgt   1680

atgcgtttcg gtatcgatat gaataccgac cacacgctgg aagaagtggg caaacagttc   1740

gacgtaacgc gtgagcgtat tcgtcagatt gaggcgaaag cgctgcgtaa gctgcgtcac   1800

ccaagccgct ctgaagtgct gcgcagcttc ctcgacgatt aa                      1842
```

<210> SEQ ID NO 108
<211> LENGTH: 4029
<212> TYPE: DNA
<213> ORGANISM: Unknown
<220> FEATURE:
<223> OTHER INFORMATION: Description of Unknown:
DNA-directed RNA polymerase subunit beta sequence

<400> SEQUENCE: 108

```
atggtttact cctataccga gaaaaaacgt attcgtaagg attttggaaa gcgtccacaa     60
gttctggaca ttccatatct cctttctatc cagcttgact cgttccagaa gttcatcgag    120
caagatccgg aaggtcaata tggtctggaa gcagcattcc gctccgtatt tccaatccaa    180
agctatagcg gtaattctga gctgcagtac gtcagctacc gtttaggcga acccgtcttt    240
gatgtgaaag agtgtcagat tcgtggcgtc acgtattctg ctcctctgcg cgtaaaactg    300
cgcctggtga tctacgagcg cgaagcgccg gaaggcaccg ttaaagacat caaagaacaa    360
gaagtttaca tgggcgaaat tccgctcatg acggataacg gtacctttgt tatcaacggt    420
actgagcgcg ttatcgtttc tcagctccac cgtagtcctg gtgtcttctt cgacagcgat    480
aagggtaaaa cccactcgtc cggtaaagtg ctgtataacg cacgtatcat cccttaccgt    540
ggttcatggc tggacttcga gttcgacccg aaagacaacc tgttcgtccg tattgaccgt    600
cgccgtaaac tgccagcgac catcattctg cgcgcgttga attacaccac tgaacagatc    660
ctcgacctgt tcttcgataa agtggtttac caaattcgcg acaacaagct gcagatggag    720
cttattcctg agcgcctgcg tggtgagacc gcttcatttg atattgaagc gaacggcacc    780
gtttacgtcg aaaaaggccg ccgtattact gcgcgccata ttcgccagct tgagaaagat    840
gctgttgccc acatcgaagt gccggttgag tatattgccg gtaaagtggt cgctaaagac    900
tacgttgatg agagcaccgg tgaactgctg atcgcagcga acatggaact gtcactggat    960
ctgctggcta aactcagcca gtccggtcac aagcgcattg aaaccctgtt caccaacgat   1020
ctggatcacg gtgcgtacat gtctgagacg gtacgtgtcg acccaaccag cgatcgcctg   1080
agcgctctgg ttgagatcta ccgcatgatg cgtcctggtg agccaccaac gcgtgaagcg   1140
gctgaaaacc tgtttgagaa cctgttcttc tctgaagacc gctatgatct gtctgcggtt   1200
ggtcgtatga agttcaaccg ttctctgctg cgcgacgaga tcgaaggttc cggtatcctg   1260
agcaaagacg acatcattca ggtgatgaag aagctcatcg gtatccgtaa cggtattggc   1320
gaagtggatg atatcgacca cctcggcaac cgtcgtatcc gttccgttgg cgaaatggct   1380
gaaaaccagt tccgtgttgg ccttgtgcgc gtagagcgtg cggtgaaaga gcgtctgtcc   1440
ctgggcgatc tggataccct gatgccacag gacatgatca acgccaagcc aatttctgcg   1500
gcagtgaaag agttcttcgg ctccagccag ctgtcacagt ttatggacca gaacaacccg   1560
ttgtctgaga tcacgcataa gcgtcgtatc tctgcactgg gtccgggcgg tctgacgcgt   1620
gagcgtgcag gcttcgaagt tcgagacgta cacccgacgc actacggtcg cgtatgtcca   1680
atcgaaacgc cggaaggtcc aaacatcggt ctgatcaact ccttgtctgt gtatgcacag   1740
accaatgagt acggtttcct ggaaacccca taccgtcgcg ttcgcgaagg cgtggtgacc   1800
gacgaaattc attacctctc tgctattgaa gagggtaact acgttatcgc tcaggcaaac   1860
accaatctcg acgacgaagg tcacttcgta gacgacctgg tcacctgccg tagcaaaggc   1920
gaatcgagtc tcttcaaccg cgatcaagtt gactacatgg acgtttccac ccagcaggtg   1980
gtttccgtcg gtgcgtcact gatcccgttc ctggagcacg atgacgccaa ccgcgcattg   2040
```

-continued atgggtgcaa acatgcaacg tcaggcggtt cctactctgc gtgctgataa gccgctggta 2100
ggtaccggta tggagcgtgc ggttgcggtt gactccggtg ttactgccgt agcgaaacgt 2160
ggtggtaccg tgcagtacgt ggatgcatcc cgtatcgtta ttaaagttaa cgaagacgaa 2220
atgtatccgg gcgaagccgg tatcgacatt tacaacctga ccaaatatac ccgttctaac 2280
cagaacacct gcatcaacca gatgccttgc gtgaacctgg gtgagccaat cgaacgtggt 2340
gatgtgctgg ctgatggccc ttcaaccgat ctcggcgaac tggcactcgg tcagaacatg 2400
cgcgtcgcgt tcatgccgtg gaacggctac aacttcgaag actccattct ggtctcggag 2460
cgcgttgttc aggaagatcg cttcaccact atccacattc aggaactggc gtgtgtgtct 2520
cgtgacacca agctggggcc agaagagatc accgctgaca tccctaacgt gggtgaagct 2580
gcgctctcta aactggatga gtccggtatc gtgtatatcg gtgcggaagt gaccggtggg 2640
gacattctgg ttggtaaggt aacacctaaa ggtgaaaccc agctgacgcc agaagagaaa 2700
ctgctgcgtg cgatcttcgg tgaaaaagcg tctgacgtta aagactcttc tctgcgcgta 2760
ccaaacggtg tgtcagggac aatcatcgac gttcaggtct ttacccgcga tggcgtggaa 2820
aaagacaagc gtgcgctgga aatcgaagag atgcagctga agcaggcgaa gaaagacctg 2880
tctgaagaat tgcagatcct cgaagccggc ttgttcagcc gtattaacta cctgctggtt 2940
gccggcggtg ttgaagcgga aaaactggag aagctgccac gtgagcgctg gctcgaactg 3000
ggcctgaccg acgaagagaa gcaaaatcag ctggaacagc tggccgagca gtacgacgag 3060
ctgaagcacg agtttgagaa aaaacttgaa gccaagcgcc gtaaaatcac tcagggcgat 3120
gacctggcac ctggcgtgct gaaaatcgtg aaagtgtatc tggccgttaa acgtcagatc 3180
cagcctggtg acaaaatggc aggtcgtcac gggaacaaag gtgttatctc caagatcaac 3240
ccgatcgaag atatgccata cgatgagttc ggtacgccgg tcgacatcgt actgaacccg 3300
ctgggcgttc catcacgtat gaacattggt cagattcttg aaacccacct gggtatggct 3360
gcgaaaggca ttggcgagaa aattaacgct atgcttaaga agcaggaaga agtgtccaag 3420
ctgcgtgaat tcattcagcg tgcttacgat ctgggcagcg atctgcgtca gaaagttgac 3480
ctgaacacct tcaccgatga cgaagtgctg cgcctggcag agaatctgaa aaaaggtatg 3540
ccaattgcaa caccagtgtt tgacggcgcg aaagagagcg aaatcaaaga gctgttacag 3600
ctcggcggcc tgccttcttc tggccagatc acgctgtttg atggtcgtac cggtgagcag 3660
ttcgaacgtc aggttaccgt tggctacatg tacatgctga agctgaacca cctggttgat 3720
gacaaaatgc atgcgcgttc taccggttct tacagcctcg ttactcagca gccgctgggt 3780
ggtaaggcgc agttcggtgg tcagcgcttc ggtgagatgg aagtgtgggc actggaagca 3840
tacggtgccg cgtataccct gcaggaaatg ctgaccgtga agtctgatga cgttaacggc 3900
cgtaccaaga tgtataaaaa catcgttgac ggcaaccatc agatggaacc gggcatgccg 3960
gaatctttca acgtactgtt gaaagagatc cgctcgctgg gtatcaacat cgagctggaa 4020
gacgagtaa 4029

<210> SEQ ID NO 109
<211> LENGTH: 1700
<212> TYPE: DNA
<213> ORGANISM: Unknown
<220> FEATURE:
<223> OTHER INFORMATION: Description of Unknown:
DP68 Glutamine--tRNA ligase sequence

<400> SEQUENCE: 109

-continued atgagcaagc ccactgtcga ccctacctcg aattccaagg ccggacctgc cgtcccggtc 60
aatttcctgc gcccgatcat ccaggcggac ctggattcgg gcaagcacac gcagatcgtc 120
acccgcttcc cgccagagcc caacggctac ctgcacatcg gtcacgccaa gtcgatctgt 180
gtgaacttcg gcctggccca ggagttcggt ggcgtcacgc acctgcgttt cgacgacacc 240
aacccggcca aggaagacca ggaatacatc gacgccatcg aaagcgacat caagtggctg 300
ggcttcgaat ggtccggtga agtgcgctat gcgtccaagt atttcgacca gttgttcgac 360
tgggccgtcg agctgatcaa ggccggcaag gcctacgtcg acgacctgac cccggagcag 420
gccaaggaat accgtggcac gctgaccgag ccgggcaaga acagcccgtt ccgtgaccgt 480
tcggtagaag agaacctcga ctggttcaac cgcatgcgcg ccggtgagtt cccggacggc 540
gcccgcgtgc tgcgcgccaa gatcgacatg gcctcgccga acatgaacct gcgcgacccg 600
atcatgtacc gcatccgcca cgcccatcac caccagaccg gtgacaagtg gtgcatctac 660
ccgaactatg acttcaccca cggtcagtcg gacgccatcg aaggcatcac ccactccatc 720
tgcaccctgg agttcgaaag ccatcgcccg ctgtatgagt ggttcctcga cagcctgccg 780
gttccggcgc acccgcgtca gtacgagttc agccgcctga acctgaacta caccatcacc 840
agcaagcgca agctcaagca gttggtggac gaaaagcacg tgcatggctg ggatgacccg 900
cgcatgtcca ccctgtcggg tttccgccgt cgcggctaca ccccggcgtc gatccgcagc 960
ttctgcgaca tggtcggcac caaccgctcc gacggcgtgg tcgattacgg catgctcgag 1020
ttcagcatcc gtcaggacct ggacgccaac gcgccgcgtg ccatgtgcgt attgcgcccg 1080
ttgaaagtcg tgatcaccaa ctatccggaa gacaaggtcg accacctcga actgccgcgt 1140
cacccgcaga aagaagaact tggcgtgcgc aagctgccgt tcgcgcgtga aatctacatc 1200
gaccgtgatg acttcatgga agagccgccg aaaggctaca agcgcctgga gcctaacggc 1260
gaagtgcgcc tgcgcggcag ctacgtgatc cgtgccgatg aagcgatcaa ggacgccgat 1320
ggcaacatcg tcgaactgcg atgctcctac gacccggaaa ccctgggcaa gaaccctgaa 1380
ggccgcaagg tcaaaggcgt cgttcactgg gtgccggctg ctgccagcat cgagtgcgaa 1440
gtgcgcctgt acgatcgtct gttccgttcg ccgaaccctg agaaggctga agacagcgcc 1500
agcttcctgg acaacatcaa ccctgactcc ctgcaagttc tcacgggttg tcgtgccgag 1560
ccatcgcttg gcgacgcaca gccggaagac cgtttccagt tcgagcgcga aggttacttc 1620
tgcgcggata tcaaggactc caaacctggt catccggtct tcaaccgtac cgtgaccttg 1680
cgtgattcgt ggggccagtg 1700

<210> SEQ ID NO 110
<211> LENGTH: 2418
<212> TYPE: DNA
<213> ORGANISM: Unknown
<220> FEATURE:
<223> OTHER INFORMATION: Description of Unknown:
DP68 DNA gyrase subunit B sequence

<400> SEQUENCE: 110
atgagcgaag aaaacacgta cgactcgacc agcattaaag tgctgaaagg tttggatgcc 60
gtacgcaaac gtcccggtat gtacatcggc gacaccgatg atggtagcgg tctgcaccac 120
atggtgttcg aggtggtcga caactccatc gacgaagctt tggccggtca ctgcgacgac 180
atcagcatta tcatccaccc ggatgagtcc atcaccgtgc gcgacaacgg tcgcggtatt 240
ccggtcgatg tgcacaaaga agaaggcgta tcggcggcag aggtcatcat gaccgtgctt 300

-continued

```
cacgccggcg gtaagttcga cgacaactcc tataaagttt ccggcggttt gcacggtgta    360
ggtgtgtcgg tggtgaacgc tctgtccgaa gagcttatcc tgactgttcg ccgtagcggc    420
aagatctggg aacagaccta cgtgcatggt gttccacaag aaccgatgaa aatcgttggc    480
gacagtgaat ccaccggtac gcagatccac ttcaagcctt cggcagaaac cttcaagaat    540
atccacttca gttgggacat cctggccaag cgtattcgtg aactgtcgtt ccttaactcc    600
ggtgtgggta tcgtcctcaa ggacgagcgc agcggcaagg aagagttgtt caagtacgaa    660
ggcggcttgc gtgcgttcgt tgagtacctg aacaccaaca agactgcggt caaccaggtg    720
ttccacttca acatccagcg tgaagacggt atcggcgttg aaatcgccct gcagtggaac    780
gacagcttca acgagaacct gttgtgcttc accaacaaca ttccacagcg cgacggcggt    840
actcacttgg tgggtttccg ttccgcactg acgcgtaacc tgaacaccta catcgaagcg    900
gaaggcttgg ccaagaagca caaagtggcc actaccggtg acgatgcgcg tgaaggcctg    960
acggcgatta tctcggtgaa agtgccggat ccaaagttca gctcccagac caaagacaag   1020
ctggtgtctt ccgaagtgaa gaccgcagtg gaacaggaga tggcgaagta cttctccgac   1080
ttcctgctgg aaaacccgaa cgaagccaag ttggttgtcg gcaagatgat cgacgcggcg   1140
cgtgcccgtg aagcggcgcg taaagcccgt gagatgaccc gccgtaaagg cgcgttggat   1200
atcgccggcc tgccgggcaa actggctgac tgccaggaga aggaccctgc cctctccgaa   1260
ctgtacctgg tggaaggtga ctctgctggc ggttccgcca agcagggtcg taaccgtcgc   1320
acccaggcta tcctgccgtt gaagggtaag atcctcaacg tcgagaaggc ccgcttcgac   1380
aagatgattt cctctcagga agtcggcacc ttgatcacgg cgttgggctg cggtattggc   1440
cgcgatgagt acaacatcga caaactgcgt taccacaaca tcatcatcat gaccgatgct   1500
gacgtcgacg gttcgcacat ccgtaccctg ctgctgacct tcttcttccg tcagttgccg   1560
gagctgatcg agcgtggcta catctacatc gctcagccgc cgttgtacaa agtgaaaaag   1620
ggcaagcaag agcagtacat caaagacgac gacgccatgg aagagtacat gacgcagtcg   1680
gccctggaag atgccagcct gcacttgaac gacgaagccc cgggcatttc cggtgaggcg   1740
ctggagcgtt tggttaacga cttccgcatg gtaatgaaga ccctcaagcg tctgtcgcgc   1800
ctgtaccctc aggagctgac cgagcacttc atctacctgc cttccgtgag cctggagcag   1860
ttgggcgatc acgcccacat gcagaattgg ctggctcagt acgaagtacg tctgcgcacc   1920
gtcgagaagt ctggcctggt ttacaaagcc agcttgcgtg aagaccgtga acgtaacgtg   1980
tggctgccgg aggttgaact gatctcccac ggcctgtcga actacgtcac cttcaaccgc   2040
gacttcttcg gcagcaacga ctacaagacc gtggttaccc tcggcgcgca attgagcacc   2100
ctgttggacg acggtgctta catccagcgt ggcgagcgta agaaagcggt caaggagttc   2160
aaggaagccc tggactggtt gatggctgaa agcaccaagc gccacaccat ccagcgatac   2220
aaaggtctgg gcgagatgaa cccggatcaa ctgtgggaaa ccaccatgga tcctgctcag   2280
cgtcgcatgc tacgcgtgac catcgaagac gccattggcg cagaccagat cttcaacacc   2340
ctgatgggtg atgcggtcga gcctcgccgt gacttcatcg agagcaacgc cttggcggtg   2400
tctaacctgg atttctga                                                 2418
```

<210> SEQ ID NO 111
<211> LENGTH: 2832
<212> TYPE: DNA
<213> ORGANISM: Unknown
<220> FEATURE:
<223> OTHER INFORMATION: Description of Unknown:

DP68 Isoleucine--tRNA ligase sequence

<400> SEQUENCE: 111

```
atgaccgact ataaagccac gctaaacctt ccggacaccg ccttcccaat gaaggccggc     60
ctgccacagc gcgaaccgca gatcctgcag cgctgggaca gtattggcct gtacggaaag    120
ttgcgcgaaa ttggcaagga tcgtccgaag ttcgtcctgc acgacggccc tccttatgcc    180
aacggcacga ttcacatcgg tcatgcgctg aacaaaattc tcaaggacat gatcctgcgt    240
tcgaaaaccc tgtcgggctt cgacgcgcct tatgttccgg gctgggactg ccacggcctg    300
ccgatcgaac acaaagtcga agtgacctac ggcaagaacc tgggcgcgga taaaacccgc    360
gaactgtgcc gtgcctacgc caccgagcag atcgaagggc agaagtccga attcatccgc    420
ctgggcgtgc tgggcgagtg ggacaacccg tacaagacca tgaacttcaa gaacgaggcc    480
ggtgaaatcc gtgccttggc tgaaatcgtc aaaggcggtt tcgtgttcaa gggcctcaag    540
cccgtgaact ggtgcttcga ctgcggttcg gccctggctg aagcggaagt cgagtacgaa    600
gacaagaagt cctcgaccat cgacgtggcc ttcccgatcg ccgacgacga caagctggct    660
caagcctttg gcctgtccag cctgccaaag cctgcagcca tcgtgatctg gaccaccacc    720
ccgtggacca tcccggccaa ccaggcgctg aacgtgcacc cggaattcac ctacgccctg    780
gtggacgtcg gtgatcgcct gctggtgctg gctgaagaaa tggtcgaggc ctgcctggcg    840
cgctacgagc tgcaaggttc ggtcatcgcc accaccaccg gcactgcgct ggagctgatc    900
aatttccgtc acccgttcta tgaccgtctg tcgccggtgt acctggctga ctacgtagag    960
ctgggttcgg gtactggtgt ggttcactcc gcgccggcct acggcgttga tgactttgtg   1020
acctgcaaag cctacggcat ggtcaacgat gacatcctca acccggtgca gagcaatggc   1080
gtgtacgcgc cgtcgctgga gttctttggc ggccagttca tcttcaaggc caacgagccg   1140
atcatcgaca aactgcgtga agtcggttcg ctgctgcaca ccgaaaccat caagcacagc   1200
tacatgcact gctggcgtca caagaccccg ctgatctacc gcgctaccgc gcagtggttt   1260
atcggcatgg acaaagagcc gaccagcggc gacaccctgc gtgtgcgctc gctcaaagcg   1320
atcgaagaga ccaagtttgt cccggcctgg ggccaggcgc gcctgcactc gatgatcgcc   1380
aaccgcccgg actggtgcat ctcccgccag cgcaactggg gcgtgccgat tccgttcttc   1440
ctgaacaagg aaagcggcga gctgcaccca cgtaccgttg aactgatgga agcagtggcg   1500
ctgcgcgttg agcaggaagg catcgaagcc tggttcaagc tggacgccgc cgaactgctg   1560
ggcgacgaag cgccgctgta cgacaagatc agcgacaccc tcgacgtgtg gttcgactcg   1620
ggtaccaccc actggcacgt gctgcgcggt tcgcacccga tgggtcacgc caccggcccg   1680
cgtgccgacc tgtacctgga aggctcggac caacaccgtg gctggttcca ctcgtcgttg   1740
ctgaccggct gcgccatcga caaccacgcg ccgtaccgcg aactgctgac ccacggcttc   1800
accgtcgacg agacgggccg caagatgtcc aagtcgctga aaaacgtgat cgagccgaaa   1860
aagatcaacg acaccctggg cgccgatatc atgcgtctgt gggtcgcctc gaccgattac   1920
tcgggcgaaa tcgccgtgtc ggaccagatc ctggcccgta gcgccgatgc ctaccgccgt   1980
atccgtaata ccgcacgctt cctgctgtcg aacctgaccg gtttcaaccc ggccaccgac   2040
atcctgccgg ccgaggacat gctcgccctg gaccgttggg ccgtggaccg tacgctgttg   2100
ctgcagcgcg agttgcagga acactacggc gaataccgtt tctggaacgt gtactccaag   2160
atccacaact tctgcgtgca ggagctgggt ggtttctacc tcgatatcat caaggaccgc   2220
cagtacacca ccggcgccaa cagcaaggcg cgccgctcgg cgcagaccgc gctgtaccac   2280
```

-continued atctctgaag cgctggtgcg ctggatcgca ccgatcctgg ccttcaccgc tgacgaactg 2340
tgggaatacc tgccgggcga gcgtaacgaa tcggtgatgc tcaacacctg gtacgaaggc 2400
ctgaccgaat tgccggccaa cttcgaactg ggccgcgagt actgggaagg cgtgatggcc 2460
gtcaaggttg cggtgaacaa ggagctggaa gttcagcgcg cggccaaggc cgtcggtggc 2520
aacctgcaag ccgaagtcac cctgtttgcc gaggaaggcc tgaccgccga cctggccaag 2580
ctgagcaacg aactgcgctt cgtactgatc acctcgaccg cgagcctggc accgtttgcc 2640
caggcacctg cggacgcagt ggccaccgaa gtgccgggcc tcaagctcaa agtggtcaag 2700
tcggcctttc ctaagtgcgc ccgttgctgg cactgccgtg aagacgtcgg cgtgaaccca 2760
gagcatccgg aaatctgcgg tcgttgcgtc gacaacatca gcggtgctgg cgaggttcgc 2820
cactatgcct aa 2832

<210> SEQ ID NO 112
<211> LENGTH: 1785
<212> TYPE: DNA
<213> ORGANISM: Unknown
<220> FEATURE:
<223> OTHER INFORMATION: Description of Unknown:
DP68 NADH-quinone oxidoreductase subunit C/D sequence

<400> SEQUENCE: 112
atgactacag gcagtgctct gtacatcccg ccttacaagg cagacgacca ggatgtggtt 60
gtcgaactca ataaccgttt tggccctgac gccttcaccg cccaggccac acgcaccggt 120
atgccggtgc tgtgggtggc gcgcgccaag ctcgtcgaag tcctgagctt cctgcgcaac 180
ctgcccaagc cgtacgtcat gctttatgac ctgcatggcg tggacgagcg tctgcgcacc 240
aagcgtcaag gtttgccgag cggtgccgat ttcaccgtgt tctaccactt gatgtcgctg 300
gaacgtaaca gcgacgtgat gatcaaggtc gcgctgtccg aaagcgactt gagcatcccg 360
accgtcaccg gtatctggcc gaatgccagc tggtacgagc gcgaagtttg ggacatgttc 420
ggtatcgact tcccgggcca cccgcacctg acgcgcatca tgatgccgcc gacctgggaa 480
ggtcacccgc tgcgcaagga ctttcctgcc cgcgcaaccg aattcgaccc gttcagcctc 540
aacctcgcca agcagcagct tgaagaagaa gctgcacgct tccgtccgga agactggggc 600
atgaaacgct ccggcaccaa cgaggactac atgttcctca acctgggccc gaaccaccct 660
tcggctcacg gtgccttccg tatcatcctg caactggacg gcgaagaaat cgtcgactgt 720
gtgccggaca tcggttacca ccaccgtggt gccgagaaga tggccgagcg ccagtcctgg 780
cacagcttca tcccgtacac cgaccgtatc gactacctcg gcggcgtgat gaacaacctg 840
ccgtacgtgc tgtcggtcga gaagctggcc ggtatcaagg tgccggaccg cgtcgacacc 900
atccgcatca tgatggccga gttcttccgc atcaccagcc acctgctgtt cctgggtacc 960
tatatccagg acgttggcgc catgaccccg gtgttcttca ccttcaccga ccgtcaacgc 1020
gcctacaagg tgatcgaagc catcaccggt ttccgcctgc acccggcctg gtatcgcatc 1080
ggcggcgtgg cgcacgacct gccgaacggc tgggagcgcc tggtcaagga attcatcgac 1140
tggatgccca agcgtctgga cgagtaccaa aaggctgcgc tggacaacag catcctcaag 1200
ggtcgtacca tcggcgtcgc gcagtacaac accaaagaag ccctggaatg gggcgtcact 1260
ggtgccggcc tgcgttcgac cggctgcgac ttcgacctgc gtaaagcacg gccgtactcg 1320
ggctacgaga acttcgagtt cgaagtgccg ctggccgcca atggcgatgc ctacgaccgg 1380
tgcatcgtgc gcgttgaaga aatgcgccag agcctgaaga tcatcgagca gtgcatgcgc 1440
aacatgccgg ctggcccgta caaggcggat catccgctga ccacaccgcc gccgaaagag 1500
cgcacgctgc agcacatcga aaccctgatc acgcacttcc tgcaagtttc gtggggcccg 1560
gtgatgccgg ccaacgaatc cttccagatg atcgaagcga ccaagggtat caacagttat 1620
tacctgacga gcgatggcgg caccatgagc taccgcaccc ggattcgtac cccaagcttt 1680
gcccacttgc agcagatccc ttcggtgatc aaaggcgaga tggtcgcgga cttgattgcg 1740
tacctgggta gtatcgattt cgttatggcc gacgtggacc gctaa 1785

<210> SEQ ID NO 113
<211> LENGTH: 1059
<212> TYPE: DNA
<213> ORGANISM: Unknown
<220> FEATURE:
<223> OTHER INFORMATION: Description of Unknown:
DP68 Protein RecA sequence

<400> SEQUENCE: 113
atggacgaca acaagaagaa agccttggct gcggccctgg gtcagatcga acgtcaattc 60
ggcaagggtg ccgtaatgcg tatgggcgat cacgaccgtc aggcgatccc ggctatttcc 120
actggctctc tgggtctgga catcgcactc ggcattggcg gcctgccaaa aggccgtatc 180
gttgaaatct acggtcctga atcttccggt aaaaccaccc tgaccctgtc ggtgattgcc 240
caggcgcaaa aaatgggcgc cacctgtgcg ttcgtcgacg ccgagcacgc cctggacccg 300
gaatacgccg gtaagctggg cgtcaacgtt gacgacctgc tggtttccca gccggacacc 360
ggtgagcaag ccctggaaat caccgacatg ctggtgcgct ccaacgccat cgacgtgatc 420
gtggtcgact ccgtggctgc cctggtaccg aaagctgaaa tcgaaggcga aatgggcgac 480
atgcacgtgg gcctgcaagc ccgcctgatg tcccaggcgc tgcgtaaaat taccggtaac 540
atcaagaacg ccaactgcct ggtgatcttc atcaaccaga tccgtatgaa gatcggcgta 600
atgttcggca gcccggaaac cactaccggt ggtaacgcgc tgaagttcta cgcttcggtc 660
cgtctggaca tccgccgtac cggcgcggtg aaggaaggtg acgaagttgt tggtagcgaa 720
actcgcgtta aagtcgtgaa gaacaaggtc gctccgcctt tccgtcaggc agagttccag 780
attctctacg gcaagggtat ctacctgaac ggcgagatga ttgacctggg cgtactgcac 840
ggtttcgtcg agaagtccgg tgcctggtat gcctacaacg gcagcaagat cggtcagggc 900
aaggccaact cggccaagtt cctggcagac aacccggata tcgctgccac gcttgagaag 960
cagattcgcg acaagctgct gaccccagcg ccagacgtga aagctgccgc caaccgcgag 1020
ccggttgaag aagtggaaga agctgacact gatatctga 1059

<210> SEQ ID NO 114
<211> LENGTH: 1851
<212> TYPE: DNA
<213> ORGANISM: Unknown
<220> FEATURE:
<223> OTHER INFORMATION: Description of Unknown:
DP68 RNA polymerase sigma factor RpoD sequence

<400> SEQUENCE: 114
atgtccggaa aagcgcaaca acagtctcgt attaaagagt tgatcaccct tggtcgtgag 60
cagaaatatc tgacttacgc agaggtcaac gatcacctgc ctgaggatat ttcagatcct 120
gagcaggtgg aagacatcat ccgcatgatt aatgacatgg ggatccccgt acacgagagt 180
gctccggatg cggacgccct tatgttggcc gactccgata ccgacgaggc agctgctgaa 240
gaagcggctg ctgcgctggc agcggtggag accgacatcg gtcgtacgac tgaccctgtg 300
cgcatgtata tgcgtgaaat gggtaccgtc gagctgctga cacgtgaagg cgaaatcgaa 360
atcgccaaac gtattgaaga gggtatccgt gaagtgatgg gcgcaatcgc gcacttccct 420
ggcacggttg accacattct ctccgagtac actcgcgtca ccaccgaagg tggccgcctg 480
tctgacgttc tgagcggcta catcgacccg gacgacggca ttgcgccgcc tgccgccgaa 540
gtaccgccgc ccgtcgatgc gaaagccgcg aaggctgacg acgacaccga agacgacgat 600
gctgaagcca gcagcgacga cgaagatgaa gttgaaagcg gcccggaccc gatcatcgca 660
gcccagcgtt tcggtgcggt ttccgatcaa atggaaatca cccgcaaggc cctgaaaaag 720
cacggtcgct ccaacaagct ggcgattgcc gagctggtgg ccctggctga gctgttcatg 780
ccgatcaagc tggtaccgaa gcaattcgaa ggcttggttg agcgtgttcg cagtgccctt 840
gaacgtctgc gtgcgcaaga acgcgcaatc atgcagctgt gtgtacgtga tgcacgtatg 900
ccgcgggctg acttcctgcg ccagttcccg ggcaacgaag tagacgaaag ctggaccgac 960
gcactggcca aaggcaaggc gaaatacgcc gaagccattg gtcgcctgca gccggacatc 1020
atccgttgcc agcagaagct gaccgcgctt gagaccgaaa ccggtctgac gattgctgaa 1080
atcaaagaca tcaaccgtcg catgtcgatc ggtgaggcca aggcccgccg cgcgaagaaa 1140
gagatggttg aagcgaactt gcgtctggtg atctcgatcg ccaagaagta caccaaccgt 1200
ggtctgcaat tcctcgatct gatccaggaa ggcaacatcg gcttgatgaa ggcggtggac 1260
aagttcgaat accgtcgcgg ctacaagttc tcgacttatg ccacctggtg gatccgtcag 1320
gcgatcactc gctcgatcgc cgaccaggct cgcaccatcc gtattccggt gcacatgatc 1380
gagacgatca acaagctcaa ccgtatttcc cggcagatgt tgcaggaaat gggtcgcgaa 1440
ccgaccccgg aagagctggg cgaacgcatg gaaatgcctg aggataaaat ccgcaaggta 1500
ttgaagatcg ctaaagagcc gatctccatg gaaacgccga ttggtgatga cgaagactcc 1560
cacctgggtg acttcatcga agactcgacc atgcagtcgc caatcgatgt cgccactgtt 1620
gagagcctta aagaagcgac tcgcgacgta ctgtccggcc tcactgcccg tgaagccaag 1680
gtactgcgca tgcgtttcgg catcgacatg aataccgacc acacccttga ggaagtcggt 1740
aagcagtttg acgtgacccg cgagcggatc cgtcagatcg aagccaaggc gctgcgcaag 1800
ttgcgccacc cgacgcgaag cgagcatctg cgctccttcc tcgacgagtg a 1851

<210> SEQ ID NO 115
<211> LENGTH: 4074
<212> TYPE: DNA
<213> ORGANISM: Unknown
<220> FEATURE:
<223> OTHER INFORMATION: Description of Unknown:
DP68 DNA-directed RNA polymerase subunit beta sequence

<400> SEQUENCE: 115
atggcttact catatactga gaaaaaacgt atccgcaagg actttagcaa gttgccggac 60
gtcatggatg tcccgtacct tctggctatc cagctggatt cgtatcgtga attcttgcag 120
gcgggagcga ccaaagatca gttccgcgac gtgggcctgc atgcggcctt caaatccgtt 180
ttcccgatca tcagctactc cggcaatgct gcgctggagt acgtgggtta tcgcctgggc 240
gaaccggcat ttgatgtcaa agaatgcgtg ttgcgcggtg ttacgtacgc cgtacctttg 300
cgggtaaaag tccgcctgat cattttcgac aaagaatcgt cgaacaaagc gatcaaggac 360
atcaaagagc aagaagtcta catgggcgaa atcccactga tgactgaaaa cggtaccttc 420

-continued

```
gtaatcaacg gtaccgagcg tgttattgtt tcccagctgc accgttcccc gggcgtgttc    480
ttcgaccacg accgcggcaa gacgcacagc tccggtaaac tcctgtactc cgcgcggatc    540
attccgtacc gcggttcgtg gttggacttc gagttcgacc cgaaagactg cgtgttcgtg    600
cgtatcgacc gtcgtcgcaa gctgccggcc tcggtactgc tgcgcgcgct cggttacacc    660
actgagcagg tgctggacgc tttctacacc accaacgtat tcagcctgaa ggatgaaacc    720
ctcagcctgg agctgattgc ttcgcgtctg cgtggtgaaa ttgccgttct ggacattcag    780
gacgaaaacg gcaaagtgat cgttgaagcg ggtcgtcgta ttactgcgcg ccacatcaac    840
cagatcgaaa aagccggcat caagtcgctg gaagtgcctc tggactacgt cctgggtcgc    900
accaccgcca aggttatcgt tcacccggct acaggcgaaa tcctggctga gtgcaacacc    960
gagctgaaca ccgaaatcct ggcaaaaatc gccaaggccc aggttgttcg catcgagacc   1020
ctgtacacca acgacatcga ctgcggtccg ttcatctccg acacactgaa gatcgactcc   1080
accagcaacc aattggaagc gctggtcgag atctatcgca tgatgcgtcc tggtgagcca   1140
ccgaccaaag acgctgccga gaccctgttc aacaacctgt tcttcagccc tgagcgttat   1200
gacctgtctg cggtcggccg gatgaagttc aaccgtcgta tcggtcgtac cgagatcgaa   1260
ggttcgggcg tgctgtgcaa ggaagatatc gtcgcggtac tgaagactct ggtcgacatc   1320
cgtaacggta aaggcatcgt cgatgacatc gaccacctgg gtaaccgtcg tgttcgctgc   1380
gtaggcgaaa tggccgaaaa ccagttccgc gttggccttg tgcgtgttga acgtgcggtc   1440
aaagagcgtc tgtcgatggc tgaaagcgaa ggcctgatgc cgcaagacct gatcaacgcc   1500
aagccagtgg ctgcggcagt gaaagagttc ttcggttcca gccagctttc ccagttcatg   1560
gaccagaaca acccgctctc cgagatcacc cacaagcgcc gtgtttctgc actgggcccg   1620
ggcggtctga cccgtgagcg tgctggcttt gaagttcgtg acgtacaccc gacgcactac   1680
ggtcgtgttt gcccgatcga aacgccggaa ggtccgaaca tcggtctgat caactccctg   1740
gccgcttatg cgcgcaccaa ccagtacggc ttcctcgaga gcccgtaccg cgtggtgaaa   1800
gacgctctgg tcaccgacga gatcgtattc ctgtccgcca tcgaagaagc tgatcacgtg   1860
atcgctcagg cttcggccac gatgaacgac aagaaagtcc tgatcgacga gctggtagct   1920
gttcgtcact tgaacgagtt caccgtcaag gcgccggaag acgtcacctt gatggacgtt   1980
tcgccgaagc aggtagtttc ggttgcagcg tcgctgatcc cgttcctgga acacgatgac   2040
gccaaccgtg cgttgatggg ttccaacatg cagcgtcaag ctgtaccaac cctgcgcgct   2100
gacaagccgc tggtaggtac cggcatggag cgtaacgtag cccgtgactc cggcgtttgc   2160
gtcgtagccc gtcgtggcgg cgtgatcgac tccgttgatg ccagccgtat cgtggttcgt   2220
gttgccgatg atgaagttga aactggcgaa gccggtgtcg acatctacaa cctgaccaaa   2280
tacacccgct cgaaccagaa cacctgcatc aaccagcgtc cgctggtgag caagggtgac   2340
cgcgttcagc gtagcgacat catggccgac ggcccgtcca ctgacatggg tgaactggct   2400
ctgggtcaga acatgcgcat cgcgttcatg gcatggaacg gcttcaactt cgaagactcc   2460
atctgcctgt ccgagcgtgt tgttcaagaa gaccgtttca ccacgatcca cattcaggaa   2520
ctgacctgtg tggcacgtga taccaagctt gggccagagg aaatcactgc agacatcccg   2580
aacgtgggtg aagctgcact gaacaagctg gacgaagccg gtatcgttta cgtaggtgct   2640
gaagttggcg caggcgacat cctggtaggt aaggtcactc cgaaaggcga gacccaactg   2700
actccggaag agaagctgct gcgtgccatc ttcggtgaaa aagccagcga cgttaaagac   2760
acctccctgc gtgtacctac cggtaccaag ggtactgtta tcgacgtaca ggtcttcacc   2820
```

cgtgacggcg ttgagcgtga tgctcgtgca ctgtccatcg agaagactca actcgacgag 2880
atccgcaagg acctgaacga agagttccgt atcgttgaag gcgcgacctt cgaacgtctg 2940
cgttccgctc tggtaggcca caaggctgaa ggcggcgcag gtctgaagaa aggtcaggac 3000
atcaccgacg aagtactcga cggtcttgag cacggccagt ggttcaaact gcgcatggct 3060
gaagatgctc tgaacgagca gctcgagaag gcccaggcct acatcgttga tcgccgtcgt 3120
ctgctggacg acaagttcga agacaagaag cgcaaactgc agcagggcga tgacctggct 3180
ccaggcgtgc tgaaaatcgt caaggtttac ctggcaatcc gtcgccgcat ccagccgggc 3240
gacaagatgg ccggtcgtca cggtaacaaa ggtgtggtct ccgtgatcat gccggttgaa 3300
gacatgccgc acgatgccaa tggcaccccg gtcgacgtcg tcctcaaccc gttgggcgta 3360
ccttcgcgta tgaacgttgg tcagatcctc gaaacccacc tgggcctcgc ggccaaaggt 3420
ctgggcgaga agatcaaccg tatgatcgaa gagcagcgca aggttgctga cctgcgtaag 3480
ttcctgcacg agatctacaa cgagatcggc ggtcgcaacg aagagctgga caccttctcc 3540
gaccaggaaa tcctggactt ggcgaagaac ctgcgcggcg gcgttccaat ggctaccccg 3600
gtgttcgacg gtgccaagga aagcgaaatc aaggccatgc tgaaactggc agacctgccg 3660
gaaagcggcc agatgcagct gttcgacggc cgtaccggca acaagtttga gcgcccggtt 3720
actgttggct acatgtacat gctgaagctg aaccacttgg tagacgacaa gatgcacgct 3780
cgttctaccg gttcgtacag cctggttacc cagcagccgc tgggtggtaa ggctcagttc 3840
ggtggtcagc gtttcgggga gatggaggtc tgggcactgg aagcatacgg tgctgcatac 3900
actctgcaag aaatgctcac agtgaagtcg gacgatgtga acggtcggac caagatgtac 3960
aaaaacatcg tggacggcga tcaccgtatg gagccgggca tgcccgagtc cttcaacgtg 4020
ttgatcaaag aaattcgttc cctcggcatc gatatcgatc tggaaaccga ataa 4074

<210> SEQ ID NO 116
<211> LENGTH: 1674
<212> TYPE: DNA
<213> ORGANISM: Unknown
<220> FEATURE:
<223> OTHER INFORMATION: Description of Unknown:
DP69 Glutamine--tRNA ligase sequence

<400> SEQUENCE: 116
gtgcgcgagg acctggccag cggaaagcac caggcgatca agacccgctt cccgccggag 60
ccgaacggct acctgcacat cggccacgcc aagtcgatct gcctgaactt cggcatcgcc 120
ggtgagttca gcggcgtctg caacctgcgt ttcgacgaca ccaatccggc caaggaagac 180
ccggagtacg tggccgcgat ccaggacgac gtgcgctggc tgggctttga atggaacgag 240
ctgcgccacg cctcggacta cttccagacc tattacctgg ccgccgagaa gctgatcgaa 300
cagggcaagg cctacgtctg cgacctgtcg gccgaggaag tgcgcgccta ccgcggcacc 360
ctgaccgagc cgggccgccc gtcgccgtgg cgtgaccgca gcgtcgagga gaacctcgac 420
ctgttccgcc gcatgcgtgc cggtgaattc cccgatggcg cgcgcaccgt gcgcgccaag 480
atcgacatgg ccagcggcaa catcaacctg cgtgatccgg cgctgtaccg catcaagcac 540
gtcgagcacc agaacaccgg caacgcgtgg ccgatctacc cgatgtacga cttcgcccat 600
gcgctgggcg attcgatcga gggcatcacc cactcgctgt gcacgctgga attcgaagac 660
caccgcccgc tgtacgactg gtgcgtggac aacgtcgact tcgcccacga tgacgcgctg 720
acccagccgc tggtcgacgc cggcctgccg cgcgaagcgg ccaaaccgcg ccagatcgag 780
ttctcgcgcc tgaacatcaa ctacacggtg atgagcaagc gcaagctgat ggcgctggtc 840
accgaacagc tggtggacgg ctgggaagac ccgcgcatgc cgaccctgca gggcctgcgt 900
cgccgtggct acaccccggc agcgatgcgc ctgttcgccg agcgcgtggg catcagcaag 960
cagaattcgc tgatcgattt cagcgtgctg gaaggcgcgc tgcgcgaaga cctggacagc 1020
gccgcaccgc gccgcatggc cgtggtcgac ccggtcaagc tggtgctgac caacctggcc 1080
gaaggccacg aagagcagct gaccttcagc aaccacccga aggacgagag cttcggtacc 1140
cgcgaagtgc cgttcgcacg tgaagtgtgg atcgaccgcg aggacttcgc cgaagtgccg 1200
ccgaagggct ggaagcgcct ggttcccggt ggtgaagtgc gcctgcgcgg cgccggcatc 1260
atccgctgcg acgacgtgat caaggatgcc gacggcacca tcaccgagct gcgcggctgg 1320
ctggatccgg aatcgcgccc gggcatggaa ggcgccaacc gcaaggtcaa gggcaccatc 1380
cactgggtca gcgcggtgca cggtgtgccg gccgagatcc gcctgtatga ccgcctgttc 1440
tcggtgccga acccggacga tgaatcggaa ggcaagacct accgcgacta cctcaatccg 1500
gactcgcgcc gcaccgtcac cggctatgtc gagccggcgg ctgccagcgc tgcgccggaa 1560
cagtcgttcc agttcgagcg caccggctac ttcgttgccg accgccgcga ccacaccgaa 1620
gccaagccgg tgttcaaccg cagcgtgacc ctgcgcgaca cctggtcggc ctga 1674

<210> SEQ ID NO 117
<211> LENGTH: 2460
<212> TYPE: DNA
<213> ORGANISM: Unknown
<220> FEATURE:
<223> OTHER INFORMATION: Description of Unknown:
DP69 DNA gyrase subunit B sequence

<400> SEQUENCE: 117
atgaccgacg aacagaacac cccggcaaac aacggcaact acgacgccaa cagcattacg 60
gccctggaag gcctggaggc tgtccgcaag cgcccaggca tgtacatcgg cgacgtccat 120
gacggcaccg gcctgcatca catggtgttc gaggtcgtcg acaactcaat cgacgaagcc 180
ctcgccggcc atgccgacca cgtctcggtg acgatccatg ccgatggctc ggtaggcgtg 240
tccgacaacg gtcgcggcat cccgacgggc aagcacgagc agatgagcaa gaagctcgac 300
cgcgatgtgt ctgcagccga agtggtgatg acggtcctgc acgcaggcgg caagttcgac 360
gacaacagct acaaggtttc cggcggcctg cacggcgtgg gcgtcagcgt ggtcaacgcg 420
ctgtcgcaga agctggtcct ggatatctac cagggtggct tccactacca gcaggagtac 480
gccgacggcg cagcactgca tccgctgaag cagatcggcc ccagcaccaa gcgcgggacc 540
accctgcgct tctggccctc ggtaaaggct ttccacgaca acgtggaatt ccactacgac 600
atcctggccc ggcgcctgcg cgaactgtcc ttcctcaatt ccggcgtcaa gatcgtgctg 660
gtggacgagc gtggtgatgg ccgccgcgac gacttccatt acgagggcgg catccgcagc 720
ttcgtggagc atctggcgca gttgaagacg ccgttgcacc cgaacgtgat ctcggtgacc 780
ggcgaatcca atggcatcac cgtggaagtg gcgctgcagt ggaccgactc ctaccaggag 840
acgatgtact gcttcaccaa caacattccg cagaaggacg gcggtaccca cctggccggc 900
ttccgtggcg cattgacccg cgtgctcaac aactacatcg agcagaacgg catcgccaag 960
caggccaaga tcaacctgac cggcgatgac atgcgcgaag gcatgatcgc ggtgctgtcg 1020
gtgaaggtgc cggatcccag cttctccagc cagaccaagg aaaagctggt cagctcggat 1080
gtgcgcccgg ccgtggaaag cgcgttcggc cagcgcctgg aagagttcct gcaggaaaac 1140
ccgaacgaag ccaaggccat cgccggcaag atcgtcgacg ctgcccgtgc ccgcgaagcg 1200
gcgcgcaagg cccgcgacct gacccgccgc aagggtgcgc tggatatcgc cggcctgccg 1260
ggcaagctgg ccgactgcca ggaaaaggat ccggcgctgt ccgaactgtt catcgtcgag 1320
ggtgactcgg caggtggttc ggccaagcag ggtcgcaacc gcaagaacca ggcggtgctg 1380
ccgctgcgcg gcaagatcct caacgtggaa cgtgcgcgct tcgaccgcat gctggcgtcc 1440
gaccaggtgg gtacgctgat caccgcgctg ggtaccggca tcggtcgtga cgagtacaac 1500
ccggacaagc tgcggtacca caagatcatc atcatgaccg acgccgacgt cgacggcgcg 1560
cacatccgca ccctgctgct gacgttcttc taccgtcaga tgccggagct gatcgagcgc 1620
ggttatgtct atatcggcct gccgccgttg tacaagatca agcagggcaa gcaggagctg 1680
tacctgaagg acgacccggc gctggacagc tatctggcca gcagcgcggt ggagaacgct 1740
gggctggtgc cggccagcgg cgagccgccg atcgacggcg tggcactgga aaagctgctg 1800
ctcgcctacg ctgccgcgca ggacacgatc aaccgcaata cccaccgcta cgaccgcaac 1860
ctgctcgaag cgctggtcga cttcatgccg ctggagctgg aaaacctgcg cactgcaggt 1920
cctggcgaag gtctggacgc gttggccaag cacctcaacc agggcaacct cggcagcgcc 1980
cgcttcaccc tggaactgca ggaacccaac gagcagcgtc cggcggccgt actggtgacc 2040
cgcagccaca tgggcgaaca gcacatccag gtgctgccgc tgtccgcgct ggaaagcggc 2100
gaactgcgcg gcatccatca ggcagcgcag ctgctgcacg gtctggtccg cgaaggcgcg 2160
gtcatcaccc gtggcgccaa gtcgatcgag atcgactcgt tcgcacaggc ccgcaactgg 2220
ctgttggacg aagccaagcg cggccggcag atccagcgat tcaagggtct gggcgaaatg 2280
aatccggaac agctgtggga taccaccgtc aatcccgata cccgtcgcct gctgcaggtg 2340
cgcatcgaag acgcggtggc cgctgaccag atcttcagca ccctgatggg tgatgtggtc 2400
gaaccgcgtc gtgacttcat cgaagacaac gcgttgaagg tcgccaacct ggatatctga 2460

<210> SEQ ID NO 118
<211> LENGTH: 2835
<212> TYPE: DNA
<213> ORGANISM: Unknown
<220> FEATURE:
<223> OTHER INFORMATION: Description of Unknown:
DP69 Isoleucine--tRNA ligase sequence

<400> SEQUENCE: 118
gtgagccagg actacaagac caccctcaac ctgccggcca ccgaattccc gatgcgcggc 60
gacctgccca agcgcgagcc gggcattctg gcgcgctggg aagagcaggg gctctaccag 120
cagctgcgcg acaacgccgc cggccgcccg ctgttcgtgc tgcatgacgg cccgccgtac 180
gccaatgcgc gcatccacct gggccatgcg gtcaacaaga tcctcaagga catcatcgtc 240
aagtcgcgct acctggccgg cttcgatgcg ccctacgtgc cgggctggga ctgccatggc 300
ctgccgatcg aaatcgcggt ggaaaagaag tggggcaagg tcggggtgaa gctcgatgcg 360
gtcgagttcc ggcagaagtg ccgcgagttc gccgaagaac agatcgacat ccagcgtgcc 420
gacttcaagc gcctgggcgt caccggcgac tgggacaacc cgtacaagac cctaagcttc 480
gatttcgagg ccaacgagat ccgtgcgctg tccaagatcg tggccaacgg ccatctgctg 540
cgtggcgcca agccggtcta ctggtgcttc gactgcggct cggcactggc cgaggccgag 600
atcgagtacc acgagaagac ctcgccggcg atcgacgtgg cctacaccgc gcgtgatccg 660
caggcggtgg cgcaggcgtt cggcgtcagc ctgccggccg atgtcgaagt ggcggtgccg 720

-continued

```
atctggacca ccactccgtg gacgctgccg gcttcgctgg cggtgtcgct gggcgcggac    780
atccgctacg tgctggccga aggcccggcg cacaacggca agcgccgttg gctggtgctg    840
gctgctgcgc tggccgaacg gtcgctgcag cgctacggcg tggacgcggt ggtgctgcac    900
ggtgaagccg aaggttcggc gctggaaaac cagctgctgg cgcacccgtt ctacccggag    960
cgcgagatcc ccgtgctcaa cggcgaacac gtgtccgacg aggacggtac cggtgcggtg   1020
cacactgccc ccggccacgg ccaggaagac tacgtggtca gccagaagta cggcctgctg   1080
gagaagtaca acgccggcca gatcaatccg gtcgacggtg cgggcgtgta cctggcgtcc   1140
accccgcccg ccggtgacct ggtgctggcc ggtacccaca tctggaaggc gcagcagccg   1200
atcatcgaag tgctggccgc cagcggcgcg ctgctcaagg ccgtggagat cgtgcacagt   1260
tatccgcatt gttggcgcca caagaagacc ccgctggtgt tccgcgccac cccgcagtgg   1320
ttcatttcga tggacaaggc caacctgcgc aacgatgcgc tggccgcgat cgataccgtc   1380
ggctggttcc cgagctgggg caaggcgcgc atccaaagca tgatcgacgg ccgcccggac   1440
tggaccatct cgcgccagcg cacctggggc gtgccgatcg cgctgttcac ccaccgccag   1500
accggcgaga tccacccgcg ttcggtggag ctgatgcagc aggtggccga ccgcgttgaa   1560
gccgaaggca tcgacgtgtg gtactcgctg gatgcggctg aactgctggg cgctgaagcg   1620
gccgactacg agaaggtcac cgacatcctc gatgtctggt tcgattccgg cgtgacccac   1680
gaagccgtgc tggctgcccg tggcttcggc aagccggccg atctgtacct ggaaggttcg   1740
gaccagcatc gcggctggtt ccagtcctcg ctgctgaccg gcgtggccat cgacaagcgc   1800
gcgccgtaca agcagtgcct cacccacggt ttcaccgtgg acgagcacgg ccgcaagatg   1860
tccaagtcgc tgggcaacgg catcgaaccg caggaaatca tgaacaagct gggcgcggac   1920
atcctgcgcc tgtggatcgc ctcggccgac tacagcaacg agatgtcgct gtcgcaggaa   1980
atcctcaagc gcaccgccga cgcctaccgc cgcctgcgca acaccgcccg cttcctgctg   2040
ggcaacctgg acggtttcga tccggcccag cacctgcgcc cgctcaacga gatggtcgcg   2100
ctggaccgct ggatcgtgca tcgcgcctgg gagctgcagg agaagatcaa ggcggcgtat   2160
gacaactacg acatggccga gatcgtgcag ttgctgctga acttctgcag cgtggacctg   2220
ggctcgctgt acctggacgt gaccaaggat cgcctgtata cgatgccgac cgattcggat   2280
ggtcgtcgtt cggcgcagag cgcgatgtac cacatcgccg aagcgttcac ccgctgggtg   2340
gcgccgatcc tgaccttcac cgccgacgag ctgtggggct acctgccggg cgatcgtgcc   2400
ggccacgtgc tgttcactac ctggtacgag ggcctggcac cgctgccgac cgatgcacag   2460
ctcaacgctg ccgacttcga tcagctgctg gccgtgcgcg agcaggtggc caaggtgctg   2520
gagccgatgc gcgccaatgg tgcgatcggt gccgcgctgg aagcggagat caccatcgcc   2580
gccagcgaag agcaggccgc gcgctggcag ccgctggccg atgaactgcg tttcctgttc   2640
atcagtggtg acgtgcaggt gcgtccggcg accaccgacg aggtgttcgt cagcgcgcag   2700
ccgacgcaga agtccaagtg cgtgcgctgc tggcaccacc gtgccgacgt tggcagcaat   2760
gccgaccacc cggaactgtg cggccgctgc gtgaccaaca tcgccggtgc cggcgaagcg   2820
cggagctggt tctga                                                    2835
```

<210> SEQ ID NO 119
<211> LENGTH: 2076
<212> TYPE: DNA
<213> ORGANISM: Unknown
<220> FEATURE:

-continued

<223> OTHER INFORMATION: Description of Unknown:
DP69 Glycine--tRNA ligase beta subunit sequence

<400> SEQUENCE: 119
atgagccact tgtctcccct gctgattgaa ctgggcaccg aagagttgcc ggtcaaggcg 60
ctgccgggcc tggcccaggc cttcttcgac ggtgttgtcg atggcctgcg caagcgcggc 120
gtcgaactgg agctgggcga tgcccgcccg ctgtcgaccc cgcgccgcct ggccgtgctg 180
ctgccgggcg ttggcctgga acagccggaa caacacagcg aagtgctggg cccgtacctg 240
aacatcgcgc tggacgccga aggccagccg accaaggcgc tgcagggttt cgcggccaag 300
gccgggatcg actggaccgc gctggagaag accaccgaca acaagggtga gcgcttcgtg 360
caccgtgcgg tgactccggg cgcgcgcacc gctgcgctgc tgccggagat cctgcgcgag 420
gccatcgccg gcatgccgat tcccaagccg atgcgctggg gcgaccacag ctggggcttc 480
gcccgcccgg tgcactggct ggtgctgctg catggcggcg acgtggtcga ggccgaactg 540
tttggcctga aggccgaccg catgagccgc ggccaccgct tcctgcacga caagaccgtg 600
tggctgaccc agccgcagga ctatgtcgaa tcgctgcgcg ccgccttcgt gctggtcgat 660
ccggccgagc gccgccggcg catcgttgcc gaagtggaag ccgctgccgc caccgccggt 720
ggcagcgcac gcatcaccga ggacaacctg gagcaggtgg tgaacctggt cgagtggccg 780
gcggcagtgt tgtgcagctt cgagcgcgcg ttcctggcgg taccgcagga agcgctgatc 840
gagacgatgg agatcaacca gaagttcttc ccggtgctgg atgacggcgg caagctgacc 900
gagaagttca tcggcatcgc caacatcgag tccaaggacg tggccgaagt ggccaagggc 960
tacgagcgcg tgatccgccc gcgcttcgcc gatgccaagt tcttcttcga cgaagacctg 1020
aagcagggcc tgcaggcgat gggcgagggc ctgaagacgg tgacctacca ggccaagctg 1080
ggcagcgtgg ccgacaaggt cgcgcgcgtg gcggcgctgg ccgaggtgat cgctgcgcag 1140
gtgggggccg acccggtgct ggccaagcgt gccgcgcagc tggccaagaa cgacctgcag 1200
tcgcgcatgg tcaatgagtt cccggaactg cagggcatcg ctggccgcca ctacgcggtg 1260
gccggtggcg agtcgccgga ggtggcgctg gccatcgacg aggcctacca gccgcgcttc 1320
ggtggcgatg acatcgcgct gtcgccgctg ggcaaggtgc tggcgatcgc cgagcgtgtg 1380
gacacgctgg ccggcggttt cgccgcgggc ctgaagccga ccggcaacaa ggacccgttc 1440
gccctgcgcc gcaacgcgct gggcctggcc cgcacgatta tcgaaagtgg cttcgagctg 1500
gacctgcgcg cgctgctggc cagcgccaat gccgggctga ccgtgcgcaa cgtgcaggcc 1560
gacgtggctg agctgtacga cttcatcctc gaccgcctga agggctacta cagcgacaag 1620
ggcgtgccgg ccagccactt caatgcggtg gctgagctga agccggtctc gctgtacgat 1680
ttcgaccgtc gcctggacgc catcggtatc ttcgcggcgc tgccggaggc cgaggcgctg 1740
gcagcggcca acaagcgcat ccgcaacatc ctgcgcaagg ccgaaggcga tattccgggc 1800
cagatcgatg cggccctgtt gcaggaagat gccgagcgcg cgctggcgga agccgtgact 1860
gcagccatcg acgacaccgg cgccagcctg caccagaagg actacgtggc cgtgctggcg 1920
cgcctggccc gcctgcgtcc gcaggtcgat gcgttcttcg atggggtgat ggtcaatgcc 1980
gaggatccgg cactgcgcgg caaccgcctg gcgctgctga cgatgctggg cgagcgcttg 2040
ggcaaggtcg cggcgatcga gcatctgtcg agctga 2076

<210> SEQ ID NO 120
<211> LENGTH: 1410
<212> TYPE: DNA

<213> ORGANISM: Unknown
<220> FEATURE:
<223> OTHER INFORMATION: Description of Unknown:
DP69 Glutamine synthetase sequence

<400> SEQUENCE: 120
atgtccgtgg aaaccgtaga gaagctgatc aaggacaacc agatcgagtt cgtcgatctg 60
cgcttcgtcg acatgcgtgg tgtcgaacag catgtgacct tcccggtcag catcgtcgag 120
ccgtcgctgt ttgaagaagg caagatgttc gatggcagct cgatcgccgg ctggaagggc 180
atcaacgagt cggacatggt gctgctgccg gacaccgcca gcgcctacgt cgacccgttc 240
tacgccgatc cgaccatcgt gatcagctgc gacatcctcg acccggccac catgcagccg 300
tatggccgtt gcccgcgcgg catcgccaag cgcgccgagt cctacctgaa gtcctcgggc 360
atcgccgaaa ccgcgttctt cggcccggag ccggagttct tcatcttcga ctcggtgcgt 420
ttcgccaatg aaatgggcaa caccttcttc aaggtcgact cggaagaagc ggcgtggaac 480
agcggcgcca agtacgacgg cgccaacagc ggctaccgtc cgggcgtgaa gggcggttat 540
ttccccgttc cgccgaccga caccctgcac gacctgcgtg cggagatgtg caagaccctg 600
gaacaggtcg gcatcgaagt ggaagtgcag caccacgaag tggccaccgc cggccagtgc 660
gagatcggca ccaagttcag caccctggtg cagaaggccg acgaactgct gcggatgaag 720
tacgtcatca agaacgtcgc ccaccgcaac ggcaagaccg tcaccttcat gcccaagccg 780
atcgtcggcg acaacggcag cggcatgcac gtgcaccagt cgctgtccaa gggcggcacc 840
aacctgttct ccggtgacgg ctacggtggc ctgagccaga tggcgctgtg gtacatcggc 900
ggcatcttca agcatgccaa ggcgatcaac gcctttgcca actcgggtac caacagctac 960
aagcgcctgg tgccgggctt cgaagccccg gtgatgctgg cctactcggc gcgcaaccgt 1020
tcggcctcgt gccgcattcc gtgggtgtcc aacccgaagg cgcgtcgcat tgaaatgcgc 1080
ttccccgatc cgatccagtc gggctacctg accttcaccg cgctgatgat ggccggcctg 1140
gacggcatca agaaccagat cgacccgggc gcaccgagcg acaaggatct gtacgacctg 1200
ccgccggaag aagagaagct gattccgcag gtctgctcct cgctggacca ggccctggaa 1260
gcgctggaca aggaccgtga gttcctcaag gccggtggcg tgatgagcga tgacttcatc 1320
gacggctaca tcgcgctgaa gatgcaggaa gtgaccaagt tccgcgcggc gacccacccg 1380
ctggaatacc agttgtacta cgccagctga 1410

<210> SEQ ID NO 121
<211> LENGTH: 1515
<212> TYPE: DNA
<213> ORGANISM: Unknown
<220> FEATURE:
<223> OTHER INFORMATION: Description of Unknown:
DP69 Glucose-6-phosphate isomerase sequence

<400> SEQUENCE: 121
atgacaacga acaacggatt cgactcgctg cattcccacg cccagcgcct gaagggcgca 60
agcatcccca gcctgctcgc cgccgaaccc ggccgcgtac aggacctggc gctgcgggtc 120
ggtccgttgt atgtcaactt cgcccggcag aaatacgatg ccgcggcgtt gcaggcgctg 180
ttggcgctgg ctgccgaacg tgatgtcggc ggcgccatca cgcgcctgtt ccgtggcgag 240
caggtcaatc tgaccgaagg ccgcgccgca ctgcacaccg cactgcgcgg cgacgtggtc 300
gatgcgccgg ttgccgccga ggcctatgcc acggcccgcg aaatccgcca gcgcatgggc 360
gtgctggtgc gcgcactgga agacagtggc gtgaccgatg tggtcagtgt cggcatcggc 420
ggttccgatc tcggtccgcg tctggtcgcc gacgcactgc gtccagtcac tggcgctcgc 480
ctgcgcgtgc atttcgtgtc taacgtggac ggcgctgcca tgcagcgcac gctggccacg 540
ctggatccgg cgaagaccgc cggcatcctc atttccaaga ccttcggtac ccaggaaacc 600
ctgctcaacg gccagatcct gcacgattgg ctgggtggca gcgagcgcct gtacgcggtc 660
agcgccaatc cggaacgcgc cgccaaggcc ttcgccatcg ccgccgagcg cgtgctgccg 720
atgtgggact gggtaggggg gcgctattcg ctgtggtcgg ccgtcggttt cccgatcgca 780
ctggccatcg gcttcgagcg tttcgagcag ttgctggaag gcgccgcgca gatggatgcg 840
catgcgctgg acgcgccgct ggagcgcaac ctgccggtgc tgcacggcct gaccgacatc 900
tggaaccgca atctgctggg ctctgccacg catgcggtga tgacctacga ccagcgcttg 960
gcgctgctgc cggcctacct gcagcagctg gtgatggaaa gcctgggcaa gcgcgtgcag 1020
cgcgatggcc agccggtcac caccgacacc gtgccggtgt ggtggggcgg tgccggcacc 1080
gatgtgcagc acagcttctt ccaggccctg caccagggca ccagcatcat tccggccgat 1140
ttcatcggct gcgtgcacaa cgacgatccg tatacggtca accaccaggc gttgatggcc 1200
aacctgctgg cgcagaccga agcgctggcc aacggccagg gcagtgacga tccgcaccgc 1260
gattatccgg gtggccgccc gagcacgatg atcctgctcg acgcgctcac cccgcaggcg 1320
ctgggcgcct tgatcgcgat gtacgaacac gccgtgtacg tgcagtcggt gatctggaac 1380
atcaacgcct tcgaccagtt cggtgtcgag ctgggcaagc agctggccag tggcctgctg 1440
cccgctctgc agggtgagga tgtcgaggtc aacgacccgc tgacccgtga gctgctggcc 1500
cagctgaagg gctga 1515

<210> SEQ ID NO 122
<211> LENGTH: 2640
<212> TYPE: DNA
<213> ORGANISM: Unknown
<220> FEATURE:
<223> OTHER INFORMATION: Description of Unknown:
DP69 Leucine--tRNA ligase sequence

<400> SEQUENCE: 122
atgaccagcg tcgaacccaa cgtttacgat ccgcagcagg ttgaatccgc cgcccagaag 60
tactgggacg ctacccgtgc cttcgaggtc gatgaagcct cggacaagcc gaagtactac 120
tgcctgtcga tgcttccgta tccgtccggt gcgctgcaca tgggccacgt gcgcaattac 180
acgatcggcg acgtgatcag ccgctacaag cgcatgaccg gccacaacgt gctgcagccg 240
atgggctggg acgcgtttgg cctgccggcg gaaaacgctg cgatcaagaa caagaccgcg 300
ccggccgcct ggacctacaa gaacatcgac cacatgcgca gccagctgca gtcgctgggc 360
tatgccatcg actggtcgcg cgagttcgcc acctgccgcc cggactatta cgtccacgag 420
cagcgcatgt tcacccgcct gatgcgcaag ggcctggcct accgccgcaa cgcggtggtg 480
aactgggacc cggtcgacca gaccgtgctg gccaacgagc aggtcatcga cggccgtggc 540
tggcgctccg gcgcgcttgt ggaaaagcgc gagatcccgc agtggttcct gcgcatcacc 600
gactacgccc aggaactgct ggacggcctg gatgagctgg acggctggcc ggagtcggtc 660
aagaccatgc agcgcaactg gatcggccgc tccgaagggc tggaaatcca gttcgacgtg 720
cgcgacgtcg atggtgccgc actggatccg ctgcgcgtgt tcaccacccg cccggacacc 780
gtgatgggcg tgactttcgt gtcgatcgcg gccgaacatc cgctggcgct gcatgccgcg 840
aagaacaacc cggaactggc tgcgctgctg tcggaaatga agcagggcgg cgtgtccgag 900
gccgagctgg agacccagga aaagcgcggc atggataccg gcctgcgcgc cgtgcatccg 960
gttaccggtg cccaggtgcc ggtgtgggtc gccaacttcg tgctgatggg ctacggcact 1020
ggcgcggtga tggccgtacc gggccacgac cagcgcgaca atgaattcgc caacaagtac 1080
aacctgccga tccgccaggt catcgcgctg aagtcgctgc gcaaggacga aggcgcctac 1140
gacgcgacgc gctggcagga ctggtacggc gacaagaccc gcgagaccga actggtcaac 1200
tccgaagagt tcgacggcct ggacttccag ggcgctttcg aggcgctggc cgaacggttc 1260
gagcgcaagg cccagggaca gcgccgggtg aactaccgcc tgcgcgactg gggcgtgagc 1320
cgccagcgct actggggctg cccgattccg gtgatctact gcgacaagtg tggcgcggta 1380
ccggtgccgg aagaccagct gccggtggtg ctgccggaag acgtggcgtt cgccggtacc 1440
ggttcgccga tcaagaccga tccggaatgg cgcaagacca cctgcccgga ctgcggcggt 1500
gcggccgagc gtgagaccga caccttcgac accttcatgg agtcgagctg gtactacgcc 1560
cgctacacct cgccgggcgc ccgcgatgcg gtcgacaagc gcggcaacta ctggctgccg 1620
gtggaccagt acatcggtgg catcgaacac gcgatcctgc acctgatgta tttccgcttc 1680
taccacaagc tgctgcgcga cgcgcggatg gtggacagca acgaacccgc gcggaacctg 1740
ctgtgccagg gcatggtgat cgctgagacc tactaccgcc cgaacccgga cggctcgaag 1800
gactggatca acccggccga tgtggaagtg cagcgcgacg agcgcggccg catcaccggc 1860
gccaccctga tcgccgacgg tcagccggtg gtggtcggtg gtaccgagaa gatgtccaag 1920
tcgaagaaca acggcgtgga cccgcaggcg atggtcggca agtacggcgc cgataccgtg 1980
cgcctgttct cgatgttcgc tgcaccgccg gaacagtcgc tggaatggaa cgaagccggc 2040
gtggacggca tggcccgctt cctgcgccgc ctgtgggcac aggtgcagaa gcacgctgcc 2100
gagggtgccg caccggcgct cgacgcggcc gcgctggatg ccggccagaa ggccctgcgc 2160
cgcaagaccc acgagaccat cggcaaggtc ggcgacgact acggccgccg ccacagcttc 2220
aacaccgcca ttgccgcggt gatggagctg atgaacgcgc tggccaagtt cgaggacggc 2280
agtgaacagg ggcgcgccgt gcgccaggaa gcactgcagg ccatcgtgct gctgctcaac 2340
ccgatcaccc cgcatgccag ccacgccctg tggcaggtac tgggccatgg cgaaacgctg 2400
ctggaagatc agccgttccc gcaggccgac agcagtgcgc tggtgcgcga tgcgctgact 2460
ttggccgtgc aggtcaatgg caagctgcgt ggcaccatcg aggtcgccgc cgatgccgcg 2520
cgcgagcaga tcgaagcgct ggccctggcc gagccgaacg cggccaagtt cctggaaggc 2580
ctgacggtgc gcaagatcat catcgttccc ggcaagatcg tgaacatcgt cgctgcctga 2640

<210> SEQ ID NO 123
<211> LENGTH: 2070
<212> TYPE: DNA
<213> ORGANISM: Unknown
<220> FEATURE:
<223> OTHER INFORMATION: Description of Unknown:
DP70 Glycine--tRNA ligase beta subunit sequence

<400> SEQUENCE: 123
atgtctaaac atacagtatt gttcgaattg ggctgtgaag aacttccacc taaaagcctc 60
aaaaaattac gtgatgcact gcatgctgaa acggtaaaag gcttaaaaga tgcaggctta 120
gcattcgact caatcgaagc ttatgcagca ccgcgtcgtt tggcacttaa aattgtgaat 180
atcgatggcg ctcagcctga tacacaaaaa cgctttgacg gccctgcaaa agaagcggct 240
tatgatgctg aaggcaaacc aagcaaagca ttagaaggct ttatgcgtgg tcaaggcatc 300

```
actgcggatc aagtcaccac gttccaagcg ggtaaagttg aaaaggtttg ctatttaaaa    360

gatgttaaag gtcaaagcct tgaggtttta ctgccacaaa ttctacaagc agctttggac    420

aatcttccaa ttgcaaaacg tatgcgttca gcggcaagcc gtactgaatt cgtgcgtcct    480

gtaaaatggg tggtgttgct caaagacaat gatgtgattg cagccactat tcaagatcac    540

aaagcaggca atgtgactta tggtcatcgt ttccatgccc ctgaagcgat tactttggct    600

catgcagatg aatatcttgc caagttaaaa gcggcttatg tggttgctga ctttgcagaa    660

cgccaagcca tcattgacca acaagtcaaa gcgttggctg atgaagttaa tgcgattgcg    720

attgtaccaa gcgacctgcg tgatgaagtg accgcattgg tggaatggcc tgttgcgcta    780

cgtgccagct ttgaggagcg tttccttgct gtaccgcaag aagctttgat taccacgatg    840

caagacaacc aaaaatactt ctgtttggtg aatagtgata acaagctaca gccttatttc    900

attactgttt caaatattga gtctaaagat ccgattcaaa ttattgaagg caatgaaaaa    960

gtggttcgtc cacgtttgtc ggatgctgaa ttcttcttct tgcaagatca aaagcaacca   1020

ctagcttctc gtaaagaaaa actggctaac atggtgttcc aagcacaatt gggtacgctg   1080

tgggataagt cacaacgtat tgcaaaattg gctgtggctt tatcgaacat cacgggtgca   1140

actgcggctg atgctgaaaa agcagcattg ctggcaaaat gtgacttaac ctctgaattg   1200

gtgggtgaat tccctgaact tcaaggcatt gcgggaacct attacgcacg cattgaaggt   1260

gaaaaccatg aagtggctga agctttaggc gaacagtatt tacctaaatt tgcaggcgat   1320

gttttaccgc aaacaaaaac aggcacaacc attgcccttg ccgaccgttt agacacgctc   1380

acgggtattt ttggtattgg tcaagcacct acaggttcta aagatccgtt tgcattacgt   1440

cgttctgcaa tcggtatttt acgtttggtg actgaaaaca atcttgatgt gtcgattgaa   1500

gatttaatcc agctggcatt aaacgcttat ggcgatgttg tagcggatca tgcgaagact   1560

ttagcggatg ctgttgcatt ccttgaaggt cgttaccgtg ccaagtatga agaccaaggc   1620

gttgcagttg atgtgattca agcggttcaa gcattatcac caaaatcacc tttagatttt   1680

gataagcgtg tgactgcggt aaatcatttc cgtgcattgc ctgaagctgc tgcactggct   1740

gctgcaaata agcgtgttgc caacattctt gccaaagaag cagaactaac aggcgcagtg   1800

gttgaagcaa acttggttga agaggctgaa aaagcattat tcgctgtact tgctaaaatt   1860

acgcctgaag ttgaaccatt atttgctgcc aaagattaca ccactgcatt gtctaagctt   1920

gctgctttac gtgcgcctgt ggatgcattc tttgaaggcg tcatggtcat ggcagatgat   1980

gcagaattga aagccaaccg tttacgttta ttggctcaat tacgtggttt gtttacaagt   2040

gttgcggata tttcggtgtt gcagcactaa                                     2070
```

<210> SEQ ID NO 124
<211> LENGTH: 2472
<212> TYPE: DNA
<213> ORGANISM: Unknown
<220> FEATURE:
<223> OTHER INFORMATION: Description of Unknown:
      DP70 DNA gyrase subunit B sequence

<400> SEQUENCE: 124

```
atgagttcag aagatcaagc tgcttctcaa acagaacaaa ccaatgaaaa ggcttatgat     60

tcctctagta tcaaagtatt acgtggccta gatgctgttc gtaagcgtcc gggtatgtat    120

attggtgata cggacgatgg ttcaggttta catcacatgg tgtttgaggt ggtcgataat    180

gcgattgatg aagccttagc gggtcactgt gatgaaatct tagtcaccat ccatgaagat    240
```

```
gagtctgtaa gtgttgcaga taacggtcgt gggattccaa cggatattca ccctgaagaa    300
ggggtatctg ccgctgaagt gattttaacc attttgcatg ctggcggtaa gtttgatgat    360
aatagctata aagtttccgg tggtttacac ggggtaggtg tttctgttgt aaatgccttg    420
tcgagtaaat tattactaaa tattcgtcgt gcaggaaaag tatatgaaca ggaatatcac    480
catggtgatc ctgtctatcc attacgcgcg attggtgata ctgaagaaac cggtaccacc    540
gttcgtttct atccgagtga attaaccttc tctcaaacga tttttaatgt tgatatttta    600
gcgcgtcgtt tgcgcgaact ttcattctta aatgcagggg ttcgtattgt attacgtgat    660
gaacgtatca atgctgaaca tgtatttgat tatgaaggtg gtttgtctga atttgtaaaa    720
tatatcaatc aaggtaaaac ccacttgaat gagatttttc attttaccag tgaagttgtg    780
gaaacaggaa ttactgttga agtagcatta cagtggaatg atacttatca agaaaatgtc    840
cgttgcttta ccaataacat cccacaaaaa gatggtggta cgcatttagc cggtttccgt    900
gccgcgttaa cacggggttt aaaccagtat cttgatagtg aaaatattct taagaaagaa    960
aaagttgctg tcacaggtga tgatgcccgt gaaggtttaa cggcgattgt ttcagtgaaa   1020
gtgcctgatc caaaattctc atcacaaacc aaagaaaaat tggtttccag tgaagtgaaa   1080
actgctgtag agcaggcgat gaacaagtct ttttctgaat atcttttaga aaatccacaa   1140
gcggctaaat cgattgccgg caaaattatt gatgctgcac gtgcacgtga tgctgcgcgt   1200
aaagcacgtg aaatgacacg tcgtaagagt gcattagata ttgctggtct gcctggtaaa   1260
ctggcggatt gccaagaaaa agatccagca ttgtctgaac tttacttggt cgaaggtgac   1320
tcggcgggcg gttctgcaaa acagggtcgt aaccgtaaga tgcaagctat tctgccgctt   1380
aaaggtaaaa tcttaaacgt agaacgtgca cgttttgaca aaatgatttc atcgcaagaa   1440
gtgggcacgc tgattactgc actgggctgt ggtattggtc gtgaggaata caatcctgat   1500
aaattgcgtt atcacaaaat cattatcatg accgatgccg acgtcgatgg ttcgcacatt   1560
cgtacgctcc tgttgacctt cttcttccgt caaatgccag aacttgtgga acgtggttat   1620
atttatattg cacagccacc gttgtataag ttgaaaaaag gtaagcaaga gcaatatctt   1680
aaagataatg atgctttaga aacctatctt atttcgaatg ccattgatga gcttgaactg   1740
catattagtg ctgaggcacc tgcgattcgt ggtgaatctt tggctaaagt gattgctgat   1800
tatcaaacct cacaaaaaag tttaaatcgt ttaacgctac gttatcctgc aagcttgctg   1860
gatggtttac ttggtttgga tgcatttaaa cttgatcaaa atcatgatga agattatgta   1920
aaacaatggt ctgaacaatt gcgtgcagca attgaacaac accaaccaag tttgcgtcct   1980
gaaatcacct tagaagcttt tgaaaaagag catgcagatg gtgagaaagt gacgcattat   2040
tggccacgtg taacggtcta tgtacataac ttgccgcatc attatttact tgattctgga   2100
ttattggctt caagtgaata caagcgttta ctgcaaaatt cgaagagttg gttcacattg   2160
cttgaagatg gcgcttattt gcaaaaaggt gagcgtaaaa ttcatgtcgc cactttccat   2220
caagtttggc aacatatttt atccgactcg cgtcgtggca tgatgatcca gcgctataaa   2280
ggtttgggtg agatgaacgc ggaacagctt tgggaaacca ccatggatcc tgaaaaccgt   2340
aacatgttgc aagtcaccat taatgatgcg attgaagcgg atcgtatgtt ctcttgtttg   2400
atgggagatg atgtggaacc acgtcgtgcc ttcattgaag aaaatgcttt aaatgcggat   2460
attgacgctt aa                                                       2472
```

<210> SEQ ID NO 125

<211> LENGTH: 2625
<212> TYPE: DNA
<213> ORGANISM: Unknown
<220> FEATURE:
<223> OTHER INFORMATION: Description of Unknown:
DP70 Leucine--tRNA ligase sequence

<400> SEQUENCE: 125
atgactactt ctcacattga ccctgaatat caagcgagcg cgattgaatc cactgtccaa 60
caagactggg aaactcgcaa agcctttaaa gttgccgaca ctgtagaagg taaacatcgt 120
tatatcctct cgatgttccc ttatccaagt ggcaagctgc atatgggtca tgtgcgtaac 180
tacaccattg gcgacgtgat tagccgtttc caccgtctca aaggtgaaac tgtcctacaa 240
ccgatgggtt gggatgcttt tggtctgcct gcggaaaatg cagcgattgc acaccaagtt 300
gcccctgcaa aatggacctt tgaaaacatc gcgtacatgc gtgaccagtt aaaaaaattg 360
ggtctgtcag tcgattggga tcgtgaattt gcgacctgta cgccagagta ttatcactgg 420
gaacaatggt tatttgtaca gctgtataaa aaagggctga tttatcgcaa actttcaacg 480
gtaaactggg atcctgtcga tcagactgta cttgctaatg aacaagttga aaatggtcgt 540
ggttggcgtt cgggtgcatt ggttgaaaaa cgtgatattc caatgtatta cttccgtatt 600
accgattatg cacaagaatt attagacgat ttagattcgc ttaaagatgg ttggccgcaa 660
caagtcttga ccatgcaacg caactggatt ggtcgttcac aaggcatgga aatcaccttt 720
ccatctgcga accctgaaat ctatgcagat gatttaacgg tttataccac acgtggtgac 780
accttgatgg gcgtgacgta tgttgcggtt gccgctgaac atccaatggc gcttaaagcg 840
gctgaaacaa atcccgaatt ggctgcattt attgaagaat gccgtatggg ttcagtggct 900
gaagcagatc ttgccactgc cgagaaaaaa ggcatggcca ctggtttgtc tgtgaagcat 960
cctgtaacgg gtgaagtggt tccagtgtgg attgcgaact atgtattgat gtcatacggt 1020
tcaggtgcgg tgatggcagt tccagcacac gacgaacgtg atttcgaatt tgccaacaaa 1080
tatggtttaa ccctccagca agtgattgat gccaaaggtg cagacgatgc tgaattttct 1140
gcaactgaat ggcaggaatg gtatggctcg aaagaaggca aactggttaa ttctggcgaa 1200
tttgacggtt tagacttcca agctgcattt gatgcattca ttgcaaaatt agaaccacaa 1260
aaactggcaa atacgaaagt tcagttccgt ctacgtgact ggggtgtttc gcgtcagcgt 1320
tattggggtt gtccaattcc aatgatcaac tgtgaaactt gtggtcaagt acctgtacct 1380
gaagaacaac ttccagtaat tttaccaact gacgtggtgc cagatggttc aggcaatccg 1440
ttaaataaaa tgcctgaatt ttatgaaacc caatgtccat gttgtggtgc aggtgcacgc 1500
cgtgaaaccg atactttgga tacgttcgta gagtcatctt ggtactatgc acgttatgca 1560
tctccagatt tcactggcgg tttagttaaa cctgaagctg caaaatcatg gctaccagtc 1620
aaccaatata ttggcggtgt ggaacatgca attttgcatt tattgtatgc ccgtttcttc 1680
cataaattga tgcgtgatga aggcgtcgtt gaaggcaatg aacctttcgc taacttactg 1740
actcaaggta tggttttagc tgataccttc taccgtgaag ccgaatcagg taagaaaaca 1800
tggtttaatc ctgcggatat tgaattagaa aaagacgaaa aaggtcgtgt tctttctgct 1860
aaatacacag gtgatggcca agaagttgtg gttggcggtc aagaaaaaat gtcgaaatcg 1920
aaaaataatg gcatcgaccc gcaatcgatt attgatcaat acggcgcaga tactgcacgt 1980
gtatttatga tgtttgcggc cccacccgat caatcgcttg aatggtctga tgccggtgtg 2040
gaaggtgcaa accgtttctt gaaacgtgta tggcgtttaa ccacaggttt cttagaaaaa 2100

```
ggcaaccatg ctgctgtaat tgatgttgcg aatttgtcat cagcggcaca agacttacgt   2160
cgtaaaaccc acgaaaccat tcaaaaagtc ggtgatgaca ttgaacgtcg tcatgccttc   2220
aatactgcca ttgcagcgca aatggaatta ttgaatgctt gcaataaatt tgaagccaaa   2280
gatgataatg acgttgcggt tgaacgcgat gctattgtta gcttactcac tttacttgca   2340
ccatttgcac cacatttaag tcagacccta ttggctcaat tcggtattga gttaactgaa   2400
accttgttcc ctactgtgga tgagtctgcg ctaacccgca acacacaaac tattgtggta   2460
caggtcaatg gtaaacttcg tggcaagttg gaagtgtctg ttgatctctc taaagaagat   2520
attttggatc aagccaaagc attgcctgaa gtacaacaat tcttaaccgg tccaaccaag   2580
aaagaaattg tggtgccgaa taaattggtc aatttggtgg tttaa                   2625
```

<210> SEQ ID NO 126
<211> LENGTH: 1671
<212> TYPE: DNA
<213> ORGANISM: Unknown
<220> FEATURE:
<223> OTHER INFORMATION: Description of Unknown:
DP70 Glucose-6-phosphate isomerase sequence

<400> SEQUENCE: 126

```
atgaatagta ttgaaaaatt tcccttgcat gatacggatc tgattcagga aaaactaaaa     60
agttttgccc aacaagagca agagattaat ttaaattatt tatttaaaaa aaataaaaaa    120
cgttttgatg aatattccgt tcatgcgggt cagttatgtt ttgattatag taagcaccgt    180
gttgatgagc gtattattaa cgagcttatt tgttatgcgg aatcacaaca tttgggtaac    240
tggattcagc gcttattttc tttagaaaaa attaattaca ctgaaaatcg cgcagcgatg    300
cattgggctt tgcgtttgcc gaagcaagat agtacacatg cagatttggc agcgcaggta    360
catagtcagc ttgatcgtat gtatcaattg gtcgagaaaa ttcatcaggg gcagtatcga    420
ggagctacag gtgaggtcat ccatgatgtg gtcaatattg gtgtcggtgg atcagatctt    480
ggtcctttaa tggtgtctca agcgctgact gattttaaag ttcaaacggc tcaaaaatta    540
aaagtccatt ttgtttcgac gatggatggc agccaacttt cagatctttt acatcagttt    600
cgcccagaaa ccaccttgtt tattatttca tccaagtctt ttggcaccat tgatacgctt    660
tccaatgcac aaacggcaaa atgctggctt gagcaatctt taggaacgtc gaaatcagtt    720
ctaagatgtc actttgttgg tgtttcaacc aagcccgata agatgaccga gtggggaatc    780
agcactgaaa atcaattctt attgtgggat tgggtcggtg ggcgctattc actatggtcg    840
tgtattggtt tgcctattgc attaagtatt ggggtcgagg gctttaaaca gttgcttgct    900
ggtgcttatg aaatggatca gcattttcag aacacaccac ttgaacaaaa tattcctgtg    960
ttgatgggtt tactgggaat atggaataac aacttcctga atattcaaac tcatgcggta   1020
cttccttatg atggtcggct gaaatatttt gcggcttatt tacagcaatt ggaaatggag   1080
tcgaatggta agtcgattca gcgttctggt gaaaaagtcg tattagatac ctgcccaatt   1140
ttatggggtg aagttggacc aaatgcacaa catgcttttt atcagctgct gcatcaaggt   1200
acacatgctg tgagttgtga ctttattgca cctgtgaaac gctataatgc caatcaattt   1260
acctatgttg aaaatgcaga ggctttagtt gaacaacacc atttagcctt atcgaattgt   1320
ttggcacaat cacgtctatt ggcctttggt aatcatgttc tagatccgaa agaagtagaa   1380
agttcaccga aatataaaca atatgcaggc aaccaaccga ccacaacaat tttgttaaaa   1440
gagttgaatc cgcgcagttt aggtatgctc attgcgatgt atgagcacaa ggtatttgtg   1500
```

caatccgtga tgtggaatat taatccattt gaccaatggg gcgtagaaaa aggtaaagaa 1560
attgccaatc aactgttacc gattctcaat caagagcaag ctgatgtttc tgatcttgat 1620
tcttcaacgc aaggtctatt aagaatttta ctgggaaaag ctgatggcta a 1671

<210> SEQ ID NO 127
<211> LENGTH: 1788
<212> TYPE: DNA
<213> ORGANISM: Unknown
<220> FEATURE:
<223> OTHER INFORMATION: Description of Unknown:
DP70 NADH-quinone oxidoreductase subunit C/D sequence

<400> SEQUENCE: 127
atggctgaaa ctgacattgc tatgccagaa tcaacgcctg ttgattcacg cccagcattt 60
gcaattgtag aagagctcaa agccaaattt ggtgagaact tctatgtgca agcgactttt 120
gaagattttc caacggtctg ggttgagcgc gcgcgcgtac aagatgtttt aatgttcttg 180
cgtaaagtat cacgtccata cgtgatgctg ttcgacttgt ctgcggtaga tgagcgttta 240
cgtacccacc gtgacggttt acctgcatca gacttcactg tgttttatca tttgttgtcg 300
ctagagcgca acagtgatat tcgtattaaa gttgcgttga gtgagagtga tctcaatctt 360
ccaaccgcaa ccaacatttg gccaaatgcc aactggtacg aacgtgaagc ttacgatatg 420
ttcgggatca atttcgaagg gcatccaatg ctccgtcgta ttttgttgcc aacctattgg 480
gaaggtcacc cactgcgtaa agaatattct gcacgtgcga ctgaatatac accgtatatg 540
cagaaccaag cgaagcagga tttcgagcaa gaacatttac gttttgttcc tgaagattgg 600
ggtctatcac gcggtaatgc cgatgaagat ttcatgttct tgaacttagg tccaaaccat 660
ccatctgcgc acggtgcatt ccgtatcatt ttgcagttgg acggtgaaga agtgaaagac 720
tgtgtgcctg atattggcta tcaccaccgt ggtgtggaaa agatggctga acgtcaaact 780
tggcattcat tcattccata taccgaccgt gttgactact tgggtggttg tgcgcaaaac 840
atgccttatg tgatgggtgt ggagcaaatg gcaggaatta ctgttcctga ccgtgcacaa 900
tgtatccgtg tcatgatgtc tgaattattc cgtatcaata accatttatt gtttattggt 960
actgcaattc aagatgccgg cggtatgacg ccagtcttct atatgtttgc cgatcgtcaa 1020
aagatctatg atgcgattga agcgattaca ggctaccgta tgcatccagc atggttccgt 1080
attggcggga ctgcgcacga ccttccaaac aattggcaac atctgattcg tgaaattctc 1140
gaatggatgc cgaagcgtat gaatgaatac tatacagctg cactacgcaa ctcagtattt 1200
attggtcgta cccgtaatgt tgcacaatac gatgcaaaat ctgcattggc ttggggtgta 1260
acaggtacag gtctacgcgc gacagggatt gatttcgacg tgcgtaaata ccgtccgtat 1320
agcggttatg aaaactacga cttcgacgtg cctttagaat acgaaggcga tgcttacgct 1380
cgtgtgatgg ttcacttccg tgaaattgaa gaatcactga aaattgtgaa gcagtgcttg 1440
gataacatgc catctggtcc atataaagcg gatcatcctt tggctgttcc accaccaaaa 1500
gacaagacat tacaagatat tgaaactttg attacgcact tcttgagcgt gtcatggggt 1560
cctgtgatgc ctgcgggtga agcgtctgta atggctgaag tggtaaaagg tgcatcgaac 1620
tactacttga cttcagacaa gtcaaccatg agttatcgta cccgtattcg tacaccaact 1680
ttcacgcact tacagcaaat gccttctgtg attaatggca gtcttgtatc tgacttgatc 1740
atttatttag cgaccattga cgtcgtaatg gctgacgtgg atcgctag 1788

<210> SEQ ID NO 128

<211> LENGTH: 1044
<212> TYPE: DNA
<213> ORGANISM: Unknown
<220> FEATURE:
<223> OTHER INFORMATION: Description of Unknown:
DP70 Protein RecA sequence

<400> SEQUENCE: 128
atggatgata ataaaagtaa ggcgcttaat gctgccctaa gccagattga aaaacaattt 60
ggtaaaaata ccgtaatgcg tcttggtgat aataccgtat tggccgttga agcggtctct 120
acaggttctt taacactaga cattgcactt ggtattggtg gcttaccaaa aggtcgtatc 180
gttgaaattt acggtcctga atcttctggt aaaaccacaa tgacattgca agcgattgca 240
caatgtcaaa aagccggtgg tacttgtgct tttatcgatg cagaacatgc actcgatcct 300
cagtatgcac gtaagcttgg tgtcgacctt gacaacctgt tggtttctca accagaccac 360
ggtgaacaag cccttgaaat tgcagacatg ttagtccgct ctggtgctat tgacatgatc 420
gttgtcgatt ccgtggctgc actgacacct cgcgctgaaa ttgaaggtga aatgggcgac 480
tcacatatgg gcttacaagc acgtttgatg agtcaggcat tacgtaaaat tactggtaat 540
gcaaaacgct caaactgtat ggtgatcttc attaaccaaa tccgtatgaa gattggtgta 600
atgtttggta gccctgaaac cacaacaggt ggtaatgcac tcaaattcta cgcttctgta 660
cgtttggata tccgtcgtat tggtcaagtg aaagaaggcg atgaaattgt cggttcagaa 720
acccgcgtta aagtcgtaaa aaataaaatg gcacctcctt ttaaggaagc gttattccaa 780
attttatatg gcaaaggtgt caatcaactg ggtgaactgg ttgatcttgc tgttgcgcaa 840
gaactggtac aaaaagcagg tgcttggtat tcatatcaag gcaataaaat tggtcaaggt 900
aaaaacaacg tgatccgcca tttagaggaa aatcctcaaa ttgcacaaga acttgatcgc 960
ctgattcgtg aaaaattgtt gacaccaacg accacgccta ttgaagaaaa agatgaagta 1020
gaaccagact ttctagatgc ttaa 1044

<210> SEQ ID NO 129
<211> LENGTH: 1887
<212> TYPE: DNA
<213> ORGANISM: Unknown
<220> FEATURE:
<223> OTHER INFORMATION: Description of Unknown:
DP70 RNA polymerase sigma factor RpoD sequence

<400> SEQUENCE: 129
atgagcgata tgacttcccc tacttcgcaa gtagcggctc tgattagccg aggcaaagag 60
caaggttact taacttacgc tgaggttaac gatcatctcc cagactcgat cacggaaagc 120
gaacagattg aagacattat tcaaatgctt caagatgtcg gcattccagt gcatgaacgt 180
gcgcctgaat ctgatgacac catgttcgac ggtaacaatg cagaagcaac cgatgaagtc 240
gctgaagaag aagcggcagc tgttcttgct tcagttgaaa gcgaacctgg tcgtaccacc 300
gatccagtac gtatgtacat gcgtgaaatg ggaacggttg aactattaac gcgtgaaggc 360
gaaattagca ttgcaaaacg cattgaagaa ggtattcgtg acgttcttca ttcgattgcg 420
tactggccaa atgcagttga agttgtatta aaagaatata gcgatgttgc tgaaggcgaa 480
cgtcgtcttg ctgatatttt atctggttat ttagacccag aatctgacga agaaattcca 540
gaagttttag aagaagaagc tgaaattgtt gaagatgatg aagcgacgac taaaaccact 600
aaagatgtaa aattggacga tgacgaagaa gaagaatctg aaagtgatga tgattctgaa 660
ggtgagtctg gtccagatcc agaaattgca cgtgttcgtt tcactgaatt agaagatgcg 720

```
tggaaagtaa ccaaagccac cattgaaaag catggccgta acagcaaaca agcagatgaa    780
gcgcttgaag ctcttgcaac tgtgtttatg atgttcaaat ttacaccacg tttatttgaa    840
atcatttcag aaatgattcg tggcacgcat gaacaaattc gtacagcaga acgtgaagtg    900
atgcgttacg cagttcgtcg tggtcgtatg gaccgtaccc aattccgtac atcgttccca    960
ggccaagagt caaatccagc ttggttagat gaacaaattg ctaaagcacc tgcggatcaa   1020
aaaggttatt tagaaaaagt acgtccagat gttgttgcat tccagcaaaa gattgccgat   1080
atcgaaaaag aattgggctt agatgttaaa gacatcaaag acatttctaa acgtatggct   1140
gtgggtgaag cgaaagcacg tcgcgcgaaa aaagaaatgg ttgaagcaaa cttacgtttg   1200
gtgatttcga ttgcgaaaaa atataccaac cgtggtttac aattccttga cttgattcaa   1260
gaaggtaaca tcggtttgat gaaagccgta gacaagtttg aataccgtcg tggttataaa   1320
ttctcgactt atgcaacttg gtggattcgt caggcgatta cccgttcgat tgccgatcaa   1380
gcacgtacca tccgtattcc agtacacatg atcgaaacca ttaacaagat caaccgtgta   1440
tctcgtcaac ttcttcaaga aatgggccgt gagcctaccc ctgaagaatt aggcgaacgt   1500
ctggaaatgg acgaagttaa agtacgtaaa gtgctgaaaa ttgccaaaga accgatttcg   1560
atggaaacac cgattggtga tgacgaagat tcgcatcttg gtgacttcat tgaagatggt   1620
aacattacct ctccaattga tgccgcgact tctgaaggct taaaagaagc aacacgtgaa   1680
gtgctggaaa acttgaccga acgtgaagcg aaagtcttaa aaatgcgttt tggtattgat   1740
atgccaaccg accatacttt agaagaagtg ggtaaacaat ttgatgtaac acgtgaacgt   1800
attcgtcaga ttgaagccaa agctttacgt aaattacgtc acccttctcg ttctgaacac   1860
ttacgttcat tcctagaaaa tgactaa                                       1887
```

<210> SEQ ID NO 130
<211> LENGTH: 1671
<212> TYPE: DNA
<213> ORGANISM: Unknown
<220> FEATURE:
<223> OTHER INFORMATION: Description of Unknown:
DP71 Glutamine--tRNA ligase sequence

<400> SEQUENCE: 130

```
atgagtgagg ctgaagcccg cccaacaaat tttatccgtc agattattga tgaagatctg     60
gcgaccggga aacacaatac cgttcacacc cgtttcccgc ctgagcctaa tggctatttg    120
catatcggcc atgcgaagtc tatctgcctg aatttcggca ttgcgcaaga ctaccagggt    180
cagtgcaatc tgcgttttga cgatactaac ccggcaaaag aagacatcga attcgttgag    240
tcgatcaaat acgacgtcca gtggctgggc ttcgactgga gcggtgatat tcactactcc    300
tcagactatt tcgatcaact gcacgcatac gcgctggagc taatcaacaa aggtctggcg    360
tacgttgacg aactgtctcc cgatcaaatt cgcgaatacc gtggttcgct gaccgcaccg    420
ggcaaaaaca gcccgtatcg cgatcgcagc gtggaagaaa atatcgcgct gtttgaaaaa    480
atgcgtaacg gtgaattcgc cgaaggtgcc gcttgcctgc gtgccaaaat cgatatggcg    540
tcgccattct tcgtgatgcg cgatccggtc atctaccgta ttaagtttgc cgaacatcat    600
cagactggca caaaatggtg catctacccg atgtacgatt tcactcactg catttccgat    660
gcgctggaag ggatcaccca ttcactgtgt acgctggaat tccaggacaa ccgccgtctg    720
tacgactggg tactggataa catcactatt ccatgccatc cgcgtcagta tgagttctcc    780
cgtctgaatc ttgaatactc catcatgtcc aagcgtaagc tgaacctgct ggtgacggat    840
```

-continued

```
aagattgtag aaggttggga cgatccgcgt atgccgacgg tttccggtct gcgtcgccgt    900

ggttataccg ccgcgtctat ccgcgaattc tgccgtcgta tcggcgtgac caagcaggac    960

aacaacgttg aaatgatggc gctggaatcc tgtattcgtg acgatctgaa cgaaaacgca   1020

ccgcgcgcca tggccgttat taacccggtt aaagttgtca ttgagaactt caccggtgat   1080

gacgtgcaaa tggtgaaaat gccgaatcat ccgagcaaac cggaaatggg cacccgcgaa   1140

gtgccgttca cccgtgagat ttacatcgat caggctgatt tccgcgaaga agcgaacaaa   1200

cagtacaaac gtctggtgct gggcaaagaa gttcgcctgc gcaatgcgta tgtgatcaaa   1260

gcggaacaca tcgagaaaga cgcggaaggg aatatcacca ccatcttctg ttcttacgat   1320

atcgatacgc tgagcaaaga tcccgctgat ggccgtaagg tgaaaggcgt gattcactgg   1380

gtttctgctt ctgaaggtaa accggcagaa tttcgcctgt atgaccgtct gttcagtgtt   1440

gcgaaccctg gccaggctga agatttcctg accaccatca acccggaatc tctggtgatt   1500

gctcagggct tcgttgagcc gtctctggtc gctgctcagg cagaagtcag tgtgcagttc   1560

gaacgtgaag gttacttctg tgccgacagc cgctattcaa gtgctgagca tctggtgttc   1620

aaccgcaccg tcggccttcg cgacacctgg gaaagcaaac ccgtcgcctg a            1671
```

<210> SEQ ID NO 131
<211> LENGTH: 2415
<212> TYPE: DNA
<213> ORGANISM: Unknown
<220> FEATURE:
<223> OTHER INFORMATION: Description of Unknown:
DP71 DNA gyrase subunit B sequence

<400> SEQUENCE: 131

```
atgtcgaatt cttatgactc ctcaagtatc aaggtattaa aagggctgga cgcggtgcgt     60

aagcgccccg gcatgtatat cggcgatacc gatgacggca ctggtctgca ccacatggta    120

ttcgaggttg tggacaacgc tatcgacgaa gccctcgcgg gccactgtaa agagattcag    180

gtcacgatcc atgcggataa ctctgtttcc gtacaggatg atggtcgtgg tattcctacc    240

ggcattcacg aagaagaggg cgtttctgct gctcaggtca tcatgaccgt acttcatgcc    300

ggcggtaaat ttgacgataa ctcgtacaaa gtctccggcg gtctgcatgg cgtgggtgtt    360

tccgtcgtta acgccctgtc ggaaaaactg gagctggtta tccgccgtga aggcaaagtg    420

cacacccaga cttacgtcca cggtgagccg caggatccgc tgaaagtggt tggcgatacc    480

gaggcgaccg gtacgaccgt gcgcttctgg ccaagctacg ccaccttcac caatcaaaca    540

gaattcgagt atgacattct ggcgaaacgc ctccgtgagc tgtcattcct gaactctggt    600

gtggcgatcc gcctgctcga caaacgcgat ggcaagaacg atcacttcca ttatgaaggc    660

ggtatcaaag ctttcgtgga atacctgaac aaaaacaaaa ccccaatcca cccaaccgtg    720

ttctatttct ccaccgtgaa agacgatatc ggtgtggaag tggcgttgca gtggaatgat    780

ggtttccagg aaaatattta ctgctttacc aacaatatcc ctcagcgcga cggcggcacc    840

catctggtag gcttccgttc tgcgatgacc cgtacgctta acgcgtatat ggataaagaa    900

ggctacagca agaaatccaa aatcagcgcc accggtgatg atgcccgtga aggcctgatc    960

gccgtggttt cggtaaaagt gccggatcct aagttctcct ctcagaccaa agacaaactg   1020

gtttcttccg aagtgaagac cgccgttgag tctctgatga acgagaagct ggttgattat   1080

ctgatggaaa acccggccga cgcgaaaatc gttgtcggta aaatcatcga tgcagcccgt   1140

gcgcgtgaag ccgcgcgtaa agcacgtgaa atgacccgtc gtaaaggcgc gctcgatctg   1200
```

gccggtctgc caggcaaact ggctgactgt caggaacgcg acccggcaca ttccgaactg 1260
tacttagtgg aaggggactc agcgggcggc tctgcaaaac aaggccgtaa ccgtaagaac 1320
caggcgattc tgccgttgaa agggaaaatc ctcaacgttg agaaagcgcg cttcgacaaa 1380
atgctctctt ctcaggaagt ggcgacgctg attaccgcgc tcggttgcgg tatcggccgt 1440
gacgaataca acccggataa actgcgttat cacagcatca tcatcatgac cgatgccgac 1500
gtcgatggtt cgcacatccg taccctgtta ctgacattct tctaccgtca gatgcctgaa 1560
attgtagagc gtggccacgt gtttatcgcg cagcctccgc tgtacaaagt gaaaaaaggc 1620
aaacaggaac agtacattaa agatgatgaa gcgatggatc agtatcaaat ctctatcgcg 1680
atggacgggg caacgttaca cgccaacgcc catgcaccag cactggcggg cgaaccgctg 1740
gagaaactgg tggctgaaca tcacagcgtg cagaaaatga ttggccgtat ggaacgtcgt 1800
tatccgcgtg cgctgctgaa taatctggtc tatcagccaa cgctggcggg tgctgaactt 1860
gccgacgaag cgaaagtgaa ggaatggatt gaaacgctgg tgtctcgtct gaacgagaaa 1920
gagcagcacg gcagcagcta cagtgcgatc gtgcgcgaaa atcttgaaca ccagctgttc 1980
gagccaatcc tgcgcattcg tactcacggt gtggataccg actacgatct cgatgcagac 2040
ttcattcagg gcggcgaata ccgcaaaatc tgtaccctgg gtgaaaaact gcgcggcctg 2100
atcgaagaag atgcttacat cgaacgtggc gaacgccgtc agccagtgac cagcttcgag 2160
caggcgctgg aatggctggt gaaagagtcg cgtcgcggtc tgtcgattca gcgttataaa 2220
ggtctgggtg aaatgaaccc tgagcaattg tgggaaacca cgatggatcc gacacaacgc 2280
cgcatgctgc gcgtgacggt gaaagatgct atcgcggcgg accagctgtt caccacgctg 2340
atgggcgatg cggttgaacc gcgccgcgcc ttcatcgaag agaacgccct taaagctgcc 2400
aatatcgata tctga 2415

<210> SEQ ID NO 132
<211> LENGTH: 2817
<212> TYPE: DNA
<213> ORGANISM: Unknown
<220> FEATURE:
<223> OTHER INFORMATION: Description of Unknown:
DP71 Isoleucine--tRNA ligase sequence

<400> SEQUENCE: 132
atgagtgact acaagaacac cctgaatttg ccggaaacag ggttcccgat gcgtggcgat 60
ctggccaagc gtgaacctga catgctgaag aattggtatg accaggatct gtacgggatt 120
attcgtgctg ccaagaaagg caagaaaacc tttatcttgc atgacggccc tccgtatgcg 180
aacggcagca ttcatattgg tcactcagta aacaaaattc ttaaagacat gatcgttaag 240
tccaaaggac tggcgggctt tgatgcgccg tatgttccgg gctgggattg tcatggtctg 300
ccgattgaac tgaaagttga acagctgatc ggtaagccgg gcgaaaaagt cacggcggcg 360
gaattccgtg aagcctgccg caagtacgct gctgaacagg ttgaaggtca gaagaaagac 420
ttcatccgtc tgggcgtgct cggtgactgg gatcatccgt acctgaccat ggacttcaaa 480
acagaagcca acatcattcg tgccctgggt aaaatcatcg gcaacggtca cctgcataaa 540
ggtgcgaaac ctgttcactg gtgtaccgat tgcggatctt cactggctga agccgaagtc 600
gaatattacg acaaagtgtc tccgtctatc gacgtgacgt ttaatgcgac ggatgccgcc 660
gctgttgctg cgaaattcgg tgccactgct ttcaatggcc cggtttctct ggtcatctgg 720
accaccaccc cgtggaccat gccagctaac cgcgcgattt cactcaacgc tgagttctct 780

-continued tatcagctgg tgcagattga aggtcagtgc ctgatcctgg ctaccgatct ggtagaaagc 840
gtgatgaatc gcgccggtat cgctgagtgg actgtgctgg gcgaatgtaa aggtgcggat 900
cttgaattgc ttcgattcca gcatccgttc ctcggtttcg atgttccggc gatcctcggc 960
gatcacgtta ctctcgatgc cggtaccggt gctgtacata ccgcacctgg ccacggtcct 1020
gatgactttg tcattggcca gaaatacggt ctggaagtcg caaacccggt tggaccgaac 1080
ggctgctacc tgccgggcac ttatccgacg ctggatggca aattcgtctt taaagcgaat 1140
gatctgatcg ttgaattgct gcgtgagaag ggcgcactgc tgcacgttga gaaaatgaac 1200
cacagctatc cgtgctgctg gcgtcacaaa acgccgatca tcttccgcgc tacgccacaa 1260
tggttcatca gcatggatca gaaaggtttg cgtcagaagt ctctggaaga gatcaaaggc 1320
gtgcagtgga tccctgactg ggtcaggcg cgtatcgaaa acatggtcgc taaccgtcct 1380
gactggtgta tctcccgcca gcgtacgtgg ggcgtaccga tgtctctgtt cgtgcataaa 1440
gataccgaac agcttcatcc gcgcagcctt gagctgatgg aagaagtggc aaaacgcgtg 1500
gaagccgatg gcattcaggc atggtgggat ctgaaccctg aagagatttt gggtgcagac 1560
gctgccgatt acgtcaaagt gccggatacg ctggacgtct ggtttgactc cggttccacg 1620
cactcctccg ttgtggatgt gcgccctgag ttcaacggtc attcaccgga tctgtatctg 1680
gaaggttctg accagcatcg cggctggttc atgtcttctc tgatgatttc tacggcgatg 1740
aaaggcaaag cgccttacaa acaagtactg actcacggtt tcaccgtcga tggtcagggc 1800
cgtaaaatgt ctaaatccat cggtaacacc atcgcgcctc aggatgtgat gaataagctg 1860
ggtggcgaca tcctgcgttt gtgggtggca tctacggatt acaccggcga aatcgccgtg 1920
tccgacgaaa tcctcaaacg tgctgccgat tcttatcgcc gtatccgtaa caccgcgcgc 1980
ttcctgctgg cgaaccttaa cggtttcgat ccggcgctgc acagcgtggc accggaagag 2040
atggttgtgc tggatcgctg ggcggttggc cgcgcgaaag ctgcacaaga cgagatcatt 2100
gctgcgtacg aagcctatga tttccacggc gttgttcagc gtctgatgca gttctgctcg 2160
atcgaaatgg gttcgttcta tctggatatc attaaagatc gccagtacac cgcgaagagc 2220
gacagcgttg cgcgccgcag ctgccagacc gcgctgtatc acatctgcga agcactggtt 2280
cgctggatgg cgccaatcat gtccttcact gccgatgaaa tctgggctga actgccaggt 2340
catcgcgaga agttcgtctt tactgaagaa tggtacgacg gtctgtttgg cctgatcggt 2400
aacgaatcca tgaacgatgc gttctgggat gagctgctga aagtgcgtgg tgaagtgaac 2460
aaagtgatcg aacaggcgcg tgctgataaa cgtctgggcg gttctctgga agcagccgtg 2520
accttatatg cagacgacgc gctggcaaca gacctgcgtt ctctgggtaa cgaactgcgc 2580
tttgtgctcc tgacttccgg tgcgaaagtc gccgcgctgt ctgaagctga tgactcagcg 2640
caggccagcg aattgttgaa aggactgaaa attggtctgg cgaaagcaga aggcgagaag 2700
tgcccgcgct gctggcattt caccactgat atcggccaga atgcggaaca cagtgacatc 2760
tgtggccgtt gtgtgactaa cattgccggt gacggcgaag agcgtaagtt tgcataa 2817

<210> SEQ ID NO 133
<211> LENGTH: 1560
<212> TYPE: DNA
<213> ORGANISM: Unknown
<220> FEATURE:
<223> OTHER INFORMATION: Description of Unknown:
DP71 NADH-quinone oxidoreductase subunit C/D sequence

<400> SEQUENCE: 133
atgtcagaac ttactcatat taatgcttcc ggcgacgccc acatggtgga tgtctccggt 60
aaagacgaca ccgttcgtga agcccgtgcc gaagcctttg ttgaaatggc cgaaagcacg 120
ctggcgatga tcatcggcgg taatcaccat aagggtgacg tgttcgcgac cgcgcggatt 180
gccggtattc aggcagcgaa gaaaacctgg gatctgatcc cgctgtgtca tccgctgttg 240
ctgaccaagg tggaagtgaa tcttgaagcg cagccagaat ttaatcgtgt acgtattgaa 300
tcccgctgcc gcctgagcgg taaaaccggc gtcgagatgg aagcgctgac cttcaagcct 360
gaagactggg gaatgaagcg cggcaccgaa aacgaggact tcatgttcct caacctcgga 420
cctaaccatc cgtctgcgca cggtgcgttc cgcatcatcc tgcagcttga tggcgaagaa 480
attgtcgact gtgtaccgga cgtcggttac caccaccgtg gtgctgagaa gatgggcgag 540
cgccagtcat ggcacagcta cattccatac acggaccgta tcgaatacct cggcggttgc 600
gttaacgaga tgccatacgt actggctgtt gaaaaactgg cgggtatcgt cgtgccggat 660
cgcgttaaca ccatccgcgt gatgctgtct gaactgttcc gtatcaacag ccacctgctg 720
tacatctcta cgtttattca ggacgtgggc gcgatgacgc cagtgttctt cgcctttacc 780
gatcgtcaga aaatttacga tctggtggaa gcgatcaccg gtttccgtat gcacccggcc 840
tggttccgta ttggtggcgt tgcacacgac ctgccgaaag gctgggagcg tctgctgcgt 900
gaattccttg actggatgcc agcccgtctg gattcctacg tcaaggcagc gctgaaaaac 960
accattctga ttggacgttc caaaggcgta gcagcataca acgccgatga tgcgctggcg 1020
tggggcacca ccggtgctgg cctgcgtgcg accgggatcg acttcgatgt ccgcaaatgg 1080
cgtccatatt caggttacga aaacttcgat tttgaagtgc cggtcggcga tggcgtcagt 1140
gattgctatt cccgcgtgat gctaaaagtg gaagagcttc gtcagagcct gcgcattctg 1200
gaacagtgct acaaaaacat gccggaaggc ccgttcaagg cggatcaccc gctgaccacg 1260
ccgccaccga aagagcgtac gctgcaacac atcgaaaccc tgatcactca cttcctgcaa 1320
gtgtcgtggg gtccgatcat gcctgcgcaa gaatctttcc agatggttga agccaccaaa 1380
gggatcaaca gctactacct gaccagtgac ggcagcacca tgagctaccg cacgcgcgtc 1440
cgtacgccaa gcttcccgca tttgcagcag atcccgtccg taatccgtgg cagcctggta 1500
tccgacctga tcgtgtatct gggcagtatc gattttgtaa tgtcagatgt ggaccgctaa 1560

<210> SEQ ID NO 134
<211> LENGTH: 1065
<212> TYPE: DNA
<213> ORGANISM: Unknown
<220> FEATURE:
<223> OTHER INFORMATION: Description of Unknown:
DP71 Protein RecA sequence

<400> SEQUENCE: 134
atggctattg atgagaacaa gcaaaaagcg ttagctgcag cactgggcca gattgaaaag 60
caattcggta aaggctccat catgcgtctg ggtgaagatc gctctatgga cgtggaaacg 120
atctctaccg gctctttgtc tctggatatc gcgttaggcg ccggtggttt gccgatgggc 180
cgtatcgttg agatttatgg cccggaatcc tccggtaaaa ctacgctgac ccttcaggtt 240
attgctgccg cacagcgcga aggcaaaacc tgtgcgttca tcgatgcgga acatgcactt 300
gaccctatct acgcgaagaa attgggcgta gatatcgaca acctgttgtg ttctcagccg 360
gataccggcg aacaggctct ggaaatctgt gacgcgctga cccgttcagg cgcggtcgac 420
gttatcatcg tcgactccgt tgctgcactg acgccaaaag cagaaatcga aggcgaaatc 480
ggtgactctc acatgggcct tgcggcacgt atgatgagcc aggcaatgcg taagcttgcc 540
ggtaacctga aaaacgccaa caccttgctg atcttcatca accagatccg tatgaaaatc 600
ggtgtgatgt tcggtaaccc ggaaaccacc accggtggta acgccctgaa attctacgcc 660
tctgtgcgtc tggatatccg ccgcatcggc gctatcaaag aaggcgacgt ggtgatcggc 720
agtgaaacgc gcgtgaaagt tgtgaagaac aaaatcgctg cgcctttcaa acaggctgaa 780
ttccagatcc tatacggcga aggcatcaac attaacggcg agctgatcga tttgggcgtt 840
aagcacaaac tggtcgaaaa agccggtgca tggtacagct acaacggcga gaagattggt 900
cagggtaaat ctaactcctg caactatctg aaagaaaacc cgaaaatcgc tgctgaactg 960
gataaaaaac tgcgtgatat gttgttgagt ggcactggtg aactggccgc tgcaaccaca 1020
gcagaacttg cagacgacga tatggaaacc agcgaagagt tttaa 1065

<210> SEQ ID NO 135
<211> LENGTH: 1794
<212> TYPE: DNA
<213> ORGANISM: Unknown
<220> FEATURE:
<223> OTHER INFORMATION: Description of Unknown:
DP71 RNA polymerase sigma factor RpoD sequence

<400> SEQUENCE: 135
ggtaaggagc aaggctatct gacctttgct gaggtcaatg accatctgcc ggaagatatc 60
gtcgactccg accagatcga agacatcatc cagatgatta acgacatggg catccaggtt 120
cttgaagaag cgccggacgc cgatgatttg atgctggccg aaaaccgccc tgataccgat 180
gaagatgctg cagaagcagc ggctcaggtg ctttccagcg ttgaatctga aattggccgt 240
accaccgacc ctgtgcgtat gtatatgcgc gaaatgggta ccgttgagct cctgacccgt 300
gaaggcgaaa tcgacatcgc caaacgtatc gaagacggta tcaatcaggt ccagtgctcc 360
gttgctgaat atcctgaagc tatcacctat ttgttagagc aatatgaccg tgttgaagca 420
ggcgaagcac gtctgtctga tttgatcacc ggttttgttg atccgaacgc cgaagaagaa 480
atcgcgccga ctgcgactca cgtgggttct gaactgacca ctgaagagca aaatgatacc 540
gacgacgatg aagaagacga cgacgatgct gaagacgaca acagcatcga cccggaactg 600
gcgcgtcaga agttcaccga tctgcgtgag caacatgaag cgacccgtgc cgtcatcaag 660
aaaaatggcc gtagccacaa aagcgccgca gaagaaattc tgaagctgtc cgatgtgttt 720
aaacagttcc gtctggtacc aaaacagttc gatttcctgg tgaacagcat gcgctccatg 780
atggatcgcg tccgtactca ggaacgtctg atcatgaaag tgtgcgttga acagtgcaaa 840
atgccgaaga aaaacttcgt caatctgttc gccggtaacg aaaccagcag tacctggttt 900
gatgctgctc tggcaatggg taaaccatgg tctgagaagc tgaaagaagt gaccgaagac 960
gtgcagcgcg gcctgatgaa actgcgccaa atcgaagaag aaactggcct gactatcgaa 1020
caggtaaaag acattaaccg tcgcatgtcg atcggcgaag cgaaagcacg ccgcgcgaag 1080
aaagagatgg ttgaagcgaa cttacgtctg gttatctcta tcgcgaagaa atacaccaac 1140
cgtggcttgc agttccttga cctgattcag gaaggtaaca tcggcctgat gaaagccgtt 1200
gataagtttg aatatcgccg tggttataag ttctctactt atgcgacctg gtggatccgt 1260
caggctatca cccgctccat cgccgaccag gcacgtacca tccgtattcc ggtgcatatg 1320
attgagacca tcaacaaact caaccgtatt tcgcgccaga tgttgcagga gatgggccgt 1380
gagccgacgc cggaagagct ggctgaacgc atgctgatgc cggaagacaa gatccgtaaa 1440

-continued gtgctgaaaa ttgctaaaga gccaatctcc atggaaacgc caatcggcga cgatgaagat 1500
tcgcatctgg gtgatttcat cgaggatact accctcgagc tgccgctgga ttctgcgacc 1560
tctgaaagcc tgcgttctgc aacgcacgac gttctggctg gcctgaccgc acgtgaagcg 1620
aaagttctgc gtatgcgttt cggtatcgat atgaacactg accacactct ggaagaagtg 1680
ggcaaacagt tcgacgtaac ccgtgaacgt atccgtcaga tcgaagccaa agcgttgcgt 1740
aaactacgcc acccaagccg ctccgaagtg ctgcgcagct tcctcgacga ctag 1794

<210> SEQ ID NO 136
<211> LENGTH: 2487
<212> TYPE: DNA
<213> ORGANISM: Unknown
<220> FEATURE:
<223> OTHER INFORMATION: Description of Unknown:
DP71 DNA-directed RNA polymerase subunit beta sequence

<400> SEQUENCE: 136
atggaccaga acaacccgtt gtctgagatc acgcacaaac gtcgtatctc tgcactgggc 60
ccgggcggtt tgacccgtga acgtgctggc tttgaagttc gagacgtaca cccgacgcac 120
tacggtcgcg tatgtccaat cgaaacgcca gaaggtccaa acatcggtct gatcaactca 180
ttatctgtct atgcacagac aaatgagtat ggtttcctgg aaacccctta ccgccgtgtg 240
cgtgaaggta tggttaccga tgaaattaac tacctgtctg ccatcgaaga aggcaacttt 300
gttatcgctc aggcgaactc caacctggat gacgaaggcc acttcctgga agatttagtc 360
acttgtcgta gcaaaggcga atcaagcctg ttcagccgcg accaggttga ctacatggac 420
gtttctaccc agcagatcgt atccgttggt gcttcactga ttccattcct ggaacacgat 480
gacgccaacc gtgcattgat gggtgcgaac atgcaacgtc aggcagttcc tactctgcgt 540
gctgataagc cgctggtagg tactggtatg gaacgtgctg ttgcggttga ctccggtgtt 600
actgccgttg ccaaacgtgg tggtactgtt cagtacgtag atgcatcccg tatcgttatt 660
cgtgttaacg aagaagagat gaatccaggc gaagcaggta tcgacattta taacctgact 720
aagtacaccc gttctaacca gaacacctgc atcaaccaga tgccgtgtgt gaatctgggc 780
gagccaatcg agcgcggcga cgtgctggca gatggtccgt caacagatct gggcgaactg 840
gcactgggtc agaacatgcg tgtcgcgttc atgccttgga acggttacaa cttcgaagac 900
tccatcttgg tctccgaacg tgttgtgcag gaagatcgct tcacgaccat ccatatccag 960
gaactggcat gtgtgtcccg tgacacaaag ttagggcctg aagagatcac tgctgatatc 1020
cctaacgtgg gtgaagctgc gctctccaaa ctggatgagt ccggtattgt gtatatcggt 1080
gctgaagtga ccggtggtga cattctggtc ggtaaagtta cgcctaaagg cgaaacccag 1140
ctgactccag aagagaaact gctgcgtgcg atcttcggtg agaaagcgtc tgacgttaaa 1200
gattcttctc tgcgtgtacc aaacggcgtt tccggtacga ttattgacgt gcaagtcttt 1260
acccgcgatg gcgtggaaaa agataagcgt gcgttagaaa tcgaagaaat gcagctgaaa 1320
caggctaaga aagacctgac tgaagagctg caaattctgg aagctggtct gtttgcacgt 1380
atccagtccg cgctggttgc tggcggtgtt gaagccgata agctgggcaa attgccacgc 1440
gatcgttggc ttgaactgtc actgactgac gaagacaaac agaatcagtt ggaacagctt 1500
gctgaacagt acgacgaact gaaatccgag tttgagaaaa aactcgaagc taaacgtcgt 1560
aaaatcactc agggcgatga cctagcacca ggtgtgctga aatcgttaa agtgtacctg 1620 gccgttaaac gtcagatcca acctggtgac aaaatggcag gccgccacgg taacaaaggt 1680
gttatctcca agatcaaccc gatcgaagat atgccttacg atgaaaacgg gactcctgtt 1740
gacatcgtac tgaacccgct gggcgttcca tcacgtatga acattggtca gattttagaa 1800
acccacctgg gtatggccgc gaaaggtatt ggtgaaaaaa tcaatgccat gcttaagaaa 1860
catgaagaag tttctaagct gcgcgagttc atccagcgtg cctatgatct gggcgacgac 1920
gtacgtcaga aagttgatct gaccaccttc accgatgatg aagtattgcg tttggctgaa 1980
aacctgaaaa agggtatgcc aattgcaaca ccagtcttcg acggtgcgaa agagacagag 2040
atcaagcaac tgcttgaaat gggcggcgtc ccaacctctg gccagatcac actgtttgac 2100
ggccgtaccg gcgagcaatt cgagcgccag gttaccgtcg gctacatgta catgctgaaa 2160
ctgaaccacc tggttgacga taagatgcat gcgcgttcta ccggttctta cagccttgtt 2220
actcagcagc cgctgggtgg taaagctcag ttcggtggtc agcgcttcgg tgagatggaa 2280
gtgtgggcac tggaagcata cggtgccgct tataccctgc aggaaatgct gactgttaag 2340
tccgatgacg tgaacggccg tactaagatg tataaaaaca tcgtagatgg cgatcaccgg 2400
atggaaccag gcatgccgga atcattcaac gtactgttga aagaaatccg ctctctgggt 2460
atcaacatcg agctggaaga cgagtaa 2487

<210> SEQ ID NO 137
<211> LENGTH: 1547
<212> TYPE: DNA
<213> ORGANISM: Unknown
<220> FEATURE:
<223> OTHER INFORMATION: Description of Unknown:
DP72 16S rRNA sequence

<400> SEQUENCE: 137
ttcggagagt ttgatcctgg ctcaggacga acgctggcgg cgtgcctaat acatgcaagt 60
cgagcggaca gaagggagct tgctcccgga tgttagcggc ggacgggtga gtaacacgtg 120
ggtaacctgc ctgtaagact gggataactc cgggaaaccg gagctaatac cggatagttc 180
cttgaaccgc atggttcaag gatgaaagac ggtttcggct gtcacttaca gatggacccg 240
cggcgcatta gctagttggt ggggtaatgg ctcaccaagg cgacgatgcg tagccgacct 300
gagagggtga tcggccacac tgggactgag acacggccca gactcctacg ggaggcagca 360
gtagggaatc ttccgcaatg gacgaaagtc tgacggagca acgccgcgtg agtgatgaag 420
gttttcggat cgtaaagctc tgttgttagg gaagaacaag tgcgagagta actgctcgca 480
ccttgacggt acctaaccag aaagccacgg ctaactacgt gccagcagcc gcggtaatac 540
gtaggtggca agcgttgtcc ggaattattg ggcgtaaagg gctcgcaggc ggtttcttaa 600
gtctgatgtg aaagcccccg gctcaaccgg ggagggtcat tggaaactgg gaaacttgag 660
tgcagaagag gagagtggaa ttccacgtgt agcggtgaaa tgcgtagaga tgtggaggaa 720
caccagtggc gaaggcgact ctctggtctg taactgacgc tgaggagcga aagcgtgggg 780
agcgaacagg attagatacc ctggtagtcc acgccgtaaa cgatgagtgc taagtgttag 840
ggggtttccg ccccttagtg ctgcagctaa cgcattaagc actccgcctg gggagtacgg 900
tcgcaagact gaaactcaaa ggaattgacg ggggcccgca caagcggtgg agcatgtggt 960
ttaattcgaa gcaacgcgaa gaaccttacc aggtcttgac atcctctgac aaccctagag 1020
atagggcttt cccttcgggg acagagtgac aggtggtgca tggttgtcgt cagctcgtgt 1080
cgtgagatgt tgggttaagt cccgcaacga gcgcaaccct tgatcttagt tgccagcatt 1140
tagttgggca ctctaaggtg actgccggtg acaaaccgga ggaaggtggg gatgacgtca 1200
aatcatcatg ccccttatga cctgggctac acacgtgcta caatggacag aacaaagggc 1260
tgcgagaccg caaggtttag ccaatcccat aaatctgttc tcagttcgga tcgcagtctg 1320
caactcgact gcgtgaagct ggaatcgcta gtaatcgcgg atcagcatgc cgcggtgaat 1380
acgttcccgg gccttgtaca caccgcccgt cacaccacga gagtttgcaa cacccgaagt 1440
cggtgaggta acctttatgg agccagccgc cgaaggtggg gcagatgatt ggggtgaagt 1500
cgtaacaagg tagccgtatc ggaaggtgcg gctggatcac ctccttt 1547

<210> SEQ ID NO 138
<211> LENGTH: 841
<212> TYPE: DNA
<213> ORGANISM: Unknown
<220> FEATURE:
<223> OTHER INFORMATION: Description of Unknown:
DP73 16S rRNA sequence

<400> SEQUENCE: 138
aacggagagt ttgatcctgg ctcaggacga acgctggcgg cgtgcctaat acatgcaagt 60
cgagcggaca gaagggagct tgctcccgga cgttagcggc ggacgggtga gtaacacgtg 120
ggcaacctgc ccttagact gggataactc cgggaaaccg gagctaatac cggataatcc 180
ctttctccac ctggagagag ggtgaaagat ggcttcggct atcactaagg gatgggcccg 240
cggcgcatta gctagttggt aaggtaacgg cttaccaagg cgacgatgcg tagccgacct 300
gagagggtga tcggccacac tgggactgag acacggccca gactcctacg ggaggcagca 360
gtagggaatc ttccgcaatg gacgaaagtc tgacggagca acgccgcgtg agtgaggaag 420
gccttcgggt cgtaaagctc tgttgtgagg gaagaagcgg tgccgttcga atagggcggt 480
accttgacgg tacctcacca gaaagccacg gctaactacg tgccagcagc cgcggtaata 540
cgtaggtggc aagcgttgtc cggaattatt gggcgtaaag cgcgcgcagg cggcttctta 600
agtctgatgt gaaatctcgg ggctcaaccc cgagcggcca ttggaaactg gggagcttga 660
gtgcagaaga ggagagtgga attccacgtg tagcggtgaa atgcgtagag atgtggagga 720
acaccagtgg cgaaggcgac tctctggtct gtaactgacg ctgaggcgcg aaagcgtggg 780
gagcaaacag gattagatac cctggtagtc cacgccgtaa acgatgagtg ctaggtgtta 840
g 841

<210> SEQ ID NO 139
<211> LENGTH: 1105
<212> TYPE: DNA
<213> ORGANISM: Unknown
<220> FEATURE:
<223> OTHER INFORMATION: Description of Unknown:
DP74 16S rRNA sequence

<400> SEQUENCE: 139
gcctaataca tgcaagtcgt gcggaccttt taaaagcttg cttttaaaag gttagcggcg 60
aacgggtgag taacacgtgg gcaacctgcc tgtaagatcg ggataatgcc gggaaaccgg 120
ggctaatacc ggatagtttt ttcctccgca tggaggaaaa aggaaagacg gcttcggctg 180
tcacttacag atgggcccgc ggcgcattag cttgttggtg gggtaacggc tcaccaaggc 240
aacgatgcgt agccgacctg agagggtgat cggccacatt gggactgaga cacggcccaa 300
actcctacgg gaggcagcag tagggaatct tccgcaatgg acgaaagtct gacggagcaa 360
cgccgcgtga gtgaagaagg ccttcgggtc gtaaaactct gttgccgggg aagaacaagt 420

-continued

```
gccgttcgaa cagggcggcg ccttgacggt acccggccag aaagccacgg ctaactacgt    480

gccagcagcc gcggtaatac gtaggtggca agcgttgtcc ggaattattg ggcgtaaagc    540

gcgcgcaggc ggcttcttaa gtctgatgtg aaatcttgcg gctcaaccgc aagcggtcat    600

tggaaactgg gaggcttgag tgcagaagag gagagtggaa ttccacgtgt agcggtgaaa    660

tgcgtagaga tgtggaggaa caccagtggc gaaggcggct ctctggtctg taactgacgc    720

tgaggcgcga aagcgtgggg agcaaacagg attagatacc ctggtagtcc acgccgtaaa    780

cgatgagtgc taagtgttag agggtttccg ccctttagtg ctgcagctaa cgcattaagc    840

actccgcctg gggagtacgg ccgcaaggct gaaactcaaa ggaattgacg ggggcccgca    900

caagcggtgg agcatgtggt ttaattcgaa gcaacgcgaa gaaccttacc aggtcttgac    960

atcctctgac ctccctggag acagggcctt ccccttcggg ggacagagtg acaggtggtg   1020

catggttgtc gtcagctcgt gtcgtgagat gttgggttaa gtcccgcaac gagcgcaacc   1080

cttgacctta gttgccagca ttcag                                         1105
```

<210> SEQ ID NO 140
<211> LENGTH: 1515
<212> TYPE: DNA
<213> ORGANISM: Unknown
<220> FEATURE:
<223> OTHER INFORMATION: Description of Unknown:
DP75 16S rRNA sequence

<400> SEQUENCE: 140

```
tgaagagttt gatcatggct cagattgaac gctggcggca ggcctaacac atgcaagtcg     60

agcggtagag agaagcttgc ttctcttgag agcggcggac gggtgagtaa tgcctaggaa    120

tctgcctggt agtgggggat aacgttcgga aacggacgct aataccgcat acgtcctacg    180

ggagaaagca ggggaccttc gggccttgcg ctatcagatg agcctaggtc ggattagcta    240

gttggtgagg taatggctca ccaaggcgac gatccgtaac tggtctgaga ggatgatcag    300

tcacactgga actgagacac ggtccagact cctacgggag gcagcagtgg ggaatattgg    360

acaatgggcg aaagcctgat ccagccatgc cgcgtgtgtg aagaaggtct tcggattgta    420

aagcacttta agttgggagg aagggttgta gattaatact ctgcaatttt gacgttaccg    480

acagaataag caccggctaa ctctgtgcca gcagccgcgg taatacagag ggtgcaagcg    540

ttaatcggaa ttactgggcg taaagcgcgc gtaggtggtt cgttaagttg gatgtgaaag    600

ccccgggctc aacctgggaa ctgcattcaa aactgacgag ctagagtatg gtagagggtg    660

gtggaatttc ctgtgtagcg gtgaaatgcg tagatatagg aaggaacacc agtggcgaag    720

gcgaccacct ggactgatac tgacactgag gtgcgaaagc gtggggagca aacaggatta    780

gataccctgg tagtccacgc cgtaaacgat gtcaactagc cgttggaatc cttgagattt    840

tagtggcgca gctaacgcat taagttgacc gcctggggag tacggccgca aggttaaaac    900

tcaaatgaat tgacgggggc ccgcacaagc ggtggagcat gtggtttaat tcgaagcaac    960

gcgaagaacc ttaccaggcc ttgacatcca atgaactttc cagagatgga tgggtgcctt   1020

cgggaacatt gagacaggtg ctgcatggct gtcgtcagct cgtgtcgtga gatgttgggt   1080

taagtcccgt aacgagcgca acccttgtcc ttagttacca gcacgttatg gtgggcactc   1140

taaggagact gccggtgaca aaccggagga aggtggggat gacgtcaagt catcatggcc   1200

cttacggcct gggctacaca cgtgctacaa tggtcggtac aaagggttgc caagccgcga   1260

ggtggagcta atcccataaa accgatcgta gtccggatcg cagtctgcaa ctcgactgcg   1320
```

tgaagtcgga atcgctagta atcgcgaatc agaatgtcgc ggtgaatacg ttcccgggcc 1380
ttgtacacac cgcccgtcac accatgggag tgggttgcac cagaacggga ggacggttac 1440
cacggtgtga ttcatgactg gggtgaagtc gtaacaaggt agccgtaggg gaacctgcgg 1500
ctggatcacc tcctt 1515

<210> SEQ ID NO 141
<211> LENGTH: 1479
<212> TYPE: DNA
<213> ORGANISM: Unknown
<220> FEATURE:
<223> OTHER INFORMATION: Description of Unknown:
DP76 16S rRNA sequence

<400> SEQUENCE: 141
cttgagagtt tgatcctggc tcagaacgaa cgctggcggc aggcttaaca catgcaagtc 60
gagcgccccg caaggggagc ggcagacggg tgagtaacgc gtgggaatct accttttgct 120
acggaacaac agttggaaac gactgctaat accgtatgtg cccttcgggg gaaagattta 180
tcggcaaagg atgagcccgc gttggattag ctagttggtg aggtaaaggc tcaccaaggc 240
gacgatccat agctggtctg agaggatgat cagccacact gggactgaga cacggcccag 300
actcctacgg gaggcagcag tggggaatat tggacaatgg gcgcaagcct gatccagcca 360
tgccgcgtga gtgatgaagg ccctagggtt gtaaagctct ttcaccggtg aagataatga 420
cggtaaccgg agaagaagcc ccggctaact tcgtgccagc agccgcggta atacgaaggg 480
ggctagcgtt gttcggattt actgggcgta aagcgcacgt aggcggattt ttaagtcagg 540
ggtgaaatcc cggggctcaa ccccggaact gcctttgata ctggaagtct tgagtatggt 600
agaggtgagt ggaattccga gtgtagaggt gaaattcgta gatattcgga ggaacaccag 660
tggcgaaggc ggctcactgg accattactg acgctgaggt gcgaaagcgt ggggagcaaa 720
caggattaga taccctggta gtccacgccg taaacgatga atgttagccg tcggggggtt 780
tacctttcgg tggcgcagct aacgcattaa acattccgcc tggggagtac ggtcgcaaga 840
ttaaaactca aaggaattga cgggggcccg cacaagcggt ggagcatgtg gtttaattcg 900
aagcaacgcg cagaacctta ccagcccttg acataccggt cgcggacaca gagatgtgtc 960
tttcagttcg gctggaccgg atacaggtgc tgcatggctg tcgtcagctc gtgtcgtgag 1020
atgttgggtt aagtcccgca acgagcgcaa ccctcgcctt tagttgccag catttagttg 1080
ggcactctaa agggactgcc agtgataagc tggaggaagg tggggatgac gtcaagtcct 1140
catggccctt acgggctggg ctacacacgt gctacaatgg tggtgacagt gggcagcaag 1200
cacgcgagtg tgagctaatc tccaaaagcc atctcagttc ggattgcact ctgcaactcg 1260
agtgcatgaa gttggaatcg ctagtaatcg cggatcagca tgccgcggtg aatacgttcc 1320
cgggccttgt acacaccgcc cgtcacacca tgggagttgg ttttacccga aggcactgtg 1380
ctaaccgcaa ggaggcaggt gaccacggta gggtcagcga ctggggtgaa gtcgtaacaa 1440
ggtagccgta ggggaacctg cggctggatc acctcctttt 1479

<210> SEQ ID NO 142
<211> LENGTH: 1549
<212> TYPE: DNA
<213> ORGANISM: Unknown
<220> FEATURE:
<223> OTHER INFORMATION: Description of Unknown:
DP77 16S rRNA sequence

<400> SEQUENCE: 142

```
tcggagagtt tgatcctggc tcaggatgaa cgctggcggc gtgcctaata catgcaagtc     60
gagcgaactg attagaagct tgcttctatg acgttagcgg cggacgggtg agtaacacgt    120
gggcaacctg cctgtaagac tgggataact tcgggaaacc gaagctaata ccggatagga    180
tcttctcctt catgggagat gattgaaaga tggtttcggc tatcacttac agatgggccc    240
gcggtgcatt agctagttgg tgaggtaacg gctcaccaag gcaacgatgc atagccgacc    300
tgagagggtg atcggccaca ctgggactga gacacggccc agactcctac gggaggcagc    360
agtagggaat cttccgcaat ggacgaaagt ctgacggagc aacgccgcgt gagtgatgaa    420
ggctttcggg tcgtaaaact ctgttgttag ggaagaacaa gtacaagagt aactgcttgt    480
accttgacgg tacctaacca gaaagccacg gctaactacg tgccagcagc cgcggtaata    540
cgtaggtggc aagcgttatc cggaattatt gggcgtaaag cgcgcgcagg cggtttctta    600
agtctgatgt gaaagcccac ggctcaaccg tggagggtca ttggaaactg gggaacttga    660
gtgcagaaga gaaaagcgga attccacgtg tagcggtgaa atgcgtagag atgtggagga    720
acaccagtgg cgaaggcggc tttttggtct gtaactgacg ctgaggcgcg aaagcgtggg    780
gagcaaacag gattagatac cctggtagtc cacgccgtaa acgatgagtg ctaagtgtta    840
gagggtttcc gccctttagt gctgcagcta acgcattaag cactccgcct ggggagtacg    900
gtcgcaagac tgaaactcaa aggaattgac gggggcccgc acaagcggtg gagcatgtgg    960
tttaattcga agcaacgcga agaaccttac caggtcttga catcctctga caactctaga   1020
gatagagcgt tccccttcgg gggacagagt gacaggtggt gcatggttgt cgtcagctcg   1080
tgtcgtgaga tgttgggtta agtcccgcaa cgagcgcaac ccttgatctt agttgccagc   1140
attcagttgg gcactctaag gtgactgccg gtgacaaacc ggaggaaggt ggggatgacg   1200
tcaaatcatc atgcccctta tgacctgggc tacacacgtg ctacaatgga tggtacaaag   1260
ggctgcaaga ccgcgaggtc aagccaatcc cataaaacca ttctcagttc ggattgtagg   1320
ctgcaactcg cctacatgaa gctggaatcg ctagtaatcg cggatcagca tgccgcggtg   1380
aatacgttcc cgggccttgt acacaccgcc cgtcacacca cgagagtttg taacacccga   1440
agtcggtgga gtaaccgtaa ggagctagcc gcctaaggtg ggacagatga ttggggtgaa   1500
gtcgtaacaa ggtagccgta tcggaaggtg cggctggatc acctccttt               1549
```

```
<210> SEQ ID NO 143
<211> LENGTH: 1536
<212> TYPE: DNA
<213> ORGANISM: Unknown
<220> FEATURE:
<223> OTHER INFORMATION: Description of Unknown:
      DP78 16S rRNA sequence

<400> SEQUENCE: 143
```

```
ttgaagagtt tgatcatggc tcagattgaa cgctggcggc aggcctaaca catgcaagtc     60
ggacggtagc acagagagct tgctcttggg tgacgagtgg cggacgggtg agtaatgtct    120
ggggatctgc ccgatagagg gggataacca ctggaaacgg tggctaatac cgcataacgt    180
cgcaagacca aagaggggga ccttcgggcc tctcactatc ggatgaaccc agatgggatt    240
agctagtagg cggggtaatg gcccacctag gcgacgatcc ctagctggtc tgagaggatg    300
accagccaca ctggaactga gacacggtcc agactcctac gggaggcagc agtggggaat    360
attgcacaat gggcgcaagc ctgatgcagc catgccgcgt gtatgaagaa ggccttcggg    420
ttgtaaagta ctttcagcgg ggaggaaggc gacggggtta ataaccctgt cgattgacgt    480
```

tacccgcaga agaagcaccg gctaactccg tgccagcagc cgcggtaata cggagggtgc 540
aagcgttaat cggaattact gggcgtaaag cgcacgcagg cggtctgtta agtcagatgt 600
gaaatccccg ggcttaacct gggaactgca tttgaaactg gcaggcttga gtcttgtaga 660
ggggggtaga attccaggtg tagcggtgaa atgcgtagag atctggagga ataccggtgg 720
cgaaggcggc cccctggaca aagactgacg ctcaggtgcg aaagcgtggg gagcaaacag 780
gattagatac cctggtagtc cacgccgtaa acgatgtcga cttggaggtt gttcccttga 840
ggagtggctt ccggagctaa cgcgttaagt cgaccgcctg gggagtacgg ccgcaaggtt 900
aaaactcaaa tgaattgacg ggggcccgca caagcggtgg agcatgtggt ttaattcgat 960
gcaacgcgaa gaaccttacc tactcttgac atccagcgaa cttagcagag atgctttggt 1020
gccttcggga acgctgagac aggtgctgca tggctgtcgt cagctcgtgt tgtgaaatgt 1080
tgggttaagt cccgcaacga gcgcaaccct tatcctttgt tgccagcgat tcggtcggga 1140
actcaaagga gactgccggt gataaaccgg aggaaggtgg ggatgacgtc aagtcatcat 1200
ggcccttacg agtagggcta cacacgtgct acaatggcgc atacaaagag aagcgacctc 1260
gcgagagcaa gcggacctca caaagtgcgt cgtagtccgg atcggagtct gcaactcgac 1320
tccgtgaagt cggaatcgct agtaatcgtg gatcagaatg ccacggtgaa tacgttcccg 1380
ggccttgtac acaccgcccg tcacaccatg ggagtgggtt gcaaaagaag taggtagctt 1440
aaccttcggg agggcgctta ccactttgtg attcatgact ggggtgaagt cgtaacaagg 1500
taaccgtagg ggaacctgcg gttggatcac ctcctt 1536

<210> SEQ ID NO 144
<211> LENGTH: 1532
<212> TYPE: DNA
<213> ORGANISM: Unknown
<220> FEATURE:
<223> OTHER INFORMATION: Description of Unknown:
DP79 16S rRNA sequence

<400> SEQUENCE: 144
tgaagagttt gatcatggct cagattgaac gctggcggca ggcctaacac atgcaagtcg 60
agcggtagag agaagcttgc ttctcttgag agcggcggac gggtgagtaa tacctaggaa 120
tctgcctgat agtgggggat aacgttcgga aacggacgct aataccgcat acgtcctacg 180
ggagaaagca ggggaccttc gggccttgcg ctatcagatg agcctaggtc ggattagcta 240
gttggtgagg taatggctca ccaaggctac gatccgtaac tggtctgaga ggatgatcag 300
tcacactgga actgagacac ggtccagact cctacgggag gcagcagtgg ggaatattgg 360
acaatgggcg aaagcctgat ccagccatgc cgcgtgtgtg aagaaggtct tcggattgta 420
aagcacttta agttgggagg aagggcagtt acctaatacg tgactgtctt gacgttaccg 480
acagaataag caccggctaa ctctgtgcca gcagccgcgg taatacagag ggtgcaagcg 540
ttaatcggaa ttactgggcg taaagcgcgc gtaggtggtt tgttaagttg aatgtgaaat 600
ccccgggctc aacctgggaa ctgcatccaa aactggcaag ctagagtatg gtagagggta 660
gtggaatttc ctgtgtagcg gtgaaatgcg tagatatagg aaggaacacc agtggcgaag 720
gcgactacct ggactgatac tgacactgag gtgcgaaagc gtggggagca aacaggatta 780
gataccctgg tagtccacgc cgtaaacgat gtcaactagc cgttgggagt cttgaactct 840
tagtggcgca gctaacgcat taagttgacc gcctggggag tacggccgca aggttaaaac 900
tcaaatgaat tgacgggggc ccgcacaagc ggtggagcat gtggtttaat tcgaagcaac 960

-continued gcgaagaacc ttaccaggcc ttgacatcca atgaactttc tagagataga ttggtgcctt 1020
cgggaacatt gagacaggtg ctgcatggct gtcgtcagct cgtgtcgtga gatgttgggt 1080
taagtcccgt aacgagcgca acccttgtcc ttagttacca gcacgtaatg gtgggcactc 1140
taaggagact gccggtgaca aaccggagga aggtggggat gacgtcaagt catcatggcc 1200
cttacggcct gggctacaca cgtgctacaa tggtcggtac aaagggttgc caagccgcga 1260
ggtggagcta atcccataaa accgatcgta gtccggatcg cagtctgcaa ctcgactgcg 1320
tgaagtcgga atcgctagta atcgtgaatc agaatgtcac ggtgaatacg ttcccgggcc 1380
ttgtacacac cgcccgtcac accatgggag tgggttgcac cagaagtagc tagtctaacc 1440
ttcgggagga cggttaccac ggtgtgattc atgactgggg tgaagtcgta acaaggtagc 1500
cgtaggggaa cctgcggctg gatcacctcc tt 1532

<210> SEQ ID NO 145
<211> LENGTH: 1136
<212> TYPE: DNA
<213> ORGANISM: Unknown
<220> FEATURE:
<223> OTHER INFORMATION: Description of Unknown:
DP80 16S rRNA sequence

<400> SEQUENCE: 145
cttgagagtt tgatcctggc tcagagcgaa cgctggcggc aggcttaaca catgcaagtc 60
gagcgggcac cttcgggtgt cagcggcaga cgggtgagta acacgtggga acgtaccctt 120
cggttcggaa taacgctggg aaactagcgc taataccgga tacgcccttt tggggaaagg 180
tttactgccg aaggatcggc ccgcgtctga ttagctagtt ggtggggtaa cggcctacca 240
aggcgacgat cagtagctgg tctgagagga tgatcagcca cactgggact gagacacggc 300
ccagactcct acgggaggca gcagtgggga atattggaca atgggcgcaa gcctgatcca 360
gccatgccgc gtgagtgatg aaggccttag ggttgtaaag ctcttttgtc cgggacgata 420
atgacggtac cggaagaata agccccggct aacttcgtgc cagcagccgc ggtaatacga 480
agggggctag cgttgctcgg aatcactggg cgtaaagggc gcgtaggcgg ccattcaagt 540
cgggggtgaa agcctgtggc tcaaccacag aattgccttc gatactgttt ggcttgagtt 600
tggtagaggt tggtggaact gcgagtgtag aggtgaaatt cgtagatatt cgcaagaaca 660
ccagtggcga aggcggccaa ctggaccaat actgacgctg aggcgcgaaa gcgtggggag 720
caaacaggat tagataccct ggtagtccac gccgtaaacg atgaatgcta gctgttgggg 780
tgcttgcacc tcagtagcgc agctaacgct ttaagcattc cgcctgggga gtacggtcgc 840
aagattaaaa ctcaaaggaa ttgacggggg cccgcacaag cggtggagca tgtggtttaa 900
ttcgaagcaa cgcgcagaac cttaccatcc cttgacatgt cgtgccatcc ggagagatcc 960
ggggttccct tcggggacgc gaacacaggt gctgcatggc tgtcgtcagc tcgtgtcgtg 1020
agatgttggg ttaagtcccg caacgagcgc aacccacgtc cttagttgcc atcatttagt 1080
tgggcactct agggagactg ccggtgataa gccgcgagga aggtgtggat gacgtc 1136

<210> SEQ ID NO 146
<211> LENGTH: 1547
<212> TYPE: DNA
<213> ORGANISM: Unknown
<220> FEATURE:
<223> OTHER INFORMATION: Description of Unknown:
DP81 16S rRNA sequence

<400> SEQUENCE: 146
aacggagagt ttgatcctgg ctcaggacga acgctggcgg cgtgcctaat acatgcaagt 60
cgagcggaca gaagggagct tgctcccgga cgttagcggc ggacgggtga gtaacacgtg 120
ggcaacctgc cccttagact gggataactc cgggaaaccg gagctaatac cggataatcc 180
ctttctccac ctggagagag ggtgaaagat ggcttcggct atcactaggg gatgggcccg 240
cggcgcatta gctagttggt aaggtaacgg cttaccaagg cgacgatgcg tagccgacct 300
gagagggtga tcggccacac tgggactgag acacggccca gactcctacg ggaggcagca 360
gtagggaatc ttccgcaatg gacgaaagtc tgacggagca acgccgcgtg agtgaggaag 420
gctttcgggt cgtaaagctc tgttgtgagg gaagaagcgg taccgttcga atagggcggt 480
accttgacgg tacctcacca gaaagccacg gctaactacg tgccagcagc cgcggtaata 540
cgtaggtggc aagcgttgtc cggaattatt gggcgtaaag cgcgcgcagg cggcttctta 600
agtctgatgt gaaatctcgg ggctcaaccc cgagcggcca ttggaaactg gggagcttga 660
gtgcagaaga ggagagtgga attccacgtg tagcggtgaa atgcgtagag atgtggagga 720
acaccagtgg cgaaggcgac tctctggtct gtaactgacg ctgaggcgcg aaagcgtggg 780
gagcaaacag gattagatac cctggtagtc cacgccgtaa acgatgagtg ctaggtgtta 840
ggggtttcga tgcccgtagt gccgaagtta acacattaag cactccgcct ggggagtacg 900
gccgcaaggc tgaaactcaa aggaattgac ggggacccgc acaagcagtg gagcatgtgg 960
tttaattcga agcaacgcga agaaccttac caggtcttga catcctttga ccacccaaga 1020
gattgggctt ccccttcggg ggcaaagtga caggtggtgc atggttgtcg tcagctcgtg 1080
tcgtgagatg ttgggttaag tcccgcaacg agcgcaaccc ttgatcttag ttgccagcat 1140
tgagttgggc actctaaggt gactgccggt gacaaaccgg aggaaggtgg ggatgacgtc 1200
aaatcatcat gccccttatg acctgggcta cacacgtgct acaatggatg gtacaaaggg 1260
cagcgaaacc gcgaggtgaa gccaatccca taaagccatt ctcagttcgg attgcaggct 1320
gcaactcgcc tgcatgaagc cggaattgct agtaatcgcg gatcagcatg ccgcggtgaa 1380
tacgttcccg ggtcttgtac acaccgcccg tcacaccacg agagtttgta acacccgaag 1440
tcggtgaggc aacctttgg agccagccgc ctaaggtggg acaaatgatt ggggtgaagt 1500
cgtaacaagg tagccgtatc ggaaggtgcg gctggatcac ctccttt 1547

<210> SEQ ID NO 147
<211> LENGTH: 1547
<212> TYPE: DNA
<213> ORGANISM: Unknown
<220> FEATURE:
<223> OTHER INFORMATION: Description of Unknown:
DP82 16S rRNA sequence

<400> SEQUENCE: 147
aacggagagt ttgatcctgg ctcaggacga acgctggcgg cgtgcctaat acatgcaagt 60
cgagcggaca gaagggagct tgctcccgga cgttagcggc ggacgggtga gtaacacgtg 120
ggcaacctgc cccttagact gggataactc cgggaaaccg gagctaatac cggataatcc 180
ctttctccac ctggagagag ggtgaaagat ggcttcggct atcactaagg gatgggcccg 240
cggcgcatta gctagttggt aaggtaacgg cttaccaagg caacgatgcg tagccgacct 300
gagagggtga tcggccacac tgggactgag acacggccca gactcctacg ggaggcagca 360
gtagggaatc ttccgcaatg gacgaaagtc tgacggagca acgccgcgtg agtgaggaag 420

```
gccttcgggt cgtaaagctc tgttgtgagg gaagaagcgg taccgttcga atagggcggt    480

accttgacgg tacctcacca gaaagccacg gctaactacg tgccagcagc cgcggtaata    540

cgtaggtggc aagcgttgtc cggaattatt gggcgtaaag cgcgcgcagg cggcttctta    600

agtctgatgt gaaatctcgg ggctcaaccc cgagcggcca ttggaaactg gggagcttga    660

gtgcagaaga ggagagtgga attccacgtg tagcggtgaa atgcgtagag atgtggagga    720

acaccagtgg cgaaggcgac tctctggtct gtaactgacg ctgaggcgcg aaagcgtggg    780

gagcaaacag gattagatac cctggtagtc cacgccgtaa acgatgagtg ctaggtgtta    840

ggggtttcga tgcccgtagt gccgaagtta acacattaag cactccgcct ggggagtacg    900

gccgcaaggc tgaaactcaa aggaattgac ggggacccgc acaagcagtg gagcatgtgg    960

tttaattcga agcaacgcga agaaccttac caggtcttga catcctttga ccacccaaga   1020

gattgggctt ccccttcggg ggcaaagtga caggtggtgc atggttgtcg tcagctcgtg   1080

tcgtgagatg ttgggttaag tcccgcaacg agcgcaaccc ttgatcttag ttgccagcat   1140

tcagttgggc actctaaggt gactgccggt gacaaaccgg aggaaggtgg ggatgacgtc   1200

aaatcatcat gccccttatg acctgggcta cacacgtgct acaatggatg gtacaaaggg   1260

cagcgaaacc gcgaggtgaa gccaatccca taaagccatt ctcagttcgg attgcaggct   1320

gcaactcgcc tgcatgaagc cggaattgct agtaatcgcg gatcagcatg ccgcggtgaa   1380

tacgttcccg ggtcttgtac acaccgcccg tcacaccacg agagtttgta acacccgaag   1440

tcggtgaggc aacctttgg agccagccgc ctaaggtggg acaaatgatt ggggtgaagt   1500

cgtaacaagg tagccgtatc ggaaggtgcg gctggatcac ctccttt                 1547
```

```
<210> SEQ ID NO 148
<211> LENGTH: 1548
<212> TYPE: DNA
<213> ORGANISM: Unknown
<220> FEATURE:
<223> OTHER INFORMATION: Description of Unknown:
      DP83 16S rRNA sequence

<400> SEQUENCE: 148

acggagagtt tgatcctggc tcaggacgaa cgctggcggc gtgcctaata catgcaagtc     60

gagcggagtt tcaagaagct tgctttttga aacttagcgg cggacgggtg agtaacacgt    120

gggcaacctg ccccttagac tgggataact ccgggaaacc ggagctaata ccggataatc    180

cctttctcca cctggagaga gggtgaaaga tggcttcggc tatcactaag ggatgggccc    240

gcggcgcatt agctagttgg taaggtaacg gcttaccaag gcaacgatgc gtagccgacc    300

tgagagggtg atcggccaca ctgggactga gacacggccc agactcctac gggaggcagc    360

agtagggaat cttccgcaat ggacgaaagt ctgacggagc aacgccgcgt gagtgaggaa    420

ggccttcggg tcgtaaagct ctgttgtgag ggaagaagcg gtaccgttcg aatagggcgg    480

taccttgacg gtacctcacc agaaagccac ggctaactac gtgccagcag ccgcggtaat    540

acgtaggtgg caagcgttgt ccggaattat tgggcgtaaa gcgcgcgcag gcggcttctt    600

aagtctgatg tgaaatctcg gggctcaacc ccgagcggcc attggaaact ggggagcttg    660

agtgcagaag aggagagtgg aattccacgt gtagcggtga aatgcgtaga gatgtggagg    720

aacaccagtg gcgaaggcga ctctctggtc tgtaactgac gctgaggcgc gaaagcgtgg    780

ggagcaaaca ggattagata ccctggtagt ccacgccgta aacgatgagt gctaggtgtt    840

aggggtttcg atgcccgtag tgccgaagtt aacacattaa gcactccgcc tggggagtac    900
```

ggccgcaagg ctgaaactca aaggaattga cggggacccg cacaagcagt ggagcatgtg 960
gtttaattcg aagcaacgcg aagaacctta ccaggtcttg acatcctttg accacccaag 1020
agattgggct tccccttcgg gggcaaagtg acaggtggtg catggttgtc gtcagctcgt 1080
gtcgtgagat gttgggttaa gtcccgcaac gagcgcaacc cttgatctta gttgccagca 1140
ttcagttggg cactctaagg tgactgccgg tgacaaaccg gaggaaggtg gggatgacgt 1200
caaatcatca tgccccttat gacctgggct acacacgtgc tacaatggat ggtacaaagg 1260
gcagcgaagc cgcgaggtga agccaatccc ataaagccat tctcagttcg gattgcaggc 1320
tgcaactcgc ctgcatgaag ccggaattgc tagtaatcgc ggatcagcat gccgcggtga 1380
atacgttccc gggtcttgta cacaccgccc gtcacaccac gagagtttgt aacacccgaa 1440
gtcggtgagg caacctttg gagccagccg cctaaggtgg gacaaatgat tggggtgaag 1500
tcgtaacaag gtagccgtat cggaaggtgc ggctggatca cctccttt 1548

<210> SEQ ID NO 149
<211> LENGTH: 1480
<212> TYPE: DNA
<213> ORGANISM: Unknown
<220> FEATURE:
<223> OTHER INFORMATION: Description of Unknown:
DP84 16S rRNA sequence

<400> SEQUENCE: 149
tacggagagt ttgatcctgg ctcaggatga acgctggcgg cgtgcttaac acatgcaagt 60
cgaacggtga agccaagctt gcttggtgga tcagtggcga acgggtgagt aacacgtgag 120
caacctgccc tggactctgg gataagcgct ggaaacggcg tctaatactg gatatgagct 180
ctcatcgcat ggtgggggtt ggaaagattt tttggtctgg gatgggctcg cggcctatca 240
gcttgttggt gaggtaatgg ctcaccaagg cgtcgacggg tagccggcct gagagggtga 300
ccggccacac tgggactgag acacggccca gactcctacg ggaggcagca gtggggaata 360
ttgcacaatg ggcgaaagcc tgatgcagca acgccgcgtg agggatgacg gccttcgggt 420
tgtaaacctc ttttagcagg gaagaagcga aagtgacggt acctgcagaa aaagcgccgg 480
ctaactacgt gccagcagcc gcggtaatac gtagggcgca agcgttatcc ggaattattg 540
ggcgtaaaga gctcgtaggc ggtttgtcgc gtctgctgtg aaatcccgag gctcaacctc 600
gggcctgcag tgggtacggg cagactagag tgcggtaggg gagattggaa ttcctggtgt 660
agcggtggaa tgcgcagata tcaggaggaa caccgatggc gaaggcagat ctctgggccg 720
taactgacgc tgaggagcga aagggtgggg agcaaacagg cttagatacc ctggtagtcc 780
accccgtaaa cgttgggaac tagttgtggg gaccattcca cggtttccgt gacgcagcta 840
acgcattaag ttccccgcct ggggagtacg gccgcaaggc taaaactcaa aggaattgac 900
ggggacccgc acaagcggcg gagcatgcgg attaattcga tgcaacgcga agaaccttac 960
caaggcttga catacaccag aacgggccag aaatggtcaa ctctttggac actggtgaac 1020
aggtggtgca tggttgtcgt cagctcgtgt cgtgagatgt tgggttaagt cccgcaacga 1080
gcgcaaccct cgttctatgt tgccagcacg taatggtggg aactcatggg atactgccgg 1140
ggtcaactcg gaggaaggtg gggatgacgt caaatcatca tgccccttat gtcttgggct 1200
tcacgcatgc tacaatggcc ggtacaaagg gctgcaatac cgtgaggtgg agcgaatccc 1260
aaaaagccgg tcccagttcg gattgaggtc tgcaactcga cctcatgaag tcggagtcgc 1320
tagtaatcgc agatcagcaa cgctgcggtg aatacgttcc cgggtcttgt acacaccgcc 1380

-continued cgtcaagtca tgaaaggagc cgtcgaaggt gggatcggta attaggacta agtcgtaaca 1440
aggtagccgt accggaaggt gcggctggat cacctccttt 1480

<210> SEQ ID NO 150
<211> LENGTH: 924
<212> TYPE: DNA
<213> ORGANISM: Unknown
<220> FEATURE:
<223> OTHER INFORMATION: Description of Unknown:
DP85 16S rRNA sequence

<400> SEQUENCE: 150
acggtcgggg gcatcagtat tcagtcgtca gaggtgaaat tcttggattg actgaagact 60
aactactgcg aaagcatttg ccaaggacgt tttcattaat caagaacgaa agttagggga 120
tcgaagatga tcagataccg tcgtagtctt aaccataaac tatgccgact agagatcggg 180
tggtgctttt tgcgcactcg gcatcttacg agaaatcaaa gtctttgggt tctgggggga 240
gtatggtcgc aaggctgaaa cttaaaggaa ttgacggagg ggcaccacca ggagtggagc 300
ctgcggctta atttgactca acacggggaa actcaccagg tccagacgta ataaggattg 360
acaagttaga gacttctctt gatcttacgg gtggtggtgc atggccgttt ttagtccttg 420
gagtgatttg tctgcttaat tgcgataacg gacgagacct taacctgcta aatagggctg 480
cgagcatctg ctcgtgggct cttcttagag ggactatggg tatcaaaccc atggaagttt 540
gaggcaacaa caggtctgtg atgcccttag acgttctggg ccgcacgcgc gctacactga 600
cggagccagc aagcataacc ttggtcgaga ggcctgggta atctcgtgaa actccgtcgt 660
gctggggata gagcattgta atttttgctc ttcaacgagg aattcctagt aagcgcaagt 720
catcagcttg cgttgattac gtccctgccc cttgtacaca ccgcccgtcg ctactaccga 780
ttgaatggct tagtgaggct tcaagaccgg cgcggcctgc ggggcaactc gcgcgctgcg 840
ctgggaattt agtcaaactt ggtcatttag aggtcgtaaa agtcgtaaca aggtttccgt 900
aggtgaacct gcggaaggat catt 924

<210> SEQ ID NO 151
<211> LENGTH: 881
<212> TYPE: DNA
<213> ORGANISM: Unknown
<220> FEATURE:
<223> OTHER INFORMATION: Description of Unknown:
DP86 16S rRNA sequence

<400> SEQUENCE: 151
cgatgcgtag ccgacctgag agggtgatcg gccacactgg gactgagaca cggcccagac 60
tcctacggga ggcagcagta gggaatcttc cgcaatggac gaaagtctga cggagcaacg 120
ccgcgtgagt gatgaaggtt ttcggatcgt aaagctctgt tgttagggaa gaacaagtgc 180
cgttcaaata gggcggcacc ttgacggtac ctaaccagaa agccacggct aactacgtgc 240
cagcagccgc ggtaatacgt aggtggcaag cgttgtccgg aattattggg cgtaaagggc 300
tcgcaggcgg tttcttaagt ctgatgtgaa agcccccggc tcaaccgggg agggtcattg 360
gaaactgggg aacttgagtg cagaagagga gagtggaatt ccacgtgtag cggtgaaatg 420
cgtagagatg tggaggaaca ccagtggcga aggcgactct ctggtctgta actgacgctg 480
aggagcgaaa gcgtggggag cgaacaggat tagataccct ggtagtccac gccgtaaacg 540
atgagtgcta agtgttaggg ggtttccgcc ccttagtgct gcagctaacg cattaagcac 600
tccgcctggg gagtacggtc gcaagactga aactcaaagg aattgacggg ggcccgcaca 660
agcggtggag catgtggttt aattcgaagc aacgcgaaga accttaccag gtcttgacat 720
cctctgacaa tcctagagat aggacgtccc cttcgggggc agagtgacag gtggtgcatg 780
gttgtcgtca gctcgtgtcg tgagatgttg ggttaagtcc cgcaacgagc gcaacccttg 840
atcttagttg ccagcattca gttgggtgtt ctttgaaaac t 881

<210> SEQ ID NO 152
<211> LENGTH: 1563
<212> TYPE: DNA
<213> ORGANISM: Unknown
<220> FEATURE:
<223> OTHER INFORMATION: Description of Unknown:
DP87 16S rRNA sequence

<400> SEQUENCE: 152
tttgagagtt tgatcctggc tcaggacgaa cgctggcggc gtgcctaata catgcaagtc 60
gaacgaactc tggtattgat tggtgcttgc atcatgattt acatttgagt gagtggcgaa 120
ctggtgagta acacgtggga aacctgccca gaagcggggg ataacacctg gaaacagatg 180
ctaataccgc ataacaactt ggaccgcatg gtccgagctt gaaagatggc ttcggctatc 240
acttttggat ggtcccgcgg cgtattagct agatggtggg gtaacggctc accatggcaa 300
tgatacgtag ccgacctgag agggtaatcg gccacattgg gactgagaca cggcccaaac 360
tcctacggga ggcagcagta gggaatcttc cacaatggac gaaagtctga tggagcaacg 420
ccgcgtgagt gaagaagggt ttcggctcgt aaaactctgt tgttaaagaa gaacatatct 480
gagagtaact gttcaggtat tgacggtatt taaccagaaa gccacggcta actacgtgcc 540
agcagccgcg gtaatacgta ggtggcaagc gttgtccgga tttattgggc gtaaagcgag 600
cgcaggcggt tttttaagtc tgatgtgaaa gccttcggct caaccgaaga agtgcatcgg 660
aaactgggaa acttgagtgc agaagaggac agtggaactc catgtgtagc ggtgaaatgc 720
gtagatatat ggaagaacac cagtggcgaa ggcggctgtc tggtctgtaa ctgacgctga 780
ggctcgaaag tatgggtagc aaacaggatt agataccctg gtagtccata ccgtaaacga 840
tgaatgctaa gtgttggagg gtttccgccc ttcagtgctg cagctaacgc attaagcatt 900
ccgcctgggg agtacggccg caaggctgaa actcaaagga attgacgggg gcccgcacaa 960
gcggtggagc atgtggttta attcgaagct acgcgaagaa ccttaccagg tcttgacata 1020
ctatgcaaat ctaagagatt agacgttccc ttcggggaca tggatacagg tggtgcatgg 1080
ttgtcgtcag ctcgtgtcgt gagatgttgg gttaagtccc gcaacgagcg caacccttat 1140
tatcagttgc cagcattaag ttgggcactc tggtgagact gccggtgaca aaccggagga 1200
aggtggggat gacgtcaaat catcatgccc cttatgacct gggctacaca cgtgctacaa 1260
tggatggtac aacgagttgc gaactcgcga gagtaagcta atctcttaaa gccattctca 1320
gttcggattg taggctgcaa ctcgcctaca tgaagtcgga atcgctagta atcgcggatc 1380
agcatgccgc ggtgaatacg ttcccgggcc ttgtacacac cgcccgtcac accatgagag 1440
tttgtaacac ccaaagtcgg tggggtaacc ttttaggaac cagccgccta aggtgggaca 1500
gatgattagg gtgaagtcgt aacaaggtag ccgtaggaga acctgcggct ggatcacctc 1560
ctt 1563

<210> SEQ ID NO 153
<211> LENGTH: 1546
<212> TYPE: DNA
<213> ORGANISM: Unknown

<220> FEATURE:
<223> OTHER INFORMATION: Description of Unknown:
DP88 16S rRNA sequence

<400> SEQUENCE: 153

```
tagtgggttt gatcctggct caggacgaac gctggcggcg tgcctaatac atgcaagtcg     60
agcggacaga tgggagcttg ctccctgatg ttagcggcgg acgggtgagt aacacgtggg    120
taacctgcct gtaagactgg gataactccg ggaaaccggg gctaataccg gatggttgtc    180
tgaaccgcat ggttcagaca taaaaggtgg cttcggctac cacttacaga tggacccgcg    240
gcgcattagc tagttggtga ggtaacggct caccaaggcg acgatgcgta gccgacctga    300
gagggtgatc ggccacactg ggactgagac acggcccaga ctcctacggg aggcagcagt    360
agggaatctt ccgcaatgga cgaaagtctg acggagcaac gccgcgtgag tgatgaaggt    420
tttcggatcg taaagctctg ttgttaggga agaacaagtg ccgttcaaat agggcggcac    480
cttgacggta cctaaccaga aagccacggc taactacgtg ccagcagccg cggtaatacg    540
taggtggcaa gcgttgtccg gaattattgg gcgtaaaggg ctcgcaggcg gtttcttaag    600
tctgatgtga aagcccccgg ctcaaccggg gagggtcatt ggaaactggg gaacttgagt    660
gcagaagagg agagtggaat tccacgtgta gcggtgaaat gcgtagagat gtggaggaac    720
accagtggcg aaggcgactc tctggtctgt aactgacgct gaggagcgaa agcgtgggga    780
gcgaacagga ttagataccc tggtagtcca cgccgtaaac gatgagtgct aagtgttagg    840
gggtttccgc cccttagtgc tgcagctaac gcattaagca ctccgcctgg ggagtacggt    900
cgcaagactg aaactcaaag gaattgacgg gggcccgcac aagcggtgga gcatgtggtt    960
taattcgaag caacgcgaag aaccttacca ggtcttgaca tcctctgaca atcctagaga   1020
taggacgtcc ccttcggggg cagagtgaca ggtggtgcat ggttgtcgtc agctcgtgtc   1080
gtgagatgtt gggttaagtc ccgcaacgag cgcaaccctt gatcttagtt gccagcattc   1140
agttgggcac tctaaggtga ctgccggtga caaaccggag gaaggtgggg atgacgtcaa   1200
atcatcatgc cccttatgac ctgggctaca cacgtgctac aatggacaga acaaagggca   1260
gcgaaaccgc gaggttaagc caatcccaca aatctgttct cagttcggat cgcagtctgc   1320
aactcgactg cgtgaagctg gaatcgctag taatcgcgga tcagcatgcc gcggtgaata   1380
cgttcccggg ccttgtacac accgcccgtc acaccacgag agtttgtaac acccgaagtc   1440
ggtgaggtaa cctttatgga gccagccgcc gaaggtggga cagatgattg gggtgaagtc   1500
gtaacaaggt agccgtatcg gaaggtgcgg ctggatcacc tccttt                  1546
```

<210> SEQ ID NO 154
<211> LENGTH: 1285
<212> TYPE: DNA
<213> ORGANISM: Unknown
<220> FEATURE:
<223> OTHER INFORMATION: Description of Unknown:
DP89 16S rRNA sequence

<400> SEQUENCE: 154

```
gtaacggctc accaaggcaa cgatgcgtag ccgacctgag agggtgatcg gccacactgg     60
gactgagaca cggcccagac tcctacggga ggcagcagta gggaatcttc cgcaatggac    120
gaaagtctga cggagcaacg ccgcgtgagt gatgaaggtt ttcggatcgt aaagctctgt    180
tgttagggaa gaacaagtac cgttcgaata gggcggtacc ttgacggtac ctaaccagaa    240
agccacggct aactacgtgc cagcagccgc ggtaatacgt aggtggcaag cgttgtccgg    300
```

-continued aattattggg cgtaaagggc tcgcaggcgg tttcttaagt ctgatgtgaa agcccccggc 360
tcaaccgggg agggtcattg gaaactgggg aacttgagtg cagaagagga gagtggaatt 420
ccacgtgtag cggtgaaatg cgtagagatg tggaggaaca ccagtggcga aggcgactct 480
ctggtctgta actgacgctg aggagcgaaa gcgtggggag cgaacaggat tagataccct 540
ggtagtccac gccgtaaacg atgagtgcta agtgttaggg ggtttccgcc ccttagtgct 600
gcagctaacg cattaagcac tccgcctggg gagtacggtc gcaagactga aactcaaagg 660
aattgacggg ggcccgcaca agcggtggag catgtggttt aattcgaagc aacgcgaaga 720
accttaccag gtcttgacat cctctgacaa tcctagagat aggacgtccc cttcgggggc 780
agagtgacag gtggtgcatg gttgtcgtca gctcgtgtcg tgagatgttg ggttaagtcc 840
cgcaacgagc gcaacccttg atcttagttg ccagcattca gttgggcact ctaaggtgac 900
tgccggtgac aaaccggagg aaggtgggga tgacgtcaaa tcatcatgcc ccttatgacc 960
tgggctacac acgtgctaca atggacagaa caaagggcag cgaaaccgcg aggttaagcc 1020
aatcccacaa atctgttctc agttcggatc gcagtctgca actcgactgc gtgaagctgg 1080
aatcgctagt aatcgcggat cagcatgccg cggtgaatac gttcccgggc cttgtacaca 1140
ccgcccgtca caccacgaga gtttgtaaca cccgaagtcg gtgaggtaac cttttaggag 1200
ccagccgccg aaggtgggac agatgattgg ggtgaagtcg taacaaggta gccgtatcgg 1260
aaggtgcggc tggatcacct ccttt 1285

<210> SEQ ID NO 155
<211> LENGTH: 1563
<212> TYPE: DNA
<213> ORGANISM: Unknown
<220> FEATURE:
<223> OTHER INFORMATION: Description of Unknown:
DP90 16S rRNA sequence

<400> SEQUENCE: 155
tttgagagtt tgatcctggc tcaggacgaa cgctggcggc gtgcctaata catgcaagtc 60
gaacgaactc tggtattgat tggtgcttgc atcatgattt acatttgagt gagtggcgaa 120
ctggtgagta acacgtggga aacctgccca gaagcggggg ataacacctg gaaacagatg 180
ctaataccgc ataacaactt ggaccgcatg gtccgagctt gaaagatggc ttcggctatc 240
acttttggat ggtcccgcgg cgtattagct agatggtggg gtaacggctc accatggcaa 300
tgatacgtag ccgacctgag agggtaatcg gccacattgg gactgagaca cggcccaaac 360
tcctacggga ggcagcagta gggaatcttc cacaatggac gaaagtctga tggagcaacg 420
ccgcgtgagt gaagaagggt ttcggctcgt aaaactctgt tgttaaagaa gaacatatct 480
gagagtaact gttcaggtat tgacggtatt taaccagaaa gccacggcta actacgtgcc 540
agcagccgcg gtaatacgta ggtggcaagc gttgtccgga tttattgggc gtaaagcgag 600
cgcaggcggt tttttaagtc tgatgtgaaa gccttcggct caaccgaaga agtgcatcgg 660
aaactgggaa acttgagtgc agaagaggac agtggaactc catgtgtagc ggtgaaatgc 720
gtagatatat ggaagaacac cagtggcgaa ggcggctgtc tggtctgtaa ctgacgctga 780
ggctcgaaag tatgggtagc aaacaggatt agataccctg gtagtccata ccgtaaacga 840
tgaatgctaa gtgttggagg gtttccgccc ttcagtgctg cagctaacgc attaagcatt 900
ccgcctgggg agtacggccg caaggctgaa actcaaagga attgacgggg gcccgcacaa 960
gcggtggagc atgtggttta attcgaagct acgcgaagaa ccttaccagg tcttgacata 1020
ctatgcaaat ctaagagatt agacgttccc ttcggggaca tggatacagg tggtgcatgg 1080
ttgtcgtcag ctcgtgtcgt gagatgttgg gttaagtccc gcaacgagcg caacccttat 1140
tatcagttgc cagcattaag ttgggcactc tggtgagact gccggtgaca aaccggagga 1200
aggtggggat gacgtcaaat catcatgccc cttatgacct gggctacaca cgtgctacaa 1260
tggatggtac aacgagttgc gaactcgcga gagtaagcta atctcttaaa gccattctca 1320
gttcggattg taggctgcaa ctcgcctaca tgaagtcgga atcgctagta atcgcggatc 1380
agcatgccgc ggtgaatacg ttcccgggcc ttgtacacac cgcccgtcac accatgagag 1440
tttgtaacac ccaaagtcgg tggggtaacc ttttaggaac cagccgccta aggtgggaca 1500
gatgattagg gtgaagtcgt aacaaggtag ccgtaggaga acctgcggct ggatcacctc 1560
ctt 1563

<210> SEQ ID NO 156
<211> LENGTH: 1265
<212> TYPE: DNA
<213> ORGANISM: Unknown
<220> FEATURE:
<223> OTHER INFORMATION: Description of Unknown:
DP92 16S rRNA sequence

<400> SEQUENCE: 156
cgatgcgtag ccgacctgag agggtgatcg gccacactgg gactgagaca cggcccagac 60
tcctacggga ggcagcagta gggaatcttc cgcaatggac gaaagtctga cggagcaacg 120
ccgcgtgagt gatgaaggtt ttcggatcgt aaagctctgt tgttagggaa gaacaagtac 180
cgttcgaata gggcggtacc ttgacggtac ctaaccagaa agccacggct aactacgtgc 240
cagcagccgc ggtaatacgt aggtggcaag cgttgtccgg aattattggg cgtaaagggc 300
tcgcaggcgg tttcttaagt ctgatgtgaa agcccccggc tcaaccgggg agggtcattg 360
gaaactgggg aacttgagtg cagaagagga gagtggaatt ccacgtgtag cggtgaaatg 420
cgtagagatg tggaggaaca ccagtggcga aggcgactct ctggtctgta actgacgctg 480
aggagcgaaa gcgtggggag cgaacaggat tagataccct ggtagtccac gccgtaaacg 540
atgagtgcta agtgttaggg ggtttccgcc ccttagtgct gcagctaacg cattaagcac 600
tccgcctggg gagtacggtc gcaagactga aactcaaagg aattgacggg ggcccgcaca 660
agcggtggag catgtggttt aattcgaagc aacgcgaaga accttaccag gtcttgacat 720
cctctgacaa tcctagagat aggacgtccc cttcgggggc agagtgacag gtggtgcatg 780
gttgtcgtca gctcgtgtcg tgagatgttg ggttaagtcc cgcaacgagc gcaacccttg 840
atcttagttg ccagcattca gttgggcact ctaaggtgac tgccggtgac aaaccggagg 900
aaggtgggga tgacgtcaaa tcatcatgcc ccttatgacc tgggctacac acgtgctaca 960
atggacagaa caaagggcag cgaaaccgcg aggttaagcc aatcccacaa atctgttctc 1020
agttcggatc gcagtctgca actcgactgc gtgaagctgg aatcgctagt aatcgcggat 1080
cagcatgccg cggtgaatac gttcccgggc cttgtacaca ccgcccgtca caccacgaga 1140
gtttgtaaca cccgaagtcg gtgaggtaac cttttaggag ccagccgccg aaggtgggac 1200
agatgattgg ggtgaagtcg taacaaggta gccgtatcgg aaggtgcggc tggatcacct 1260
ccttt 1265

<210> SEQ ID NO 157
<211> LENGTH: 1548
<212> TYPE: DNA

<213> ORGANISM: Unknown
<220> FEATURE:
<223> OTHER INFORMATION: Description of Unknown:
DP93 16S rRNA sequence

<400> SEQUENCE: 157
attgagagtt tgatcctggc tcaggatgaa cgctggcggc gtgcctaata catgcaagtc 60
gaacgcacag cgaaaggtgc ttgcaccttt caagtgagtg gcgaacgggt gagtaacacg 120
tggacaacct gcctcaaggc tggggataac atttggaaac agatgctaat accgaataaa 180
acttagtgtc gcatgacaaa aagttaaaag gcgcttcggc gtcacctaga gatggatccg 240
cggtgcatta gttagttggt ggggtaaagg cctaccaaga caatgatgca tagccgagtt 300
gagagactga tcggccacat tgggactgag acacggccca aactcctacg ggaggctgca 360
gtagggaatc ttccacaatg ggcgaaagcc tgatggagca acgccgcgtg tgtgatgaag 420
gctttcgggt cgtaaagcac tgttgtatgg gaagaacagc tagaatagga aatgatttta 480
gtttgacggt accataccag aaagggacgg ctaaatacgt gccagcagcc gcggtaatac 540
gtatgtcccg agcgttatcc ggatttattg ggcgtaaagc gagcgcagac ggtttattaa 600
gtctgatgtg aaagcccgga gctcaactcc ggaatggcat tggaaactgg ttaacttgag 660
tgcagtagag gtaagtggaa ctccatgtgt agcggtggaa tgcgtagata tatggaagaa 720
caccagtggc gaaggcggct tactggactg caactgacgt tgaggctcga aagtgtgggt 780
agcaaacagg attagatacc ctggtagtcc acaccgtaaa cgatgaacac taggtgttag 840
gaggtttccg cctcttagtg ccgaagctaa cgcattaagt gttccgcctg gggagtacga 900
ccgcaaggtt gaaactcaaa ggaattgacg ggacccgca caagcggtgg agcatgtggt 960
ttaattcgaa gcaacgcgaa gaaccttacc aggtcttgac atcctttgaa gcttttagag 1020
atagaagtgt tctcttcgga gacaaagtga caggtggtgc atggtcgtcg tcagctcgtg 1080
tcgtgagatg ttgggttaag tcccgcaacg agcgcaaccc ttattgttag ttgccagcat 1140
tcagatgggc actctagcga gactgccggt gacaaaccgg aggaaggcgg ggacgacgtc 1200
agatcatcat gccccttatg acctgggcta cacacgtgct acaatggcgt atacaacgag 1260
ttgccaaccc gcgagggtga gctaatctct taaagtacgt ctcagttcgg attgtagtct 1320
gcaactcgac tacatgaagt cggaatcgct agtaatcgcg gatcagcacg ccgcggtgaa 1380
tacgttcccg ggtcttgtac acaccgcccg tcacaccatg ggagtttgta atgcccaaag 1440
ccggtggcct aacctttag gaaggagccg tctaaggcag gacagatgac tggggtgaag 1500
tcgtaacaag gtagccgtag gagaacctgc ggctggatca cctccttt 1548

<210> SEQ ID NO 158
<211> LENGTH: 1421
<212> TYPE: DNA
<213> ORGANISM: Unknown
<220> FEATURE:
<223> OTHER INFORMATION: Description of Unknown:
DP94 16S rRNA sequence

<400> SEQUENCE: 158
atctgcccag aagcagggga taacacttgg aaacaggtgc taataccgta taacaacaaa 60
atccgcatgg attttgtttg aaaggtggct tcggctatca cttctggatg atcccgcggc 120
gtattagtta gttggtgagg taaaggccca ccaagacgat gatacgtagc cgacctgaga 180
gggtaatcgg ccacattggg actgagacac ggcccaaact cctacgggag gcagcagtag 240
ggaatcttcc acaatggacg aaagtctgat ggagcaatgc cgcgtgagtg aagaagggtt 300

-continued tcggctcgta aaactctgtt gttaaagaag aacacctttg agagtaactg ttcaagggtt 360
gacggtattt aaccagaaag ccacggctaa ctacgtgcca gcagccgcgg taatacgtag 420
gtggcaagcg ttgtccggat ttattgggcg taaagcgagc gcaggcggtt ttttaagtct 480
gatgtgaaag ccttcggctt aaccggagaa gtgcatcgga aactgggaga cttgagtgca 540
gaagaggaca gtggaactcc atgtgtagcg gtggaatgcg tagatatatg gaagaacacc 600
agtggcgaag gcggctgtct agtctgtaac tgacgctgag gctcgaaagc atgggtagcg 660
aacaggatta gataccctgg tagtccatgc cgtaaacgat gagtgctaag tgttggaggg 720
tttccgccct tcagtgctgc agctaacgca ttaagcactc cgcctgggga gtacgaccgc 780
aaggttgaaa ctcaaaggaa ttgacggggg cccgcacaag cggtggagca tgtggtttaa 840
ttcgaagcta cgcgaagaac cttaccaggt cttgacatct tctgccaatc ttagagataa 900
gacgttccct tcggggacag aatgacaggt ggtgcatggt tgtcgtcagc tcgtgtcgtg 960
agatgttggg ttaagtcccg caacgagcgc aacccttatt atcagttgcc agcattcagt 1020
tgggcactct ggtgagactg ccggtgacaa accggaggaa ggtggggatg acgtcaaatc 1080
atcatgcccc ttatgacctg ggctacacac gtgctacaat ggacggtaca acgagttgcg 1140
aagtcgtgag gctaagctaa tctcttaaag ccgttctcag ttcggattgt aggctgcaac 1200
tcgcctacat gaagttggaa tcgctagtaa tcgcggatca gcatgccgcg gtgaatacgt 1260
tcccgggcct tgtacacacc gcccgtcaca ccatgagagt ttgtaacacc caaagccggt 1320
gagataacct tcgggagtca gccgtctaag gtgggacaga tgattagggt gaagtcgtaa 1380
caaggtagcc gtaggagaac ctgcggctgg atcacctcct t 1421

<210> SEQ ID NO 159
<211> LENGTH: 1388
<212> TYPE: DNA
<213> ORGANISM: Unknown
<220> FEATURE:
<223> OTHER INFORMATION: Description of Unknown:
DP95 16S rRNA sequence

<400> SEQUENCE: 159
tgctaatacc gcatagatcc aagaaccgca tggttcttgg ctgaaagatg gcgtaagcta 60
tcgcttttgg atggacccgc ggcgtattag ctagttggtg aggtaatggc tcaccaaggc 120
gatgatacgt agccgaactg agaggttgat cggccacatt gggactgaga cacggcccaa 180
actcctacgg gaggcagcag tagggaatct tccacaatgg acgcaagtct gatggagcaa 240
cgccgcgtga gtgaagaagg ctttcgggtc gtaaaactct gttgttggag aagaatggtc 300
ggcagagtaa ctgttgtcgg cgtgacggta tccaaccaga aagccacggc taactacgtg 360
ccagcagccg cggtaatacg taggtggcaa gcgttatccg gatttattgg gcgtaaagcg 420
agcgcaggcg gtttttttaag tctgatgtga aagccctcgg cttaaccgag gaagcgcatc 480
ggaaactggg aaacttgagt gcagaagagg acagtggaac tccatgtgta gcggtgaaat 540
gcgtagatat atggaagaac accagtggcg aaggcggctg tctggtctgt aactgacgct 600
gaggctcgaa agcatgggta gcgaacagga ttagataccc tggtagtcca tgccgtaaac 660
gatgaatgct aggtgttgga gggtttccgc ccttcagtgc cgcagctaac gcattaagca 720
ttccgcctgg ggagtacgac cgcaaggttg aaactcaaag gaattgacgg gggcccgcac 780
aagcggtgga gcatgtggtt taattcgaag caacgcgaag aaccttacca ggtcttgaca 840
tcttttgatc acctgagaga tcaggtttcc ccttcggggg caaaatgaca ggtggtgcat 900
ggttgtcgtc agctcgtgtc gtgagatgtt gggttaagtc ccgcaacgag cgcaaccctt 960
atgactagtt gccagcattt agttgggcac tctagtaaga ctgccggtga caaaccggag 1020
gaaggtgggg atgacgtcaa atcatcatgc cccttatgac ctgggctaca cacgtgctac 1080
aatggatggt acaacgagtt gcgagaccgc gaggtcaagc taatctctta aagccattct 1140
cagttcggac tgtaggctgc aactcgccta cacgaagtcg gaatcgctag taatcgcgga 1200
tcagcacgcc gcggtgaata cgttcccggg ccttgtacac accgcccgtc acaccatgag 1260
agtttgtaac acccgaagcc ggtggcgtaa cccttttagg gagcgagccg tctaaggtgg 1320
gacaaatgat tagggtgaag tcgtaacaag gtagccgtag gagaacctgc ggctggatca 1380
cctccttt 1388

<210> SEQ ID NO 160
<211> LENGTH: 1219
<212> TYPE: DNA
<213> ORGANISM: Unknown
<220> FEATURE:
<223> OTHER INFORMATION: Description of Unknown:
DP96 16S rRNA sequence

<400> SEQUENCE: 160
acacggccca aactcctacg ggaggcagca gtagggaatc ttccacaatg gacgcaagtc 60
tgatggagca acgccgcgtg agtgaagaag gctttcgggt cgtaaaactc tgttgttgga 120
gaagaatggt cggcagagta actgttgtcg gcgtgacggt atccaaccag aaagccacgg 180
ctaactacgt gccagcagcc gcggtaatac gtaggtggca agcgttatcc ggatttattg 240
ggcgtaaagc gagcgcaggc ggtttttaa gtctgatgtg aaagccctcg gcttaaccga 300
ggaagcgcat cggaaactgg gaaacttgag tgcagaagag gacagtggaa ctccatgtgt 360
agcggtgaaa tgcgtagata tatggaagaa caccagtggc gaaggcggct gtctggtctg 420
taactgacgc tgaggctcga aagcatgggt agcgaacagg attagatacc ctggtagtcc 480
atgccgtaaa cgatgaatgc taggtgttgg agggtttccg cccttcagtg ccgcagctaa 540
cgcattaagc attccgcctg gggagtacga ccgcaaggtt gaaactcaaa ggaattgacg 600
ggggcccgca caagcggtgg agcatgtggt ttaattcgaa gcaacgcgaa gaaccttacc 660
aggtcttgac atcttttgat cacctgagag atcaggtttc cccttcgggg gcaaaatgac 720
aggtggtgca tggttgtcgt cagctcgtgt cgtgagatgt tgggttaagt cccgcaacga 780
gcgcaaccct tatgactagt tgccagcatt tagttgggca ctctagtaag actgccggtg 840
acaaaccgga ggaaggtggg gatgacgtca aatcatcatg ccccttatga cctgggctac 900
acacgtgcta caatggatgg tacaacgagt tgcgagaccg cgaggtcaag ctaatctctt 960
aaagccattc tcagttcgga ctgtaggctg caactcgcct acacgaagtc ggaatcgcta 1020
gtaatcgcgg atcagcacgc cgcggtgaat acgttcccgg gccttgtaca caccgcccgt 1080
cacaccatga gagtttgtaa cacccgaagc cggtggcgta acccttttag ggagcgagcc 1140
gtctaaggtg ggacaaatga ttagggtgaa gtcgtaacaa ggtagccgta ggagaacctg 1200
cggctggatc acctcccttt 1219

<210> SEQ ID NO 161
<211> LENGTH: 1546
<212> TYPE: DNA
<213> ORGANISM: Unknown
<220> FEATURE:
<223> OTHER INFORMATION: Description of Unknown:

DP97 16S rRNA sequence

<400> SEQUENCE: 161

```
aatgagagtt tgatcctggc tcaggacgaa cgctggcggc gtgcctaata catgcaagtc     60
gagcgatgat taaagatagc ttgctatttt tatgaagagc ggcgaacggg tgagtaacgc    120
gtgggaaatc tgccgagtag cgggggacaa cgtttggaaa cgaacgctaa taccgcataa    180
caatgagaat cgcatgattc ttatttaaaa gaagcaattg cttcactact tgatgatccc    240
gcgttgtatt agctagttgg tagtgtaaag gactaccaag gcgatgatac atagccgacc    300
tgagagggtg atcggccaca ctgggactga gacacggccc agactcctac gggaggcagc    360
agtagggaat cttcggcaat gggggcaacc ctgaccgagc aacgccgcgt gagtgaagaa    420
ggttttcgga tcgtaaaact ctgttgttag agaagaacgt taagtagagt ggaaaattac    480
ttaagtgacg gtatctaacc agaaagggac ggctaactac gtgccagcag ccgcggtaat    540
acgtaggtcc caagcgttgt ccggatttat tgggcgtaaa gcgagcgcag gtggtttctt    600
aagtctgatg taaaaggcag tggctcaacc attgtgtgca ttggaaactg ggagacttga    660
gtgcaggaga ggagagtgga attccatgtg tagcggtgaa atgcgtagat atatggagga    720
acaccggagg cgaaagcggc tctctggcct gtaactgaca ctgaggctcg aaagcgtggg    780
gagcaaacag gattagatac cctggtagtc cacgccgtaa acgatgagtg ctagctgtag    840
ggagctataa gttctctgta gcgcagctaa cgcattaagc actccgcctg gggagtacga    900
ccgcaaggtt gaaactcaaa ggaattgacg gggcccgca caagcggtgg agcatgtggt    960
ttaattcgaa gcaacgcgaa gaaccttacc aggtcttgac atactcgtga tatccttaga   1020
gataaggagt tccttcggga cacgggatac aggtggtgca tggttgtcgt cagctcgtgt   1080
cgtgagatgt tgggttaagt cccgcaacga gcgcaaccct tattactagt tgccatcatt   1140
aagttgggca ctctagtgag actgccggtg ataaaccgga ggaaggtggg gatgacgtca   1200
aatcatcatg ccccttatga cctgggctac acacgtgcta caatggatgg tacaacgagt   1260
cgccaacccg cgagggtgcg ctaatctctt aaaaccattc tcagttcgga ttgcaggctg   1320
caactcgcct gcatgaagtc ggaatcgcta gtaatcgcgg atcagcacgc cgcggtgaat   1380
acgttcccgg gccttgtaca caccgcccgt cacaccacgg aagttgggag tacccaaagt   1440
aggttgccta accgcaagga gggcgcttcc taaggtaaga ccgatgactg gggtgaagtc   1500
gtaacaaggt agccgtatcg gaaggtgcgg ctggatcacc tccttt                  1546
```

<210> SEQ ID NO 162
<211> LENGTH: 1546
<212> TYPE: DNA
<213> ORGANISM: Unknown
<220> FEATURE:
<223> OTHER INFORMATION: Description of Unknown:
DP98 16S rRNA sequence

<400> SEQUENCE: 162

```
aatgagagtt tgatcctggc tcaggacgaa cgctggcggc gtgcctaata catgcaagtc     60
gagcgatgat taaagatagc ttgctatttt tatgaagagc ggcgaacggg tgagtaacgc    120
gtgggaaatc tgccgagtag cgggggacaa cgtttggaaa cgaacgctaa taccgcataa    180
caatgagaat cgcatgattc ttatttaaaa gaagcaattg cttcactact tgatgatccc    240
gcgttgtatt agctagttgg tagtgtaaag gactaccaag gcgatgatac atagccgacc    300
tgagagggtg atcggccaca ctgggactga gacacggccc agactcctac gggaggcagc    360
```

-continued

```
agtagggaat cttcggcaat gggggcaacc ctgaccgagc aacgccgcgt gagtgaagaa    420
ggttttcgga tcgtaaaact ctgttgttag agaagaacgt taagtagagt ggaaaattac    480
ttaagtgacg gtatctaacc agaaagggac ggctaactac gtgccagcag ccgcggtaat    540
acgtaggtcc caagcgttgt ccggatttat tgggcgtaaa gcgagcgcag gtggtttctt    600
aagtctgatg taaaaggcag tggctcaacc attgtgtgca ttggaaactg ggagacttga    660
gtgcaggaga ggagagtgga attccatgtg tagcggtgaa atgcgtagat atatggagga    720
acaccggagg cgaaagcggc tctctggcct gtaactgaca ctgaggctcg aaagcgtggg    780
gagcaaacag gattagatac cctggtagtc cacgccgtaa acgatgagtg ctagctgtag    840
ggagctataa gttctctgta gcgcagctaa cgcattaagc actccgcctg gggagtacga    900
ccgcaaggtt gaaactcaaa ggaattgacg ggggcccgca caagcggtgg agcatgtggt    960
ttaattcgaa gcaacgcgaa gaaccttacc aggtcttgac atactcgtga tatccttaga   1020
gataaggagt tccttcggga cacgggatac aggtggtgca tggttgtcgt cagctcgtgt   1080
cgtgagatgt tgggttaagt cccgcaacga gcgcaaccct tattactagt tgccatcatt   1140
aagttgggca ctctagtgag actgccggtg ataaaccgga ggaaggtggg gatgacgtca   1200
aatcatcatg ccccttatga cctgggctac acacgtgcta caatggatgg tacaacgagt   1260
cgccaacccg cgagggtgcg ctaatctctt aaaaccattc tcagttcgga ttgcaggctg   1320
caactcgcct gcatgaagtc ggaatcgcta gtaatcgcgg atcagcacgc cgcggtgaat   1380
acgttcccgg gccttgtaca caccgcccgt cacaccacgg aagttgggag tacccaaagt   1440
aggttgccta accgcaagga gggcgcttcc taaggtaaga ccgatgactg gggtgaagtc   1500
gtaacaaggt agccgtatcg gaaggtgcgg ctggatcacc tccttt                  1546
```

```
<210> SEQ ID NO 163
<211> LENGTH: 1263
<212> TYPE: DNA
<213> ORGANISM: Unknown
<220> FEATURE:
<223> OTHER INFORMATION: Description of Unknown:
      DP100 16S rRNA sequence

<400> SEQUENCE: 163
```

```
tttgagagtt tgatcctggc tcaggacgaa cgctggcggc gtgcctaata catgcaagtc     60
gaacgaactc tggtattgat tggtgcttgc atcatgattt acatttgagt gagtggcgaa    120
ctggtgagta acacgtggga aacctgccca gaagcggggg ataacacctg gaaacagatg    180
ctaataccgc ataacaactt ggaccgcatg gtccgagctt gaaagatggc ttcggctatc    240
acttttggat ggtcccgcgg cgtattagct agatggtggg gtaacggctc accatggcaa    300
tgatacgtag ccgacctgag agggtaatcg gccacattgg gactgagaca cggcccaaac    360
tcctacggga ggcagcagta gggaatcttc cacaatggac gaaagtctga tggagcaacg    420
ccgcgtgagt gaagaagggt ttcggctcgt aaaactctgt tgttaaagaa gaacatatct    480
gagagtaact gttcaggtat tgacggtatt taaccagaaa gccacggcta actacgtgcc    540
agcagccgcg gtaatacgta ggtggcaagc gttgtccgga tttattgggc gtaaagcgag    600
cgcaggcggt tttttaagtc tgatgtgaaa gccttcggct caaccgaaga agtgcatcgg    660
aaactgggaa acttgagtgc agaagaggac agtggaactc catgtgtagc ggtgaaatgc    720
gtagatatat ggaagaacac cagtggcgaa ggcggctgtc tggtctgtaa ctgacgctga    780
ggctcgaaag tatgggtagc aaacaggatt agataccctg gtagtccata ccgtaaacga    840
```

tgaatgctaa gtgttggagg gtttccgccc ttcagtgctg cagctaacgc attaagcatt 900
ccgcctgggg agtacggccg caaggctgaa actcaaagga attgacgggg gcccgcacaa 960
gcggtggagc atgtggttta attcgaagct acgcgaagaa ccttaccagg tcttgacata 1020
ctatgcaaat ctaagagatt agacgttccc ttcggggaca tggatacagg tggtgcatgg 1080
ttgtcgtcag ctcgtgtcgt gagatgttgg gttaagtccc gcaacgagcg caacccttat 1140
tatcagttgc cagcattaag ttgggcactc tggtgagact gccggtgaca aaccggagga 1200
aggtggggat gacgtcaaat catcatgccc cttatgacct gggctacaca cgtgctacaa 1260
tgg 1263

<210> SEQ ID NO 164
<211> LENGTH: 1457
<212> TYPE: DNA
<213> ORGANISM: Unknown
<220> FEATURE:
<223> OTHER INFORMATION: Description of Unknown:
DP101 16S rRNA sequence

<400> SEQUENCE: 164
atgagagttt gatcttggct caggatgaac gctggcggcg tgcctaatac atgcaagtcg 60
aacgaacttc cgttaattga ttatgacgta cttgtactga ttgagatttt aacacgaagt 120
gagtggcgaa cgggtgagta acacgtgggt aacctgccca gaagtagggg ataacacctg 180
gaaacagatg ctaataccgt ataacagaga aaaccgcatg gttttctttt aaaagatggc 240
tctgctatca cttctggatg gacccgcggc gtattagcta gttggtgagg caaaggctca 300
ccaaggcagt gatacgtagc cgacctgaga gggtaatcgg ccacattggg actgagacac 360
ggcccagact cctacgggag gcagcagtag ggaatcttcc acaatggacg caagtctgat 420
ggagcaacgc cgcgtgagtg aagaagggtt tcggctcgta aagctctgtt gttaaagaag 480
aacgtgggta agagtaactg tttacccagt gacggtattt aaccagaaag ccacggctaa 540
ctacgtgcca gcagccgcgg taatacgtag gtggcaagcg ttatccggat ttattgggcg 600
taaagcgagc gcaggcggtc ttttaagtct aatgtgaaag ccttcggctc aaccgaagaa 660
gtgcattgga aactgggaga cttgagtgca gaagaggaca gtggaactcc atgtgtagcg 720
gtgaaatgcg tagatatatg gaagaacacc agtggcgaag gcggctgtct ggtctgcaac 780
tgacgctgag gctcgaaagc atgggtagcg aacaggatta gataccctgg tagtccatgc 840
cgtaaacgat gattactaag tgttggaggg tttccgccct tcagtgctgc agctaacgca 900
ttaagtaatc cgcctgggga gtacgaccgc aaggttgaaa ctcaaaagaa ttgacggggg 960
cccgcacaag cggtggagca tgtggtttaa ttcgaagcta cgcgaagaac cttaccaggt 1020
cttgacatct tctgacagtc taagagatta gaggttccct tcggggacag aatgacaggt 1080
ggtgcatggt tgtcgtcagc tcgtgtcgtg agatgttggg ttaagtcccg caacgagcgc 1140
aacccttatt actagttgcc agcattaagt tgggcactct agtgagactg ccggtgacaa 1200
accggaggaa ggtggggacg acgtcaaatc atcatgcccc ttatgacctg ggctacacac 1260
gtgctacaat ggatggtaca acgagtcgcg agaccgcgag gttaagctaa tctcttaaaa 1320
ccattctcag ttcggactgt aggctgcaac tcgcctacac gaagtcggaa tcgctagtaa 1380
tcgcggatca gcatgccgcg gtgaatacgt tcccgggcct tgtacacacc gcccgtcaca 1440
ccatgagagt ttgtaac 1457

<210> SEQ ID NO 165

-continued

```
<211> LENGTH: 1415
<212> TYPE: DNA
<213> ORGANISM: Unknown
<220> FEATURE:
<223> OTHER INFORMATION: Description of Unknown:
      DP101 ITS sequence

<400> SEQUENCE: 165

tccgtaggtg aacctgcgga aggatcatta ctgtgattta gtactacact gcgtgagcgg     60

aacgaaaaca acaacaccta aaatgtggaa tatagcatat agtcgacaag agaaatctac    120

gaaaaacaaa caaaactttc aacaacggat ctcttggttc tcgcatcgat gaagagcgca    180

gcgaaatgcg atacctagtg tgaattgcag ccatcgtgaa tcatcgagtt cttgaacgca    240

cattgcgccc ctcggcattc cgggggggcat gcctgtttga gcgtcgtttc catcttgcgc    300

gtgcgcagag ttgggggagc ggagcggacg acgtgtaaag agcgtcggag ctgcgactcg    360

cctgaaaggg agcgaagctg gccgagcgaa ctagactttt tttcagggac gcttggcggc    420

cgagagcgag tgttgcgaga caacaaaaag ctcgacctca aatcaggtag gaatacccgc    480

tgaacttaag catatcaata agcggaggaa aagaaaccaa cagggattgc ctcagtagcg    540

gcgagtgaag cggcaagagc tcagatttga aatcgtgctt tgcggcacga gttgtagatt    600

gcaggttgga gtctgtgtgg aaggcggtgt ccaagtccct tggaacaggg cgcccaggag    660

ggtgagagcc ccgtgggatg ccggcggaag cagtgaggcc cttctgacga gtcgagttgt    720

ttgggaatgc agctccaagc gggtggtaaa ttccatctaa ggctaaatac tggcgagaga    780

ccgatagcga acaagtactg tgaaggaaag atgaaaagca ctttgaaaag agagtgaaac    840

agcacgtgaa attgttgaaa gggaagggta ttgcgcccga catggggatt gcgcaccgct    900

gcctctcgtg ggcggcgctc tgggctttcc ctgggccagc atcggttctt gctgcaggag    960

aaggggttct ggaacgtggc tcttcggagt gttatagcca gggccagatg ctgcgtgcgg   1020

ggaccgagga ctgcggccgt gtaggtcacg gatgctggca gaacggcgca acaccgcccg   1080

tcttgaaaca tggaccaagg agtctaacgt ctatgcgagt gtttgggtgt gaaacccgta   1140

cgcgtaatga aagtgaacgt aggtcggacc ccctgccctc ggggagggga gcacgatcga   1200

ccgatcccga tgtttatcgg aaggatttga gtaggagcat agctgttggg acccgaaaga   1260

tggtgaacta tgcctgaata gggtgaagcc agaggaaact ctggtggagg ctcgtagcgg   1320

ttctgacgtg caaatcgatc gtcgaatttg ggtatagggg cgaaagacta atcgaaccat   1380

ctagtagctg gttcctgccg aagtttccct cagga                                1415
```

METHODS AND COMPOSITIONS FOR TREATING MUSCULOSKELETAL DISEASES

CROSS REFERENCE TO RELATED APPLICATIONS

This application is a continuation of International Application PCT/US2019/049823, filed Sep. 5, 2019, which claims the benefit of U.S. Provisional Application No. 62/727,503 filed Sep. 5, 2018; U.S. Provisional Application No. 62/728,018, filed Sep. 6, 2018; 62/728,019, filed Sep. 6, 2018; U.S. Provisional Application No. 62/728,020, filed Sep. 6, 2018, and U.S. Provisional Application No. 62/863,722, filed Jun. 19, 2019 each of which is hereby incorporated by reference in its entirety for all purposes.

SEQUENCE LISTING

The instant application contains a Sequence Listing which has been submitted via EFS-Web and is hereby incorporated herein by reference in its entirety. Said ASCII copy, created on Nov. 22, 2019, is named SBI001WOUSC1_SequenceListing.txt, and is 382,298 bytes in size.

BACKGROUND

The disclosure relates to methods and compositions for treating or preventing musculoskeletal diseases, including osteoporosis, osteopenia, osteoarthritis, suboptimal fracture healing, and osteomyelitis.

Daily consumption of fresh fruits, vegetables, seeds and other plant-derived ingredients of salads and juices is recognized as part of a healthy diet and associated with weight loss, weight management and overall healthy life styles. This is demonstrated clinically and epidemiologically in the "China Study" (Campbell, T. C. and Campbell T. M. 2006. The China Study: startling implications for diet, weight loss and long-term health. Benbella books pp 419) where a lower incidence of inflammatory-related indications were observed in rural areas where diets are whole food plant-based. The benefit from these is thought to be derived from the vitamins, fiber, antioxidants and other molecules that are thought to benefit the microbial flora through the production of prebiotics. These can be in the form of fermentation products from the breakdown of complex carbohydrates and other plant-based polymers. There has been no clear mechanistic association between microbes in whole food plant-based diets and the benefits conferred by such a diet. The role of these microbes as probiotics, capable of contributing to gut colonization and thereby influencing a subject's microbiota composition in response to a plant-based diet, has been underappreciated.

Musculoskeletal disorders, including osteoporosis, osteopenia, Paget's disease, stunting, osteoarthritis, osteomyelitis, delayed or non-union fractures, are potentially disabling conditions whose current treatments are often accompanied by potentially serious negative side effects. Often therapies treat symptoms, while leaving underlying causes, such as chronic inflammation, unaddressed. Therefore, treatments with reduced side-effects and increased efficacy towards alleviating underlying causes represent a long-felt unmet need.

SUMMARY OF THE INVENTION

Provided for herein is a method of reducing bone loss, comprising administering to a subject in need thereof a pharmaceutical composition comprising an effective amount of at least two heterologous microbes selected from at least two groups selected from proteobacteria, lactic acid bacteria, and yeast, formulated for oral administration.

In some aspects, at least two of the heterologous microbes have at least 97% similarity to Seq ID Nos: 1-66 at the at 16S rRNA or fungal ITS sequence. In some aspects, at least two of the heterologous microbes have at least 98% similarity to Seq ID Nos: 1-66 at the at 16S rRNA or fungal ITS sequence. In some aspects, at least two of the heterologous microbes have at least 98.5% similarity to Seq ID Nos: 1-66 at the at 16S rRNA or fungal ITS sequence. In some aspects, at least two of the heterologous microbes have at least 99% similarity to Seq ID Nos: 1-66 at the at 16S rRNA or fungal ITS sequence. In some aspects, at least two of the heterologous microbes have 100% similarity to Seq ID Nos: 1-66 at the at 16S rRNA or fungal ITS sequence.

In some aspects, the pharmaceutical composition comprises an effective amount of at least three each heterologous microbes, selected from at least two groups selected from proteobacteria, lactic acid bacteria, and yeast, formulated for oral administration.

In some aspects, the pharmaceutical composition further comprises at least one additional microbe from table 4 or table 7. In some aspects, the pharmaceutical composition further comprises a cryoprotectant. In some aspects, the cryoprotectant extends room temperature survival of at least one microbe.

In some aspects, the pharmaceutical composition further comprises a prebiotic.

Also provided for herein is a method of reducing bone loss, comprising administering to a subject in need thereof a medical food composition comprising an effective amount of at least two heterologous microbes selected from at least two groups selected from proteobacteria, lactic acid bacteria, and yeast, formulated for oral administration. In some aspects, at least two of the heterologous microbes have at least 97% similarity to Seq ID Nos: 1-66 at the at 16S rRNA or fungal ITS sequence. In some aspects, the medical food composition comprises an effective amount of at least three of each heterologous microbes selected from at least two groups selected from proteobacteria, lactic acid bacteria, and yeast, formulated for oral administration. In some aspects, the medical food composition further comprises at least one additional microbe from table 4 or table 7. In some aspects, the medical food composition further comprises a cryoprotectant. In some aspects, the cryoprotectant extends room temperature survival of at least one microbe. In some aspects, the medical food composition further comprises a prebiotic.

Also provided for herein is a probiotic composition comprising an effective amount of at least two heterologous microbes selected from at least two groups selected from proteobacteria, lactic acid bacteria, and yeast, formulated for oral administration. In some aspects, at least two of the heterologous microbes have at least 97% similarity to Seq ID Nos: 1-66 at the at 16S rRNA or fungal ITS sequence. In some aspects, the probiotic composition comprises an effective amount of at least three of each heterologous microbes selected from at least two groups selected from proteobacteria, lactic acid bacteria, and yeast, formulated for oral administration. In some aspects, the probiotic composition further comprises at least one additional microbe from table 4 or table 7. In some aspects, the probiotic composition further comprises a cryoprotectant. In some aspects, the cryoprotectant extends room temperature survival of at least one microbe. In some aspects, the medical food composition further comprises a prebiotic.

Also provided for herein is a method of treating osteoarthritis, comprising administering to a subject in need thereof a pharmaceutical composition comprising an effective amount of at least two heterologous microbes selected from at least two groups selected from proteobacteria, lactic acid bacteria, and yeast, formulated for oral administration. In some aspects, at least two of the heterologous microbes have at least 97% similarity to Seq ID Nos: 1-66 at the at 16S rRNA or fungal ITS sequence. In some aspects, the pharmaceutical composition comprises an effective amount of at least three each heterologous microbes, selected from at least two groups selected from proteobacteria, lactic acid bacteria, and yeast, formulated for oral administration. In some aspects, the pharmaceutical composition further comprises at least one additional microbe from table 4 or table 7. In some aspects, the pharmaceutical composition further comprises a cryoprotectant.

Also provided for herein is a method of treating osteomyelitis, comprising administering to a subject in need thereof a pharmaceutical composition comprising an effective amount of at least two heterologous microbes selected from at least two groups selected from proteobacteria, lactic acid bacteria, and yeast, formulated for oral administration. In some aspects, at least two of the heterologous microbes have 97% similarity to Seq ID Nos: 1-66 at the at 16S rRNA or fungal ITS sequence. In some aspects, the pharmaceutical composition comprises an effective amount of at least three each heterologous microbes, selected from at least two groups selected from proteobacteria, lactic acid bacteria, and yeast, formulated for oral administration. In some aspects, the pharmaceutical composition further comprises at least one additional microbe from table 4 or table 7. In some aspects, the pharmaceutical composition further comprises a cryoprotectant.

Also provided for herein is a method of improving healing of non-union or delayed union fractures, comprising administering to a subject in need thereof a pharmaceutical composition comprising an effective amount of at least two heterologous microbes selected from at least two groups selected from proteobacteria, lactic acid bacteria, and yeast, formulated for oral administration. In some aspects, at least two of the heterologous microbes have at least 97% similarity to Seq ID Nos: 1-66 at the at 16S rRNA or fungal ITS sequence. In some aspects, the pharmaceutical composition comprises an effective amount of at least three each heterologous microbes, selected from at least two groups selected from proteobacteria, lactic acid bacteria, and yeast, formulated for oral administration. In some aspects, the pharmaceutical composition further comprises at least one additional microbe from table 4 or table 7. In some aspects, the pharmaceutical composition further comprises a cryoprotectant.

Also provided for herein is a pharmaceutical composition comprising an isolated population of bacterial cells comprising three or more strains present in whole food plant-based diets, wherein each strain is capable of modulating production of one or more short chain fatty acids, vitamin K2, and/or flavones such as apigenin, narigenin, hesperidin, nobiletin, tangeretin in the mammalian gut.

Also provided for herein is a synthetic combination comprising a purified bacterial population, wherein said population comprises at least three unique isolates selected from the group consisting of *Pseudomonas, Leuconostoc, Acinetobacter, Aeromonas, Curtobacterium, Escherichia, Lactobacillus, Serratia, Streptococcus*, and *Stenotrophomonas, Leuconostoc, Pediococous, Deboromyces, Pichia, Hanseniaspora*, where the purified bacterial population is capable of modulating production of one or more short chain fatty acids, flavones, and/or vitamin K2 in a mammalian gut.

Also provided for herein is a synthetic combination comprising a purified bacterial population, wherein said population comprises at least 3 isolates from Table 4 or Table 7 where the at least 3 isolates are capable of modulating production of one or more short chain fatty acids selected from the group consisting of acetate, butyrate, and propionate; or the enzymes acetolactate synthase I, N-acetylglutamate synthase, acetate kinase, Acetyl-CoA synthetase, acetyl-CoA hydrolase, Glucan 1,4-alpha-glucosidase, Bile acid symporter Acr3; and/or capable of modulating production of flavones and/or vitamin K2 and wherein the isolates are present in an amount effective to adhere to a mammalian mucosal lining, thereby modulating the bone health markers of a mammal treated with the synthetic combination, as compared to a reference mammal Also provided for herein is a synthetic population that mimics the composition seen in human stool from patients with desirable bone mineral density or other markers of normal bone health.

Also provided for herein is a synthetic microbial consortia comprising a purified bacterial population of lactic acid bacteria and gamma proteobacteria, wherein the synthetic consortia is capable of modulating production of one or more short chain fatty acids selected from the group consisting of acetate, butyrate, and propionate; and/or capable of modulating production of flavones and/or vitamin K2; and wherein the isolates are present in an amount effective to adhere to a mammalian mucosal lining, thereby modulating the bone health markers, such as bone density, of a mammal treated with the synthetic combination, as compared to a reference mammal.

Also provided for herein is a synthetic microbial consortia comprising a purified bacterial population isolated from a first plant-based sample selected from samples 1-21 in Table 3 artificially associated with a purified bacterial population isolated from a second plant-based sample from selected from samples 1-21 in Table 3, wherein the synthetic microbial consortia is capable of modulating the bone density of a mammal treated with the synthetic microbial consortia, as compared to a reference mammal.

Also provided for herein is a synthetic microbial composition that is not completely viable and can act by releasing metabolites that act in the GI tract of a patient reducing symptoms of osteoporosis or osteopenia.

BRIEF DESCRIPTION OF FIGURES

These and other features, aspects, and advantages of the present invention will become better understood with regard to the following description, and accompanying drawings, where:

FIG. 1A shows bacterial diversity observed in a green chard.

FIG. 1B shows bacterial diversity in red cabbage.

FIG. 1C shows bacterial diversity in romaine lettuce.

FIG. 1D shows bacterial diversity in celery sticks.

FIG. 1E shows bacterial diversity observed in butterhead lettuce grown hydroponically.

FIG. 1F shows bacterial diversity in organic baby spinach.

FIG. 1G shows bacterial diversity in green crisp gem lettuce

FIG. 1H shows bacterial diversity in red oak leaf lettuce.

FIG. 1I shows bacterial diversity in green oak leaf lettuce.

FIG. 1J shows bacterial diversity in cherry tomatoes.

FIG. 1K shows bacterial diversity in crisp red gem lettuce.

FIG. 1L shows bacterial diversity in broccoli juice.

FIG. 2A-C show graphs depicting the taxonomic composition of microbial samples taken from Broccoli Heads (FIG. 2A), Blueberries (FIG. 2B), and Pickled Green Olives (FIG. 2C).

FIG. 18 Mean proportion differences and confidence intervals at 95% of metabolic pathways of interest identified during different treatments and timepoints.

DETAILED DESCRIPTION

Figure 1A:
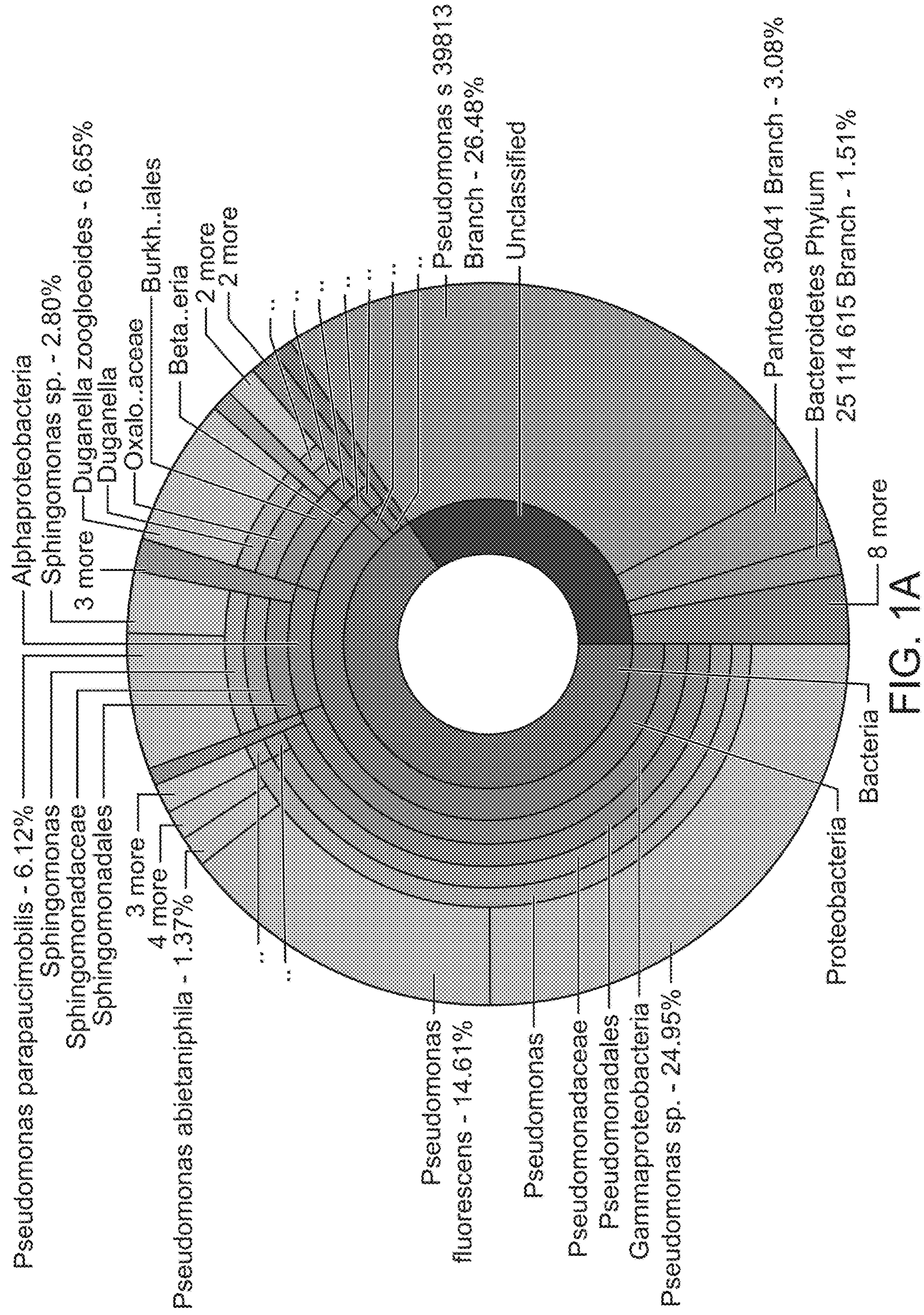
FIGS. 1A-L show plots depicting the diversity of microbial species detected in samples taken from 12 plants usually consumed raw by humans.

Musculoskeletal disorders, including osteoporosis and osteopenia, represent a medical challenge presently without a satisfactory remedy. Approximately 10 million Americans over the age of 50 are currently living with osteoporosis or osteopenia culminating in 1.5 million fractures annually. The high incidence of disease leads to an annual economic burden of $17 billion that couples with significantly reduced quality of life. The current standards of care including anti-resorptive and anabolic therapies are limited due to their side effects and restrictive costs, leading to the current unmet need for a safe, effective, and low cost therapeutic that prevents bone loss.

Osteoarthritis (OA), another musculoskeletal disorder, is one of most prevalent diseases in the world, afflicting 31 million individuals in the US, and projected to impact 45 million by 2030. The United States reports the highest incidence of OA with 13% of US adult population affected, and more than 80% of persons over the age of 75 having some degree of disease. OA is a degenerative disease with multiple origins, characterized by progressive cartilage erosion, joint effusion, synovial hyperplasia, subchondral bone sclerosis, and osteophyte formation. Three main types of osteoarthritis are typically identified: aging-related, obesity-related, and post-traumatic. All of these varieties, however, share a root cause of deleterious inflammation.

Affected patients are left in a perpetual state of pain and discomfort, relying on non-steroidal anti-inflammatory drugs (NSAIDs) and opioid pain killers for relief, until end stage disease requires a total joint replacement to restore functionality to the ailing joint. A need for a therapy that modulates systemic inflammation to reduce or reverse the symptoms of osteoarthritis with naturally occurring products is needed for patients to avoid the side effects of current therapies.

Another musculoskeletal disorder involves fractures that do not properly heal. Fractures are a common orthopedic problem, with over 2 million occurring per year in the U.S. With treatment, most broken bones will heal over a 6 to 8-week period without clinically relevant delay. Delayed union and nonunion, the failure of a fractured bone to heal, occurs in approximately 5-10% of all fractures. Moreover, delayed and nonunion is associated with significant morbidity. (Amin et al. 2014)

Importantly, multiple clinical studies have demonstrated that obesity/type 2 diabetes (T2D) are risk factors for fracture nonunion. This is supported by previous studies demonstrating that mice fed a high-fat diet to induce obesity/T2D have impaired fracture healing. Despite this, little is known about the mechanism(s) that increase the risk of nonunion in obese patients, and there are no accepted therapeutic approaches to address the delay in healing that obese/T2D patients experience. (Zura et al. 2016) Thus, strategies to mitigate the deleterious effect of obesity/T2D on fracture are a critical unmet need.

One additional indication is osteomyelitis, which is inflammation of the bone or bone marrow. Although sometimes caused by infection, treatment of osteomyelitis could by aided by administration of probiotic compositions described herein. Modulation of the host immune system by intentionally dosed microbes could mitigate damage done by an overactive immune system or decrease recovery time by improving targeting of the immune system.

Advantages and Utility

Briefly, and as described in more detail below, described herein are methods and compositions for using microbial agents (probiotics) and agents that promote growth of certain microbes (prebiotics) for management (including prevention and treatment) of musculoskeletal disorders, including osteoporosis, osteopenia, Paget's disease, stunting, osteoarthritis, osteomyelitis, and delayed or non-union fractures.

Several features of the current approach should be noted. It is based on development of synergistic combinations of microbes as on those found in fruits and vegetables consumed as part of a plant-based diet. The combinations are based, in part, on analyses of biochemical pathways catalyzed by genes in these microbes and selection of microbial combinations that promote beneficial metabolic changes in a subject through the biochemical reactions they catalyze such as the production of short chain fatty acids (SCFA).

Advantages of this approach are numerous. They include reduction of the morbidity associated with musculoskeletal disorders, such as osteoporosis or osteopenia, without the use of traditional drugs and the side effects they can sometimes cause. The invention can also reduce chronic inflammation.

The invention is useful for providing health benefits associated with consumption of a plant-based diet, as the diet microbes and fibers are delivered in concentrated form. This can reduce the burden on a subject to ingest potentially unreasonable or inconvenient amounts of particular plants and/or plant-based products, such as fermented foods.

Definitions

Terms used in the claims and specification are defined as set forth below unless otherwise specified.

The term "ameliorating" refers to any therapeutically beneficial result in the treatment of a disease state, e.g., a metabolic disease state, including prophylaxis, lessening in the severity or progression, remission, or cure thereof.

The term "in situ" refers to processes that occur in a living cell growing separate from a living organism, e.g., growing in tissue culture.

The term "in vivo" refers to processes that occur in a living organism.

The term "mammal" as used herein includes both humans and non-humans and include but is not limited to humans, non-human primates, canines, felines, murines, bovines, equines, and porcines.

As used herein, the term "derived from" includes microbes immediately taken from an environmental sample and also microbes isolated from an environmental source and subsequently grown in pure culture. The term "derived from" also includes material isolated from the recited source, and materials obtained using the isolated materials (e.g., cultures of microorganisms made from microorganisms isolated from the recited source).

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (www.ncbi.nlm.nih.gov/).

In some cases, alignment of an entire sequence is not necessary for identification or comparison purposes regarding a microbial entity. In such a case, a so-called diagnostic subsequence can be used. The term "diagnostic subsequence" refers to a portion of a known sequence which would be identified and used by one of skill in the art to identify or compare two or more microbial entities. One, non-limiting example is utilization of subsequences of 16S rRNA sequences found in Asgari et al (2018, bioRxiv).

The term "effective amount" is an amount that is effective to ameliorate a symptom of a disease. An effective amount can also be an amount effective for prophylaxis of a particular disease. More generally, an effective amount is an amount sufficient to produce a desired effect, e.g., an amount effective for alteration of the microbial content of a subject's microbiota.

The term "defined microbial assemblage" or "DMA" refers to a combination of two or more microbial strains (bacterial or fungal) wherein the two or more microbial strains are chosen because they are predicted to achieve a particular synergistic result when applied in concert. DMA compositions preferably further comprise prebiotics or other fiber sources predicted to heighten the desired effect of the microbial strains applied. A DMA is rationally designed to achieve a particular benefit, such as increase SCFA production in the gut lumen.

The term "SBD" refers to a DMA when it is used as a therapeutic intervention in a preclinical or clinical study.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition.

As used herein, the term "preventing" includes completely or substantially reducing the likelihood or occurrence or the severity of initial clinical or aesthetical symptoms of a condition.

As used herein, the term "about" includes variation of up to approximately +/−10% and that allows for functional equivalence in the product.

As used herein, the term "colony-forming unit" or "cfu" is an individual cell that is able to clone itself into an entire colony of identical cells.

As used herein all percentages are weight percent unless otherwise indicated.

As used herein, "viable organisms" are organisms that are capable of growth and multiplication. In some embodiments, viability can be assessed by numbers of colony-forming units that can be cultured. In some embodiments viability can be assessed by other means, such as quantitative polymerase chain reaction.

"Microbiota" refers to the community of microorganisms that occur (sustainably or transiently) in and on a plant or an animal subject, typically a mammal such as a human, including eukaryotes, archaea, bacteria, and viruses (including bacterial viruses i.e., phage).

"Microbiome" refers to the genetic content of the communities of microbes that live inside and on the human body, or inside or outside a plant, both sustainably and transiently, including eukaryotes, archaea, bacteria, and viruses (including bacterial viruses (i.e., phage)), wherein "genetic content" includes genomic DNA, RNA such as ribosomal RNA, the epigenome, plasmids, and all other types of genetic information.

The term "subject" refers to any animal subject including humans, laboratory animals (e.g., primates, rats, mice), livestock (e.g., cows, sheep, goats, pigs, turkeys, and chickens), and household pets (e.g., dogs, cats, and rodents). The subject may be suffering from a dysbiosis, including, but not limited to, an infection due to a gastrointestinal pathogen or may be at risk of developing or transmitting to others an infection due to a gastrointestinal pathogen.

The "colonization" of a host organism includes the non-transitory residence of a bacterium or other microscopic organism. As used herein, "reducing colonization" of a host subject's gastrointestinal tract (or any other microbiotal niche) by a pathogenic bacterium includes a reduction in the residence time of the pathogen in the gastrointestinal tract as well as a reduction in the number (or concentration) of the pathogen in the gastrointestinal tract or adhered to the luminal surface of the gastrointestinal tract. Measuring reductions of adherent pathogens may be demonstrated, e.g., by a biopsy sample, or reductions may be measured indirectly, e.g., by measuring the pathogenic burden in the stool of a mammalian host.

A "combination" of two or more bacteria includes the physical co-existence of the two bacteria, either in the same material or product or in physically connected products, as well as the temporal co-administration or co-localization of the two bacteria.

As used herein "heterologous" designates organisms to be administered that are not naturally present in the same proportions as in the therapeutic composition as in subjects to be treated with the therapeutic composition. These can be organisms that are not normally present in individuals in need of the composition described herein, or organisms that are not present in sufficient proportion in said individuals. These organisms can comprise a synthetic composition of organisms derived from separate plant sources or can comprise a composition of organisms derived from the same plant source, or a combination thereof.

Compositions disclosed herein can be used to treat osteoporosis or osteopenia. Osteoporosis is a systemic skeletal disease characterized by decreasing bone mass and micro-architectural deterioration of bone tissue that leads to an increased risk for bone fragility and fracture. In patients without fragility fracture, osteoporosis is often diagnosed by low bone mineral density (BMD). The international reference standard for the description of osteoporosis in post-menopausal women and in men is a femoral neck or lumbar spine BMD of 2.5 standard deviations (SD) or more below the young female adult mean. Osteopenia is a less severe form of low BMD, defined by the international standard as between 1 and 2.5 SD below the young female average. As defined herein "osteoporosis or osteopenia" indicates a condition where the subject's bone mass per unit volume is reduced. Osteoporosis indicates bone mass reduction to a level below that required for the adequate mechanical support function of the bone. Osteopenia is a milder disease where bone mass per unit is reduced but not to the extent seen in osteoporosis. Patients with osteopenia may subsequently suffer from osteoporosis.

As used herein, "bone density" indicates "bone mineral density" (BMD).

In some embodiments, compositions disclosed herein can be used to treat osteoarthritis. As used herein, the term "osteoarthritis" (abbreviated as "OA"), refers to the disease also known as osteoarthrosis and degenerative joint disease, characterized by inflammation and damage to, or loss of cartilage in any joint or joints, and joint pain. Clinical standards for diagnosing osteoarthritis in subjects including mammalian subjects such as canines and humans are well known and include for example swelling or enlargement of joints, joint tenderness or pain, decreased range of motion in joints, visible joint deformities such as bony growths, and crepitus. Symptoms can be identified by clinical observation and history, or imaging including MRI and X-ray. Criteria for diagnosing the presence or absence of OA and severity or degree of OA include but are not limited to the ACR Criteria for knee OA (R. Altman et al., Development of criteria for the classification and reporting of osteoarthritis: Classification of osteoarthritis of the knee: Diagnostic and Therapeutic Criteria Committee of the American Rheumatism Association. ARTHRITIS RHEUM. August 29(8): 1039-1049 (1986)), functional status criteria according to WOMAC (N. Bellamy et al., 1988, Validation study of WOMAC: a health status instrument for measuring clinically important patient relevant outcomes to antirheumatic drug therapy in patients with osteoarthritis of the hip or knee. J RHEUMATOL 15:1833-1840), and radiological standards for evaluating OA disease severity according to the Kellgren and Lawrence method for knee OA (Kellgren, J. and J. S. Lawrence, Radiological assessment of osteoarthrosis. ANN RHEUM DIS 16:494-502).

In some embodiments, compositions disclosed herein can be used to improve fracture healing. The term "fracture", as used herein, refers to a disruption in the integrity of a living bone involving injury to bone marrow, periosteum, and adjacent soft tissues. Many types of fractures exist such as, for example, pathological, stress, non-union, delayed-union, and greenstick fractures. A fracture includes open and closed fractures.

The term "fracture line" refers to the line across where disruption of the integrity of the living bone has occurred.

The term "non-union" fracture refers to the fractures which are not completely healed nine months after the initial fracture. These are commonly found in clavicle fractures that are not healed usually within three months, and are usually painful and require surgical fixation.

The term "delayed-union" refers to a fracture that has not healed at least about six months post injury.

In some embodiments, compositions disclosed herein can be used to prevent or treat osteomyelitis. As used herein, "osteomyelitis" is defined as inflammation of the bone or bone marrow. In some embodiments, osteomyelitis is caused by an infection.

Throughout this application, various embodiments of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range.

It is appreciated that certain features of the invention, which are, for clarity, described in the context of separate embodiments, can also be provided in combination in a single embodiment. Conversely, various features of the invention, which are, for brevity, described in the context of a single embodiment, can also be provided separately or in any suitable subcombination or as suitable in any other described embodiment of the invention. Certain features described in the context of various embodiments are not to be considered essential features of those embodiments, unless the embodiment is inoperative without those elements.

It must be noted that, as used in the specification and the appended claims, the singular forms "a," "an" and "the" include plural referents unless the context clearly dictates otherwise.

The following abbreviations are used in this specification and/or Figures: ac=acetic acid; but=butyric acid; ppa=propionic acid; etoh=ethanol; lac_L=lactic acid.

Methods of the Invention

The administration of the microbial composition can be accomplished orally or rectally, although administration is not limited to these methods. In some embodiments, the microbial composition is administered orally. In some embodiments, the microbial composition is delivered rectally. In some embodiments, the administration of the microbial composition occurs at regular intervals. In some embodiments, the administration occurs daily.

The microbial composition can be administered via typical pharmacological means, such as slurries, capsules, microcapsules, or solutions, although means of administration are not limited to these methods. In some embodiments, an enteric capsule or enteric microcapsule is used. In some embodiments the pharmaceutical composition involving the microbial composition described herein will be fresh or frozen prior to application. In some embodiments, said pharmaceutical composition will be lyophilized or otherwise treated to increase stability or otherwise obtain a benefit from said treatment.

Compositions of the Invention

In certain embodiments, compositions of the invention comprise probiotic compositions formulated for administration or consumption, with a prebiotic and any necessary or useful excipient. In other embodiments, compositions of the invention comprise probiotic compositions formulated for consumption without a prebiotic. Probiotic compositions of the invention are preferably isolated from foods normally consumed raw and isolated for cultivation. Preferably, microbes are isolated from different foods normally consumed raw, but multiple microbes from the same food source may be used.

It is known to those of skill in the art how to identify microbial strains. Bacterial strains are commonly identified by 16S rRNA gene sequence. Fungal species can be identified by sequence of the internal transcribed space (ITS) regions of rDNA.

One of skill in the art will recognize that the 16S rRNA gene and the ITS region comprise a small portion of the overall genome, and so sequence of the entire genome (whole genome sequence) may also be obtained and compared to known species.

Additionally, multi-locus sequence typing (MLST) is known to those of skill in the art. This method uses the sequences of 7 known bacterial genes, typically 7 housekeeping genes, to identify bacterial species based upon sequence identity of known species as recorded in the publicly available PubMLST database. Housekeeping genes are genes involved in basic cellular functions.

In certain embodiments, bacterial entities of the invention are identified by comparison of the 16S rRNA sequence to those of known bacterial species, as is well understood by those of skill in the art. In certain embodiments, fungal species of the invention are identified based upon comparison of the ITS sequence to those of known species (Schoch et al PNAS 2012). In certain embodiments, microbial strains of the invention are identified by whole genome sequencing and subsequent comparison of the whole genome sequence to a database of known microbial genome sequences. While microbes identified by whole genome sequence comparison, in some embodiments, are described and discussed in terms of their closest defined genetic match, as indicated by 16S rRNA gene sequence, it should be understood that these microbes are not identical to their closest genetic match and are novel microbial entities. This can be shown by examining the Average Nucleotide Identity (ANI) of microbial entities of interest as compared to the reference strain that most closely matches the genome of the microbial entity of interest. ANI is further discussed in example 6.

In other embodiments, microbial entities described herein are functionally equivalent to previously described strains with homology at the 16S rRNA or ITS region. In certain embodiments, functionally equivalent bacterial strains have at least 95% identity at the 16S rRNA region and functionally equivalent fungal strains have at least 95% identity at the ITS region. In certain embodiments, functionally equivalent bacterial strains have at least 96% identity at the 16S rRNA region and functionally equivalent fungal strains have at least 96% identity at the ITS region. In certain embodiments, functionally equivalent bacterial strains have at least 97% identity at the 16S rRNA region and functionally equivalent fungal strains have at least 97% identity at the ITS region. In certain embodiments, functionally equivalent bacterial strains have at least 98% identity at the 16S rRNA region and functionally equivalent fungal strains have at least 98% identity at the ITS region. In certain embodiments, functionally equivalent bacterial strains have at least 99% identity at the 16S rRNA region and functionally equivalent fungal strains have at least 99% identity at the ITS region. In certain embodiments, functionally equivalent bacterial strains have at least 99.5% identity at the 16S rRNA region and functionally equivalent fungal strains have at least 99.5% identity at the ITS region. In certain embodiments, functionally equivalent bacterial strains have 100% identity at the 16S rRNA region and functionally equivalent fungal strains have 100% identity at the ITS region.

16S rRNA sequences for strains tolerant of relevant stressors (described in table 7) are found in SEQ ID NOs 1-63. 16S rRNA is one way to classify bacteria into operational taxonomic units (OTUs). Bacterial strains with 97% sequence identity at the 16S rRNA locus are considered to belong to the same OTU. A similar calculation can be done with fungi using the ITS locus in place of the bacterial 16S rRNA sequence.

In some embodiments, the invention provides a probiotic composition for the treatment of osteoporosis, osteopenia, Paget's disease, or stunting comprising a mixture of Lactic acid bacteria, such as *Pediococcus* spp, *Leuconostoc* spp, *Lactobacillus* spp, *Lactobacillus crispatus, Lactobacillus plantarum, Lactobacillus reuteri*, combined with non-lactic acid bacteria isolated or identified from samples described in Table 3 or described in Table 4. In some embodiments, the invention provides a fermented probiotic composition for the treatment of bone diseases comprising a mixture of *Pediococcus pentosaceus* and/or *Leuconostoc mesenteroides* and at least one non-lactic acid bacterium, preferably a bacterium classified as a gamma proteobacterium or a filamentous fungus or yeast. Some embodiments comprise the probiotic being in a capsule or microcapsule adapted for enteric delivery.

The compositions disclosed herein are derived from edible plants and can comprise a mixture of microorganisms, comprising bacteria, fungi, archaea, and/or other indigenous or exogenous microorganisms, all of which work together to form a microbial ecosystem with a role for each of its members.

In some embodiments, species of interest are isolated from plant-based food sources normally consumed raw. These isolated compositions of microorganisms from individual plant sources can be combined to create a new mixture of organisms. Particular species from individual plant sources can be selected and mixed with other species cultured from other plant sources, which have been similarly isolated and grown. In some embodiments, species of interest are grown in pure cultures before being prepared for consumption or administration. In some embodiments, the organisms grown in pure culture are combined to form a synthetic combination of organisms.

In some embodiments, the microbial composition comprises proteobacteria or gamma proteobacteria. In some embodiments, at least one species from each of 4 groups is present, the four groups being: Lactic Acid bacteria, Bacilli, proteobacteria, and yeast. In some embodiments, at least one microbe from a group other than the four stated above is also present. In some embodiments, the microbial composition comprises several species of *Pseudomonas*. In some embodiments, species from another genus are also present. In some embodiments, a species from the genus *Duganella* is also present. In some embodiments of said microbial composition, the population comprises at least three unique isolates selected from the group consisting of *Pseudomonas, Acinetobacter, Aeromonas, Curtobacterium, Escherichia, Lactobacillus, Serratia, Streptococcus*, and *Stenotrophomonas*. In some embodiments, the bacteria are selected based upon their ability to degrade fibers, including plant fibers, and to modulate production of one or more branch chain fatty acids, short chain fatty acids, and/or flavones in a mammalian gut.

In some embodiments, microbial compositions comprise isolates that are capable of modulating production or activity of the enzymes involved in fatty acid metabolism, such as acetolactate synthase I, N-acetylglutamate synthase, acetate kinase, Acetyl-CoA synthetase, acetyl-CoA hydrolase, Glucan 1,4-alpha-glucosidase, or Bile acid symporter Acr3.

In some embodiments, the administered microbial compositions colonize the treated mammal's digestive tract. In some embodiments, these colonizing microbes comprise bacterial assemblages present in whole food plant-based diets. In some embodiments, these colonizing microbes comprise *Pseudomonas* with a diverse species denomination that is present and abundant in whole food plant-based diets. In some embodiments, these colonizing microbes reduce free fatty acids absorbed into the body of a host by absorbing the free fatty acids in the gastrointestinal tract of mammals. In some embodiments, these colonizing microbes comprise genes encoding metabolic functions related to desirable health outcomes such as increased bone mineral density, prevention of loss of bone mineral density, improved bone turnover markers, or improved low-grade inflammatory metabolic indicators, etc.

Some embodiments comprise bacteria that are not completely viable but act by releasing metabolites that act in the gastro-intestinal tract of a patient promoting bone health or other desirable outcome. Some embodiments comprise a prebiotic composition derived from metabolites present in whole food plant-based materials, identified and enriched as part of the formula for oral delivery.

Prebiotics

Prebiotics, in accordance with the teachings of this invention, comprise compositions that promote the growth of beneficial bacteria in the intestines. Prebiotic substances can be consumed by a relevant probiotic, or otherwise assist in keeping the relevant probiotic alive or stimulate its growth. When consumed in an effective amount, prebiotics also beneficially affect a subject's naturally-occurring gastrointestinal microflora and thereby impart health benefits apart from just nutrition. Prebiotic foods enter the colon and serve as substrate for the endogenous bacteria, thereby indirectly providing the host with energy, metabolic substrates, and essential micronutrients. The body's digestion and absorption of prebiotic foods is dependent upon bacterial metabolic activity, which salvages energy for the host from nutrients that escaped digestion and absorption in the small intestine.

Prebiotics help probiotics flourish in the gastrointestinal tract, and accordingly, their health benefits largely are indirect. Metabolites generated by colonic fermentation by intestinal microflora, such as short-chain fatty acids, can play important functional roles in the health of the host. Prebiotics can be useful agents for enhancing the ability of intestinal microflora to provide benefits to their host.

Prebiotics, in accordance with the embodiments of this invention, include, without limitation, mucopolysaccharides, oligosaccharides, polysaccharides, amino acids, vitamins, nutrient precursors, proteins, and combinations thereof.

According to particular embodiments, compositions comprise a prebiotic comprising a dietary fiber, including, without limitation, polysaccharides and oligosaccharides. These compounds have the ability to increase the number of probiotics, and augment their associated benefits. For example, an increase of beneficial Bifidobacteria likely changes the intestinal pH to support the increase of Bifidobacteria, thereby decreasing pathogenic organisms.

Non-limiting examples of oligosaccharides that are categorized as prebiotics in accordance with particular embodiments include fructooligosaccharides, inulins, isomalto-oligosaccharides, lactilol, lactosucrose, lactulose, pyrodextrins, soy oligosaccharides, transgalacto-oligosaccharides, cellulose, and xylo-oligosaccharides.

According to other particular embodiments, compositions comprise a prebiotic comprising an amino acid.

Prebiotics are found naturally in a variety of foods including, without limitation, cabbage, bananas, berries, asparagus, garlic, wheat, oats, barley (and other whole grains), flaxseed, tomatoes, Jerusalem artichoke, onions and chicory, greens (e.g., dandelion greens, spinach, collard greens, chard, kale, mustard greens, turnip greens), and legumes (e.g., lentils, kidney beans, chickpeas, navy beans, white beans, black beans). Generally, according to particular embodiments, compositions comprise a prebiotic present in a sweetener composition or functional sweetened composition in an amount sufficient to promote health and wellness.

In particular embodiments, prebiotics also can be added to high-potency sweeteners or sweetened compositions. Non-limiting examples of prebiotics that can be used in this manner include fructooligosaccharides, xylooligosaccharides, galactooligosaccharides, and combinations thereof.

Many prebiotics have been discovered from dietary intake including, but not limited to: antimicrobial peptides, polyphenols, Okara (soybean pulp by product from the manufacturing of tofu), polydextrose, lactosucrose, malto-oligosaccharides, gluco-oligosaccharides (GOS), fructo-oligosaccharides (FOS), xantho-oligosaccharides, soluble dietary fiber in general. Types of soluble dietary fiber include, but are not limited to, *psyllium*, pectin, or inulin. Phytoestrogens (plant-derived isoflavone compounds that have estrogenic effects) have been found to have beneficial growth effects of intestinal microbiota through increasing microbial activity and microbial metabolism by increasing the blood testosterone levels, in humans and farm animals. Phytoestrogen compounds include but are not limited to: Oestradiol, Daidzein, Formononetin, Biochainin A, Genistein, and Equol.

Dosage for the compositions described herein are deemed to be "effective doses," indicating that the probiotic or prebiotic composition is administered in a sufficient quantity to alter the physiology of a subject in a desired manner. In some embodiments, the desired alterations include reducing osteoporosis or osteopenia and sequelae associated with these conditions. In some embodiments, the desired alterations occur in a post-menopausal subject. Vitamin K2 and osteoporosis:

Vitamin K is found in many fruits and vegetables including broccoli, grapes, lettuce, and olives and plays a role in a wide range of biological activities including calcium metabolism, cell proliferation, oxidative stress, and inflammation. Vitamin K2 (menaquinone) plays a vital role in bone synthesis and is produced by bacteria residing in the gastrointestinal tract. Vitamin K2 affects the proliferation and differentiation of osteoblasts, leading to increased osteoblast activity and bone matrix production. Specifically, Vitamin K2 stimulates the expression of osteoprotegerin (OPG) and inhibits the expression of receptor activator of nuclear factor kappa-B ligand (RANKL) on osteoblasts, leading to increased proliferation and activation. Vitamin K2 has also been shown to inhibit osteoclastic bone resorption, preventing the breakdown of bone.

In some embodiments, the compositions of the invention improve Vitamin K2 absorption. In some embodiments, the compositions of the invention produce Vitamin K2 in the gut of a subject. In some embodiments, the microbes of the invention are selected based upon their having genes involved in biosynthetic pathways for producing Vitamin K2.

In some embodiments, the composition comprises a cryoprotectant. In general, a cryoprotectant functions through work by dissolving in water, lowering the melting point or a composition containing cells, and preventing or limiting intracellular and extracellular crystals from forming in cells during a freezing process. A cryoprotectant can allow for preservation of strain viability for prolonged periods of time, including extending viability for years. In some embodiments, the cryoprotectant is a prebiotic. In some embodiments, the cryoprotectant includes glycerol, trehalose, or Dimethyl sulfoxide (DMSO). In some embodiments, the cryoprotectant is derived from a plant source. In some embodiments, viability, measured at room temperature, is increased for at least one microbe by addition of cryoprotectant to a composition comprising said microbe wherein the composition is stored frozen. In some embodiments, viability is increased by at least 10, 15, 25, 35, 45, 50, 55, 65, 75, 85, 95, or 100 percent. Typically, A cryoprotectant (e.g., glycerol, trehalose, or DMSO) concentration of about 5% to 15% is used and permits survival of a substantial fraction of isolated cells after freezing and thawing from cryogenic temperatures. One skilled in the art will recognize a cryoprotectant formulation can adjusted dependent on the cellular species to be preserved. For example, certain species (e.g., gamma proteobacteria) are sensitive to cryopreservation and lose considerable viability after few days in cryostorage. In some embodiments, biological materials (such as microbial strains including bacteria and fungi) are refrigerated at temperatures of −20° C. or at −80° C., e.g., with use of laboratory freezers. In some embodiments, biological materials are stored using the vapor phase of liquid nitrogen that brings the temperature to −170° C.

Methods of Use

Included within the scope of this disclosure are methods for treatment of musculoskeletal disorders including osteoporosis, osteopenia, Paget's disease, stunting, osteoarthritis, osteomyelitis, and delayed or non-union fractures.

These methods include treatment with a prebiotic composition (e.g., a composition comprising or consisting of FOS, GOS, or other appropriate polysaccharide), optionally in conjunction with a probiotic composition, one or more digestible saccharides (e.g. lactose, glucose, or galactose), a buffer, or a combination thereof. These methods optionally are used in combination with other treatments to reduce the musculoskeletal disorder. Any suitable treatment can be used. In some embodiments the additional treatment is administered before, during, or after treatment with a prebiotic composition, or any combination thereof. In an embodiment, when the musculoskeletal disorder or disorders are not completely or substantially completely eliminated by treatment with a prebiotic composition, the additional treatment is administered after prebiotic treatment is terminated. The additional treatment is used on an as-needed basis.

In an embodiment, a subject to be treated for one or more symptoms of a musculoskeletal disorder is a human. In an embodiment, the human subject is a preterm newborn, a full term newborn, an infant up to one year of age, a young child (e.g., 1 yr to 12 yrs), a teenager (e.g., 13-19 yrs), an adult (e.g., 20-64 yrs), a pregnant women, or an elderly adult (65 yrs and older).

In an embodiment, the condition to be treated is osteoporosis or osteopenia. In an embodiment, the condition to be treated is osteoporosis or osteopenia, and treating osteoporosis further involves administration of any one or combination of known anti-osteoporosis medications or treatments. These include, but are not limited to, bisphosphonates (alendronate, risedronate, ibandronate, zolendronate), biologics (denosumab, romosozumab), selective estrogen receptor mediators (Raloxifene), or anabolic agents (teriparatide, abaloparatide).

In an embodiment, the condition to be treated is osteoarthritis. In an embodiment, the condition to be treated is osteoarthritis, and treating the condition further involves administration of any one or combination of known anti-osteoarthritis medications or treatments. These include, but are not limited to, surgery, analgesics, non-steroidal anti-inflammatory drugs (aspirin, celecoxib, diclofenac, diflunisal, etodolac, ibuprofen, indomethacin, ketoprofen, ketorolac, nabumetone, naproxen, oxaprozin, piroxicam), menthol, weight loss regimens, physical exercise, acupuncture, narcotics (Codeine, Fentanyl, Hydrocodone, hydroporphone, meperidine, methadone, oxycodone), and physical therapy.

In an embodiment, the condition to be treated is a delayed or non-union fracture. In an embodiment, the condition to be treated is a delayed or non-union fracture, and treating the condition further involves administration of any one or combination of known treatments to improve delayed or non-union fractures. These include, but are not limited to surgical bone grafts or fixations and bone stimulation.

In an embodiment, the condition to be treated is osteomyelitis. The methods disclosed herein, optionally, are used in combination with other treatments to treat or prevent osteomyelitis. Typical treatments for osteomyelitis include, but are not limited to, intravenous or oral antibiotics (clindamycin, cefotetan, ticarcillin/clavulanate, ceftriaxone, metronidazole, piperacillin/tazobactam, fluoroquinolone, cefepime, ciprofloxacin, imipenem/cilastin, vancomycin, trimethoprim/sulfamethoxazole, minocycline, nafcillin, oxacillin, cefazolin, penicillin) and surgery. Any suitable treatment for osteomyelitis can be used. These include, but are not limited to, removal of diseased tissue and antibiotics, administered either orally or intravenously.

Timing and Dose of Probiotics and Prebiotics

In an embodiment, probiotic bacteria, such as a *Pediococcus* species or a *Leuconostoc* species, are given prior to beginning treatment with a prebiotic. In an embodiment, probiotic bacteria, such as a *Pediococcus* species or a *Leuconostoc* species, are given in conjunction with treatment with a prebiotic (e.g., comprising or consisting essentially of FOS, GOS, or other appropriate polysaccharide), for part or all of the treatment with the prebiotic. Thus, in an embodiment, some or all doses of a prebiotic (e.g., comprising or consisting essentially of FOS, GOS, or other appropriate polysaccharide) are accompanied by a dose of bacteria, e.g., live cultured bacteria, e.g., a *Pediococcus* species or a *Leuconostoc* species. In an embodiment, bacteria, e.g., a *Pediococcus* species or a *Leuconostoc* species, are given initially with a prebiotic (e.g., comprising or consisting essentially of FOS, GOS, or other appropriate polysaccharide), but then use of the bacteria is discontinued. For example, the initial one, two, three, four, five, six, seven, eight, nine, ten, or more than ten days of treatment with a prebiotic (e.g., comprising or consisting essentially of FOS, GOS, or other appropriate polysaccharide) further comprises doses of bacteria, with the use of bacteria discontinued after that time. In an embodiment, bacteria, (e.g., bacteria in yogurt), or bacteria by themselves, can be given for the first two days of treatment; then the administration of bacteria is discontinued. In another embodiment, probiotic bacteria, either alone or in combination with other substances or treatments are used after the treatment with a prebiotic (comprising or consisting essentially of FOS, GOS, or other appropriate polysaccharide) is terminated. The bacteria can be taken for any suitable period after the termination of treatment with prebiotic and can be taken daily or at regular or irregular intervals. Doses can be as described below.

Any suitable amount of probiotic per serving can be used that allows an effective microbiota in the GI as demonstrated by an increase in bone mineral density, improved bone architecture, protection from loss of bone mineral density, improved bone turnover markers, or improvement in other markers of osteoporosis or osteopenia. Markers of osteoporosis or osteopenia can include elevated levels of Inflammatory cytokines in the blood including: Tumor necrosis factor alpha (TNF$\alpha$), Interleukin-17 (IL-17), Interleukin-4 (IL-4), Interferon gamma (IFN$\gamma$), Receptor activator of nuclear factor kappa-B ligand (RANKL). They can also include increased one resorption blood markers (breakdown) crosslinked C-telopeptide of type 1 collagen (CTX), or decreased Bone formation blood markers: osteocalcin, alkaline phosphatase, N-terminal propeptide of type 1 collagen.

Any suitable amount of probiotic per serving can be used that allows an effective microbiota in the GI as demonstrated by an increase in healthy bone healing, including decreased incidence of delayed or non-union fractures or increased normal fracture callus formation. Markers of fracture healing defects include delayed healing, non-union fracture healing, or changes in fracture callus architecture (including increased size or adiposity of the fracture callus).

Typically, probiotics are given as live cultured bacteria. The dose can be 0.001 mg to 1 mg, or 0.5 mg to 5 mg, or 1 mg to 1000 mg, or 2 mg to 200 mg, or 2 mg to 100 mg, or 2 mg to 50 mg, or 4 mg to 25 mg, or 5 mg to 20 mg, or 10 mg to 15 mg, or 50 mg to 200 mg, or 200 mg to 1000 mg, or 10, 11, 12, 12.5, 13, 14, or 15 mg per serving. In an embodiment, *L. acidophilus* is used in a dose of 12.5 mg per serving. The probiotic bacteria can also be 0.5% w/w to 20% w/w of the final composition. The dose of probiotics can be given in combination with one or more prebiotics. Another common way of specifying the amount of probiotics is as a colony forming unit (cfu). In an embodiment, one or more strains of probiotic bacteria are ingested in an amount of between 1×10^5 and 1×10^12 cfu's per serving. In an embodiment, one or more strains of probiotic bacteria are ingested in an amount of 1×10^5 to 1×10^9 cfu's, or 1×10^6 cfu's to 1×10^10 cfu's, or 1×10^6 cfu's to 1×10^9 cfu's, or 1×10^5 cfu's to 1×10^6 cfu's, or 1×10^5 cfu's to 1×10^12 cfu's, or 1×10^9 cfu's per serving. In another embodiment, one or more strains of probiotic bacteria are administered as part of a dairy product. In an embodiment, a typical serving size for a dairy product such as fluid milk is 240 g. In other embodiments, a serving size is 245 g, or 240 g to 245 g, or 227 to 300 g. In an embodiment the dairy product is yogurt. Yogurt can have a serving size of 4 oz, or 6 oz, or 8 oz, or 4 oz to 10 oz, or half cup, or 1 cup, or 113 g, or 170 g, or 227 g, or 245 g or 277 g, or 100 g to 350 g.

In an embodiment, probiotic bacteria are given as live cultured bacteria, e.g., in combination with a prebiotic (e.g., comprising or consisting essentially of FOS, GOS, or other appropriate polysaccharide) and, optionally, other substances. The dose can be 1 mg to 1000 mg, or 2 mg to 200 mg, or 2 mg to 100 mg, or 2 mg to 50 mg, or 4 mg to 25 mg, or 5 mg to 20 mg, or 10 mg to 15 mg, or 10, 11, 12, 12.5, 13, 14, or 15 mg of probiotic bacterial cell culture dry weight. In an embodiment, *L. acidophilus* is used in a dose of 12.5 mg. In an embodiment, as the administration of a prebiotic (e.g., comprising or consisting essentially of FOS, GOS, or other appropriate polysaccharide) dose to a subject increases, the dose of bacteria increases as well. For example, an initial dose of a prebiotic (e.g., comprising or consisting essentially of FOS, GOS, or other appropriate polysaccharides) can be 0.6 g to 1.0 g, e.g., 0.8 g, given in combination with 10-15 mg, e.g., 12.5 mg, of *L. acidophilus*. The dose of a prebiotic (e.g., comprising or consisting essentially of FOS, GOS, or other appropriate polysaccharide) can be increased incrementally by 0.6 g to 1.0 g, e.g., 0.8 g, and the accompanying dose of *L. acidophilus* can be increased by 10-15 mg, e.g., 12.5 mg, of *L. acidophilus*.

FOS, GOS, or Other Appropriate Polysaccharide Formulations

A. Formulations Introduction

In one aspect a prebiotic composition for the treatment of one or more musculoskeletal disorder is provided. In an embodiment a prebiotic composition comprises inulin, FOS, lactulose, GOS, raffinose, stachyose, or a combination thereof. In addition, other plant-derived polysaccharides such as xylan, pectin, isomalto-oligosaccharides, gentio-oligosaccharides, 4-O-methyl glucuronoxylan (GX), neutral arabinoxylan (AX), heteroxylan (HX) can be combined with the probiotics to enhance bacterial metabolic function. Some of these can be derived from plant material found in the plant host from which the probiotics were isolated from. Therefore, the probiotics are adapted to assimilate and digest the rich complexity and variety of polysaccharides present in the plant that play a role during digestion by the consumption of an animal.

In an embodiment a prebiotic composition comprises or consists of FOS, GOS, or other appropriate polysaccharide. In another embodiment a prebiotic composition comprises FOS, GOS, other, and one or more digestible saccharides. Digestible saccharides are saccharides that are digestible by humans and include, but are not limited to lactose, glucose, and galactose. In an embodiment a prebiotic composition comprises FOS, GOS, or other appropriate polysaccharide, and less than 20% weight/weight of one or more digestible saccharides (e.g. lactose, glucose, or galactose). In an embodiment a prebiotic composition comprises FOS, GOS, or other appropriate polysaccharide, and less than 10% of one or more digestible saccharides. In an embodiment a prebiotic composition comprises FOS, GOS, or other appropriate polysaccharide, and less than 5% of one or more digestible saccharides. In another embodiment a prebiotic composition contains less than 5% lactose. In another embodiment a prebiotic composition contains less than 4% lactose. In another embodiment a prebiotic composition contains less than 3% lactose. In another embodiment a prebiotic composition contains less than 2% lactose. In another embodiment a prebiotic composition contains less than 1% lactose. In another embodiment a prebiotic composition contains less than 0.5% lactose. In another embodiment a prebiotic composition contains less than 0.4% lactose. In another embodiment a prebiotic composition contains less than 0.3% lactose. In another embodiment a prebiotic composition contains less than 0.2% lactose. In another embodiment a prebiotic composition contains less than 0.1% lactose. In another embodiment a prebiotic composition contains less than 0.05% lactose. In another embodiment a prebiotic composition contains less than 0.01% lactose. In another embodiment a prebiotic composition contains less than 0.005% lactose. In an embodiment a prebiotic composition comprises FOS, GOS, or other appropriate polysaccharide, and essentially no lactose. In an embodiment a prebiotic composition does not contain any lactose. In another embodiment a prebiotic composition contains FOS, GOS, or other appropriate polysaccharide, and at least one probiotic bacteria strain. In another embodiment a prebiotic composition comprises FOS, GOS, or other appropriate polysaccharide, and optionally one or more of lactose, at least one probiotic bacteria strain, or a buffer. Additional ingredients include ingredients to improve handling, preservatives, antioxidants, flavorings and the like.

In an embodiment, a prebiotic composition comprises FOS, GOS, or other appropriate polysaccharide, or a probiotic. In other embodiment, a prebiotic composition is in the form of a powder, tablet, capsule, or liquid. In an embodiment, a prebiotic composition can be administered with a dairy product and is in the form of milk or other common dairy product such as a yogurt, shake, smoothie, cheese, and the like.

In embodiments where a prebiotic composition comprises less than 100% by weight of FOS, GOS, or other appropriate polysaccharide, the remaining ingredients can be any suitable ingredients intended for the consumption of the subject in need thereof, e.g., human, including, but not limited to, other prebiotics (e.g., FOS), a buffer, one or more digestible saccharides (e.g. lactose, glucose, or galactose), ingredients intended to inhibit clumping and increase pourability, such as silicone dioxide and microcrystalline cellulose, or similar ingredients as are well-known in the art. Remaining ingredients can also include ingredients to improve handling, preservatives, antioxidants, flavorings, and the like.

B. Buffer Components

One or more buffers, optionally with a calcium counter ion, can also be administered in methods and compositions described herein. Any buffer suitable for consumption by the subject being treated, e.g., human, are useful for the compositions herein. The buffer neutralizes stomach acidity, which can, e.g., allow live bacteria to reach the gut. Buffers include citrates, phosphates, and the like. One embodiment utilizes a buffer with a calcium counter ion, such as Calcium Phosphate Tribasic. The calcium can serve to restore the calcium that many lactose intolerant subjects are missing in their diet. Calcium phosphate can protect *Lactobacillus acidophilus* from bile. Calcium phosphate can help neutralize stomach acidity.

In an embodiment, a buffer such as calcium phosphate is given prior to beginning treatment with a prebiotic composition (such as a composition comprising or consisting essentially of FOS, GOS, or other appropriate polysaccharide), optionally in conjunction with administration of bacteria. As used herein FOS indications one or more fructo-oligosaccharides and GOS indicates one or more galacto-oligosaccharides. In an embodiment, a buffer such as calcium phosphate is given in conjunction with treatment with a prebiotic composition (e.g., a composition comprising or consisting essentially of FOS, GOS, or other appropriate polysaccharide), for part or all of the treatment with lactose. Thus, in an embodiment, some or all doses of a prebiotic composition are accompanied by a dose of a buffer such as calcium phosphate. In an embodiment, a buffer such as calcium phosphate is given initially with a prebiotic composition (such as a composition comprising or consisting essentially of FOS, GOS, or other appropriate polysaccharide), but then its use is discontinued. For example, the initial one, two, three, four, five, six, seven, eight, nine, ten, or more than ten days of treatment with a prebiotic composition can include doses of a buffer such as calcium phosphate, with the use of the buffer discontinued after that time. In an embodiment, a buffer such as calcium phosphate can be given for the first two days of treatment, and then the administration of buffer is discontinued. In an embodiment, a buffer such as calcium phosphate, either alone or in combination with other substances or treatments is used after the treatment with a prebiotic composition is terminated. A buffer such as calcium phosphate can be taken for any suitable period after the termination of treatment with lactose, and can be taken daily or at regular or irregular intervals. Doses can be as described below.

Numerous buffers suitable for human consumption are known in the art, and any suitable buffer can be used in the methods and compositions described herein. Calcium triphosphate is an exemplary buffer, and its counterion supplies a nutrient that is often lacking in lactose-intolerant subjects, i.e. calcium. In an embodiment a buffer can be used in a dose from 2 mg to 2000 mg, or 4 mg to 400 mg, or 4 mg to 200 mg, or 4 mg to 100 mg, or 8 mg to 50 mg, or 10 mg to 40 mg, or 20 mg to 30 mg, or 20, 21, 22, 23, 24, 25, 26, 27, 28, 29, or 30 mg. In another embodiment a prebiotic composition further comprises an amount of a buffer from 1-50 mg, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mg. In an embodiment, buffer is used in a dose of 25 mg. In an embodiment, calcium phosphate is used in a dose of 25 mg. The dose can be given in combination with a prebiotic composition (e.g., a composition comprising or consisting essentially of FOS, GOS, or other appropriate polysaccharide). In an embodiment, as a prebiotic composition dose increases, the dose of buffer increases as well. For example, an initial dose of a prebiotic composition can be 0.6 g to 1.0 g, e.g., 0.8 g, given in combination with 20-30 mg, e.g., 25 mg, of buffer, e.g., calcium phosphate. The dose of a prebiotic composition can be increased incrementally by 0.6 g to 1.0 g, e.g., 0.8 g, and the accompanying dose of buffer, e.g., calcium phosphate, can be increased by 20-30 mg, e.g., 25 mg, of buffer, e.g., calcium phosphate.

C. Compositions Comprising GOS and at Least One Probiotic Bacteria Strain

In an embodiment, a prebiotic composition comprises FOS, GOS, or other appropriate polysaccharide, and at least one probiotic bacteria strain. The FOS, GOS, or other appropriate polysaccharide can comprise more than 1% of the weight of the composition while the at least one probiotic bacteria strain will typically comprise less than 10%, 5%, 4%, 3%, or 2% by weight of the compositions. For example, the FOS, GOS, or other appropriate polysaccharide can be present at 1-99.75% by weight and the at least one probiotic bacteria strain at 0.25-2% by weight, or the FOS, GOS, or other appropriate polysaccharide can be present at 89-96% by weight and the bacteria at 1.2-3.7% by weight. In an embodiment, FOS, GOS, or other appropriate polysaccharide are present at 92% by weight and at least one probiotic bacteria strain, (e.g., *L. mesenteroides, P. pentosaceus, Lactobacillus* or other members from Table 4), is present at 1.5% by weight. In an embodiment, FOS, GOS, or other appropriate polysaccharide are present at 2% by weight and at least one probiotic bacteria strain, (e.g., *L. mesenteroides, P. pentosaceus*, or other members from Table 4), is present at 1.5% by weight. In another embodiment, FOS, GOS, or other appropriate polysaccharide are present at 93% by weight and at least one probiotic bacteria strain, (e.g., *L. mesenteroides, P. pentosaceus*, or other members from Table 4), is present at 1.5% by weight. In another embodiment, FOS, GOS, or other appropriate polysaccharide are present at 94% by weight and at least one probiotic bacteria strain, (e.g., *L. mesenteroides, P. pentosaceus*, or other members from Table 4), is present at 1.5% by weight. In another embodiment, FOS, GOS, or other appropriate polysaccharide are present at 95% by weight and at least one probiotic bacteria strain, (e.g., *L. mesenteroides, P. pentosaceus*, or other members from Table 4), is present at 1.5% by weight. In another embodiment, FOS, GOS, or other appropriate polysaccharide are present at 96% by weight and at least one probiotic bacteria strain, (e.g *L. mesenteroides, P. pentosaceus*, or other members from Table 4), is present at 1.5% by weight. In another embodiment, FOS, GOS, or other appropriate polysaccharide are present at 97% by weight and at least one probiotic bacteria strain, (e.g., *L. mesenteroides, P. pentosaceus*, or other members from Table 4), is present at 1.5% by weight. In another embodiment, FOS, GOS, or other appropriate polysaccharide are present at 98% by weight and at least one probiotic bacteria strain, (e.g., *L. mesenteroides, P. pentosaceus*, or other members from Table 4), is present at 1.5% by weight. In another embodiment, FOS, GOS, or other appropriate polysaccharide are present at 98.5% by weight and at least one probiotic bacteria strain, (e.g., *L. mesenteroides, P. pentosaceus*, or other members from Table 4), is present at 1.5% by weight. If the at least one probiotic bacteria strain and FOS, GOS, or other appropriate polysaccharide do not make up 100% by weight of the prebiotic composition, the remaining ingredients can be any suitable ingredients intended for consumption by the subject in need thereof, e.g., human, including, but not limited to, other prebiotics (e.g., FOS), one or more buffers, digestible saccharides (e.g. lactose, glucose, or galactose), ingredients intended to inhibit clumping and increase pourability, such as silicone dioxide and microcrystalline cellulose, or similar ingredients as are well-known in the art. Remaining ingredients can also include ingredients to improve handling, preservatives, antioxidants, flavorings and the like.

D. Compositions Comprising FOS, GOS, or Other Appropriate Polysaccharide and a Buffer In another embodiment, a prebiotic composition comprises FOS, GOS, or other appropriate polysaccharide and a buffer (e.g., calcium phosphate tribasic). For example, FOS, GOS, or other appropriate polysaccharide can be present at 1-100% by weight and the buffer at 0.50-4% by weight, or FOS, GOS, or other appropriate polysaccharide can be present at 1-96% by weight and the buffer at 1 to 3.75% by weight. In an embodiment, FOS, GOS, or other appropriate polysaccharide are present at 1% by weight and buffer is present at 3% by weight. In an embodiment, FOS, GOS, or other appropriate polysaccharide are present at 5% by weight and buffer is present at 3% by weight. In an embodiment, FOS, GOS, or other appropriate polysaccharide are present at 10% by weight and buffer is present at 3% by weight. In an embodiment, FOS, GOS, or other appropriate polysaccharide are present at 15% by weight and buffer is present at 15% by weight. In an embodiment, FOS, GOS, or other appropriate polysaccharide are present at 20% by weight and buffer is present at 3% by weight. In an embodiment, FOS, GOS, or other appropriate polysaccharide are present at 25% by weight and buffer is present at 3% by weight. In an embodiment, FOS, GOS, or other appropriate polysaccharide are present at 30% by weight and buffer is present at 3% by weight. In an embodiment, FOS, GOS, or other appropriate polysaccharide are present at 35% by weight and buffer is present at 3% by weight. In an embodiment, FOS, GOS, or other appropriate polysaccharide are present at 40% by weight and buffer is present at 3% by weight. In an embodiment, FOS, GOS, or other appropriate polysaccharide are present at 50% by weight and buffer is present at 3% by weight. In an embodiment, FOS, GOS, or other appropriate polysaccharide are present at 60% by weight and buffer is present at 3% by weight. In an embodiment, FOS, GOS, or other appropriate polysaccharide are present at 70% by weight and buffer is present at 3% by weight. In another embodiment, FOS, GOS, or other appropriate polysaccharide are present at 90% by weight and buffer is present at 3% by weight. In another embodiment, FOS, GOS, or other appropriate polysaccharide are present at 92% by weight and buffer is present at 3% by weight. In another embodiment, FOS, GOS, or other appropriate polysaccharide are present at 93% by weight and buffer is present at 3% by weight. In another embodiment, FOS, GOS, or other appropriate polysaccharide are present at 94% by weight and buffer is present at 3% by weight. In another embodiment, FOS, GOS, or other appropriate polysaccharide are present at 95% by weight and buffer is present at 3% by weight. In another embodiment, FOS, GOS, or other appropriate polysaccharide are present at 96% by weight and buffer is present at 3% by weight. In another embodiment, FOS, GOS, or other appropriate polysaccharide are present at 97% by weight and buffer is present at 2% by weight. In another embodiment, FOS, GOS, or other appropriate polysaccharide are present at 98% by weight and buffer is present at 1% by weight. In another embodiment, FOS, GOS, or other appropriate polysaccharide are present at 99% by weight and buffer is present at 1% by weight. In another embodiment, FOS, GOS, or other appropriate polysaccharide are present at 100% by weight and buffer is present at less than 1% by weight. If the buffer and FOS, GOS, or other appropriate polysaccharide do not make up 100% by weight of the composition, the remaining ingredients can be any suitable ingredients intended for consumption by the subject (e.g., a human) including, but not limited to, probiotics (e.g., beneficial bacteria) or other prebiotics (e.g., FOS), but also including ingredients intended to inhibit clumping and increase pourability, such as silicone dioxide and microcrystalline cellulose, or similar ingredients as are well-known in the art. Remaining ingredients can also include ingredients to improve handling, preservatives, antioxidants, flavorings and the like.

E. Compositions Comprising a Digestible Saccharide, a Probiotic Bacteria, and FOS, GOS, or Other Appropriate Polysaccharide In an embodiment, a prebiotic composition comprises a digestible saccharide (e.g. lactose, glucose, or galactose), at least one probiotic bacterium (e.g., *L. mesenteroides, P. pentosaceus*, or other members from Table 4), and FOS, GOS, or other appropriate polysaccharide. In an embodiment, lactose can be present at 1-20% by weight, bacteria at 0.25-20.10% by weight, and FOS, GOS, or other appropriate polysaccharide at 1-98.75% by weight. In another embodiment lactose can be present at 5-20% by weight, bacteria at 0.91-1.95% by weight, and FOS, GOS, or other appropriate polysaccharide at 1 to 96% by weight. In another embodiment, lactose is present at 20% by weight, bacteria at 1.5% by weight, and FOS, GOS, or other appropriate polysaccharide are present at 1% by weight. In another embodiment, lactose is present at 20% by weight, bacteria at 1.5% by weight, and FOS, GOS, or other appropriate polysaccharide are present at 50% by weight. In another embodiment, lactose is present at 20% by weight, bacteria at 1.5% by weight, and FOS, GOS, or other appropriate polysaccharide are present at 60% by weight. In another embodiment, lactose is present at 20% by weight, bacteria at 1.5% by weight, and FOS, GOS, or other appropriate polysaccharide are present at 70% by weight. In another embodiment, lactose is present at 5% by weight, bacteria at 1.5% by weight, and FOS, GOS, or other appropriate polysaccharide are present at 90% by weight. In another embodiment, lactose is present at 5% by weight, bacteria at 1.5% by weight, and FOS, GOS, or other appropriate polysaccharide are present at 92% by weight. In another embodiment, lactose is present at 5% by weight, bacteria at 1.5% by weight, and FOS, GOS, or other appropriate polysaccharide are present at 93% by weight. In another embodiment, lactose is present at 5% by weight, bacteria at 1% by weight, and FOS, GOS, or other appropriate polysaccharide are present at 94% by weight. In another embodiment, lactose is present at 4.5% by weight, bacteria at 1.5% by weight, and FOS, GOS, or other appropriate polysaccharide are present at 94% by weight. In another embodiment, lactose is present at 4.5% by weight, bacteria at 0.5% by weight, and FOS, GOS, or other appropriate polysaccharide are present at 95% by weight. In another embodiment, lactose is present at 3.5% by weight, bacteria at 0.5% by weight, and FOS, GOS, or other appropriate polysaccharide are present at 96% by weight. In another embodiment, lactose is present at 2.5% by weight, bacteria at 0.5% by weight, and FOS, GOS, or other appropriate polysaccharides are present at 97% by weight. In another embodiment, lactose is present at 1.5% by weight, bacteria at 0.5% by weight, and FOS, GOS, or other appropriate polysaccharide are present at 98% by weight. In another embodiment, lactose is present at 0.5% by weight, bacteria at 0.5% by weight, and FOS, GOS, or other appropriate polysaccharide are present at 99% by weight. If the bacteria, FOS, GOS, or other appropriate polysaccharide and lactose do not make up 100% of the composition, the remaining ingredients can be any suitable ingredients intended for consumption by the subject, e.g., a human, including, but not limited to a buffer, digestible saccharides (e.g., lactose, glucose, or galactose), ingredients intended to inhibit clumping and increase pourability, such as silicone dioxide and microcrystalline cellulose, or similar ingredients as are well-known in the art. Remaining ingredients can also include ingredients to improve handling, preservatives, antioxidants, flavorings and the like.

F. Compositions Comprising FOS, GOS, or Other Appropriate Polysaccharide, a Probiotic Bacteria, and Buffer In an embodiment, a prebiotic composition comprises FOS, GOS, or other appropriate polysaccharide, a probiotic bacteria strain, and buffer. In an embodiment, FOS, GOS, or other appropriate polysaccharide can be present at 1-100% by weight, a probiotic bacteria strain at 0.25-2% by weight, and the buffer at 0.50-4% by weight. In another embodiment, FOS, GOS, or other appropriate polysaccharide can be present at 1-95% by weight, a probiotic bacteria strain at 0.91-1.95% by weight, and the buffer at 1.2-30.75% by weight. In another embodiment, FOS, GOS, or other appropriate polysaccharide are present at 1% by weight, a probiotic bacteria strain at 1.5% by weight, and buffer is present at 3% by weight. In another embodiment, FOS, GOS, or other appropriate polysaccharide are present at 5% by weight, a probiotic bacteria strain at 1.5% by weight, and buffer is present at 3% by weight. In another embodiment, FOS, GOS, or other appropriate polysaccharide are present at 10% by weight, a probiotic bacteria strain at 1.5% by weight, and buffer is present at 3% by weight. In another embodiment, FOS, GOS, or other appropriate polysaccharide are present at 15% by weight, a probiotic bacteria strain at 1.5% by weight, and buffer is present at 3% by weight. In another embodiment, FOS, GOS, or other appropriate polysaccharide are present at 20% by weight, a probiotic bacteria strain at 1.5% by weight, and buffer is present at 3% by weight. In another embodiment, FOS, GOS, or other appropriate polysaccharide are present at 25% by weight, a probiotic bacteria strain at 1.5% by weight, and buffer is present at 3% by weight. In another embodiment, FOS, GOS, or other appropriate polysaccharide are present at 30% by weight, a probiotic bacteria strain at 1.5% by weight, and buffer is present at 3% by weight. In another embodiment, FOS, GOS, or other appropriate polysaccharide are present at 35% by weight, a probiotic bacteria strain at 1.5% by weight, and buffer is present at 3% by weight. In another embodiment, FOS, GOS, or other appropriate polysaccharide are present at 40% by weight, a probiotic bacteria strain at 1.5% by weight, and buffer is present at 3% by weight. In another embodiment, FOS, GOS, or other appropriate polysaccharide are present at 50% by weight, a probiotic bacteria strain at 1.5% by weight, and buffer is present at 3% by weight. In another embodiment, FOS, GOS, or other appropriate polysaccharide are present at 60% by weight, a probiotic bacteria strain at 1.5% by weight, and buffer is present at 3% by weight. In another embodiment, FOS, GOS, or other appropriate polysaccharide are present at 70% by weight, a probiotic bacteria strain at 1.5% by weight, and buffer is present at 3% by weight. In another embodiment, FOS, GOS, or other appropriate polysaccharide are present at 90% by weight, a probiotic bacteria strain at 1.5% by weight, and buffer is present at 3% by weight. In another embodiment, FOS, GOS, or other appropriate polysaccharide are present at 92% by weight, a probiotic bacteria strain at 1.5% by weight, and buffer is present at 3% by weight. In another embodiment, FOS, GOS, or other appropriate polysaccharide are present at 93% by weight, a probiotic bacteria strain at 1.5% by weight, and buffer is present at 3% by weight. In another embodiment, FOS, GOS, or other appropriate polysaccharide are present at 94% by weight, a probiotic bacteria strain at 1.5% by weight, and buffer is present at 3% by weight. In another embodiment, FOS, GOS, or other appropriate polysaccharide are present at 95% by weight, a probiotic bacteria strain at 1.5% by weight, and buffer is present at 3% by weight. In another embodiment, FOS, GOS, or other appropriate polysaccharide are present at 96% by weight, a probiotic bacteria strain at 1.5% by weight, and buffer is present at 2% by weight. In another embodiment, FOS, GOS, or other appropriate polysaccharide are present at 97% by weight, a probiotic bacteria strain at 1.5% by weight, and buffer is present at 1.5% by weight. In another embodiment, FOS, GOS, or other appropriate polysaccharide are present at 99% by weight, a probiotic bacteria strain at 0.5% by weight, and buffer is present at 0.5% by weight. In another embodiment, FOS, GOS, or other appropriate polysaccharide are present at 100% by weight, a probiotic bacteria strain at less than 0.5% by weight, and buffer is present at less than 0.5% by weight. If the probiotic bacteria strain, buffer, and FOS, GOS, or other appropriate polysaccharide do not make up 100% of the composition, the remaining ingredients can be any suitable ingredients intended for the consumption of a subject (e.g., human) including, but not limited to, other prebiotics (e.g., FOS), digestible saccharides (e.g., lactose, glucose or galactose), ingredients intended to inhibit clumping and increase pourability, such as silicone dioxide and microcrystalline cellulose, or similar ingredients as are well-known in the art. Remaining ingredients can also include ingredients to improve handling, preservatives, antioxidants, flavorings and the like.

G. Compositions Comprising a Digestible Saccharide, FOS, GOS, or Other Appropriate Polysaccharide, and a Buffer In an embodiment, a prebiotic composition comprises a digestible saccharide (e.g. lactose, glucose, or galactose), FOS, GOS, or other appropriate polysaccharide, and a buffer. For example, lactose can be present at 1-20% by weight, FOS, GOS, or other appropriate polysaccharide at 1-100% by weight, and the buffer at 0.50-4% by weight, or the lactose can be present at 5-20% by weight, FOS, GOS, or other appropriate polysaccharide at 1-96% by weight, and the buffer at 1.2-30.75% by weight. In an embodiment, lactose is present at 20% by weight, FOS, GOS, or other appropriate polysaccharide at 1% by weight, and buffer is present at 3% by weight. In an embodiment, lactose is present at 5% by weight, FOS, GOS, or other appropriate polysaccharide at 1% by weight, and buffer is present at 3% by weight. In an embodiment, lactose is present at 20% by weight, FOS, GOS, or other appropriate polysaccharide at 10% by weight, and buffer is present at 3% by weight. In an embodiment, lactose is present at 20% by weight, FOS, GOS, or other appropriate polysaccharide at 15% by weight, and buffer is present at 3% by weight. In an embodiment, lactose is present at 20% by weight, FOS, GOS, or other appropriate polysaccharide at 20% by weight, and buffer is present at 3% by weight. In an embodiment, lactose is present at 20% by weight, FOS, GOS, or other appropriate polysaccharide at 25% by weight, and buffer is present at 3% by weight. In an embodiment, lactose is present at 20% by weight, FOS, GOS, or other appropriate polysaccharide at 30% by weight, and buffer is present at 3% by weight. In an embodiment, lactose is present at 20% by weight, FOS, GOS, or other appropriate polysaccharide at 35% by weight, and buffer is present at 3% by weight. In an embodiment, lactose is present at 20% by weight, FOS, GOS, or other appropriate polysaccharide at 40% by weight, and buffer is present at 3% by weight. In an embodiment, lactose is present at 20% by weight, FOS, GOS, or other appropriate polysaccharide at 50% by weight, and buffer is present at 3% by weight. In an embodiment, lactose is present at 20% by weight, FOS, GOS, or other appropriate polysaccharide at 60% by weight, and buffer is present at 3% by weight. In an embodiment, lactose is present at 20% by weight, FOS, GOS, or other appropriate polysaccharide at 70% by weight, and buffer is present at 3% by weight. In another embodiment, lactose is present at 5% by weight, FOS, GOS, or other appropriate polysaccharide at 90% by weight, and buffer is present at 3% by weight. In another embodiment, lactose is present at 5% by weight, FOS, GOS, or other appropriate polysaccharide at 92% by weight, and buffer is present at 3% by weight. In another embodiment, lactose is present at 4% by weight, FOS, GOS, or other appropriate polysaccharide at 93% by weight, and buffer is present at 3% by weight. In another embodiment, lactose is present at 3% by weight, FOS, GOS, or other appropriate polysaccharide at 94% by weight, and buffer is present at 3% by weight. In another embodiment, lactose is present at 2% by weight, FOS, GOS, or other appropriate polysaccharide at 95% by weight, and buffer is present at 3% by weight. In another embodiment, lactose is present at 1% by weight, FOS, GOS, or other appropriate polysaccharide at 96% by weight, and buffer is present at 3% by weight. If a suitable prebiotic, buffer and lactose do not make up 100% of the composition by weight, the remaining ingredients can be any suitable ingredients intended for consumption by a subject (e.g., human) including, but not limited to, bacteria, ingredients intended to inhibit clumping and increase pourability, such as silicone dioxide and microcrystalline cellulose, or similar ingredients as are well-known in the art. Remaining ingredients can also include ingredients to improve handling, preservatives, antioxidants, flavorings and the like.

H. Compositions Comprising a Digestible Saccharide, Bacteria, GOS, and a Buffer

In an embodiment, a composition comprises a digestible saccharide (e.g. lactose, glucose, or galactose), bacteria, FOS, GOS, or other appropriate polysaccharide, and buffer. For example, lactose can be present at 1-20% by weight, bacteria at 0.25-2.10% by weight, FOS, GOS, or other appropriate polysaccharide at 1-100% by weight, and the buffer at 0.50-4% by weight, or the lactose can be present at 5-20% by weight, bacteria at 0.91-1.95% by weight, FOS, GOS, or other appropriate polysaccharide at 70-95% by weight, and the buffer at 1.2-30.75% by weight. In an embodiment, lactose is present at 20% by weight, bacteria at 1.47% by weight, FOS, GOS, or other appropriate polysaccharide at 1% by weight, and buffer is present at 3% by weight. In an embodiment, lactose is present at 20% by weight, bacteria at 1.47% by weight, FOS, GOS, or other appropriate polysaccharide at 10% by weight, and buffer is present at 3% by weight. In an embodiment, lactose is present at 20% by weight, bacteria at 1.47% by weight, FOS, GOS, or other appropriate polysaccharide at 15% by weight, and buffer is present at 3% by weight. In an embodiment, lactose is present at 20% by weight, bacteria at 1.47% by weight, FOS, GOS, or other appropriate polysaccharide at 20% by weight, and buffer is present at 3% by weight. In an embodiment, lactose is present at 20% by weight, bacteria at 1.47% by weight, FOS, GOS, or other appropriate polysaccharide at 25% by weight, and buffer is present at 3% by weight. In an embodiment, lactose is present at 20% by weight, bacteria at 1.47% by weight, FOS, GOS, or other appropriate polysaccharide at 30% by weight, and buffer is present at 3% by weight. In an embodiment, lactose is present at 20% by weight, bacteria at 1.47% by weight, FOS, GOS, or other appropriate polysaccharide at 35% by weight, and buffer is present at 3% by weight. In an embodiment, lactose is present at 20% by weight, bacteria at 1.47% by weight, FOS, GOS, or other appropriate polysaccharide at 40% by weight, and buffer is present at 3% by weight. In an embodiment, lactose is present at 20% by weight, bacteria at 1.47% by weight, FOS, GOS, or other appropriate polysaccharide at 50% by weight, and buffer is present at 3% by weight. In an embodiment, lactose is present at 20% by weight, bacteria at 1.47% by weight, FOS, GOS, or other appropriate polysaccharide at 60% by weight, and buffer is present at 3% by weight. In an embodiment, lactose is present at 20% by weight, bacteria at 1.47% by weight, FOS, GOS, or other appropriate polysaccharide at 70% by weight, and buffer is present at 3% by weight. In an embodiment, lactose is present at 5% by weight, bacteria at 1.47% by weight, FOS, GOS, or other appropriate polysaccharide at 90% by weight, and buffer is present at 3% by weight. In an embodiment, lactose is present at 3% by weight, bacteria at 1.47% by weight, FOS, GOS, or other appropriate polysaccharide at 92% by weight, and buffer is present at 3% by weight. In an embodiment, lactose is present at 2% by weight, bacteria at 1.47% by weight, FOS, GOS, or other appropriate polysaccharide at 93% by weight, and buffer is present at 3% by weight. In an embodiment, lactose is present at 1% by weight, bacteria at 1.47% by weight, FOS, GOS, or other appropriate polysaccharide at 94% by weight, and buffer is present at 3% by weight. In an embodiment, lactose is present at 0.5% by weight, bacteria at 1.47% by weight, FOS, GOS, or other appropriate polysaccharide at 95% by weight, and buffer is present at 3% by weight. If the bacteria, FOS, GOS, or other, buffer and lactose do not make up 100% of the composition by weight, the remaining ingredients can be any suitable ingredients intended for consumption by a subject, e.g., human, including, but not limited to, ingredients intended to inhibit clumping and increase pourability, such as silicone dioxide and microcrystalline cellulose, or similar ingredients as are well-known in the art. Remaining ingredients can also include ingredients to improve handling, preservatives, antioxidants, flavorings and the like.

I. Additional Ingredients

Additional ingredients include ingredients to improve handling, preservatives, antioxidants, flavorings and the like. For example, in an embodiment, a prebiotic composition in powdered form can include flavorings such that when mixed in a liquid (e.g., water), the powder can flavor the liquid with various flavors such as grape, strawberry, lime, lemon, chocolate, and the like. In an embodiment, the compositions include microcrystalline cellulose or silicone dioxide. Preservatives can include, for example, benzoic acid, alcohols, for example, ethyl alcohol, and hydroxybenzoates. Antioxidants can include, for example, butylated hydroxyanisole (BHA), butylated hydroxytoluene (BHT), tocopherols (e.g., Vitamin E), and ascorbic acid (Vitamin C).

Timing and Dosage of Probiotic and Treatments Known to Combat Musculoskeletal Disorders In an embodiment, probiotic microbes, such as *L. mesenteroides* and *P. pentosaceus*, are given prior to beginning treatment with a drug typically prescribed for treatment of a musculoskeletal disorder.

Thus, in an embodiment, some or all doses of a treatment or drug are accompanied by a dose of microbes, e.g., live cultured bacteria or yeast, e.g., *L. mesenteroides, P. pentosaceus*. In an embodiment, microbes, e.g., *L. mesenteroides, P. pentosaceus*, are given initially with another treatment or drug, but then use of the microbes is discontinued. For example, the initial one, two, three, four, five, six, seven, eight, nine, ten, or more than ten days of treatment with a treatment or drug further comprises doses of microbes, with the use of microbes discontinued after that time. In an embodiment, microbes, (e.g., bacteria in yogurt), or microbes by themselves, can be given for the first two days of treatment; then the administration of microbes is discontinued. In another embodiment, probiotic microbes, either alone or in combination with other substances or treatments are used after the treatment with a drug or treatment for musculoskeletal disorders is terminated. The microbes can be taken for any suitable period after the termination of treatment with the drug and can be taken daily or at regular or irregular intervals. Doses can be as described below. Any suitable amount of probiotic per serving can be used that allows an effective microbiota in the GI as demonstrated by, for example, decreased symptoms of a given musculoskeletal disorder.

Examples of anti-osteoprosis combination partners are but are not limited to, bisphosphonates (alendronate, risedronate, ibandronate, zolendronate), biologics (denosumab, romosozumab), selective estrogen receptor mediators (Raloxifene), or anabolic agents (teriparatide, abaloparatide). In an embodiment, probiotic microbes, such as *L. mesenteroides, P. pentosaceus*, are given in conjunction with treatment, such as, but are not limited to, bisphosphonates (alendronate, risedronate, ibandronate, zolendronate), biologics (denosumab, romosozumab), selective estrogen receptor mediators (Raloxifene), or anabolic agents (teriparatide, abaloparatide).

Examples of anti-osteoarthritis combination partners are surgery, analgesics, non-steroidal anti-inflammatory drugs, menthol, weight loss regimens, physical exercise, acupuncture, narcotics, teriparatide, abaloparatide, and physical therapy.

Examples of treatments for osteomyelitis that may be used in combination with compositions disclosed herein, include, but are not limited to surgery and antibiotics. In some embodiments, antibiotics are given intravenously. In some embodiments, antibiotics are given orally. Typically, compositions disclosed herein are given after cessation of antibiotic therapy; however, in some cases, a suitable antibiotic or a suitable delivery route of antibiotic allows for concurrent use of compositions described herein and antibiotic therapy.

Examples of treatments for delayed or non-union fractures include bone stimulation and surgery, such as bone grafts or fixations.

Dosage Forms

A. General

Compositions described herein include any suitable form, including liquid or powder. Powdered compositions can be as pure powder, or can be in the form of capsules, tablets, or the like. Powder can be packaged in bulk (e.g., in a container containing sufficient prebiotic or other substances for a subject to follow for an entire course of treatment with increasing doses of prebiotic, or a portion of a course of treatment), or as individual packets (e.g., packets containing a single dose of prebiotic plus other components, or packets containing the dose of prebiotic and other components needed for a particular day of a prebiotic treatment regimen). If packaged in bulk, the powder can be in any suitable container, such as a packet, sachet, canister, ampoule, ramekin, or bottle. The container can also include one or more scoops or similar serving devices of a size or sizes appropriate to measure and serve one or more doses of prebiotic and, optionally, other ingredients included in the powder. Liquid compositions contain prebiotic and, optionally, other ingredients, in a suitable liquid, e.g., water or buffer. Liquid compositions can be provided in bulk (e.g., in a container containing sufficient prebiotic or other substances for one subject in need thereof to follow an entire course of treatment with increasing doses of prebiotic, or a portion of a course of treatment), or as individual containers, such as cans, bottles, soft packs, and the like (e.g., containers containing a single dose of prebiotic plus other components in suitable liquid, or containers containing the dose of prebiotic and other components needed for a particular day of a prebiotic treatment regimen). The container can also include one or more measuring cups or similar serving devices of a size or sizes appropriate to measure and serve one or more doses of prebiotic and, optionally, other ingredients included in the liquid.

In an embodiment, compositions described herein comprise one or more excipients. In an embodiment, the one or more excipients comprise one or more antiadherents, one or more binders, one or more coatings, one or more disintegrants, one or more fillers, one or more flavors, one or more colors, one or more lubricants, one or more glidants, one or more sorbents, one or more preservatives, one or more sweeteners, or a combination thereof. In an embodiment, the antiadherent is magnesium stearate. In an embodiment, the one or more binders are cellulose, microcrystalline cellulose, hydroxypropyl cellulose, xylitol, sorbitol, maltitol, gelatin, polyvinylpyrrolidone, polyethylene glycol, methyl cellulose, hydroxypropyl methylcellulose, or a combination thereof. In an embodiment, the one or more coatings are a hydroxypropyl methylcellulose film, shellac, corn protein zein, gelatin, methyl acrylate-methacrylic acid copolymers, cellulose acetate succinate, hydroxy propyl methyl cellulose phthalate, hydroxy propyl methyl cellulose acetate succinate, polyvinyl acetate phthalate, methyl methacrylate-methacrylic acid copolymers, sodium alginate, stearic acid, or a combination thereof. In an embodiment, the one or more disintegrants are crosslinked polyvinylpyrrolidone (crospovidone), crosslinked sodium carboxymethyl cellulose (croscarmellose sodium), sodium starch glycolate, or a combination thereof. In an embodiment, the one or more fillers are calcium carbonate, magnesium stearate, dibasic calcium phosphate, cellulose, vegetable oil, vegetable fat, or a combination thereof. In an embodiment, the one or more flavors are mint, cherry, anise, peach, apricot, licorice, raspberry, vanilla, or a combination thereof. In an embodiment, the one or more lubricants are talc, silica, vegetable stearin, magnesium stearate, stearic acid, or a combination thereof. In an embodiment, the one or more glidants are fumed silica, talc, magnesium carbonate, or a combination thereof. In an embodiment, the one or more sorbents are fatty acids, waxes, shellac, plastics, plant fibers, or a combination thereof. In an embodiment, the one or more preservatives are vitamin A, vitamin E, vitamin C, retinyl palmitate, selenium, cysteine, methionine, citric acid, sodium citrate, methyl paraben, propyl paraben, or a combination thereof. In an embodiment, the one or more sweeteners are *stevia*, aspartame, sucralose, neotame, acesulfame potassium, saccharin or a combination thereof.

B. Oral Dosage Forms and Components

In one aspect provided herein are methods and compositions formulated for oral delivery to a subject in need thereof. In an embodiment a composition is formulated to deliver a composition comprising a prebiotic to a subject in need thereof. In another embodiment, a pharmaceutical composition is formulated to deliver a composition comprising a prebiotic to a subject in need thereof. In another embodiment a composition is formulated to deliver a composition comprising prebiotic and a probiotic to a subject in need thereof 1. Forms In an embodiment, a composition is administered in solid, semi-solid, micro-emulsion, gel, or liquid form. Examples of such dosage forms include tablet forms disclosed in U.S. Pat. Nos. 3,048,526, 3,108,046, 4,786,505, 4,919,939, and 4,950,484; gel forms disclosed in U.S. Pat. Nos. 4,904,479, 6,482,435, 6,572,871, and 5,013,726; capsule forms disclosed in U.S. Pat. Nos. 4,800,083, 4,532,126, 4,935,243, and 6,258,380; or liquid forms disclosed in U.S. Pat. Nos. 4,625,494, 4,478,822, and 5,610,184; each of which is incorporated herein by reference in its entirety.

Forms of the compositions that can be used orally include tablets, push-fit capsules made of gelatin, as well as soft, sealed capsules made of gelatin and a plasticizer, such as glycerol or sorbitol. Tablets can be made by compression or molding, optionally with one or more accessory ingredients including freeze-dried plant material serving both as prebiotic and as a filler. Compressed tablets can be prepared by compressing in a suitable machine the active ingredient in a free-flowing form such as a powder or granules, optionally mixed with binders (e.g., povidone, gelatin, hydroxypropylmethyl cellulose), inert diluents, preservative, antioxidant, disintegrant (e.g., sodium starch glycolate, cross-linked povidone, cross-linked sodium carboxymethyl cellulose) or lubricating, surface active or dispersing agents. Molded tablets can be made by molding in a suitable machine a mixture of the powdered compound moistened with an inert liquid diluent. The tablets can optionally be coated or scored and can be formulated so as to provide slow or controlled release of the active ingredient therein. Tablets can optionally be provided with an enteric coating, to provide release in parts of the gut (e.g., colon, lower intestine) other than the stomach. All formulations for oral administration can be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds (prebiotics or probiotics) can be dissolved or suspended in suitable liquids, such as fatty oils, liquid paraffin, or liquid polyethylene glycols. In addition, stabilizers can be added. Dragee cores are provided with suitable coatings. For this purpose, concentrated sugar solutions can be used, which can optionally contain gum arabic, talc, polyvinyl pyrrolidone, carbopol gel, polyethylene glycol, or titanium dioxide, lacquer solutions, and suitable organic solvents or solvent mixtures. Dyestuffs or pigments can be added to the tablets or Dragee coatings for identification or to characterize different combinations of active compound doses.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethylene glycol or an oil medium, for example peanut oil, liquid paraffin, or olive oil.

Oral liquid preparations can be in the form of, for example, aqueous or oily suspensions, solutions, emulsions syrups or elixirs, or can be presented as a dry product for reconstitution with water or other suitable vehicle before use. Such liquid preparations can contain conventional additives, such as suspending agents, for example sorbitol, methyl cellulose, glucose syrup, gelatin, hydroxyethyl cellulose, carboxymethyl cellulose, aluminum stearate gel or hydrogenated edible fats, emulsifying agents, for example lecithin, sorbitan monooleate, acacia; nonaqueous vehicles (which can include edible oils), for example almond oil, oily esters such as glycerine, propylene glycol, or ethyl alcohol; preservatives, for example methyl or propyl p-hydoxybenzoate or sorbic acid, and, if desired, conventional flavoring or coloring agents.

In an embodiment, a provided composition includes a softgel formulation. A softgel can contain a gelatin-based shell that surrounds a liquid fill. The shell can be made of gelatin, plasticiser (e.g., glycerin and/or sorbitol), modifier, water, color, antioxidant, or flavor. The shell can be made with starch or carrageenan. The outer layer can be enteric coated. In an embodiment, a softgel formulation can include a water or oil soluble fill solution, or suspension of a composition, for example, a prebiotic composition, covered by a layer of gelatin.

An enteric coating can control the location of where a prebiotic composition is absorbed in the digestive system. For example, an enteric coating can be designed such that a prebiotic composition does not dissolve in the stomach but rather travels to the small intestine, where it dissolves. An enteric coating can be stable at low pH (such as in the stomach) and can dissolve at higher pH (for example, in the small intestine). Material that can be used in enteric coatings includes, for example, alginic acid, cellulose acetate phthalate, plastics, waxes, shellac, and fatty acids (e.g., stearic acid, palmitic acid). Enteric coatings are described, for example, in U.S. Pat. Nos. 5,225,202, 5,733,575, 6,139,875, 6,420,473, 6,455,052, and 6,569,457, all of which are herein incorporated by reference in their entirety. The enteric coating can be an aqueous enteric coating. Examples of polymers that can be used in enteric coatings include, for example, shellac (trade name EmCoat 120 N, Marcoat 125); cellulose acetate phthalate (trade name aquacoat CPD®, Sepifilm™ LP, Klucel, Aquacoat® ECD, and Metolose®); polyvinylacetate phthalate (trade name Sureteric®); and methacrylic acid (trade name Eudragit®).

In an embodiment, an enteric coated prebiotic composition is administered to a subject. In another embodiment, an enteric coated probiotic composition is administered to a subject. In another embodiment, an enteric coated probiotic and prebiotic composition is administered to a subject. In an embodiment, probiotic bacteria can be administered to a subject using an enteric coating. The stomach has an acidic environment that can kill probiotics. An enteric coating can protect probiotics as they pass through the stomach and small intestine.

Enteric coatings can be used to (1) prevent the gastric juice from reacting with or destroying the active substance, (2) prevent dilution of the active substance before it reaches the intestine, (3) ensure that the active substance is not released until after the preparation has passed the stomach, and (4) prevent live bacteria contained in the preparation from being killed because of the low pH-value in the stomach.

Enteric coatings can also be used for avoiding irritation of or damage to the mucous membrane of the stomach caused by substances contained in the oral preparation, and for counteracting or preventing formation or release of substances having an unpleasant odor or taste in the stomach. Finally, such coatings can be used for preventing nausea or vomiting on intake of oral preparations.

In an embodiment a prebiotic composition is provided as a tablet, capsule, or caplet with an enteric coating. In an embodiment the enteric coating is designed to hold the tablet, capsule, or caplet together when in the stomach. The enteric coating is designed to hold together in acid conditions of the stomach and break down in non-acid conditions and therefore release the drug in the intestines.

Softgel delivery systems can also incorporate phospholipids or polymers or natural gums to entrap a composition, for example, a prebiotic composition, in the gelatin layer with an outer coating to give desired delayed/control release effects, such as an enteric coating.

Formulations of softgel fills can be at pH 2.5-7.5.

A softgel formulation can be sealed tightly in an automatic manner. A softgel formulation can easily be swallowed, allow for product identification using colors and several shapes, allow uniformity, precision and accuracy between dosages, be safe against adulteration, provide good availability and rapid absorption, and offer protection against contamination, light and oxidation. Furthermore, softgel formulations can avoid unpleasant flavors due to content encapsulation.

A composition comprising a softgel formulation can be in any of number of different sizes, including, for example, round, oblong, oval, tube, droplet, or suppositories.

In an embodiment a composition is provided in a dosage form which comprises an effective amount of prebiotic and one or more release controlling excipients as described herein. Suitable modified release dosage vehicles include, but are not limited to, hydrophilic or hydrophobic matrix devices, water-soluble separating layer coatings, enteric coatings, osmotic devices, multi-particulate devices, and combinations thereof. In an embodiment the dosage form is a tablet, caplet, capsule or lollipop. In another embodiment, the dosage form is a liquid, oral suspension, oral solution, or oral syrup. In yet another embodiment, the dosage form is a gel capsule, soft gelatin capsule, or hard gelatin capsule.

In an embodiment, the dosage form is a gelatin capsule having a size indicated in Table 1.

TABLE 1

| Gel Cap Sizes Allowable For Human Consumption Empty Gelatin Capsule Physical Specifications | | | |
|---|---|---|---|
| | Outer Diameter Size (mm) | Height or Locked Length (mm) | Actual Volume (ml) |
| 000 | 9.97 | 26.14 | 1.37 |
| 00 | 8.53 | 23.30 | 0.95 |
| 0 | 7.65 | 21.7 | 0.68 |
| 1 | 6.91 | 19.4 | 0.50 |
| 2 | 6.35 | 18.0 | 0.37 |
| 3 | 5.82 | 15.9 | 0.3 |
| 4 | 5.31 | 14.3 | 0.21 |
| 5 | 4.91 | 11.1 | 0.13 |

Note:
sizes and volumes are approximate.

In another embodiment a composition comprising a prebiotic is provided in effervescent dosage forms. The compositions can also comprise non-release controlling excipients.

In another embodiment, a composition comprising a prebiotic is provided in a dosage form that has at least one component that can facilitate release of the prebiotic. In a further embodiment the dosage form can be capable of giving a discontinuous release of the compound in the form of at least two consecutive pulses separated in time from 0.1 up to 24 hours. The compositions can comprise one or more release controlling and non-release controlling excipients, such as those excipients suitable for a disruptable semi-permeable membrane and as swellable substances.

In another embodiment the prebiotic mixture is a plant or plant extract, either in solid or liquid form.

In another embodiment a composition comprising a prebiotic is provided in an enteric coated dosage form. The composition can also comprise non-release controlling excipients.

In another embodiment a composition comprising a prebiotic is provided in a dosage form for oral administration to a subject in need thereof, which comprises one or more pharmaceutically acceptable excipients or carriers, enclosed in an intermediate reactive layer comprising a gastric juice-resistant polymeric layered material partially neutralized with alkali and having cation exchange capacity and a gastric juice-resistant outer layer.

In an embodiment a composition comprising a prebiotic is provided in the form of enteric-coated granules, for oral administration. The compositions can further comprise cellulose, disodium hydrogen phosphate, hydroxypropyl cellulose, hypromellose, lactose, mannitol, and sodium lauryl sulfate.

In another embodiment a composition comprising a prebiotic is provided in the form of enteric-coated pellets, for oral administration. The compositions can further comprise glyceryl monostearate 40-50, hydroxypropyl cellulose, hypromellose, magnesium stearate, methacrylic acid copolymer type C, polysorbate 80, sugar spheres, talc, and triethyl citrate.

In an embodiment a composition comprising a prebiotic is provided in the form of enteric-coated granules, for oral administration. The compositions can further comprise carnauba wax, crospovidone, diacetylated monoglycerides, ethylcellulose, hydroxypropyl cellulose, hypromellose phthalate, magnesium stearate, mannitol, sodium hydroxide, sodium stearyl fumarate, talc, titanium dioxide, and yellow ferric oxide.

In another embodiment a composition comprising a prebiotic can further comprise calcium stearate, crospovidone, hydroxypropyl methylcellulose, iron oxide, mannitol, methacrylic acid copolymer, polysorbate 80, povidone, propylene glycol, sodium carbonate, sodium lauryl sulfate, titanium dioxide, and triethyl citrate.

The compositions provided herein can be in unit-dosage forms or multiple-dosage forms. Unit-dosage forms, as used herein, refer to physically discrete units suitable for administration to human or non-human animal subject in need thereof and packaged individually. Each unit-dose can contain a predetermined quantity of an active ingredient(s) sufficient to produce the desired therapeutic effect, in association with other pharmaceutical carriers or excipients. Examples of unit-dosage forms include, but are not limited to, ampoules, syringes, and individually packaged tablets and capsules. Unit-dosage forms can be administered in fractions or multiples thereof. A multiple-dosage form is a plurality of identical unit-dosage forms packaged in a single container, which can be administered in segregated unit-dosage form. Examples of multiple-dosage forms include, but are not limited to, vials, bottles of tablets or capsules, or bottles of pints or gallons. In another embodiment the multiple dosage forms comprise different pharmaceutically active agents. For example a multiple dosage form can be provided which comprises a first dosage element comprising a composition comprising a prebiotic and a second dosage element comprising lactose or a probiotic, which can be in a modified release form.

In this example a pair of dosage elements can make a single unit dosage. In an embodiment a kit is provided comprising multiple unit dosages, wherein each unit comprises a first dosage element comprising a composition comprising a prebiotic and a second dosage element comprising probiotic, lactose or both, which can be in a modified release form. In another embodiment the kit further comprises a set of instructions.

In an embodiment, compositions can be formulated in various dosage forms for oral administration. The compositions can also be formulated as a modified release dosage form, including immediate-, delayed-, extended-, prolonged-, sustained-, pulsatile-, controlled-, extended, accelerated-, fast-, targeted-, programmed-release, and gastric retention dosage forms. These dosage forms can be prepared according to known methods and techniques (see, Remington: The Science and Practice of Pharmacy, supra; Modified-Release Drug Delivery Technology, Rathbone et al., Eds., Drugs and the Pharmaceutical Science, Marcel Dekker, Inc.: New York, N.Y., 2002; Vol. 126, which is herein incorporated by reference in its entirety).

In an embodiment, the compositions are in one or more dosage forms. For example, a composition can be administered in a solid or liquid form. Examples of solid dosage forms include but are not limited to discrete units in capsules or tablets, as a powder or granule, or present in a tablet conventionally formed by compression molding. Such compressed tablets can be prepared by compressing in a suitable machine the three or more agents and a pharmaceutically acceptable carrier. The molded tablets can be optionally coated or scored, having indicia inscribed thereon and can be so formulated as to cause immediate, substantially immediate, slow, controlled or extended release of a composition comprising a prebiotic. Furthermore, dosage forms of the invention can comprise acceptable carriers or salts known in the art, such as those described in the Handbook of Pharmaceutical Excipients, American Pharmaceutical Association (1986), incorporated by reference herein in its entirety.

In an embodiment, an effective amount of a composition comprising a prebiotic is mixed with a pharmaceutical excipient to form a solid preformulation composition comprising a homogeneous mixture of compounds described herein. When referring to these compositions as "homogeneous," it is meant that the agents are dispersed evenly throughout the composition so that the composition can be subdivided into unit dosage forms such as tablets, caplets, or capsules. This solid preformulation composition can then be subdivided into unit dosage forms of the type described above comprising from, for example, 1 g to 20 mg of a prebiotic composition. A prebiotic composition can be formulated, in the case of caplets, capsules or tablets, to be swallowed whole, for example with water.

The compositions described herein can be in liquid form. The liquid formulations can comprise, for example, an agent in water-in-solution and/or suspension form; and a vehicle comprising polyethoxylated castor oil, alcohol, and/or a polyoxyethylated sorbitan mono-oleate with or without flavoring. Each dosage form comprises an effective amount of an active agent and can optionally comprise pharmaceutically inert agents, such as conventional excipients, vehicles, fillers, binders, disintegrants, pH adjusting substances, buffer, solvents, solubilizing agents, sweeteners, coloring agents, and any other inactive agents that can be included in pharmaceutical dosage forms for oral administration. Examples of such vehicles and additives can be found in Remington's Pharmaceutical Sciences, 17th edition (1985).

2. Manufacturing

The dosage forms described herein can be manufactured using processes that are well known to those of skill in the art. For example, for the manufacture of tablets, an effective amount of a prebiotic can be dispersed uniformly in one or more excipients, for example, using high shear granulation, low shear granulation, fluid bed granulation, or by blending for direct compression. Excipients include diluents, binders, disintegrants, dispersants, lubricants, glidants, stabilizers, surfactants and colorants. Diluents, also termed "fillers," can be used to increase the bulk of a tablet so that a practical size is provided for compression. Non-limiting examples of diluents include lactose, cellulose, microcrystalline cellulose, mannitol, dry starch, hydrolyzed starches, powdered sugar, talc, sodium chloride, silicon dioxide, titanium oxide, dicalcium phosphate dihydrate, calcium sulfate, calcium carbonate, alumina and kaolin. Binders can impart cohesive qualities to a tablet formulation and can be used to help a tablet remain intact after compression. Non-limiting examples of suitable binders include starch (including corn starch and pregelatinized starch), gelatin, sugars (e.g., glucose, dextrose, sucrose, lactose and sorbitol), celluloses, polyethylene glycol, waxes, natural and synthetic gums, e.g., acacia, tragacanth, sodium alginate, and synthetic polymers such as polymethacrylates and polyvinylpyrrolidone. Lubricants can also facilitate tablet manufacture; non-limiting examples thereof include magnesium stearate, calcium stearate, stearic acid, glyceryl behenate, and polyethylene glycol. Disintegrants can facilitate tablet disintegration after administration, and non-limiting examples thereof include starches, alginic acid, crosslinked polymers such as, e.g., crosslinked polyvinylpyrrolidone, croscarmellose sodium, potassium or sodium starch glycolate, clays, celluloses, starches, gums and the like. Non-limiting examples of suitable glidants include silicon dioxide, talc, and the like. Stabilizers can inhibit or retard drug decomposition reactions, including oxidative reactions. Surfactants can also include and can be anionic, cationic, amphoteric or nonionic. If desired, the tablets can also comprise nontoxic auxiliary substances such as pH buffering agents, preservatives, e.g., antioxidants, wetting or emulsifying agents, solubilizing agents, coating agents, flavoring agents, and the like.

In an embodiment, a softgel formulation is made with a gelatin mass for the outer shell, and a composition including one or more substances, for example prebiotics and/or probiotics, for the capsule fill can be prepared. To make the gelatin mass, gelatin powder can be mixed with water and glycerin, heated, and stirred under vacuum. Additives, for example, flavors or colors, can be added to molten gelatin using a turbine mixer and transferred to mobile vessels. The gelatin mass can be kept in a steam-jacketed storage vessel at a constant temperature.

The encapsulation process can begin when the molten gel is pumped to a machine and two thin ribbons of gel are formed on either side of machine. These ribbons can then pass over a series of rollers and over a set of die that determine the size and shapes of capsules. A fill composition, for example a prebiotic and/or probiotic fill composition, can be fed to a positive displacement pump, which can dose the fill and inject it between two gelatin ribbons prior to sealing them together through the application of heat and pressure. To remove excess water, the capsules can pass through a conveyer into tumble dryers where a portion of the water can be removed. The capsules can then be placed on, for example, trays, which can be stacked and transferred into drying rooms. In the drying rooms, dry air can be forced over capsules to remove any excess moisture.

3. Release Formulations

Immediate-release formulations of an effective amount of a prebiotic composition can comprise one or more combinations of excipients that allow for a rapid release of a pharmaceutically active agent (such as from 1 minute to 1 hour after administration). In an embodiment an excipient can be microcrystalline cellulose, sodium carboxymethyl cellulose, sodium starch glycolate, corn starch, colloidal silica, Sodium Laurel Sulphate, Magnesium Stearate, Prosolve SMCC (HD90), croscarmellose Sodium, Crospovidone NF, Avicel PH200, and combinations of such excipients.

"Controlled-release" formulations (also referred to as sustained release (SR), extended-release (ER, XR, or XL), time-release or timed-release, controlled-release (CR), or continuous-release) refer to the release of a prebiotic composition from a dosage form at a particular desired point in time after the dosage form is administered to a subject. Controlled-release formulations can include one or more excipients, including but not limited to microcrystalline cellulose, sodium carboxymethyl cellulose, sodium starch glycolate, corn starch, colloidal silica, Sodium Laurel Sulphate, Magnesium Stearate, Prosolve SMCC (HD90), croscarmellose Sodium, Crospovidone NF, or Avicel PH200. Generally, controlled-release includes sustained but otherwise complete release. A sudden and total release in the large intestine at a desired and appointed time or a release in the intestines such as through the use of an enteric coating are both considered controlled-release. Controlled-release can occur at a predetermined time or in a predetermined place within the digestive tract. It is not meant to include a passive, uncontrolled process as in swallowing a normal tablet. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,556; 5,871,776; 5,902,632; and 5,837,284 each of which is incorporated herein by reference in its entirety.

In an embodiment a controlled release dosage form begins its release and continues that release over an extended period of time. Release can occur beginning almost immediately or can be sustained. Release can be constant, can increase or decrease over time, can be pulsed, can be continuous or intermittent, and the like. Generally, however, the release of at least one pharmaceutically active agent from a controlled-release dosage form will exceed the amount of time of release of the drug taken as a normal, passive release tablet. Thus, for example, while all of at least one pharmaceutically active agent of an uncoated aspirin tablet should be released within, for example, four hours, a controlled-release dosage form could release a smaller amount of aspirin over a period of six hours, 12 hours, or even longer. Controlled-release in accordance with the compositions and methods described herein generally means that the release occurs for a period of six hours or more, such as 12 hours or more.

In another embodiment a controlled release dosage refers to the release of an agent, from a composition or dosage form in which the agent is released according to a desired profile over an extended period of time. In an embodiment, controlled-release results in dissolution of an agent within 20-720 minutes after entering the stomach. In another embodiment, controlled-release occurs when there is dissolution of an agent within 20-720 minutes after being swallowed. In another embodiment, controlled-release occurs when there is dissolution of an agent within 20-720 minutes after entering the intestine. In another embodiment, controlled-release results in substantially complete dissolution after at least 1 hour following administration. In another embodiment, controlled-release results in substantially complete dissolution after at least 1 hour following oral administration. For example, controlled-release compositions allow delivery of an agent to a subject in need thereof over an extended period of time according to a predetermined profile. Such release rates can provide therapeutically effective levels of agent for an extended period of time and thereby provide a longer period of pharmacologic or diagnostic response as compared with conventional rapid release dosage forms. Such longer periods of response provide for many inherent benefits that are not achieved with immediate-release dosages. When used in connection with the dissolution profiles discussed herein, the term "controlled-release" refers to wherein all or less than all of the total amount of a dosage form, made according to methods and compositions described herein, delivers an active agent over a period of time greater than 1 hour.

In one aspect, controlled-release refers to delayed release of an agent, from a composition or dosage form in which the agent is released according to a desired profile in which the release occurs after a period of time.

When present in a controlled-release oral dosage form, the compositions described herein can be administered at a substantially lower daily dosage level than immediate-release forms.

In an embodiment, the controlled-release layer is capable of releasing 30 to 40% of the one or more active agents (e.g., prebiotic and/or probiotic) contained therein in the stomach of a subject in need thereof in 5 to 10 minutes following oral administration. In another embodiment, the controlled-release layer is capable of releasing 90% of the one or more active agents (e.g., prebiotic and/or probiotic) is released in 40 minutes after oral administration.

In some embodiments, the controlled-release layer comprises one or more excipients, including but not limited to silicified microcrystalline cellulose (e.g., HD90), croscarmellose sodium (AC-Di-Sol), hydroxyl methyl propyl cellulose, magnesium stearate, or stearic acid. In an embodiment, a controlled release formulation weighs between 100 mg to 3 g.

Pharmaceutical carriers or vehicles suitable for administration of the compounds provided herein include all such carriers known to those skilled in the art to be suitable for the particular mode of administration. In addition, the compositions can one or more components that do not impair the desired action, or with components that supplement the desired action, or have another action.

In another embodiment, an effective amount of the prebiotic is formulated in an immediate release form. In this embodiment the immediate-release form can be included in an amount that is effective to shorten the time to its maximum concentration in the blood. By way of example, certain immediate-release pharmaceutical preparations are taught in United States Patent Publication US 2005/0147710A1 entitled, "Powder Compaction and Enrobing," which is incorporated herein in its entirety by reference.

The dosage forms described herein can also take the form of pharmaceutical particles manufactured by a variety of methods, including but not limited to high-pressure homogenization, wet or dry ball milling, or small particle precipitation (nano spray). Other methods to make a suitable powder formulation are the preparation of a solution of active ingredients and excipients, followed by precipitation, filtration, and pulverization, or followed by removal of the solvent by freeze-drying, followed by pulverization of the powder to the desired particle size.

In a further aspect the dosage form can be an effervescent dosage form. Effervescent means that the dosage form, when mixed with liquid, including water and saliva, evolves a gas.

Some effervescent agents (or effervescent couple) evolve gas by means of a chemical reaction which takes place upon exposure of the effervescent disintegration agent to water or to saliva in the mouth. This reaction can be the result of the reaction of a soluble acid source and an alkali monocarbonate or carbonate source. The reaction of these two general compounds produces carbon dioxide gas upon contact with water or saliva. An effervescent couple (or the individual acid and base separately) can be coated with a solvent protective or enteric coating to prevent premature reaction. Such a couple can also be mixed with previously lyophilized particles (such as a prebiotic). The acid sources can be any which are safe for human consumption and can generally include food acids, acid and hydrite antacids such as, for example: citric, tartaric, amalic, fumeric, adipic, and succinics. Carbonate sources include dry solid carbonate and bicarbonate salt such as, preferably, sodium bicarbonate, sodium carbonate, potassium bicarbonate and potassium carbonate, magnesium carbonate and the like. Reactants which evolve oxygen or other gasses and which are safe for human consumption are also included. In an embodiment citric acid and sodium bicarbonate are used.

In another aspect the dosage form can be in a candy form (e.g., matrix), such as a lollipop or lozenge. In an embodiment an effective amount of a prebiotic is dispersed within a candy matrix. In an embodiment the candy matrix comprises one or more sugars (such as dextrose or sucrose). In another embodiment the candy matrix is a sugar-free matrix. The choice of a particular candy matrix is subject to wide variation. Conventional sweeteners such as sucrose can be utilized, or sugar alcohols suitable for use with diabetic patients, such as sorbitol or mannitol can be employed. Other sweeteners, such as the aspartame, can also be easily incorporated into a composition in accordance with compositions described herein. The candy base can be very soft and fast dissolving, or can be hard and slower dissolving. Various forms will have advantages in different situations.

A candy mass composition comprising an effective amount of the prebiotic can be orally administered to a subject in need thereof so that an effective amount of the prebiotic will be released into the subject's mouth as the candy mass dissolves and is swallowed. A subject in need thereof includes a human adult or child.

In an embodiment a candy mass is prepared that comprises one or more layers which can comprise different amounts or rates of dissolution of the prebiotic. In an embodiment a multilayer candy mass (such as a lollipop) comprises an outer layer with a concentration of the prebiotic differing from that of one or more inner layers. Such a drug delivery system has a variety of applications.

The choices of matrix and the concentration of the drug in the matrix can be important factors with respect to the rate of drug uptake. A matrix that dissolves quickly can deliver drug into the subject's mouth for absorption more quickly than a matrix that is slow to dissolve. Similarly, a candy matrix that contains the prebiotic in a high concentration can release more of the prebiotic in a given period of time than a candy having a low concentration. In an embodiment a candy matrix such as one disclosed in U.S. Pat. No. 4,671,953 or US Application Publication No. 2004/0213828 (which are herein incorporated by reference in their entirety) is used to deliver the prebiotic.

The dosage forms described herein can also take the form of pharmaceutical particles manufactured by a variety of methods, including but not limited to high-pressure homogenization, wet or dry ball milling, or small particle precipitation (e.g., nGimat's NanoSpray). Other methods useful to make a suitable powder formulation are the preparation of a solution of active ingredients and excipients, followed by precipitation, filtration, and pulverization, or followed by removal of the solvent by freeze-drying, followed by pulverization of the powder to the desired particle size. In an embodiment the pharmaceutical particles have a final size of 3-1000 μM, such as at most 3, 4, 5, 6, 7, 8, 9, 10, 20, 30, 40, 50, 60, 70, 80, 90, 100, 150, 200, 250, 300, 350, 400, 450, 500, 550, 600, 650, 700, 750, 800, 850, 900, 950, 1000 μM. In another embodiment the pharmaceutical particles have a final size of 10-500 μM. In another embodiment the pharmaceutical particles have a final size of 50-600 μM. In another embodiment the pharmaceutical particles have a final size of 100-800 μM.

In an embodiment an oral dosage form (such as a powder, tablet, or capsule) is provided comprising a prebiotic composition comprising 0.7 g of FOS, GOS, or other FOS, GOS, or other appropriate polysaccharide, 0.2 g of lactose, 0.01 g of glucose, 0.01 g of galactose, 0.1-0.2 g of a binder, 0.1-0.2 g of a dispersant, 0.1-0.2 g of a solubilizer, wherein the FOS, GOS, or other FOS, GOS, or other appropriate polysaccharide are composed of 1-25% disaccharides, 1-25% trisaccharides, 1-25% tetrasaccharides, and 1-25% pentasaccharides. The oral dosage form can be in the form of a powder, capsule, or tablet. Suitable amounts of binders, dispersants, and solubilizers are known in the art for preparation of oral tablets or capsules.

In another embodiment an oral dosage form (such as a powder, tablet or capsule) is provided comprising a prebiotic composition comprising 1-99.9% by weight of FOS, GOS, or other FOS, GOS, or other appropriate polysaccharide 0.5-20% by weight of lactose, 0.1-2% by weight of glucose, 0.1-2% by weight of galactose, 0.05-2% by weight of a binder, 0.05-2% by weight of a dispersant, 0.05-2% by weight of a solubilizer, wherein the FOS, GOS, or other FOS, GOS, or other appropriate polysaccharide are composed of 1-25% by weight disaccharides, 1-25% by weight trisaccharides, 1-25% by weight tetrasaccharides, and 1-25% by weight pentasaccharides.

In another embodiment an oral dosage form (such as a powder, tablet, or capsule) is provided comprising a prebiotic composition comprising 1, 10, 20, 30, 40, 50, 60, 70, 80, 90, 95, 99.5, 100% by weight of FOS, GOS, or other FOS, GOS, or other appropriate polysaccharide 0, 5, 10, 15, or 20% by weight of lactose, 0.1, 0.5, 1, or 2% by weight of glucose, 0.1, 0.5, 1, or 2% by weight of galactose, 0.05, 0.1, 0.5, 1, or 2% by weight of a binder, 0.05, 0.1, 0.5, 1, or 2% by weight of a dispersant, 0.05, 0.1, 0.5, 1, or 2% by weight of a solubilizer, wherein the FOS, GOS, or other FOS, GOS, or other appropriate polysaccharide are composed of 1, 5, 10, 15, 20, or 25% by weight disaccharides, 1, 5, 10, 15, 20, or 25% by weight trisaccharides, 1, 5, 10, 15, 20, or 25% by weight tetrasaccharides, and 1, 5, 10, 15, 20, or 25% by weight pentasaccharides.

In another embodiment, an oral dosage form is provided comprising a prebiotic composition, wherein the oral dosage form is a syrup. The syrup can comprise 1%, 5%, 10%, 15%, 20%, 25%, 30%, 35%, 40%, 45%, 50%, 55%, 60%, 65%, 70%, 75%, 80%, or 85% solid. The syrup can comprise 15%, 20%, 25%, 30%, 35%, 40%, 45%, or 50% liquid, for example, water. The solid can comprise a prebiotic composition. The solid can be, for example, 1-96%, 10-96%, 20-96%, 30-96%, 40-96%, 50-96%, 60-96%, 70-96%, 80-96%, or 90-96% prebiotic composition. The solid can be, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96% prebiotic composition. In an embodiment a prebiotic composition comprises FOS, GOS, or other FOS, GOS, or other appropriate polysaccharide. In another embodiment a prebiotic composition comprises FOS, GOS, or other FOS, GOS, or other appropriate polysaccharide and another prebiotic. In another embodiment a prebiotic composition comprises FOS, GOS or other and inulin or GOS and FOS.

In an embodiment, the softgel capsule is 0.25 mL, 0.5 mL, 1.0 mL, 1.25 mL, 1.5 mL, 1.75 mL, or 2.0 mL. In another embodiment, a softgel capsule comprises 0.1 g to 2.0 g of prebiotic composition. In another embodiment, a softgel capsule comprises 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 g of a prebiotic composition. In an embodiment the prebiotic composition comprises FOS, GOS, or other FOS, GOS, or other appropriate polysaccharide. In another embodiment the prebiotic composition consists essentially of FOS, GOS, or other FOS, GOS, or other appropriate polysaccharide. In another embodiment, a softgel capsule comprises FOS, GOS, or other FOS, GOS, or other appropriate polysaccharide and inulin or FOS.

In another embodiment, the prebiotic composition is delivered in a gelatin capsule containing an amount of FOS, GOS, or other FOS, GOS, or other appropriate polysaccharide within the ranges listed in Table 2. In another embodiment, the number of pills taken per day is within the ranges listed in Table 2.

TABLE 2

Exemplary GOS Dosing Units
Exemplary GOS Composition
Dosages in Gel Caps

| Size | GOS/ Pill (g) | # pills per day |
|---|---|---|
| 000 | 1-2 | 1-15 |
| 00 | 0.6-1.5 | 1-25 |
| 0 | 0.4-1.1 | 1-38 |
| 1 | 0.3-0.8 | 1-50 |
| 2 | 0.25-0.6 | 1-60 |
| 3 | 0.2-0.5 | 1-75 |
| 4 | 0.14-0.3 | 1-107 |

In another embodiment, a prebiotic composition is provided that does not contain a preservative. In another embodiment, a prebiotic composition is provided that does not contain an antioxidant. In another embodiment, a prebiotic composition is provided that does not contain a preservative or an antioxidant. In an embodiment a prebiotic composition comprising FOS, GOS, or other FOS, GOS, or other appropriate polysaccharide does not contain a preservative or an antioxidant.

In another embodiment, a prebiotic composition is formulated as a viscous fluid. In another embodiment, a prebiotic composition is formulated such that its water content is low enough that it does not support microbial growth. In an embodiment, this composition is an intermediate-moisture food, with a water activity between 0.6 and 0.85; in another embodiment this composition is a low-moisture food, with a water activity less than 0.6. Low-moisture foods limit microbial growth significantly and can be produced by one of ordinary skill in the art. For example, these products could be produced similarly to a liquid-centered cough drop. In another embodiment, a prebiotic composition is formulated as a viscous fluid without a preservative in a gel capsule. In another embodiment, a prebiotic composition comprising FOS, GOS, or other FOS, GOS, or other appropriate polysaccharide is a viscous fluid. In another embodiment, a prebiotic composition comprises a high percentage of FOS, GOS, or other FOS, GOS, or other appropriate polysaccharide that does not support microbial growth. In another embodiment, the prebiotic composition comprises FOS, GOS, or other FOS, GOS, or other appropriate polysaccharide and inulin or FOS.

In another embodiment, an oral dosage form is provided comprising a prebiotic composition, wherein the oral dosage form is a softgel. In an embodiment the softgel comprises a syrup. In an embodiment the syrup comprises a prebiotic composition. In an embodiment the prebiotic composition comprises FOS, GOS, or other FOS, GOS, or other appropriate polysaccharide. In another embodiment the prebiotic composition comprises more than 80% FOS, GOS, or other FOS, GOS, or other appropriate polysaccharide. In another embodiment the prebiotic composition comprises between 80-99.9% FOS, GOS, or other. In another embodiment the prebiotic composition comprises more than 80% FOS, GOS, or other FOS, GOS, or other appropriate polysaccharide. In another embodiment the prebiotic composition comprises 80, 81, 82, 83, 84, 85, 86, 87, 88, 89, 90, 91, 92, 93, 94, 95, 96, 97, 98, 99, or 99.9% FOS, GOS, or other FOS, GOS, or other appropriate polysaccharide.

In an embodiment a FOS, GOS, or other FOS, GOS, or other appropriate polysaccharide composition is formulated for delivery in a soft gel capsule. In an embodiment a FOS, GOS, or other FOS, GOS, or other appropriate polysaccharide composition formulated for delivery in a soft gel capsule is a high percentage FOS, GOS, or other FOS, GOS, or other appropriate polysaccharide composition, such as a 90-100% FOS, GOS, or other FOS, GOS, or other appropriate polysaccharide composition (e.g., 90, 91, 92, 93, 94, 95, 96, 97, 98, 99 or 100% FOS, GOS, or other FOS, GOS, or other appropriate polysaccharide composition by weight). In another embodiment a FOS, GOS, or other FOS, GOS, or other appropriate polysaccharide composition formulated for delivery in a soft gel capsule comprises 95% FOS, GOS, or other FOS, GOS, or other appropriate polysaccharide. In another embodiment a FOS, GOS, or other FOS, GOS, or other appropriate polysaccharide composition formulated for delivery in a soft gel capsule comprises 96% FOS, GOS, or other FOS, GOS, or other appropriate polysaccharide. In another embodiment, the FOS, GOS, or other FOS, GOS, or other appropriate polysaccharide composition is formulated such that its water content is low enough that it does not support microbial growth. In another embodiment, the FOS, GOS, or other FOS, GOS, or other appropriate polysaccharide composition is formulated as a viscous fluid without a preservative in a gel capsule. In another embodiment, the FOS, GOS, or other FOS, GOS, or other appropriate polysaccharide composition is formulated as a viscous fluid without an antioxidant in a gel capsule. In another embodiment the soft gel capsule comprises 0.1-2 g of a FOS, GOS, or other FOS, GOS, or other appropriate polysaccharide composition.

In another embodiment a prebiotic composition can be formulated as described, in U.S. Pat. No. 6,750,331, which is herein incorporated by reference in its entirety. A prebiotic composition can be formulated to comprise an oligosaccharide, a foaming component, a water-insoluble dietary fiber (e.g., cellulose or lignin), or a neutralizing component. In an embodiment a prebiotic composition can be in the form of a chewable tablet.

In an embodiment a foaming component can be at least one member selected from the group consisting of sodium hydrogencarbonate, sodium carbonate, and calcium carbonate. In an embodiment a neutralizing component can be at least one member selected from the group consisting of citric acid, L-tartaric acid, fumaric acid, L-ascorbic acid, DL-malic acid, acetic acid, lactic acid, and anhydrous citric acid. In an embodiment a water-insoluble dietary fiber can be at least one member selected from the group consisting of crystalline cellulose, wheat bran, oat bran, cone fiber, soy fiber, and beet fiber. The formulation can contain a sucrose fatty acid ester, powder sugar, fruit juice powder, and/or flavoring material.

Formulations of the provided invention can include additive components selected from various known additives. Such additives include, for example, saccharides (excluding oligosaccharides), sugar alcohols, sweeteners and like excipients, binders, disintegrators, lubricants, thickeners, surfactants, electrolytes, flavorings, coloring agents, pH modifiers, fluidity improvers, and the like. Specific examples of the additives include wheat starch, potato starch, corn starch, dextrin and like starches; sucrose, glucose, fructose, maltose, xylose, lactose and like saccharides (excluding oligosaccharides); sorbitol, mannitol, maltitol, xylitol and like sugar alcohols; calcium phosphate, calcium sulfate and like excipients; starch, saccharides, gelatin, gum arabic, dextrin, methyl cellulose, polyvinylpyrrolidone, polyvinyl alcohol, hydroxypropylcellulose, xanthan gum, pectin, gum tragacanth, casein, alginic acid and like binders and thickeners; leucine, isoleucine, L-valine, sugar esters, hardened oils, stearic acid, magnesium stearate, talc, macrogols and like lubricants; CMC, CMC-Na, CMC-Ca and like disintegrators; polysorbate, lecithin and like surfactants; aspartame, alitame and like dipeptides; silicon dioxide and like fluidity improvers; and *stevia*, saccharin, and like sweeteners. The amounts of these additives can be properly selected based on their relation to other components and properties of the preparation, production method, etc.

In an embodiment, a FOS, GOS, or other FOS, GOS, or other appropriate polysaccharide composition is a chewable oral dosage formulation. In an embodiment the chewable formulation can comprises between 1-99.9% FOS, GOS, or other FOS, GOS, or other appropriate polysaccharide. In an embodiment, a FOS, GOS, or other FOS, GOS, or other appropriate polysaccharide composition comprises 80% FOS, GOS, or other FOS, GOS, or other appropriate polysaccharide 5% L-ascorbic acid, 2% anhydrous citric acid, 3% sodium hydrogencarbonate, 3% calcium carbonate, 2% sucrose fatty acid, 3% fruit juice powder, and 2% potassium carbonate.

In another embodiment, a FOS, GOS, or other FOS, GOS, or other appropriate polysaccharide composition comprises 85% FOS, GOS, or other FOS, GOS, or other appropriate polysaccharide, 5% L-ascorbic acid, 3% sodium hydrogencarbonate, 2% sodium carbonate, 2% sucrose fatty acid ester, 2% fruit juice powder, and 1% potassium carbonate.

In another embodiment, a FOS, GOS, or other FOS, GOS, or other appropriate polysaccharide composition comprises 90% FOS, GOS, or other FOS, GOS, or other appropriate polysaccharide, 2% L-ascorbic acid, 1% anhydrous citric acid, 2% sodium hydrogencarbonate, 2% sodium carbonate, 2% sucrose fatty acid ester, and 1% potassium carbonate.

In another embodiment, a FOS, GOS, or other FOS, GOS, or other appropriate polysaccharide composition comprises 95% FOS, GOS, or other FOS, GOS, or other appropriate polysaccharide, 2% L-ascorbic acid, 1% sodium hydrogencarbonate, and 2% fruit juice powder. In another embodiment, a FOS, GOS, or other FOS, GOS, or other appropriate polysaccharide composition comprises 95% FOS, GOS, or other FOS, GOS, or other appropriate polysaccharide and 5% of L-ascorbic acid, anhydrous citric acid, sodium hydrogencarbonate, calcium carbonate, sucrose fatty acid, fruit juice powder, or potassium carbonate.

In another embodiment, a FOS, GOS, or other FOS, GOS, or other appropriate polysaccharide composition comprises 95% FOS, GOS, or other FOS, GOS, or other appropriate polysaccharide and 5% of L-ascorbic acid, anhydrous citric acid, sodium hydrogencarbonate, calcium carbonate, sucrose fatty acid, fruit juice powder, and potassium carbonate.

Combination Therapy

In some embodiments, the compositions of the present invention can be used in conjunction with traditional treatments for a musculoskeletal disorder, such as an anti-osteoporosis or osteopenia therapy. In some embodiments, the present invention is administered together with at least one other agent. In some embodiments, the present invention is administered before the at least one other agent. In other embodiments, the present invention is administered after cessation of another therapy. The therapy includes, but is not limited to, approved therapies for osteoporosis, osteopenia, Paget's disease, stunting, osteoarthritis, osteomyelitis, delayed or on-union fractures, or any combination of the foregoing.

Some therapies for osteoporosis or osteopenia that are known in the art include: estrogen, estrogen agonists, estrogen antagonists, and bisphosphonates. One of skill in the art would understand that the present invention may be used to supplement, increase efficacy of, or otherwise improve upon any of a number of known therapies for osteoporosis or osteopenia.

Medical Foods

An alternate embodiment of the present invention is a formulation as a medical food.

The consuming public has come to understand that foods possess more than basic nutrition (protein, carbohydrate, fat, etc). For example, 95% of consumers agree that "certain foods have health benefits that go beyond basic nutrition and may reduce the risk of disease or other health concerns." More than 50% of consumers believe that foods can replace the use of drugs. Replacing the use of drugs may have the benefit of reducing the incidence of adverse side effects suffered by patients following a pharmaceutical drug treatment regimen. In fact, medical foods are assumed to be generally safe, as people have historically consumed these foods safely in non-medical contexts.

The compositions of the invention may be administered under the supervision of a medical specialist, or may be self-administered. Medical foods could take the form of nutritional shakes or other liquids or meal replacements. Medical foods of the present invention could also take the form of a powder capable of being consumed upon addition to suitable food or liquid.

A medical food formulation of the present invention could confer benefits of a synthetic composition of microbes isolated from nutritionally beneficial plants, as well as the benefits of prebiotics, or other nutritionally beneficial inclusions, but not consumed to obtain nutrition from them but rather to provide a metabolic function different than a foodstuff. For example, medical foods of the invention may also include at least one vitamin, or vitamin precursor. Preferred vitamins possess antioxidant properties and include vitamins A, C and E, and/or their biochemical precursors. Another embodiment of the medical foods of the invention also includes at least one trace element, preferably selected from the group consisting of zinc, manganese and selenium. Medical foods of the invention also may include at least one additional antioxidant selected from the group consisting of carotenoids, N-acetylcysteine and L-glutamine. It is known to those of skill in the art how to construct medical foods containing these elements.

Medical foods of the present invention would include effective doses of microbes deemed useful for the indication and effective doses of any vitamin, prebiotic, or other beneficial additive not consumed to obtain nutrition but to add a therapeutic benefit mediated by the production of SCFA or other immuno-stimulant molecules when passing through the GI tract.

Typically, the dietary supplements and medical foods of the present invention are consumed at least once daily, and preferably administered two times per day, preferably once in the morning and once in the afternoon. A typical treatment regime for the dietary supplements or medical foods will continue for four to eight weeks. Depending on such factors as the medical condition being treated and the response of the patient, the treatment regime may be extended. A medical food of the present invention will typically be consumed in two servings per day as either a meal replacement or as a snack between meals.

Anyone perceived to be at risk from a musculoskeletal disorder, including, or already suffering from any of the foregoing, can potentially benefit from ingesting the compositions of the invention. According to the invention it is believed to be possible to effectively ameliorate symptoms and conditions associated with musculoskeletal disorders with natural compounds, which do not show any severe side effects. Furthermore, the present methods are expected to be well-tolerated, for example without causing any discomfort or nausea, and simple to apply.

Additional Embodiments

[Add Additional Embodiments Regarding Non-Osteoporosis Indications]

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

Example 1: Microbial Preparations and Metagenomic Analyses

A sample set of 15 vegetables typically eaten raw was selected to analyze the microbial communities by whole genome shotgun sequencing and comparison to microbial databases. The 15 fruits and vegetable samples are shown in Table 3 and represent ingredients in typical salads or eaten fresh. The materials were sourced at the point of distribution in supermarkets selling both conventional and organic farmed vegetables, either washed and ready to eat or without washing.

The samples were divided into 50 g portions, thoroughly rinsed with tap water and blended for 30 seconds on phosphate buffer pH 7.4 (PBS) in a household blender. The resulting slurry was strained by serial use of a coarse and then a fine household sieve followed by filtration through a 40 mm sieve. The cell suspension containing the plant microbiota, chloroplasts and plant cell debris was centrifuged at slow speed for removing plant material and the resulting supernatant centrifuged at high speed to pellet microbial cells. The pellet resuspended in a buffer containing a proprietary plant cell lysis buffer consisting of chelating agents such as EDTA or Versetene EDTA-based chelating agents to remove divalent ions and a suitable non-ionic detergent such as Tween-20, Tween 80, Triton X, and washed then with PBS. For sample #12 (broccoli) the cell pellet was washed and a fraction of the biomass separated and only the top part of the pellet collected. This was deemed "broccoli juice" for analyses. The resulting microbiota prep was inspected under fluorescence microscopy with DNA stains to visualize plant and microbial cells based on cell size and DNA structure (nuclei for plants) and selected for DNA isolation based on a minimum ratio of 9:1 microbe to plant cells. The DNA isolation was based on the method reported by Marmur (1961), or using commercial DNA extraction kits based on magnetic beads such as Thermo Charge Switch resulting in a quality suitable for DNA library prep and free of PCR inhibitors.

The DNA was used to construct a single read 150 base pair libraries and a total of 26 million reads sequenced per sample according to the standard methods done by CosmosID (www.cosmosid.com) for samples #1 to #12 or 300 base pair-end libraries and sequenced in an Illumina NextSeq instrument covering 4 Gigabases per sample for samples #13 to #15. The unassembled reads were then mapped to the CosmosID for first 12 samples or OneCodex for the last 3 samples databases containing 36,000 reference bacterial genomes covering representative members from diverse taxa. The mapped reads were tabulated and represented using a "sunburst" plot to display the relative abundance for each genome identified corresponding to that bacterial strain and normalized to the total of identified reads for each sample. In addition, phylogenetic trees were constructed based on the classification for each genome in the database with a curated review. There are genomes that have not been updated in the taxonomic classifier and therefore reported as unclassified here but it does not reflect a true lack of clear taxonomic position, it reflects only the need for manual curation and updating of those genomes in the taxonomic classifier tool. Lastly, samples 16 to 21 were analyzed using Kraken2 taxonomic sequence classification approach (Wood and Salzberg, 2014). The unassembled reads were filtered out by mapping the reads to each plant host genome sequences if available. Taxonomic labels were assigned to each sequencing read by Kraken2 according to the standard Kraken2 database that includes complete RefSeq genome sequences (O'Leary et al. 2016). Then, the abundance of species in each metagenomic sample was estimated using Bracken (Lu et al. 2017). The relative abundances were presented in pie chart at each taxonomic level.

In addition to the shotgun metagenomics survey, relevant microbes were isolated from fruits and vegetables listed in Table 3 using potato dextrose agar, nutrient agar or MRS agar and their genomes sequenced to cover 50× and analyzed their metabolic potential by using genome-wide models. For example, a yeast isolated from blueberries was sequenced and its genome showed identity to *Aureobasidium subglaciale* assembled in contigs with an N50 of 71 Kb and annotated to code for 10, 908 genes. Similarly, bacterial genomes from the same sample were sequenced and annotated for strains with high identity to *Pseudomonas* and *Rahnella*.

TABLE 3

| Samples analyzed. | |
|---|---|
| Sample number | sample description |
| 1 | Chard |
| 2 | Red cabbage |
| 3 | Romaine lettuce |
| 4 | Celery |
| 5 | Butterhead lettuce |
| 6 | Baby spinach |
| 7 | Crisp green gem lettuce |
| 8 | Red oak leaf lettuce |
| 9 | Green oak leaf lettuce |
| 10 | Cherry tomato |
| 11 | Crisp red gem lettuce |
| 12 | Broccoli juice |
| 13 | Broccoli head |
| 14 | Blueberries |
| 15 | Pickled olives |
| 16 | Gingseng |
| 17 | Blackberries |
| 18 | Squash gourd |
| 19 | Broccolini |
| 20 | Fermented cabbage |
| 21 | Fermented pepper paste |

Results

For most samples, bacterial abundances of fresh material contain 10ˆ4 to 10ˆ8 microbes per gram of vegetable as estimated by direct microscopy counts or viable counts. Diverse cell morphologies were observed including rods, elongated rods, cocci and fungal hyphae. Microorganisms were purified from host cells, DNA was isolated and sequenced using a shotgun approach mapping reads to 35,000 bacterial genomes applying a k-mer method using Cosmos ID (https://www.cosmosid.com/). All samples were dominated by gamma proteobacteria, primarily Pseudomonadacea, presumably largely endophytes as some samples were triple washed before packaging. *Pseudomonas* cluster was the dominant genera for several samples with 10-90% of the bacterial relative abundance detected per sample and mapped to a total of 27 different genomes indicating it is a diverse group. A second relevant bacterial strain identified was *Duganella zoogloeoides* ATCC 25935 as it was present in almost all the samples ranging from 1-6% of the bacterial relative abundance detected per sample or can reach 29% of the bacterial relative abundance detected per sample in organic romaine. Red cabbage was identified to contain a relatively large proportion of lactic acid bacteria as it showed 22% *Lactobacillus crispatus*, a species commercialized as probiotic and recognized relevant in vaginal healthy microbial community. Another vegetable containing lactic acid bacteria was red oak leaf lettuce containing 1.5% of the bacterial relative abundance detected per sample *Lactobacillus reuteri*. Other bacterial species recognized as probiotics included *Bacillus, Bacteroidetes, Propionibacterium* and *Streptococcus*. A large proportion of the abundant taxa in most samples was associated with plant microbiota and members recognized to act as biocontrol agents against fungal diseases or growth promoting agents such as *Pseudomonas fluorescens*. The aggregated list of unique bacteria detected by the k-mer method is 287 (Table 4).

Blueberries contain a mixture of bacteria and fungi dominated by *Pseudomonas* and *Propionibacterium* but the yeast *Aureobasidium* was identified as a relevant member of the community. A lesser abundant bacterial species was *Rahnella*. Pickled olives are highly enriched in lactic acid bacteria after being pickled in brine allowing the endogenous probiotic populations to flourish by acidifying the environment and eliminating most of the acid-sensitive microbes including bacteria and fungi. This resulted in a large amount of *Lactobacillus* species and *Pediococcus* recognized as probiotics and related to osteoporosis treatment. Other fermented samples included fermented cabbage and chili pepper paste. Fermented cabbage contained *Pediococcus pentosaceus* as well as dominant gamma proteobacteria. Fermented chili pepper paste enriched for *Lactobacillus* with 31% of the bacterial population but also *Leuconostoc mesenteroides* and *Pediococcus pentosaceus* were enriched. One unexpected sample containing lactic acid bacteria was squash gourd showing 59% *Lactococcus* but also *Leuconostoc* was present at 3.5% of the bacterial population. In addition to the bacterial populations, some samples also contained yeast not shown in Kraken2 plots from which *Pichia* was isolated, such as fermented chili pepper paste.

The shotgun sequencing method allows for the analysis of the metagenome including genes coding for metabolic reactions involved in the assimilation of nutrient, fermentative processes to produce short chain fatty acids, flavonoids and other relevant molecules in human nutrition.

TABLE 4

Bacteria identified in a 15 sample survey identified by whole genome matching to reference genomes. The fruits and vegetables were selected based on their recognition as part of the whole food plant-based diet and some antidiabetic and obesogenic properties. There is general recognition of microbes in these vegetables relevant for plant health but not previously recognized for their use in human health.

| Strain identified by k-mer based on entire genome | Strain number | Collection |
|---|---|---|
| *Acinetobacter baumannii* | — | |
| *Acinetobacter soli* | — | |
| *Acinetobacter* 41764 Branch | — | |
| *Acinetobacter* 41930 Branch | — | |
| *Acinetobacter* 41981 Branch | — | |
| *Acinetobacter* 41982 Branch | — | |
| *Acinetobacter baumannii* 348935 | — | |
| *Acinetobacter baumannii* 40298 Branch | — | |
| *Acinetobacter beijerinckii* 41969 Branch | — | |
| *Acinetobacter beijerinckii* CIP 110307 | CIP 110307 | WFCC |
| *Acinetobacter bohemicus* ANC 3994 | — | |
| *Acinetobacter guillouiae* 41985 Branch | — | |
| *Acinetobacter guillouiae* 41986 Branch | — | |
| *Acinetobacter gyllenbergii* 41690 Branch | — | |
| *Acinetobacter haemolyticus* TG19602 | — | |

TABLE 4-continued

Bacteria identified in a 15 sample survey identified by whole genome matching to reference genomes. The fruits and vegetables were selected based on their recognition as part of the whole food plant-based diet and some antidiabetic and obesogenic properties. There is general recognition of microbes in these vegetables relevant for plant health but not previously recognized for their use in human health.

| Strain identified by k-mer based on entire genome | Strain number | Collection |
|---|---|---|
| *Acinetobacter harbinensis* strain HITLi 7 | — | |
| *Acinetobacter johnsonii* 41886 Branch | — | |
| *Acinetobacter johnsonii* ANC 3681 | — | |
| *Acinetobacter junii* 41994 Branch | — | |
| *Acinetobacter lwoffii* WJ10621 | — | |
| *Acinetobacter* sp 41945 Branch | — | |
| *Acinetobacter* sp 41674 Branch | — | |
| *Acinetobacter* sp 41698 Branch | — | |
| *Acinetobacter* sp ETR1 | — | |
| *Acinetobacter* sp NIPH 298 | — | |
| *Acinetobacter tandoii* 41859 Branch | — | |
| *Acinetobacter tjernbergiae* 41962 Branch | — | |
| *Acinetobacter towneri* 41848 Branch | — | |
| *Acinetobacter venetianus* VE C3 | — | |
| *Actinobacterium* LLX17 | — | |
| *Aeromonas bestiarum* strain CECT 4227 | CECT 4227 | CECT |
| *Aeromonas caviae* strain CECT 4221 | CECT 4221 | CECT |
| *Aeromonas hydrophila* 4AK4 | — | |
| *Aeromonas media* 37528 Branch | — | |
| *Aeromonas media* strain ARB 37524 Branch | — | |
| *Aeromonas salmonicida* subsp 37538 Branch | — | |
| *Aeromonas* sp ZOR0002 | — | |
| *Agrobacterium* 22298 Branch | — | |
| *Agrobacterium* 22301 Branch | — | |
| *Agrobacterium* 22313 Branch | — | |
| *Agrobacterium* 22314 Branch | — | |
| *Agrobacterium* sp ATCC 31749 | ATCC 31749 | ATCC |
| *Agrobacterium tumefaciens* 22306 Branch | — | |
| *Agrobacterium tumefaciens* strain MEJ076 | — | |
| *Agrobacterium tumefaciens* strain S2 | — | |
| *Alkanindiges illinoisensis* DSM 15370 | DSM 15370 | WFCC |
| alpha proteobacterium L41A | — | |
| *Arthrobacter* 20515 Branch | — | |
| *Arthrobacter arilaitensis* Re117 | — | |
| *Arthrobacter chlorophenolicus* A6 | — | |
| *Arthrobacter nicotinovorans* 20547 Branch | — | |
| *Arthrobacter phenanthrenivorans* Sphe3 | — | |
| *Arthrobacter* sp 20511 Branch | — | |
| *Arthrobacter* sp PAO19 | — | |
| *Arthrobacter* sp W1 | — | |
| *Aureimonas* sp. Leaf427 | — | |
| *Aureobasidium pullulans* | — | |
| *Bacillaceae* Family 24 4101 12691 Branch | — | |
| *Bacillus* sp. LL01 | — | |
| *Bacillus* 12637 Branch | — | |
| *Bacillus aerophilus* strain C772 | — | |
| *Bacillus thuringiensis* serovar 12940 Branch | — | |
| *Brevundimonas nasdae* strain TPW30 | — | |
| *Brevundimonas* sp 23867 Branch | — | |
| *Brevundimonas* sp EAKA | — | |
| *Buchnera aphidicola* str 28655 Branch | — | |
| *Burkholderiales* Order 15 6136 Node 25777 | — | |
| *Buttiauxella agrestis* 35837 Branch | — | |
| *Candidatus Burkholderia verschuerenii* | — | |
| *Carnobacterium* 5833 Branch | — | |
| *Carnobacterium maltaromaticum* ATCC 35586 | ATCC 35586 | ATCC |
| *Chryseobacterium* 285 Branch | — | |
| *Chryseobacterium daeguense* DSM 19388 | DSM 19388 | WFCC |
| *Chryseobacterium formosense* | — | |
| *Chryseobacterium* sp YR005 | — | |
| *Clavibacter* 20772 Branch | — | |
| *Clostridium diolis* DSM 15410 | DSM 15410 | WFCC |
| *Comamonas* sp B 9 | — | |
| *Curtobacterium flaccumfaciens* 20762 Branch | — | |
| *Curtobacterium flaccumfaciens* UCD AKU | — | |
| *Curtobacterium* sp UNCCL17 | — | |
| *Deinococcus aquatilis* DSM 23025 | DSM 23025 | WFCC |
| *Debaromyces hansenii* | ATCC 36239 | ATCC |
| *Duganella zoogloeoides* | ATCC 25935 | |
| *Dyadobacter* 575 Branch | — | |
| *Elizabethkingia anophelis* | — | |
| *Empedobacter falsenii* strain 282 | — | |

TABLE 4-continued

Bacteria identified in a 15 sample survey identified by whole genome matching to reference genomes. The fruits and vegetables were selected based on their recognition as part of the whole food plant-based diet and some antidiabetic and obesogenic properties. There is general recognition of microbes in these vegetables relevant for plant health but not previously recognized for their use in human health.

| Strain identified by k-mer based on entire genome | Strain number | Collection |
|---|---|---|
| *Enterobacter* sp 638 | — | |
| *Enterobacteriaceae* Family 9 3608 Node 35891 | — | |
| *Enterobacteriaceae* Family 9 593 Node 36513 | — | |
| *Epilithonimonas lactis* | — | |
| *Epilithonimonas tenax* DSM 16811 | DSM 16811 | WFCC |
| *Erwinia* 35491 Branch | — | |
| *Erwinia amylovora* 35816 Branch | — | |
| *Erwinia pyrifoliae* 35813 Branch | — | |
| *Erwinia tasmaniensis* Et1 99 | DSM 17950 | WFCC |
| *Escherichia coli* ISC11 | — | |
| *Exiguobacterium* 13246 Branch | — | |
| *Exiguobacterium* 13260 Branch | — | |
| *Exiguobacterium sibiricum* 255 15 | DSM 17290 | WFCC |
| *Exiguobacterium* sp 13263 Branch | — | |
| *Exiguobacterium undae* 13250 Branch | — | |
| *Exiguobacterium undae* DSM 14481 | DSM 14481 | WFCC |
| *Flavobacterium* 237 Branch | — | |
| *Flavobacterium aquatile* LMG 4008 | LMG 4008 | WFCC |
| *Flavobacterium chungangense* LMG 26729 | LMG 26729 | WFCC |
| *Flavobacterium daejeonense* DSM 17708 | DSM 17708 | WFCC |
| *Flavobacterium hibernum* strain DSM 12611 | DSM 12611 | WFCC |
| *Flavobacterium hydatis* | — | |
| *Flavobacterium johnsoniae* UW101 | ATCC 17061D-5 | ATCC |
| *Flavobacterium reichenbachii* | — | |
| *Flavobacterium soli* DSM 19725 | DSM 19725 | WFCC |
| *Flavobacterium* sp 238 Branch | — | |
| *Flavobacterium* sp EM1321 | — | |
| *Flavobacterium* sp MEB061 | — | |
| *Hanseniaspora uvarum* | ATCC 18859 | |
| *Hanseniaspora occidentalis* | ATCC 32053 | |
| *Herminiimonas arsenicoxydans* | — | |
| *Hymenobacter swuensis* DY53 | — | |
| *Janthinobacterium* 25694 Branch | — | |
| *Janthinobacterium agaricidamnosum* NBRC 102515 | DSM 9628 | WFCC |
| *Janthinobacterium lividum* strain RIT308 | — | |
| *Janthinobacterium* sp RA13 | — | |
| *Kocuria* 20614 Branch | — | |
| *Kocuria rhizophila* 20623 Branch | — | |
| *Lactobacillus acetotolerans* | — | |
| *Lactobacillus brevis* | — | |
| *Lactobacillus buchneri* | — | |
| *Lactobacillus futsaii* | — | |
| *Lactobacillus kefiranofaciens* | — | |
| *Lactobacillus panis* | — | |
| *Lactobacillus parafarraginis* | — | |
| *Lactobacillus plantarum* | — | |
| *Lactobacillus rapi* | — | |
| *Lactobacillus crispatus* 5565 Branch | — | |
| *Lactobacillus plantarum* WJL | — | |
| *Lactobacillus reuteri* 5515 Branch | — | |
| *Leuconostoc mesenteroides* | ATCC 8293 | |
| *Luteibacter* sp 9135 | — | |
| *Massilia timonae* CCUG 45783 | — | |
| *Methylobacterium extorquens* 23001 Branch | — | |
| *Methylobacterium* sp 22185 Branch | — | |
| *Methylobacterium* sp 285MFTsu5 1 | — | |
| *Methylobacterium* sp 88A | — | |
| *Methylotenera versatilis* 7 | — | |
| *Microbacterium laevaniformans* OR221 | — | |
| *Microbacterium oleivorans* | — | |
| *Microbacterium* sp MEJ108Y | — | |
| *Microbacterium* sp UCD TDU | — | |
| *Microbacterium testaceum* StLB037 | — | |
| *Micrococcus luteus* strain RIT304 | NCTC 2665 | NCTC |
| *Mycobacterium abscessus* 19573 Branch | — | |
| *Neosartorya fischeri* | — | |
| *Oxalobacteraceae bacterium* AB 14 | — | |
| *Paenibacillus* sp FSL 28088 Branch | — | |
| *Paenibacillus* sp FSL H7 689 | — | |
| *Pantoea* sp. SL1 M5 | — | |
| *Pantoea* 36041 Branch | — | |
| *Pantoea agglomerans* strain 4 | — | |

TABLE 4-continued

Bacteria identified in a 15 sample survey identified by whole genome matching to reference genomes. The fruits and vegetables were selected based on their recognition as part of the whole food plant-based diet and some antidiabetic and obesogenic properties. There is general recognition of microbes in these vegetables relevant for plant health but not previously recognized for their use in human health.

| Strain identified by k-mer based on entire genome | Strain number | Collection |
|---|---|---|
| *Pantoea agglomerans* strain 4 | — | |
| *Pantoea agglomerans* strain LMAE 2 | — | |
| *Pantoea agglomerans* Tx10 | — | |
| *Pantoea* sp 36061 Branch | — | |
| *Pantoea* sp MBLJ3 | — | |
| *Pantoea* sp SL1 M5 | — | |
| *Paracoccus* sp PAMC 22219 | — | |
| *Patulibacter minatonensis* DSM 18081 | DSM 18081 | WFCC |
| *Pectobacterium carotovorum* subsp *carotovorum* strain 28625 Branch | — | |
| *Pediococcus ethanolidurans* | — | |
| *Pediococcus pentosaceus* | ATCC 33314 | |
| *Pedobacter* 611 Branch | — | |
| *Pedobacter agri* PB92 | — | |
| *Pedobacter borealis* DSM 19626 | DSM 19626 | WFCC |
| *Pedobacter kyungheensis* strain KACC 16221 | — | |
| *Pedobacter* sp R20 19 | — | |
| *Periglandula ipomoeae* | — | |
| *Planomicrobium glaciei* CHR43 | — | |
| *Propionibacterium acnes* | — | |
| *Propionibacterium* 20955 Branch | — | |
| *Propionibacterium acnes* 21065 Branch | — | |
| *Pseudomonas fluorescens* | — | |
| *Pseudomonas* sp. DSM 29167 | — | |
| *Pseudomonas* sp. Leaf15 | — | |
| *Pseudomonas syringae* | — | |
| *Pseudomonas* 39524 Branch | — | |
| *Pseudomonas* 39642 Branch | — | |
| *Pseudomonas* 39733 Branch | — | |
| *Pseudomonas* 39744 Branch | — | |
| *Pseudomonas* 39791 Branch | — | |
| *Pseudomonas* 39821 Branch | — | |
| *Pseudomonas* 39834 Branch | — | |
| *Pseudomonas* 39875 Branch | — | |
| *Pseudomonas* 39880 Branch | — | |
| *Pseudomonas* 39889 Branch | — | |
| *Pseudomonas* 39894 Branch | — | |
| *Pseudomonas* 39913 Branch | — | |
| *Pseudomonas* 39931 Branch | — | |
| *Pseudomonas* 39942 Branch | — | |
| *Pseudomonas* 39979 Branch | — | |
| *Pseudomonas* 39996 Branch | — | |
| *Pseudomonas* 40058 Branch | — | |
| *Pseudomonas* 40185 Branch | — | |
| *Pseudomonas abietaniphila* strain KF717 | — | |
| *Pseudomonas chlororaphis* strain EA105 | — | |
| *Pseudomonas cremoricolorata* DSM 17059 | DSM 17059 | WFCC |
| *Pseudomonas entomophila* L48 | — | |
| *Pseudomonas extremaustralis* 14 3 substr 14 3b | — | |
| *Pseudomonas fluorescens* BBc6R8 | — | |
| *Pseudomonas fluorescens* BS2 | ATCC 12633 | ATCC |
| *Pseudomonas fluorescens* EGD AQ6 | — | |
| *Pseudomonas fluorescens* strain AU 39831 Branch | — | |
| *Pseudomonas fluorescens* strain AU10973 | — | |
| *Pseudomonas fluorescens* strain AU14440 | — | |
| *Pseudomonas fragi* B25 | NCTC 10689 | NCTC |
| *Pseudomonas frederiksbergensis* strain SI8 | — | |
| *Pseudomonas fulva* strain MEJ086 | — | |
| *Pseudomonas fuscovaginae* 39768 Branch | — | |
| *Pseudomonas gingeri* NCPPB 3146 | NCPPB 3146 | NCPPB |
| *Pseudomonas lutea* | — | |
| *Pseudomonas luteola* XLDN4 9 | — | |
| *Pseudomonas mandeth* JR 1 | — | |
| *Pseudomonas moraviensis* R28 S | — | |
| *Pseudomonas mosselii* SJ10 | — | |
| *Pseudomonas plecoglossicida* NB 39639 Branch | — | |
| *Pseudomonas poae* RE*1 1 14 | — | |
| *Pseudomonas pseudoalcaligenes* AD6 | — | |
| *Pseudomonas psychrophila* HA 4 | — | |
| *Pseudomonas putida* DOT T1E | — | |
| *Pseudomonas putida* strain KF703 | — | |
| *Pseudomonas putida* strain MC4 5222 | — | |

TABLE 4-continued

Bacteria identified in a 15 sample survey identified by whole genome matching to reference genomes. The fruits and vegetables were selected based on their recognition as part of the whole food plant-based diet and some antidiabetic and obesogenic properties. There is general recognition of microbes in these vegetables relevant for plant health but not previously recognized for their use in human health.

| Strain identified by k-mer based on entire genome | Strain number | Collection |
|---|---|---|
| *Pseudomonas rhizosphaerae* | — | |
| *Pseudomonas rhodesiae* strain FF9 | — | |
| *Pseudomonas* sp 39813 Branch | — | |
| *Pseudomonas simiae* strain 2 36 | — | |
| *Pseudomonas simiae* strain MEB105 | — | |
| *Pseudomonas* sp 11 12A | — | |
| *Pseudomonas* sp 2 922010 | — | |
| *Pseudomonas* sp CF149 | — | |
| *Pseudomonas* sp Eur1 9 41 | — | |
| *Pseudomonas* sp LAMO17WK12 I2 | — | |
| *Pseudomonas* sp PAMC 25886 | — | |
| *Pseudomonas* sp PTA1 | — | |
| *Pseudomonas* sp R62 | — | |
| *Pseudomonas* sp WCS374 | — | |
| *Pseudomonas synxantha* BG33R | — | |
| *Pseudomonas synxantha* BG33R | — | |
| *Pseudomonas syringae* 39550 Branch | — | |
| *Pseudomonas syringae* 39596 Branch | — | |
| *Pseudomonas syringae* 40123 Branch | — | |
| *Pseudomonas syringae* CC 39499 Branch | — | |
| *Pseudomonas syringae* pv panici str LMG 2367 | — | |
| *Pseudomonas syringae* strain mixed | — | |
| *Pseudomonas tolaasii* 39796 Branch | — | |
| *Pseudomonas tolaasii* PMS117 | — | |
| *Pseudomonas veronii* 1YdBTEX2 | — | |
| *Pseudomonas viridiflava* CC1582 | — | |
| *Pseudomonas viridiflava* strain LMCA8 | — | |
| *Pseudomonas viridiflava* TA043 | — | |
| *Pseudomonas viridiflava* UASWS0038 | — | |
| *Rahnella* 35969 Branch | — | |
| *Rahnella* 35970 Branch | — | |
| *Rahnella* 35971 Branch | — | |
| *Rahnella aquatilis* HX2 | — | |
| *Rahnella* sp WP5 | — | |
| *Raoultella ornithinolytica* | — | |
| *Rhizobiales* Order 22324 Branch | — | |
| *Rhizobium* sp YR528 | — | |
| *Rhodococcus fascians* A76 | — | |
| *Rhodococcus* sp BS 15 | — | |
| *Saccharomyces cerevisiae* | — | |
| *Sanguibacter keddieii* | DSM 10542 | WFCC |
| *Serratia fonticola* AU 35657 Branch | — | |
| *Serratia fonticola* AU AP2C | — | |
| *Serratia liquefaciens* ATCC 27592 | ATCC 27592 | ATCC |
| *Serratia* sp H 35589 Branch | — | |
| *Shewanella* 37294 Branch | — | |
| *Shewanella baltica* 37301 Branch | — | |
| *Shewanella baltica* 37315 Branch | — | |
| *Shewanella baltica* OS 37308 Branch | — | |
| *Shewanella baltica* OS 37312 Branch | — | |
| *Shewanella baltica* OS185 | — | |
| *Shewanella baltica* OS223 | — | |
| *Shewanella baltica* OS678 | — | |
| *Shewanella oneidensis* MR 1 | — | |
| *Shewanella putrefaciens* HRCR 6 | — | |
| *Shewanella* sp W3 18 1 | — | |
| *Sphingobacterium* sp ML3W | — | |
| *Sphingobium japonicum* BiD32 | — | |
| *Sphingobium xenophagum* 24443 Branch | — | |
| *Sphingomonas echinoides* ATCC 14820 | ATCC 14820 | ATCC |
| *Sphingomonas parapaucimobilis* NBRC 15100 | ATCC 51231 | ATCC |
| *Sphingomonas paucimobilis* NBRC 13935 | ATCC 29837 | ATCC |
| *Sphingomonas phyllosphaerae* 5 2 | — | |
| *Sphingomonas* sp 23777 Branch | — | |
| *Sphingomonas* sp STI56 2 | — | |
| *Staphylococcus* 6317 Branch | — | |
| *Staphylococcus equorum* UMC CNS 924 | — | |
| *Staphylococcus* sp 6275 Branch | — | |
| *Staphylococcus* sp 6240 Branch | — | |
| *Staphylococcus* sp OJ82 | — | |
| *Staphylococcus xylosus* strain LSR 02N | — | |
| *Stenotrophomonas* 14028 Branch | — | |

TABLE 4-continued

Bacteria identified in a 15 sample survey identified by whole genome matching to reference genomes. The fruits and vegetables were selected based on their recognition as part of the whole food plant-based diet and some antidiabetic and obesogenic properties. There is general recognition of microbes in these vegetables relevant for plant health but not previously recognized for their use in human health.

| Strain identified by k-mer based on entire genome | Strain number | Collection |
|---|---|---|
| *Stenotrophomonas* 42816 Branch | — | |
| *Stenotrophomonas maltophilia* 42817 Branch | — | |
| *Stenotrophomonas maltophilia* PML168 | — | |
| *Stenotrophomonas maltophilia* strain ZBG7B | — | |
| *Stenotrophomonas rhizophila* | — | |
| *Stenotrophomonas* sp RIT309 | — | |
| *Streptococcus gallolyticus* subsp *gallolyticus* TX20005 | — | |
| *Streptococcus infantarius* subsp *infantarius* 2242 Branch | — | |
| *Streptococcus infantarius* subsp *infantarius* ATCC BAA 102 | ATCC BAA102 | ATCC |
| *Streptococcus macedonicus* ACA DC 198 | ATCC BAA-249 | ATCC |
| *Streptomyces olindensis* | — | |
| *Variovorax paradoxus* 110B | — | |
| *Variovorax paradoxus* ZNC0006 | — | |
| *Variovorax* sp CF313 | — | |
| *Vibrio fluvialis* 44473 Branch | — | |
| *Xanthomonas campestris* 37936 Branch | — | |
| *Xanthomonas campestris* pv *raphani* 756C | — | |

FIG. 1 shows bacterial diversity observed in a set of 21 plant-derived samples as seen by a community reconstruction based on mapping the reads from a shotgun sequencing library into the full genomes of a database containing 36,000 genomes by the k-mer method (CosmosID, OneCodex or Kraken2). The display corresponds to a sunburst plot constructed with the relative abundance for each corresponding genome identified and their taxonomic classification or pie charts. The genomes identified as unclassified have not been curated in the database with taxonomic identifiers and therefore not assigned to a group. This does not represent novel taxa and it is an artifact of the database updating process.

More specifically, FIG. 1A shows bacterial diversity observed in a green chard. The dominant group is gamma proteobacteria with different *Pseudomonas* species. The members of the group "unclassified" are largely gamma proteobacteria not included in the hierarchical classification as an artifact of the database annotation.

Figure 1B:
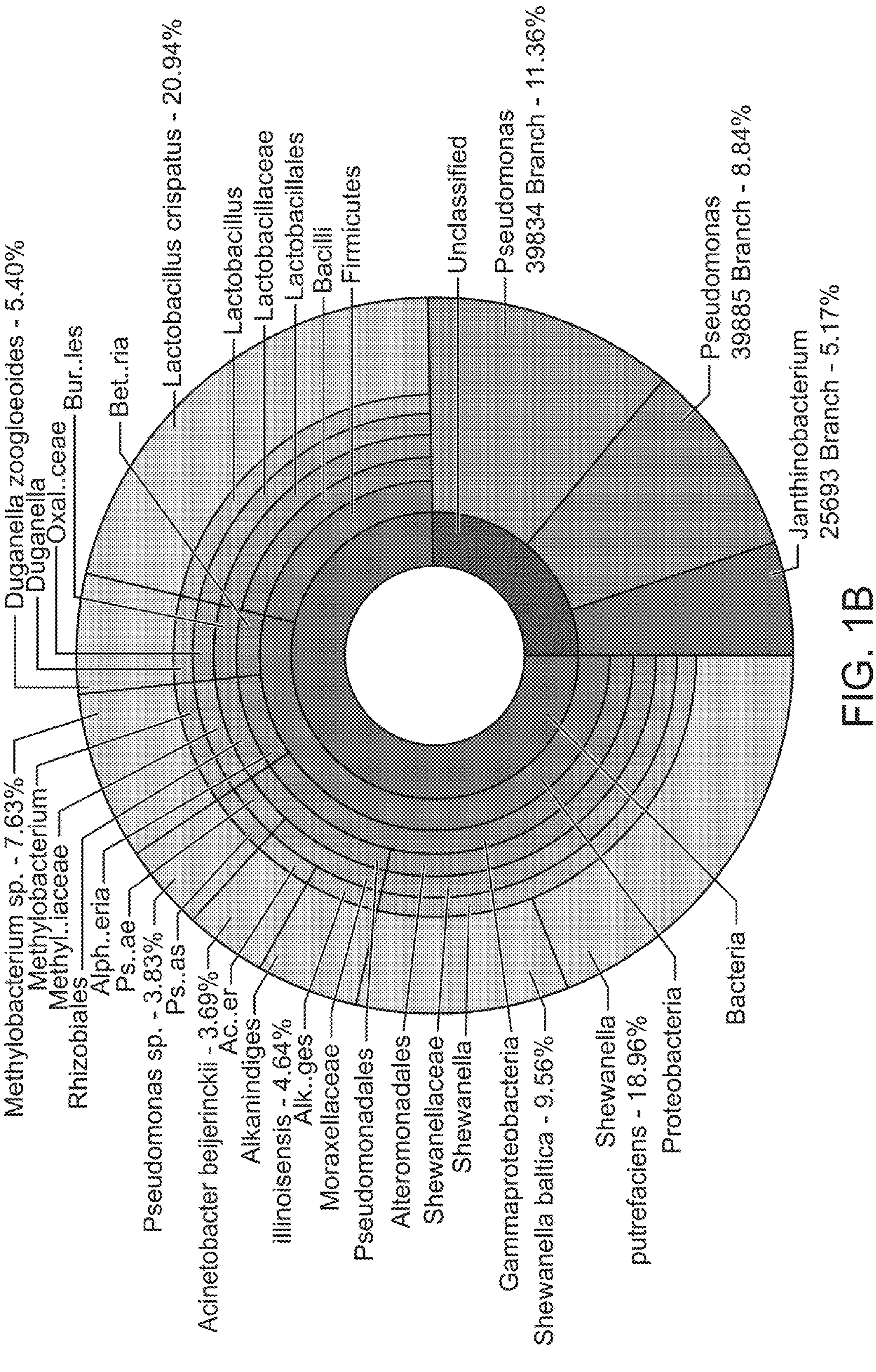

FIG. 1B shows bacterial diversity in red cabbage. There is a large abundance of *Lactobacillus* in the sample followed by a variety of *Pseudomonas* and *Shewanella.*

Figure 1C:
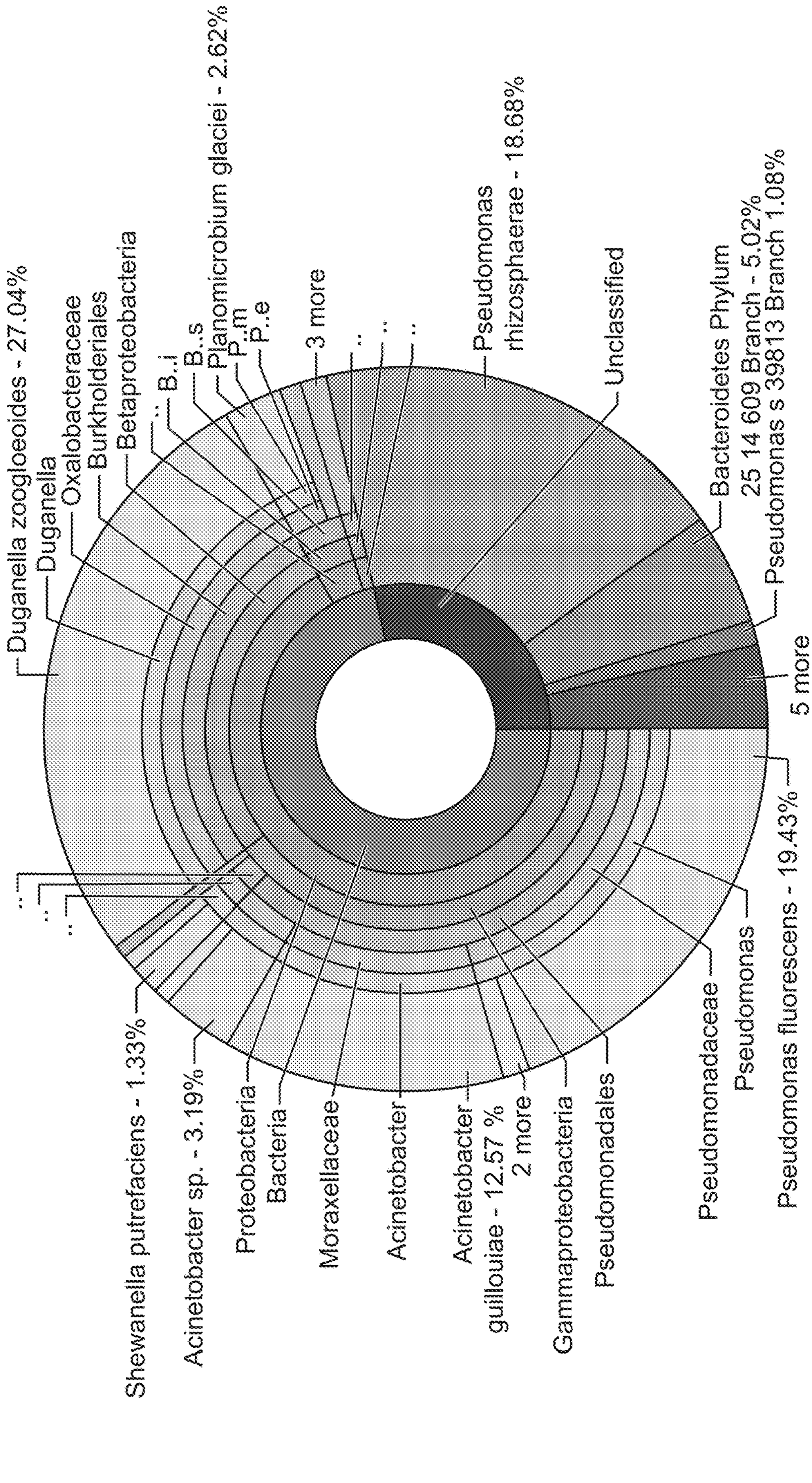

FIG. 1C shows bacterial diversity in romaine lettuce. *Pseudomonas* and *Duganella* are the dominant groups. A member of the Bacteroidetes was also identified.

Figure 1D:
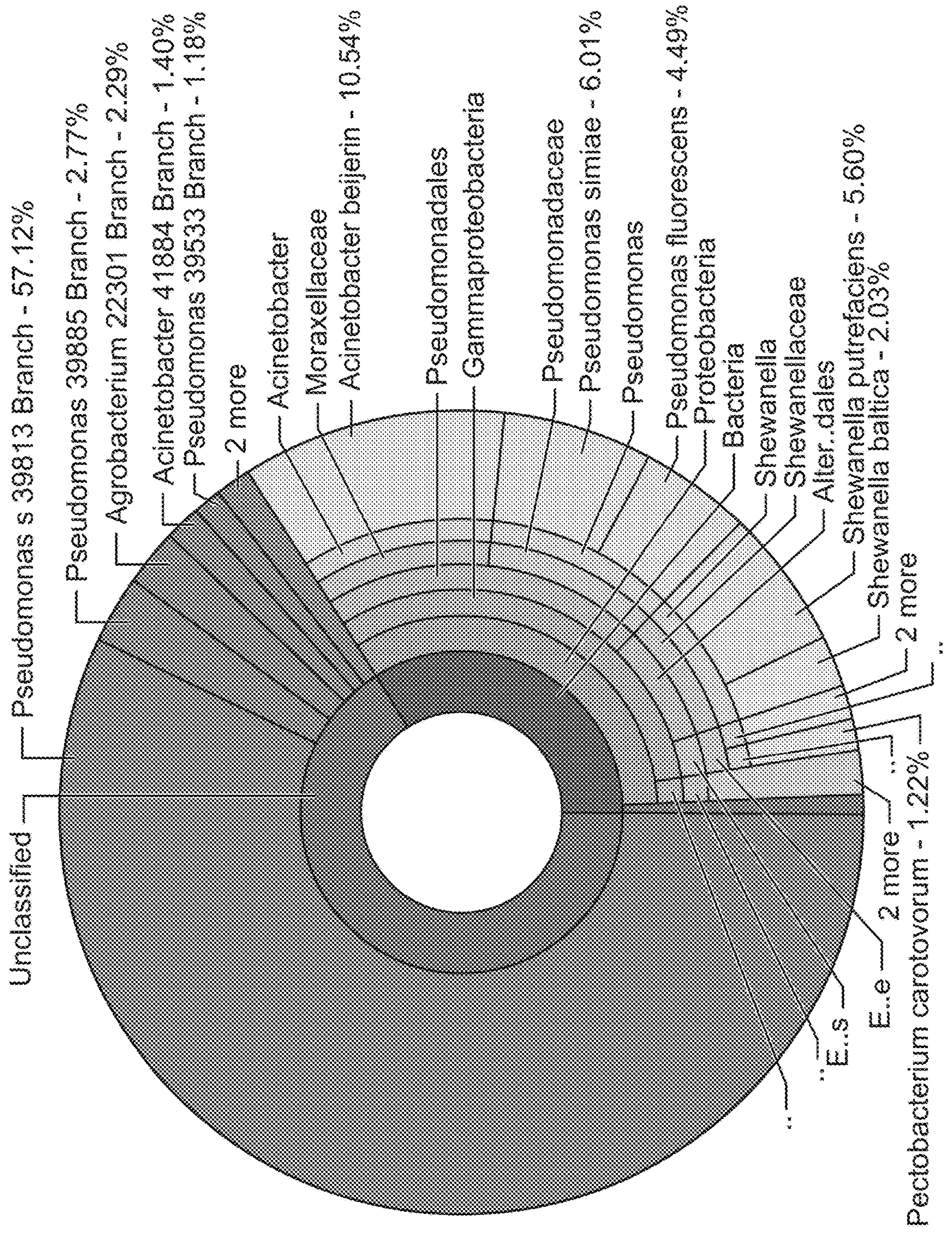

FIG. 1D shows bacterial diversity in celery sticks. This sample was dominated by a *Pseudomonas* species that was not annotated yet into the database and therefore appeared as "unclassified" same for *Agrobacterium* and *Acinetobacter.*

Figure 1E:
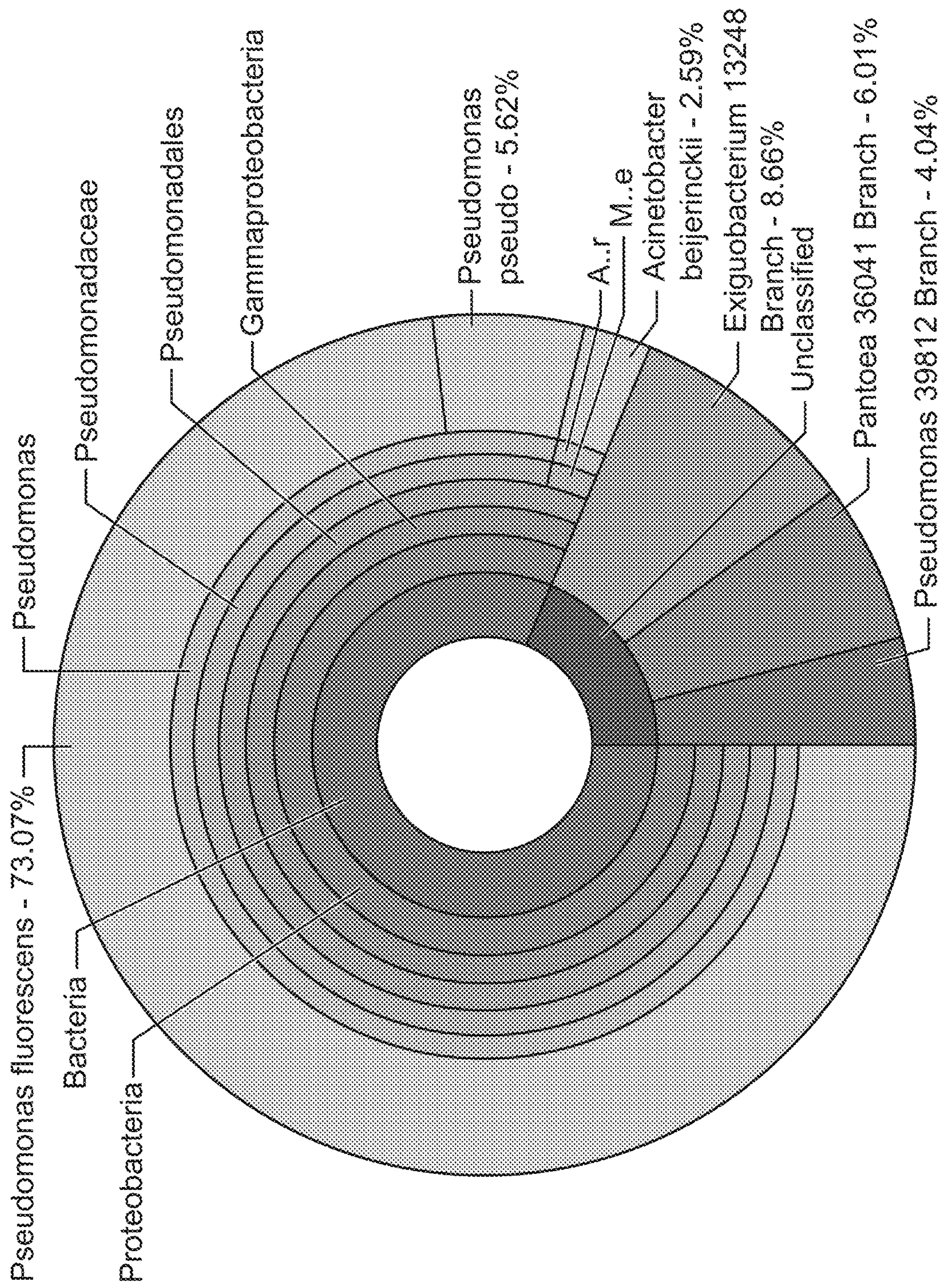

FIG. 1E shows bacterial diversity observed in butterhead lettuce grown hydroponically. The sample contains relatively low bacterial complexity dominated by *P. fluorescens* and other groups. Also, there is a 9% abundance of *Exiguobacterium.*

Figure 1F:
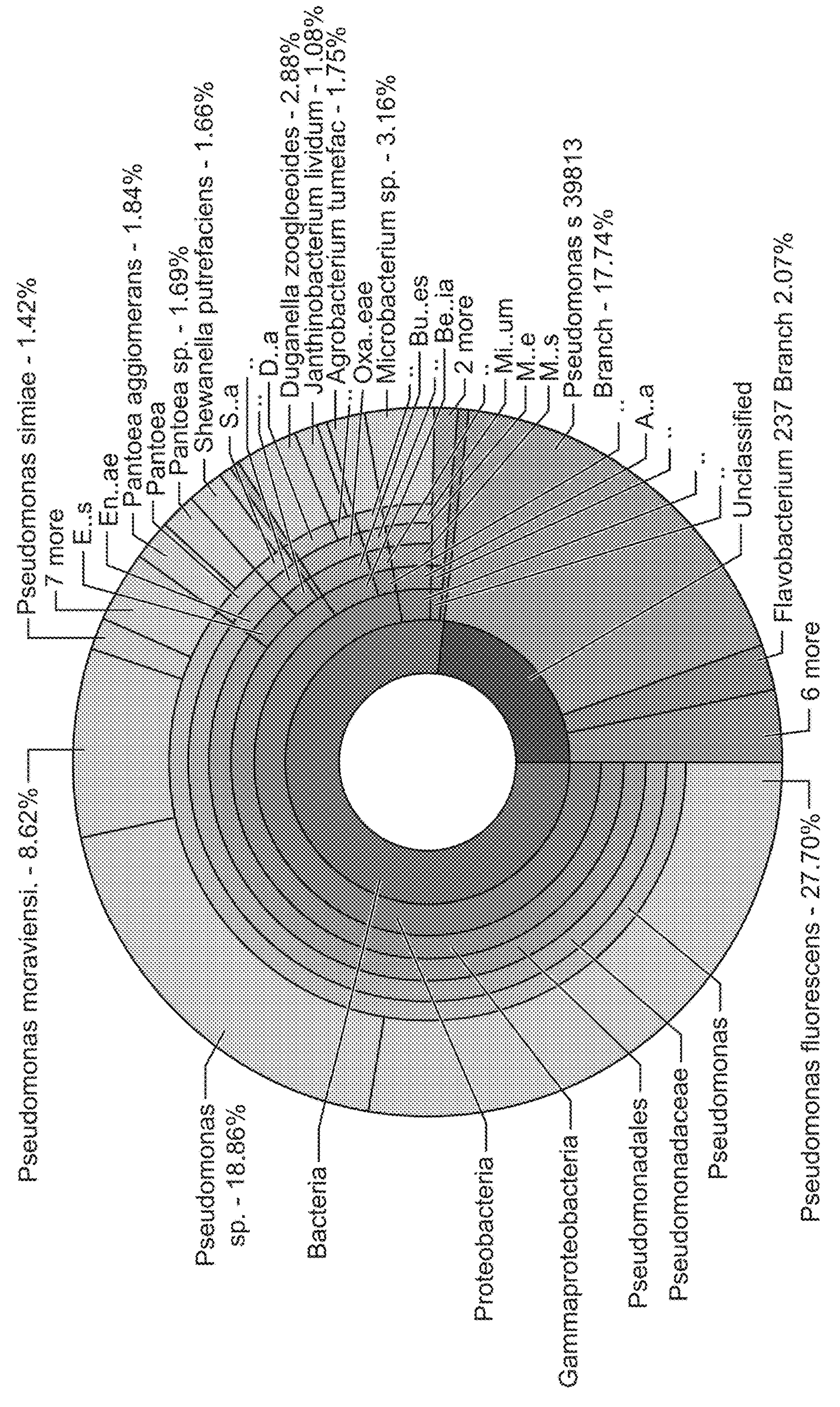

FIG. 1F shows bacterial diversity in organic baby spinach. The samples were triple-washed before distribution at the point of sale and therefore it is expected that must of the bacteria detected here are endophytes. Multiple *Pseudomonas* species observed in this sample including *P. fluorescens* and other shown as "unclassified."

Figure 1G:
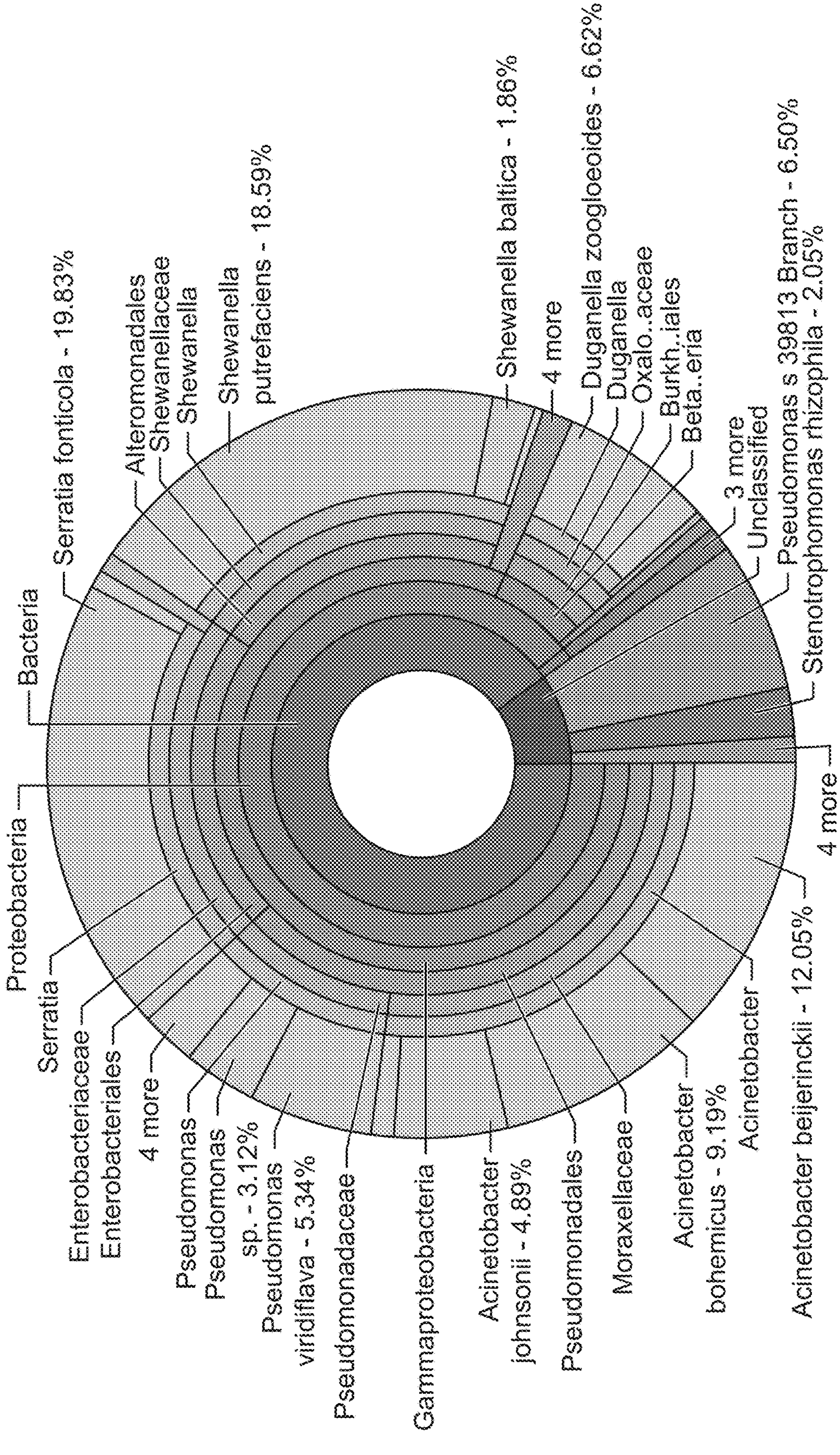

FIG. 1G shows bacterial diversity in green crisp gem lettuce. This variety of lettuce showed clear dominance of gamma proteobacteria and with *Pseudomonas, Shewanella, Serratia* as well as other groups such as *Duganella.*

Figure 1H:
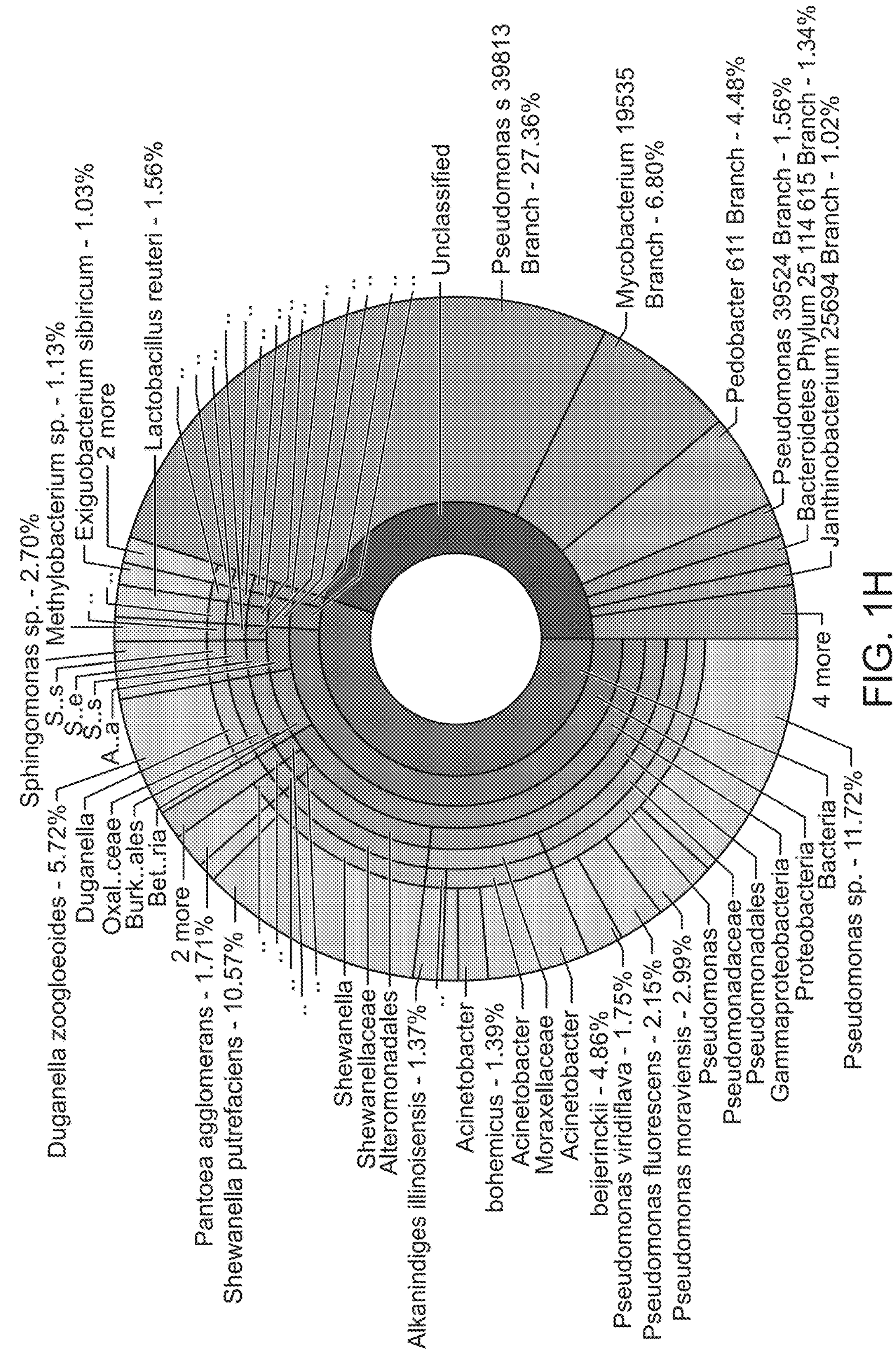

FIG. 1H shows bacterial diversity in red oak leaf lettuce. There is a relative high diversity represented in this sample with members of *Lactobacillus, Microbacterium, Bacteroidetes, Exiguobacterium* and a variety of *Pseudomonas.*

Figure 1I:
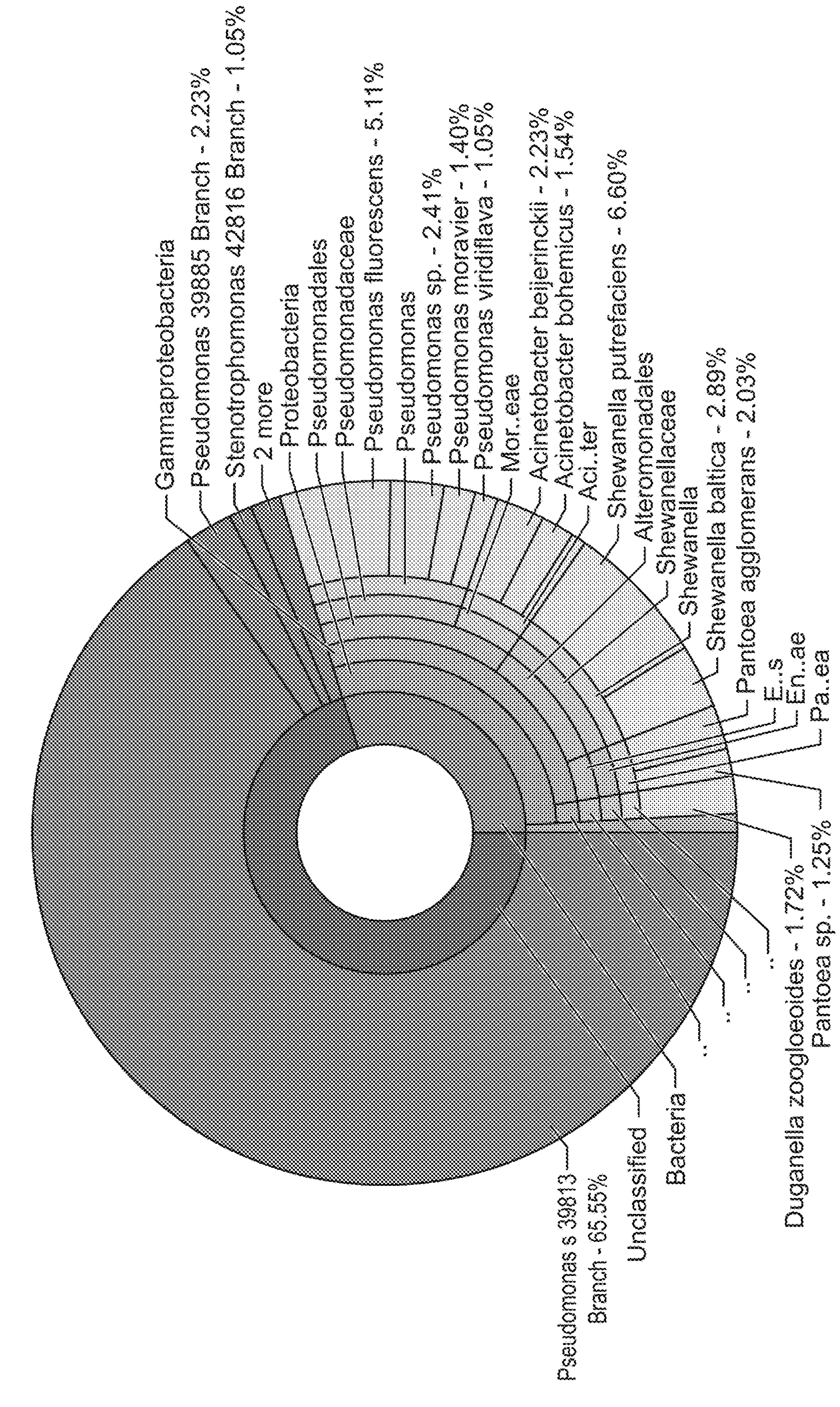

FIG. 1I shows bacterial diversity in green oak leaf lettuce. It is dominated *Pseudomonas* species including *fluorescens* and mostly gamma proteobacteria.

Figure 1J:
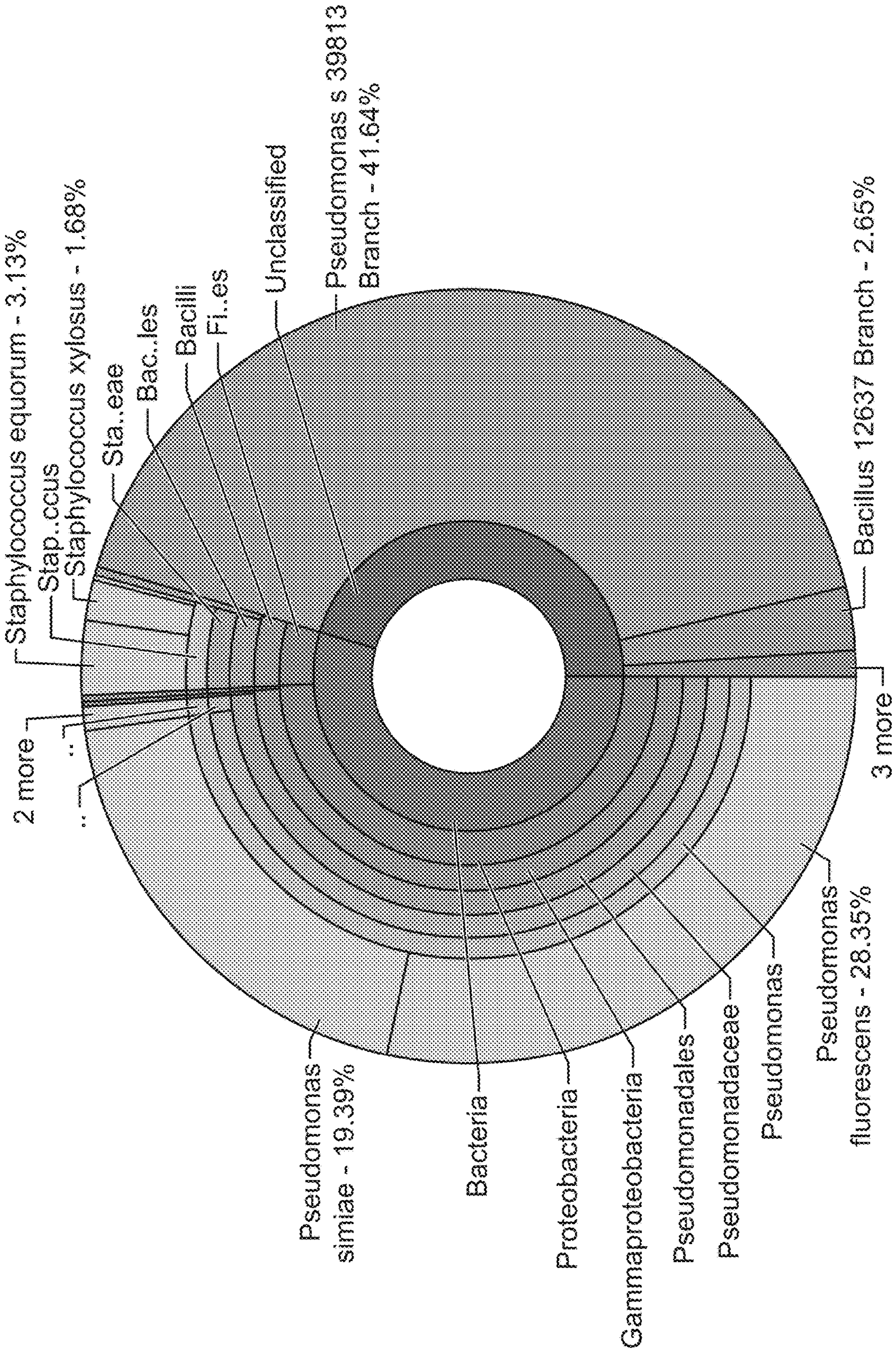

FIG. 1J shows bacterial diversity in cherry tomatoes. It is dominated by three species of *Pseudomonas* comprising more than 85% of the total diversity on which *P. fluorescens* comprises 28% of bacterial diversity.

Figure 1K:
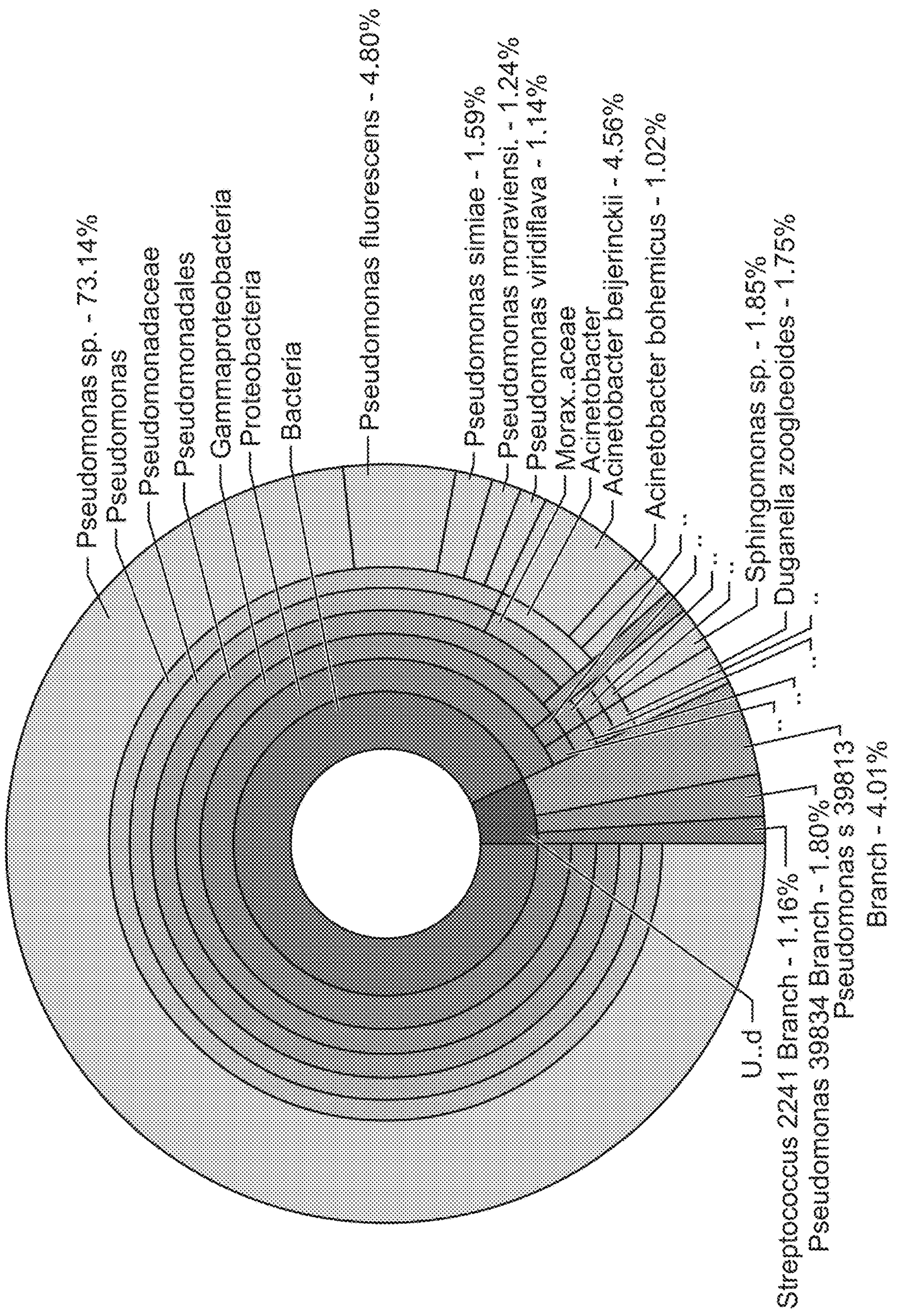

FIG. 1K shows bacterial diversity in crisp red gem lettuce. Dominance by *Pseudomonas* species covering 73% of the bacterial diversity, on which *P. fluorescens* comprises 5% of bacterial diversity.

Figure 1L:
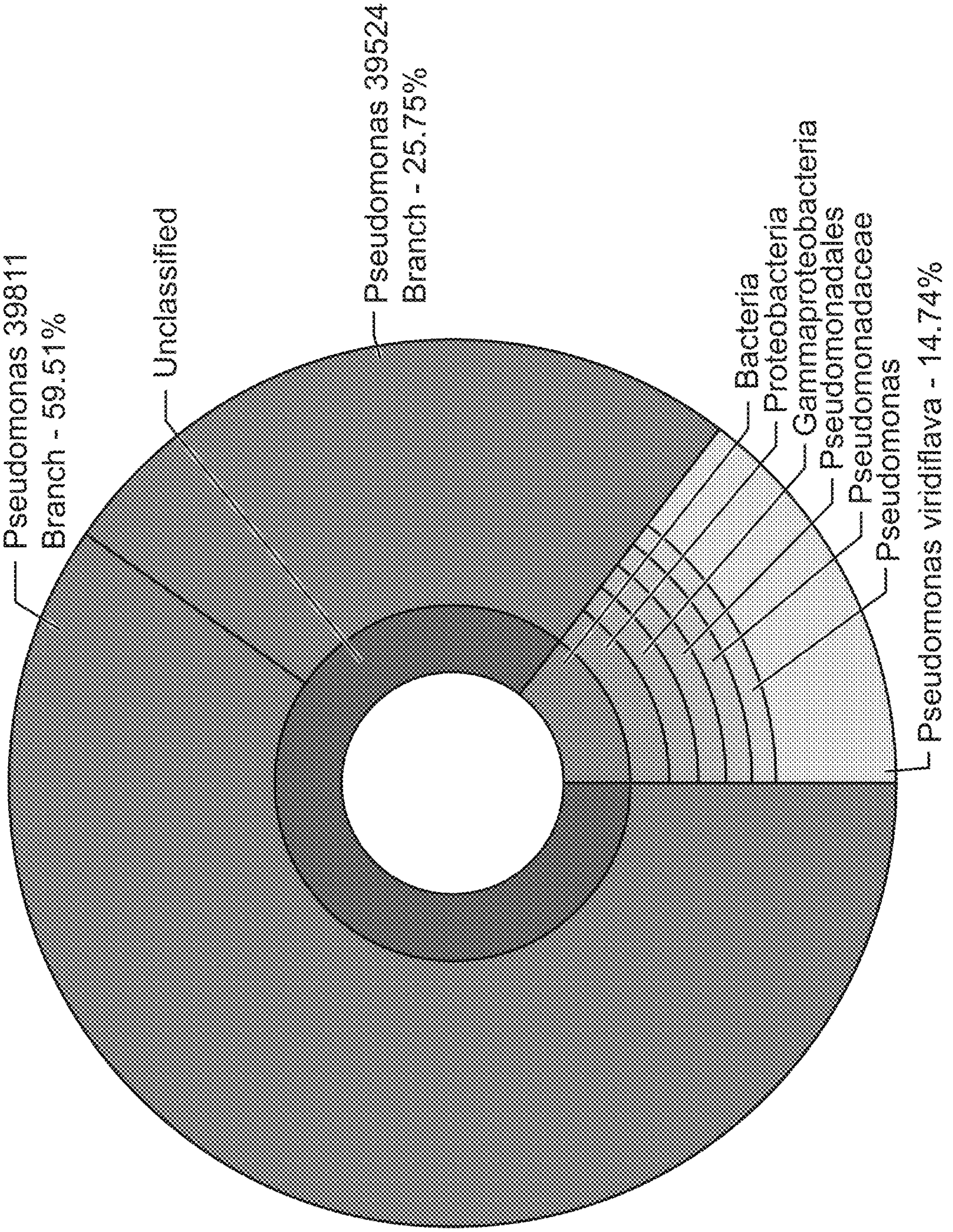

FIG. 1L shows bacterial diversity in broccoli juice. The sample is absolutely dominated by three varieties of *Pseudomonas.*

Figure 2A:
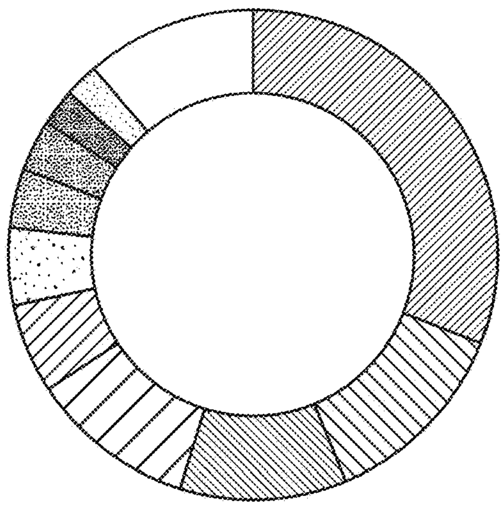

FIG. 2 shows taxonomic composition of blueberries, pickled olives and broccoli head. More specifically, FIG. 2A shows taxonomic composition of broccoli head showing a diversity of fungi and bacteria distinct from the broccoli juice dominated by few *Pseudomonas* species.

Figure 2C:
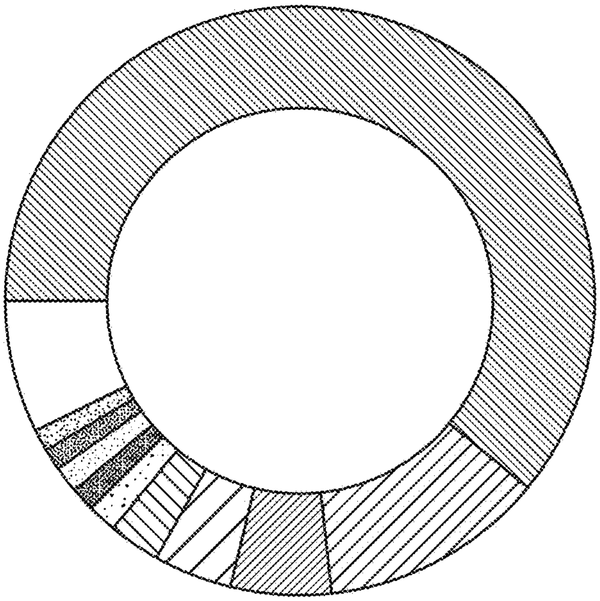

FIG. 2C shows taxonomic composition of blueberries.

FIG. 2C shows taxonomic composition of pickled olives showing a variety of lactic acid bacteria present and dominant. Some of the species are recognized as probiotics.

Figure 3A:
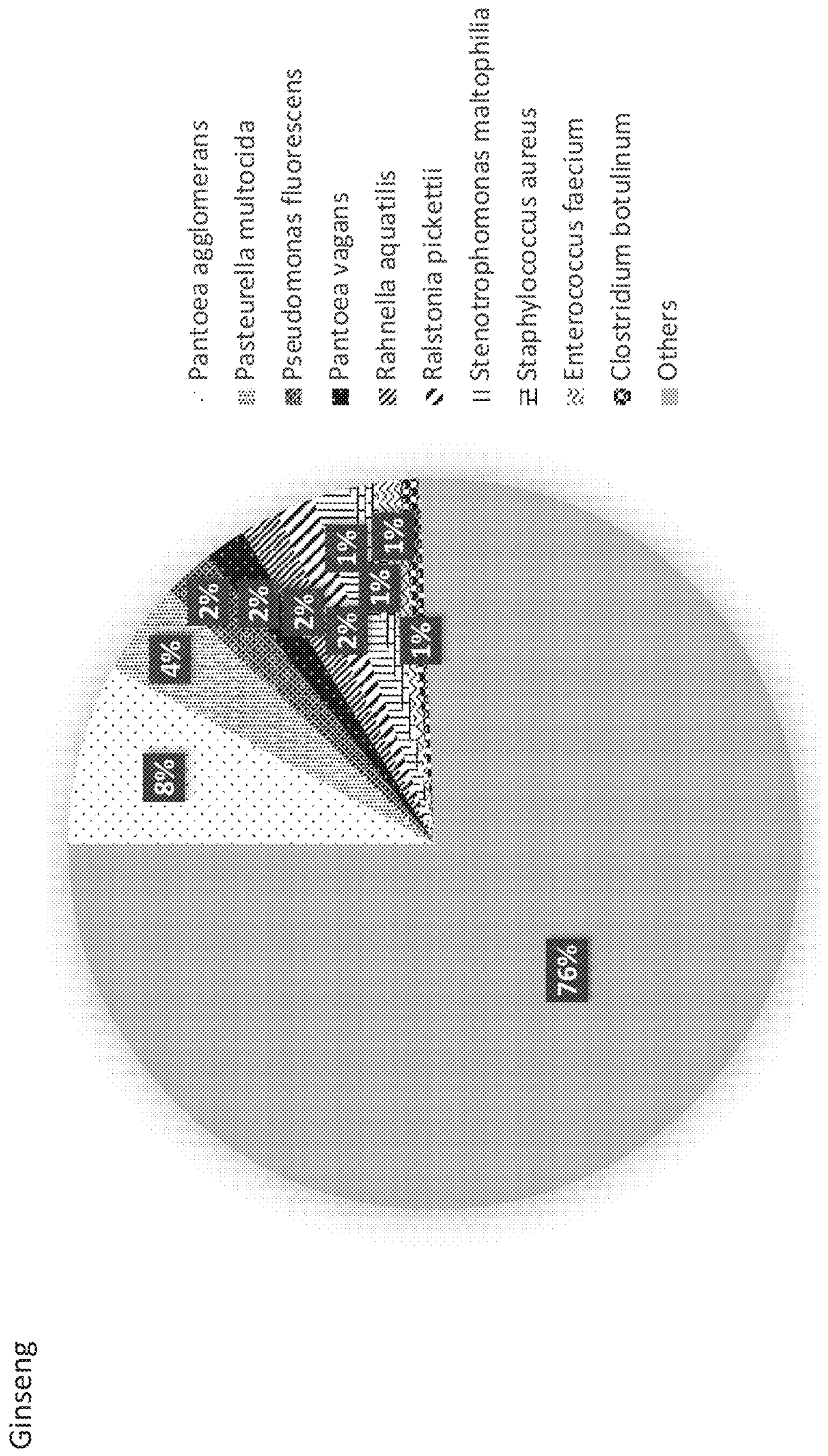
FIG. 3A shows taxonomic composition of *ginseng*. There is a relatively high diversity represented in this sample with members of *Pseudomonas, Pantoea*, and *Stenotrophomonas.*

FIG. 3A shows taxonomic composition of *ginseng*. There is a relatively high diversity represented in this sample with members of *Pseudomonas, Pantoea*, and *Stenotrophomonas.*

Figure 3B:
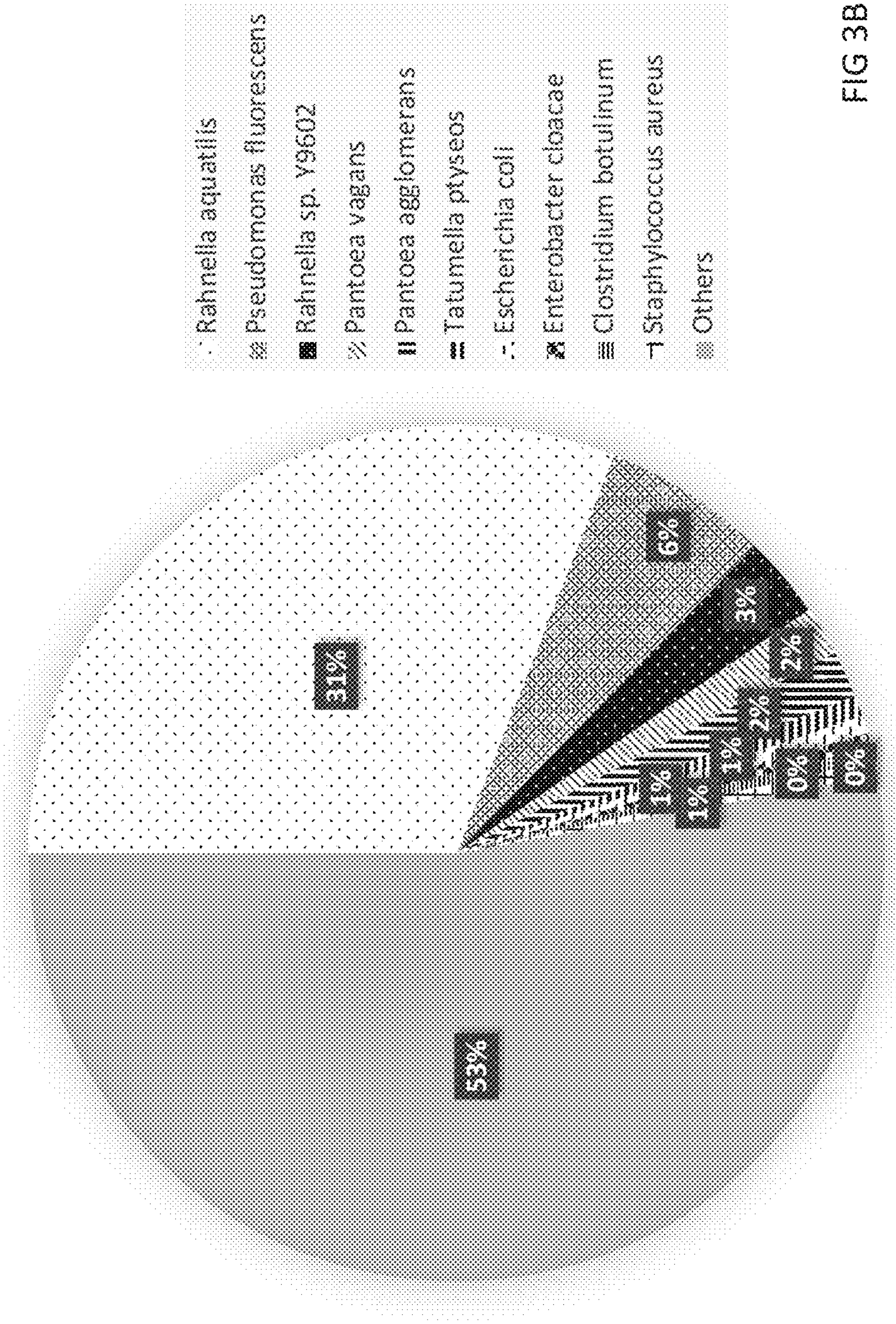
FIG. 3B shows taxonomic composition of blackberries. The most abundant member is *Rahnella aquatilis* covering 31% of total composition.

FIG. 3B shows taxonomic composition of blackberries. The most abundant member is *Rahnella aquatilis* covering 31% of total composition.

Figure 3C:
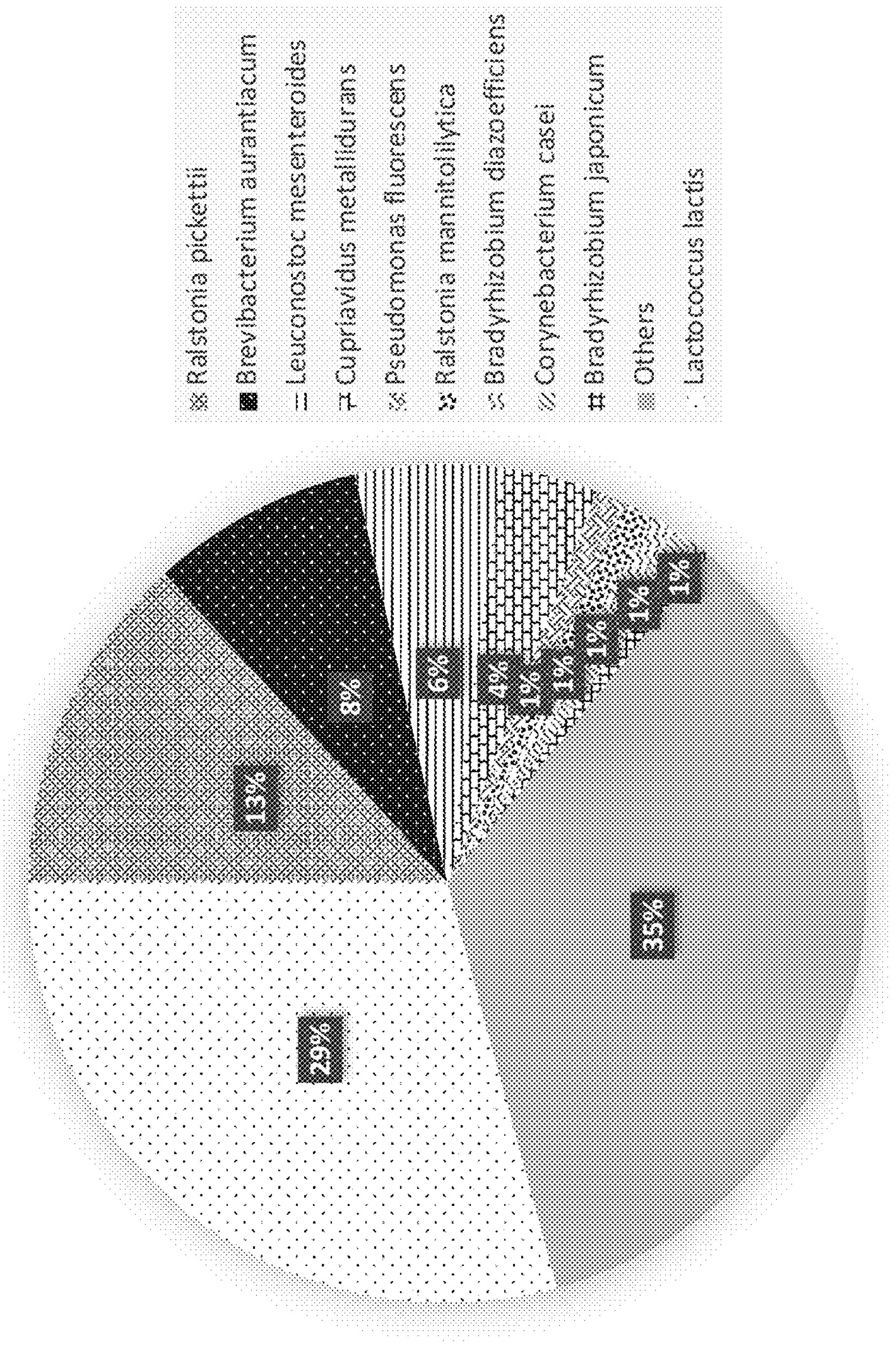
FIG. 3C shows taxonomic composition of squash gourd. The sample is dominated by *Lactococcus lactis* covering 59% of total composition but also *Leuconostoc mesenteroides* was present at 3.3% of the bacterial population.

FIG. 3C shows taxonomic composition of squash gourd. The sample is dominated by *Lactococcus lactis* covering 59% of total composition but also *Leuconostoc mesenteroides* was present at 3.3% of the bacterial population.

Figure 3D:
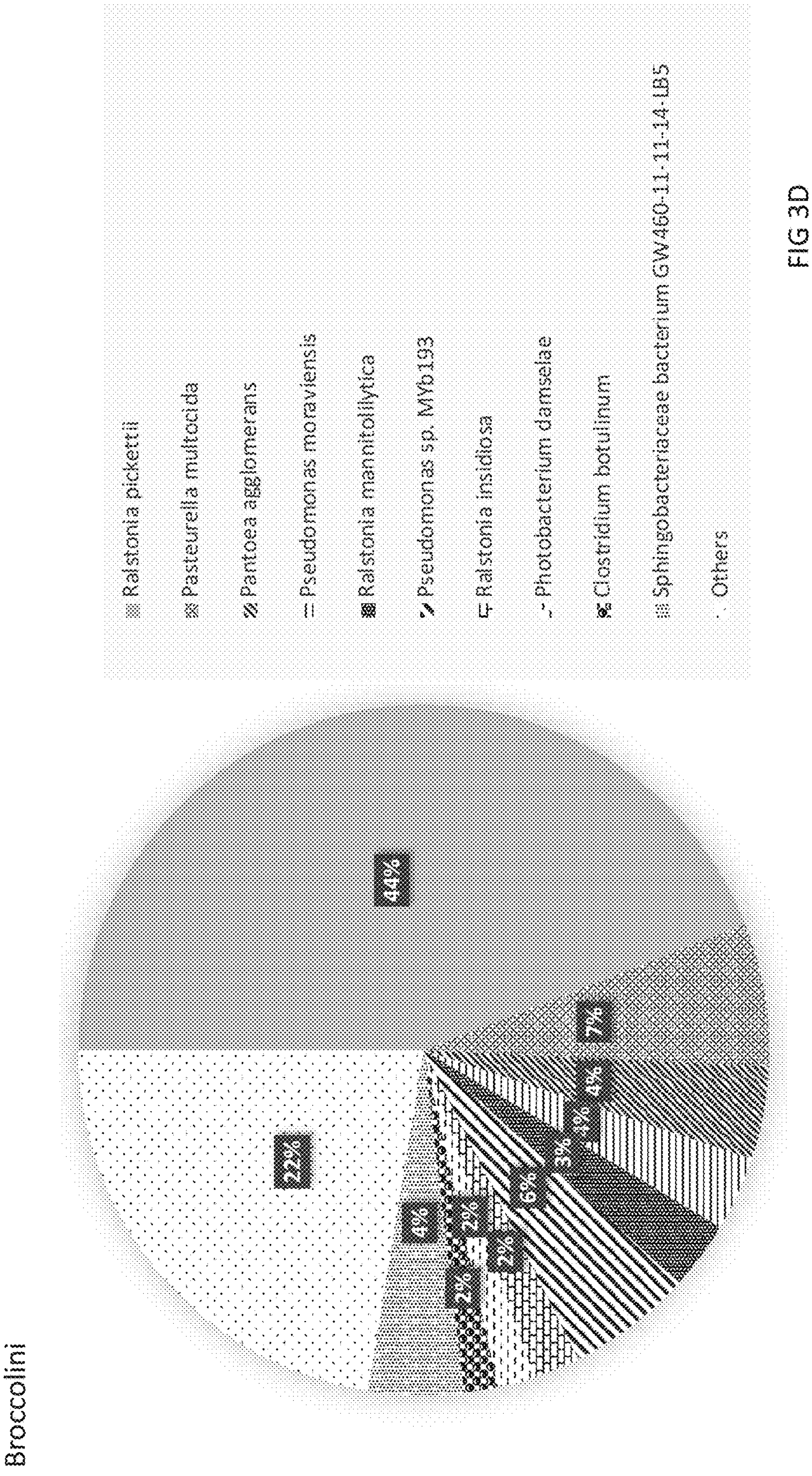
FIG. 3D shows taxonomic composition of broccolini. *Ralstonia pickettii* covers 44% of entire bacterial community.

FIG. 3D shows taxonomic composition of broccolini. *Ralstonia pickettii* covers 44% of entire bacterial community.

Figure 3E:
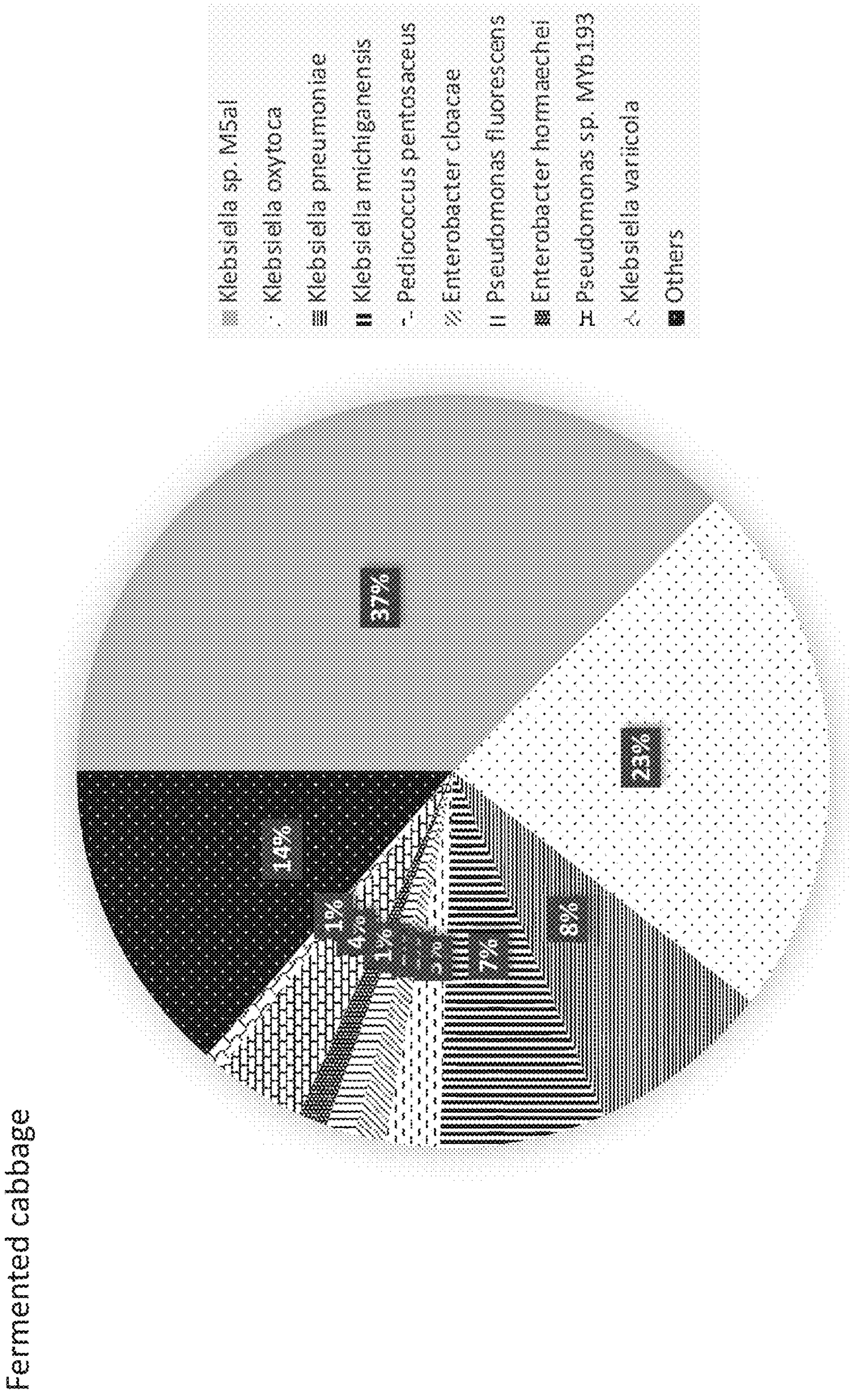
FIG. 3E shows taxonomic composition of fermented cabbage. It contained *Pediococcus pentosaceus* as well as dominant gamma proteobacteria.

FIG. 3E shows taxonomic composition of fermented cabbage. It contained *Pediococcus pentosaceus* as well as dominant gamma proteobacteria.

Figure 3F:
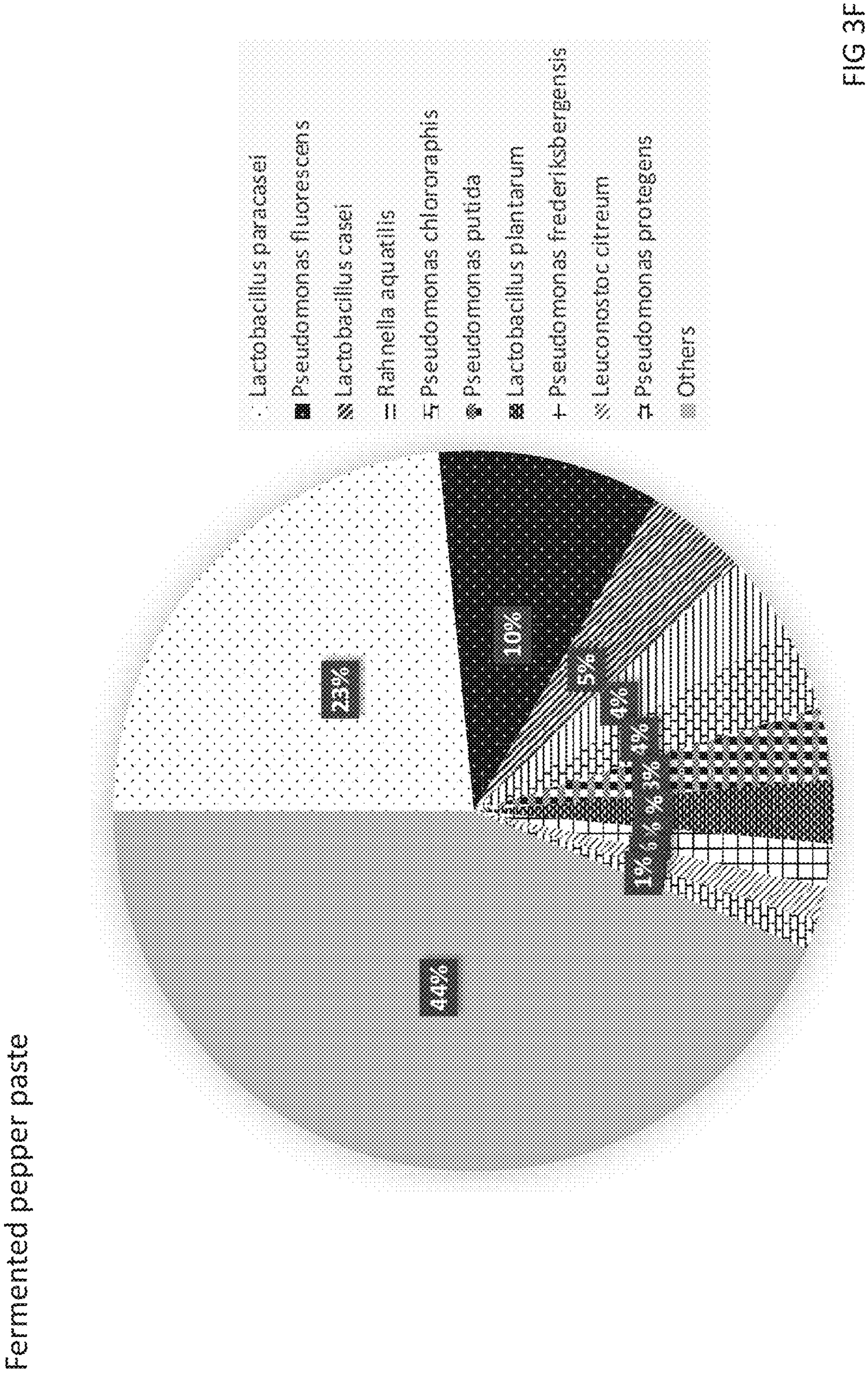
FIG. 3F shows taxonomic composition of fermented pepper paste. The sample enriched many lactic acid bacteria such as *Lactobacillus paracasei, Lactobacillus casei* and *Lactobacillus plantarum.*
Figure 4:
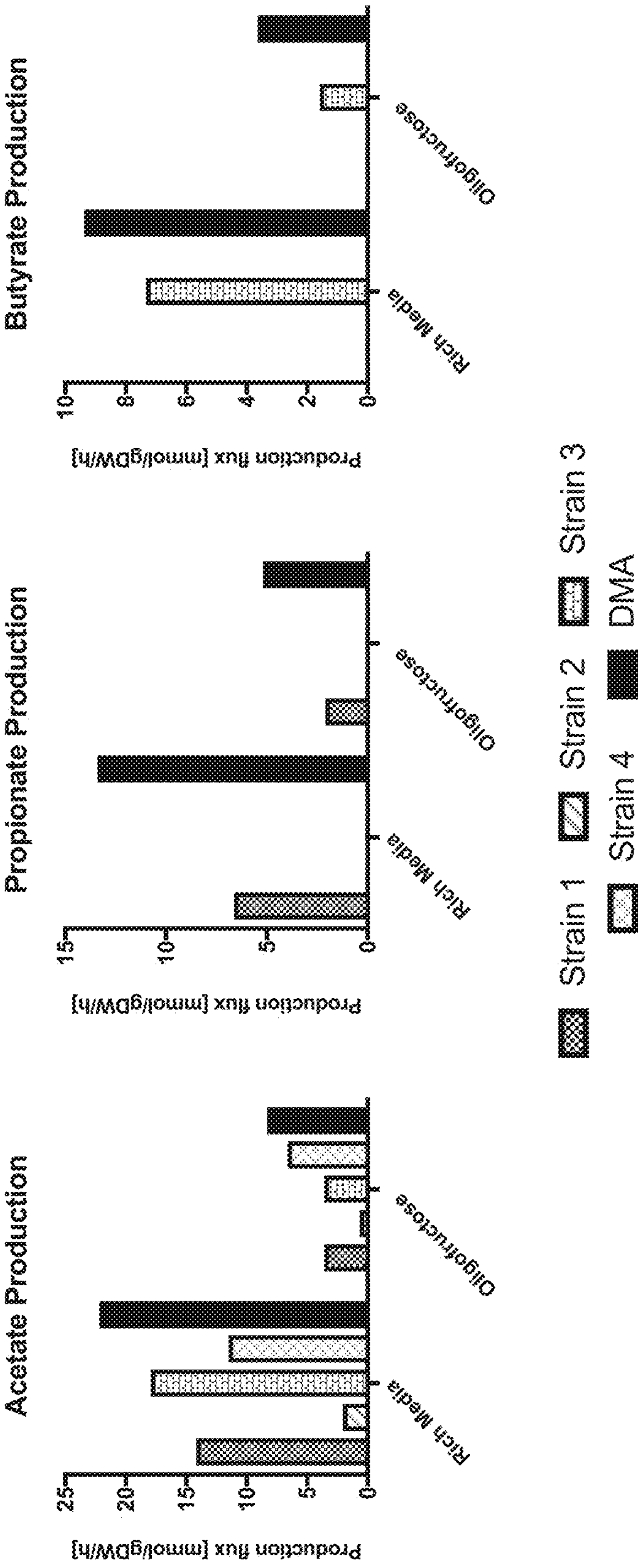
FIG. 4 shows fermentative rates by sample microbes alone or as a community under various conditions in silico. Four microbes were tested in silico for their ability to produce (A) Acetate, (B) Propionate, or (C) Butyrate under rich media or oligofructose conditions alone or as an assembled community.
Figure 5:
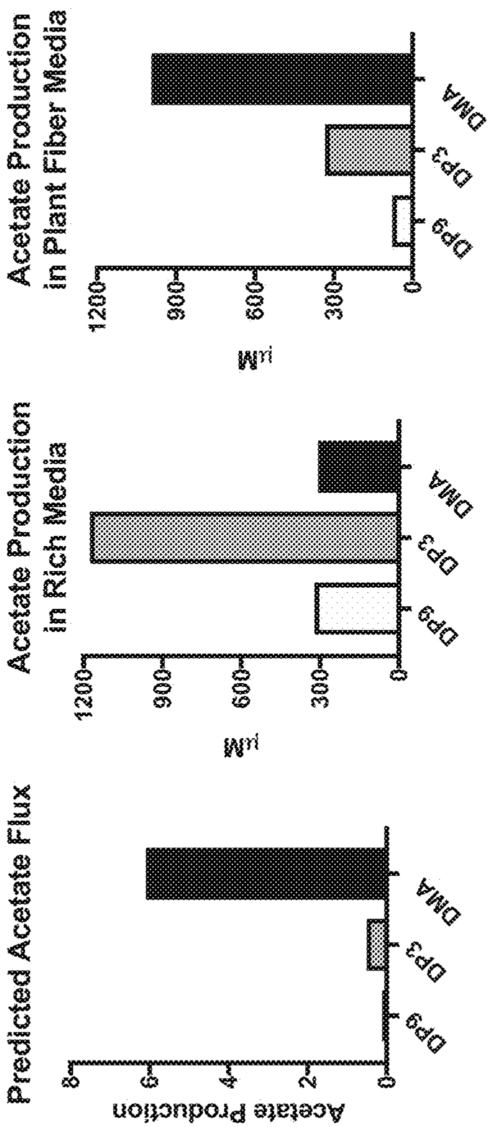
FIG. 5 shows DMA experimental validation for a combination of strains DP3 and DP9 under nutrient replete and plant fiber media showing that the strains show synergy for increased SCFA production only under plant fiber media but not under rich media.
Figure 6:
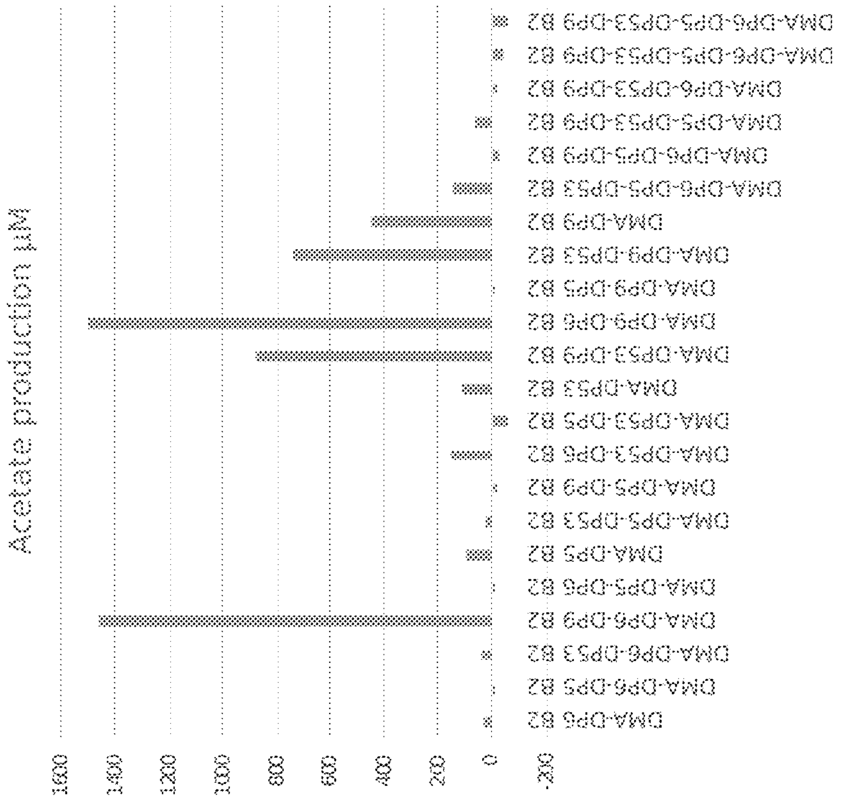
FIG. 6 shows synergistic acetate production for 4 strains tested as singles, pairs or trios. Cells were grown on blueberry extract media for 4 days in a 24 well plate at 300 RPM and 22° C. The pairs in this experiment were run in duplicate. Spent culture broth was extracted with ethyl acetate and analyzed by gas chromatography with a flame ionization detector (GC-FID) and acetate concentrations measured with a standard curve done in sterile media. The strain DP6 does not produce acetate, while strain DP9 produces 448 uM, and when the 2 are grown together the acetate production is 1500 uM and 1457 uM for both duplicate cultures respectively. This indicates the acetate increased by adding strain DP6 to DP9.
Figure 7:
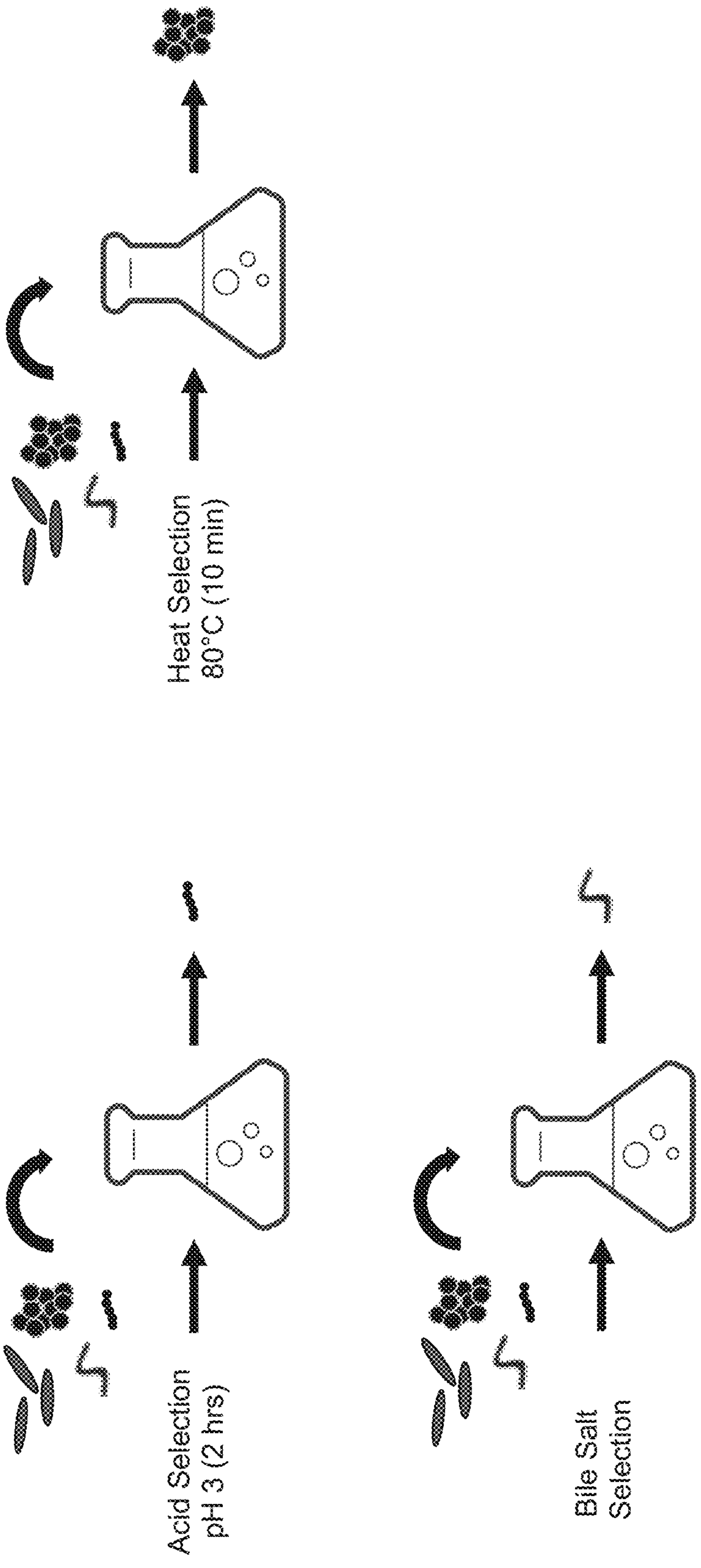
FIG. 7 shows a schematic describing a gut simulator experiment. The experiment comprises an in vitro, system that mimics various sections of the gastrointestinal tract. Isolates of interest are incubated in the presence of conditions that mimic particular stresses in the gastro-intestinal tract (such as low pH or bile salts), heat shock, or metformin. After incubation, surviving populations are recovered. Utilizing this system, the impact of various oral anti-diabetic therapies alone or in combination with probiotic cocktails of interest on the microbial ecosystem can be tested.
Figure 8:
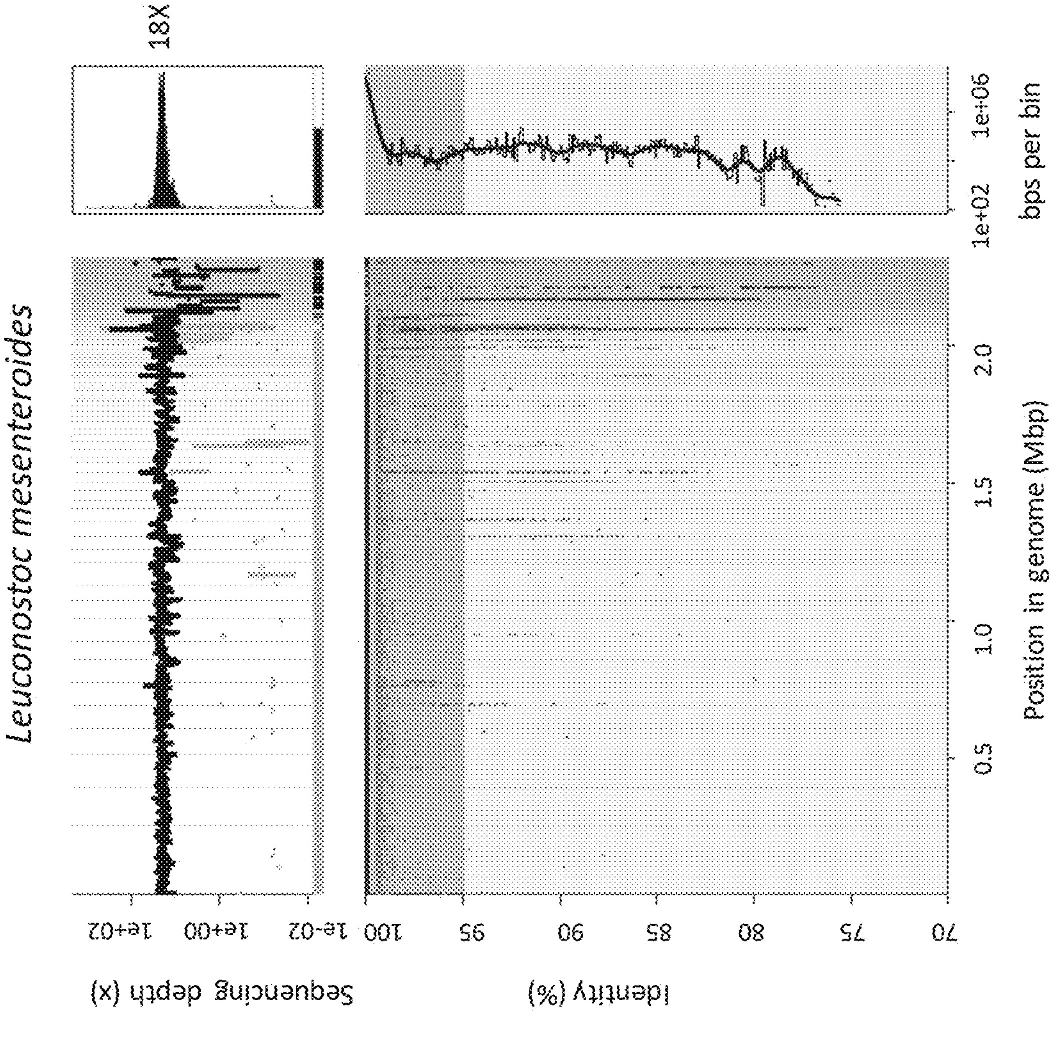
FIG. 8 shows a fragment recruitment plot sample for the shotgun sequencing on sample 22 (fermented cabbage) comparing to the reference genome of strain DP3 *Leuconostoc mesenteroides*-like and the 18× coverage indicating the isolated strain was represented in the environmental sample and it was largely genetically homogeneous.
Figure 9:
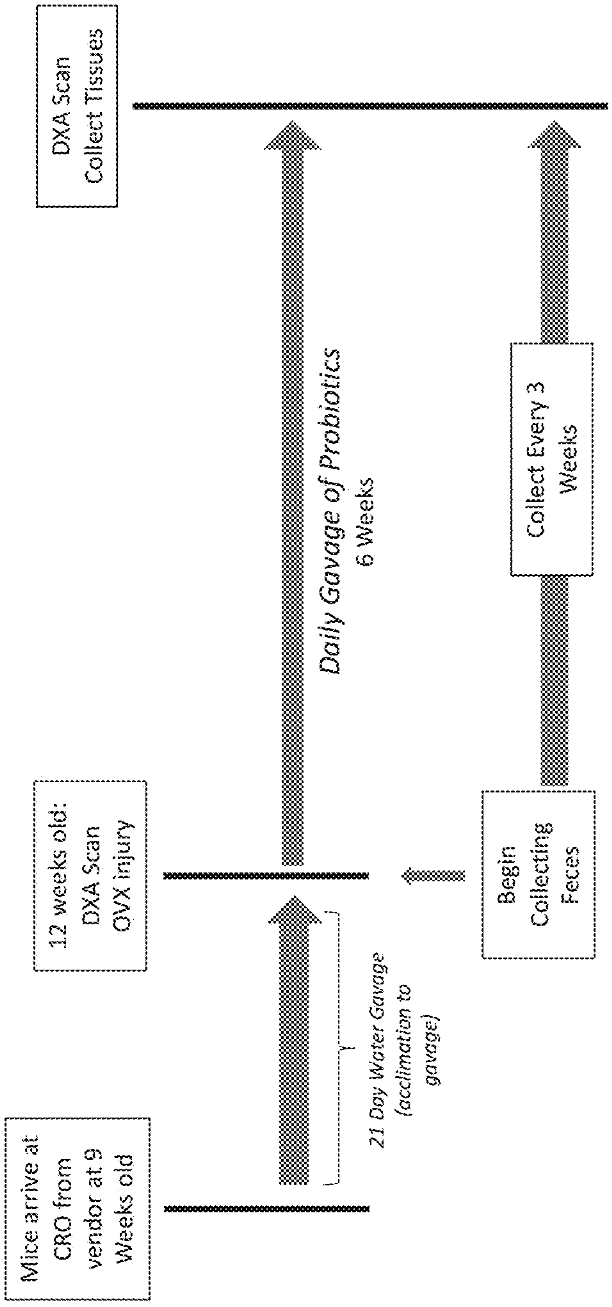
FIG. 9 shows a schematic detailing the experimental procedure for a pre-clinical model testing the disclosed invention. The experimental design is as follows: Candidate DMAs were evaluated for their therapeutic efficacy in an ovariectomized (OVX) mouse model of postmenopausal osteoporosis. All mice were group housed with 5 mice per cage in individually ventilated cages (IVCs) specifically designed for germ free husbandry [59, 60]. At 12-weeks of age, mice were weighed, had baseline feces collected, and underwent OVX (N=20) or sham (N=1.0) surgery to deplete estrogen levels and commence the bone resorption process as previously described [61]. 1-day post-surgery, mice were randomly divided into experimental groups and mice began a daily oral gavage regimen (200 uL) of saline (negative control), or SBD111 and continued for 6-weeks. Fecal samples were collected every 3 weeks to monitor the composition of the gut microbiome over time. On the last day of the study, mice received a DXA scan to evaluate systemic BMD, followed by euthanasia and collection of uterine weights, serum, cecal material, lumbar spine and femurs for downstream analysis.
Figure 10:
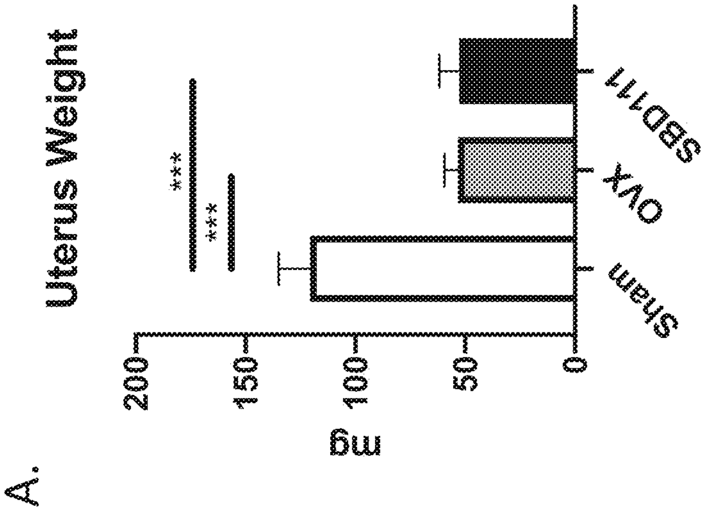
FIG. 10. Shows ovary weights taken from ovariectomized and sham-treated mice. Ovariectomized (OVX) mice were treated with either water (OVX) or DMA SBD111 for six-weeks post-surgery. At sacrifice, the uterus from each animal was removed and weighed. Uterus measurements were also taken from sham-treated mice. Decreased uterus weight in OVX and SBD111 treated animals indicates successful ovariectomy. Significant differences between groups in A were identified via 1-way ANOVA with a Tukey multiple comparison post-test (*$P<0.05$, $P<0.01$ *$P<0.001$, ****$P<0.0001$)

FIG. 3F shows taxonomic composition of fermented pepper paste. The sample enriched many lactic acid bacteria such as *Lactobacillus paracasei, Lactobacillus casei* and *Lactobacillus plantarum.*

Example 2: In Silico Modeling Outputs for Different Assemblages and DMA Formulation To generate in silico predictions for the effect of different microbial assemblages with a human host a genome-wide metabolic analysis was performed with formulated microbial communities selected from the Agora collection (Magbustoddir et al. 2016) and augmented with the genomes of bacterial members detected in the present survey. These simulations predict the "fermentative power" of each assemblage when simulated under different nutritional regimes including relatively high carbon availability (carbon replete) or carbon limited conditions when using plant fibers such as inulin, oligofructose and others as carbon source.

The method used for DNA sequencing the sample-associated microbiomes enabled to search for genes detected in the different vegetables related to propionate, butyrate, acetate and bile salt metabolism. This was done by mapping the reads obtained in the samples to reference genes selected for their intermediate role in the synthesis or degradation of these metabolites. There were organisms present in some of the 15 analyzed samples that matched the target pathways indicating their metabolic potential to produce desirable metabolites. Table 6a shows Metabolites in samples.

Assuming a diet composed of lipids, different carbohydrates and proteins the metabolic fluxes were predicted using an unconstrained model comparing the individual strain production of acetate, propionate and butyrate and compared to the metabolic fluxes with the assemblage.

In the first model, 4 strains were combined into a DMA. Strains 1-4 are predicted to produce acetate as single cultures but the combination into a DMA predicts the flux will increase when modeled on replete media and the flux decreases when modeled on plant fibers. Strain 4 is predicted to utilize the fibers better than the other 3 to produce acetate. Strain 1 is the only member of the assemblage predicted to produce propionate and when modeled with the other 3 strains the predicted flux doubles in replete media and quadruples in the fiber media illustrating the potential metabolic synergy from the assemblage. Strain 3 is the only member of the assemblage predicted to produce butyrate and when modeled with the other 3 strains the predicted flux increase slightly in replete media and doubled in the fiber media illustrating the potential metabolic synergy from the assemblage.

TABLE 6b

| Strains from first DMA model. |
|---|
| Strain 1-DP6 *Bacillus cereus*-like |
| Strain 2-DP9 *Pediococcus pentosaceus*-like |
| Strain 3-*Clostridium butyricum* DSM 10702 |
| Strain 4-DP1 *Pseudomonas fluorescens*-like |

Substrate availability plays an important role in the establishment of synergistic interactions. Carbon limitation in presence of plant fibers favors fiber depolymerization and fermentation to produce SCFA. Conversely, carbon replete conditions will prevent the establishment of synergistic metabolism to degrade fibers as it is not favored thermodynamically when the energy available from simple sugars is available. To illustrate this, a DMA was formulated containing two strains of lactic acid bacteria and run a metabolic prediction assuming a limited media with plant fibers. According to the model, *Leuconostoc* predicted flux is higher than *Pediococcus* and the DMA flux increases five times on the combined strains. When tested in the lab and measured by gas chromatography, the acetate production increases 3 times compared to the single strains. However, when grown on carbon replete media with available simple sugars, acetate production is correspondingly higher compared to the plant fiber media but there is no benefit of synergistic acetate production when the two strains are grown together into a DMA.

TABLE 6a

Metabolites in samples.

| NAME OF ENZYME | ASSOCIATED METABOLITE | GENE SYMBOL | PATHWAY | E. C. NUMBER | COMMENTS |
|---|---|---|---|---|---|
| ACETOLACTATE SYNTHASE I | (S)-2-ACETOLACTATE | | BUTANOATE METABOLISM | 2.2.1.6 | BUTYRATE PRODUCTION |
| ACETATE KINASE | PROPIONATE | ACKA | PROPANOATE METABOLISM | 2.7.2.1 | PROPIONATE |
| ACETYL-COA SYNTHETASE | PROPIONATE | AACS | PROPANOATE METABOLISM | 6.2.1.1 | PROPIONATE |
| ACETYL-COA HYDROLASE | ACETATE | | PYRUVATE METABOLISM | 3.1.2.1 | ACETATE |
| BILE SALT TRANSPORTER | BILE SALTS | ACR3 | BILE SALT TRANSPORT | | BILE SALT TOLERANCE |

DMA Formulation

Microbes in nature interact with multiple other groups and form consortia that work in synergy exchanging metabolic products and substrates resulting in thermodynamically favorable reactions as compared to the individual metabolism. For example, in the human colon, the process for plant fiber depolymerization, digestion and fermentation into butyrate is achieved by multiple metabolic groups working in concert. This metabolic synergy is reproduced in the DMA concept where strains are selected to be combined based on their ability to synergize to produce an increased amount of SCFA when grown together and when exposed to substrates such as plant fibers.

To illustrate this process, a set of 40 bacterial and fungal strains were isolated from food sources and their genomes were sequenced. The assembled and annotated genomes were then used to formulate in silico assemblages considering the human host as one of the metabolic members.

In addition to acetate, propionate, and butyrate some strains produce other isomers. For example, strain DP1 related to *P. fluorescens* and DP5 related to *Debaromyces hansenii* (yeast) produce isobutyrate when grown in carbon-replete media as single strains, however there is metabolic synergy when tested together as DMA measured as an increase in the isobutyric acid production.

To describe experimentally the process of DMA validation the following method is applied to find other candidates applicable to other products:

1. Define a suitable habitat where microbes are with the desirable attributes are abundant based on ecological hypotheses. For example, fresh vegetables are known to have anti-inflammatory effects when consumed in a whole-food plant-based diet, and therefore, it is likely they harbor microbes that can colonize the human gut.
2. Apply a selection filter to isolate and characterize only those microbes capable of a relevant gut function. For example, tolerate acid shock, bile salts and low oxygen. In addition, strains need to be compatible with target therapeutic drugs including but not limited to bisphosphonates (alendronate, risedronate, ibandronate, zolendronate), biologics (denosumab, romosozumab), selective estrogen receptor mediators (Raloxifene), or anabolic agents (teriparatide, abaloparatide).
3. Selected strains are then cultivated in vitro and their genomes sequenced at 100× coverage to assemble, annotate and use in predictive genome-wide metabolic models.
4. Metabolic fluxes are generated with unconstrained models that consider multiple strains and the human host to determine the synergistic effects from multiple strains when it is assumed, they are co-cultured under simulated substrate conditions.
5. Predicted synergistic combinations are then tested in the laboratory for validation. Single strains are grown to produce a biomass and the spent growth media removed after reaching late log phase. The washed cells are then combined in Defined Microbial Assemblages with 2-10 different strains per DMA and incubated using a culture media with plant fibers as substrates to produce short chain fatty acids to promote gut health.
6. The DMAs are then analyzed by gas chromatography to quantify the short chain fatty acid production where the synergistic effect produces an increased production in the combined assemblage as compared to the individual contributions.

Example 3: Gut Simulation Experiments

The experiment comprises an in vitro, system that mimics various sections of the gastrointestinal tract. Isolates of interest are incubated in the presence of conditions that mimic particular stresses in the gastro-intestinal tract (such as low pH or bile salts), or heat shock. After incubation, surviving populations are recovered. Utilizing this system, the impact of various oral anti-diabetic therapies alone or in combination with probiotic cocktails of interest on the microbial ecosystem can be tested. Representative isolates are shown in Table 7.

TABLE 7

| Strains | | | | | |
|---|---|---|---|---|---|
| Strain Number | Heat Shock | Isolation Temperature | Acid Shock (pH 3; 2 hr) | Genus | Species |
| DP1 | No | 25 | No | *Pseudomonas* | *fluorescens* |
| DP2 | No | 37 | No | *Hanseniaspora* | *occidentalis* |
| DP3 | No | 25 | No | *Leuconostoc* | *mesenteroides* |
| DP4 | No | 25 | No | *Aureobasidium* | *pullulans* |
| DP5 | No | 37 | No | *Debaromyces* | *hansenii* |
| DP6 | Yes | 25 | No | *Bacillus* | *wiedmannii* |
| DP7 | No | 25 | No | *Pichia* | *fermentans* |
| DP8 | No | 25 | No | *Hanseniaspora* | *opuntiae* |
| DP9 | No | 25 | No | *Pediococcus* | *pentosaceus* |
| DP10 | Yes | 25 | No | *Bacillus* | *velezensis* |
| DP11 | No | 25 | No | *Pseudomonas* | *putida* |
| DP12 | No | 25 | Yes | *Microbacterium* | sp. |
| DP13 | No | 25 | Yes | *Bacillus* | *mycoides* |
| DP14 | No | 25 | Yes | *Arthrobacter* | *luteolus* |
| DP15 | No | 25 | No | *Curtobacterium* | sp. |
| DP16 | No | 25 | No | *Lacihabitans* | *lacunae* |
| DP17 | No | 25 | No | *Rahnella* | *aquatilis* |
| DP18 | No | 25 | No | *Pseudomonas* | sp. |
| DP19 | No | 25 | No | *Curtobacterium* | *pusillum* |
| DP20 | No | 25 | No | *Stenotrophomonas* | *rhizophila* |
| DP22 | No | 25 | No | *Rahnella* | sp. |
| DP23 | No | 25 | No | *Erwinia* | *billingiae* |
| DP24 | No | 25 | No | *Filobasidium* | *globisporum* |
| DP25 | No | 25 | No | *Penicillium* | *solitum* |
| DP26 | No | 25 | No | *Methylobacterium* | sp. |
| DP27 | No | 25 | No | *Sphingomonas* | sp. |
| DP28 | No | 25 | Yes | *Aureobasidium* | *pullulans* |
| DP29 | No | 25 | Yes | *Pseudoclavibacter* | *helvolus* |
| DP30 | No | 25 | Yes | *Microbacterium* | *testaceum* |
| DP31 | No | 25 | Yes | *Sporisorium* | *reilianum* |
| DP32 | No | 25 | No | *Hafnia* | *paralvei* |
| DP33 | No | 25 | No | *Erwinia* | *persicinus* |
| DP34 | No | 25 | Yes | *Plantibacter* | *flavus* |
| DP35 | No | 25 | Yes | *Pantoea* | *ananatis* |
| DP36 | No | 25 | Yes | *Pantoea* | *vagans* |
| DP37 | No | 25 | No | *Pseudomonas* | *rhodesiae* |
| DP38 | No | 25 | No | *Rhodococcus* | sp. |
| DP39 | No | 25 | No | *Agrobacterium* | *tumefaciens* |
| DP40 | No | 37 | No | *Pantoea* | sp. |
| DP41 | Yes | 37 | No | *Corynebacterium* | *mucifaciens* |
| DP42 | No | 37 | No | *Pseudomonas* | *lundensis* |
| DP43 | No | 25 | No | *Janthinobacterium* | sp. |
| DP44 | No | 25 | No | *Herbaspirillum* | sp. |
| DP45 | No | 25 | No | *San guibacter* | *keddieii* |
| DP46 | No | 25 | Yes | *Pantoea* | *agglomerans* |
| DP47 | No | 25 | Yes | *Cronobacter* | *dublinensis* |
| DP48 | Yes | 25 | No | *Bacillus* | *paralicheniformis* |
| DP49 | Yes | 25 | No | *Bacillus* | *gibsonii* |
| DP50 | No | 25 | No | *Enterobacter* | sp. |
| DP51 | No | 25 | No | *Klebsiella* | *aerogenes* |
| DP52 | No | 25 | No | *Arthrobacter* | sp. |
| DP53 | No | 25 | No | *Pseudomonas* | *fragi* |
| DP54 | No | 25 | No | *Methylobacterium* | *adhaesivum* |
| DP55 | Yes | 25 | No | *Bacillus* | *megaterium* |
| DP56 | Yes | 25 | No | *Paenibacillus* | *lautus* |
| DP57 | Yes | 25 | No | *Bacillus* | *mycoides* |
| DP58 | No | 25 | No | *Janthinobacterium* | *svalbardensis* |
| DP59 | No | 25 | No | *Kosakonia* | *cowanii* |
| DP60 | Yes | 25 | No | *Bacillus* | *simplex* |
| DP61 | No | 25 | No | *Lelliottia* | sp. |
| DP62 | No | 25 | No | *Erwinia* | sp. |
| DP63 | No | 25 | Yes | *Pseudomonas* | *azotoformans* |
| DP64 | No | 25 | No | *Hanseniaspora* | *uvarum* |
| DP65 | No | 25 | No | *Bacillus* | sp. |
| DP66 | No | 25 | No | *Hanseniaspora* | *occidentalis* |
| DP67 | Yes | 25 | No | *Bacillus* | sp. |
| DP68 | Yes | 25 | No | *Bacillus* | *atrophaeus* |
| DP69 | Yes | 25 | No | *Bacillus* | sp. |
| DP70 | No | 25 | No | *Bacillus* | *subtilis* |
| DP71 | No | 25 | No | *Rhodotorula* | sp. |
| DP72 | Yes | 25 | No | *Bacillus* | *zhangzhouensis* |
| DP73 | Yes | 37 | No | *Bacillus* | *clausii* |
| DP74 | Yes | 25 | No | *Bacillus* | *coagulans* |

TABLE 7-continued

| Strains | | | | | |
|---|---|---|---|---|---|
| Strain Number | Heat Shock | Isolation Temperature | Acid Shock (pH 3; 2 hr) | Genus | Species |
| DP75 | No | 37 | No | *Pseudomonas* | *gessardii* |
| DP76 | No | 25 | No | *Ochrobactrum* | sp. |
| DP77 | Yes | 25 | No | *Bacillus* | *aryabhattai* |
| DP78 | No | 25 | No | *Erwinia* | *rhapontici* |
| DP79 | No | 25 | No | *Pseudomonas* | *fragi* |
| DP80 | No | 25 | No | *Methylobacterium* | *adhaesivum* |
| DP81 | Yes | 37 | No | *Bacillus* | *clausii* |

TABLE 7-continued

| Strains | | | | | |
|---|---|---|---|---|---|
| Strain Number | Heat Shock | Isolation Temperature | Acid Shock (pH 3; 2 hr) | Genus | Species |
| DP82 | Yes | 37 | No | *Bacillus* | *clausii* |
| DP83 | Yes | 37 | No | *Bacillus* | *clausii* |
| DP84 | No | 25 | No | *Microbacterium* | sp. |
| DP85 | No | 30 | No | *Methanolacinia* | *petrolearia* |
| DP86 | No | 30 | No | *Bacillus* | *velezensis* |
| DP87 | No | 30 | No | *Lactobacillus* | *plantarum* |
| DP88 | No | 30 | No | *Bacillus* | *velezensis* |
| DP89 | No | 30 | No | *Bacillus* | *subtilis* |
| DP90 | No | 30 | No | *Lactobacillus* | *plantarum* |
| DP92 | No | 30 | No | *Bacillus* | *subtilis* |
| DP93 | No | 30 | No | *Leuconostoc* | *mesenteroides* |
| DP94 | No | 30 | No | *Lactobacillus* | *brevis* |
| DP95 | No | 30 | No | *Lactobacillus* | *paracasei* |
| DP96 | No | 30 | No | *Lactobacillus* | *casei* |
| DP97 | No | 30 | No | *Lactococcus* | *garvieae* |
| DP98 | No | 30 | No | *Lactococcus* | *garvieae* |
| DP100 | No | 30 | No | *Lactobacillus* | *plantarum* |
| DP101 | No | 30 | No | *Pediococcus* | *pentosaceus* |
| DP102 | No | 30 | No | *Pichia* | *krudriaze vii* |

Example 4: Computation of Microbial Average Nucleotide Identity (ANI)

A whole-genome based method was applied, known as the average nucleotide identity (ANI), to estimate the genetic relatedness among bacterial genomes and profile hundreds of microbial species at a higher resolution taxonomic level (i.e., species- and strain-level classification). ANI is based on the average of the nucleotide identity of all orthologous genes shared between a genome pair. Genomes of the same species present ANI values above 95% and of the same genus values above 80% (Jain et al. 2018).

Taxonomic annotation of the strains combined into DMAs using ANI and the NCBI RefSeq database indicated that these microbes represent species not present in the database and most likely are new bacterial species even when the nucleotide identity based on the 16S rRNA gene is 99%:

TABLE 8

Comparative predictive power of 16S rRNA sequence analysis and Average Nucleotide Identity (ANI) analysis. While 16S rRNA sequence percentage indicates a high degree of homology, ANI analysis demonstrates that the overall genome sequence of the microbial entities isolated from plants and described herein as compared to reference strains is different enough in many cases to qualify as a different species.

| ID | Name | 16S rRNA gene (%) | Closest Ref. genome | ANI (%) |
|---|---|---|---|---|
| DP3 | *Leuconostoc mesenteroides* (NR_074957.1) | 99 | *Leuconostoc pseudomesenteroides* (JDVA01000001.1) | 91.77 |
| DP9 | *Pediococcus pentosaceus* (NR_042058.1) | 99 | *Pediococcus pentosaceus* (NC_022780.1) | 99.6 |
| DP53 | *Pseudomonas helleri* *Pseudomonas* (NR_148763.1) | 99 | *Pseudomonas psychrophila* (NZ_L1329795.1) | 86.82 |
| DP1 | *fluorescens* (NR_115715.1) | 99 | *Pseudomonas antarctica* (NZ_CP015600.1) | 94.48 |
| DP22 | *Rahnella* sp. (NR_025337.1) | 98 | *Rahnella* sp. (NC_015061.1) | 88.24 |

Example 5: Testing Composition Efficacy in a Mouse Model of Obesity Induced Bone Loss

Experimental Design

Male diet induced obese (DIO) and low-fat diet control C57BL/6J mice were purchased from the vendor at 16 weeks of age and were singly housed in individually ventilated cages (IVCs). At 5 weeks of age, mice were placed on either a low-fat diet (10% kcal, D12450B) or high-fat diet (60% kcal, D12492) (Open Source Diets; Research Diets Inc.) and remained on those respective diets for the duration of the experiment. Mice were allowed to acclimate for 2-weeks prior to the experimental initiation. At 18-weeks of age, one cohort of lean mice (N=4) and one cohort of obese mice (n=4) began control supplementation with water by daily oral gavage, while another group of obese mice (N=4) were treated with a daily oral gavage of SBD102 at a dose of $8\times10^{10}$ CFUs/kg body weight. Control groups were provided sterile water at a dose of 5 mL/kg body weight. Mice were orally gavaged with control or test article daily for 8-weeks.

Bone Mineral Density Analysis:

At the time of sacrifice, mice were anesthetized via intraperitoneal injection of ketamine (60 mg/kg) and xylazine (4 mg/kg) and scanned by Dual Energy x-ray Absorptiometry (DEXA) scan (PIXImus2 Mouse Densitometer; GE) to measure whole body bone mineral density (BMD).

Distal Femur Trabecular Bone Analysis:

To evaluate trabecular bone volumes at the distal femur, femurs were removed at the time of sacrifice and analyzed by micro computed tomography (microCT) with a Scanco microCT 40 desktop microCT scanner.

Conclusion

Figure 13:
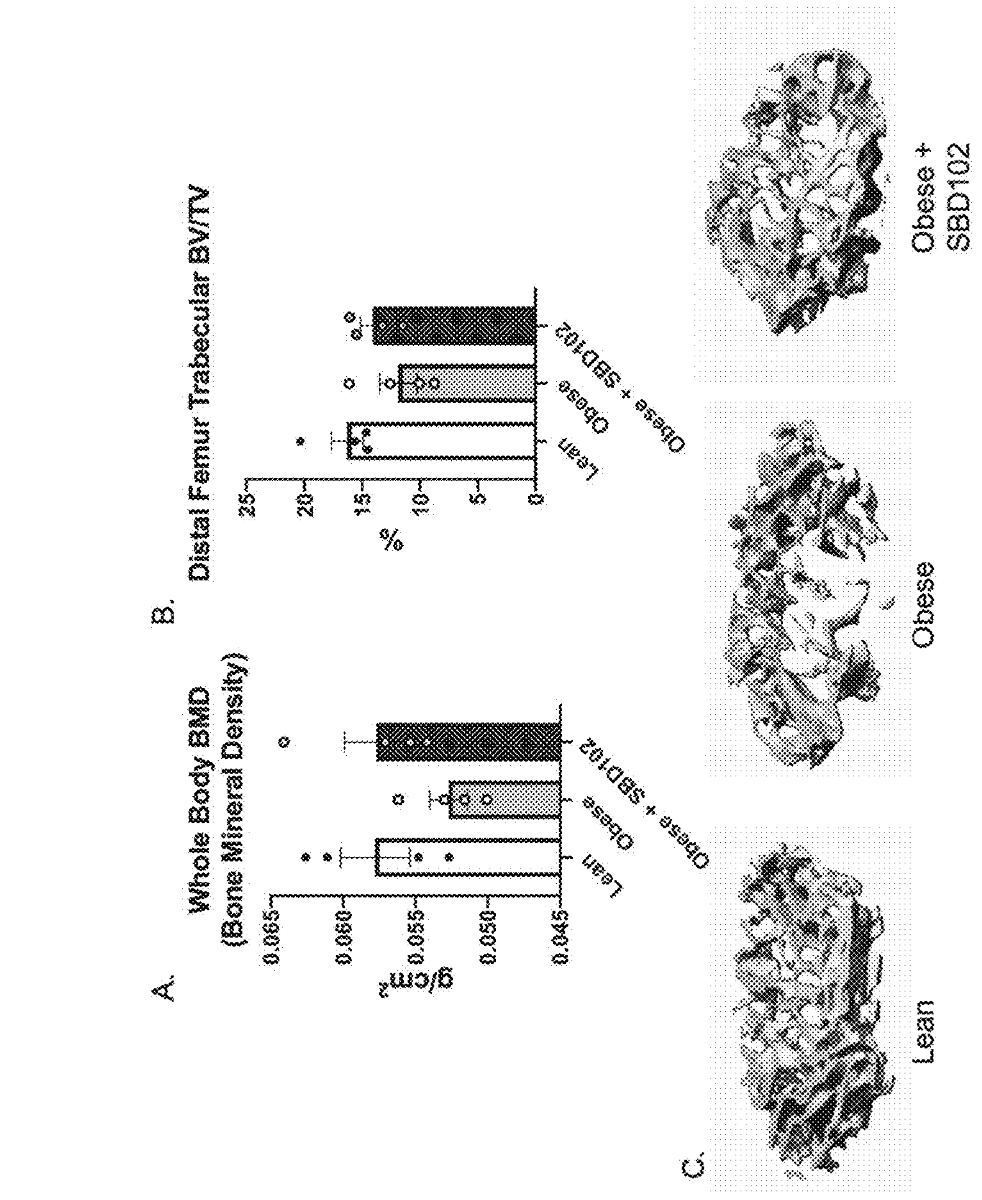
FIG. 13. C57bl/6J mice were placed on a high fat diet (60% kcal fat) for 12 weeks to induce obesity. Mice were then treated with either water control (obese) or SBD102 (obese+SBD102), a DMA consisting of prebiotic plant fibers and probiotic microbes, for 8-weeks. Bone mineral density (BMD) was measured by whole body dual x-ray absorptiometry (DXA) (A), and trabecular bone volume was measured at the distal femur by micro computed tomography (MicroCT) (B). Whole body DXA revealed an 8.5% decrease in BMD in obese mice compared to lean, that was prevented by treatment with SBD102 (A). A similar effect was observed by microCT of the distal femur, were obese mice had lower trabecular bone volume compared to lean mice that was prevented by treatment with SBD102 (B). Representative images of the microCT are depicted in (C).

Compared to lean animals, obese mice lost 8.5% of their total BMD as measured by DXA scan. Obese mice treated with SBD102 were completely protected from this loss of BMD, indicating that SBD102 prevents obesity induced bone loss in a mouse model (FIG. 13A). Substantiating these data, microCT analysis of distal femurs showed similar trends where obesity induced a decrease in trabecular bone volume (BV/TV) compared to lean animals, and treatment with SBD102 prevented that decrease (FIG. 13B, 13C). With this, treatment with DMAs like SBD102 demonstrates a viable therapeutic option for the prevention of obesity induced bone loss.

SBD102 comprised DP9, DP2, and DP53.

Example 6: Testing Composition Efficacy in Mouse Model of Postmenopausal Osteoporosis Experimental Design DMA compositions were evaluated for therapeutic efficacy in an ovariectomized (OVX) mouse model of postmenopausal osteoporosis. All mice were group-housed with 5 mice per cage in individually ventilated cages (IVCs) specifically designed for germ free husbandry [59, 60]. At 12-weeks of age, mice were weighed, had baseline feces collected, and underwent OVX surgery (N=20) or sham (N=10) surgery to deplete estrogen levels and commence the bone resorption process as previously described (Souza et al., 2019). 1-day post-surgery, mice were randomly divided into experimental groups and mice began a daily oral gavage regimen (200 uL) of saline (negative control), or SBD111 ($5\times10^9$ CFU/dose) which continued for 6-weeks. Fecal samples were collected at the beginning of the experiment, at week 3 and week 6 at the end of the experiment to monitor the composition of the gut microbiome over time. Finally, on the last day of the study, mice received a DXA scan to evaluate systemic BMD, followed by euthanasia and collection of lumbar vertebra for analysis.

SBD111 comprised: DP1 (*Pseudomonas* sp.), DP94 (*Lactobacillus brevis*), DP95 (*Leuconostoc mesenteroides*), DP100 (*Lactobacillus plantarum*), and DP102 (*Pichia krudriazevii*).

Tissue Collection and Analysis:

At the time of sacrifice, the uterus was removed and weighed to confirm that the ovaries were successfully removed, and estrogen was depleted following OVX surgery. Tissues were then collected from each mouse to evaluate bone quantity. Cecal contents were removed and flash frozen for downstream metagenomic sequencing and SCFA analysis by GC-FID to determine how our DMA impacted the composition and function of the gut microbiome. Finally, the lumbar spines were removed, processed, and analyzed by micro computed tomography (microCT) with a Scanco microCT 40 desktop microCT scanner.

Conclusion

Figure 11:
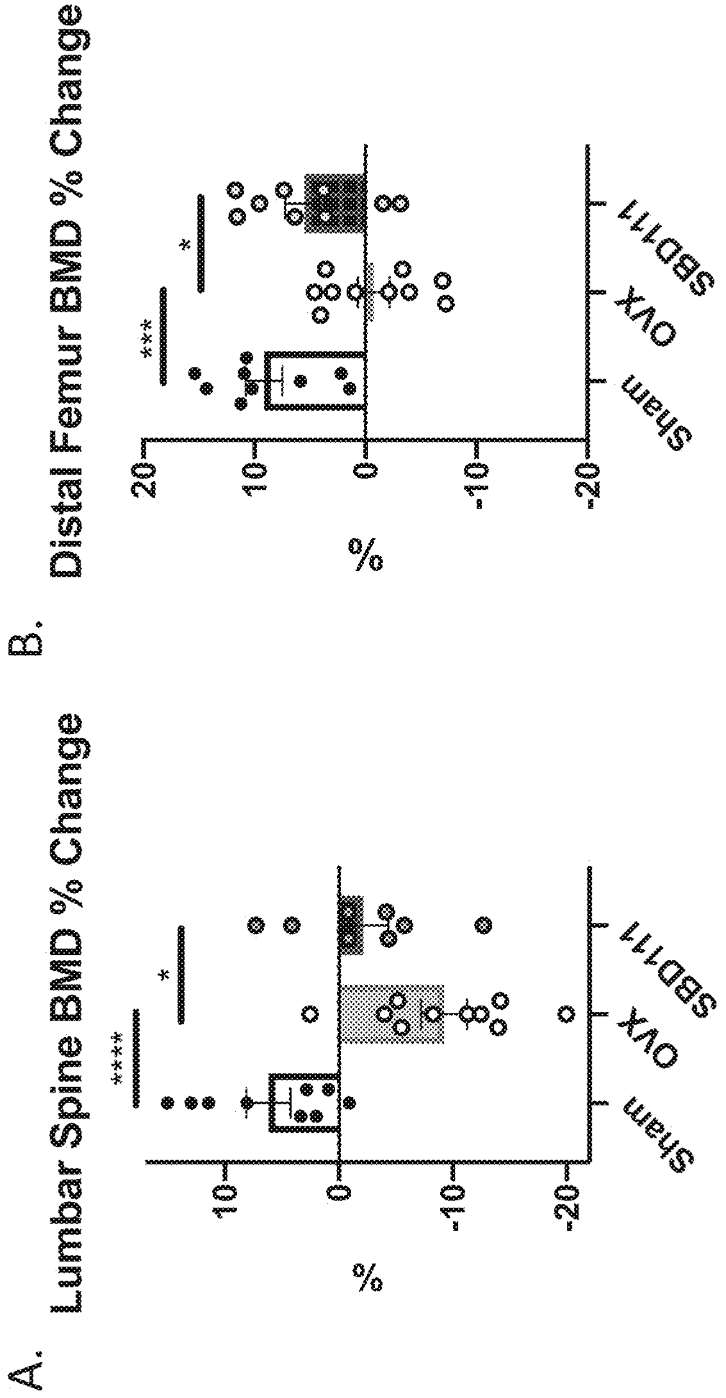
FIG. 11. Ovariectomized (OVX) mice were treated with either water (OVX) or SBD111 for six-weeks post-surgery. Mice received DXA scans before surgery and six-weeks post-surgery to determine the percent change in bone mineral density (BMD). DXA scans reveal a significant protection against OVX-induced bone loss at the lumbar spine (A) and distal femur (B) in mice treated with SBD111. Significant differences between groups in A and B were identified via 1-way ANOVA with a Tukey multiple comparison post-test (*$P<0.05$, $P<0.01$ *$P<0.001$, ****$P<0.0001$)
Figure 12:
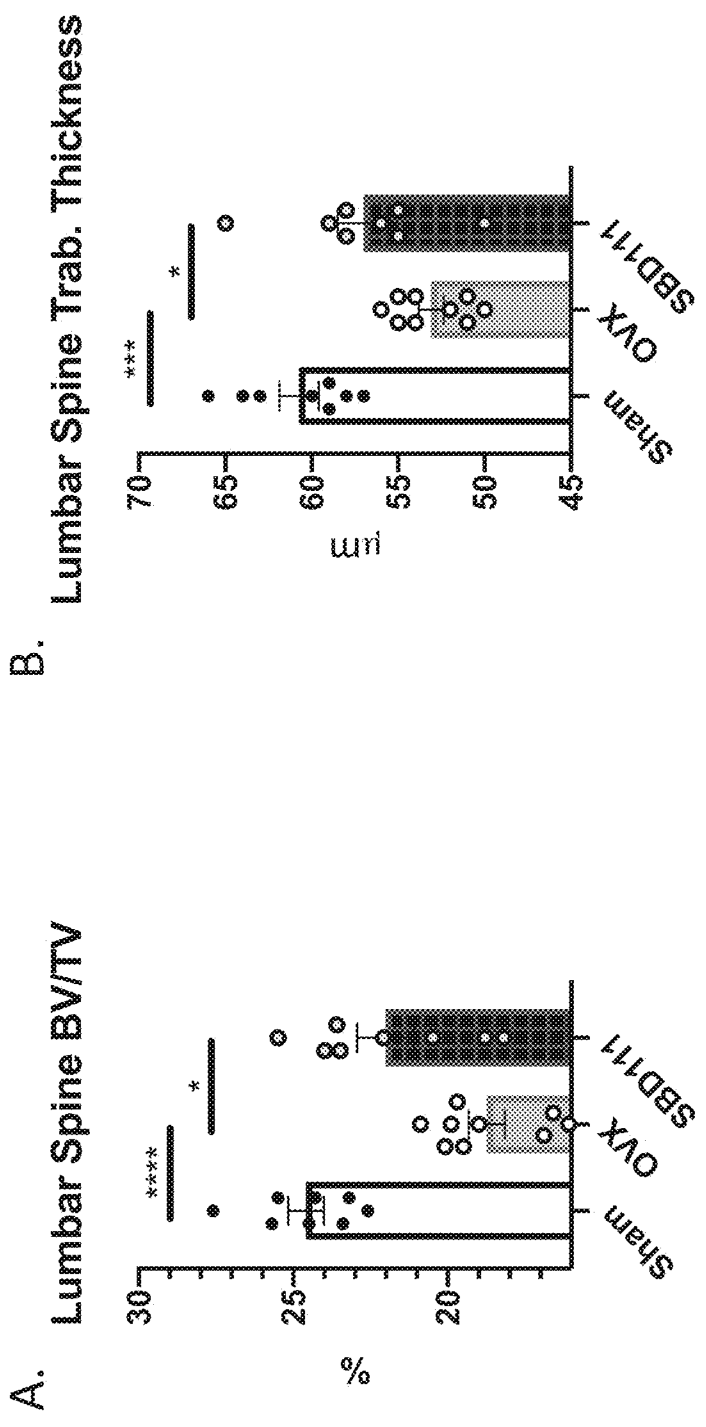
FIG. 12. Ovariectomized (OVX) mice were treated with either water (OVX) or SBD111 for six-weeks post-surgery. At sacrifice, lumbar spine (L1-L4) were removed and analyzed by micro computed tomography (MicroCT) for trabecular bone volume (BV/TV) (A) and trabecular thickness (B). MicroCT scans reveal a significant protection against OVX-induced bone loss at the lumbar spine as indicated by BV/TV (A) and Trabecular Thickness (B) in mice treated with SBD111. Significant differences between groups in A and B were identified via 1-way ANOVA with a Tukey multiple comparison post-test (*$P<0.05$, $P<0.01$ *$P<0.001$, ****$P<0.0001$)

As has been previously described, OVX surgery induced a significant loss of BMD at the lumbar spine and distal femur in comparison to mice receiving sham surgery. Strikingly, OVX mice treated with SBD111 were almost completely protected from this steroid ablation induced bone loss after 6-weeks of daily treatment (FIGS. 11A, B). Further, microCT analysis of the lumbar spine revealed significant protection from the loss of trabecular bone that is characteristic of this model in mice treated with SBD111. SBD111 treated animals retained ~70% more trabecular bone volume than OVX controls, and also had thicker trabeculae compared to OVX animals (FIG. 12A, B). With this, DMA treatment demonstrates a potential viable therapeutic option for the protection against postmenopausal bone loss.

Example 7: Orthopaedic Infection

To test the impact of our DMAs on the severity and incidence of implant-associated orthopedic infections, a well-recognized orthopedic implant surgery and infection model is used.

An orthopedic implant coated with *Staphylococcus aureus* (*S. aureus*) is generated by cutting flat stainless steel surgical wire into a 0.02×0.5×4 mm length, and bent at 1 mm to make an L shaped pin that is placed in an overnight culture of USA300 LAC::/uxmethicillin resistants *S. aureus* (2×10^6 CFUs) for 20 minutes. Next, mice are anesthetized with an intraperitoneal injection of ketamine (60 mg/kg) and xylazine (4 mg/kg), and a 4 mm incision is made on the medial aspect of the right tibia. A hole in the medial tibia is then predrilled using successive 30- and 26-gauge needles before the infected pin is placed through the defect. The surgical site is then closed using a 5-0 nylon suture.

After surgery, mice are divided into treatment groups, and daily oral gavages of defined microbial assemblages (DMAs) or saline controls are performed for four weeks. Weekly fecal samples are collected for sequencing to monitor the gut microbiome over time. For each treatment, infections are monitored longitudinally by bioluminescence of the tibia using a Xenogen IVIS® camera system. At 14, 21, and 35 days post-infection, mice are euthanized and tissues are collected including ti bias for analysis of the infection by micro-computed tomography (MicroCT) and histology, serum for cytokine analysis, and colonic tissues for immune cell and cytokine evaluation by histology and qRT-PCR.

The results demonstrate that mice treated with the compositions disclosed herein have a shorter recovery period and milder infection symptoms than mice receiving the saline control.

Example 8: Efficacy of DMAs on Improving Fracture Healing in a Mouse Model

To test the impact of DMAs on fracture healing, a well-recognized mouse model of fracture repair is used, the murine stabilized tibia fracture model. Here, 12-week old male and female mice are anesthetized with an intraperitoneal injection of ketamine (60 mg/kg) and xylazine (4 mg/kg). A 4 mm longitudinal incision is made on the anterior side of the right tibia, and a small hole is then be drilled into the tibial tuberosity using a 26-gauge needle. A transverse osteotomy is then performed with a number 11 scalpel blade at the proximal diaphysis of the tibia. The fibula remains intact. The bone fracture is then fixed with an intramedullary nailing procedure using a 26-gauge Quincke type spinal needle (BD Medical Systems), and the wound is closed using 5-0 nylon sutures. After surgery, mice are divided into treatment groups, and begin daily oral gavages for four weeks of defined microbial assemblages (DMAs) or saline controls. Weekly fecal samples are collected for sequencing to monitor the gut microbiome over time. For each treatment, Fractures are evaluated for strength, fracture callus formation, and union proficiency by X-ray, MicroCT, biomechanical torsion testing of the tibia, and histological/histomorphometric analysis of the tibia at 7, 14, 21, and 35 days post fracture. Additionally, serum, colon, and cecal material are collected from each mouse, from which serum is analyzed for inflammatory cytokine levels, colonic tissues are evaluated by qRT-PCR for immune cell and cytokine levels, and cecal material is shotgun sequenced for microbiome analysis.

The results demonstrate that mice treated with the compositions disclosed herein demonstrate the efficacy of DMAs on improving fracture healing in a mouse model.

Example 9: Evaluation of Anti-Osteoarthritis Efficacy in a Mouse Model

DMAs are evaluated for their therapeutic efficacy in a mouse model of post-traumatic osteoarthritis. All mice are group housed with 3 mice per cage in individually ventilated cages (IVCs) specifically designed for germ free husbandry. At 12-weeks of age, mice have baseline feces collected, and receive either a sham injury (n=12) or a destabilization of the medial meniscus (DMM) (n=72) injury to induce arthritis. Briefly, a 5-mm-long incision is made through the skin on the medial side of the knee. Under a dissecting microscope, another incision through the synovial membrane is made along the medial side of the patellar tendon, opening the joint space. Using a #11 scalpel, the medial meniscotibial ligament (MMTL) is transected, enabling the medial meniscus to move freely. After surgery, 4-0 silk sutures are used to close the incision using an interrupted pattern. 1-week post-surgery, mice are randomly divided into experimental groups and fresh fecal samples are again collected. Mice then begin a daily oral gavage regimen (200 μL) of saline (negative control), DMA #1, DMA #2, DMA #3, DMA #4, or DMA #5 and continue for 12-weeks. Monthly fecal samples are collected to monitor the composition of the gut microbiome over time. On the last day of the study, mice are euthanized, and tissues are collected including serum, colon, cecal material, knees, and synovial membranes for analysis. Serum is analyzed for inflammatory cytokine levels; colonic tissues are evaluated by qRT-PCR for immune cell and cytokine levels; cecal material is shotgun sequenced for microbiome analysis; knees are evaluated by histology for total cartilage area and hypertrophic chondrocyte markers, and synovial membranes are assessed by qRT-PCR for inflammatory cytokine levels.

The results demonstrate that mice treated with the compositions disclosed herein anti-osteoarthritis efficacy in a mouse model.

Example 10: Monitoring the Effect of DMAs on Microbial Flora of a Mammal

Alterations of the gut microbiota have been linked with changes in the host homeostasis such as chronic inflammation. In order to evaluate changes in the gut microbiota composition in OVX mice, fecal pellets were collected from OVX and sham mice during baseline and week 6 of treatment and the gut microbiota was characterized. Briefly, DNA was extracted using the ZymoBIOMICS DNA extraction Kit and quantified using a Qubit 2.0 flurometer with the dsDNA HS assay kit. Metagenomic libraries were prepared using the Illumina Nextera Flex DNA library preparation kit and an equimolar mixture of the libraries was sequenced on an Illumina NovaSeq Si instrument on a 2×150 bp paired end run. Raw reads from the sequencing run were analyzed using SolexaQA (Cox et al. 2010) for trimming and removing of Illumina adaptors using a Phred score cutoff of 20 and minimum fragment length of 50 bp. Mouse sequencing reads were removed by mapping metagenomic reads against the *Mus musculus* genome GRCm38 using Bowtie2 with default parameters (Langmead et al. 2012). Taxonomic classification of the short-read metagenomes was determined using MetaPhlan2, which uses clade-specific marker genes from approximately 17,000 reference genomes to estimate the relative abundance of microbial members present in the sample (Troung et al. 2015).

Figure 14:
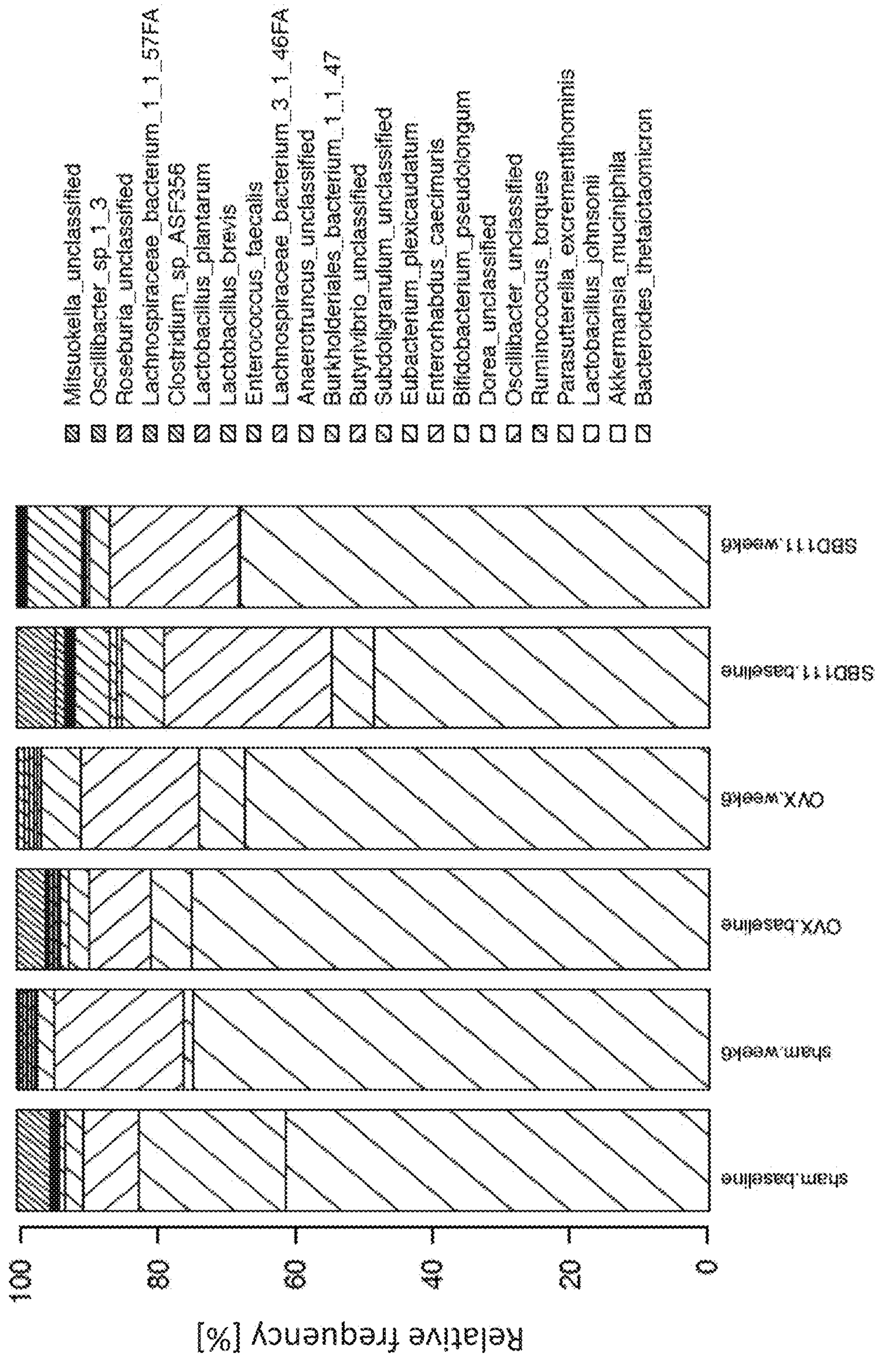
FIG. 14. Shows the composition of the gut microbial community of the sham and OVX mice at the baseline and six-weeks post-surgery time points with SBD111. Overall, *Bacteroides thetaiotaomicron* was the most prevalent taxon detected among the mice groups encompassing more than 50% of the total community on average, followed by *Lactobacillus johnsonii* with abundance values between 8.8% and 24.2%, excepting the sham baseline group where *Akkermansia municiphila* was the second most abundant taxon (21.3% on average). In the case of the SBD111 group, *Bifidobacterium pseudolongum* showed an increase in abundance at week 6 (from 5% to 7.8% of the total community).

FIG. 14 shows the composition of the gut microbial community of the sham and ovx mice at the baseline and week 6 time points with different DMA combinations. Overall, *Bacteroides thetaiotaomicron* was the most prevalent taxon detected among the mice groups encompassing more than 50% of the total community on average, followed by *Lactobacillus johnsonii* with abundance values between 8.8% and 24.2%, excepting the sham baseline group where *Akkermansia municiphila* was the second most abundant taxon (21.3% on average). In the case of the SBD111 group, *Bifidobacterium pseudolongum* showed an increase in abundance at week 6 (from 5% to 7.8% of the total community). *Bifidobacterium pseudolongum* has been shown previously to modulate the immune system and decrease systemic inflammation. Inflammation plays a large role in osteoclastogenesis and the breakdown of bone, so the increased abundance of *Bifidobacterium pseudolongum* likely decreases systemic inflammatory mediators and thus decreases the resorption of bone, leading to improved BMD and trabecular bone volume in mice treated with SBD111 compared to OVX mice.

Further, *Eubacterium plexicaudatum* and *Lactobacillus johnsonii* increase in the sham group after 6 weeks while *Akkermansia muciniphila* decreases. These changes should be considered as part of a growth changes in the microbiome due to age and not associated to a changing phenotype due to the interventions.

In the OVX group there is a decrease in the Burkholderiales bacterium and *Oscillibacter* sp. SBD111 exhibits an increase in *Bacteroides thetaiotaomicron* in Lachnospiracea bacterium and a decrease in Burkholderiales, *Parasutterella excremintihomini* that can be associated to the phenotypes of prevention to bone loss.

Example 11: Functional Profile of the Gut Microbiota Under DMA Treatment L-Rhamnose Degradation In order to compare the rhamnose degradation in each group at week 6, relative abundances of genes related to L-rhamnose degradation pathway in individual mouse were calculated by mapping of sequencing reads against UniRef90 using HuMANN2 and characterizing gene families (Franzosa et al., 2018). Gene families that were annotated to the same MetaCyC reaction ID were averaged in each individual.

Figure 19A:
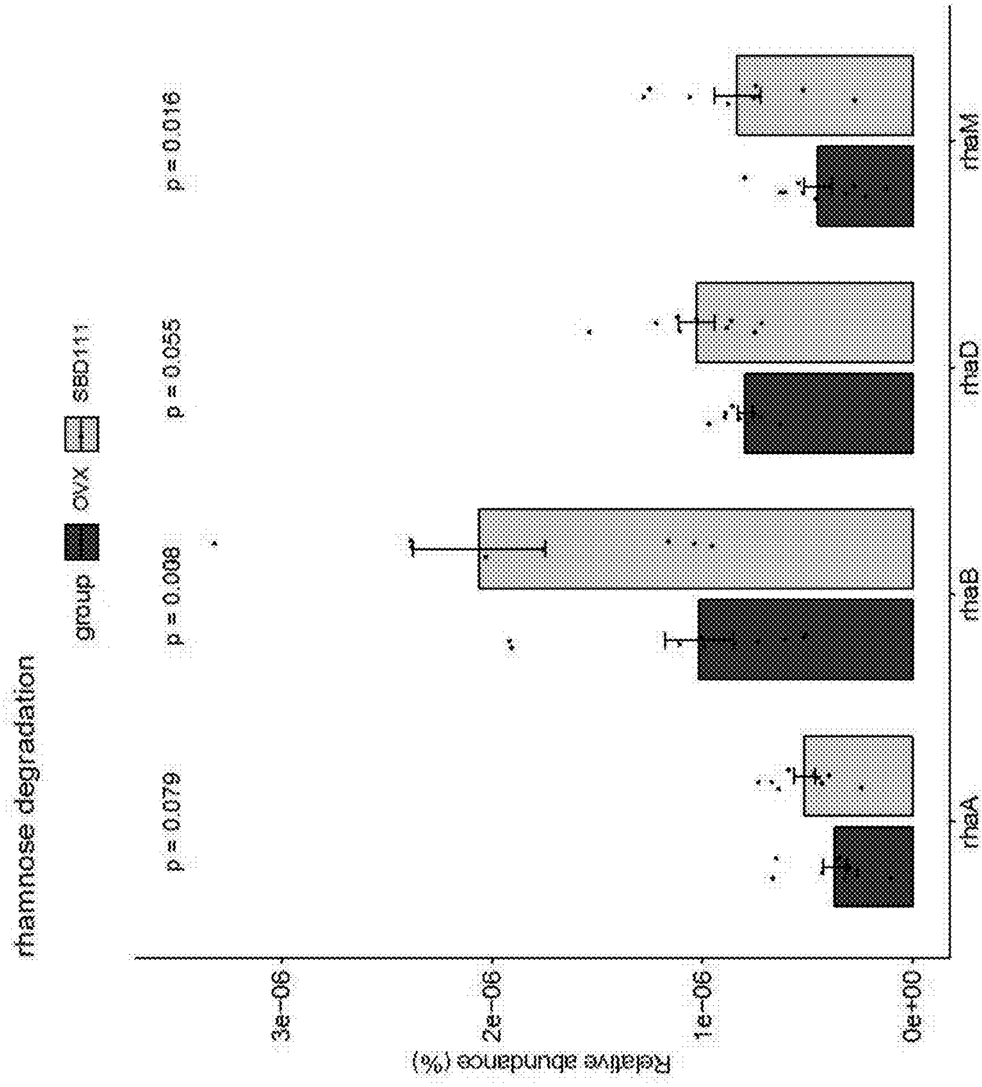
FIG. 19A Comparison of relative abundance of genes related to L-rhamnose degradation between OVX group and SBD111-treated group. Differences between groups were assessed by Mann-Whitney U test (*P<0.05, **P<0.01). rhaD, rhamnulose-1-phosphage aldolase; rhaB, rhamnulokinase; rhaA, L-rhamnose isomerase; rhaM, L-rhamnose mutarotase.

FIG. 19A shows the comparison of relative abundance of genes related to L-rhamnose degradation between OVX group and SBD111-treated group. Differences between groups were assessed by Mann-Whitney U test. Comparison of gene abundance between OVX and SBD111 groups indicated significantly higher abundance at week 6 in the SBD111 group in comparison with the OVX one. The L-rhamnose degradation pathway has been implicated in increased short chain fatty acid production. Further, increased short chain fatty acid production has been shown to improve BMD in OVX mice, and thus an increase in L-rhamnose degradation may partially explain the increased BMD and trabecular bone volume in SBD111 treated mice via increased SCFA production.

rhaD, rhamnulose-1-phosphage aldolase; rhaB, rhamnulokinase; rhaA L-rhamnose isomerase; rhaM, L-rhamnose mutarotase.

TABLE 9

Pathways significantly enriched or depleted after 6 weeks in both SBD111 and OVX in response to ovariectomy surgery and treatment. The mean relative frequency between baseline and six-week time points were compared for each mice group (OVX, sham, and SBD111). Mann-Whitney U test (P > 0.05).

| | OVX | sham | p-values |
|---|---|---|---|
| L-rhamnose degradation I | 0.57 | 0.77 | 0.02 |
| | OVX | DMA5 | |
| L-arginine biosynthesis I (via L-ornithine) | 0.80 | 0.58 | 0.01 |
| L-arginine biosynthesis II (acetyl cycle) | 0.41 | 0.26 | 0.02 |
| L-arginine biosynthesis III (via N-acetyl-L-citrulline) | 0.42 | 0.26 | 0.01 |
| L-rhamnose degradation I | 0.57 | 0.82 | 0.03 |
| dTDP-L-rhamnose biosynthesis I | 0.86 | 0.58 | 0.05 |

Short-Chain Fatty Acids (SCFA) Gene Abundance

SCFA, produced mainly from microbial fermentation of dietary fiber, appear to be a major mediator of the beneficial effects induced by the gut microbiome (Tan et al., 2014). In order to compare the potential production level of short-chain fatty acids in each group at week 6, relative abundances of marker genes related to SCFA productions in individual mouse were calculated by mapping of sequencing reads against UniRef90 using HuMANN2 HUMAnN2 and characterizing gene families (Franzosa et al. 2018). Gene families that were annotated to the same MetaCyC reaction ID were averaged in each individual.

Figure 19B:
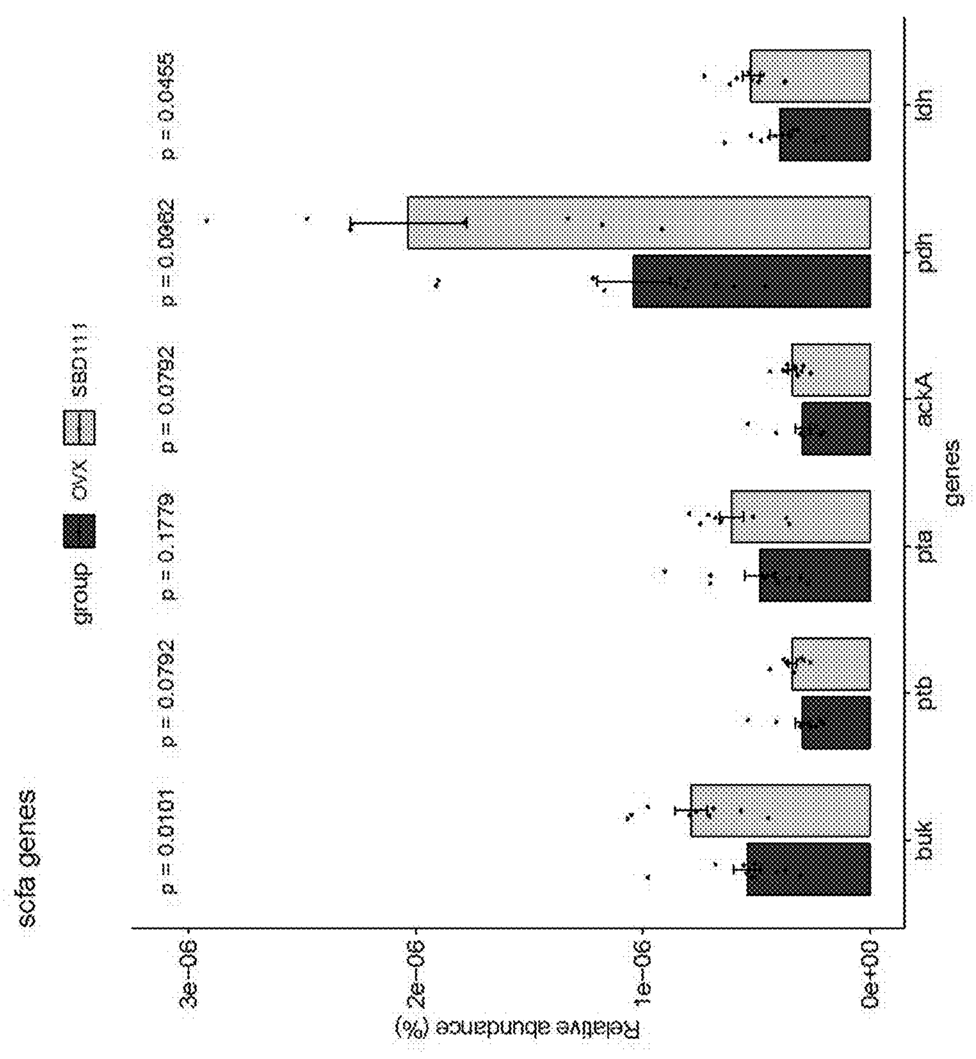
FIG. 19B Comparison of relative abundance of genes related to SCFA production between OVX group and SBD111-treated group. Differences between groups were assessed by Mann-Whitney U test (*P<0.05, **P<0.01). Butyrate kinase (buk) and phosphotransbutyrylase (ptb) were selected as marker genes representing butyrate production. Pyruvate dehydrogenase (pdh), phosphate acetyltransferase (pta) and acetate kinase (ackA) represent acetate production. L-lactate dehydrogenase (ldh) are involved in lactate production pathway.

FIG. 19B shows the comparison of relative abundance of genes related to SCFA production between OVX group and SBD111-treated group. Differences between groups were assessed by Mann-Whitney U test. Butyrate kinase (buk) and phosphotransbutyrylase (ptb) were selected as marker genes representing butyrate production. Pyruvate dehydrogenase (pdh), phosphate acetyltransferase (pta) and acetate kinase (ackA) represent acetate production. L-lactate dehydrogenase (ldh) are involved in lactate production pathway. All genes presented in the figure are significantly more abundant in SBD111-treated groups compared to OVX group. Increased short chain fatty acid production has been shown to improve BMD in OVX mice, and thus an increase in genes related to SCFA biosynthesis may partially explain the increased BMD and trabecular bone volume in SBD111 treated mice.

Glycoside Hydrolase

Microbial fermentation of complex non-digestible dietary carbohydrates and host-derived glycans in human intestines has important health consequences. Bacteria that colonize the mammalian gut possess large number of genes that encode carbohydrate active enzymes, which play an important role in the community by initiating the breakdown of complex substrates such as plant cell walls, starch particles and mucins.

Glycoside hydrolases (GH) are one of the carbohydrate active enzyme families that catalyze the hydrolysis of glycosidic bonds in plant fibers. In order to compare the potential capabilities of glycoside hydrolase activity in each group at week 6, relative abundances of gene families related to glycoside hydrolase in individual mouse were calculated by mapping sequencing reads against UniRef90 using HUMAnN2 and characterizing gene families (Franzosa et al. 2018). UniRef90 gene families that were annotated to the same GH families were averaged in each individual.

Figure 19C:
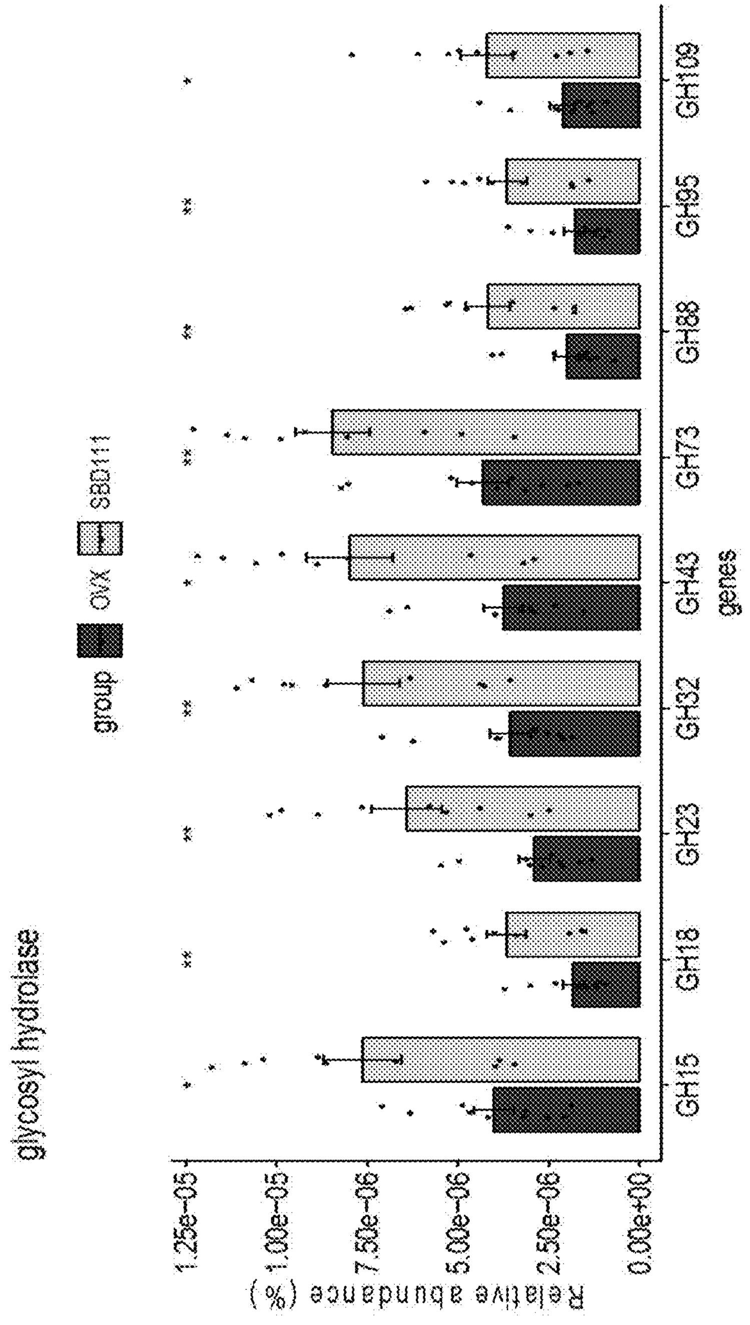
FIG. 19C Comparison of relative abundance of genes related to glycoside hydrolase between OVX group and SBD111-treated group. Differences between groups were assessed by Mann-Whitney U test (*P<0.05, **P<0.01). GH15, glucoamylase; GH18, chitinase; GH23, peptidoglycan lyase; GH32, invertase; GH43, (3-xylosidase; GH73, lysozyme; GH88, unsaturated glucuronyl hydrolases; GH95, α-L-fucosidase; GH109, α-N-acetylgalactosaminidase.

FIG. 19C shows the comparison of relative abundance of genes related to glycoside hydrolase between OVX group and SBD111-treated group at week 6. Differences between groups were assessed by Mann-Whitney U test (*P<0.05, P<0.01). Comparison of gene abundance between OVX and SBD111 groups indicated significantly higher abundance at week 6 in the SBD111 group in comparison with the OVX one. Results are shown in FIG. 19**C. Increased abundance of GH genes likely indicates increased fermentation of non-digestible dietary fiber, leading to increased SCFA production. Increased short chain fatty acid production has been shown to improve BMD in OVX mice, and thus an increase in glycoside hydrolase may partially explain the increased BMD and trabecular bone volume in SBD111 treated mice through increased production of SCFA.

GH15, glucoamylase; GH18, chitinase; GH23, peptidoglycan lyase; GH32, invertase; GH43, (3-xylosidase; GH73, lysozyme; GH88, unsaturated glucuronyl hydrolases; GH95, α-L-fucosidase; GH109, α-N-acetylgalactosaminidase.

Vitamin K2 Biosynthesis

Figure 19D:
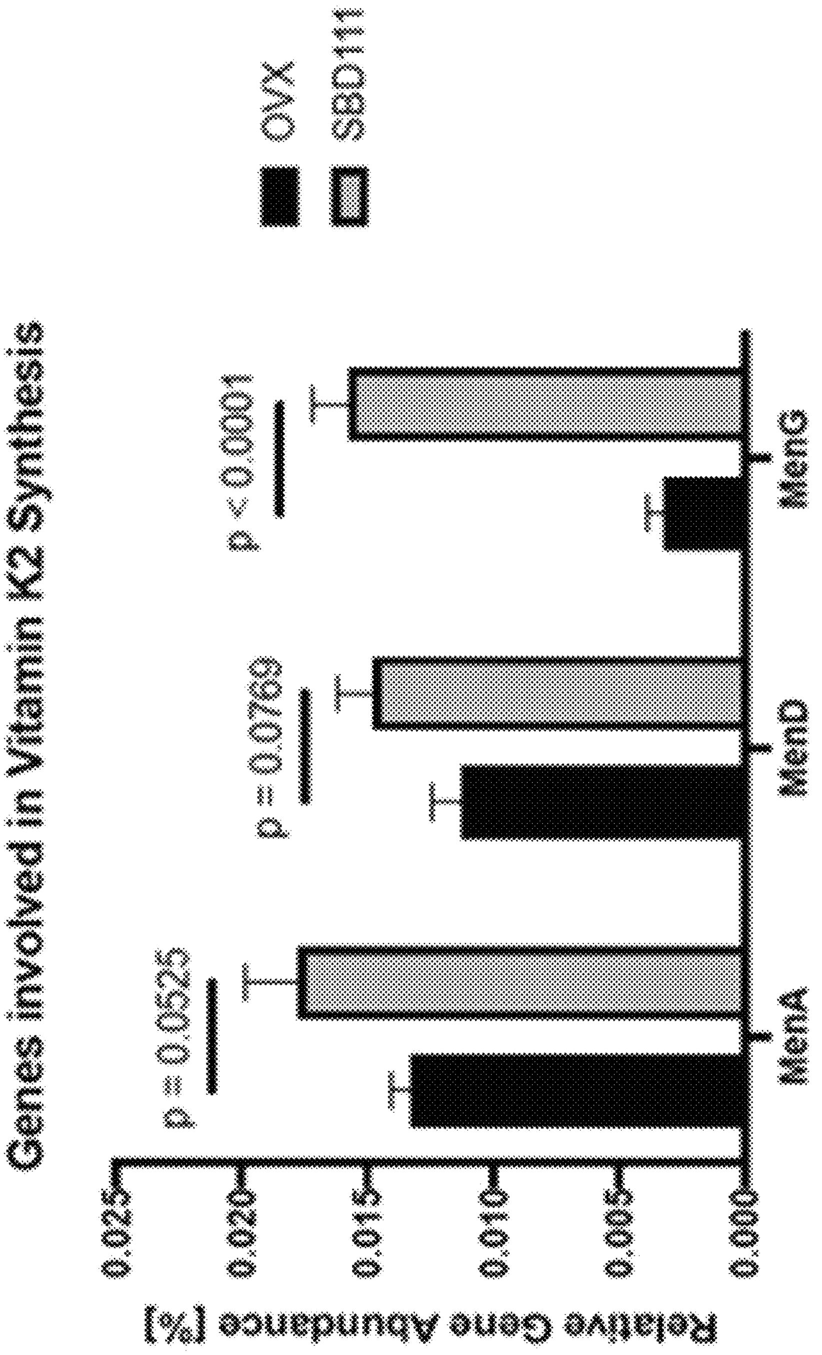
FIG. 19D Comparison of relative abundance of genes related to vitamin K2 biosynthesis between OVX group and SBD111-treated group. Differences between groups were assessed by Mann-Whitney U test (*P<0.05, **P<0.01). MenA, 1,4-dihydroxy-2-naphthoate prenyltransferase; MenD, 2-succinyl-5-enolpyruvyl-6-hydroxy-3-cyclohexene-1-carboxylate synthase, and MenG, demethylmenaquinone methyltransferase.

Functional characterization of the short-read metagenomes was determined using HUMAnN2 (Abubucker et al. 2012) with default parameters and the UniRef90 database (Suzek et al. 2015). Identifying genes involved in vitamin K2 (menaquinone) biosynthesis in the gut metagenomes is useful because vitamin K2 exhibits beneficial effects on human health. Although some studies have reported a positive effect of vitamin K2 consumption on bone health (Hess et al. 2015, Heaney 2013), the mechanism and factors involved in this relation are still unclear. Comparison of changes in gene abundance at the baseline and week 6 between OVX and SBD111 groups indicated higher significant increase in abundance at week 6 in the SBD111 group in comparison with the OVX one. Results are shown in FIG. 19D. As vitamin K2 has been shown to play a role in osteoblast functionality, an increase in Vitamin K2 biosynthesis may in part explain the increased BMD and trabecular bone volume in SBD111 treated mice compared to OVX mice.

Alkaline Phosphatase

Alkaline phosphatase (ALP) is a ubiquitous membrane-bound glycoprotein that catalyzes the hydrolysis of phosphate monoesters at basic pH values and is produced by both eukaryotic and prokaryotic cells. In the intestine, ALP has been shown to improve intestinal barrier integrity, exerting its effects through dephosphorylation of proinflammatory molecules including lipopolysaccharide (LPS), flagellin, and adenosine triphosphate (ATP) released from cells during stressful events. Diminished activity of ALP could increase the risk of disease through changes in the microbiome, intestinal inflammation, and intestinal permeability. With this, the increased gene abundance of ALP In order to compare the potential capabilities of alkaline phosphatase activity in each group at week 6, relative abundances of gene families related to alkaline phosphatase in individual mouse were calculated by mapping sequencing reads against UniRef90 using HUMAnN2 and characterizing gene families (Franzosa et al., 2018).

Figure 19E:
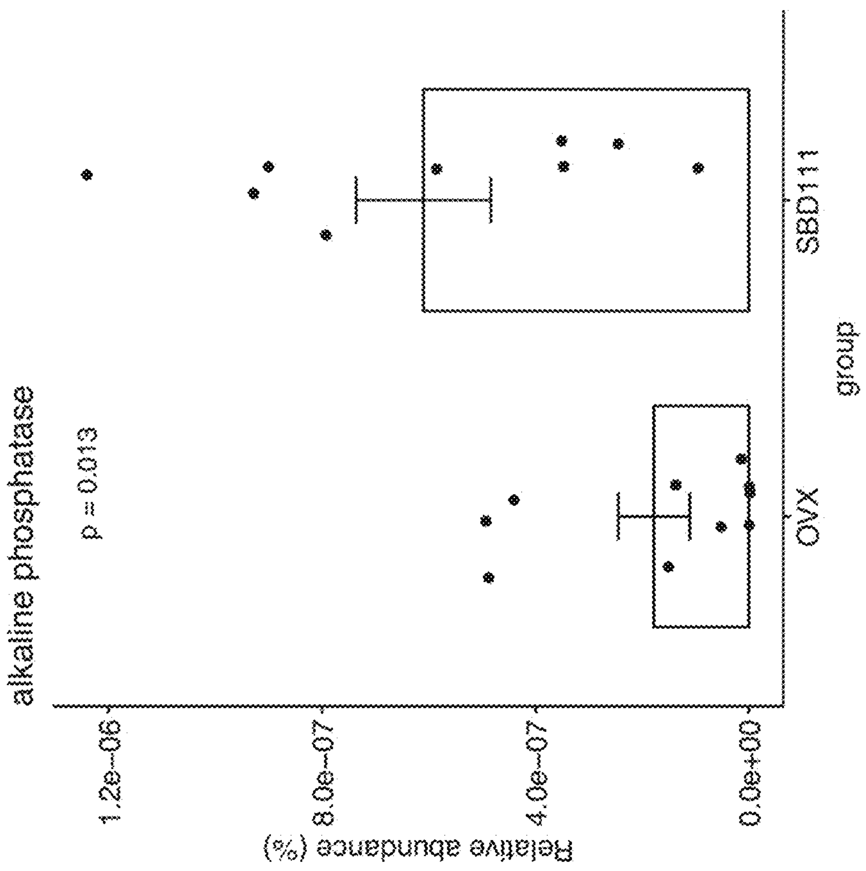
FIG. 19E Comparison of relative abundance of alkaline phosphate gene between OVX group and SBD111-treated group at 6 weeks. Differences between groups were assessed by Mann-Whitney U test (*P<0.05, **P<0.01).

FIG. 19E shows the comparison of relative abundance of alkaline phosphatase between OVX group and SBD111-treated group. Alkaline phosphatase was found to be increased in samples from SBD111 treated mice. Differences between groups were assessed by Mann-Whitney U test. With this, increased ALP in the microbiome could improve gut barrier integrity and decrease systemic inflammation, leading to improved BMD in SBD111 treated mice compared to OVX.

Additional Changes

Changes in additional metabolic pathways were also observed. Some comparisons of interest are displayed in Table 10 and Table 11.

TABLE 10

Comparison of the pathways enriched or depleted in both SBD111 and OVX after 6 weeks with respect to baseline in response to ovariectomy surgery and treatment. Mann-Whitney U test ($P < 0.05$).

| | Pathway | Baseline mean rel. freq. (%) | 6 Weeks mean rel. freq. (%) | p-values |
|---|---|---|---|---|
| DMA5 | L-arginine biosynthesis I (via L-ornithine) | 0.75 | 0.58 | 0.03 |
| DMA5 | L-arginine biosynthesis III (via N-acetyl-L-citrulline) | 0.36 | 0.26 | 0.04 |
| DMA5 | L-arginine biosynthesis IV (archaebacteria) | 0.82 | 0.64 | 0.03 |
| DMA5 | L-rhamnose degradation I | 0.48 | 0.82 | 0.01 |
| OVX | L-arginine biosynthesis I (via L-ornithine) | 0.58 | 0.80 | 0.02 |
| OVX | L-arginine biosynthesis II (acetyl cycle) | 0.21 | 0.41 | 0.00 |
| OVX | L-arginine biosynthesis III (via N-acetyl-L-citrulline) | 0.26 | 0.42 | 0.01 |
| OVX | L-arginine biosynthesis IV (archaebacteria) | 0.64 | 0.86 | 0.02 |

TABLE 11

Metabolic pathways of interest and observed changes in both SBD111 and OVX mice in response to ovariectomy surgery and treatment.

| Pathway | Metabolic effect | Observed changes |
|---|---|---|
| UMP biosynthesis | Immune system stimulation humans; DNA, RNA synthesis | Increased in SBD111 at week 6 |
| coenzyme A biosynthesis II (mammalian) | Fatty acid metabolism cofactor | Increased in SBD111 at week 6 |
| adenine and adenosine salvage III | Nucleotide synthesis, immune system | Increased in SBD111 at week 6 |
| 5-aminoimidazole ribonucleotide biosynthesis II | Alternative glucose oxidation | Increased in SBD111 at week 6 |
| pentose phosphate pathway (non-oxidative branch) | Alternative glucose oxidation, active in ovarian tissue, skeletal muscles | Increased in SBD111 at week 6 |
| L-rhamnose degradation I | Bone health, connective tissues, SCFA upregulation | Increased in SBD111 at week 6 |
| superpathway of 5-aminoimidazole ribonucleotide biosynthesis | purine biosynthesis | Increased in SBD111 at week 6 |
| superpathway of L-aspartate and L-asparagine biosynthesis | formation of succinate & fumarate in anaerobic conditions | Increased in SBD111 at week 6 |
| L-arginine biosynthesis IV | BMD, immunomodulatory, anti-aging | Decreased in SBD111 at week 6 |
| L-arginine biosynthesis I (via L-orinthine) | downstream intermediate releases acetate | Decreased in SBD111 at week 6 |
| flavin biosynthesis III (fungi) | energetic metabolism, redox homeostasis and protein folding, vitamin B2 | Increased in SBD111 at week 6 |
| L-histidine degradation I | catabolite repression, L-glutamate, amino acid d egredation | Increased in SBD111 at week 6 |
| D-fructuronate degredatoin | Female-specific factor, gut microbiota | Decreased in OVX vs SBD111 |
| inosine-5'-phosphate biosynthesis I | RNA and DNA synthesis, IMPDH in T cells, immune system | Decrease in SBD111 vs OVX |
| sulfate reduction I (assimilatory) | Colonic sulfide metabolism, hydrogen sulfide, intestinal disorders | Appeared in OVX |

TABLE 11-continued

Metabolic pathways of interest and observed changes in both SBD111 and OVX mice in response to ovariectomy surgery and treatment.

| Pathway | Metabolic effect | Observed changes |
|---|---|---|
| dTDP-L-rhamnose biosynthesis I | Enterobacterial common antigen | Increased in OVX vs SBD111 |
| tetrapyrrole biosynthesis I (from glutamate) | production of vitamin B12, antioxidant properties | Decrease in SBD111 vs OVX |
| L-arginine biosynthesis II (acetyl cycle) | inflammation regulation | Increase in OVX |

TABLE 12

Comparison of genes enriched or depleted in SBD111 and OVX after 6 weeks with respect to baseline in response to ovariectomy surgery and treatment. Mann-Whitney U test ($P < 0.05$).

| Family | Genes | SBD111 mean rel. freq. (%) | OVX mean rel. freq. (%) | p-values |
|---|---|---|---|---|
| UniRef90_D6D0Y9 | D6D0Y9_Alpha-1,2-mannosidase, putative | 0.017 | 0.014 | 0.037 |
| UniRef90_Q8A1H4 | Q8A1H4_Glycosyl hydrolase, family 88 | 0.018 | 0.015 | 0.039 |
| UniRef90_R9KRQ6 | R9KRQ6_Beta-galactosidase | 0.004 | 0.001 | 0.007 |
| UniRef90_Q8A1F2 | Q8A1F2_Phospholipid/glycerol acyltransferase | 0.017 | 0.014 | 0.035 |
| UniRef90_Q8A222 | Q8A222_N-acetylgalactosamine-6-sulfatase | 0.017 | 0.013 | 0.033 |
| UniRef90_Q8A9I7 | Q8A9I7_dTDP-4-dehydrorhamnose 3,5-epimer | 0.014 | 0.010 | 0.017 |
| UniRef90_J9CIK2 | J9CIK2_Tetrapyrrole methylase family protein | 0.016 | 0.012 | 0.032 |
| UniRef90 _R7KTS6 | R7KTS6_Zinc ABC transporter zinc-binding prot | 0.019 | 0.015 | 0.042 |
| UniRef90_R6UVU4 | R6UVU4_GDP-L-fucose synthase | 0.015 | 0.011 | 0.044 |
| UniRef90_Q8A3K1 | Q8A3K1_L-rhamnose-proton symporter | 0.017 | 0.013 | 0.043 |
| UniRef90_Q8A7Q2 | Q8A7Q2_Glycoside transferase family 2 | 0.017 | 0.012 | 0.027 |
| UniRef90_Q8A3K8 | Q8A3K8_Glycoside transferase family 4 | 0.019 | 0.015 | 0.021 |
| UniRef90_Q8A7J9 | Q8A7J9_Phosphatidylglycerophosphatase A | 0.016 | 0.011 | 0.028 |
| UniRef90_R5UG56 | R5UG56_Gliding motility-associated protein G | 0.015 | 0.011 | 0.019 |
| UniRef90_Q8A677 | Q8A677_Guanylate kinase | 0.018 | 0.013 | 0.013 |
| UniRef90_Q8A3L8 | Q8A3L8_Glycoside transferase family 4 | 0.021 | 0.016 | 0.036 |
| UniRef90_Q5LI10 | Q5LI10_Argininosuccinate lyase | 0.017 | 0.013 | 0.043 |
| UniRef90_Q8AALO | Q8AAL0_Arabinose-proton symporter (Arabino | 0.019 | 0.014 | 0.046 |
| UniRef90_Q8A0G3 | Q8A0G3_NADH-quinone oxidoreductase subuni | 0.019 | 0.014 | 0.039 |
| UniRef90_Q8A0F5 | Q8A0F5_NADH-quinone oxidoreductase subuni | 0.018 | 0.013 | 0.050 |
| UniRef90_Q8A3K7 | Q8A3K7_Glycoside transferase family 2 | 0.018 | 0.013 | 0.006 |
| UniRef90_D6D807 | D6D807_Asparaginase | 0.019 | 0.014 | 0.031 |
| UniRef90_R9H5P6 | R9H5P6_Serine acetyltransferase | 0.017 | 0.011 | 0.010 |
| UniRef90_R5B6J1 | R5B6J1_Tyrosine-tRNA ligase | 0.072 | 0.108 | 0.001 |
| UniRef90_R7J544 | R7J544_L-aspartate oxidase | 0.038 | 0.051 | 0.009 |

Figure 15:
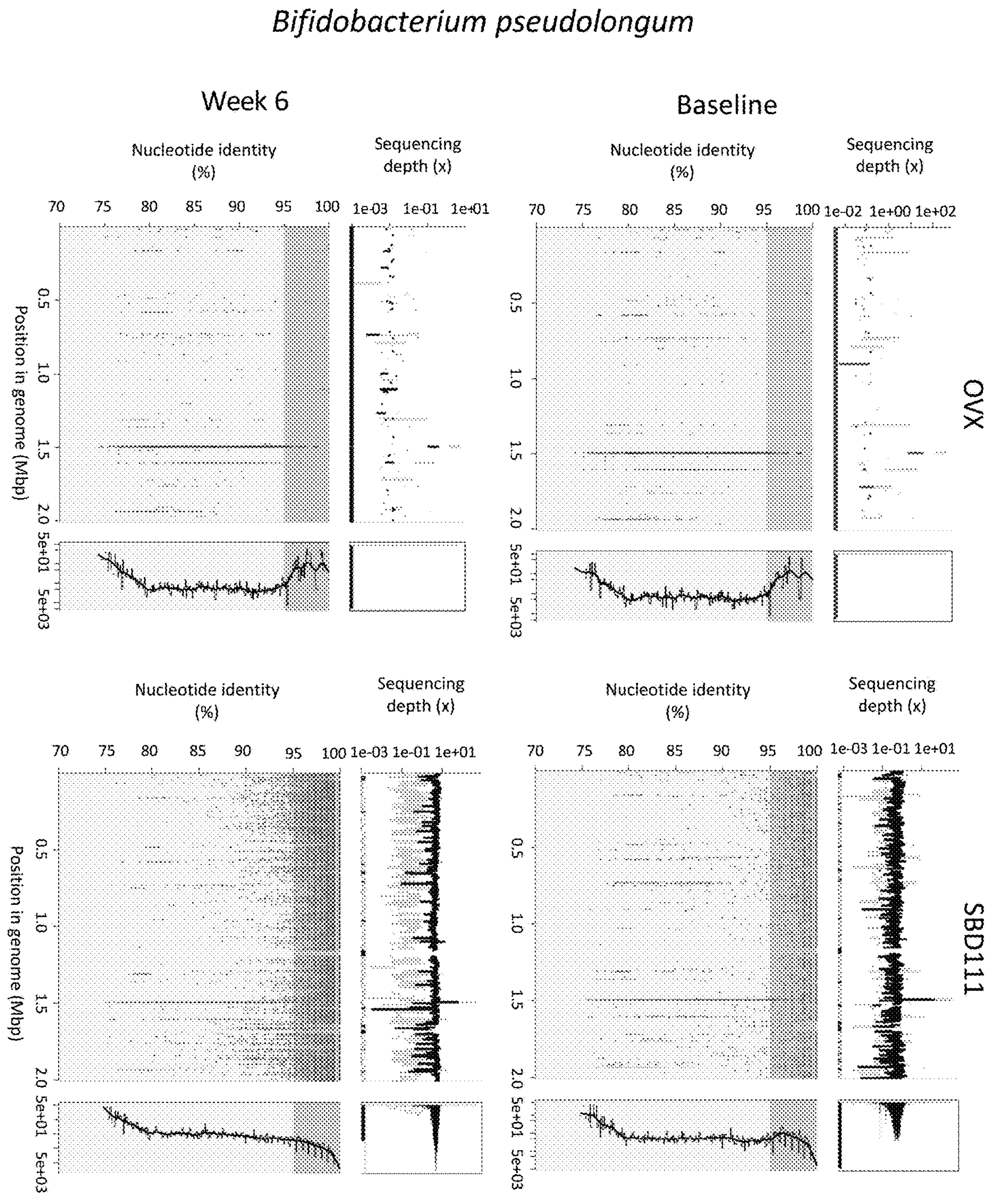
FIG. 15. Fragment recruitment plots showing fragment recruitment of the *Bifidobacterium pseudolongum* reference genome in the gut metagenomes from mice treated withOVX and SBD111 at the baseline and six-weeks post-surgery. Recruitment plots were built using scripts available at the enveomics toolbox (Rodriguez-R and Konstantinidis 2016). Table 13 shows the individuals changes in *B. pseudolongum* as seem by coverage.
Figure 16:
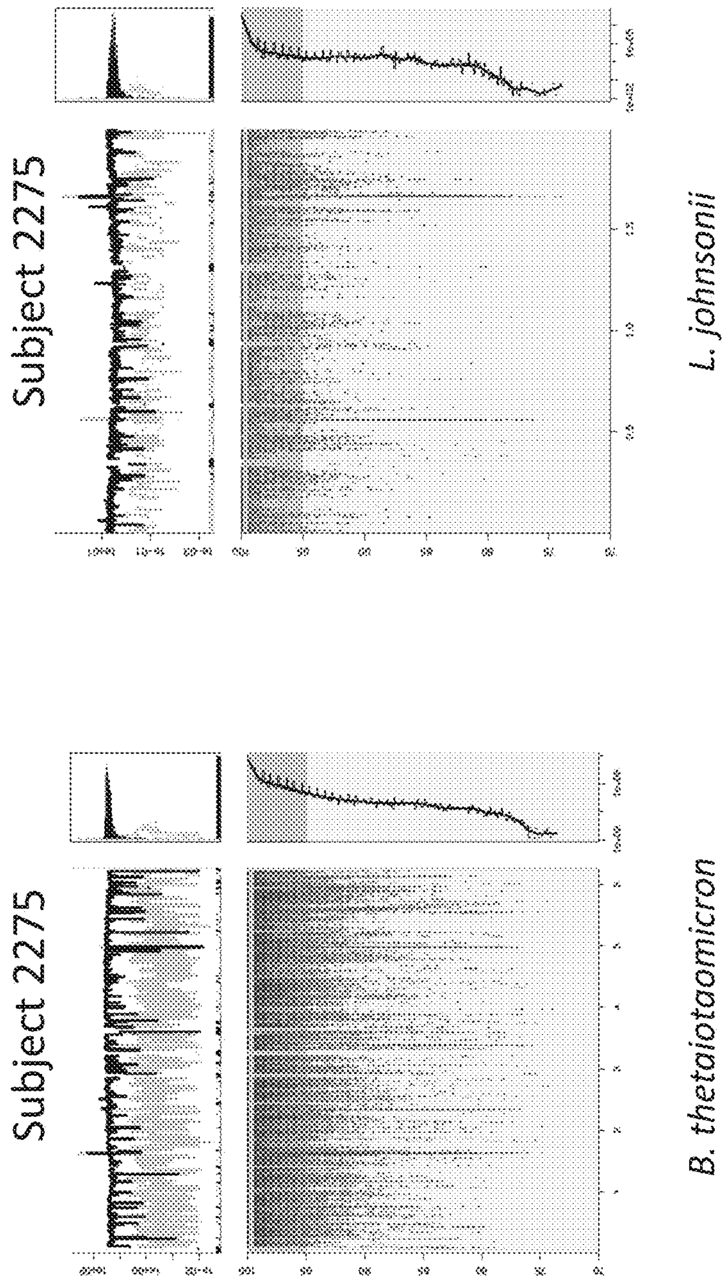
FIG. 16. Fragment recruitment plots showing fragment recruitment of the *Bifidobacterium pseudolongum* and *Lactobacillus johnsonii* reference genomes in the gut metagenomes from mice treated with SBD111 taken at the week 6 time point. These show that the microbes were present at week 6 post-surgery. The recruitment plots were built using scripts available at the enveomics toolbox (Rodriguez-R and Konstantinidis 2016).
Figure 17:
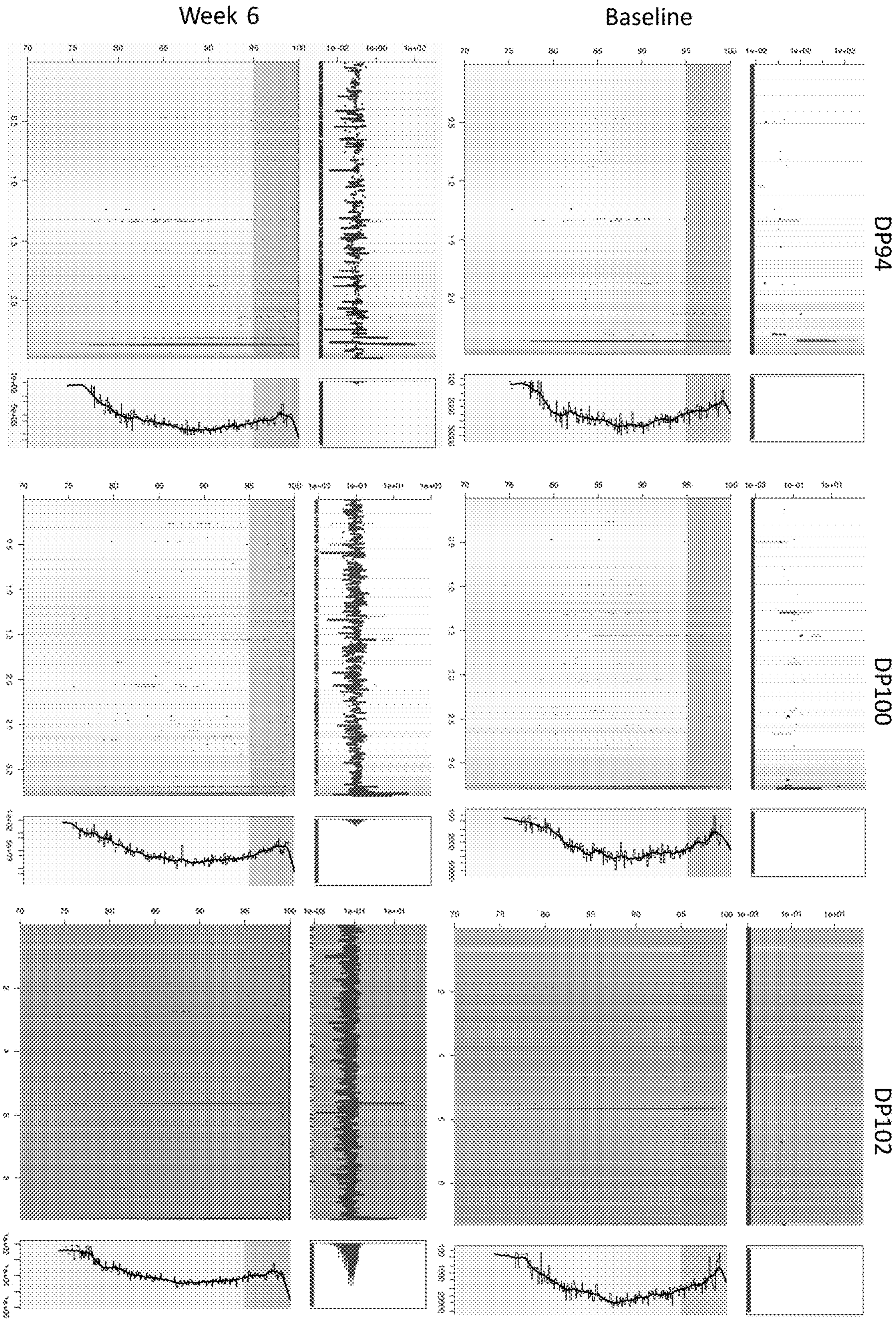
FIG. 17 Fragment recruitment of the genomes from the microbes used in SDB111 in the gut metagenomes from mice treated with SBD111 at the baseline and week 6 time points. Recruitment plots were built using scripts available at the enveomics toolbox (Rodriguez-R and Konstantinidis 2016).
Figure 18A:
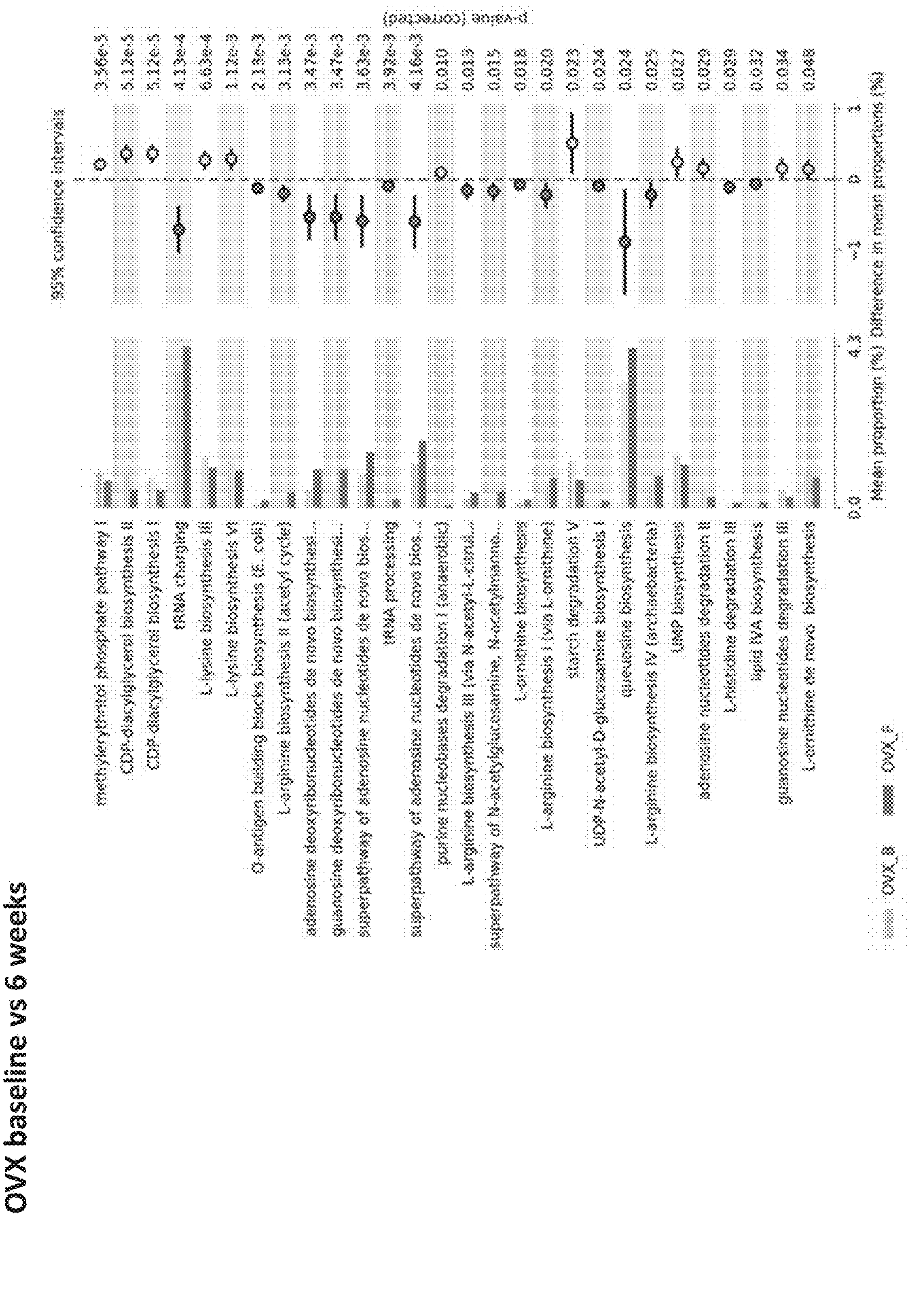
FIG. 18A Metabolic pathways significantly different between baseline and 6 weeks of treatment in OVX mice (Tukey-Kramer post-hoc test, P<0.05).
Figure 18B:
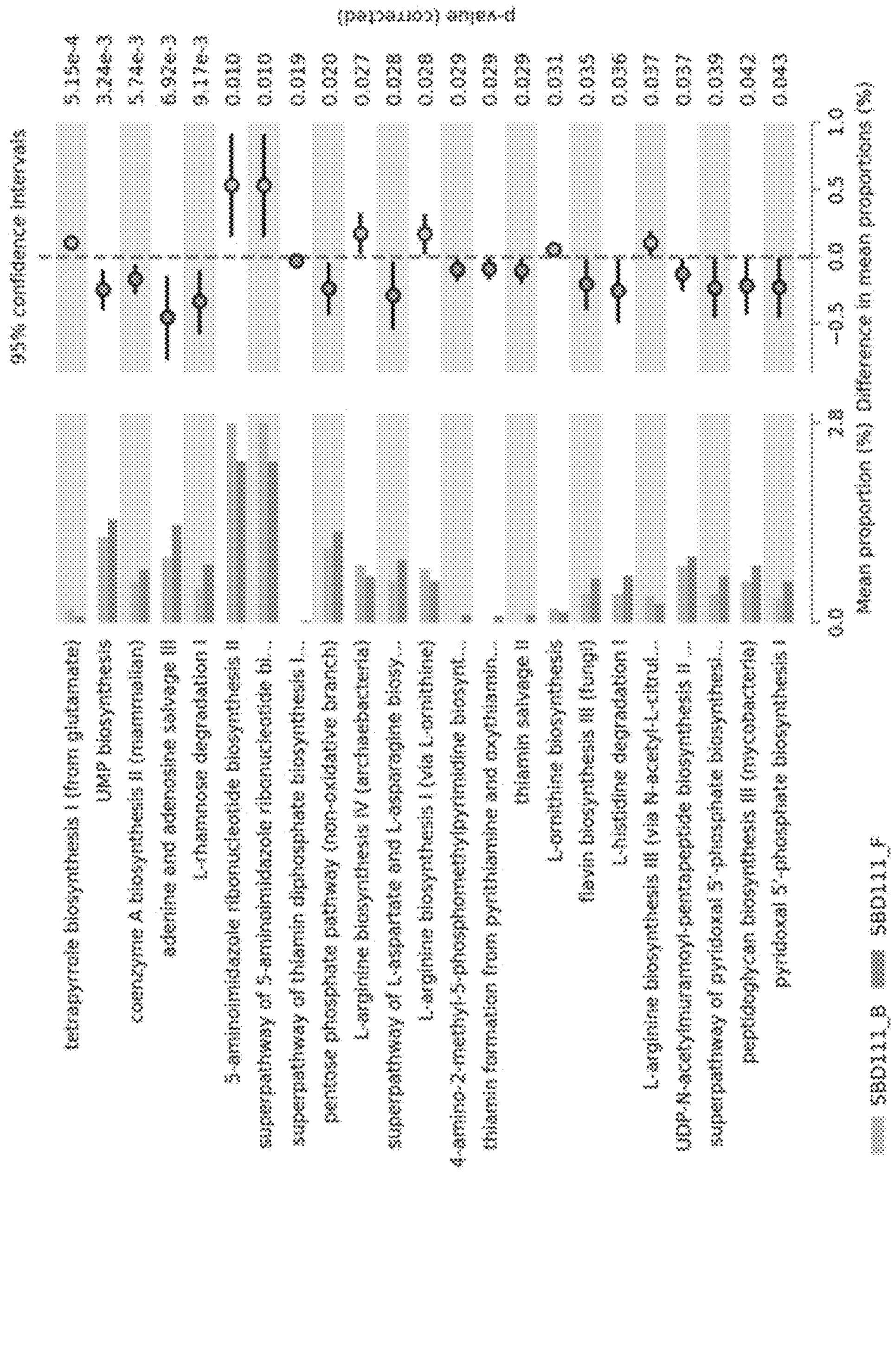
FIG. 18B Metabolic pathways significantly different between baseline and 6 weeks of treatment in SBD111-treated OVX mice (Tukey-Kramer post-hoc test, P<0.05).
Figure 18C:
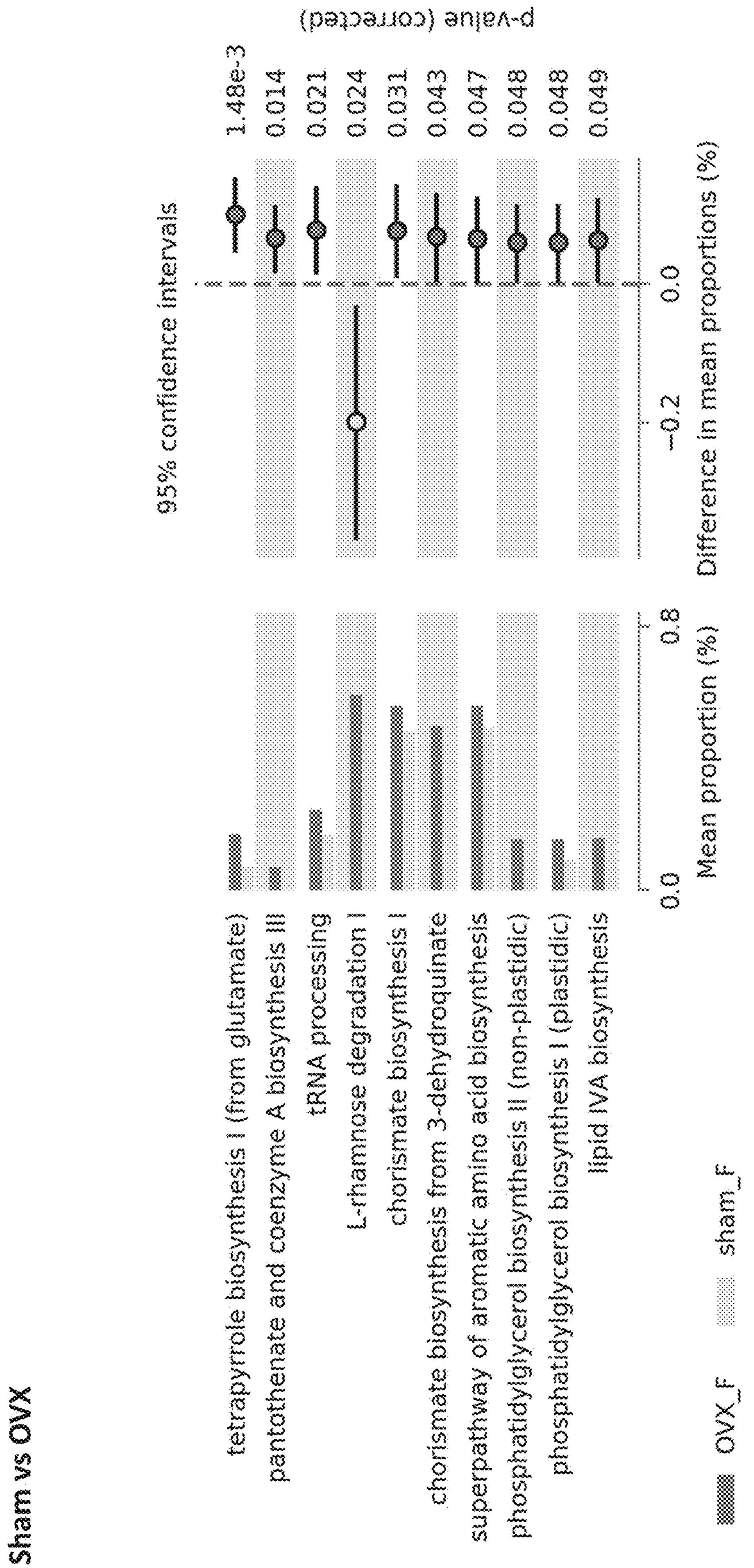
FIG. 18C Metabolic pathways significantly different between untreated OVX mice (OVX) and mice given a sham surgery (sham) after 6 weeks of treatment (Tukey-Kramer post-hoc test, P<0.05).
Figure 18D:
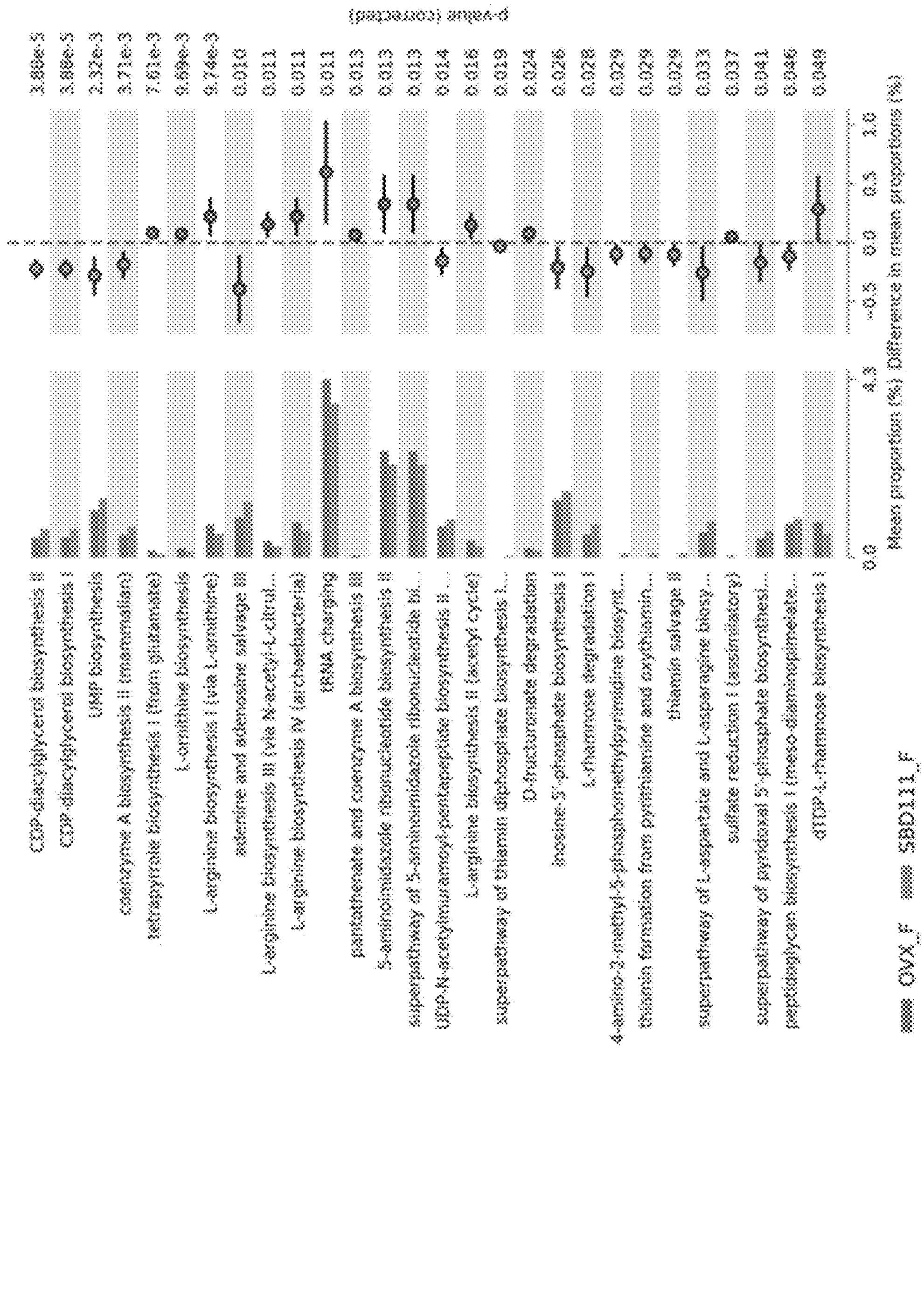
FIG. 18D Metabolic pathways significantly different between untreated OVX (OVX) mice and mice treated with SBD111 after 6 weeks of treatment (Tukey-Kramer post-hoc test, P<0.05).

Example 12: Increase in Relative Abundance and Intra-Population Diversity of *Bifidobacterium pseudolongum* in Week-6 SBD111-Treated Group FIG. 15 shows the fragment recruitment of the *Bifidobacterium pseudolongum* reference genome in the gut from SBD111-treated group at the baseline and week 6 time points. Recruitment plots were built using scripts available at the enveomics toolbox (Rodriguez-R and Konstantinidis 2016).

TABLE 13

Average coverage of *B. pseudolongum* genome in the gut metagenomes of mice treated with SBD111 at the baseline and week 6 time points.

| Subject ID | Baseline | week 6 |
|---|---|---|
| 2266 | 0.95 | 3.19 |
| 2268 | 1.32 | 3.55 |
| 2269 | 1.35 | 2.32 |
| 2270 | 2.7 | 1.37 |
| 2271 | 0.52 | 0.29 |
| 2272 | 0.69 | 3.92 |
| 2273 | 0.37 | 1.75 |
| 2274 | 0.55 | 4.32 |
| 2275 | 2.57 | 1.39 |

The fragment recruitment plot shows that *B. pseudolongum* was not present in the gut microbiome at the baseline and after 6 weeks in the ovx mouse group since metagenomic reads did not map at any nucleotide identity across the genome sequence (left panel of the plot) with an even coverage.

Opposite, the recruitment plot at the baseline of one of the mice treated with SBD111 shows that there is one *B. pseudolongum* population in the gut metagenome with genome coverage values of 0.5× and metagenomic reads mapped more than 98% nucleotide identity (dark thick line, top right panel). After 6 weeks, an increase in the abundance of this population was observed (average coverage values of 4.32×) in addition to the increase of discrete populations (light lines in the bottom panel) indicating an increase in the intra-population diversity (reads mapped between 95% and 98% nucleotide identity) of *B. pseudolongum* in the gut metagenome.

In conclusion, the SDB111-treated group showed an increase in the abundance of *B. pseudolongum* after 6 weeks (table 12) as well as the diversity of *B. pseudolongum* in the gut community. Accordingly, the results demonstrate that the administration of a SDB111 resulted in an increase in abundance and diversity of a beneficial microbial population. *Bifidobacterium pseudolongum* has been shown previously to modulate the immune system and decrease systemic inflammation. Inflammation plays a large role in osteoclastogenesis and the breakdown of bone, so the increased abundance of *Bifidobacterium pseudolongum* likely decreases systemic inflammatory mediators and thus decreases the resorption of bone, leading to improved BMD and trabecular bone volume in mice treated with SBD111 compared to OVX mice.

Example 13: Cryopreservant Demonstrating Improved Shelf Life

Cryopreservation was performed using DP53 (*Pseudomonas fragi*) under conditions using DMSO at 10% or a cryogenic buffer ("Cryobuffer") at 10% and were compared to PBS as negative control to assess viability at different timepoints after cryo storage at −80° C. A cell pellet containing 1×10^9 CFUs/ml measured by colony counts in nutrient agar media were placed in a cryogenic vial and stored at −80° C.

Figure 20:
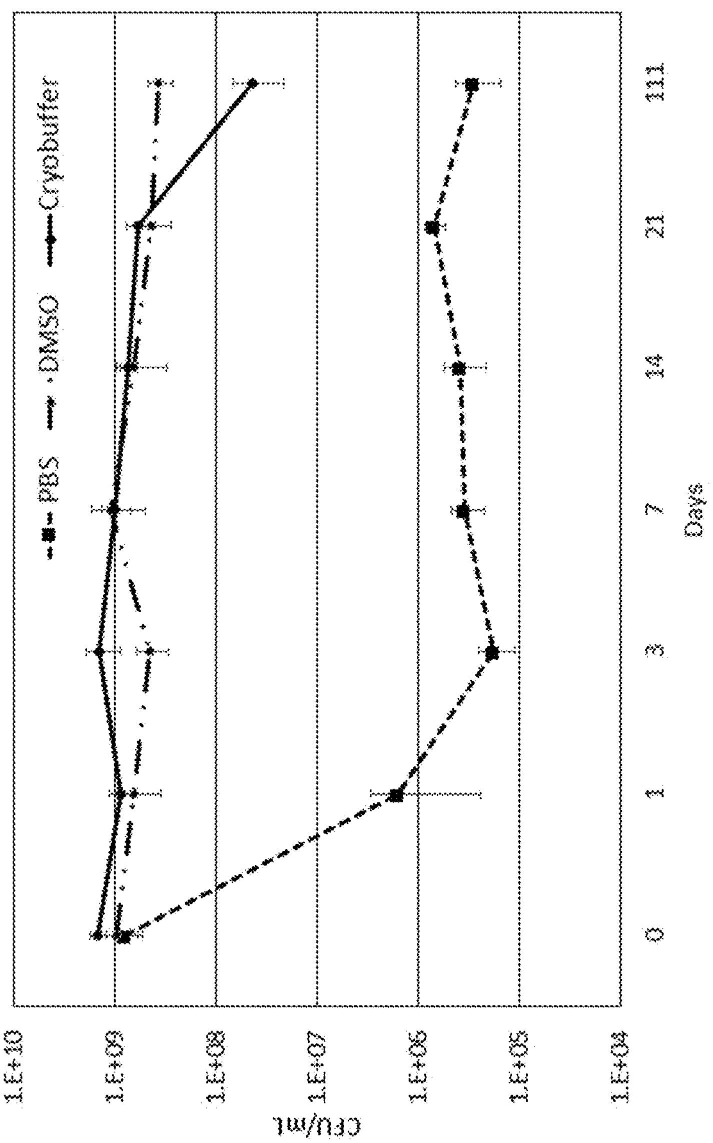
FIG. 20 shows viability at different timepoints after cryopreservation using PBS, DMSO, or Cryobuffer solutions to store bacteria.

As shown in FIG. 20, the vials with PBS without cryoprotectant showed 1×10^6 CFU/ml after 1 day while DMSO and Cryobuffer remained high. After 3 days there was further loss of viability in PBS to 1.75×10^5 CFU/ml while DMSO and Cryobuffer maintained the same titer. The vials containing DMSO generally maintained the same titer out to day 111, while the vials containing the Cryobuffer generally maintained the same titer out to day 21 and about a log difference in viability at day 111. Thus, the results demonstrate the use of cryogenic buffer enables cryopreservation and extension of shelf life. Accordingly, the use of cryogenic buffer enables cryopreservation when conducting preclinical or clinical experiments as the product can have the same amount of viable cells at different time points.

INCORPORATION BY REFERENCE

All references, issued patents, and patent applications cited within the body of the instant specification are hereby incorporated by reference in their entirety, for all purposes. Additionally, Compositions of Oligofructose and Commensal Microorganisms and Methods Thereof, WO2018170034, filed on Mar. 14, 2018 is hereby incorporated by reference.

Sequence Listing

| Seq ID No. | Description | Sequence |
|---|---|---|
| 1 | DP1 16S rRNA | AGTCAGACATGCAAGTCGAGCGGTAGAGAGAAGCTTGCTTCTCTTGA<br>GAGCGGCGGACGGGTGAGTAAAGCCTAGGAATCTGCCTGGTAGTGGG<br>GGATAACGTTCGGAAACGGACGCTAATACCGCATACGTCCTACGGGA<br>GAAAGCAGGGGACCTTCGGGCCTTGCGCTATCAGATGAGCCTAGGTC<br>GGATTAGCTAGTTGGTGAGGTAATGGCTCACCAAGGCGACGATCCGT<br>AACTGGTCTGAGAGGATGATCAGTCACACTGGAACTGAGACACGGTC<br>CAGACTCCTACGGGAGGCAGCAGTGGGGAATATTGGACAATGGGCGA<br>AAGCCTGATCCAGCCATGCCGCGTGTGTGAAGAAGGTCTTCGGATTG<br>TAAAGCACTTTAAGTTGGGAGGAAGGGCATTAACCTAATACGTTAGT<br>GTTTTGACGTTACCGACAGAATAAGCACCGGCTAACTCTGTGCCAGC<br>AGCCGCGGTAATACAGAGGGTGCAAGCGTTAATCGGAATTACTGGGC<br>GTAAAGCGCGCGTAGGTGGTTTGTTAAGTTGGATGTGAAATCCCCGG<br>GCTCAACCTGGGAACTGCATTCAAAACTGACTGACTAGAGTATGGTA<br>GAGGGTGGTGGAATTTCCTGTGTAGCGGTGAAATGCGTAGATATAGG<br>AAGGAACACCAGTGGCGAAGGCGACCACCTGGACTAATACTGACACT |

-continued

Sequence Listing

| Seq ID No. | Description | Sequence |
|---|---|---|
| | | GAGGTGCGAAAGCGTGGGGAGCAAACAGGATTAGATACCCTGGTAGT<br>CCACGCCGTAAACGATGTCAACTAGCCGTTGGGAGCCTTGAGCTCTTA<br>GTGGCGCAGCTAACGCATTAAGTTGACCGCCTGGGGAGTACGGCCGC<br>AAGGTTAAAACTCAAATGAATTGACGGGGGCCCGCACAAGCGGTGGA<br>GCATGTGGTTTAATTCGAAGCAACGCGAAGAACCTTACCAGGCCTTG<br>ACATCCAATGAACTTTCTAGAGATAGATTGGTGCCTTCGGGAACATTG<br>AGACAGGTGCTGCATGGCTGTCGTCAGCTCGTGTCGTGAGATGTTGG<br>GTTAAGTCCCGTAACGAGCGCAACCCTTGTCCTTAGTTACCAGCACGT<br>AATGGTGGGCACTCTAAGGAGACTGCCGGTGACAAACCGGAGGAAG<br>GTGGGGATGACGTCAAGTCATCATGGCCCTTACGGCCTGGGCTACAC<br>ACGTGCTACAATGGTCGGTACAGAGGGTTGCCAAGCCGCGAGGTGGA<br>GCTAATCCCATAAAACCGATCGTAGTCCGGATCGCAGTCTGCAACTC<br>GACTGCGTGAAGTCGGAATCGCTAGTAATCGCGAATCAGAATGTCGC<br>GGTGAATACGTTCCCGGGCCTTGTACACACCGCCCGTCACACCATGG<br>GAGTGGGTTGCACCAGAAGTAGCTAGTCTAACCTTCGGGAGGACGGT<br>TACCACGGTGTGATTCATGACTGGGGTGAAGTCGTAACAAGGTAGCC<br>GTAGGGGAACCTGCGGCTGGATCACCTCCTT |
| 2 | DP2 ITS sequence | TTGTTGCTCGAGTTCTTGTTTAGATCTTTTACAATAATGTGTATCTTTA<br>ATGAAGATGNGNGCTTAATTGCGCTGCTTTATTAGAGTGTCGCAGTAG<br>AAGTAGTCTTGCTTGAATCTCAGTCAACGTTTACACACATTGGAGTTT<br>TTTTACTTTAATTTAATTCTTTCTGCTTTGAATCGAAAGGTTCAAGGCA<br>AAAAACAAACACAAACAATTTTATTTTATTATAATTTTTTAAACTAAA<br>CCAAAATTCCTAACGGAAATTTTAAAATAATTTAAAACTTTCAACAAC<br>GGATCTCTTGGTTCTCGCATCGATGAAAAACGTACCGAATTGCGATAA<br>GTAATGTGAATTGCAAATACTCGTGAATCATTGAATTTTTGAACGCAC<br>ATTGCGCCCTTGAGCATTCTCAAGGGCATGCCTGTTTGAGCGTCATTT<br>CCTTCTCAAAAAATAATTTTTTATTTTTTGGTTGTGGGCGATACTCAGG<br>GTTAGCTTGAAATTGGAGACTGTTTCAGTCTTTTTTAATTCAACACTTA<br>NCTTCTTTGGAGACGCTGTTCTCGCTGTGATGTATTTATGGATTTATTC<br>GTTTTACTTTACAAGGGAAATGGTAATGTACCTTAGGCAAAGGGTTGC<br>TTTTAATATTCATCAAGTTTGACCTCAAATCAGGTAGGATTACCCGCT<br>GAACTTAAGCATATCAATAAGCGGAGGAAAAGAAACCAACTGGGATT<br>ACCTTAGTAACGGCGAGTGAAGCGGTAAAAGCTCAAATTTGAAATCT<br>GGTACTTTCAGTGCCCGAGTTGTAATTTGTAGAATTTGTCTTTGATTA<br>GGTCCTTGTCTATGTTCCTTGGAACAGGACGTCATAGAGGGTGAGANT<br>CCCGTTTGNNGAGGATACCTTTTCTCTGTANNACTTTTTCNAAGAGTC<br>GAGTTGNTTGGGAATGCAGCTCAAANNGGGTNGNAAATTCCATCTAA<br>AGCTAAATATTNGNCNAGAGACCGANAGCGACANTACAGNGATGGA<br>AAGANGAAA |
| 3 | DP3 16S rRNA | ATTGAGAGTTTGATCCTGGCTCAGGATGAACGCTGGCGGCGTGCCTA<br>ATACATGCAAGTCGAACGCACAGCGAAAGGTGCTTGCACCTTTCAAG<br>TGAGTGGCGAACGGGTGAGTAACACGTGGACAACCTGCCTCAAGGCT<br>GGGGATAACATTTGGAAACAGATGCTAATACCGAATAAAACTCAGTG<br>TCGCATGACACAAAGTTAAAAGGCGCTTTGGCGTCACCTAGAGATGG<br>ATCCGCGGTGCATTAGTTAGTTGGTGGGGTAAAGGCCTACCAAGACA<br>ATGATGCATAGCCGAGTTGAGAGACTGATCGGCCACATTGGGACTGA<br>GACACGGCCCAAACTCCTACGGGAGGCTGCAGTAGGGAATCTTCCAC<br>AATGGGCGAAAGCCTGATGGAGCAACGCCGCGTGTGTGATGAAGGCT<br>TTCGGGTCGTAAAGCACTGTTGTACGGGAAGAACAGCTAGAATAGGG<br>AATGATTTTAGTTTGACGGTACCATACCAGAAAGGGACGGCTAAATA<br>CGTGCCAGCAGCCGCGGTAATACGTATGTCCCGAGCGTTATCCGGATT<br>TATTGGGCGTAAAGCGAGCGCAGACGGTTGATTAAGTCTGATGTGAA<br>AGCCCGGAGCTCAACTCCGGAATGGCATTGGAAACTGGTTAACTTGA<br>GTGCAGTAGAGGTAAGTGGAACTCCATGTGTAGCGGTGGAATGCGTA<br>GATATATGGAAGAACACCAGTGGCGAAGGCGGCTTACTGGACTGTAA<br>CTGACGTTGAGGCTCGAAAGTGTGGGTAGCAAACAGGATTAGATACC<br>CTGGTAGTCCACACCGTAAACGATGAACACTAGGTGTTAGGAGGTTT<br>CCGCCTCTTAGTGCCGAAGCTAACGCATTAAGTGTTCCGCCTGGGGAG<br>TACGACCGCAAGGTTGAAACTCAAAGGAATTGACGGGGACCCGCACA<br>AGCGGTGGAGCATGTGGTTTAATTCGAAGCAACGCGAAGAACCTTAC<br>CAGGTCTTGACATCCTTTGAAGCTTTTAGAGATAGAAGTGTTCTCTTC<br>GGAGACAAAGTGACAGGTGGTGCATGGTCGTCGTCAGCTCGTGTCGT<br>GAGATGTTGGGTTAAGTCCCGCAACGAGCGCAACCCTTATTGTTAGTT<br>GCCAGCATTCAGATGGGCACTCTAGCGAGACTGCCGGTGACAAACCG<br>GAGGAAGGCGGGGACGACGTCAGATCATCATGCCCCTTATGACCTGG<br>GCTACACACGTGCTACAATGGCGTATACAACGAGTTGCCAACCCGCG<br>AGGGTGAGCTAATCTCTTAAAGTACGTCTCAGTTCGGATTGTAGTCTG<br>CAACTCGACTACATGAAGTCGGAATCGCTAGTAATCGCGGATCAGCA<br>CGCCGCGGTGAATACGTTCCCGGGTCTTGTACACACCGCCCGTCACAC |

-continued

Sequence Listing

| Seq ID No. | Description | Sequence |
|---|---|---|
| | | CATGGGAGTTTGTAATGCCCAAAGCCGGTGGCCTAACCTTTTAGGAA GGAGCCGTCTAAGGCAGGACAGATGACTGGGGTGAAGTCGTAACAA GGTAGCCGTAGGAGAACCTGCGGCTGGATCACCTCCTTT |
| 4 | DP4 16S rRNA | TTGAAGAGTTTGATCATGGCTCAGATTGAACGCTGGCGGCAGGCCTA ACACATGCAAGTCGAGCGGCAGCGGAAAGTAGCTTGCTACTTTGCCG GCGAGCGGCGGACGGGTGAGTAATGTCTGGGAAACTGCCTGATGGAG GGGGATAACTACTGGAAACGGTAGCTAATACCGCATGACCTCGAAAG AGCAAAGTGGGGGATCTTCGGACCTCACGCCATCGGATGTGCCCAGA TGGGATTAGCTAGTAGGTGAGGTAATGGCTCACCTAGGCGACGATCC CTAGCTGGTCTGAGAGGATGACCAGCCACACTGGAACTGAGACACGG TCCAGACTCCTACGGGAGGCAGCAGTGGGGAATATTGCACAATGGGC GCAAGCCTGATGCAGCCATGCCGCGTGTGTGAAGAAGGCCTTAGGGT TGTAAAGCACTTTCAGCGAGGAGGAAGGCATCATACTTAATACGTGT GGTGATTGACGTTACTCGCAGAAGAAGCACCGGCTAACTCCGTGCCA GCAGCCGCGGTAATACGGAGGGTGCAAGCGTTAATCGGAATTACTGG GCGTAAAGCGCACGCAGGCGGTTTGTTAAGTCAGATGTGAAATCCCC GCGCTTAACGTGGGAACTGCATTTGAAACTGGCAAGCTAGAGTCTTG TAGAGGGGGGTAGAATTCCAGGTGTAGCGGTGAAATGCGTAGAGATC TGGAGGAATACCGGTGGCGAAGGCGGCCCCCTGGACAAAGACTGAC GCTCAGGTGCGAAAGCGTGGGGAGCAAACAGGATTAGATACCCTGGT AGTCCACGCCGTAAACGATGTCGACTTGGAGGTTGTTCCCTTGAGGA GTGGCTTCCGGAGCTAACGCGTTAAGTCGACCGCCTGGGGAGTACGG CCGCAAGGTTAAAACTCAAATGAATTGACGGGGGCCCGCACAAGCGG TGGAGCATGTGGTTTAATTCGATGCAACGCGAAGAACCTTACCTACTC TTGACATCCACGGAATTTGGCAGAGATGCCTTAGTGCCTTCGGGAACC GTGAGACAGGTGCTGCATGGCTGTCGTCAGCTCGTGTTGTGAAATGTT GGGTTAAGTCCCGCAACGAGCGCAACCCTTATCCTTTGTTGCCAGCGA TTCGGTCGGGAACTCAAAGGAGACTGCCGGTGATAAACCGGAGGAAG GTGGGGATGACGTCAAGTCATCATGGCCCTTACGAGTAGGGCTACAC ACGTGCTACAATGGCGCATACAAAGAGAAGCGACCTCGCGAGAGCA AGCGGACCTCACAAAGTGCGTCGTAGTCCGGATCGGAGTCTGCAACT CGACTCCGTGAAGTCGGAATCGCTAGTAATCGTGGATCAGAATGCCA CGGTGAATACGTTCCCGGGCCTTGTACACACCGCCCGTCACACCATGG GAGTGGGTTGCAAAAGAAGTAGGTAGCTTAACCTTCGGGAGGGCGCT TACCACTTTGTGATTCATGACTGGGGTGAAGTCGTAACAAGGTAACC GTAGGGGAACCTGCGGTTGGATCACCTCCTT |
| 5 | DP5 ITS sequence | GCGCTTATTGCGCGGCGAAAAAACCTTACACACAGTGTTTTTTGTTAT TACANNAACTTTTGCTTTGGTCTGGACTAGAAATAGTTTGGGCCAGAG GTTACTAAACTAAACTTCAATATTTATATTGAATTGTTATTTATTTAAT TGTCAATTTGTTGATTAAATTCAAAAAATCTTCAAAACTTTCAACAAC GGATCTCTTGGTTCTCGCATCGATGAAGAACGCAGCGAAATGCGATA AGTAATATGAATTGCAGATTTTCGTGAATCATCGAATCTTTGAACGCA CATTGCGCCCTCTGGTATTCCAGAGGGCATGCCTGTTTGAGCGTCATT TCTCTCTCAAACCTTCGGGTTTGGTATTGAGTGATACTCTTAGTCGAA CTAGGCGTTTGCTTGAAATGTATTGGCATGAGTGGTACTGGATAGTGC TATATGACTTTCAATGTATTAGGTTTATCCAACTCGTTGAATAGTTTA ATGGTATATTTCTCGGTATTCTAGGCTCGGCCTTACAATATAACAAAC AAGTTTGACCTCAAATCAGGTAGGATTACCCGCTGAACTTAAGCATAT CAATAAGCGGAGGAAAAGAAACCAACAGGGATTGCCTTAGTAACGG CGAGTGAAGCGGCAAAAGCTCAAATTTGAAATCTGGCACCTTCGGTG TCCGAGTTGTAATTTGAAGAAGGTAACTTTGGAGTTGGCTCTTGTCTA TGTTCCTTGGAACAGGACGTCACAGAGGGTGAGAATCCCGTGCGATG AGATGCCCAATTCTATGTAAAGTGCTTTCGAAGAGTCGAGTTGTTTGG GAATGCAGCTCTAAGTGGGTGGTAAATTCCATCTAAAGCTAAATATT GGCGAGAGACCGATAGCGAACAAGTACAGTGATGGAAAGATGAAAA GAACTTTGAAAAGAGAGTGAAAAAGTACGTGAAATTGTTGAAAGGG AAAGGGCTTGAGATCAGACTTGGTATTTTGCGATCCTTTCCTTCTTGG TTGGGTTCCTCGCAGCTTACTGGGNCAGCATCGGTTTGGATGG |
| 6 | DP6 16S rRNA | GAAAGGCGGCTTCGGCTGTCACTTATGGATGGACCCGCGTCGCATTA GCTAGTTGGTGAGGTAACGGCTCACCAAGGCAACGATGCGTAGCCGA CCTGAGAGGGTGATCGGCCACACTGGGACTGAGACACGGCCCAGACT CCTACGGGAGGCAGCAGTAGGGAATCTTCCGCAATGGACGAAAGTCT GACGGAGCAACGCCGCGTGAGTGATGAAGGCTTTCGGGTCGTAAAAC TCTGTTGTTAGGGAAGAACAAGTGCTAGTTGAATAAGCTGCACCTTG ACGGTACCTAACCAGAAAGCCACGGCTAACTACGTGCCAGCAGCCGC GGTAATACGTAGGTGGCAAGCGTTATCCGGAATTATTGGGCGTAAAG CGCGCGCAGGTGGTTTCTTAAGTCTGATGTGAAAGCCCACGGCTCAA CCGTGGAGGGTCATTGGAAACTGGGAGACTTGAGTGCAGAAGAGGA AAGTGGAATTCCATGTGTAGCGGTGAAATGCGTAGAGATATGGAGGA ACACCAGTGGCGAAGGCGACTTTCTGGTCTGTAACTGACACTGAGGC |

-continued

Sequence Listing

| Seq ID No. | Description | Sequence |
|---|---|---|
| | | GCGAAAGCGTGGGGAGCAAACAGGATTAGATACCCTGGTAGTCCACG CCGTAAACGATGAGTGCTAAGTGTTAGAGGGTTTCCGCCCTTTAGTGC TGAAGTTAACGCATTAAGCACTCCGCCTGGGGAGTACGGCCGCAAGG CTGAAACTCAAAGGAATTGACGGGGGCCCGCACAAGCGGTGGAGCAT GTGGTTTAATTCGAAGCAACGCGAAGAACCTTACCAGGTCTTGACAT CCTCTGAAAACCCTAGAGATAGGGCTTCTCCTTCGGGAGCAGAGTGA CAGGTGGTGCATGGTTGTCGTCAGCTCGTGTCGTGAGATGTTGGGTTA AGTCCCGCAACGAGCGCAACCCTTGATCTTAGTTGCCATCATTAAGTT GGGCACTCTAAGGTGACTGCCGGTGACAAACCGGAGGAAGGTGGGG ATGACGTCAAATCATCATGCCCCTTATGACCTGGGCTACACACGTGCT ACAATGGACGGTACAAAGAGCTGCAAGACCGCGAGGTGGAGCTAAT CTCATAAAACCGTTCTCAGTTCGGATTGTAGGCTGCAACTCGCCTACA TGAAGCTGGAATCGCTAGTAATCGCGGATCAGCAT |
| 7 | DP7 ITS | CCACNCTGCGTGGGCGACACGAAACACCGAAACCGAACGCACGCCGT CAAGCAAGAAATCCACAAAACTTTCAACAACGGATCTCTTGGTTCTC GCATCGATGAAGAGCGCAGCGAAATGCGATACCTAGTGTGAATTGCA GCCATCGTGAATCATCGAGTTCTTGAACGCACATTGCGCCCGCTGGTA TTCCGGCGGGCATGCCTGTCTGAGCGTCGTTTCCTTCTTGGAGCGGAG CTTCAGACCTGGCGGGCTGTCTTTCGGGACGGCGCGCCCAAAGCGAG GGGCCTTCTGCGCGAACTAGACTGTGCGCGCGGGGCGGCCGGCGAAC TTATACCAAGCTCGACCTCAGATCAGGCAGGAGTACCCGCTGAACTT AAGCATATCAATAAGCGGAGGAAAAGAAACCAACAGGGATTGCCCC AGTAGCGGCGAGTGAAGCGGCAAAAGCTCAGATTTGGAATCGCTTCG GCGAGTTGTGAATTGCAGGTTGGCGCCTCTGCGGCGGCGGCGGTCCA AGTCCCTTGGAACAGGGCGCCATTGAGGGTGAGAGCCCCGTGGGACC GTTTGCCTATGCTCTGAGGCCCTTCTGACGAGTCGAGTTGTTTGGGAA TGCAGCTCTAAGCGGGTGGTAAATTCCATCTAAGGCTAAATACTGGC GAGAGACCGATAGCGAACAAGTACTGTGAAGGAAAGATGAAAAGCA CTTTGAAAAGAGAGTGAAACAGCACGTGAAATTGTTGAAAGGGAAG GGTATTGCGCCCGACATGGAGCGTGCGCACCGCTGCCCCTCGTGGGC GGCGCTCTGGGCGTGCTCTGGGCCAGCATCGGTTTTTGCCGCGGGAG AAGGGCGGCGGGCATGTAGCTCTTC |
| 8 | DP8 ITS | GTTGCTCGAGTTCTTGTTTAGATCTTTTACNATAATGTGTATCTTTAAT GAAGATGTGCGCTTAATTGCGCTGCTTTATTAGAGTGTCGCAGTAGAA GTAGTCTTGCTTGAATCTCAGTCAACGTTTACACACATTGGAGTTTTTT TACTTTAATTTAATTCTTTCTGCTTTGAATCGAAAGGTTCAAGGCAAA AAACAAACACAAACAATTTTATTTTATTATAATTTTTTAAACTAAACC AAAATTCCTAACGGAAATTTTAAAATAATTTAAAACTTTCAACAACG GATCTCTTGGTTCTCGCATCGATGAAAAACGTAGCGAATTGCGATAA GTAATGTGAATTGCAAATACTCGTGAATCATTGAATTTTTGAACGCAC ATTGCGCCCTTGAGCATTCTCAAGGGCATGCCTGTTTGAGCGTCATTT CCTTCTCAAAAGATAATTTTTTATTTTTTGGTTGTGGGCGATACTCAGG GTTAGCTTGAAATTGGAGACTGTTTCAGTCTTTTTTAATTCAACACTTA NCTTCTTTGGAGACGCTGTTCTCGCTGTGATGTATTTATGGATTTATTC GTTTTACTTTACAAGGGAAATGGTAATGTACCTTAGGCAAAGGGTTGC TTTTAATATTCATCAAGTTTGACCTCAAATCAGGTAGGATTACCCGCT GAACTTAAGCATATCAATAAGCGGAGGAAAAGAAACCAACTGGGATT ACCTTAGTAACGGCGAGTGAAGCGGTAAAAGCTCAAATTTGAAATCT GGTACTTTCANNGCCCGAGTTGTAATTTGTAGAATTTGTCTTTGATTA GGTCCTTGTCTATGTTCCTTGGANCAGGACGTCATANAGGGTGANTCC CNTTTGGCGANGANACCTTTTCTCTGTANACTTTTTCNANAGTCGAGT TGTTTNGGATGCAGCTCNAAGTGGGGNGG |
| 9 | DP9 16S rRNA | ATGAGAGTTTGATCTTGGCTCAGGATGAACGCTGGCGGCGTGCCTAA TACATGCAAGTCGAACGAACTTCCGTTAATTGATTATGACGTACTTGT ACTGATTGAGATTTTAACACGAAGTGAGTGGCGAACGGGTGAGTAAC ACGTGGGTAACCTGCCCAGAAGTAGGGGATAACACCTGGAAACAGAT GCTAATACCGTATAACAGAGAAAACCGCATGGTTTTCTTTTAAAAGAT GGCTCTGCTATCACTTCTGGATGGACCCGCGGCGTATTAGCTAGTTGG TGAGGCAAAGGCTCACCAAGGCAGTGATACGTAGCCGACCTGAGAGG GTAATCGGCCACATTGGGACTGAGACACGGCCCAGACTCCTACGGGA GGCAGCAGTAGGGAATCTTCCACAATGGACGCAAGTCTGATGGAGCA ACGCCGCGTGAGTGAAGAAGGGTTTCGGCTCGTAAAGCTCTGTTGTT AAAGAAGAACGTGGGTAAGAGTAACTGTTTACCCAGTGACGGTATTT AACCAGAAAGCCACGGCTAACTACGTGCCAGCAGCCGCGGTAATACG TAGGTGGCAAGCGTTATCCGGATTTATTGGGCGTAAAGCGAGCGCAG GCGGTCTTTTAAGTCTAATGTGAAAGCCTTCGGCTCAACCGAAGAAGT GCATTGGAAACTGGGAGACTTGAGTGCAGAAGAGGACAGTGGAACTC CATGTGTAGCGGTGAAATGCGTAGATATATGGAAGAACACCAGTGGC GAAGGCGGCTGTCTGGTCTGCAACTGACGCTGAGGCTCGAAAGCATG GGTAGCGAACAGGATTAGATACCCTGGTAGTCCATGCCGTAAACGAT |

-continued

Sequence Listing

| Seq ID No. | Description | Sequence |
|---|---|---|
| | | GATTACTAAGTGTTGGAGGGTTTCCGCCCTTCAGTGCTGCAGCTAACG<br>CATTAAGTAATCCGCCTGGGGAGTACGACCGCAAGGTTGAAACTCAA<br>AAGAATTGACGGGGGCCCGCACAAGCGGTGGAGCATGTGGTTTAATT<br>CGAAGCTACGCGAAGAACCTTACCAGGTCTTGACATCTTCTGACAGTC<br>TAAGAGATTAGAGGTTCCCTTCGGGGACAGAATGACAGGTGGTGCAT<br>GGTTGTCGTCAGCTCGTGTCGTGAGATGTTGGGTTAAGTCCCGCAACG<br>AGCGCAACCCTTATTACTAGTTGCCAGCATTAAGTTGGGCACTCTAGT<br>GAGACTGCCGGTGACAAACCGGAGGAAGGTGGGGACGACGTCAAAT<br>CATCATGCCCCTTATGACCTGGGCTACACACGTGCTACAATGGATGGT<br>ACAACGAGTCGCGAGACCGCGAGGTTAAGCTAATCTCTTAAAACCAT<br>TCTCAGTTCGGACTGTAGGCTGCAACTCGCCTACACGAAGTCGGAATC<br>GCTAGTAATCGCGGATCAGCATGCCGCGGTGAATACGTTCCCGGGCC<br>TTGTACACACCGCCCGTCACACCATGAGAGTTTGTAACACCCAAAGC<br>CGGTGGGGTAACCTTTTAGGAGCTAGCCGTCTAAGGTGGGACAGATG<br>ATTAGGGTGAAGTCGTAACAAGGTAGCCGTAGGAGAACCTGCGGCTG<br>GATCACCTCCTT |
| 10 | DP10 16S rRNA | CAGATAGTTGGTGAGGTAACGGCTCACCAAGGCAACGATGCGTAGCC<br>GACCTGAGAGGGTGATCGGCCACACTGGGACTGAGACACGGCCCAGA<br>CTCCTACGGGAGGCAGCAGTAGGGAATCTTCCGCAATGGACGAAAGT<br>CTGACGGAGCAACGCCGCGTGAGTGATGAAGGTTTTCGGATCGTAAA<br>GCTCTGTTGTTAGGGAAGAACAAGTGCCGTTCAAATAGGGCGGCACC<br>TTGACGGTACCTAACCAGAAAGCCACGGCTAACTACGTGCCAGCAGC<br>CGCGGTAATACGTAGGTGGCAAGCGTTGTCCGGAATTATTGGGCGTA<br>AAGGGCTCGCAGGCGGTTTCTTAAGTCTGATGTGAAAGCCCCCGGCT<br>CAACCGGGGAGGGTCATTGGAAACTGGGGAACTTGAGTGCAGAAGA<br>GGAGAGTGGAATTCCACGTGTAGCGGTGAAATGCGTAGAGATGTGGA<br>GGAACACCAGTGGCGAAGGCGACTCTCTGGTCTGTAACTGACGCTGA<br>GGAGCGAAAGCGTGGGGAGCGAACAGGATTAGATACCCTGGTAGTCC<br>ACGCCGTAAACGATGAGTGCTAAGTGTTAGGGGGTTTCCGCCCCTTA<br>GTGCTGCAGCTAACGCATTAAGCACTCCGCCTGGGGAGTACGGTCGC<br>AAGACTGAAACTCAAAGGAATTGACGGGGGCCCGCACAAGCGGTGG<br>AGCATGTGGTTTAATTCGAAGCAACGCGAAGAACCTTACCAGGTCTT<br>GACATCCTCTGACAATCCTAGAGATAGGACGTCCCCTTCGGGGGCAG<br>AGTGACAGGTGGTGCATGGTTGTCGTCAGCTCGTGTCGTGAGATGTTG<br>GGTTAAGTCCCGCAACGAGCGCAACCCTTGATCTTAGTTGCCAGCATT<br>CAGTTGGGCACTCTAAGGTGACTGCCGGTGACAAACCGGAGGAAGGT<br>GGGGATGACGTCAAATCATCATGCCCCTTATGACCTGGGCTACACAC<br>GTGCTACAATGGACAGAACAAAGGGCAGCGAAACCGCGAGGTTAAG<br>CCAATCCCACAAATCTGTTCTCAGTTCGGATCGCAGTCTGCAACTCGA<br>CTGCGTGAAGCTGGAATCGCTAGTAATCGCGGATCAGCATGCCGCGG<br>TGAATACGTTCCCGGGCCTTGTACACACCGCCCGTCACACCACGAGA<br>GTTTGTAACACCCGAAGTCGGTGAGGTAACCTTTTAGGAGCCAGCCG<br>CCGAAGGTGGGACAGATGATTGGGGTGAAGTCGTAACAAGGTAGCCG<br>TATCGGAAGGTGCGGCTGGATCACCTCCTTT |
| 11 | DP11 16S rRNA | TGAAGAGTTTGATCATGGCTCAGATTGAACGCTGGCGGCAGGCCTAA<br>CACATGCAAGTCGAGCGGTAGAGAGAAGCTTGCTTCTCTTGAGAGCG<br>GCGGACGGGTGAGTAATGCCTAGGAATCTGCCTGGTAGTGGGGGATA<br>ACGTTCGGAAACGGACGCTAATACCGCATACGTCCTACGGGAGAAAG<br>CAGGGGACCTTCGGGCCTTGCGCTATCAGATGAGCCTAGGTCGGATT<br>AGCTAGTTGGTGAGGTAATGGCTCACCAAGGCGACGATCCGTAACTG<br>GTCTGAGAGGATGATCAGTCACACTGGAACTGAGACACGGTCCAGAC<br>TCCTACGGGAGGCAGCAGTGGGGAATATTGGACAATGGGCGAAAGCC<br>TGATCCAGCCATGCCGCGTGTGTGAAGAAGGTCTTCGGATTGTAAAG<br>CACTTTAAGTTGGGAGGAAGGGTTGTAGATTAATACTCTGCAATTTTG<br>ACGTTACCGACAGAATAAGCACCGGCTAACTCTGTGCCAGCAGCCGC<br>GGTAATACAGAGGGTGCAAGCGTTAATCGGAATTACTGGGCGTAAAG<br>CGCGCGTAGGTGGTTCGTTAAGTTGGATGTGAAAGCCCCGGGCTCAA<br>CCTGGGAACTGCATTCAAAACTGACGAGCTAGAGTATGGTAGAGGGT<br>GGTGGAATTTCCTGTGTAGCGGTGAAATGCGTAGATATAGGAAGGAA<br>CACCAGTGGCGAAGGCGACCACCTGGACTGATACTGACACTGAGGTG<br>CGAAAGCGTGGGGAGCAAACAGGATTAGATACCCTGGTAGTCCACGC<br>CGTAAACGATGTCAACTAGCCGTTGGAATCCTTGAGATTTTAGTGGCG<br>CAGCTAACGCATTAAGTTGACCGCCTGGGGAGTACGGCCGCAAGGTT<br>AAAACTCAAATGAATTGACGGGGGCCCGCACAAGCGGTGGAGCATGT<br>GGTTTAATTCGAAGCAACGCGAAGAACCTTACCAGGCCTTGACATCC<br>AATGAACTTTCCAGAGATGGATGGGTGCCTTCGGGAACATTGAGACA<br>GGTGCTGCATGGCTGTCGTCAGCTCGTGTCGTGAGATGTTGGGTTAAG<br>TCCCGTAACGAGCGCAACCCTTGTCCTTAGTTACCAGCACGTTATGGT<br>GGGCACTCTAAGGAGACTGCCGGTGACAAACCGGAGGAAGGTGGGG<br>ATGACGTCAAGTCATCATGGCCCTTACGGCCTGGGCTACACACGTGCT<br>ACAATGGTCGGTACAAAGGGTTGCCAAGCCGCGAGGTGGAGCTAATC |

-continued

Sequence Listing

| Seq ID No. | Description | Sequence |
|---|---|---|
| | | CCATAAAACCGATCGTAGTCCGGATCGCAGTCTGCAACTCGACTGCG TGAAGTCGGAATCGCTAGTAATCGCGAATCAGAATGTCGCGGTGAAT ACGTTCCCGGGCCTTGTACACACCGCCCGTCACATCCCACACGAATTG CTTG |
| 12 | DP12 16S rRNA | TACGGAGAGTTTGATCCTGGCTCAGGATGAACGCTGGCGGCGTGCTT AACACATGCAAGTCGAACGGTGAAGCCAAGCTTGCTTGGTGGATCAG TGGCGAACGGGTGAGTAACACGTGAGCAACCTGCCCTGGACTCTGGG ATAAGCGCTGGAAACGGCGTCTAATACTGGATATGAGCCTTCATCGC ATGGTGGGGGTTGGAAAGATTTTTTGGTCTGGGATGGGCTCGCGGCCT ATCAGCTTGTTGGTGAGGTAATGGCTCACCAAGGCGTCGACGGGTAG CCGGCCTGAGAGGGTGACCGGCCACACTGGGACTGAGACACGGCCCA GACTCCTACGGGAGGCAGCAGTGGGGAATATTGCACAATGGGCGAAA GCCTGATGCAGCAACGCCGCGTGAGGGATGACGGCCTTCGGGTTGTA AACCTCTTTTAGCAGGGAAGAAGCGAAAGTGACGGTACCTGCAGAAA AAGCGCCGGCTAACTACGTGCCAGCAGCCGCGGTAATACGTAGGGCG CAAGCGTTATCCGGAATTATTGGGCGTAAAGAGCTCGTAGGCGGTTT GTCGCGTCTGCTGTGAAATCCCGAGGCTCAACCTCGGGCCTGCAGTG GGTACGGGCAGACTAGAGTGCGGTAGGGGAGATTGGAATTCCTGGTG TAGCGGTGGAATGCGCAGATATCAGGAGGAACACCGATGGCGAAGG CAGATCTCTGGGCCGTAACTGACGCTGAGGAGCGAAAGGGTGGGGAG CAAACAGGCTTAGATACCCTGGTAGTCCACCCCGTAAACGTTGGGAA CTAGTTGTGGGGACCATTCCACGGTTTCCGTGACGCAGCTAACGCATT AAGTTCCCCGCCTGGGGAGTACGGCCGCAAGGCTAAAACTCAAAGGA ATTGACGGGGACCCGCACAAGCGGCGGAGCATGCGGATTAATTCGAT GCAACGCGAAGAACCTTACCAAGGCTTGACATACACCAGAACGGGCC AGAAATGGTCAACTCTTTGGACACTGGTGAACAGGTGGTGCATGGTT GTCGTCAGCTCGTGTCGTGAGATGTTGGGTTAAGTCCCGCAACGAGC GCAACCCTCGTTCTATGTTGCCAGCACGTAATGGTGGGAACTCATGGG ATACTGCCGGGGTCAACTCGGAGGAAGGTGGGGATGACGTCAAATCA TCATGCCCCTTATGTCTTGGGCTTCACGCATGCTACAATGGCCGGTAC AAAGGGCTGCAATACCGTGAGGTGGAGCGAATCCCAAAAAGCCGGTC CCAGTTCGGATTGAGGTCTGCAACTCGACCTCATGAAGTCGGAGTCG CTAGTAATCGCAGATCAGCAACGCTGCGGTGAATACGTTCCCGGGTC TTGTACACACCGCCCGTCAAGTCATGAAAGTCGGTAACACCTGAAGC CGGTGGCCCAACCCTTGTGGAGGGAGCCGTCGAAGGTGGGATCGGTA ATTAGGACTAAGTCGTAACAAGGTAGCCGTACCGGAAGGTGCGGCTG GATCACCTCCTTT |
| 13 | DP13 16S rRNA | AGTTAGCGGCGGACGGGTGAGTAACACGTGGGTAACCTGCCTATAAG ACTGGGATAACTCCGGGAAACCGGGGCTAATACCGGATAACATTTTG CACCGCATGGTGCGAAATTGAAAGGCGGCTTCGGCTGTCACTTATAG ATGGACCTGCGGCGCATTAGCTAGTTGGTGAGGTAACGGCTCACCAA GGCGACGATGCGTAGCCGACCTGAGAGGGTGATCGGCCACACTGGGA CTGAGACACGGCCCAGACTCCTACGGGAGGCAGCAGTAGGGAATCTT CCGCAATGGACGAAAGTCTGACGGAGCAACGCCGCGTGAACGATGA AGGCTTTCGGGTCGTAAAGTTCTGTTGTTAGGGAAGAACAAGTGCTA GTTGAATAAGCTGGCACCTTGACGGTACCTAACCAGAAAGCCACGGC TAACTACGTGCCAGCAGCCGCGGTAATACGTAGGTGGCAAGCGTTAT CCGGAATTATTGGGCGTAAAGCGCGCGCAGGTGGTTTCTTAAGTCTG ATGTGAAAGCCCACGGCTCAACCGTGGAGGGTCATTGGAAACTGGGA GACTTGAGTGCAGAAGAGGAAAGTGGAATTCCATGTGTAGCGGTGAA ATGCGTAGAGATATGGAGGAACACCAGTGGCGAAGGCGACTTTCTGG TCTGCAACTGACACTGAGGCGCGAAAGCGTGGGGAGCAAACAGGATT AGATACCCTGGTAGTCCACGCCGTAAACGATGAGTGCTAAGTGTTAG AGGGTTTCCGCCCTTTAGTGCTGAAGTTAACGCATTAAGCACTCCGCC TGGGGAGTACGGCCGCAAGGCTGAAACTCAAAGGAATTGACGGGGG CCCGCACAAGCGGTGGAGCATGTGGTTTAATTCGAAGCAACGCGAAG AACCTTACCAGGTCTTGACATCCTCTGAAAACCCTAGAGATAGGGCTT CCCCTTCGGGGGCAGAGTGACAGGTGGTGCATGGTTGTCGTCAGCTC GTGTCGTGAGATGTTGGGTTAAGTCCCGCAACGAGCGCAACCCTTGA TCTTAGTTGCCATCATTAAGTTGGGCACTCTAAGGTGACTGCCGGTGA CAAACCGGAGGAAGGTGGGGATGACGTCAAATCATCATGCCCCTTAT GACCTGGGCTACACACGTGCTACAATGGACGGTACAAAGAGTCGCAA GACCGCGAGGTGGAGCTAATCTCATAAAACCGTTCTCAGTTCGGATT GTAGGCTGCAACTCGCCTACATGAAGCTGGAATCGCTAGTAATCGCG GATCAGCATGCCGCGGTGAATACGTTCCCGGGCCTTGTACACACCGC CCGTCACACCACGAGAGTTTGTAACACCCGAAGTCGGTGGGGTAACC TTTTGGAGCCAGCCGCCTAAGGTGGGACAGATGATTGGGGTGAAGTC GTAACAAGGTAGCCGTATCGGAAGGTGCGGCTGGATCACCTCCTTT |
| 14 | DP1416S rRNA | TACGGAGAGTTTGATCCTGGCTCAGGATGAACGCTGGCGGCGTGCTT AACACATGCAAGTCGAACGATGACTTCTGTGCTTGCACAGAATGATT |

-continued

Sequence Listing

| Seq ID No. | Description | Sequence |
|---|---|---|
| | | AGTGGCGAACGGGTGAGTAACACGTGAGTAACCTGCCCTTAACTTCG<br>GGATAAGCCTGGGAAACCGGGTCTAATACCGGATACGACCTCCTGGC<br>GCATGCCATGGTGGTGGAAAGCTTTAGCGGTTTTGGATGGACTCGCG<br>GCCTATCAGCTTGTTGGTTGGGGTAATGGCCCACCAAGGCGACGACG<br>GGTAGCCGGCCTGAGAGGGTGACCGGCCACACTGGGACTGAGACACG<br>GCCCAGACTCCTACGGGAGGCAGCAGTGGGGAATATTGCACAATGGG<br>CGAAAGCCTGATGCAGCGACGCCGCGTGAGGGATGACGGCCTTCGGG<br>TTGTAAACCTCTTTCAGCAGGGAAGAAGCGAAAGTGACGGTACCTGC<br>AGAAGAAGCGCCGGCTAACTACGTGCCAGCAGCCGCGGTAATACGTA<br>GGGCGCAAGCGTTATCCGGAATTATTGGGCGTAAAGAGCTCGTAGGC<br>GGTTTGTCGCGTCTGCTGTGAAAGCCCGGGGCTCAACCCCGGGTCTGC<br>AGTGGGTACGGGCAGACTAGAGTGCAGTAGGGGAGACTGGAATTCCT<br>GGTGTAGCGGTGAAATGCGCAGATATCAGGAGGAACACCGATGGCG<br>AAGGCAGGTCTCTGGGCTGTAACTGACGCTGAGGAGCGAAAGCATGG<br>GGAGCGAACAGGATTAGATACCCTGGTAGTCCATGCCGTAAACGTTG<br>GGCACTAGGTGTGGGGGACATTCCACGTTTTCCGCGCCGTAGCTAAC<br>GCATTAAGTGCCCCGCCTGGGGAGTACGGCCGCAAGGCTAAAACTCA<br>AAGGAATTGACGGGGGCCCGCACAAGCGGCGGAGCATGCGGATTAA<br>TTCGATGCAACGCGAAGAACCTTACCAAGGCTTGACATGAACCGGTA<br>AGACCTGGAAACAGGTCCCCCACTTGTGGCCGGTTTACAGGTGGTGC<br>ATGGTTGTCGTCAGCTCGTGTCGTGAGATGTTGGGTTAAGTCCCGCAA<br>CGAGCGCAACCCTCGTTCTATGTTGCCAGCGGGTTATGCCGGGGACTC<br>ATAGGAGACTGCCGGGGTCAACTCGGAGGAAGGTGGGGACGACGTC<br>AAATCATCATGCCCCTTATGTCTTGGGCTTCACGCATGCTACAATGGC<br>CGGTACAAAGGGTTGCGATACTGTGAGGTGGAGCTAATCCCAAAAAG<br>CCGGTCTCAGTTCGGATTGAGGTCTGCAACTCGACCTCATGAAGTTGG<br>AGTCGCTAGTAATCGCAGATCAGCAACGCTGCGGTGAATACGTTCCC<br>GGGCCTTGTACACACCGCCCGTCAAGTCACGAAAGTTGGTAACACCC<br>GAAGCCGGTGGCCTAACCCCTTGTGGGAGGGAGCCGTCGAAGGTGGG<br>ACCGGCGATTGGGACTAAGTCGTAACAAGGTAGCCGTACCGGAAGGT<br>GCGGCTGGATCACCTCCTTT |
| 15 | DP15 16S rRNA | TACGGAGAGTTTGATCCTGGCTCAGGACGAACGCTGGCGGCGTGCTT<br>AACACATGCAAGTCGAACGATGATCAGGAGCTTGCTCCTGTGATTAG<br>TGGCGAACGGGTGAGTAACACGTGAGTAACCTGCCCCTGACTCTGGG<br>ATAAGCGTTGGAAACGACGTCTAATACTGGATATGATCACTGGCCGC<br>ATGGTCTGGTGGTGGAAAGATTTTTTGGTTGGGGATGGACTCGCGGCC<br>TATCAGCTTGTTGGTGAGGTAATGGCTCACCAAGGCGACGACGGGTA<br>GCCGGCCTGAGAGGGTGACCGGCCACACTGGGACTGAGACACGGCCC<br>AGACTCCTACGGGAGGCAGCAGTGGGGAATATTGCACAATGGGCGAA<br>AGCCTGATGCAGCAACGCCGCGTGAGGGATGACGGCCTTCGGGTTGT<br>AAACCTCTTTTAGTAGGGAAGAAGCGAAAGTGACGGTACCTGCAGAA<br>AAAGCACCGGCTAACTACGTGCCAGCAGCCGCGGTAATACGTAGGGT<br>GCAAGCGTTGTCCGGAATTATTGGGCGTAAAGAGCTCGTAGGCGGTT<br>TGTCGCGTCTGCTGTGAAATCCCGAGGCTCAACCTCGGGCTTGCAGTG<br>GGTACGGGCAGACTAGAGTGCGGTAGGGGAGATTGGAATTCCTGGTG<br>TAGCGGTGGAATGCGCAGATATCAGGAGGAACACCGATGGCGAAGG<br>CAGATCTCTGGGCCGTAACTGACGCTGAGGAGCGAAAGCGTGGGGAG<br>CGAACAGGATTAGATACCCTGGTAGTCCACGCCGTAAACGTTGGGCG<br>CTAGATGTAGGGACCTTTCCACGGTTTCTGTGTCGTAGCTAACGCATT<br>AAGCGCCCCGCCTGGGGAGTACGGCCGCAAGGCTAAAACTCAAAGG<br>AATTGACGGGGGCCCGCACAAGCGGCGGAGCATGCGGATTAATTCGA<br>TGCAACGCGAAGAACCTTACCAAGGCTTGACATACACCGGAAACGGC<br>CAGAGATGGTCGCCCCCTTGTGGTCGGTGTACAGGTGGTGCATGGTTG<br>TCGTCAGCTCGTGTCGTGAGATGTTGGGTTAAGTCCCGCAACGAGCGC<br>AACCCTCGTTCTATGTTGCCAGCGCGTTATGGCGGGGACTCATAGGAG<br>ACTGCCGGGGTCAACTCGGAGGAAGGTGGGGATGACGTCAAATCATC<br>ATGCCCCTTATGTCTTGGGCTTCACGCATGCTACAATGGCCGGTACAA<br>AGGGCTGCGATACCGTAAGGTGGAGCGAATCCCAAAAAGCCGGTCTC<br>AGTTCGGATTGAGGTCTGCAACTCGACCTCATGAAGTCGGAGTCGCT<br>AGTAATCGCAGATCAGCAACGCTGCGGTGAATACGTTCCCGGGCCTT<br>GTACACACCGCCCGTCAAGTCATGAAAGTCGGTAACACCCGAAGCCG<br>GTGGCCTAACCCTTGTGGAAGGAGCCGTCGAAGGTGGGATCGGTGAT<br>TAGGACTAAGTCGTAACAAGGTAGCCGTACCGGAAGGTGCGGCTGGA<br>TCACCTCCTTT |
| 16 | DP16 16S rRNA | GCACTTCATCGTGGTGCACCGTGAAGGGTCTTTGGGCGTTTTACACAT<br>GCAAGCAAGTGTTCTATAATTTAGGTTATGGAACAGCCAAATGGTCA<br>GTACAGCTCAGTCCTAGGCGATGGACTCCGTAAAACGGGGACAGACT<br>ATCCTTTAATAATTAATAGGTTTATTATTTCAATAATAATCTCTAGGA<br>AGGGATATACATATATCCTTATTAGTCTAAAGGTTAATAAACCGCCTT<br>AGTCAGGACTGAGTTCTCAACAGCTACGGGTTAAACCCCAGGCAACG<br>ACGAGTAGGGGATAGTGATAGCTACAACCCCGACACTGGCCGCAAGC |

-continued

Sequence Listing

| Seq ID No. | Description | Sequence |
|---|---|---|
| | | CAGGGTACTTAAGTACGCAGCAGTGAAGAATCCTCGGCAATGCATCG<br>CAATTACCGGTGACCCAATATAAAATAATATCAGGGAGGTAGTAGGT<br>GTGACCGGGTGACCCAAAGACGAGTAGTGACATAAGTTATTATTCGC<br>GTATGTCGAACATGATAGTGACGTGTTCAACATCAAGCCCCGTCCAA<br>CCTCTGTGCCAGCAGTCGCGGTAAAACAGGAGGGGCAGCTCTTATGG<br>TCATGAATGGGCGTATAGGGCACGCAGCCAGTTAGTAAAAGCTTGAA<br>TATTTATTTTTTTAAAAAGAATGTTTGAGAGGCTATGAGTTTTTATAA<br>AGTGTACCCACGACACCAGACTTAGGGCTGAGATCCTATGAAGTCTG<br>GGGGCGGTCCTTTAGGGTGCATTGTAAAAACTGACGGTAAGGTGCGA<br>CAGCTGGGATACCGAAGCGGAGTAGAGCCCGCCTAGCCCCAGCCGTA<br>AACGATAGGGGCCGTTGTTGACTACGGTTTTCAATAAGGCTAACGCCT<br>GAGCCCCTCGCCTGTAGGGTATAGCCGCAAGGCCGACATATTAACGA<br>TGAGACCGCTGGTGAGCAAACGGGTGCGGGGCATGCTGTTCAATCAG<br>ACAGTACGCTGACAACCTTACCACTCCTTGAATCTTTTAGATTATATT<br>TCTAAAATGACAGGTGCTGCATGGCCGTCGTCAGTTCGTGGTCGTGAG<br>TCGTCCGGTTGAGTCCATGAACGAACGCAGACCCGTCTGTATACTCAG<br>TGAAAAGAAATTTAGCTGAACTATACAGTTGTACTTCTATAAAAGGT<br>ACCTGTACGGGATTATGACAGGTCGTCATGGCCTTTATGGAGTGGGCT<br>ACAGGCGTGCCACACGAGCCGTTTTAACGAGTTCCTCATTTTTATGAA<br>TAAGGTCTCTTAATCACGGCTAGTATACGGATCGTAGGCTGTAACTCG<br>CCTACGTGAAGTCGGAGTCCCGAGTAATCGCCGATCATCACGCGGCG<br>GTGAATCTACACTCTCACTGGGGTACTAACCGCTCGTCACG |
| 17 | DP17 16S rRNA | GTGATTGACGTTACTCGCAGAAGAAGCACCGGCTAACTCCGTGCCAG<br>CAGCCGCGGTAATACGGAGGGTGCAAGCGTTAATCGGAATTACTGGG<br>CGTAAAGCGCACGCAGGCGGTTTGTTAAGTCAGATGTGAAATCCCCG<br>CGCTTAACGTGGGAACTGCATTTGAAACTGGCAAGCTAGAGTCTTGT<br>AGAGGGGGGTAGAATTCCAGGTGTAGCGGTGAAATGCGTAGAGATCT<br>GGAGGAATACCGGTGGCGAAGGCGGCCCCCTGGACAAAGACTGACG<br>CTCAGGTGCGAAAGCGTGGGGAGCAAACAGGATTAGATACCCTGGTA<br>GTCCACGCTGTAAACGATGTCGACTTGGAGGTTGTGCCCTTGAGGCGT<br>GGCTTCCGGAGCTAACGCGTTAAGTCGACCGCCTGGGGAGTACGGCC<br>GCAAGGTTAAAACTCAAATGAATTGACGGGGGCCCGCACAAGCGGTG<br>GAGCATGTGGTTTAATTCGATGCAACGCGAAGAACCTTACCTACTCTT<br>GACATCCACGGAATTCGCCAGAGATGGCTTAGTGCCTTCGGGAACCG<br>TGAGACAGGTGCTGCATGGCTGTCGTCAGCTCGTGTTGTGAAATGTTG<br>GGTTAAGTCCCGCAACGAGCGCAACCCTTATCCTTTGTTGCCAGCACG<br>TAATGGTGGGAACTCAAAGGAGACTGCCGGTGATAAACCGGAGGAA<br>GGTGGGGATGACGTCAAGTCATCATGGCCCTTACGAGTAGGGCTACA<br>CACGTGCTACAATGGCATATACAAAGAGAAGCGAACTCGCGAGAGCA<br>AGCGGACCTCATAAAGTATGTCGTAGTCCGGATTGGAGTCTGCAACT<br>CGACTCCATGAAGTCGGAATCGCTAGTAATCGTAGATCAGAATGCTA<br>CGG |
| 18 | DP18 16S rRNA | TGAAGAGTTTGATCATGGCTCAGATTGAACGCTGGCGGCAGGCCTAA<br>CACATGCAAGTCGAGCGGATGAAAGGAGCTTGCTCCTGGATTCAGCG<br>GCGGACGGGTGAGTAATGCCTAGGAATCTGCCTGGTAGTGGGGGACA<br>ACGTTTCGAAAGGAACGCTAATACCGCATACGTCCTACGGGAGAAAG<br>CAGGGGACCTTCGGGCCTTGCGCTATCAGATGAGCCTAGGTCGGATT<br>AGCTAGTTGGTGAGGTAATGGCTCACCAAGGCGACGATCCGTAACTG<br>GTCTGAGAGGATGATCAGTCACACTGGAACTGAGACACGGTCCAGAC<br>TCCTACGGGAGGCAGCAGTGGGGAATATTGGACAATGGGCGAAAGCC<br>TGATCCAGCCATGCCGCGTGTGTGAAGAAGGTCTTCGGATTGTAAAG<br>CACTTTAAGTTGGGAGGAAGGGCAGTAAATTAATACTTTGCTGTTTTG<br>ACGTTACCGACAGAATAAGCACCGGCTAACTCTGTGCCAGCAGCCGC<br>GGTAATACAGAGGGTGCAAGCGTTAATCGGAATTACTGGGCGTAAAG<br>CGCGCGTAGGTGGTTTGTTAAGTTGAATGTGAAATCCCCGGGCTCAAC<br>CTGGGAACTGCATCCAAAACTGGCAAGCTAGAGTATGGTAGAGGGTG<br>GTGGAATTTCCTGTGTAGCGGTGAAATGCGTAGATATAGGAAGGAAC<br>ACCAGTGGCGAAGGCGACCACCTGGACTGATACTGACACTGAGGTGC<br>GAAAGCGTGGGGAGCAAACAGGATTAGATACCCTGGTAGTCCACGCC<br>GTAAACGATGTCAACTAGCCGTTGGGAGCCTTGAGCTCTTAGTGGCG<br>CAGCTAACGCATTAAGTTGACCGCCTGGGGAGTACGGCCGCAAGGTT<br>AAAACTCAAATGAATTGACGGGGGCCCGCACAAGCGGTGGAGCATGT<br>GGTTTAATTCGAAGCAACGCGAAGAACCTTACCAGGCCTTGACATCC<br>AATGAACTTTCCAGAGATGGATTGGTGCCTTCGGGAACATTGAGACA<br>GGTGCTGCATGGCTGTCGTCAGCTCGTGTCGTGAGATGTTGGGTTAAG<br>TCCCGTAACGAGCGCAACCCTTGTCCTTAGTTACCAGCACGTTATGGT<br>GGGCACTCTAAGGAGACTGCCGGTGACAAACCGGAGGAAGGTGGGG<br>ATGACGTCAAGTCATCATGGCCCTTACGGCCTGGGCTACACACGTGCT<br>ACAATGGTCGGTACAAAGGGTTGCCAAGCCGCGAGGTGGAGCTAATC<br>CCATAAAACCGATCGTAGTCCGGATCGCAGTCTGCAACTCGACTGCG<br>TGAAGTCGGAATCGCTAGTAATCGCGAATCAGAATGTCGCGGTGAAT |

-continued

Sequence Listing

| Seq ID No. | Description | Sequence |
|---|---|---|
| | | ACGTTCCCGGGCCTTGTACACACCGCCCGTCACACCATGGGAGTGGG TTGCACCAGAAGTAGCTAGTCTAACCTTCGGGAGGACGGTTACCACG GTGTGATTCATGACTGGGGTGAAGTCGTAACAAGGTAGCCGTAGGGG AACCTGCGGCTGGATCACCTCCTT |
| 19 | DP19 16S rRNA | TACGGAGAGTTTGATCCTGGCTCAGGACGAACGCTGGCGGCGTGCTT AACACATGCAAGTCGAACGATGATGCCCAGCTTGCTGGGTGGATTAG TGGCGAACGGGTGAGTAACACGTGAGTAACCTGCCCCTGACTCTGGG ATAAGCGTTGGAAACGACGTCTAATACTGGATACGACTGCCGGCCGC ATGGTCTGGTGGTGGAAAGATTTTTTGGTTGGGGATGGACTCGCGGCC TATCAGCTTGTTGGTGAGGTAATGGCTCACCAAGGCGACGACGGGTA GCCGGCCTGAGAGGGTGACCGGCCACACTGGGACTGAGACACGGCCC AGACTCCTACGGGAGGCAGCAGTGGGGAATATTGCACAATGGGCGAA AGCCTGATGCAGCAACGCCGCGTGAGGGATGACGGCCTTCGGGTTGT AAACCTCTTTTAGTAGGGAAGAAGCGAAAGTGACGGTACCTGCAGAA AAAGCACCGGCTAACTACGTGCCAGCAGCCGCGGTAATACGTAGGGT GCAAGCGTTGTCCGGAATTATTGGGCGTAAAGAGCTCGTAGGCGGTT TGTCGCGTCTGCTGTGAAATCCCGAGGCTCAACCTCGGGCTTGCAGTG GGTACGGGCAGACTAGAGTGCGGTAGGGGAGATTGGAATTCCTGGTG TAGCGGTGGAATGCGCAGATATCAGGAGGAACACCGATGGCGAAGG CAGATCTCTGGGCCGTAACTGACGCTGAGGAGCGAAAGCGTGGGGAG CGAACAGGATTAGATACCCTGGTAGTCCACGCCGTAAACGTTGGGCG CTAGATGTAGGGACCTTTCCACGGTTTCTGTGTCGTAGCTAACGCATT AAGCGCCCCGCCTGGGGAGTACGGCCGCAAGGCTAAAACTCAAAGG AATTGACGGGGGCCCGCACAAGCGGCGGAGCATGCGGATTAATTCGA TGCAACGCGAAGAACCTTACCAAGGCTTGACATACACCGGAAACGGC CAGAGATGGTCGCCCCCTTGTGGTCGGTGTACAGGTGGTGCATGGTTG TCGTCAGCTCGTGTCGTGAGATGTTGGGTTAAGTCCCGCAACGAGCGC AACCCTCGTTCTATGTTGCCAGCGCGTTATGGCGGGGACTCATAGGAG ACTGCCGGGGTCAACTCGGAGGAAGGTGGGGATGACGTCAAATCATC ATGCCCCTTATGTCTTGGGCTTCACGCATGCTACAATGGCCGGTACAA AGGGCTGCGATACCGTAAGGTGGAGCGAATCCCAAAAAGCCGGTCTC AGTTCGGATTGAGGTCTGCAACTCGACCTCATGAAGTCGGAGTCGCT AGTAATCGCAGATCAGCAACGCTGCGGTGAATACGTTCCCGGGCCTT GTACACACCGCCCGTCAAGTCATGAAAGTCGGTAACACCCGAAGCCG GTGGCCTAACCCTTGTGGAAGGAGCCGTCGAAGGTGGGATCGGTGAT TAGGACTAAGTCGTAACAAGGTAGCCGTACCGGAAGGTGCGGCTGGA TCACCTCCTTT |
| 20 | DP20 16S rRNA | TGAAGAGTTTGATCCTGGCTCAGAGTGAACGCTGGCGGTAGGCCTAA CACATGCAAGTCGAACGGCAGCACAGTAAGAGCTTGCTCTTATGGGT GGCGAGTGGCGGACGGGTGAGGAATACATCGGAATCTACCTTTTCGT GGGGGATAACGTAGGGAAACTTACGCTAATACCGCATACGACCTTCG GGTGAAAGCAGGGGACCTTCGGGCCTTGCGCGGATAGATGAGCCGAT GTCGGATTAGCTAGTTGGCGGGGTAAAGGCCCACCAAGGCGACGATC CGTAGCTGGTCTGAGAGGATGATCAGCCACACTGGAACTGAGACACG GTCCAGACTCCTACGGGAGGCAGCAGTGGGGAATATTGGACAATGGG CGCAAGCCTGATCCAGCCATACCGCGTGGGTGAAGAAGGCCTTCGGG TTGTAAAGCCCTTTTGTTGGGAAAGAAAAGCAGTCGGCTAATACCCG GTTGTTCTGACGGTACCCAAAGAATAAGCACCGGCTAACTTCGTGCC AGCAGCCGCGGTAATACGAAGGGTGCAAGCGTTACTCGGAATTACTG GGCGTAAAGCGTGCGTAGGTGGTTGTTTAAGTCTGTTGTGAAAGCCCT GGGCTCAACCTGGGAATTGCAGTGGATACTGGGCGACTAGAGTGTGG TAGAGGGTAGTGGAATTCCCGGTGTAGCAGTGAAATGCGTAGAGATC GGGAGGAACATCCATGGCGAAGGCAGCTACCTGGACCAACACTGACA CTGAGGCACGAAAGCGTGGGGAGCAAACAGGATTAGATACCCTGGTA GTCCACGCCCTAAACGATGCGAACTGGATGTTGGGTGCAATTTGGCA CGCAGTATCGAAGCTAACGCGTTAAGTTCGCCGCCTGGGGAGTACGG TCGCAAGACTGAAACTCAAAGGAATTGACGGGGGCCCGCACAAGCG GTGGAGTATGTGGTTTAATTCGATGCAACGCGAAGAACCTTACCTGGT CTTGACATGTCGAGAACTTTCCAGAGATGGATTGGTGCCTTCGGGAAC TCGAACACAGGTGCTGCATGGCTGTCGTCAGCTCGTGTCGTGAGATGT TGGGTTAAGTCCCGCAACGAGCGCAACCCTTGTCCTTAGTTGCCAGCA CGTAATGGTGGGAACTCTAAGGAGACCGCCGGTGACAAACCGGAGG AAGGTGGGGATGACGTCAAGTCATCATGGCCCTTACGACCAGGGCTA CACACGTACTACAATGGTAGGGACAGAGGGCTGCAAACCCGCGAGG GCAAGCCAATCCCAGAAACCCTATCTCAGTCCGGATTGGAGTCTGCA ACTCGACTCCATGAAGTCGGAATCGCTAGTAATCGCAGATCAGCATT GCTGCGGTGAATACGTTCCCGGGCCTTGTACACACCGCCCGTCACACC ATGGGAGTTTGTTGCACCAGAAGCAGGTAGCTTAACCTTCGGGAGGG CGCTTGCCACGGTGTGGCCGATGACTGGGGTGAAGTCGTAACAAGGT AGCCGTATCGGAAGGTGCGGCTGGATCACCTCCTTT |

-continued

Sequence Listing

| Seq ID No. | Description | Sequence |
|---|---|---|
| 22 | DP22 16S rRNA | TTGAAGAGTTTGATCATGGCTCAGATTGAACGCTGGCGGCAGGCCTA<br>ACACATGCAAGTCGAGCGGCAGCGGGAAGTAGCTTGCTACTTTGCCG<br>GCGAGCGGCGGACGGGTGAGTAATGTCTGGGAAACTGCCTGATGGAG<br>GGGGATAACTACTGGAAACGGTAGCTAATACCGCATGACCTCGCAAG<br>AGCAAAGTGGGGGACCTTCGGGCCTCACGCCATCGGATGTGCCCAGA<br>TGGGATTAGCTAGTAGGTGAGGTAATGGCTCACCTAGGCGACGATCC<br>CTAGCTGGTCTGAGAGGATGACCAGCCACACTGGAACTGAGACACGG<br>TCCAGACTCCTACGGGAGGCAGCAGTGGGGAATATTGCACAATGGGC<br>GCAAGCCTGATGCAGCCATGCCGCGTGTGTGAAGAAGGCCTTAGGGT<br>TGTAAAGCACTTTCAGCGAGGAGGAAGGGTTCAGTGTTAATAGCACT<br>GAACATTGACGTTACTCGCAGAAGAAGCACCGGCTAACTCCGTGCCA<br>GCAGCCGCGGTAATACGGAGGGTGCAAGCGTTAATCGGAATTACTGG<br>GCGTAAAGCGCACGCAGGCGGTTTGTTAAGTCAGATGTGAAATCCCC<br>GAGCTTAACTTGGGAACTGCATTTGAAACTGGCAAGCTAGAGTCTTGT<br>AGAGGGGGGTAGAATTCCAGGTGTAGCGGTGAAATGCGTAGAGATCT<br>GGAGGAATACCGGTGGCGAAGGCGGCCCCCTGGACAAAGACTGACG<br>CTCAGGTGCGAAAGCGTGGGGAGCAAACAGGATTAGATACCCTGGTA<br>GTCCACGCTGTAAACGATGTCGACTTGGAGGTTGTGCCCTTGAGGCGT<br>GGCTTCCGGAGCTAACGCGTTAAGTCGACCGCCTGGGGAGTACGGCC<br>GCAAGGTTAAAACTCAAATGAATTGACGGGGGCCCGCACAAGCGGTG<br>GAGCATGTGGTTTAATTCGATGCAACGCGAAGAACCTTACCTACTCTT<br>GACATCCAGAGAATTCGCTAGAGATAGCTTAGTGCCTTCGGGAACTC<br>TGAGACAGGTGCTGCATGGCTGTCGTCAGCTCGTGTTGTGAAATGTTG<br>GGTTAAGTCCCGCAACGAGCGCAACCCTTATCCTTTGTTGCCAGCGAG<br>TAATGTCGGGAACTCAAAGGAGACTGCCGGTGATAAACCGGAGGAA<br>GGTGGGGATGACGTCAAGTCATCATGGCCCTTACGAGTAGGGCTACA<br>CACGTGCTACAATGGCATATACAAAGAGAAGCAAACTCGCGAGAGCA<br>AGCGGACCTCATAAAGTATGTCGTAGTCCGGATTGGAGTCTGCAACT<br>CGACTCCATGAAGTCGGAATCGCTAGTAATCGTAGATCAGAATGCTA<br>CGGTGAATACGTTCCCGGGCCTTGTACACACCGCCCGTCACACCATGG<br>GAGTGGGTTGCAAAAGAAGTAGGTAGCTTAACCTTCGGGAGGGCGCT<br>TACCACTTTGTGATTCATGACTGGGGTGAAGTCGTAACAAGGTAACC<br>GTAGGGGAACCTGCGGTTGGATCACCTCCTT |
| 23 | DP23 16S rRNA | TTGAAGAGTTTGATCATGGCTCAGATTGAACGCTGGCGGCAGGCCTA<br>ACACATGCAAGTCGAACGGTAGCACAGAGAGCTTGCTCTTGGGTGAC<br>GAGTGGCGGACGGGTGAGTAATGTCTGGGAAACTGCCCGATGGAGGG<br>GGATAACTACTGGAAACGGTAGCTAATACCGCATAACGTCTTCGGAC<br>CAAAGTGGGGGACCTTCGGGCCTCACACCATCGGATGTGCCCAGATG<br>GGATTAGCTAGTAGGTGGGGTAATGGCTCACCTAGGCGACGATCCCT<br>AGCTGGTCTGAGAGGATGACCAGCCACACTGGAACTGAGACACGGTC<br>CAGACTCCTACGGGAGGCAGCAGTGGGGAATATTGCACAATGGGCGC<br>AAGCCTGATGCAGCCATGCCGCGTGTATGAAGAAGGCCTTCGGGTTG<br>TAAAGTACTTTCAGCGGGGAGGAAGGCGATACGGTTAATAACCGTGT<br>CGATTGACGTTACCCGCAGAAGAAGCACCGGCTAACTCCGTGCCAGC<br>AGCCGCGGTAATACGGAGGGTGCAAGCGTTAATCGGAATTACTGGGC<br>GTAAAGCGCACGCAGGCGGTCTGTCAAGTCAGATGTGAAATCCCCGG<br>GCTTAACCTGGGAACTGCATTTGAAACTGGCAGGCTTGAGTCTCGTAG<br>AGGGGGGTAGAATTCCAGGTGTAGCGGTGAAATGCGTAGAGATCTGG<br>AGGAATACCGGTGGCGAAGGCGGCCCCCTGGACGAAGACTGACGCTC<br>AGGTGCGAAAGCGTGGGGAGCAAACAGGATTAGATACCCTGGTAGTC<br>CACGCTGTAAACGATGTCGACTTGGAGGTTGTGCCCTTGAGGCGTGG<br>CTTCCGGAGCTAACGCGTTAAGTCGACCGCCTGGGGAGTACGGCCGC<br>AAGGTTAAAACTCAAATGAATTGACGGGGGCCCGCACAAGCGGTGGA<br>GCATGTGGTTTAATTCGATGCAACGCGAAGAACCTTACCTGGCCTTGA<br>CATCCACAGAATTCGGCAGAGATGCCTTAGTGCCTTCGGGAACTGTG<br>AGACAGGTGCTGCATGGCTGTCGTCAGCTCGTGTTGTGAAATGTTGGG<br>TTAAGTCCCGCAACGAGCGCAACCCTTATCCTTTGTTGCCAGCGATTC<br>GGTCGGGAACTCAAAGGAGACTGCCGGTGATAAACCGGAGGAAGGT<br>GGGGATGACGTCAAGTCATCATGGCCCTTACGGCCAGGGCTACACAC<br>GTGCTACAATGGCGCATACAAAGAGAAGCGACCTCGCGAGAGCAAG<br>CGGACCTCATAAAGTGCGTCGTAGTCCGGATCGGAGTCTGCAACTCG<br>ACTCCGTGAAGTCGGAATCGCTAGTAATCGTAGATCAGAATGCTACG<br>GTGAATACGTTCCCGGGCCTTGTACACACCGCCCGTCACACCATGGG<br>AGTGGGTTGCAAAAGAAGTAGGTAGCTTAACCTTCGGGAGGGCGCTT<br>ACCACTTTGTGATTCATGACTGGGGTGAAGTCGTAACAAGGTAACCG<br>TAGGGGAACCTGCGGTTGGATCACCTCCTT |
| 24 | DP24 16S rRNA | AGCATTTGATTATGGTGCTTACTGATTGCTATCTAGGGGTTTAACACA<br>TGCTAGTCAATGATCTTTTAGATTATGGCGTACGGGCTAGGAATACTT<br>AGAATGATAACTCTATGATCGCAGTAATAGCGTAAAAGGTATAATAC<br>CGCATAGAGGTTCGCTTCGTATCTCAATAGGTAGTTGGTGAGGTAAA<br>GCTCAACAAGCCGATGATGAGTAATATTGGATGAAAGTCTTAAATAT |

-continued

Sequence Listing

| Seq ID No. | Description | Sequence |
|---|---|---|
| | | AGCAGTGGAAATGAAAAAGTCCACCGTTATTTATTAACGCAGCAGTG GAGAATCGTCGTAATGTGCAGTATTCATTTATGGATAAGCATGAACG CGCTACCTAGATTCGGATAGGAGATAGCATCTTCTACCGATAAAAGA ACTTAGAATAATGATCTAGTTCTCATTAGTGGGTGACAATCGCCGTGC CAGCATCAGCGGTAAAACGGCTTCCGCAAGCAATAGTAATTTAAATT GGTGTAAAGGGTACGTAGCCGGCCTTATTAGGCTAGAGTTAGATACG GGTAAGTACAATACTTGGAGTAGGGCTGATATCTTATGATCCCAAGG GGAGTGCTAAAGGCGAAGGCAACTTACTGGTAATAACTGACGGTGAG GTACGAAGGTCAGGGCATGGAAAGAGATTAGATACCTCATTACTCCT GACAGTAAACGATGTAGATTAAAGATTGGAATAATTCTGTCTTAACG CTAACGCATTAAATCTACCACCTGTAGAGTATAGTCGCAAGGCCGAA ATACAAATAATTAGACGGCTCTAGAGCAAACGGAGTGAAGCATGTTA TTTAATACGATAACCCGCGTAAAATCTTACCAGTTCTTGAATCTTAGA CAGGTGTTGCATGGTTGTCGTCAGCTCGTGCTAATGGTGTCTGGTTAA TTCCAAATAACGAGCGCAATCCTTACTTCTAGTTTTCTAGGAGTCTCC ATTTGACATACGTGTCAATGGTTTAAGGAATATGACAAACCCTCATGG CCCTTATGGACTGGGCAATAGACGTGCCACAAGAATCTAGACAAAAT GACGCGAAATGGTAACAATGAGCTAATCATCAAAGAAGATTAATGTA CGAATTATGGGCTGGAACTCGCCCATATGAAGTAGGAATTCCGAGTA ATCGCGTATCAGAACGACGCGGTGAACATCATCTCTGGAGTGTACTA ACTGCTCGTCACGGGACGAAAGGGAGTGTATTATGAAGTGGGGCTAA TTGGTTAACTCCGGTGAGTGTCACGAATAATCCTTCCCGATTGTTCTG AAGTCGAAACAAGGTAACCGTAAGGGAACTTGCGGTTGA |
| 25 | DP25 16S rRNA | TACGGAGAGTTTGATCCTGGCTCAGGATGAACGCTGGCGGCGTGCTT AACACATGCAAGTCGAACGGTGAAGCCAAGCTTGCTTGGTGGATCAG TGGCGAACGGGTGAGTAACACGTGAGCAACCTGCCCTGGACTCTGGG ATAAGCGCTGGAAACGGCGTCTAATACTGGATATGAGCTCCTTCCGC ATGGTGGGGGTTGGAAAGATTTTTCGGTCTGGGATGGGCTCGCGGCC TATCAGCTTGTTGGTGAGGTAATGGCTCACCAAGGCGTCGACGGGTA GCCGGCCTGAGAGGGTGACCGGCCACACTGGGACTGAGACACGGCCC AGACTCCTACGGGAGGCAGCAGTGGGGAATATTGCACAATGGGCGGA AGCCTGATGCAGCAACGCCGCGTGAGGGATGACGGCCTTCGGGTTGT AAACCTCTTTTAGCAGGGAAGAAGCGAAAGTGACGGTACCTGCAGAA AAAGCGCCGGCTAACTACGTGCCAGCAGCCGCGGTAATACGTAGGGC GCAAGCGTTATCCGGAATTATTGGGCGTAAAGAGCTCGTAGGCGGTT TGTCGCGTCTGCTGTGAAATCCCGAGGCTCAACCTCGGGCCTGCAGTG GGTACGGGCAGACTAGAGTGCGGTAGGGGAGATTGGAATTCCTGGTG TAGCGGTGGAATGCGCAGATATCAGGAGGAACACCGATGGCGAAGG CAGATCTCTGGGCCGTAACTGACGCTGAGGAGCGAAAGGGTGGGGAG CAAACAGGCTTAGATACCCTGGTAGTCCACCCCGTAAACGTTGGGAA CTAGTTGTGGGGACCATTCCACGGTTTCCGTGACGCAGCTAACGCATT AAGTTCCCCGCCTGGGGAGTACGGCCGCAAGGCTAAAACTCAAAGGA ATTGACGGGGACCCGCACAAGCGGCGGAGCATGCGGATTAATTCGAT GCAACGCGAAGAACCTTACCAAGGCTTGACATATACGAGAACGGGCC AGAAATGGTCAACTCTTTGGACACTCGTAAACAGGTGGTGCATGGTT GTCGTCAGCTCGTGTCGTGAGATGTTGGGTTAAGTCCCGCAACGAGC GCAACCCTCGTTCTATGTTGCCAGCACGTAATGGTGGGAACTCATGGG ATACTGCCGGGGTCAACTCGGAGGAAGGTGGGGATGACGTCAAATCA TCATGCCCCTTATGTCTTGGGCTTCACGCATGCTACAATGGCCGGTAC AAAGGGCTGCAATACCGTAAGGTGGAGCGAATCCCAAAAAGCCGGTC CCAGTTCGGATTGAGGTCTGCAACTCGACCTCATGAAGTCGGAGTCG CTAGTAATCGCAGATCAGCAACGCTGCGGTGAATACGTTCCCGGGTC TTGTACACACCGCCCGTCAAGTCATGAAAGTCGGTAACACCTGAAGC CGGTGGCCCAACCCTTGTGGAGGGAGCCGTCGAAGGTGGGATCGGTA ATTAGGACTAAGTCGTAACAAGGTAGCCGTACCGGAAGGTGCGGCTG GATCACCTCCTTT |
| 26 | DP26 16S rRNA | CTTGAGAGTTTGATCCTGGCTCAGAGCGAACGCTGGCGGCAGGCTTA ACACATGCAAGTCGAGCGGGCATCTTCGGATGTCAGCGGCAGACGGG TGAGTAACACGTGGGAACGTACCCTTCGGTTCGGAATAACGCTGGGA AACTAGCGCTAATACCGGATACGCCCTTTTGGGGAAAGGTTTACTGCC GAAGGATCGGCCCGCGTCTGATTAGCTAGTTGGTGGGGTAACGGCCT ACCAAGGCGACGATCAGTAGCTGGTCTGAGAGGATGATCAGCCACAC TGGGACTGAGACACGGCCCAGACTCCTACGGGAGGCAGCAGTGGGG AATATTGGACAATGGGCGCAAGCCTGATCCAGCCATGCCGCGTGAGT GATGAAGGCCTTAGGGTTGTAAAGCTCTTTTGTCCGGGACGATAATG ACGGTACCGGAAGAATAAGCCCCGGCTAACTTCGTGCCAGCAGCCGC GGTAATACGAAGGGGGCTAGCGTTGCTCGGAATCACTGGGCGTAAAG GGCGCGTAGGCGGCCATTCAAGTCGGGGGTGAAAGCCTGTGGCTCAA CCACAGAATTGCCTTCGATACTGTTTGGCTTGAGTATGGTAGAGGTTG GTGGAACTGCGAGTGTAGAGGTGAAATTCGTAGATATTCGCAAGAAC ACCGGTGGCGAAGGCGGCCAACTGGACCATTACTGACGCTGAGGCGC |

-continued

Sequence Listing

| Seq ID No. | Description | Sequence |
|---|---|---|
| | | GAAAGCGTGGGGAGCAAACAGGATTAGATACCCTGGTAGTCCACGCC<br>GTAAACGATGAATGCCAGCTGTTGGGGTGCTTGCACCTCAGTAGCGC<br>AGCTAACGCTTTAAGCATTCCGCCTGGGGAGTACGGTCGCAAGATTA<br>AAACTCAAAGGAATTGACGGGGGCCCGCACAAGCGGTGGAGCATGT<br>GGTTTAATTCGAAGCAACGCGCAGAACCTTACCATCCCTTGACATGGC<br>ATGTTACCCGGAGAGATTCGGGGTCCACTTCGGTGGCGTGCACACAG<br>GTGCTGCATGGCTGTCGTCAGCTCGTGTCGTGAGATGTTGGGTTAAGT<br>CCCGCAACGAGCGCAACCCACGTCCTTAGTTGCCATCATTCAGTTGGG<br>CACTCTAGGGAGACTGCCGGTGATAAGCCGCGAGGAAGGTGTGGATG<br>ACGTCAAGTCCTCATGGCCCTTACGGGATGGGCTACACACGTGCTAC<br>AATGGCGGTGACAGTGGGACGCGAAGGAGCGATCTGGAGCAAATCC<br>CCAAAAACCGTCTCAGTTCAGATTGCACTCTGCAACTCGAGTGCATGA<br>AGGCGGAATCGCTAGTAATCGTGGATCAGCATGCCACGGTGAATACG<br>TTCCCGGGCCTTGTACACACCGCCCGTCACACCATGGGAGTTGGTCTT<br>ACCCGACGGCGCTGCGCCAACCGCAAGGAGGCAGGCGACCACGGTA<br>GGGTCAGCGACTGGGGTGAAGTCGTAACAAGGTAGCCGTAGGGGAA<br>CCTGCGGCTGGATCACCTCCTTT |
| 27 | DP27 16S rRNA | CTTGAGAGTTTGATCCTGGCTCAGAACGAACGCTGGCGGCATGCCTA<br>ACACATGCAAGTCGAACGATGCTTTCGGGCATAGTGGCGCACGGGTG<br>CGTAACGCGTGGGAATCTGCCCTCAGGTTCGGAATAACAGCTGGAAA<br>CGGCTGCTAATACCGGATGATATCGCAAGATCAAAGATTTATCGCCT<br>GAGGATGAGCCCGCGTTGGATTAGGTAGTTGGTGGGGTAAAGGCCTA<br>CCAAGCCGACGATCCATAGCTGGTCTGAGAGGATGATCAGCCACACT<br>GGGACTGAGACACGGCCCAGACTCCTACGGGAGGCAGCAGTGGGGA<br>ATATTGGACAATGGGCGCAAGCCTGATCCAGCAATGCCGCGTGAGTG<br>ATGAAGGCCCTAGGGTTGTAAAGCTCTTTTACCCGGGAAGATAATGA<br>CTGTACCGGGAGAATAAGCCCCGGCTAACTCCGTGCCAGCAGCCGCG<br>GTAATACGGAGGGGGCTAGCGTTGTTCGGAATTACTGGGCGTAAAGC<br>GCACGTAGGCGGCTTTGTAAGTCAGAGGTGAAAGCCTGGAGCTCAAC<br>TCCAGAACTGCCTTTGAGACTGCATCGCTTGAATCCAGGAGAGGTCA<br>GTGGAATTCCGAGTGTAGAGGTGAAATTCGTAGATATTCGGAAGAAC<br>ACCAGTGGCGAAGGCGGCTGACTGGACTGGTATTGACGCTGAGGTGC<br>GAAAGCGTGGGGAGCAAACAGGATTAGATACCCTGGTAGTCCACGCC<br>GTAAACGATGATAACTAGCTGTCCGGGCACTTGGTGCTTGGGTGGCG<br>CAGCTAACGCATTAAGTTATCCGCCTGGGGAGTACGGCCGCAAGGTT<br>AAAACTCAAAGGAATTGACGGGGGCCTGCACAAGCGGTGGAGCATGT<br>GGTTTAATTCGAAGCAACGCGCAGAACCTTACCAGCGTTTGAC |
| 28 | DP28 16S rRNA | ATAGTCGGGGGCATCAGTATTCAATTGTCAGAGGTGAAATTCTTGGAT<br>TTATTGAAGACTAACTACTGCGAAAGCATTTGCCAAGGATGTTTTCAT<br>TAATCAGTGAACGAAAGTTAGGGGATCGAAGACGATCAGATACCGTC<br>GTAGTCTTAACCATAAACTATGCCGACTAGGGATCGGGCGATGTTATC<br>ATTTTGACTCGCTCGGCACCTTACGAGAAATCAAAGTCTTTGGGTTCT<br>GGGGGGAGTATGGTCGCAAGGCTGAAACTTAAAGAAATTGACGGAA<br>GGGCACCACCAGGCGTGGAGCCTGCGGCTTAATTTGACTCAACACGG<br>GGAAACTCACCAGGTCCAGACACAATAAGGATTGACAGATTGAGAGC<br>TCTTTCTTGATTTTGTGGGTGGTGGTGCATGGCCGTTCTTAGTTGGTGG<br>AGTGATTTGTCTGCTTAATTGCGATAACGAACGAGACCTTAACCTGCT<br>AAATAGCCCGGCCCGCTTTGGCGGGTCGCCGGCTTCTTAGAGGGACT<br>ATCGGCTCAAGCCGATGGAAGTTTGAGGCAATAACAGGTCTGTGATG<br>CCCTTAGATGTTCTGGGCCGCACGCGCGCTACACTGACAGAGCCAAC<br>GAGTTCATTTCCTTGCCCGGAAGGGTTGGGTAATCTTGTTAAACTCTG<br>TCGTGCTGGGGATAGAGCATTGCAATTATTGCTCTTCAACGAGGAATG<br>CCTAGTAAGCGTACGTCATCAGCGTGCGTTGATTACGTCCCTGCCCTT<br>TGTACACACCGCCCGTCGCTACTACCGATTGAATGGCTGAGTGAGGC<br>CTTCGGACTGGCCCAGGGAGGTCGGCAACGACCACCCAGGGCCGGAA<br>AGTTGGTCAAACTCCGTCATTTAGAGGAAGTAAAAGTCGTAACAAGG<br>TTTCCGTAGGTGAACCTGCGGAAGGATCA |
| 29 | DP29 16S rRNA | TACGGAGAGTTTGATCCTGGCTCAGGACGAACGCTGGCGGCGTGCTT<br>AACACATGCAAGTCGAACGATGAAGCCCAGCTTGCTGGGTTGATTAG<br>TGGCGAACGGGTGAGTAACACGTGAGCAACGTGCCCATAACTCTGGG<br>ATAACCTCCGGAAACGGTGGCTAATACTGGATATCTAACACGATCGC<br>ATGGTCTGTGTTTGGAAAGATTTTTTGGTTATGGATCGGCTCACGGCC<br>TATCAGCTTGTTGGTGAGGTAATGGCTCACCAAGGCGACGACGGGTA<br>GCCGGCCTGAGAGGGTGACCGGCCACACTGGGACTGAGACACGGCCC<br>AGACTCCTACGGGAGGCAGCAGTGGGGAATATTGCACAATGGGCGAA<br>AGCCTGATGCAGCAACGCCGCGTGAGGGATGACGGCATTCGGGTTGT<br>AAACCTCTTTTAGTAGGGAAGAAGCGAAAGTGACGGTACCTGCAGAA<br>AAAGCACCGGCTAACTACGTGCCAGCAGCCGCTGTAATACGTAGGGT<br>GCAAGCGTTGTCCGGAATTATTGGGCGTAAAGAGCTCGTAGGCGGTT<br>TGTCGCGTCTGCTGTGAAATCCCGAGGCTCAACCTCGGGTCTGCAGTG |

-continued

Sequence Listing

| Seq ID No. | Description | Sequence |
|---|---|---|
| | | GGTACGGGCAGACTAGAGTGTGGTAGGGGAGATTGGAATTCCTGGTG TAGCGGTGGAATGCGCAGATATCAGGAGGAACACCGATGGCGAAGG CAGATCTCTGGGCCATTACTGACGCTGAGGAGCGAAAGCATGGGGAG CGAACAGGATTAGATACCCTGGTAGTCCATGCCGTAAACGTTGGGCG CTAGATGTGGGGACCATTCCACGGTTTCCGTGTCGTAGCTAACGCATT AAGCGCCCCGCCTGGGGAGTACGGCCGCAAGGCTAAAACTCAAAGG AATTGACGGGGGCCCGCACAAGCGGCGGAGCATGCGGATTAATTCGA TGCAACGCGAAGAACCTTACCAAGGCTTGACATATACCGGAAACGTT CAGAAATGTTCGCC |
| 30 | DP30 16S rRNA | TACGGAGAGTTTGATCCTGGCTCAGGATGAACGCTGGCGGCGTGCTT AACACATGCAAGTCGAACGGTGAAGCCAAGCTTGCTTGGTGGATCAG TGGCGAACGGGTGAGTAACACGTGAGCAACCTGCCCTGGACTCTGGG ATAAGCGCTGGAAACGGCGTCTAATACTGGATATGAGACGTGATCGC ATGGTCGTGTTTGGAAAGATTTTTCGGTCTGGGATGGGCTCGCGGCCT ATCAGCTTGTTGGTGAGGTAATGGCTCACCAAGGCGTCGACGGGTAG CCGGCCTGAGAGGGTGACCGGCCACACTGGGACTGAGACACGGCCCA GACTCCTACGGGAGGCAGCAGTGGGGAATATTGCACAATGGGCGAAA GCCTGATGCAGCAACGCCGCGTGAGGGATGACGGCCTTCGGGTTGTA AACCTCTTTTAGCAGGGAAGAAGCGAAAGTGACGGTACCTGCAGAAA AAGCGCCGGCTAACTACGTGCCAGCAGCCGCGGTAATACGTAGGGCG CAAGCGTTATCCGGAATTATTGGGCGTAAAGAGCTCGTAGGCGGTTT GTCGCGTCTGCTGTGAAATCCCGAGGCTCAACCTCGGGCCTGCAGTG GGTACGGGCAGACTAGAGTGCGGTAGGGGAGATTGGAATTCCTGGTG TAGCGGTGGAATGCGCAGATATCAGGAGGAACACCGATGGCGAAGG CAGATCTCTGGGCCGTAACTGACGCTGAGGAGCGAAAGGGTGGGGAG CAAACAGGCTTAGATACCCTGGTAGTCCACCCCGTAAACGTTGGGAA CTAGTTGTGGGGACCATTCCACGGTTTCCGTGACGCAGCTAACGCATT AAGTTCCCCGCCTGGGGAGTACGGCCGCAAGGCTAAAACTCAAAGGA ATTGACGGGGACCCGCACAAGCGGCGGAGCATGCGGATTAATTCGAT GCAACGCGAAGAACCTTACCAAGGCTTGACATATACGAGAACGGGCC AGAAATGGTCAACTCTTTGGACACTCGTAAACAGGTGGTGCATGGTT GTCGTCAGCTCGTGTCGTGAGATGTTGGGTTAAGTCCCGCAACGAGC GCAACCCTCGTTCTATGTTGCCAGCACGTAATGGTGGGAACTCATGGG ATACTGCCGGGGTCAACTCGGAGGAAGGTGGGGATGACGTCAAATCA TCATGCCCCTTATGTCTTGGGCTTCACGCATGCTACAATGGCCGGTAC AAAGGGCTGCAATACCGTGAGGTGGAGCGAATCCCAAAAAGCCGGTC CCAGTTCGGATTGAGGTCTGCAACTCGACCTCATGAAGTCGGAGTCG CTAGTAATCGCAGATCAGCAACGCTGCGGTGAATACGTTCCCGGGTC TTGTACACACCGCCCGTCAAGTCATGAAAGTCGGTAACACCTGAAGC CGGTGGCCCAACCCTTGTGGAGGGAGCCGTCGAAGGTGGGATCGGTA ATTAGGACTAAGTCGTAACAAGGTAGCCGTACCGGAAGGTGCGGCTG GATCACCTCCTTT |
| 31 | DP31 16S rRNA | CAGCCGGGGGCATTAGTATTTGCACGCTAGAGGTGAAATTCTTGGATT GTGCAAAGACTTCCTACTGCGAAAGCATTTGCCAAGAATGTTTTCATT AATCAAGAACGAAGGTTAGGGTATCGAAAACGATTAGATACCGTTGT AGTCTTAACAGTAAACTATGCCGACTCCGAATCGGTCGATGCTCATTT CACTGGCTCGATCGGCGCGGTACGAGAAATCAAAGTTTTTGGGTTCTG GGGGGAGTATGGTCGCAAGGCTGAAACTTAAAGAAATTGACGGAAG GGCACCACCAGGAGTGGAGCCTGCGGCTTAATTTGACTCAACACGGG AAAACTCACCGGGTCCGGACATAGTAAGGATTGACAGATTGATGGCG CTTTCATGATTCTATGGGTGGTGGTGCATGGCCGTTCTTAGTTGGTGG AGTGATTTGTCTGGTTAATTCCGATAACGAACGAGACCTTGACCTGCT AAATAGACGGGTTGACATTTTGTTGGCCCCTTATGTCTTCTTAGAGGG ACAATCGACCGTCTAGGTGATGGAGGCAAAAGGCAATAACAGGTCTG TGATGCCCTTAGATGTTCCGGGCTGCACGCGCGCTACACTGACAGAG ACAACGAGTGGGGCCCCTTGTCCGAAATGACTGGGTAAACTTGTGAA ACTTTGTCGTGCTGGGGATGGAGCTTTGTAATTTTTGCTCTTCAACGA GGAATTCCTAGTAAGCGCAAGTCATCAGCTTGCGTTGACTACGTCCCT GCCCTTTGTACACACCGCCCGTCGCTACTACCGATTGAATGGCTTAGT GAGGACTTGGGAGAGTACATCGGGGAGCCAGCAATGGCACCCTGACG GCTCAAACTCTTACAAACTTGGTCATTTAGAGGAAGTAAAAGTCGTA ACAAGGTATCTGTAGGTGAACCTGCAGATGGATCATTTC |
| 32 | DP32 16S rRNA | ACTGAGCATTGACGTTACTCGCAGAAGAAGCACCGGCTAACTCCGTG CCAGCAGCCGCGGTAATACGGAGGGTGCAAGCGTTAATCGGAATTAC TGGGCGTAAAGCGCACGCAGGCGGTTTGTTAAGTCAGATGTGAAATC CCCGAGCTTAACTTGGGAACTGCATTTGAAACTGGCAAGCTAGAGTC TTGTAGAGGGGGGTAGAATTCCAGGTGTAGCGGTGAAATGCGTAGAG ATCTGGAGGAATACCGGTGGCGAAGGCGGCCCCCTGGACAAAGACTG ACGCTCAGGTGCGAAAGCGTGGGGAGCAAACAGGATTAGATACCCTG GTAGTCCACGCTGTAAACGATGTCGACTTGGAGGTTGTGCCCTTGAGG |

-continued

Sequence Listing

| Seq ID No. | Description | Sequence |
|---|---|---|
| | | CGTGGCTTCCGGAGCTAACGCGTTAAGTCGACCGCCTGGGGAGTACG<br>GCCGCAAGGTTAAAACTCAAATGAATTGACGGGGGCCCGCACAAGCG<br>GTGGAGCATGTGGTTTAATTCGATGCAACGCGAAGAACCTTACCTACT<br>CTTGACATCCAGAGAATTCGCTAGAGATAGCTTAGTGCCTTCGGGAA<br>CTCTGAGACAGGTGCTGCATGGCTGTCGTCAGCTCGTGTTGTGAAATG<br>TTGGGTTAAGTCCCGCAACGAGCGCAACCCTTATCCTTTGTTGCCAGC<br>GAGTAATGTCGGGAACTCAAAGGAGACTGCCGGTGATAAACCGGAG<br>GAAGGTGGGGATGACGTCAAGTCATCATGGCCCTTACGAGTAGGGCT<br>ACACACGTGCTACAATGGCATATACAAAGAGAAGCGAACTCGCGAGA<br>GCAAGCGGACCTCATAAAGTATGTCGTAGTCCGGATTGGAGTCTGCA<br>ACTCGACTCCATGAAGTCGGAATCGCTAGTAATCGTAGATCAGAATG<br>CTACGGTGAATACGTTCCCGGGCCTTGTACACACCGCCCGTCACACCA<br>TGGGAGTGGGTTGCAAAAGAAGTAGGTAGCTTAACCTTCGGGAGGGC<br>GCTTACCACTTTGTGATTCATGACTGGGGTGAAGTCGTAACAAGGTAA<br>CCGTAGGGGAACCTGCGGTTGGATCACCTCCTT |
| 33 | DP33 16S rRNA | GGAGGAAGGCGTAGAGATCTGGAGGAATACCGGTGGCGAAGGCGGC<br>CCCCTGGACAAAGACTGACGCTCAGGTGCGAAAGCGTGGGGAGCAA<br>ACAGGATTAGATACCCTGGTAGTCCACGCCGTAAACGATGTCGACTT<br>GGAGGTTGTGCCCTTGAGGCGTGGCTTCCGGAGCTAACGCGTTAAGT<br>CGACCGCCTGGGGAGTACGGCCGCAAGGTTAAAACTCAAATGAATTG<br>ACGGGGGCCCGCACAAGCGGTGGAGCATGTGGTTTAATTCGATGCAA<br>CGCGAAGAACCTTACCTGGCCTTGACATCCACGGAATTCGGCAGAGA<br>TGCCTTAGTGCCTTCGGGAACCGTGAGACAGGTGCTGCATGGCTGTCG<br>TCAGCTCGTGTTGTGAAATGTTGGGTTAAGTCCCGCAACGAGCGCAA<br>CCCTTATCCTTTGTTGCCAGCACGTAATGGTGGGAACTCAAAGGAGAC<br>TGCCGGTGATAAACCGGAGGAAGGTGGGGATGACGTCAAGTCATCAT<br>GGCCCTTACGGCCAGGGCTACACACGTGCTACAATGGCGCATACAAA<br>GAGAAGCGACCTCGCGAGAGCAAGCGGACCTCATAAAGTGCGTCGTA<br>GTCCGGATCGGAGTCTGCAACTCGACTCCGTGAAGTCGGAATCGCTA<br>GTAATCGTAGATCAGAATGCTACGGTGAATACGTTCCCGGGCCTTGTA<br>CACACCGCCCGTCACACCATGGGAGTGGGTTGCAAAAGAAGTAGGTA<br>GCTTAACCTTCGGGAGGGCGCTTACCACTTTGTGATTCATGACTGGGG<br>TGAAGTCGTAACAAGGTAACCGTAGGGGAACCTGCGGTTGGATCACC<br>TCCTT |
| 34 | DP34 16S rRNA | TACGGAGAGTTTGATCCTGGCTCAGGACGAACGCTGGCGGCGTGCTT<br>AACACATGCAAGTCGAACGATGAAGCCCAGCTTGCTGGGTGGATTAG<br>TGGCGAACGGGTGAGTAACACGTGAGTAACCTGCCCTTGACTCTGGG<br>ATAAGCGTTGGAAACGACGTCTAATACCGGATACGAGCTTCCACCGC<br>ATGGTGAGTTGCTGGAAAGAATTTTGGTCAAGGATGGACTCGCGGCC<br>TATCAGCTTGTTGGTGAGGTAATGGCTCACCAAGGCGACGACGGGTA<br>GCCGGCCTGAGAGGGTGACCGGCCACACTGGGACTGAGACACGGCCC<br>AGACTCCTACGGGAGGCAGCAGTGGGGAATATTGCACAATGGGCGAA<br>AGCCTGATGCAGCAACGCCGCGTGAGGGACGACGGCCTTCGGGTTGT<br>AAACCTCTTTTAGCAGGGAAGAAGCGAAAGTGACGGTACCTGCAGAA<br>AAAGCACCGGCTAACTACGTGCCAGCAGCCGCGGTAATACGTAGGGT<br>GCAAGCGTTGTCCGGAATTATTGGGCGTAAAGAGCTCGTAGGCGGTT<br>TGTCGCGTCTGCTGTGAAATCCCGAGGCTCAACCTCGGGTCTGCAGTG<br>GGTACGGGCAGACTAGAGTGCGGTAGGGGAGATTGGAATTCCTGGTG<br>TAGCGGTGGAATGCGCAGATATCAGGAGGAACACCGATGGCGAAGG<br>CAGATCTCTGGGCCGCTACTGACGCTGAGGAGCGAAAGGGTGGGGAG<br>CAAACAGGCTTAGATACCCTGGTAGTCCACCCCGTAAACGTTGGGCG<br>CTAGATGTGGGGACCATTCCACGGTTTCCGTGTCGTAGCTAACGCATT<br>AAGCGCCCCGCCTGGGGAGTACGGCCGCAAGGCTAAAACTCAAAGG<br>AATTGACGGGGGCCCGCACAAGCGGCGGAGCATGCGGATTAATTCGA<br>TGCAACGCGAAGAACCTTACCAAGGCTTGACATATACGAGAACGGGC<br>CAGAAATGGTCAACTCTTTGGACACTCGTAAACAGGTGGTGCATGGT<br>TGTCGTCAGCTCGTGTCGTGAGATGTTGGGTTAAGTCCCGCAACGAGC<br>GCAACCCTCGTTCTATGTTGCCAGCACGTAATGGTGGGAACTCATGGG<br>ATACTGCCGGGGTCAACTCGGAGGAAGGTGGGGACGACGTCAAATCA<br>TCATGCCCCTTATGTCTTGGGCTTCACGCATGCTACAATGGCCAGTAC<br>AAAGGGCTGCAATACCGTAAGGTGGAGCGAATCCCAAAAAGCTGGTC<br>CCAGTTCGGATTGAGGTCTGCAACTCGACCTCATGAAGTCGGAGTCG<br>CTAGTAATCGCAGATCAGCAACGCTGCGGTGAATACGTTCCCGGGCC<br>TTGTACACACCGCCCGTCAAGTCATGAAAGTCGGTAACACCCGAAGC<br>CAGTGGCCTAACCGCAAGGATGGAGCTGTCTAAGGTGGGATCGGTAA<br>TTAGGACTAAGTCGTAACAAGGTAGCCGTACCGGAAGGTGCGGCTGG<br>ATCACCTCCTTT |
| 35 | DP35 16S rRNA | TTGAAGAGTTTGATCATGGCTCAGATTGAACGCTGGCGGCAGGCCTA<br>ACACATGCAAGTCGGACGGTAGCACAGAGAGCTTGCTCTTGGGTGAC<br>GAGTGGCGGACGGGTGAGTAATGTCTGGGGATCTGCCCGATAGAGGG |

-continued

Sequence Listing

| Seq ID No. | Description | Sequence |
|---|---|---|
| | | GGATAACCACTGGAAACGGTGGCTAATACCGCATAACGTCGCAAGAC CAAAGAGGGGGACCTTCGGGCCTCTCACTATCGGATGAACCCAGATG GGATTAGCTAGTAGGCGGGGTAATGGCCCACCTAGGCGACGATCCCT AGCTGGTCTGAGAGGATGACCAGCCACACTGGAACTGAGACACGGTC CAGACTCCTACGGGAGGCAGCAGTGGGGAATATTGCACAATGGGCGC AAGCCTGATGCAGCCATGCCGCGTGTATGAAGAAGGCCTTCGGGTTG TAAAGTACTTTCAGCGGGGAGGAAGGCGATGAGGTTAATAACCGCGT CGATTGACGTTACCCGCAGAAGAAGCACCGGCTAACTCCGTGCCAGC AGCCGCGGTAATACGGAGGGTGCAAGCGTTAATCGGAATTACTGGGC GTAAAGCGCACGCAGGCGGTCTGTTAAGTCAGATGTGAAATCCCCGG GCTTAACCTGGGAACTGCATTTGAAACTGGCAGGCTTGAGTCTTGTAG AGGGGGGTAGAATTCCAGGTGTAGCGGTGAAATGCGTAGAGATCTGG AGGAATACCGGTGGCGAAGGCGGCCCCCTGGACAAAGACTGACGCTC AGGTGCGAAAGCGTGGGGAGCAAACAGGATTAGATACCCTGGTAGTC CACGCCGTAAACGATGTCGACTTGGAGGTTGTTCCCTTGAGGAGTGG CTTCCGGAGCTAACGCGTTAAGTCGACCGCCTGGGGAGTACGGCCGC AAGGTTAAAACTCAAATGAATTGACGGGGGCCCGCACAAGCGGTGGA GCATGTGGTTTAATTCGATGCAACGCGAAGAACCTTACCTACTCTTGA CATCCAGCGAACTTAGCAGAGATGCTTTGGTGCCTTCGGGAACGCTG AGACAGGTGCTGCATGGCTGTCGTCAGCTCGTGTTGTGAAATGTTGGG TTAAGTCCCGCAACGAGCGCAACCCTTATCCTTTGTTGCCAGCGATTC GGTCGGGAACTCAAAGGAGACTGCCGGTGATAAACCGGAGGAAGGT GGGGATGACGTCAAGTCATCATGGCCCTTACGAGTAGGGCTACACAC GTGCTACAATGGCGCATACAAAGAGAAGCGACCTCGCGAGAGCAAG CGGACCTCACAAAGTGCGTCGTAGTCCGGATCGGAGTCTGCAACTCG ACTCCGTGAAGTCGGAATCGCTAGTAATCGTGGATCAGAATGCCACG GTGAATACGTTCCCGGGCCTTGTACACACCGCCCGTCACACCATGGG AGTGGGTTGCAAAAGAAGTAGGTAGCTTAACCTTCGGGAGGGCGCTT ACCACTTTGTGATTCATTACTGGGGTGAAGTCGTAACAAGGTAACCGT AGGGGAACCTGCGGTTGGATCACCTCCTT |
| 36 | DP36 16S rRNA | TTGAAGAGTTTGATCATGGCTCAGATTGAACGCTGGCGGCAGGCCTA ACACATGCAAGTCGGACGGTAGCACAGAGAGCTTGCTCTTGGGTGAC GAGTGGCGGACGGGTGAGTAATGTCTGGGGATCTGCCCGATAGAGGG GGATAACCACTGGAAACGGTGGCTAATACCGCATAACGTCGCAAGAC CAAAGAGGGGGACCTTCGGGCCTCTCACTATCGGATGAACCCAGATG GGATTAGCTAGTAGGCGGGGTAATGGCCCACCTAGGCGACGATCCCT AGCTGGTCTGAGAGGATGACCAGCCACACTGGAACTGAGACACGGTC CAGACTCCTACGGGAGGCAGCAGTGGGGAATATTGCACAATGGGCGC AAGCCTGATGCAGCCATGCCGCGTGTATGAAGAAGGCCTTCGGGTTG TAAAGTACTTTCAGCGGGGAGGAAGGCGATGCGGTTAATAACCGCGT CGATTGACGTTACCCGCAGAAGAAGCACCGGCTAACTCCGTGCCAGC AGCCGCGGTAATACGGAGGGTGCAAGCGTTAATCGGAATTACTGGGC GTAAAGCGCACGCAGGCGGTCTGTTAAGTCAGATGTGAAATCCCCGG GCTTAACCTGGGAACTGCATTTGAAACTGGCAGGCTTGAGTCTTGTAG AGGGGGGTAGAATTCCAGGTGTAGCGGTGAAATGCGTAGAGATCTGG AGGAATACCGGTGGCGAAGGCGGCCCCCTGGACAAAGACTGACGCTC AGGTGCGAAAGCGTGGGGAGCAAACAGGATTAGATACCCTGGTAGTC CACGCCGTAAACGATGTCGACTTGGAGGTTGTTCCCTTGAGGAGTGG CTTCCGGAGCTAACGCGTTAAGTCGACCGCCTGGGGAGTACGGCCGC AAGGTTAAAACTCAAATGAATTGACGGGGGCCCGCACAAGCGGTGGA GCATGTGGTTTAATTCGATGCAACGCGAAGAACCTTACCTACTCTTGA CATC |
| 37 | DP37 16S rRNA | TGAAGAGTTTGATCATGGCTCAGATTGAACGCTGGCGGCAGGCCTAA CACATGCAAGTCGAGCGGTAGAGAGAAGCTTGCTTCTCTTGAGAGCG GCGGACGGGTGAGTAATGCCTAGGAATCTGCCTGGTAGTGGGGGATA ACGTTCGGAAACGAACGCTAATACCGCATACGTCCTACGGGAGAAAG CAGGGGACCTTCGGGCCTTGCGCTATCAGATGAGCCTAGGTCGGATT AGCTAGTTGGTGGGGTAATGGCTCACCAAGGCGACGATCCGTAACTG GTCTGAGAGGATGATCAGTCACACTGGAACTGAGACACGGTCCAGAC TCCTACGGGAGGCAGCAGTGGGGAATATTGGACAATGGGCGAAAGCC TGATCCAGCCATGCCGCGTGTGTGAAGAAGGTCTTCGGATTGTAAAG CACTTTAAGTTGGGAGGAAGGGCCATTACCTAATACGTGATGGTTTTG ACGTTACCGACAGAATAAGCACCGGCTAACTCTGTGCCAGCAGCCGC GGTAATACAGAGGGTGCAAGCGTTAATCGGAATTACTGGGCGTAAAG CGCGCGTAGGTGGTTTGTTAAGTTGGATGTGAAATCCCCGGGCTCAAC CTGGGAACTGCATTCAAAACTGACTGACTAGAGTATGGTAGAGGGTG GTGGAATTTCCTGTGTAGCGGTGAAATGCGTAGATATAGGAAGGAAC ACCAGTGGCGAAGGCGACCACCTGGACTGATACTGACACTGAGGTGC GAAAGCGTGGGGAGCAAACAGGATTAGATACCCTGGTAGTCCACGCC GTAAACGATGTCAACTAGCCGTTGGGAGCCTTGAGCTCTTAGTGGCG CAGCTAACGCATTAAGTTGACCGCCTGGGGAGTACGGCCGCAAGGTT |

-continued

Sequence Listing

| Seq ID No. | Description | Sequence |
|---|---|---|
| | | AAAACTCAAATGAATTGACGGGGGCCCGCACAAGCGGTGGAGCATGT GGTTTAATTCGAAGCAACGCGAAGAACCTTACCAGGCCTTGACATCC AATGAACTTTCTAGAGATAGATTGGTGCCTTCGGGAACATTGAGACA GGTGCTGCATGGCTGTCGTCAGCTCGTGTCGTGAGATGTTGGGTTAAG TCCCGTAACGAGCGCAACCCTTGTCCTTAGTTACCAGCACGTAATGGT GGGCACTCTAAGGAGACTGCCGGTGACAAACCGGAGGAAGGTGGGG ATGACGTCAAGTCATCATGGCCCTTACGGCCTGGGCTACACACGTGCT ACAATGGTCGGTACAGAGGGTTGCCAAGCCGCGAGGTGGAGCTAATC CCATAAAACCGATCGTAGTCCGGATCGCAGTCTGCAACTCGACTGCG TGAAGTCGGAATCGCTAGTAATCGCGAATCAGAATGTCGCGGTGAAT ACGTTCCCGGGCCTTGTACACACCGCCCGTCACACCATGGGAGTGGG TTGCACCAGAAGTAGCTAGTCTAACCTTCGGGGGGACGGTTACCACG GTGTGATTCATGACTGGGGTGAAGTCGTAACAAGGTAGCCGTAGGGG AACCTGCGGCTGGATCACCTCCTT |
| 38 | DP38 16S rRNA | TACGGAGAGTTTGATCCTGGCTCAGGACGAACGCTGGCGGCGTGCTT AACACATGCAAGTCGAGCGGTAAGGCCTTTCGGGGTACACGAGCGGC GAACGGGTGAGTAACACGTGGGTGATCTGCCCTGCACTCTGGGATAA GCTTGGGAAACTGGGTCTAATACCGGATATGACCACAGCATGCATGT GTTGTGGTGGAAAGATTTATCGGTGCAGGATGGGCCCGCGGCCTATC AGCTTGTTGGTGGGGTAATGGCCTACCAAGGCGACGACGGGTAGCCG ACCTGAGAGGGTGACCGGCCACACTGGGACTGAGACACGGCCCAGAC TCCTACGGGAGGCAGCAGTGGGGAATATTGCACAATGGGCGGAAGCC TGATGCAGCGACGCCGCGTGAGGGATGAAGGCCTTCGGGTTGTAAAC CTCTTTCAGCAGGGACGAAGCGTGAGTGACGGTACCTGCAGAAGAAG CACCGGCTAACTACGTGCCAGCAGCCGCGGTAATACGTAGGGTGCGA GCGTTGTCCGGAATTACTGGGCGTAAAGAGTTCGTAGGCGGTTTGTCG CGTCGTTTGTGAAAACCCGGGGCTCAACTTCGGGCTTGCAGGCGATA CGGGCAGACTTGAGTGTTTCAGGGGAGACTGGAATTCCTGGTGTAGC GGTGAAATGCGCAGATATCAGGAGGAACACCGGTGGCGAAGGCGGG TCTCTGGGAAACAACTGACGCTGAGGAACGAAAGCGTGGGTAGCAAA CAGGATTAGATACCCTGGTAGTCCACGCCGTAAACGGTGGGCGCTAG GTGTGGGTTCCTTCCACGGGATCTGTGCCGTAGCTAACGCATTAAGCG CCCCGCCTGGGGAGTACGGCCGCAAGGCTAAAACTCAAAGGAATTGA CGGGGGCCCGCACAAGCGGCGGAGCATGTGGATTAATTCGATGCAAC GCGAAGAACCTTACCTGGGTTTGACATACACCGGAAAACCGTAGAGA TACGGTCCCCCTTGTGGTCGGTGTACAGGTGGTGCATGGCTGTCGTCA GCTCGTGTCGTGAGATGTTGGGTTAAGTCCCGCAACGAGCGCAACCC TTGTCTTATGTTGCCAGCACGTAATGGTGGGGACTCGTAAGAGACTGC CGGGGTCAACTCGGAGGAAGGTGGGGACGACGTCAAGTCATCATGCC CCTTATGTCCAGGGCTTCACACATGCTACAATGGCCAGTACAGAGGG CTGCGAGACCGTGAGGTGGAGCGAATCCCTTAAAGCTGGTCTCAGTT CGGATCGGGGTCTGCAACTCGACCCCGTGAAGTCGGAGTCGCTAGTA ATCGCAGATCAGCAACGCTGCGGTGAATACGTTCCCGGGCCTTGTAC ACACCGCCCGTCACGTCATGAAAGTCGGTAACACCCGAAGCCGGTGG CCTAACCCCTTACGGGGAGGGAGCCGTCGAAGGTGGGATCGGCGATT GGGACGAAGTCGTAACAAGGTAGCCGTACCGGAAGGTGCGGCTGGAT CACCTCCTTT |
| 39 | DP39 16S rRNA | CTTGAGAGTTTGATCCTGGCTCAGAACGAACGCTGGCGGCAGGCTTA ACACATGCAAGTCGAACGCCCCGCAAGGGGAGTGGCAGACGGGTGA GTAACGCGTGGGAATCTACCGTGCCCTGCGGAATAGCTCCGGGAAAC TGGAATTAATACCGCATACGCCCTACGGGGGAAAGATTTATCGGGGT ATGATGAGCCCGCGTTGGATTAGCTAGTTGGTGGGGTAAAGGCCTAC CAAGGCGACGATCCATAGCTGGTCTGAGAGGATGATCAGCCACATTG GGACTGAGACACGGCCCAAACTCCTACGGGAGGCAGCAGTGGGGAA TATTGGACAATGGGCGCAAGCCTGATCCAGCCATGCCGCGTGAGTGA TGAAGGCCTTAGGGTTGTAAAGCTCTTTCACCGGAGAAGATAATGAC GGTATCCGGAGAAGAAGCCCCGGCTAACTTCGTGCCAGCAGCCGCGG TAATACGAAGGGGGCTAGCGTTGTTCGGAATTACTGGGCGTAAAGCG CACGTAGGCGGATATTTAAGTCAGGGGTGAAATCCCAGAGCTCAACT CTGGAACTGCCTTTGATACTGGGTATCTTGAGTATGGAAGAGGTAAGT GGAATTCCGAGTGTAGAGGTGAAATTCGTAGATATTCGGAGGAACAC CAGTGGCGAAGGCGGCTTACTGGTCCATTACTGACGCTGAGGTGCGA AAGCGTGGGGAGCAAACAGGATTAGATACCCTGGTAGTCCACGCCGT AAACGATGAATGTTAGCCGTCGGGCAGTATACTGTTCGGTGGCGCAG CTAACGCATTAAACATTCCGCCTGGGGAGTACGGTCGCAAGATTAAA ACTCAAAGGAATTGACGGGGGCCCGCACAAGCGGTGGAGCATGTGGT TTAATTCGAAGCAACGCGCAGAACCTTACCAGCTCTTGACATTCGGG GTTTGGGCAGTGGAGACATTGTCCTTCAGTTAGGCTGGCCCCAGAAC AGGTGCTGCATGGCTGTCGTCAGCTCGTGTCGTGAGATGTTGGGTTAA GTCCCGCAACGAGCGCAACCCTCGCCCTTAGTTGCCAGCATTTAGTTG GGCACTCTAAGGGGACTGCCGGTGATAAGCCGAGAGGAAGGTGGGG |

-continued

Sequence Listing

| Seq ID No. | Description | Sequence |
|---|---|---|
| | | ATGACGTCAAGTCCTCATGGCCCTTACGGGCTGGGCTACACACGTGCT<br>ACAATGGTGGTGACAGTGGGCAGCGAGACAGCGATGTCGAGCTAATC<br>TCCAAAAGCCATCTCAGTTCGGATTGCACTCTGCAACTCGAGTGCATG<br>AAGTTGGAATCGCTAGTAATCGCAGATCAGCATGCTGCGGTGAATAC<br>GTTCCCGGGCCTTGTACACACCGCCCGTCACACCATGGGAGTTGGTTT<br>TACCCGAAGGTAGTGCGCTAACCGCAAGGAGGCAGCTAACCACGGTA<br>GGGTCAGCGACTGGGGTGAAGTCGTAACAAGGTAGCCGTAGGGGAA<br>CCTGCGGCTGGATCACCTCCTTT |
| 40 | DP40 16S rRNA | TTGACGTTACCCGCAGAAGAAGCACCGGCTAACTCCGTGCCAGCAGC<br>CGCGGTAATACGGAGGGTGCAAGCGTTAATCGGAATTACTGGGCGTA<br>AAGCGCACGCAGGCGGTCTGTTAAGTCAGATGTGAAATCCCCGGGCT<br>TAACCTGGGAACTGCATTTGAAACTGGCAGGCTTGAGTCTTGTAGAG<br>GGGGGTAGAATTCCAGGTGTAGCGGTGAAATGCGTAGAGATCTGGAG<br>GAATACCGGTGGCGAAGGCGGCCCCCTGGACAAAGACTGACGCTCAG<br>GTGCGAAAGCGTGGGGAGCAAACAGGATTAGATACCCTGGTAGTCCA<br>CGCCGTAAACGATGTCGACTTGGAGGTTGTTCCCTTGAGGAGTGGCTT<br>CCGGAGCTAACGCGTTAAGTCGACCGCCTGGGGAGTACGGCCGCAAG<br>GTTAAAACTCAAATGAATTGACGGGGGCCCGCACAAGCGGTGGAGCA<br>TGTGGTTTAATTCGATGCAACGCGAAGAACCTTACCTACTCTTGACAT<br>CCAGAGAACTTTCCAGAGATGGATTGGTGCCTTCGGGAACTCTGAGA<br>CAGGTGCTGCATGGCTGTCGTCAGCTCGTGTTGTGAAATGTTGGGTTA<br>AGTCCCGCAACGAGCGCAACCCTTATCCTTTGTTGCCAGCGCGTGATG<br>GCGGGAACTCAAAGGAGACTGCCGGTGATAAACCGGAGGAAGGTGG<br>GGATGACGTCAAGTCATCATGGCCCTTACGAGTAGGGCTACACACGT<br>GCTACAATGGCGCATACAAAGAGAAGCGACCTCGCGAGAGCAAGCG<br>GACCTCACAAAGTGCGTCGTAGTCCGGATCGGAGTCTGCAACTCGAC<br>TCCGTGAAGTCGGAATCGCTAGTAATCGTGGATCAGAATGCCACGGT<br>GAATACGT |
| 41 | DP41 16S rRNA | GTGGAGAGTTTGATCCTGGCTCAGGATGAACGCTGGCGGCGTGCTTA<br>ACACATGCAAGTCGAACGGAAAGGCCCAAGCTTGCTTGGGTACTCGA<br>GTGGCGAACGGGTGAGTAACACGTGGGTGATCTGCCCTGCACTTCGG<br>GATAAGCCTGGGAAACTGGGTCTAATACCGGATAGGACGATGGTTTG<br>GATGCCATTGTGGAAAGTTTTTTCGGTGTGGGATGAGCTCGCGGCCTA<br>TCAGCTTGTTGGTGGGGTAATGGCCTACCAAGGCGTCGACGGGTAGC<br>CGGCCTGAGAGGGTGTACGGCCACATTGGGACTGAGATACGGCCCAG<br>ACTCCTACGGGAGGCAGCAGTGGGGAATATTGCACAATGGGCGCAAG<br>CCTGATGCAGCGACGCCGCGTGGGGGATGACGGCCTTCGGGTTGTAA<br>ACTCCTTTCGCTAGGGACGAAGCGTTTTGTGACGGTACCTGGAGAAG<br>AAGCACCGGCTAACTACGTGCCAGCAGCCGCGGTAATACGTAGGGTG<br>CGAGCGTTGTCCGGAATTACTGGGCGTAAAGAGCTCGTAGGTGGTTT<br>GTCGCGTCGTTTGTGTAAGCCCGCAGCTTAACTGCGGGACTGCAGGC<br>GATACGGGCATAACTTGAGTGCTGTAGGGGAGACTGGAATTCCTGGT<br>GTAGCGGTGGAATGCGCAGATATCAGGAGGAACACCGATGGCGAAG<br>GCAGGTCTCTGGGCAGTAACTGACGCTGAGGAGCGAAAGCATGGGTA<br>GCGAACAGGATTAGATACCCTGGTAGTCCATGCCGTAAACGGTGGGC<br>GCTAGGTGTGAGTCCCTTCCACGGGGTTCGTGCCGTAGCTAACGCATT<br>AAGCGCCCCGCCTGGGGAGTACGGCCGCAAGGCTAAAACTCAAAGG<br>AATTGACGGGGGCCCGCACAAGCGGCGGAGCATGTGGATTAATTCGA<br>TGCAACGCGAAGAACCTTACCTGGGCTTGACATACACCAGATCGCCG<br>TAGAGATACGGTTTCCCTTTGTGGTTGGTGTACAGGTGGTGCATGGTT<br>GTCGTCAGCTCGTGTCGTGAGATGTTGGGTTAAGTCCCGCAACGAGC<br>GCAACCCTTGTCTTATGTTGCCAGCACGTGATGGTGGGGACTCGTGAG<br>AGACTGCCGGGGTTAACTCGGAGGAAGGTGGGGATGACGTCAAATCA<br>TCATGCCCCTTATGTCCAGGGCTTCACACATGCTACAATGGTCGGTAC<br>AACGCGCATGCGAGCCTGTGAGGGTGAGCGAATCGCTGTGAAAGCCG<br>GTCGTAGTTCGGATTGGGGTCTGCAACTCGACCCCATGAAGTCGGAG<br>TCGCTAGTAATCGCAGATCAGCAACGCTGCGGTGAATACGTTCCCGG<br>GCCTTGTACACACCGCCCGTCACACCATGGGAGTGGGTTGCAAAAGA<br>AGTAGGTAGCTTAACCTTCGGGAGGGCGCTTACCACTTTGTGAT |
| 42 | DP42 16S rRNA | TGAAGAGTTTGATCATGGCTCAGATTGAACGCTGGCGGCAGGCCTAA<br>CACATGCAAGTCGAGCGGTAGAGAGGTGCTTGCACCTCTTGAGAGCG<br>GCGGACGGGTGAGTAATACCTAGGAATCTGCCTGATAGTGGGGGATA<br>ACGTTCGGAAACGGACGCTAATACCGCATACGTCCTACGGGAGAAAG<br>CAGGGGACCTTCGGGCCTTGCGCTATCAGATGAGCCTAGGTCGGATT<br>AGCTAGTTGGTGAGGTAATGGCTCACCAAGGCTACGATCCGTAACTG<br>GTCTGAGAGGATGATCAGTCACACTGGAACTGAGACACGGTCCAGAC<br>TCCTACGGGAGGCAGCAGTGGGGAATATTGGACAATGGGCGAAAGCC<br>TGATCCAGCCATGCCGCGTGTGTGAAGAAGGTCTTCGGATTGTAAAG<br>CACTTTAAGTTGGGAGGAAGGGCATTAACCTAATACGTTAGTGTCTTG<br>ACGTTACCGACAGAATAAGCACCGGCTAACTCTGTGCCAGCAGCCGC |

-continued

Sequence Listing

| Seq ID No. | Description | Sequence |
|---|---|---|
| | | GGTAATACAGAGGGTGCAAGCGTTAATCGGAATTACTGGGCGTAAAG<br>CGCGCGTAGGTGGTTTGTTAAGTTGAATGTGAAATCCCCGGGCTCAAC<br>CTGGGAACTGCATCCAAAACTGGCAAGCTAGAGTATGGTAGAGGGTA<br>GTGGAATTTCCTGTGTAGCGGTGAAATGCGTAGATATAGGAAGGAAC<br>ACCAGTGGCGAAGGCGACTACCTGGACTGATACTGACACTGAGGTGC<br>GAAAGCGTGGGGAGCAAACAGGATTAGATACCCTGGTAGTCCACGCC<br>GTAAACGATGTCAACTAGCCGTTGGGAACCTTGAGTTCTTAGTGGCGC<br>AGCTAACGCATTAAGTTGACCGCCTGGGGAGTACGGCCGCAAGGTTA<br>AAACTCAAATGAATTGACGGGGGCCCGCACAAGCGGTGGAGCATGTG<br>GTTTAATTCGAAGCAACGCGAAGAACCTTACCAGGCCTTGACATCCA<br>ATGAACTTTCCAGAGATGGATTGGTGCCTTCGGGAACATTGAGACAG<br>GTGCTGCATGGCTGTCGTCAGCTCGTGTCGTGAGATGTTGGGTTAAGT<br>CCCGTAACGAGCGCAACCCTTGTCCTTAGTTACCAGCACGTAATGGTG<br>GGCACTCTAAGGAGACTGCCGGTGACAAACCGGAGGAAGGTGGGGA<br>TGACGTCAAGTCATCATGGCCCTTACGGCCTGGGCTACACACGTGCTA<br>CAATGGTCGGTACAAAGGGTTGCCAAGCCGCGAGGTGGAGCTAATCC<br>CATAAAACCGATCGTAGTCCGGATCGCAGTCTGCAACTCGACTGCGT<br>GAAGTCGGAATCGCTAGTAATCGTGAATCAGAATGTCACGGTGAATA<br>CGTTCCCGGGCCTTGTACACACCGCCCGTCACACCATGGGAGTGGGTT<br>GCACCAGAAGTAGCTAGTCTAACCCTCGGGAGGACGGTTACCACGGT<br>GTGATTCATGACTGGGGTGAAGTCGTAACAAGGTAGCCGTAGGGGAA<br>CCTGCGGCTGGATCACCTCCTT |
| 43 | DP43 16S rRNA | CTGAGTTTGATCCTGGCTCAGATTGAACGCTGGCGGCATGCCTTACAC<br>ATGCAAGTCGAACGGCAGCACGGAGCTTGCTCTGGTGGCGAGTGGCG<br>AACGGGTGAGTAATATATCGGAACGTACCCTGGAGTGGGGGATAACG<br>TAGCGAAAGTTACGCTAATACCGCATACGATCTAAGGATGAAAGTGG<br>GGGATCGCAAGACCTCATGCTCGTGGAGCGGCCGATATCTGATTAGC<br>TAGTTGGTAGGGTAAAAGCCTACCAAGGCATCGATCAGTAGCTGGTC<br>TGAGAGGACGACCAGCCACACTGGAACTGAGACACGGTCCAGACTCC<br>TACGGGAGGCAGCAGTGGGGAATTTTGGACAATGGGCGAAAGCCTGA<br>TCCAGCAATGCCGCGTGAGTGAAGAAGGCCTTCGGGTTGTAAAGCTC<br>TTTTGTCAGGGAAGAAACGGTGAGAGCTAATATCTCTTGCTAATGAC<br>GGTACCTGAAGAATAAGCACCGGCTAACTACGTGCCAGCAGCCGCGG<br>TAATACGTAGGGTGCAAGCGTTAATCGGAATTACTGGGCGTAAAGCG<br>TGCGCAGGCGGTTTTGTAAGTCTGATGTGAAATCCCCGGGCTCAACCT<br>GGGAATTGCATTGGAGACTGCAAGGCTAGAATCTGGCAGAGGGGGGT<br>AGAATTCCACGTGTAGCAGTGAAATGCGTAGATATGTGGAGGAACAC<br>CGATGGCGAAGGCAGCCCCCTGGGTCAAGATTGACGCTCATGCACGA<br>AAGCGTGGGGAGCAAACAGGATTAGATACCCTGGTAGTCCACGCCCT<br>AAACGATGTCTACTAGTTGTCGGGTCTTAATTGACTTGGTAACGCAGC<br>TAACGCGTGAAGTAGACCGCCTGGGGAGTACGGTCGCAAGATTAAAA<br>CTCAAAGGAATTGACGGGGACCCGCACAAGCGGTGGATGATGTGGAT<br>TAATTCGATGCAACGCGAAAAACCTTACCTACCCTTGACATGGCTGG<br>AATCCTTGAGAGATCAGGGAGTGCTCGAAAGAGAACCAGTACACAGG<br>TGCTGCATGGCTGTCGTCAGCTCGTGTCGTGAGATGTTGGGTTAAGTC<br>CCGCAACGAGCGCAACCCTTGTCATTAGTTGCTACGAAAGGGCACTC<br>TAATGAGACTGCCGGTGACAAACCGGAGGAAGGTGGGGATGACGTC<br>AAGTCCTCATGGCCCTTATGGGTAGGGCTTCACACGTCATACAATGGT<br>ACATACAGAGCGCCGCCAACCCGCGAGGGGGAGCTAATCGCAGAAA<br>GTGTATCGTAGTCCGGATTGTAGTCTGCAACTCGACTGCATGAAGTTG<br>GAATCGCTAGTAATCGCGGATCAGCATGTCGCGGTGAATACGTTCCC<br>GGGTCTTGTACACACCGCCCGTCACACCATGGGAGCGGGTTTTACCA<br>GAAGTAGGTAGCTTAACCGTAAGGAGGGCGCTTACCACGGTAGGATT<br>CGTGACTGGGGTGAAGTCGTAACAAGGTAGCCGTATCGGAAGGTGCG<br>GCTGGATCACCTCCTTT |
| 44 | DP44 16S rRNA | TGGCGGCATGCCTTACACATGCAAGTCGAACGGCAGCATAGGAGCTT<br>GCTCCTGATGGCGAGTGGCGAACGGGTGAGTAATATATCGGAACGTG<br>CCCTAGAGTGGGGGATAACTAGTCGAAAGACTAGCTAATACCGCATA<br>CGATCTACGGATGAAAGTGGGGGATCGCAAGACCTCATGCTCCTGGA<br>GCGGCCGATATCTGATTAGCTAGTTGGTGGGGTAAAAGCTCACCAAG<br>GCGACGATCAGTAGCTGGTCTGAGAGGACGACCAGCCACACTGGGAC<br>TGAGACACGGCCCAGACTCCTACGGGAGGCAGCAGTGGGGAATTTTG<br>GACAATGGGGGCAACCCTGATCCAGCAATGCCGCGTGAGTGAAGAAG<br>GCCTTCGGGTTGTAAAGCTCTTTTGTCAGGGAAGAAACGGTTCTGGAT<br>AATACCTAGGACTAATGACGGTACCTGAAGAATAAGCACCGGCTAAC<br>TACGTGCCAGCAGCCGCGGTAATACGTAGGGTGCAAGCGTTAATCGG<br>AATTACTGGGCGTAAAGCGTGCGCAGGCGGTTGTGTAAGTCAGATGT<br>GAAATCCCCGGGCTCAACCTGGGAATTGCATTTGAGACTGCACGGCT<br>AGAGTGTGTCAGAGGGGGGTAGAATTCCACGTGTAGCAGTGAAATGC<br>GTAGATATGTGGAGGAATACCGATGGCGAAGGCAGCCCCCTGGGATA<br>ACACTGACGCTCATGCACGAAAGCGTGGGGAGCAAACAGGATTAGAT |

-continued

Sequence Listing

| Seq ID No. | Description | Sequence |
|---|---|---|
| | | ACCCTGGTAGTCCACGCCCTAAACGATGTCTACTAGTTGTCGGGTCTT AATTGACTTGGTAACGCAGCTAACGCGTGAAGTAGACCGCCTGGGGA GTACGGTCGCAAGATTAAAACTCAAAGGAATTGACGGGGACCCGCAC AAGCGGTGGATGATGTGGATTAATTCGATGCAACGCGAAAAACCTTA CCTACCCTTGACATGGATGGAATCCCGAAGAGATTTGGGAGTGCTCG AAAGAGAACCATCACACAGGTGCTGCATGGCTGTCGTCAGCTCGTGT CGTGAGATGTTGGGTTAAGTCCCGCAACGAGCGCAACCCTTGTCATTA GTTGCTACGAAAGGGCACTCTAATGAGACTGCCGGTGACAAACCGGA GGAAGGTGGGGATGACGTCAAGTCCTCATGGCCCTTATGGGTAGGGC TTCACACGTCATACAATGGTACATACAGAGGGCCGCCAACCCGCGAG GGGGAGCTAATCCCAGAAAGTGTATCGTAGTCCGGATTGGAGTCTGC AACTCGACTCCATGAAGTTGGAATCGCTAGTAATCGCGGATCAGCAT GTCGCGGTGAATACGTTCCCGGGTCTTGTACACACCGCCCGTCACACC ATGGGAGCGGGTTTTACCAGAAGTGGGTAGCCTAACCGCAAGGAGGG CGCTCACCACGGTAGGATTCGTGACTGGGGTGAAGTCGTAACAAGGT AGCCGTATCGGAAGGTGCGGCTGGATCACCTCCTTT |
| 45 | DP45 16S rRNA | TACGGAGAGTTTGATCCTGGCTCAGGACGAACGCTGGCGGCGTGCTT AACACATGCAAGTCGAACGGTGACGCTAGAGCTTGCTCTGGTTGATC AGTGGCGAACGGGTGAGTAACACGTGAGTAACCTGCCCTTGACTCTG GGATAACTCCGGGAAACCGGGGCTAATACCGGATACGAGACGCGACC GCATGGTCGGCGTCTGGAAAGTTTTTCGGTCAAGGATGGACTCGCGG CCTATCAGCTTGTTGGTGAGGTAATGGCTCACCAAGGCGTCGACGGG TAGCCGGCCTGAGAGGGCGACCGGCCACACTGGGACTGAGACACGGC CCAGACTCCTACGGGAGGCAGCAGTGGGGAATATTGCACAATGGGCG AAAGCCTGATGCAGCGACGCCGCGTGAGGGATGAAGGCCTTCGGGTT GTAAACCTCTTTCAGTAGGGAAGAAGCGAAAGTGACGGTACCTGCAG AAGAAGCGCCGGCTAACTACGTGCCAGCAGCCGCGGTAATACGTAGG GCGCAAGCGTTGTCCGGAATTATTGGGCGTAAAGAGCTCGTAGGCGG TTTGTCGCGTCTGGTGTGAAAACTCAAGGCTCAACCTTGAGCTTGCAT CGGGTACGGGCAGACTAGAGTGTGGTAGGGGTGACTGGAATTCCTGG TGTAGCGGTGGAATGCGCAGATATCAGGAGGAACACCGATGGCGAA GGCAGGTCACTGGGCCACTACTGACGCTGAGGAGCGAAAGCATGGGG AGCGAACAGGATTAGATACCCTGGTAGTCCATGCCGTAAACGTTGGG CACTAGGTGTGGGGCTCATTCCACGAGTTCCGCGCCGCAGCTAACGC ATTAAGTGCCCCGCCTGGGGAGTACGGCCGCAAGGCTAAAACTCAAA GGAATTGACGGGGGCCCGCACAAGCGGCGGAGCATGCGGATTAATTC GATGCAACGCGAAGAACCTTACCAAGGCTTGACATACACCGGAATCA TGCAGAGATGTGTGCGTCTTCGGACTGGTGTACAGGTGGTGCATGGTT GTCGTCAGCTCGTGTCGTGAGATGTTGGGTTAAGTCCCGCAACGAGC GCAACCCTCGTCCTATGTTGCCAGCACGTTATGGTGGGGACTCATAGG AGACTGCCGGGGTCAACTCGGAGGAAGGTGGGGATGACGTCAAATCA TCATGCCCCTTATGTCTTGGGCTTCACGCATGCTACAATGGCCGGTAC AAAGGGCTGCGATACCGCGAGGTGGAGCGAATCCCAAAAAGCCGGT CTCAGTTCGGATTGGGGTCTGCAACTCGACCCCATGAAGTCGGAGTC GCTAGTAATCGCAGATCAGCAACGCTGCGGTGAATACGTTCCCGGGC CTTGTACACACCGCCCGTCAAGTCACGAAAGTCGGTAACACCCGAAG CCGGTGGCCTAACCCCTTGTGGGATGGAGCCGTCGAAGGTGGGATTG GCGATTGGGACTAAGTCGTAACAAGGTAGCCGTACCGGAAGGTGCGG CTGGATCACCTCCTTT |
| 46 | DP46 16S rRNA | TTGAAGAGTTTGATCATGGCTCAGATTGAACGCTGGCGGCAGGCCTA ACACATGCAAGTCGGACGGTAGCACAGAGGAGCTTGCTCCTTGGGTG ACGAGTGGCGGACGGGTGAGTAATGTCTGGGGATCTGCCCGATAGAG GGGGATAACCACTGGAAACGGTGGCTAATACCGCATAACGTCGCAAG ACCAAAGAGGGGGACCTTCGGGCCTCTCACTATCGGATGAACCCAGA TGGGATTAGCTAGTAGGCGGGGTAATGGCCCACCTAGGCGACGATCC CTAGCTGGTCTGAGAGGATGACCAGCCACACTGGAACTGAGACACGG TCCAGACTCCTACGGGAGGCAGCAGTGGGGAATATTGCACAATGGGC GCAAGCCTGATGCAGCCATGCCGCGTGTATGAAGAAGGCCTTCGGGT TGTAAAGTACTTTCAGCGGGGAGGAAGGCGACAGGGTTAATAACCCT GTCGATTGACGTTACCCGCAGAAGAAGCACCGGCTAACTCCGTGCCA GCAGCCGCGGTAATACGGAGGGTGCAAGCGTTAATCGGAATTACTGG GCGTAAAGCGCACGCAGGCGGTCTGTTAAGTCAGATGTGAAATCCCC GGGCTTAACCTGGGAACTGCATTTGAAACTGGCAGGCTTTAGTCTTGT AGAGTGGGGTAGAATTCCAGGTGTAGCGGTGAAATGCGTAGAGATGT GGAGGAACACCAGTGGCGAAGGCGGCTTTTTGGTCTGTAACTGACGC TGAGGCGCGAAAGCGTGGGGAGCAAACAGGATTAGATACCCTGGTA GTCCACGCCGTAAACGATGAGTGCTAAGTGTT |
| 47 | DP47 16S rRNA | AGGGTGCAAGCGTTAATCGGAATTACTGGGCGTAAAGCGCGCGTAGG TGGTTTGTTAAGTTGAATGTGAAATCCCCGGGCTCAACCTGGGAACTG CATTTGAAACTGGCAAGCTAGAGTCTCGTAGAGGGGGGTAGAATTCC |

-continued

Sequence Listing

| Seq ID No. | Description | Sequence |
|---|---|---|
| | | AGGTGTAGCGGTGAAATGCGTAGAGATCTGGAGGAATACCGGTGGCG<br>AAGGCGGCCCCCTGGACGAAGACTGACGCTCAGGTGCGAAAGCGTGG<br>GGAGCAAACAGGATTAGATACCCTGGTAGTCCACGCCGTAAACGATG<br>TCAACTAGCCGTTGGAAGCCTTGAGCTTTTAGTGGCGCAGCTAACGCA<br>TTAAGTTGACCGCCTGGGGAGTACGGCCGCAAGGTTAAAACTCAAAT<br>GAATTGACGGGGGCCCGCACAAGCGGTGGAGCATGTGGTTTAATTCG<br>AAGCAACGCGAAGAACCTTACCAGGCCTTGACATCCAATGAACTTTC<br>TAGAGATAGATTGGTGCCTTCGGGAACATTGAGACAGGTGCTGCATG<br>GCTGTCGTCAGCTCGTGTCGTGAGATGTTGGGTTAAGTCCCGCAACGA<br>GCGCAACCCTTGTCCTGTGTTGCCAGCGCGTAATGGCGGGGACTCGC<br>AGGAGACTGCCGGGGTCAACTCGGAGGAAGGTGGGGATGACGTCAA<br>ATCATCATGCCCCTTATGTCTTGGGCTTCACGCATGCTACAATGGCCG<br>GTACAAAGGGCTGCAATACCGTGAGGTGGAGCGAATCCCAAAAAGCC<br>GGTCCCAGTTCGGATTGAGGTCTGCAACTCGACCTCATGAAGTCGGA<br>GTCGCTAGTAATCGCAGATCAGCAACGCTGCGGTGAATACGTTCCCG<br>GGTCTTGTACACACCGCCCGTCAAGTCATGAAAGTCGGTAACACCTG<br>AAGCCGGTGGCCCAACCCTTGTGGAGGGAGCCGTCGAAGGTGGGATC<br>GGTAATTAGGACTAAGT |
| 48 | DP48 16S rRNA | CATGGAGAGTTTGATCCTGGCTCAGGACGAACGCTGGCGGCGTGCCT<br>AATACATGCAAGTCGAGCGGACAGATGGGAGCTTGCTCCCTGATGTT<br>AGCGGCGGACGGGTGAGTAACACGTGGGTAACCTGCCTGTAAGACTG<br>GGATAACTCCGGGAAACCGGGGCTAATACCGGATGCTTGATTGAACC<br>GCATGGTTCAATTATAAAAGGTGGCTTTTAGCTACCACTTACAGATGG<br>ACCCGCGGCGCATTAGCTAGTTGGTGAGGTAACGGCTCACCAAGGCA<br>ACGATGCGTAGCCGACCTGAGAGGGTGATCGGCCACACTGGGACTGA<br>GACACGGCCCAGACTCCTACGGGAGGCAGCAGTAGGGAATCTTCCGC<br>AATGGACGAAAGTCTGACGGAGCAACGCCGCGTGAGTGATGAAGGTT<br>TTCGGATCGTAAAACTCTGTTGTTAGGGAAGAACAAGTACCGTTCGA<br>ATAGGGCGGTACCTTGACGGTACCTAACCAGAAAGCCACGGCTAACT<br>ACGTGCCAGCAGCCGCGGTAATACGTAGGTGGCAAGCGTTGTCCGGA<br>ATTATTGGGCGTAAAGCGCGCGCAGGCGGTTTCTTAAGTCTGATGTGA<br>AAGCCCCCGGCTCAACCGGGGAGGGTCATTGGAAACTGGGGAACTTG<br>AGTGCAGAAGAGGAGAGTGGAATTCCACGTGTAGCGGTGAAATGCGT<br>AGAGATGTGGAGGAACACCAGTGGCGAAGGCGACTCTCTGGTCTGTA<br>ACTGACGCTGAGGCGCGAAAGCGTGGGGAGCGAACAGGATTAGATA<br>CCCTGGTAGTCCACGCCGTAAACGATGAGTGCTAAGTGTTAGAGGGT<br>TTCCGCCCTTTAGTGCTGCAGCAAACGCATTAAGCACTCCGCCTGGGG<br>AGTACGGTCGCAAGACTGAAACTCAAAGGAATTGACGGGGGCCCGCA<br>CAAGCGGTGGAGCATGTGGTTTAATTCGAAGCAACGCGAAGAACCTT<br>ACCAGGTCTTGACATCCTCTGACAACCCTAGAGATAGGGCTTCCCCTT<br>CGGGGGCAGAGTGACAGGTGGTGCATGGTTGTCGTCAGCTCGTGTCG<br>TGAGATGTTGGGTTAAGTCCCGCAACGAGCGCAACCCTTGATCTTAGT<br>TGCCAGCATTCAGTTGGGCACTCTAAGGTGACTGCCGGTGACAAACC<br>GGAGGAAGGTGGGGATGACGTCAAATCATCATGCCCCTTATGACCTG<br>GGCTACACACGTGCTACAATGGGCAGAACAAAGGGCAGCGAAGCCG<br>CGAGGCTAAGCCAATCCCACAAATCTGTTCTCAGTTCGGATCGCAGTC<br>TGCAACTCGACTGCGTGAAGCTGGAATCGCTAGTAATCGCGGATCAG<br>CATGCCGCGGTGAATACGTTCCCGGGCCTTGTACACACCGCCCGTCAC<br>ACCACGAGAGTTTGTAACACCCGAAGTCGGTGAGGTAACCTTTTGGA<br>GCCAGCCGCCGAAGGTGGGACAGATGATTGGGGTGAAGTCGTAACAA<br>GGTAGCCGTATCGGAAGGTGCGGCTGGATCACCTCCTTT |
| 49 | DP49 16S rRNA | TATGGAGAGTTTGATCCTGGCTCAGGACGAACGCTGGCGGCGTGCCT<br>AATACATGCAAGTCGAGCGGACGTTTTTGAAGCTTGCTTCAAAAACG<br>TTAGCGGCGGACGGGTGAGTAACACGTGGGCAACCTGCCTTATCGAC<br>TGGGATAACTCCGGGAAACCGGGGCTAATACCGGATAATATCTAGCA<br>CCTCCTGGTGCAAGATTAAAAGAGGGCCTTCGGGCTCTCACGGTGAG<br>ATGGGCCCGCGGCGCATTAGCTAGTTGGAGAGGTAATGGCTCCCCAA<br>GGCGACGATGCGTAGCCGACCTGAGAGGGTGATCGGCCACACTGGGA<br>CTGAGACACGGCCCAGACTCCTACGGGAGGCAGCAGTAGGGAATCTT<br>CCGCAATGGACGAAAGTCTGACGGAGCAACGCCGCGTGAGTGATGAA<br>GGGTTTCGGCTCGTAAAGCTCTGTTATGAGGGAAGAACACGTACCGT<br>TCGAATAGGGCGGTACCTTGACGGTACCTCATCAGAAAGCCACGGCT<br>AACTACGTGCCAGCAGCCGCGGTAATACGTAGGTGGCAAGCGTTGTC<br>CGGAATTATTGGGCGTAAAGCGCGCGCAGGCGGCCTTTTAAGTCTGA<br>TGTGAAATCTTGCGGCTCAACCGCAAGCGGTCATTGGAAACTGGGAG<br>GCTTGAGTACAGAAGAGGAGAGTGGAATTCCACGTGTAGCGGTGAAA<br>TGCGTAGATATGTGGAGGAACACCAGTGGCGAAGGCGACTCTCTGGT<br>CTGTAACTGACGCTGAGGCGCGAAAGCGTGGGGAGCAAACAGGATTA<br>GATACCCTGGTAGTCCACGCCGTAAACGATGAGTGCTAGGTGTTAGG<br>GGTTTCGATGCCCGTAGTGCCGAAGTTAACACATTAAGCACTCCGCCT<br>GGGGAGTACGGCCGCAAGGCTGAAACTCAAAGGAATTGACGGGGGC |

-continued

Sequence Listing

| Seq ID No. | Description | Sequence |
|---|---|---|
| | | CCGCACAAGCAGTGGAGCATGTGGTTTAATTCGAAGCAACGCGAAGA<br>ACCTTACCAGGTCTTGACATCCTTTGACCACTCTGGAGACAGAGCTTC<br>CCCTTCGGGGGCAAAGTGACAGGTGGTGCATGGTTGTCGTCAGCTCG<br>TGTCGTGAGATGTTGGGTTAAGTCCCGCAACGAGCGCAACCCTTGAC<br>CTTAGTTGCCAGCATTTAGTTGGGCACTCTAAGGTGACTGCCGGTGAC<br>AAACCGGAGGAAGGTGGGGATGACGTCAAATCATCATGCCCCTTATG<br>ACCTGGGCTACACACGTGCTACAATGGATGGTACAAAGGGTTGCGAA<br>GCCGCGAGGTGAAGCCAATCCCATAAAGCCATTCTCAGTTCGGATTG<br>TAGGCTGCAACTCGCCTGCATGAAGCTGGAATTGCTAGTAATCGCGG<br>ATCAGCATGCCGCGGTGAATACGTTCCCGGGCCTTGTACACACCGCCC<br>GTCACACCACGAGAGTTTGTAACACCCGAAGTCGGTGAGGTAACCTT<br>TTGGAGCCAGCCGCCGAAGGTGGGACAGATGATTGGGGTGAAGTCGT<br>AACAAGGTAGCCGTATCGGAAGGTGCGGCTGGATCACCTCCTTT |
| 50 | DP50 16S rRNA | TTGAAGAGTTTGATCATGGCTCAGATTGAACGCTGGCGGCAGGCCTA<br>ACACATGCAAGTCGAACGGTAGCACAGAGAGCTTGCTCTTGGGTGAC<br>GAGTGGCGGACGGGTGAGTAATGTCTGGGAAACTGCCCGATGGAGGG<br>GGATAACTACTGGAAACGGTAGCTAATACCGCATAACGTCGCAAGAC<br>CAAAGTGGGGGACCTTCGGGCCTCACACCATCGGATGTGCCCAGATG<br>GGATTAGCTAGTAGGTGGGGTAATGGCTCACCTAGGCGACGATCCCT<br>AGCTGGTCTGAGAGGATGACCAGCCACACTGGAACTGAGACACGGTC<br>CAGACTCCTACGGGAGGCAGCAGTGGGGAATATTGCACAATGGGCGC<br>AAGCCTGATGCAGCCATGCCGCGTGTATGAAGAAGGCCTTCGGGTTG<br>TAAAGTACTTTCAGCGAGGAGGAAGGCATTGTGGTTAATAACCGCAG<br>TGATTGACGTTACTCGCAGAAGAAGCACCGGCTAACTCCGTGCCAGC<br>AGCCGCGGTAATACGGAGGGTGCAAGCGTTAATCGGAATTACTGGGC<br>GTAAAGCGCACGCAGGCGGTCTGTCAAGTCGGATGTGAAATCCCCGG<br>GCTCAACCTGGGAACTGCATTCGAAACTGGCAGGCTAGAGTCTTGTA<br>GAGGGGGGTAGAATTCCAGGTGTAGCGGTGAAATGCGTAGAGATCTG<br>GAGGAATACCGGTGGCGAAGGCGGCCCCCTGGACAAAGACTGACGCT<br>CAGGTGCGAAAGCGTGGGGAGCAAACAGGATTAGATACCCTGGTAGT<br>CCACGCCGTAAACGATGTCGACTTGGAGGTTGTGCCCTTGAGGCGTG<br>GCTTCCGGAGCTAACGCGTTAAGTCGACCGCCTGGGGAGTACGGCCG<br>CAAGGTTAAAACTCAAATGAATTGACGGGGGCCCGCACAAGCGGTGG<br>AGCATGTGGTTTAATTCGATGCAACGCGAAGAACCTTACCTACTCTTG<br>ACATCCACGGAATTTAGCAGAGATGCTTTAGTGCCTTCGGGAACCGT<br>GAGACAGGTGCTGCATGGCTGTCGTCAGCTCGTGTTGTGAAATGTTGG<br>GTTAAGTCCCGCAACGAGCGCAACCCTTATCCTTTGTTGCCAGCGGTT<br>CGGCCGGGAACTCAAAGGAGACTGCCAGTGATAAACTGGAGGAAGG<br>TGGGGATGACGTCAAGTCATCATGGCCCTTACGAGTAGGGCTACACA<br>CGTGCTACAATGGCATATACAAAGAGAAGCGACCTCGCGAGAGCAAG<br>CGGACCTCATAAAGTATGTCGTAGTCCGGATCGGAGTCTGCAACTCG<br>ACTCCGTGAAGTCGGAATCGCTAGTAATCGTAGATCAGAATGCTACG<br>GTGAATACGTTCCCGGGCCTTGTACACACCGCCCGTCACACCATGGG<br>AGTGGGTTGCAAAAGAAGTAGGTAGCTTAACCTTCGGGAGGGCGCTT<br>ACCACTTTGTGATTCATGACTGGGGTGAAGTCGTAACAAGGTAACCG<br>TAGGGGAACCTGCGGTTGGATCACCTCCTT |
| 51 | DP51 16S rRNA | TTGAAGAGTTTGATCATGGCTCAGATTGAACGCTGGCGGCAGGCCTA<br>ACACATGCAAGTCGAGCGGTAGCACAGGGAGCTTGCTCCTGGGTGAC<br>GAGCGGCGGACGGGTGAGTAATGTCTGGGAAACTGCCTGATGGAGGG<br>GGATAACTACTGGAAACGGTAGCTAATACCGCATAACGTCGCAAGAC<br>CAAAGAGGGGGACCTTCGGGCCTCTTGCCATCAGATGTGCCCAGATG<br>GGATTAGCTAGTAGGTGAGGTAATGGCTCACCTAGGCGACGATCCCT<br>AGCTGGTCTGAGAGGATGACCAGCCACACTGGAACTGAGACACGGTC<br>CAGACTCCTACGGGAGGCAGCAGTGGGGAATATTGCACAATGGGCGC<br>AAGCCTGATGCAGCCATGCCGCGTGTATGAAGAAGGCCTTCGGGTTG<br>TAAAGTACTTTCAGCGAGGAGGAAGGCATTAAGGTTAATAACCTTGG<br>TGATTGACGTTACTCGCAGAAGAAGCACCGGCTAACTCCGTGCCAGC<br>AGCCGCGGTAATACGGGGGGTGCAAGCGTTAATCGGAATTACTGGGC<br>GTAAAGCGCACGCAGGCGGTTTGTCAAGTCGGATGTGAAATCCCCGG<br>GCTCAACCTGGGAACTGCATTCGAAACGGGCAAGCTAGAGTCTTGTA<br>GAGGGGGGTAGAATTCCAGGTGTAGCGGTGAAATGCGTAGAGATCTG<br>GAGGAATACCGGTGGCGAAGGCGGCCCCCTGGACAAAGACTGACGCT<br>CAGGTGCGAAAGCGTGGGGAGCAAACAGGATTAGATACCCTGGTAGT<br>CCACGCCGTAAACGATGTCGACTTGGAGGTTGTGCCCTTGAGGCGTG<br>GCTTCCGGAGCTAACGCGTTAAGTCGACCGCCTGGGGAGTACGGCCG<br>CAAGGTTAAAACTCAAATGAATTGACGGGGGCCCGCACAAGCGGTGG<br>AGCATGTGGTTTAATTCGATGCAACGCGAAGAACCTTACCTACTCTTG<br>ACATCCAGAGAACTTTCCAGAGATGGATTGGTGCCTTCGGGAACTCT<br>GAGACAGGTGCTGCATGGCTGTCGTCAGCTCGTGTTGTGAAATGTTGG<br>GTTAAGTCCCGCAACGAGCGCAACCCTTATCCTTTGTTGCCAGCGAGT<br>AATGTCGGGAACTCAAAGGAGACTGCCAGTGACAAACTGGAGGAAG |

-continued

| Seq ID No. | Description | Sequence |
|---|---|---|
| | | GTGGGGATGACGTCAAGTCATCATGGCCCTTACGAGTAGGGCTACAC ACGTGCTACAATGGCATATACAAAGAGAAGCGACCTCGCGAGAGCAA GCGGACCTCACAAAGTATGTCGTAGTCCGGATCGGAGTCTGCAACTC GACTCCGTGAAGTCGGAATCGCTAGTAATCGTAGATCAGAATGCTAC GGTGAATACGTTCCCGGGCCTTGTACACACCGCCCGTCACACCATGG GAGTGGGTTGCAAAAGAAGTAGGTAGCTTAACCTTCGGGAGGGCGCT TACCACTTTGTGATTCATGACTGGGGTGAAGTCGTAACAAGGTAACC GTAGGGGAACCTGCGGTTGGATCACCTCCTT |
| 52 | DP52 16S rRNA | ACGGAGAGTTTGATCCTGGCTCAGGATGAACGCTGGCGGCGTGCTTA ACACATGCAAGTCGAACGATGATCCCAGCTTGCTGGGGGATTAGTGG CGAACGGGTGAGTAACACGTGAGTAACCTGCCCTTGACTCTGGGATA AGCCTGGGAAACTGGGTCTAATACCGGATATGACTGTCTGACGCATG TCAGGTGGTGGAAAGCTTTTGTGGTTTTGGATGGACTCGCGGCCTATC AGCTTGTTGGTGGGGTAATGGCCTACCAAGGCGACGACGGGTAGCCG GCCTGAGAGGGTGACCGGCCACACTGGGACTGAGACACGGCCCAGAC TCCTACGGGAGGCAGCAGTGGGGAATATTGCACAATGGGCGCAAGCC TGATGCAGCGACGCCGCGTGAGGGATGACGGCCTTCGGGTTGTAAAC CTCTTTCAGTAGGGAAGAAGCGAAAGTGACGGTACCTGCAGAAGAAG CGCCGGCTAACTACGTGCCAGCAGCCGCGGTAATACGTAGGGCGCAA GCGTTATCCGGAATTATTGGGCGTAAAGAGCTCGTAGGCGGTTTGTCG CGTCTGCTGTGAAAGACCGGGGCTCAACTCCGGTTCTGCAGTGGGTA CGGGCAGACTAGAGTGCAGTAGGGGAGACTGGAATTCCTGGTGTAGC GGTGAAATGCGCAGATATCAGGAGGAACACCGATGGCGAAGGCAGG TCTCTGGGCTGTAACTGACGCTGAGGAGCGAAAGCATGGGGAGCGAA CAGGATTAGATACCCTGGTAGTCCATGCCGTAAACGTTGGGCACTAG GTGTGGGGGACATTCCACGTTTTCCGCGCCGTAGCTAACGCATTAAGT GCCCCGCCTGGGGAGTACGGCCGCAAGGCTAAAACTCAAAGGAATTG ACGGGGGCCCGCACAAGCGGCGGAGCATGCGGATTAATTCGATGCAA CGCGAAGAACCTTACCAAGGCTTGACATGAACCGGTAATACCTGGAA ACAGGTGCCCCGCTTGCGGTCGGTTTACAGGTGGTGCATGGTTGTCGT CAGCTCGTGTCGTGAGATGTTGGGTTAAGTCCCGCAACGAGCGCAAC CCTCGTTCTATGTTGCCAGCGCGTTATGGCGGGGACTCATAGGAGACT GCCGGGGTCAACTCGGAGGAAGGTGGGGACGACGTCAAATCATCATG CCCCTTATGTCTTGGGCTTCACGCATGCTACAATGGCCGGTACAAAGG GTTGCGATACTGTGAGGTGGAGCTAATCCCAAAAAGCCGGTCTCAGT TCGGATTGGGGTCTGCAACTCGACCCCATGAAGTCGGAGTCGCTAGT AATCGCAGATCAGCAACGCTGCGGTGAATACGTTCCCGGGCCTTGTA CACACCGCCCGTCAAGTCACGAAAGTTGGTAACACCCGAAGCCGGTG GCCTAACCCTTGTGGGGGGAGCCGTCGAAGGTGGGACCGGCGATTGG GACTAAGTCGTAACAAGGTAGCCGTACCGGAAGGTGCGGCTGGATCA CCTCCTTT |
| 53 | DP53 16S rRNA | TGAAGAGTTTGATCATGGCTCAGATTGAACGCTGGCGGCAGGCCTAA CACATGCAAGTCGAGCGGTAGAGAGAAGCTTGCTTCTCTTGAGAGCG GCGGACGGGTGAGTAATACCTAGGAATCTGCCTGATAGTGGGGGATA ACGTTCGGAAACGGACGCTAATACCGCATACGTCCTACGGGAGAAAG CAGGGGACCTTCGGGCCTTGCGCTATCAGATGAGCCTAGGTCGGATT AGCTAGTTGGTGAGGTAATGGCTCACCAAGGCTACGATCCGTAACTG GTCTGAGAGGATGATCAGTCACACTGGAACTGAGACACGGTCCAGAC TCCTACGGGAGGCAGCAGTGGGGAATATTGGACAATGGGCGAAAGCC TGATCCAGCCATGCCGCGTGTGTGAAGAAGGTCTTCGGATTGTAAAG CACTTTAAGTTGGGAGGAAGGGCAGTTACCTAATACGTGATTGTCTTG ACGTTACCGACAGAATAAGCACCGGCTAACTCTGTGCCAGCAGCCGC GGTAATACAGAGGGTGCAAGCGTTAATCGGAATTACTGGGCGTAAAG CGCGCGTAGGTGGTTTGTTAAGTTGAATGTGAAATCCCCGGGCTCAAC CTGGGAACTGCATCCAAAACTGGCAAGCTAGAGTATGGTAGAGGGTA GTGGAATTTCCTGTGTAGCGGTGAAATGCGTAGATATAGGAAGGAAC ACCAGTGGCGAAGGCGACTACCTGGACTGATACTGACACTGAGGTGC GAAAGCGTGGGGAGCAAACAGGATTAGATACCCTGGTAGTCCACGCC GTAAACGATGTCAACTAGCCGTTGGGAGTCTTGAACTCTTAGTGGCGC AGCTAACGCATTAAGTTGACCGCCTGGGGAGTACGGCCGCAAGGTTA AAACTCAAATGAATTGACGGGGGCCCGCACAAGCGGTGGAGCATGTG GTTTAATTCGAAGCAACGCGAAGAACCTTACCAGGCCTTGACATCCA ATGAACTTTCTAGAGATAGATTGGTGCCTTCGGGAACATTGAGACAG GTGCTGCATGGCTGTCGTCAGCTCGTGTCGTGAGATGTTGGGTTAAGT CCCGTAACGAGCGCAACCCTTGTCCTTAGTTACCAGCACGTAATGGTG GGCACTCTAAGGAGACTGCCGGTGACAAACCGGAGGAAGGTGGGGA TGACGTCAAGTCATCATGGCCCTTACGGCCTGGGCTACACACGTGCTA CAATGGTCGGTACAAAGGGTTGCCAAGCCGCGAGGTGGAGCTAATCC CATAAAACCGATCGTAGTCCGGATCGCAGTCTGCAACTCGACTGCGT GAAGTCGGAATCGCTAGTAATCGTGAATCAGAATGTCACGGTGAATA CGTTCCCGGGCCTTGTACACACCGCCCGTCACACCATG |

-continued

Sequence Listing

| Seq ID No. | Description | Sequence |
|---|---|---|
| 54 | DP54 16S rRNA | CTTGAGAGTTTGATCCTGGCTCAGAGCGAACGCTGGCGGCAGGCTTA<br>ACACATGCAAGTCGAGCGGGCACCTTCGGGTGTCAGCGGCAGACGGG<br>TGAGTAACACGTGGGAACGTACCCTTCGGTTCGGAATAACGCTGGGA<br>AACTAGCGCTAATACCGGATACGCCCTTTTGGGGAAAGGTTTACTGCC<br>GAAGGATCGGCCCGCGTCTGATTAGCTAGTTGGTGGGGTAACGGCCT<br>ACCAAGGCGACGATCAGTAGCTGGTCTGAGAGGATGATCAGCCACAC<br>TGGGACTGAGACACGGCCCAGACTCCTACGGGAGGCAGCAGTGGGG<br>AATATTGGACAATGGGCGCAAGCCTGATCCAGCCATGCCGCGTGAGT<br>GATGAAGGCCTTAGGGTTGTAAAGCTCTTTTGTCCGGGACGATAATG<br>ACGGTACCGGAAGAATAAGCCCCGGCTAACTTCGTGCCAGCAGCCGC<br>GGTAATACGAAGGGGGCTAGCGTTGCTCGGAATCACTGGGCGTAAAG<br>GGCGCGTAGGCGGCCATTCAAGTCGGGGGTGAAAGCCTGTGGCTCAA<br>CCACAGAATTGCCTTCGATACTGTTTGGCTTGAGTTTGGTAGAGGTTG<br>GTGGAACTGCGAGTGTAGAGGTGAAATTCGTAGATATTCGCAAGAAC<br>ACCAGTGGCGAAGGCGGCCAACTGGACCAATACTGACGCTGAGGCGC<br>GAAAGCGTGGGGAGCAAACAGGATTAGATACCCTGGTAGTCCACGCC<br>GTAAACGATGAATGCTAGCTGTTGGGGTGCTTGCACCTCAGTAGCGC<br>AGCTAACGCTTTAAGCATTCCGCCTGGGGAGTACGGTCGCAAGATTA<br>AAACTCAAAGGAATTGACGGGGGCCCGCACAAGCGGTGGAGCATGT<br>GGTTTAATTCGAAGCAACGCGCAGAACCTTACCATCCCTTGACATGTC<br>GTGCCATCCGGAGAGATCCGGGGTTCCCTTCGGGGACGCGAACACAG<br>GTGCTGCATGGCTGTCGTCAGCTCGTGTCGTGAGATGTTGGGTTAAGT<br>CCCGCAACGAGCGCAACCCACGTCCTTAGTTGCCATCATTTAGTTGGG<br>CACTCTAGGGAGACTGCCGGTGATAAGCCGCGAGGAAGGTGTGGATG<br>ACGTC |
| 55 | DP55 16S rRNA | TCGGAGAGTTTGATCCTGGCTCAGGATGAACGCTGGCGGCGTGCCTA<br>ATACATGCAAGTCGAGCGAACTGATTAGAAGCTTGCTTCTATGACGTT<br>AGCGGCGGACGGGTGAGTAACACGTGGGCAACCTGCCTGTAAGACTG<br>GGATAACTTCGGGAAACCGAAGCTAATACCGGATAGGATCTTCTCCT<br>TCATGGGAGATGATTGAAAGATGGTTTCGGCTATCACTTACAGATGG<br>GCCCGCGGTGCATTAGCTAGTTGGTGAGGTAACGGCTCACCAAGGCA<br>ACGATGCATAGCCGACCTGAGAGGGTGATCGGCCACACTGGGACTGA<br>GACACGGCCCAGACTCCTACGGGAGGCAGCAGTAGGGAATCTTCCGC<br>AATGGACGAAAGTCTGACGGAGCAACGCCGCGTGAGTGATGAAGGCT<br>TTCGGGTCGTAAAACTCTGTTGTTAGGGAAGAACAAGTACAAGAGTA<br>ACTGCTTGTACCTTGACGGTACCTAACCAGAAAGCCACGGCTAACTA<br>CGTGCCAGCAGCCGCGGTAATACGTAGGTGGCAAGCGTTATCCGGAA<br>TTATTGGGCGTAAAGCGCGCGCAGGCGGTTTCTTAAGTCTGATGTGAA<br>AGCCCACGGCTCAACCGTGGAGGGTCATTGGAAACTGGGGAACTTGA<br>GTGCAGAAGAGAAAAGCGGAATTCCACGTGTAGCGGTGAAATGCGTA<br>GAGATGTGGAGGAACACCAGTGGCGAAGGCGGCTTTTTGGTCTGTAA<br>CTGACGCTGAGGCGCGAAAGCGTGGGGAGCAAACAGGATTAGATAC<br>CCTGGTAGTCCACGCCGTAAACGATGAGTGCTAAGTGTTAGAGGGTT<br>TCCGCCCTTTAGTGCTGCAGCTAACGCATTAAGCACTCCGCCTGGGGA<br>GTACGGTCGCAAGACTGAAACTCAAAGGAATTGACGGGGGCCCGCAC<br>AAGCGGTGGAGCATGTGGTTTAATTCGAAGCAACGCGAAGAACCTTA<br>CCAGGTCTTGACATCCTCTGACAACTCTAGAGATAGAGCGTTCCCCTT<br>CGGGGGACAGAGTGACAGGTGGTGCATGGTTGTCGTCAGCTCGTGTC<br>GTGAGATGTTGGGTTAAGTCCCGCAACGAGCGCAACCCTTGATCTTA<br>GTTGCCAGCATTTAGTTGGGCACTCTAAGGTGACTGCCGGTGACAAA<br>CCGGAGGAAGGTGGGGATGACGTCAAATCATCATGCCCCTTATGACC<br>TGGGCTACACACGTGCTACAATGGATGGTACAAAGGGCTGCAAGACC<br>GCGAGGTCAAGCCAATCCCATAAAACCATTCTCAGTTCGGATTGTAG<br>GCTGCAACTCGCCTACATGAAGCTGGAATCGCTAGTAATCGCGGATC<br>AGCATGCT |
| 56 | DP56 16S rRNA | ATTGGAGAGTTTGATCCTGGCTCAGGACGAACGCTGGCGGCGTGCCT<br>AATACATGCAAGTCGAGCGGACCTGATGGAGTGCTTGCACTCCTGAT<br>GGTTAGCGGCGGACGGGTGAGTAACACGTAGGCAACCTGCCCTCAAG<br>ACTGGGATAACTACCGGAAACGGTAGCTAATACCGGATAATTTATTT<br>CACAGCATTGTGGAATAATGAAAGACGGAGCAATCTGTCACTTGGGG<br>ATGGGCCTGCGGCGCATTAGCTAGTTGGTGGGGTAACGGCTCACCAA<br>GGCGACGATGCGTAGCCGACCTGAGAGGGTGAACGGCCACACTGGG<br>ACTGAGACACGGCCCAGACTCCTACGGGAGGCAGCAGTAGGGAATCT<br>TCCGCAATGGGCGAAAGCCTGACGGAGCAACGCCGCGTGAGTGATGA<br>AGGTTTTCGGATCGTAAAGCTCTGTTGCCAAGGAAGAACGTCTTCTAG<br>AGTAACTGCTAGGAGAGTGACGGTACTTGAGAAGAAAGCCCCGGCTA<br>ACTACGTGCCAGCAGCCGCGGTAATACGTAGGGGGCAAGCGTTGTCC<br>GGAATTATTGGGCGTAAAGCGCGCGCAGGCGGTTCTTTAAGTCTGGT<br>GTTTAAACCCGAGGCTCAACTTCGGGTCGCACTGGAAACTGGGGAAC<br>TTGAGTGCAGAAGAGGAGAGTGGAATTCCACGTGTAGCGGTGAAATG |

-continued

Sequence Listing

| Seq ID No. | Description | Sequence |
|---|---|---|
| | | CGTAGATATGTGGAGGAACACCAGTGGCGAAGGCGACTCTCTGGGCT<br>GTAACTGACGCTGAGGCGCGAAAGCGTGGGGAGCAAACAGGATTAG<br>ATACCCTGGTAGTCCACGCCGTAAACGATGAATGCTAGGTGTTAGGG<br>GTTTCGATACCCTTGGTGCCGAAGTTAACACATTAAGCATTCCGCCTG<br>GGGAGTACGGTCGCAAGACTGAAACTCAAAGGAATTGACGGGGACC<br>CGCACAAGCAGTGGAGTATGTGGTTTAATTCGAAGCAACGCGAAGAA<br>CCTTACCAAGTCTTGACATCCCTCTGAATCCTCTAGAGATAGAGGCGG<br>CCTTCGGGACAGAGGTGACAGGTGGTGCATGGTTGTCGTCAGCTCGT<br>GTCGTGAGATGTTGGGTTAAGTCCCGCAACGAGCGCAACCCTTGATTT<br>TAGTTGCCAGCACATCATGGTGGGCACTCTAGAATGACTGCCGGTGA<br>CAAACCGGAGGAAGGCGGGGATGACGTCAAATCATCATGCCCCTTAT<br>GACTTGGGCTACACACGTACTACAATGGCTGGTACAACGGGAAGCGA<br>AGCCGCGAGGTGGAGCCAATCCTATAAAAGCCAGTCTCAGTTCGGAT<br>TGCAGGCTGCAACTCGCCTGCATGAAGTCGGAATTGCTAGTAATCGC<br>GGATCAGCATGCCGCGGTGAATACGTTCCCGGGTCTTGTACACACCG<br>CCCGTCACACCACGAGAGTTTACAACACCCGAAGTCGGTGGGGTAAC<br>CCGCAAGGGAGCCAGCCGCCGAAGGTGGGGTAGATGATTGGGGTGA<br>AGTCGTAACAAGGTAGCCGTATCGGAAGGTGCGGCTGGATCACCTCC<br>TTT |
| 57 | DP57 16S rRNA | ATTGGAGAGTTTGATCCTGGCTCAGGATGAACGCTGGCGGCGTGCCT<br>AATACATGCAAGTCGAGCGAATGGATTAAGAGCTTGCTCTTATGAAG<br>TTAGCGGCGGACGGGTGAGTAACACGTGGGTAACCTGCCCATAAGAC<br>TGGGATAACTCCGGGAAACCGGGGCTAATACCGGATAACATTTTGCA<br>CCGCATGGTGCGAAATTCAAAGGCGGCTTCGGCTGTCACTTATGGAT<br>GGACCCGCGTCGCATTAGCTAGTTGGTGAGGTAACGGCTCACCAAGG<br>CAACGATGCGTAGCCGACCTGAGAGGGTGATCGGCCACACTGGGACT<br>GAGACACGGCCCAGACTCCTACGGGAGGCAGCAGTAGGGAATCTTCC<br>GCAATGGACGAAAGTCTGACGGAGCAACGCCGCGTGAGTGATGAAG<br>GCTTTCGGGTCGTAAAACTCTGTTGTTAGGGAAGAACAAGTGCTAGTT<br>GAATAAGCTGGCACCTTGACGGTACCTAACCAGAAAGCCACGGCTAA<br>CTACGTGCCAGCAGCCGCGGTAATACGTAGGTGGCAAGCGTTATCCG<br>GAATTATTGGGCGTAAAGCGCGCGCAGGTGGTTTCTTAAGTCTGATGT<br>GAAAGCCCACGGCTCAACCGTGGAGGGTCATTGGAAACTGGGAGACT<br>TGAGTGCAGAAGAGGAAAGTGGAATTCCATGTGTAGCGGTGAAATGC<br>GTAGAGATATGGAGGAACACCAGTGGCGAAGGCGACTTTCTGGTCTG<br>TAACTGACACTGAGGCGCGAAAGCGTGGGGAGCAAACAGGATTAGA<br>TACCCTGGTAGTCCACGCCGTAAACGATGAGTGCTAAGTGTTAGAGG<br>GTTTCCGCCCTTTAGTGCTGAAGTTAACGCATTAAGCACTCCGCCTGG<br>GGAGTACGGCCGCAAGGCTGAAACTCAAAGGAATTGACGGGGGCCC<br>GCACAAGCGGTGGAGCATGTGGTTTAATTCGAAGCAACGCGAAGAAC<br>CTTACCAGGTCTTGACATCCTCTGACAACCCTAGAGATAGGGCTTCCC<br>CTTCGGGGGCAGAGTGACAGGTGGTGCATGGTTGTCGTCAGCTCGTG<br>TCGTGAGATGTTGGGTTAAGTCCCGCAACGAGCGCAACCCTTGATCTT<br>AGTTGCCATCATTAAGTTGGGCACTCTAAGGTGACTGCCGGTGACAA<br>ACCGGAGGAAGGTGGGGATGACGTCAAATCATCATGCCCCTTATGAC<br>CTGGGCTACACACGTGCTACAATGGACGGTACAAAGAGCTGCAAGAC<br>CGCGAGGTGGAGCTAATCTCATAAAACCGTTCTCAGTTCGGATTGTAG<br>GCTGCAACTCGCCTACATGAAGCTGGAATCGCTAGTAATCGCGGATC<br>AGCATGCCGCGGTGAATACGTTCCCGGGCCTTGTACACACCGCCCGTC<br>ACACCACGAGAGTTTGTAACACCCGAAGTCGGTGGGGTAACCTTTTT<br>GGAGCCAGCCGCCTAAGGTGGGACAGATGATTGGGGTGAAGTCGTAA<br>CAAGGTAGCCGTATCGGAAGGTGCGGCTGGATCACCTCCTTT |
| 58 | DP58 16S rRNA | AATGACGGTACCTGAAGAATAAGCACCGGCTAACTACGTGCCAGCAG<br>CCGCGGTAATACGTAGGGTGCAAGCGTTAATCGGAATTACTGGGCGT<br>AAAGCGTGCGCAGGCGGTTTTGTAAGTCTGATGTGAAATCCCCGGGC<br>TCAACCTGGGAATTGCATTGGAGACTGCAAGGCTAGAATCTGGCAGA<br>GGGGGGTAGAATTCCACGTGTAGCAGTGAAATGCGTAGATATGTGGA<br>GGAACACCGATGGCGAAGGCAGCCCCCTGGGTCAAGATTGACGCTCA<br>TGCACGAAAGCGTGGGGAGCAAACAGGATTAGATACCCTGGTAGTCC<br>ACGCCCTAAACGATGTCTACTAGTTGTCGGGTCTTAATTGACTTGGTA<br>ACGCAGCTAACGCGTGAAGTAGACCGCCTGGGGAGTACGGTCGCAAG<br>ATTAAAACTCAAAGGAATTGACGGGGACCCGCACAAGCGGTGGATGA<br>TGTGGATTAATTCGATGCAACGCGAAAAACCTTACCTACCCTTGACAT<br>GGCTGGAATCCTCGAGAGATTGGGGAGTGCTCGAAAGAGAACCAGTA<br>CACAGGTGCTGCATGGCTGTCGTCAGCTCGTGTCGTGAGATGTTGGGT<br>TAAGTCCCGCAACGAGCGCAACCCTTGTCATTAGTTGCTACGAAAGG<br>GCACTCTAATGAGACTGCCGGTGACAAACCGGAGGAAGGTGGGGATG<br>ACGTCAAGTCCTCATGGCCCTTATGGGTAGGGCTTCACACGTCATACA<br>ATGGTACATACAGAGCGCCGCCAACCCGCGAGGGGGAGCTAATCGCA<br>GAAAGTGTATCGTAGTCCGGATTGTAGTCTGCAACTCGACTGCATGA<br>AGTTGGAATCGCTAGTAATCGCGGATCAGCATGTCGCGGTGAATACG |

-continued

| Sequence Listing | | |
|---|---|---|
| Seq ID No. | Description | Sequence |
| | | TTCCCGGGTCTTGTACACACCGCCCGTCACACCATGGGAGCGGGTTTT ACCAGAAGTAGGTAGCTTAACCGTAAGGAGGGCGCTTACCACGGTAG GATTCGTGACTGGGGTGAAGTCGTAACAAGGTAGCCGTATCGGAAGG TGCGGCTGGATCACCTCCTTT |
| 59 | DP59 16S rRNA | TTGAAGAGTTTGATCATGGCTCAGATTGAACGCTGGCGGCAGGCCTA ACACATGCAAGTCGAACGGTAACAGGAAGCAGCTTGCTGCTTTGCTG ACGAGTGGCGGACGGGTGAGTAATGTCTGGGAAACTGCCTGATGGAG GGGGATAACTACTGGAAACGGTAGCTAATACCGCATAACGTCGCAAG ACCAAAGAGGGGGACCTTCGGGCCTCTTGCCATCAGATGTGCCCAGA TGGGATTAGCTAGTAGGTGGGGTAACGGCTCACCTAGGCGACGATCC CTAGCTGGTCTGAGAGGATGACCAGCCACACTGGAACTGAGACACGG TCCAGACTCCTACGGGAGGCAGCAGTGGGGAATATTGCACAATGGGC GCAAGCCTGATGCAGCCATGCCGCGTGTATGAAGAAGGCCTTCGGGT TGTAAAGTACTTTCAGCGGGGAGGAAGGCGATGCGGTTAATAACCGC GTCGATTGACGTTACCCGCAGAAGAAGCACCGGCTAACTCCGTGCCA GCAGCCGCGGTAATACGGAGGGTGCAAGCGTTAATCGGAATTACTGG GCGTAAAGCGCACGCAGGCGGTCTGTCAAGTCGGATGTGAAATCCCC GGGCTCAACCTGGGAACTGCATCCGAAACTGGCAGGCTTGAGTCTCG TAGAGGGGGGTAGAATTCCAGGTGTAGCGGTGAAATGCGTAGAGATC TGGAGGAATACCGGTGGCGAAGGCGGCCCCCTGGACGAAGACTGAC GCTCAGGTGCGAAAGCGTGGGGAGCAAACAGGATTAGATACCCTGGT AGTCCACGCCGTAAACGATGTCGACTTGGAGGTTGTGCCCTTGAGGC GTGGCTTCCGGAGCTAACGCGTTAAGTCGACCGCCTGGGGAGTACGG CCGCAAGGTTAAAACTCAAATGAATTGACGGGGGCCCGCACAAGCGG TGGAGCATGTGGTTTAATTCGATGCAACGCGAAGAACCTTACCTGGTC TTGACATCCACAGAACTTGGCAGAGATGCCTTGGTGCCTTCGGGAACT GTGAGACAGGTGCTGCATGGCTGTCGTCAGCTCGTGTTGTGAAATGTT GGGTTAAGTCCCGCAACGAGCGCAACCCTTATCCTTTGTTGCCAGCGG TTAGGCCGGGAACTCAAAGGAGACTGCCAGTGATAAACTGGAGGAA GGTGGGGATGACGTCAAGTCATCATGGCCCTTACGACCAGGGCTACA CACGTGCTACAATGGCGCATACAAAGAGAAGCGATCTCGCGAGAGCC AGCGGACCTCATAAAGTGCGTCGTAGTCCGGATTGGAGTCTGCAACT CGACTCCATGAAGTCGGAATCGCTAGTAATCGTGAATCAGAATGTCA CGGTGAATACGTTCCCGGGCCTTGTACACACCGCCCGTCACACCATGG GAGTGGGTTGCAAAAGAAGTAGGTAGCTTAACCTTCGGGAGGGCGCT TACCACTTTGTGATTCATGACTGGGGTGAAGTCGTAACAAGGTAACC GTAGGGGAACCTGCGGTTGGATCACCTCCTT |
| 60 | DP60 16S rRNA | TCGGAGAGTTTGATCCTGGCTCAGGACGAACGCTGGCGGCGTGCCTA ATACATGCAAGTCGAGCGAATCGATGGGAGCTTGCTCCCTGAGATTA GCGGCGGACGGGTGAGTAACACGTGGGCAACCTGCCTATAAGACTGG GATAACTTCGGGAAACCGGAGCTAATACCGGATACGTTCTTTTCTCGC ATGAGAGAAGATGGAAAGACGGTTTTGCTGTCACTTATAGATGGGCC CGCGGCGCATTAGCTAGTTGGTGAGGTAATGGCTCACCAAGGCGACG ATGCGTAGCCGACCTGAGAGGGTGATCGGCCACACTGGGACTGAGAC ACGGCCCAGACTCCTACGGGAGGCAGCAGTAGGGAATCTTCCGCAAT GGACGAAAGTCTGACGGAGCAACGCCGCGTGAACGAAGAAGGCCTT CGGGTCGTAAAGTTCTGTTGTTAGGGAAGAACAAGTACCAGAGTAAC TGCTGGTACCTTGACGGTACCTAACCAGAAAGCCACGGCTAACTACG TGCCAGCAGCCGCGGTAATACGTAGGTGGCAAGCGTTGTCCGGAATT ATTGGGCGTAAAGCGCGCGCAGGTGGTTCCTTAAGTCTGATGTGAAA GCCCACGGCTCAACCGTGGAGGGTCATTGGAAACTGGGGAACTTGAG TGCAGAAGAGGAAAGTGGAATTCCAAGTGTAGCGGTGAAATGCGTAG AGATTTGGAGGAACACCAGTGGCGAAGGCGACTTTCTGGTCTGTAAC TGACACTGAGGCGCGAAAGCGTGGGGAGCAAACAGGATTAGATACC CTGGTAGTCCACGCCGTAAACGATGAGTGCTAAGTGTTAGAGGGTTT CCGCCCTTTAGTGCTGCAGCTAACGCATTAAGCACTCCGCCTGGGGAG TACGGCCGCAAGGCTGAAACTCAAAGGAATTGACGGGGGCCCGCACA AGCGGTGGAGCATGTGGTTTAATTCGAAGCAACGCGAAGAACCTTAC CAGGTCTTGACATCCTCTGACAACCCTAGAGATAGGGCGTTCCCCTTC GGGGGACAGAGTGACAGGTGGTGCATGGTTGTCGTCAGCTCGTGTCG TGAGATGTTGGGTTAAGTCCCGCAACGAGCGCAACCCTTGATCTTAGT TGCCAGCATTCAGTTGGGCACTCTAAGGTGACTGCCGGTGACAAACC GGAGGAAGGTGGGGATGACGTCAAATCATCATGCCCCTTATGACCTG GGCTACACACGTGCTACAATGGATGGTACAAAGGGCTGCAAACCTGC GAAGGTAAGCGAATCCCATAAAGCCATTCTCAGTTCGGATTGTAGGC TGCAACTCGCCTACATGAAGCCGGAATCGCTAGTAATCGCGGATCAG CATGCCGCGGTGAATACGTTCCCGGGCCTTGTACACACCGCCCGTCAC ACCACGAGAGTTTGTAACACCCGAAGTCGGTGAGGTAACCTTTATGG AGCCAGCCGCCTAAGGTGGGACAGATGATTGGGGTGAAGTCGTAACA AGGTAGCCGTATCGGAAGGTGCGGCTGGATCACCTCCTTT |

-continued

Sequence Listing

| Seq ID No. | Description | Sequence |
|---|---|---|
| 61 | DP61 16S rRNA | GGAAGGCGGTCTGTCAAGTCGGATGTGAAATCCCCGGGCTCAACCTG GGAACTGCATTCGAAACTGGCAGGCTAGAGTCTTGTAGAGGGGGGTA GAATTCCAGGTGTAGCGGTGAAATGCGTAGAGATCTGGAGGAATACC GGTGGCGAAGGCGGCCCCCTGGACAAAGACTGACGCTCAGGTGCGAA AGCGTGGGGAGCAAACAGGATTAGATACCCTGGTAGTCCACGCCGTA AACGATGTCGACTTGGAGGTTGTTCCCTTGAGGAGTGGCTTCCGGAGC TAACGCGTTAAGTCGACCGCCTGGGGAGTACGGCCGCAAGGTTAAAA CTCAAATGAATTGACGGGGGCCCGCACAAGCGGTGGAGCATGTGGTT TAATTCGATGCAACGCGAAGAACCTTACCTACTCTTGACATCCACGGA ATTTAGCAGAGATGCTTTAGTGCCTTCGGGAACCGTGAGACAGGTGC TGCATGGCTGTCGTCAGCTCGTGTTGTGAAATGTTGGGTTAAGTCCCG CAACGAGCGCAACCCTTATCCTTTGTTGCCAGCGGTCCGGCCGGGAA CTCAAAGGAGACTGCCAGTGATAAACTGGAGGAAGGTGGGGATGAC GTCAAGTCATCATGGCCCTTACGAGTAGGGCTACACACGTGCTACAA TGGCGCATACAAAGAGAAGCGACCTCGCGAGAGCAAGCGGACCTCAT AAAGTGCGTCGTAGTCCGGATCGGAGTCTGCAACTCGACTCCGTGAA GTCGGAATCGCTAGTAATCGTAGATCAGAATGCTACGGTGAATACGT TCCCGGGCCTTGTACACACCGCCCGTCACACCATGGGAGTGGGTTGC AAAAGAAGTAGGTAGCTTAACCTTCGGGAGGGCGCTTACCACTTTGT GATTCATGACTGGGGTGAAGTCGTAACAAGGTAACCGTAGGGGAACC TGCGGTTGGATCACCTCCTT |
| 62 | DP62 16S rRNA | TGGCTCAGATTGAACGCTGGCGGCAGGCCTAACACATGCAAGTCGAA CGGTAGCACAGAGGAGCTTGCTCCTTGGGTGACGAGTGGCGGACGGG TGAGTAATGTCTGGGAAACTGCCCGATGGAGGGGGATAACTACTGGA AACGGTAGCTAATACCGCATAACGTCTTCGGACCAAAGTGGGGGACC TTCGGGCCTCACACCATCGGATGTGCCCAGATGGGATTAGCTAGTAG GTGGGGTAATGGCTCACCTAGGCGACGATCCCTAGCTGGTCTGAGAG GATGACCAGCCACACTGGAACTGAGACACGGTCCAGACTCCTACGGG AGGCAGCAGTGGGGAATATTGCACAATGGGCGCAAGCCTGATGCAGC CATGCCGCGTGTATGAAGAAGGCCTTCGGGTTGTAAAGTACTTTCAGT GGGGAGGAAGGCGTTAAGGTTAATAACCTTGGCGATTGACGTTACCC GCAGAAGAAGCACCGGCTAACTCCGTGCCAGCAGCCGCGGTAATACG GAGGGTGCAAGCGTTAATCGGAATTACTGGGCGTAAAGCGCACGCAG GCGGTCTGTCAAGTCGGATGTGAAATCCCCGGGCTCAACCTGGGAAC TGCATTCGAAACTGGCAGGCTAGAGTCTTGTAGAGGGGGGTAGAATT CCAGGTGTAGCGGTGAAATGCGTAGAGATCTGGAGGAATACCGGTGG CGAAGGCGGCCCCCTGGACAAAGACTGACGCTCAGGTGCGAAAGCGT GGGGAGCAAACAGGATTAGATACCCTGGTAGTCCACGCCGTAAACGA TGTCGACTTGGAGGTTGTTCCCTTGAGGAGTGGCTTCCGGAGCTAACG CGTTAAGTCGACCGCCTGGGGAGTACGG |
| 63 | DP63 16S rRNA | TGAAGAGTTTGATCATGGCTCAGATTGAACGCTGGCGGCAGGCCTAA CACATGCAAGTCGAGCGGTAGAGAGAAGCTTGCTTCTCTTGAGAGCG GCGGACGGGTGAGTAATGCCTAGGAATCTGCCTGGTAGTGGGGGATA ACGTTCGGAAACGGACGCTAATACCGCATACGTCCTACGGGAGAAAG CAGGGGACCTTCGGGCCTTGCGCTATCAGATGAGCCTAGGTCGGATT AGCTAGTTGGTGAGGTAATGGCTCACCAAGGCGACGATCCGTAACTG GTCTGAGAGGATGATCAGTCACACTGGAACTGAGACACGGTCCAGAC TCCTACGGGAGGCAGCAGTGGGGAATATTGGACAATGGGCGAAAGCC TGATCCAGCCATGCCGCGTGTGTGAAGAAGGTCTTCGGATTGTAAAG CACTTTAAGTTGGGAGGAAGGGTTGTAGATTAATACTCTGCAATTTTG ACGTTACCGACAGAATAAGCACCGGCTAACTCTGTGCCAGCAGCCGC GGTAATACAGAGGGTGCAAGCGTTAATCGGAATTACTGGGCGTAAAG CGCGCGTAGGTGGTTTGTTAAGTTGGATGTGAAATCCCCGGGCTCAAC CTGGGAACTGCATTCAAAACTGACTGACTAGAGTATGGTAGAGGGTG GTGGAATTTCCTGTGTAGCGGTGAAATGCGTAGATATAGGAAGGAAC ACCAGTGGCGAAGGCGACCACCTGGACTAATACTGACACTGAGGTGC GAAAGCGTGGGGAGCAAACAGGATTAGATACCCTGGTAGTCCACGCC GTAAACGATGTCAACTAGCCGTTGGAAGCCTTGAGCTTTTAGTGGCGC AGCTAACGCATTAAGTTGACCGCCTGGGGAGTACGGCCGCAAGGTTA AAACTCAAATGAATTGACGGGGGCCCGCACAAGCGGTGGAGCATGTG GTTTAATTCGAAGCAACGCGAAGAACCTTACCAGGCCTTGACATCCA ATGAACTTTCTAGAGATAGATTGGTGCCTTCGGGAACATTGAGACAG GTGCTGCATGGCTGTCGTCAGCTCGTGTCGTGAGATGTTGGGTTAAGT CCCGTAACGAGCGCAACCCTTGTTCTTAGTTACCAGCACGTTATGGTG GGCACTCTAAGGAGACTGCCGGTGACAAACCGGAGGAAGGTGGGGA TGACGTCAAGTCATCATGGCCCTTACGGCCTGGGCTACACACGTGCTA CAATGGTCGGTACAGAGGGTTGCCAAGCCGCGAGGTGGAGCTAATCC CATAAAACCGATCGTAGTCCGGATCGCAGTCTGCAACTCGACTGCGT GAAGTCGGAATCGCTAGTAATCGCGAATCAGAATGTCGCGGTGAATA CGTTCCCGGGCCTTGTACACACCGCCCGTCACACCATGGGAGTGGGTT GCACCAGAAGTAGCTAGTCTAACCTTCGGGAGGACGGTTACCACGGT |

-continued

Sequence Listing

| Seq ID No. | Description | Sequence |
|---|---|---|
| | | GTGATTCATGACTGGGGTGAAGTCGTAACAAGGTAGCCGTAGGGGAA CCTGCGGCTGGATCACCTCCTT |
| 64 | DP64 ITS sequence | TCCGTAGGTGAACCTGCGGAAGGATCATTAAATAATCAATAATTTTG GCTTGTCCATTATTATCTATTTACTGTGAACTGTATTATTACTTGACGC TTGAGGGATGCTCCACTGCTATAAGGATAGGCGGTGGGGATGTTAAC CGAGTCATAGTCAAGCTTAGGCTTGGTATCCTATTATTATTTACCAAA AGAATTCAGAATTAATATTGTAACATAGACCTAAAAAATCTATAAAA CAACTTTTAACAACGGATCTCTTGGTTCTCGCATCGATGAAGAACGTA GCAAAGTGCGATAACTAGTGTGAATTGCATATTCAGTGAATCATCGA GTCTTTGAACGCAACTTGCGCTCATTGGTATTCCAATGAGCACGCCTG TTTCAGTATCAAAACAAACCCTCTATTCAATATTTTTGTTGAATAGGA ATACTGAGAGTCTCTTGATCTTTTCTGATCTCGAACCTCTTGAAATGT ACAAAGGCCTGATCTTGTTTGAATGCCTGAACTTTTTTTAATATAAA GAGAAGCTCTTGCGGTAAACTGTGCTGGGGCCTCCCAAATAATACTCT TTTTAAATTTGATCTGAAATCAGGCGGGATTACCCGCTGAACTTAAGC ATATCAATAAGCGGAGGAAAAGAAAATAACAATGATTTCCCTAGTAA CGGCGAGTGAAGAGGAAAGAGCTCAAAGTTGGAAACTGTTTGGCTTA GCTAAACCGTATTGTAAACTGTAGAAACATTTTCCTGGCACGCCGGAT TAATAAGTCCTTTGGAACAAGGCATCATGGAGGGTGAGAATCCCGTC TTTGATCCGAGTAGTTGTCTTTTGTGATATGTTTTCAAAGAGTCAGGTT GTTTGGGAATGCAGCCTAAATTGGGTGGTAAATCTCACCTAAAGCTA AATATTTGCGAGAGACCGATAGCGAACAAGTACCGTGAGGGAAAGAT GAAAAGAACTTTGAAAAGAGAGTTAAACAGTATGTGAAATTGTTAAA AGGGAACCGTTTGGAGCCAGACTGGTTTGACTGTAATCAACCTAGAA TTCGTTCTGGGTGCACTTGCAGTCTATACCTGCCAACAACAGTTTGAT TTGGAGGAAAAAATTAGTAGGAATGTAGCCTCTCGAGGTGTTATAGC CTACTATCATACTCTGGATTGGACTGAGGAACGCAGCGAATGCCATT AGGCGAGATTGCTGGGTGCTTTCGCTAATAAATGTTAGAATTTCTGCT TCGGGTGGTGCTAATGTTTAAAGGAGGAACACATCTAGTATATTTTTT ATTCGCTTAGGTTGTTGGCTTAATGACTCTAAATGACCCGTCTTGAAA CACGGACCAAGGAGTCCACCATAAGTGCAAGTATTTGAGTGACAAAC TCATATGCGTAAGGAAACTGATTGATACGAAATCTTTTGATGGCAGTA TCACCCGGCGTTGACGTTTTATACTGAACTGACCGAGGTAAAGCACTT ATGATGGGACCCGAAAGATGGTGAACTATGCCTGAATAGGGTGAAGC CAGAGGAAACTCTGGTGGAGGCTCGTAGCGATTCTGACGTGCAAATC GATCGTCAAATTTGGGTATAGGGGCGAAAGACTAATCGAACCATCTA GTAGCTGGTTCCTGCCGAAGTTTCCCTCAGGA |
| 65 | DP65 ITS sequence | TCCGTAGGTGAACCTGCGGAAGGATCATTATTGAAAACAAGGGTGTC CAATTTAACTTGGAACCCGAACTTCTCAATTCTAACTTTGTGCATCTG TATTATGGCGAGCAGTCTTCGGATTGTGAGCCTTCACTTATAAACACT AGTCTATGAATGTAAAATTTTTATAACAAATAAAAACTTTCAACAACG GATCTCTTGGCTCTCGCATCGATGAAGAACGCAGCGAAATGCGATAC GTAATGTGAATTGCAGAATTCAGTGAATCATCGAATCTTTGAACGCAT CTTGCGCTCTCTGGTATTCCGGAGAGCATGTCTGTTTGAGTGTCATGA ATTCTTCAACCCAATCTTTTCTTGTAATCGATTGGTGTTTGGATTTTGA GCGCTGCTGGCTTCGGCCTAGCTCGTTCGTAATACATTAGCATCCCTA ATACAAGTTTGGATTGACTTGGCGTAATAGACTATTCGCTAAGGATTC GGTGGAAACATCGAGCCAACTTCATTAAGGAAGCTCCTAATTTAAAA GTCTACCTTTTGATTAGATCTCAAATCAGGCAGGATTACCCGCTGAAC TTAAGCATATCAATAAGCGGAGGAAAAGAAACTAACAAGGATTCCCC TAGTAGCGGCGAGCGAAGCGGGAAAAGCTCAAATTTGTAATCTGGCG TCTTCGACGTCCGAGTTGTAATCTCGAGAAGTGTTTTCCGTGATAGAC CGCATACAAGTCTCTTGGAACAGAGCGTCATAGTGGTGAGAACCCAG TACACGATGCGGATGCCTATTACTTTGTGATACACTTTCGAAGAGTCG AGTTGTTTGGGAATGCAGCTCAAATTGGGTGGTAAATTCCATCTAAAG CTAAATATTGGCGAGAGACCGATAGCGAACAAGTACCGTAAGGGAA AGATGAAAAGCACTTTGGAAAGAGAGTTAACAGTACGTGAAATTGTT GGAAGGGAAACACATGCAGTGATACTTGCTATTCGGGGCAACTCGAT TGGCAGGCCCGCATCAGTTTTTCGGGGCGGAAAAGCGTAGAGAGAAG GTAGCAATTTCGGTTGTGTTATAGCTCTTTACTGGATTCGCCCTGGGG GACTGAGGAACGCAGCGTGCTTTTAGCAATTCCTTCGGGAATTCCACG CTTAGGATGCGGGTTTATGGCTGTATATGACCCGTCTTGAAACACGGA CCAAGGAGTCTAACATGCTTGCGAGTATTTGGGTGTCAAACCCGGAT GCGCAATGAAAGTGAATGGAGGTGGGAAGCGCAAGCTGCACCATCG ACCGATCTGGATTTTTTAAGATGGATTTGAGTAAGAGCAAGTATGTTG GGACCCGAAAGATGGTGAACTATGCCTGAATAGGGCGAAGCCAGAG GAAACTCTGGTGGAGGCTCGTAGCGGTTCTGACGTGCAAATCGATCG TCAAATTTGGGTATAGGGGCGAAAGACTAATCGAACCATCTAGTAGC TGGTTCCTGCCGAAGTTTCCCTCAGGA |

-continued

Sequence Listing

| Seq ID No. | Description | Sequence |
|---|---|---|
| 66 | DP66 ITS sequence | TCCGTAGGTGAACCTGCGGAAGGATCATTACTGTGATTTATCCACCAC ACTGCGTGGGCGACACGAAACACCGAAACCGAACGCACGCCGTCAA GCAAGAAATCCACAAAACTTTCAACAACGGATCTCTTGGTTCTCGCAT CGATGAAGAGCGCAGCGAAATGCGATACCTAGTGTGAATTGCAGCCA TCGTGAATCATCGAGTTCTTGAACGCACATTGCGCCCGCTGGTATTCC GGCGGGCATGCCTGTCTGAGCGTCGTTTCCTTCTTGGAGCGGAGCTTC AGACCTGGCGGGCTGTCTTTCGGGACGGCGCGCCCAAAGCGAGGGGC CTTCTGCGCGAACTAGACTGTGCGCGCGGGGCGGCCGGCGAACTTAT ACCAAGCTCGACCTCAGATCAGGCAGGAGTACCCGCTGAACTTAAGC ATATCAATAAGCGGAGGAAAAGAAACCAACAGGGATTGCCCCAGTA GCGGCGAGTGAAGCGGCAAAAGCTCAGATTTGGAATCGCTTCGGCGA GTTGTGAATTGCAGGTTGGCGCCTCTGCGGCGGCGGCGGTCCAAGTC CCTTGGAACAGGGCGCCATTGAGGGTGAGAGCCCCGTGGGACCGTTT GCCTATGCTCTGAGGCCCTTCTGACGAGTCGAGTTGTTTGGGAATGCA GCTCTAAGCGGGTGGTAAATTCCATCTAAGGCTAAATACTGGCGAGA GACCGATAGCGAACAAGTACTGTGAAGGAAAGATGAAAAGCACTTTG AAAAGAGAGTGAAACAGCACGTGAAATTGTTGAAAGGGAAGGGTAT TGCGCCCGACATGGAGCGTGCGCACCGCTGCCCCTCGTGGGCGGCGC TCTGGGCGTGCTCTGGGCCAGCATCGGTTTTTGCCGCGGGAGAAGGG CGGCGGGCATGTAGCTCTTCGGAGTGTTATAGCCTGCCGCCGGCGCC GCGAGCGGGGACCGAGGACTGCGACTTTTGTCTCGGATGCTGGCACA ACGGCGCAACACCGCCCGTCTTGAAACATGGACCAAGGAGTCTAACG TCTATGCGAGTGTTTGGGTGTGAAACCCCGGGCGCGTAATGAAAGTG AACGTAGGTCGGACCGCTCCTCTCGGGGGGCGGGCACGATCGACCGA TCCTGATGTCTTCGGATGGATTTGAGTAAGAGCATAGCTGTTGGGACC CGAAAGATGGTGAACTATGCCTGAATAGGGTGAAGCCAGAGGAAACT CTGGTGGAGGCTCGTAGCGGTTCTGACGTGCAAATCGATCGTCGAATT TGGGTATAGGGGCGAAAGACTAATCGAACCATCTAGTAGCTGGTTCC TGCCGAAGTTTCCCTCAGGA |
| 67 | DP53 Glutamine--tRNA ligase | ATGAGCAAGCCCACTGTCGACCCCACTCTGAATCCAAAGGCTGGCCC TGCTGTCCCGGCTAACTTCCTGCGTCCAATCGTTCAGGCGGACCTAGA CTCGGGTAAATACACACAGATCGTGACCCGCTTTCCGCCGGAGCCAA ACGGCTATCTGCACATCGGTCATGCCAAATCCATTTGTGTGAACTTTG GGCTGGCTCAAGAGTTTGGCGGCGTGACGCATTTGCGTTTTGACGACA CCAACCCGGCAAAAGAAGACCAGGAATACATCGACGCCATCGAAAG CGACGTCAAGTGGCTGGGCTTCGAGTGGGCCGGTGAAGTGCGTTACG CGTCGCAATACTTCGATCAACTGCACGAGTGGGCGATTTACCTGATCA AAGAAGGCAAGGCCTACGTCTGCGACCTGACGCCCGAGCAAGCCAAG GAATACCGTGGCAGCCTGACCGAGCCCGGCAAGAACAGCCCGTTCCG CGACCGTAGCGTTGAAGAGAACCTGGATCTGTTCGCCCGCATGACCG CCGGTGAGTTTGAAGACGGCAAGCGTGTGCTGCGCGCCAAGATCGAC ATGACCTCGCCGAACATGAACCTGCGCGACCCGATCATGTACCGCAT CCGTCATGCCCATCACCACCAGACCGGTGACAAGTGGTGCATCTACC CCAACTATGACTTCACCCACGGTCAGTCGGATGCCATTGAAGGCATC ACCCATTCGATCTGCACCCTGGAGTTCGAAAGCCATCGTCCGCTGTAC GAATGGTTCCTGGACAGCCTGCCAGTACCGGCGCGCCCGCGTCAGTA CGAGTTCAGCCGTCTGAACCTCAACTACACCATCACCAGCAAGCGCA AGCTCAAGCAGCTGGTCGATGAAAAGCACGTCAACGGCTGGGATGAC CCGCGCATGTCGACGCTGTCGGGTTTCCGCCGTCGCGGTTACACGCCT AAATCGATTCGTAATTTCTGTGACATGGTCGGCACCAACCGTTCTGAC GGTGTTGTTGACTTCGGCATGCTGGAATTCAGCATTCGTGACGATTTG GACCACAGCGCGCCGCGCGCCATGTGCGTGCTGCGTCCATTGAAGGT GATTATTACCAACTACCCGGAAGGTCAGGTCGAAAACCTCGAGCTGC CTTGCCACCCGAAAGAAGACATGGGTGTGCGGGTGTTGCCGTTTGCC CGTGAAATCTACATCGACCGTGAAGACTTCATGGAAGAGCCGCCAAA AGGCTACAAGCGTCTTGAGCCTGCGGGCGAAGTGCGTTTGCGCGGCA GCTATGTGATCCGTGCCGACGAAGCGATCAAGGATGCCGATGGCAAC ATCGTTGAACTGCATTGCTCGTACGATCCGCTGACCCTGGGTAAAAAC CCTGAAGGTCGCAAGGTCAAGGGTGTTGTGCACTGGGTGCCGGCGGC GGCCAGCGTCGAATGCGAAGTGCGTTTGTATGATCGTCTGTTCCGCTC GCCGAACCCTGAAAAGGCCGAAGACGGCGCGGGCTTCCTGGAAAAC ATCAACCCTGACTCGCTGCAGGTACTGACCGGTTGTCGTGCTGAACCC TCGCTGGGCAATGCACAGCCGGAAGACCGTTTCCAGTTCGAGCGCGA AGGCTACTTCTGCGCAGATATCAAGGACTCGAAACCCGGTCACCCGG TATTCAACCGTACCGTGACCCTGCGTGATTCGTGGGGCCAGTGA |
| 68 | DP53 DNA gyrase subunit B | TTGAGCGAAGAAAACACGTACGACTCAACGAGCATTAAAGTGCTGAA AGGCCTTGATGCCGTACGCAAACGTCCCGGTATGTACATTGGTGATAC TGACGATGGCAGCGGTCTGCACCACATGGTGTTCGAAGTAGTCGACA ACTCCATCGACGAAGCGCTGGCTGGCCATTGCGACGACATCACCATC ACGATCCACCCGGACGAGTCCATCACCGTGCGCGATAACGGCCGCGG |

-continued

Sequence Listing

| Seq ID No. | Description | Sequence |
|---|---|---|
| | | TATTCCGGTTGACGTGCATAAAGAAGAAGGCGTATCTGCAGCCGAGG<br>TCATCATGACCGTGCTGCACGCCGGCGGTAAGTTCGATGACAACTCCT<br>ACAAAGTATCCGGCGGCTTGCACGGTGTAGGTGTTTCGGTGGTAAAC<br>GCCCTGTCCGAACTGCTGGTCTTGACTGTACGCCGCAGCGGCAAGATC<br>TGGGAACAGACCTACGTCCACGGTGTTCCTCAGGCGCCTATGGCTATT<br>GTGGGTGAAAGCGAAACCACGGGTACGCAGATCCACTTCAAGCCTTC<br>GGCTGAAACCTTCAAGAATATCCACTTTAGCTGGGACATCCTGGCCA<br>AGCGGATTCGTGAACTGTCCTTCCTGAACTCCGGTGTGGGTATCGTCC<br>TCAAGGACGAGCGCAGCGGCAAGGAGGAGCTGTTCAAGTACGAAGG<br>TGGCCTGCGTGCATTCGTTGATTACCTGAACACCAACAAGAACGCTGT<br>GAACCAGGTGTTCCACTTCAATGTTCAGCGTGAAGACGGCATCGGCG<br>TAGAAATCGCCCTGCAGTGGAACGACAGCTTCAACGAGAACCTGTTG<br>TGCTTCACCAACAACATTCCACAGCGCGATGGTGGCACGCACTTGGT<br>GGGCTTCCGCTCTGCCCTGACGCGTAACCTCAACACGTACATCGAAGC<br>TGAAGGCCTGGCCAAGAAGCACAAGGTCGCCACCACCGGTGATGACG<br>CCCGTGAAGGCTTGACCGCGATCATCTCGGTGAAAGTGCCGGATCCA<br>AAGTTCAGCTCGCAGACTAAAGACAAGCTGGTGTCTTCCGAAGTGAA<br>GACCGCTGTTGAACAGGAAATGGGCAAGTTCTTCTCCGACTTCCTGCT<br>GGAACACCCGAACGAAGCCAAGTTGATTGTCGGCAAGATGATCGACG<br>CAGCCCGTGCTCGTGAAGCTGCACGTAAAGCCCGTGAGATGACCCGT<br>CGTAAAGGCGCGTTGGACATCGCGGGCTTGCCGGGCAAGCTGGCTGA<br>CTGCCAGGAAAAAGACCCTGCTCTGTCCGAACTGTACCTGGTGGAAG<br>GTGACTCTGCTGGCGGCTCCGCCAAGCAGGGTCGCAACCGTCGTACC<br>CAAGCCATCCTGCCGTTGAAAGGTAAAATCCTCAACGTCGAGAAAGC<br>CCGTTTTGACAAGATGATCTCTTCGCAAGAAGTCGGCACCTTGATCAC<br>TGCGCTGGGCTGTGGCATCGGCCGCGAAGAGTACAACATCGACAAAC<br>TGCGCTATCACAACATCATCATCATGACCGATGCTGACGTTGACGGTT<br>CGCACATCCGTACCCTGCTGCTGACCTTCTTCTTCCGTCAGTTGCCGG<br>AGCTGATCGAGCGTGGCTACATCTACATCGCCCAGCCACCGTTGTACA<br>AAGTGAAAAAGGGCAAGCAAGAGCAGTACATCAAAGACGACGAGGC<br>CATGGAAGAGTACATGACCCAGTCGGCTCTTGAAGATGCCAGCCTGC<br>ACTTGAACGAAGATGCCCCTGGCATCTCCGGTGAGGCACTGGAGCGT<br>CTGGTGTACGACTTCCGCATGGTGATGAAGACCCTCAAGCGTTTGTCG<br>CGCCTGTACCCTCAGGAGCTGACCGAGCACTTCATCTACCTGCCGGCT<br>GTAAGCCTTGAGCAGTTGGGTGACCACGCTGCCATGCAGGACTGGAT<br>GGCCAAGTTTGAAGAGCGTCTGCGTCTGGTTGAGAAATCGGGCCTGG<br>TCTACAAAGCCAGCCTGCGTGAAGACCGTGAGCGTAATGTCTGGTTG<br>CCAGAGGTCGAACTGATCTCCCACGGCCACTCGACGTTCATCACCTTC<br>AACCGCGACTTCTTCGGCAGCAACGATTACAAAACCGTTGTGACCCT<br>GGGCGCTCAACTGAGCACCCTGCTGGATGAAGGCGCCTATATCCAGC<br>GTGGCGAACGTCGCAAGCAAGTGACCGAGTTCAAAGAAGCACTGGAC<br>TGGTTGATGGCTGAAAGCACCAAGCGTCACACCATCCAGCGCTACAA<br>AGGACTGGGTGAAATGAACCCGGATCAGCTCTGGGAAACCACGATGG<br>ACCCAAGCGTGCGTCGCATGCTGAAAGTCACCATCGAAGACGCGATC<br>GGCGCCGATCAGATCTTCAACACCTTGATGGGCGATGCTGTAGAACC<br>ACGTCGTGAATTCATCGAGAGCAACGCACTGGCAGTGTCCAACCTGG<br>ATTTCTGA |
| 69 | DP53 Isoleucine--tRNA ligase | ATGACCGACTACAAAGCCACGCTAAACCTCCCGGACACCGCCTTCCC<br>AATGAAGGCCGGCCTGCCACAGCGCGAACCGCAAATTTTGCAGCGCT<br>GGGACAGCATTGGCCTGTACGGGAAGTTGCGCGAGATTGGCAAGGAT<br>CGTCCGAAGTTCGTACTTCACGACGGTCCTCCGTACGCCAACGGCACT<br>ATCCATATCGGTCATGCGCTGAACAAGATTCTGAAAGACATGATCAT<br>CCGCTCCAAGACCCTGTCGGGTTTTGACGCGCCGTATGTGCCGGGCTG<br>GGATTGCCATGGTTTGCCGATTGAACACAAGGTCGAAGTGACCCACG<br>GTAAAAACCTGAGCGCGGATAAAACCCGCGAGCTGTGCCGTGCCTAC<br>GCCACCGAGCAGATCGAGGGGCAGAAGTCCGAGTTCATCCGTCTGGG<br>TGTGCTGGGTGATTTCGCCAACCCGTACAAGACCATGGACTTCAAAA<br>ACGAAGCCGGTGAAATCCGTGCTTTGGCTGAGATCGTCAAGGGCGGT<br>TTTGTGTTCAAGGGCCTCAAGCCGGTGAACTGGTGCTTCGATTGCGGT<br>TCGGCCCTGGCTGAAGCTGAAGTTGAATACCAGGACAAGAAGTCTGC<br>GGCCATCGACGTTGCCTTCCCGGTTGCCGACGAGGCCAAGCTGGCCG<br>AGGCCTTTGGTCTGGCGGCACTGAGCAAACCTGCTTCGATCGTGATCT<br>GGACCACCACCCCGTGGACCATTCCGGCCAACCAGGCGCTTAACGTA<br>CACCCGGAATTCACCTACGCGCTGGTCGACGTGGGCGACAAGTTGCT<br>GGTACTGGCTGAAGAACTGGTCGAATCGAGTCTGGCGCGTTACAACC<br>TGCAGGGTTCGGTCATCGCCACCACCACTGGCTCAGCGCTTGAACTAA<br>TCAACTTCCGTCACCCGTTCTATGACCGTCTGTCGCCTGTTTATCTGGC<br>CGACTACGTTGAGCTGGGTGCTGGCACTGGTGTGGTTCACTCGGCTCC<br>AGCCTACGGCGTAGACGACTTCGTGACCTGCAAAGCCTATGGCATGG<br>TCAACGACGACATCATCAACCCGGTGCAAAGCAATGGCGTTTACGTG<br>CCGTCGCTGGAGTTCTTCGGTGGCCAGTTCATCTGGAAGGCCAACCAG<br>AACATCATCGACAAGCTGATCGAAGTCGGTTCGCTGATGTTCACCGA |

-continued

Sequence Listing

| Seq ID No. | Description | Sequence |
|---|---|---|
| | | GACCATCAGCCACAGCTATATGCACTGCTGGCGCCACAAGACGCCGC TGATCTACCGTGCCACCGCCCAGTGGTTTATCGGTATGGACAAGCAGC CGACTGATGGCGATACCTTGCGCACCCGTGCGCTGCAAGCGATCGAA GACACCCAGTTCGTTCCGGCCTGGGGTCAGGCGCGCCTGCACTCGAT GATCGCCAACCGCCCGGACTGGTGCATCTCGCGTCAACGCAACTGGG GCGTGCCGATCCCGTTTTTCCTGAACAAGGAAAGCGGCGAGCTGCAC CCGCGCACCGTCGAAATGATGGAAGAAGTGGCCAAGCGCGTTGAAGT CGAAGGCATCGAGGCGTGGTTCAAGCTGGATGCTGCCGAGCTGCTGG GCGACGAAGCGCCGCTGTACGACAAGATCAGCGATACCCTCGACGTC TGGTTCGATTCGGGCACCACGCACTGGCATGTCCTTCGCGGTTCGCAC CCGATGGGTCATGAAACCGGCCCACGCGCTGATCTCTACCTTGAAGG CTCCGACCAGCACCGTGGCTGGTTCCACTCGTCGTTGCTGACCGGTTG CGCCATCGACAACCACGCGCCGTACCGCGAGCTGCTGACCCACGGTT TTACCGTGGACGAAGCGGGCCGCAAGATGTCCAAGTCGCTGGGCAAC GTGATTGCACCGCAAAAGGTCAACGACACCCTGGGCGCCGACATCAT GCGTCTGTGGGTTGCTTCGACCGACTACTCGGGCGAAATCGCGGTTTC CGACCAGATCCTGCAGCGCAGTGCGGACGCCTACCGACGTATCCGCA ATACCGCACGCTTCCTGCTGTCGAACCTGACCGGTTTCAATCCAGCCA CCGACATCCTGCCTGCCGAAGAAATGCTGGCACTGGACCGCTGGGCG GTGGATCGTGCGTTGCTGCTGCAACGTGAGCTGGAGCTGCATTACGG CGAATACCGTTTCTGGAACGTGTACTCCAAGGTGCACAACTTCTGCGT TCAGGAGCTGGGCGGTTTCTATCTCGACATCATCAAGGACCGCCAGT ACACCACCGGCGCCAACAGCAAGGCTCGCCGTTCGTGCCAGACCGCG CTGTTCCACATCTCTGAAGCGCTGGTGCGCTGGATCGCTCCGATCCTG GCGTTCACCGCTGATGAGTTGTGGCAGTACCTGCCGGGCGAGCGCAA CGAATCGGTCATGCTCAACACCTGGTACGAAGGCCTGACTGAACTGC CGGAAGGCACCGAACTGGATCGCGCCTACTGGGAGCGAATCATGGCG GTCAAGGTTGCGGTCAACAAGGAAATGGAAAACTTGCGCGCAGCCAA GGCCATTGGCGGTAACTTGCAAGCAGAAGTGACCTTGTTCGCCGAAG ATCAGCTGGCTGCTGATTTGTCCAAGTTGAGCAACGAACTGCGTTTCG TGTTGATCACCTCCACTGCCAGCGTTGCGCCTTTTGCGCAGGCTCCAG CAGATGCCGTGGTTACCGAAGTGGCTGGCCTCAAACTCAAGGTGGTC AAGTCGGCCCATGCCAAGTGCGCCCGTTGCTGGCACTGCCGTGAAGA CGTCGGCGTTAACCCCGAGCACCCTGAAATCTGCGGTCGTTGTGTAGA CAATATCAGCGGCGCTGGTGAGGTACGTCACTATGCCTAA |
| 70 | DP53 NADH-quinone oxidoreductase subunit C/D | ATGACTGCAGGCTCCGCTCTGTACATCCCGCCTTACAAGGCTGACGAC CAAGATGTGGTTGTCGAACTCAATACCCGTTTTGGCCCTGAGGCGTTC ACCGCCCAGGCCACGCGCACCGGCATGCCGGTGCTTTGGGTTAGCCG CGCAAAACTGGTCGAAGTACTGACCTTCCTGCGCAACCTGCCAAAAC CCTACGTCATGCTCTATGACCTGCACGGTGTGGACGAACGTCTGCGTA CCAAGCGTCAGGGCCTGCCATCGGGTGCAGACTTCACCGTCTTCTACC ACCTGATGTCGCTGGAACGTAACAGCGACGTCATGATCAAGGTGGCC CTGTCTGAAAAAGACCTGAGTGTCCCTACCGTGACCGGTATCTGGCCG AACGCCAACTGGTACGAGCGTGAAGTCTGGGACATGTTCGGCATCGA TTTCAAAGGCCACCCGCACCTGTCGCGCATCATGATGCCGCCGACCTG GGAAGGTCACCCGCTGCGCAAGGACTTCCCGGCCCGTGCCACAGAGT TCGATCCGTACAGCCTGACCCTGGCCAAGGTGCAGCTGGAAGAGGAA GCCGCGCGCTTCCGCCCGGAAGACTGGGGCATGAAACGCTCCGGTGA AAACGAGGACTACATGTTCCTCAACCTGGGCCCTAACCACCCTTCGGC TCACGGTGCCTTCCGCATCATCCTGCAGCTGGACGGTGAAGAGATCGT CGACTGCGTGCCTGACGTCGGTTACCACCACCGTGGCGCCGAGAAAA TGGCCGAACGCCAGTCCTGGCACAGTTTCATCCCGTACACCGACCGG ATCGATTACCTCGGCGGAGTGATGAACAACCTGCCGTACGTGCTCTCG GTCGAGAAGCTGGCCGGTATCAAAGTGCCGGATCGGGTCGACACCAT CCGCATCATGATGGCCGAATTCTTCCGTATCACCAGCCACCTGCTGTT CCTGGGTACCTATATCCAGGACGTGGGCGCCATGACCCCGGTGTTCTT CACGTTCACCGACCGTCAGCGCGCTTACAAGGTGATCGAGGCCATCA CCGGTTTCCGTCTGCACCCGGCCTGGTACCGCATCGGCGGCGTTGCCC ACGACCTGCCGAACGGCTGGGATCGCCTGGTCAAGGAATTCATCGAC TGGATGCCCAAGCGTCTGGACGAGTACCAGAAAGCCGCTCTGGACAA CAGCATCCTGCGTGGTCGTACCATCGGCGTTGCCGCCTACAACACCAA AGAGGCCCTGGAATGGGGCGTCACCGGTGCCGGCCTGCGCTCCACCG GTTGTGACTTCGATATCCGCAAGGCGCGCCCGTATTCCGGCTACGAGA ACTTCGAATTCGAAGTCCCGCTGGCAGCCAACGGCGATGCCTACGAT CGTTGCATCGTGCGCGTCGAAGAAATGCGCCAGAGCCTGAAAATCAT CGAGCAGTGCATGCGCAACATGCCGGCCGGCCCGTACAAGGCGGATC ACCCGCTGACCACGCCGCCGCCTAAAGAACGCACGCTGCAGCATATC GAGACCTTGATCACGCACTTCCTGCAAGTTTCGTGGGGCCCGGTGATG CCGGCCAACGAATCCTTCCAGATGATCGAAGCGACCAAGGGCATCAA CAGTTATTACCTGACGAGCGATGGCGGCACCATGAGCTACCGCACCC |

-continued

Sequence Listing

| Seq ID No. | Description | Sequence |
|---|---|---|
| | | GGATTCGCACCCCAAGCTTCCCGCACCTGCAACAGATCCCTTCGGTGA<br>TCAAAGGTGAAATGGTCGCGGACTTGATTGCGTACCTGGGTAGTATC<br>GATTTCGTTATGGCCGACGTGGACCGCTAA |
| 71 | DP53 Protein RecA | ATGGACGACAACAAGAAGAAAGCCTTGGCTGCGGCCCTGGGTCAGAT<br>CGAACGTCAATTCGGCAAGGGTGCCGTGATGCTGATGGGCGACCAGG<br>AGCGTCAGGCAGTCCCGGCGATCTCCACCGGCTCCCTGGGTCTGGAC<br>ATCGCACTGGGCATTGGCGGTCTGCCAAAAGGCCGTATTGTTGAAAT<br>CTACGGCCCTGAGTCGTCGGGTAAAACCACACTGACCCTGTCCGTGAT<br>TGCCCAGGCGCAAAAGGCCGGTGCTACCTGCGCCTTCGTCGATGCCG<br>AGCACGCCCTTGATCCTGAGTACGCTGCCAAACTGGGCGTAAACGTT<br>GATGACCTGCTGGTTTCACAGCCTGACACCGGCGAACAGGCACTGGA<br>AATCACCGATATGCTGGTGCGTTCCAATGCGGTTGACGTGATCATCAT<br>CGACTCCGTTGCTGCACTGACGCCAAAAGCTGAAATCGAAGGCGACA<br>TGGGCGATACCCACGTTGGCCTGCAAGCCCGTCTGATGTCGCAAGCG<br>CTGCGTAAAATCACCGGTAACATCAAGAACGCCAACTGCCTGGTTAT<br>CTTCATCAACCAGATCCGCATGAAAATCGGCGTGATGTTCGGCAGCC<br>CTGAAACCACCACCGGTGGTAACGCACTGAAGTTCTACGCTTCGGTA<br>CGTCTGGATATCCGCCGCACCGGCGCCGTAAAAGAAGGCGATGTGGT<br>GGTGGGTAGCGAAACCCGCGTGAAAGTGGTCAAGAACAAGGTGGCA<br>CCACCGTTCCGTCAGGCTGAATTCCAGATCCTGTACGGCAAGGGTATC<br>TACCTGAACGGTGAAATGATTGACCTGGGCGTACTGCATGGCTTTGTT<br>GAAAAAGCTGGCGCCTGGTACAGCTACAACGGCAGCAAAATCGGTCA<br>GGGCAAGGCCAACTCCGCCAAGTTCCTGGACGATAACCCGGACATCA<br>AGGATGCGCTGGAGAAGCAGCTGCGTGAGAAGTTGCTCGGGCCAAAA<br>ACCGATGCCGAACTGGCAGCGACGGACTGCAATGGACCTGCTCGCGC<br>GACGCGAGCACGGTCGAGTCGAGCTGACGCGCAAGTTGCGTCAGCGC<br>GGCGCTTGCCCCGACATGATCGACGCTGCCCTTGA |
| 72 | DP53 RNA polymerase sigma factor RpoD | ATGTCCGGAAAAGCGCAACAGCAGTCTCGTATCAAAGAGTTGATCAC<br>CCTCGGCCGTGAGCAGAAGTATCTGACTTACGCAGAGGTCAACGACC<br>ACCTGCCCGAAGATATTTCAGATCCGGAGCAAGTGGAAGACATCATC<br>CGCATGATTAATGACATGGGGATCCCCGTACACGAGAGTGCTCCGGA<br>TGCGGACGCCCTTATGTTGGCCGATGCCGACACCGACGAAGCAGCAG<br>CTGAAGAAGCGGCTGCAGCGTTGGCGGCAGTAGAGACCGACATTGGT<br>CGTACTACCGACCCTGTGCGCATGTATATGCGTGAAATGGGCACGGT<br>AGAACTGCTGACACGTGAAGGCGAAATCGAAATCGCCAAGCGTATCG<br>AAGAAGGCATCCGTGAAGTGATGGGCGCAATCGCGCACTTCCCTGGC<br>ACGGTTGACCATATTCTCTCCGAGTACACTCGCGTCACCACCGAAGGT<br>GGCCGCCTGTCCGACGTTCTGAGCGGTTATATCGACCCGGACGACGG<br>TATTGCGCCGCCCGCAGCCGAAGTACCTCCTCCTGTCGACACCAAGGT<br>GAAAGCCGAAGGTGATGACGAAGAGGACGACAAGGAAGATTCCGGC<br>GAAGACGAGGAAGAGGTCGAAAGCGGCCCTGATCCGATCATCGCGG<br>CCCAGCGCTTTGGCGCTGTTTTCGATCAGATGGAAATCGCTCGCAAGG<br>CCCTGAAAAAGCACGGTCGCGGCAGCAAGCAGGCAATTGCCGAGCTG<br>GTTGCACTGGCTGAGCTGTTCATGCCGATCAAACTGGTTCCGAAGCAA<br>TTCGAAGGCCTGGTTGAGCGTGTTCGCAGCGCCCTGGAGCGTCTGCGT<br>GCACAAGAGCGCGCAATCATGCAGCTGTGTGTACGTGATGCACGCAT<br>GCCGCGCACCGATTTCCTGCGTCTGTTCCCGGGCAACGAAGTCGACG<br>AAAGCTGGAGCGATGCGCTGGCCAAAGGCAAAAGCAAATATGCTGA<br>AGCCATTGGTCGCCTGCAACCGGACATCATCCGTTGCCAGCAAAAGC<br>TCTCTGCTCTGGAAGCAGAAACCGGCTTGAAGATTGCCGAGATCAAG<br>GACATCAACCGTCGCATGTCGATCGGCGAGGCCAAGGCCCGCCGCGC<br>GAAGAAAGAAATGGTTGAAGCCAACTTGCGTCTGGTGATCTCCATCG<br>CCAAGAAGTACACCAACCGTGGCCTGCAGTTCCTCGATCTGATCCAG<br>GAAGGCAACATCGGCTTGATGAAAGCGGTAGACAAGTTTGAATACCG<br>CCGCGGCTACAAATTCTCGACTTATGCCACCTGGTGGATCCGTCAGGC<br>GATCACTCGCTCGATCGCCGACCAGGCCCGCACCATCCGTATTCCGGT<br>GCACATGATCGAGACGATCAACAAGCTCAACCGTATTTCCCGTCAGA<br>TGTTGCAGGAAATGGGCCGTGAACCGACCCCGGAAGAGCTGGGCGAA<br>CGCATGGAAATGCCTGAGGATAAAATCCGCAAGGTATTGAAGATCGC<br>TAAAGAGCCGATCTCCATGGAAACCCCGATCGGTGATGACGAAGACT<br>CCCATCTGGGTGACTTCATCGAAGACTCGACCATGCAGTCGCCAATCG<br>ATGTTGCTACCGTTGAGAGCCTTAAAGAAGCGACACGCGACGTACTC<br>GGCGGCCTCACAGCCCGTGAAGCCAAGGTACTGCGCATGCGTTTCGG<br>TATCGACATGAATACCGACCACACCCTTGAGGAGGTTGGTAAACAGT<br>TCGACGTTACCCGTGAGCGGATTCGTCAGATCGAAGCCAAGGCGCTG<br>CGCAAGCTGCGCCACCCGACGAGAAGCGAGCATTTGCGCTCCTTCCT<br>CGACGAGTGA |
| 73 | DP53 DNA-directed RNA polymerase | ATGGCTTACTCATATACTGAGAAAAAACGTATCCGCAAGGACTTTAG<br>CAAGTTGCCGGACGTCATGGATGTGCCGTATCTCTTGGCAATCCAGCT<br>GGATTCGTATCGTGAATTCTTGCAGGCGGGAGCGACTAAAGATCAGT |

-continued

Sequence Listing

| Seq ID No. | Description | Sequence |
|---|---|---|
| | subunit beta | TCCGCGACGTGGGCCTGCATGCGGCCTTCAAATCCGTTTTCCCGATCA<br>TCAGCTACTCCGGCAATGCTGCGCTGGAGTACGTCGGTTATCGCTTGG<br>GCGAACCGGCATTTGATGTCAAAGAATGCGTGTTGCGTGGCGTAACG<br>TACGCCGTACCTTTGCGGGTAAAAGTTCGTTTGATCATTTTCGACAAA<br>GAATCGTCGAACAAAGCGATCAAGGACATCAAAGAGCAAGAAGTCT<br>ACATGGGTGAAATCCCCCTGATGACTGAAAACGGTACCTTCGTAATC<br>AACGGTACCGAGCGTGTAATTGTTTCCCAGCTGCACCGTTCCCCGGGC<br>GTGTTCTTTGCCACGACCGCGGCAAGACGCACAGCTCCGGTAAGCTG<br>CTTTATTCCGCGCGTATCATTCCTTACCGTGGTTCGTGGCTCGACTTCG<br>AGTTCGACCCGAAAGACTGCGTGTTCGTGCGTATTGACCGTCGTCGCA<br>AGCTGCCTGCATCGGTATTGCTGCGCGCGCTGGGTTATACCACTGAGC<br>AAGTGCTGGACGCGTTCTACACCACCAACGTGTTCCACGTTCAGGGTG<br>AGAGCATCAGCCTGGAGCTGGTTCCACAGCGTCTGCGCGGTGAAATC<br>GCGGCCATCGACATTACCGATGACAAAGGCAAGGTGATTGTTGAGCA<br>GGGTCGTCGTATCACTGCTCGTCATATCAACCAGCTGGAAAAAGCCG<br>GTGTCAAAGAGCTCGTTATGCCTCTGGACTATGTCCTGGGTCGCACAA<br>CGGCCAAGGCTATCGTGCATCCGGCTACTGGCGAAATCATTGCTGAG<br>TGCAACACCGAGCTGACCACTGAAATCCTGGCAAAAGTTGCCAAGGG<br>CCAGGTTGTTCGCATCGAAACGTTGTACACCAACGATATCGACTGCG<br>GTCCGTTCGTCTCCGACACGCTGAAGATCGACTCCACCAGCAACCAA<br>CTGGAAGCGCTGGTCGAAATCTATCGCATGATGCGTCCAGGCGAGCC<br>GCCAACCAAAGACGCTGCCGAGACTCTGTTCAACAACCTGTTCTTCAG<br>CCCTGAGCGCTATGACCTGTCTGCGGTCGGCCGGATGAAGTTCAACC<br>GTCGTATCGGTCGTACCGAGATCGAAGGTTCGGGCGTGTTGTGCAAA<br>GAAGACATCGTTGCCGTGCTGAAGACCCTGGTCGACATCCGTAACGG<br>TAAAGGCATCGTCGATGACATCGACCACCTGGGTAACCGTCGTGTTC<br>GCTGTGTAGGCGAAATGGCCGAGAACCAGTTCCGCGTTGGCCTGGTA<br>CGTGTTGAGCGTGCGGTCAAAGAGCGTCTGTCGATGGCTGAAAGCGA<br>AGGCCTGATGCCGCAAGACCTGATCAACGCCAAGCCTGTGGCTGCGG<br>CGGTGAAAGAGTTCTTCGGTTCCAGCCAGCTGTCCCAGTTCATGGACC<br>AGAACAACCCTCTGTCCGAGATCACCCACAAGCGCCGTGTTTCTGCAC<br>TGGGCCCGGGCGGTCTGACGCGTGAGCGTGCGGGCTTTGAAGTTCGT<br>GACGTACACCCGACTCACTACGGCCGTGTTTGCCCTATTGAGACGCCG<br>GAAGGTCCGAACATCGGTCTGATCAACTCCCTGGCTGCCTATGCGCGC<br>ACCAACCAGTACGGCTTCCTCGAGAGCCCGTACCGTGTAGTGAAAGA<br>CGCACTGGTAACTGACGAGATCGTTTTCCTGTCCGCCATCGAAGAAGC<br>TGATCACGTGATCGCTCAGGCCTCGGCCACGATGAACGACAAGAAAG<br>TGCTGATCGACGAGCTGGTTGCTGTTCGTCACTTGAACGAATTCACCG<br>TCAAGGCGCCGGAAGACGTCACCTTGATGGACGTTTCGCCGAAGCAG<br>GTTGTTTCGGTTGCAGCGTCGCTGATCCCGTTCCTGGAACACGATGAC<br>GCCAACCGTGCGTTGATGGGTTCCAACATGCAGCGTCAAGCTGTACC<br>AACCCTGCGCGCTGACAAGCCGCTGGTAGGTACCGGCATGGAGCGTA<br>ACGTAGCTCGTGACTCCGGCGTTTGCGTCGTGGCTCGTCGTGGCGGCG<br>TGATCGACTCTGTTGATGCCAGCCGTATCGTGGTTCGTGTTGCTGATG<br>ACGAAGTTGAAACTGGCGAAGCCGGTGTCGACATCTACAACCTGACC<br>AAATACACCCGTTCCAACCAGAACACTTGCATCAACCAGCGTCCGCT<br>GGTGCGCAAGGGTGACCGTGTACAGCGTAGCGACATCATGGCTGACG<br>GCCCGTCCACCGATATGGGTGAACTGGCGCTGGGTCAAAACATGCGC<br>ATCGCGTTCATGGCCTGGAACGGTTACAACTTCGAAGACTCCATCTGC<br>TTGTCGGAACGAGTTGTTCAAGAAGACCGCTTTACCACGATCCACATT<br>CAGGAACTGACCTGTGTGGCACGTGACACCAAGCTTGGGCCTGAAGA<br>GATCACTGCAGACATCCCTAACGTGGGTGAAGCTGCACTGAACAAAC<br>TGGACGAAGCCGGTATCGTTTACGTAGGTGCTGAAGTTGGCGCCGGC<br>GACATTCTGGTAGGTAAGGTCACTCCGAAAGGCGAGACCCAGCTGAC<br>TCCGGAAGAGAAGCTGTTGCGTGCCATCTTCGGTGAAAAAGCCAGCG<br>ACGTTAAAGACACCTCCCTGCGCGTACCTACCGGTACCAAAGGTACT<br>GTTATCGACGTGCAGGTCTTCACCCGTGACGGCGTTGAGCGTGATGCT<br>CGTGCACTGTCGATCGAGAAGACCCAGCTGGACGAGATCCGCAAGGA<br>TCTGAACGAAGAGTTCCGTATCGTTGAAGGCGCTACCTTCGAACGTCT<br>GCGCTCTGCTCTGGTTGGCCGCATTGCCGAAGGTGGTGCCGGTCTGAA<br>GAAAGGTCAGGAAATCACCAATGAAATCCTGGACGGTCTTGAGCATG<br>GTCAGTGGTTCAAACTGCGCATGGCTGAAGATGCTCTGAACGAGCAG<br>CTTGAAAAGGCTCAGGCTTACATCATCGATCGCCGTCGTCTGCTGGAC<br>GACAAGTTCGAAGACAAGAAGCGCAAACTGCAGCAGGGCGATGACC<br>TGGCTCCAGGCGTGCTGAAAATCGTCAAGGTTTACCTGGCAATCCGCC<br>GTCGCATCCAGCCGGGTGACAAGATGGCCGGTCGTCACGGTAACAAG<br>GGTGTGGTCTCCGTGATCATGCCGGTTGAAGACATGCCGTACGATGCC<br>AATGGCACCCCGGTTGATGTGGTCCTCAACCCGTTGGGCGTACCTTCG<br>CGTATGAACGTTGGTCAGATTCTCGAAACTCACCTGGGCCTCGCGGCC<br>AAAGGTCTGGGCGAGAAGATCAACCTCATGATTGAAGAACAACGCAA<br>GGTCGCTGACCTGCGTAAGTTCCTGCATGAGATCTACAACGAAATTG<br>GCGGTCGTCAAGAAAGCCTGGATGACTTCTCCGATCAGGAAATCCTG<br>GATCTGGCGAAGAACCTTCGCGGCGGTGTGCCAATGGCTACCCCGGT |

-continued

Sequence Listing

| Seq ID No. | Description | Sequence |
|---|---|---|
| | | GTTCGACGGTGCCAAGGAAAGCGAAATCAAGGCAATGCTTCGTTTGG CAGACCTGCCAGACAGCGGCCAGATGGTGCTGACTGATGGTCGTACC GGCAACAAGTTCGAGCGTCCGGTTACCGTTGGCTACATGTACATGCTG AAGCTGAACCACTTGGTAGACGACAAGATGCACGCTCGTTCTACCGG TTCTTACAGCCTGGTTACCCAGCAGCCGCTGGGTGGTAAGGCGCAGTT CGGTGGTCAGCGTTTCGGGGAGATGGAGGTCTGGGCGCTGGAAGCCT ACGGCGCGGCATACACTCTGCAAGAAATGCTCACAGTGAAGTCGGAC GATGTGAACGGCCGTACCAAGATGTACAAAAACATCGTGGACGGCGA TCACCGTATGGAGCCGGGCATGCCCGAGTCCTTCAACGTGTTGATCAA AGAAATTCGTTCCCTCGGCATCGATATCGATCTGGAAACCGAATAA |
| 74 | DP9 Glycine--tRNA ligase beta subunit | ATGGCACATAATTATTTACTAGAAATTGGATTGGAAGAAATTCCGGC CCATGTTGTAACTCCAAGTATCAAACAGTTAGTACAAAAAGTAACAG CCTTCTTAAAAGAAAATCGCTTAACATACGACTCAATTGATCATTTTT CAACTCCTCGTCGTTTGGCAATTCGAATCAATGGGTTAGGCGACCAAC AACCTGATATTGAAGAAGATGCTAAAGGCCCTGCTCGTAAAATTGCT CAAGATGCTGATGGAAATTGGACTAAGGCTGCAATTGGCTTTACACG TGGACAAGGTCTTACGGTTGACGATATTACTTTTAAAACAATCAAAG GTACGGACTATGTGTACGTCCATAAGTTAATCAAAGGAAAGATGACT AAGGAAATCCTTACGGGGATAAAAGAAGTTGTTGAATCAATTAATTT CCCAACAATGATGAAGTGGGCTAACTTTGATTTTAAATATGTACGCCC AATTCGTTGGCTGGTTTCTATTCTAGATGAAGAAGTCCTTCCTTTTAGT ATCTTAGACGTAACTGCGGGACGCCGAACAGAAGGACATCGTTTCTT AGGTGAAGCTGTCGAACTGGCTAATGCTGAAGAATATGAAGCAAAAT TACACGATCAATTTGTGATTGTTGATGCCGACGAGCGTAAACAATTAA TTTCAAACCAAATTAAAGCAATTGCTGAAAGCAATCGTTGGAACGTT ACCCCTAACCCAGGTCTTTTAGAAGAGGTTAACAATTTGGTTGAGTGG CCAACCGCTTTTAATGGGGGATTTGATGAAAAGTATTTAGCTATTCCA GAAGAGGTATTGATAACATCAATGCGTGACCACCAACGCTTCTTCTTT GTCCGCGACCAAGCTGGAAAGCTATTGCCAAACTTCATCTCCGTACG AAATGGGAATGAAGAATTTATTGAAAATGTTGTTCGTGGAAATGAAA AAGTTTTAACTGCACGTTTAGAAGACGCTGCTTTCTTCTACGAAGAAG ATCAAAAACATGATATTAATTATTATGTTGACCGACTTAAAAAGGTTA GTTTCCATGATAAGATTGGTTCAATGTACGAAAAAATGCAACGAGTT AATTCTATTGCTAAAGTTATTGGAAACACCTTAAATCTTAATCAAACG GAACTTGATGATATCGATCGCGCTACAATGATTTATAAATTTGATTTG GTAACTGGTATGGTTGGTGAGTTCTCAGAATTACAAGGAGTAATGGG TGAAAAATATGCTCAACTTAATGGTGAAAACCAAGCAGTAGCCCAAG CCATTCGCGAACATTACATGCCAAATAGCGCAGAAGGTGATTTGCCT GAAAGTGTAACGGGCGCGGTAGTCGCATTAGCTGATAAGTTTGATAA CATCTTTAGTTTTTTCTCAGCTGGTATGATTCCAAGTGGTTCAAACGAT CCATATGCATTACGCCGACATGCATATGGAATTGTTAGAATCTTAAAT AGCCGTGATTGGCAATTAGATTTAAATCAATTCAAATCACAATTTAAG ACTGAATTAGCGGAGAATGGCACAGCGTTTGGTGTGGATGTCGATCA AAACTTTGACCAAGTACTTAACTTCTTTAATGACCGTATTAAACAATT GCTTGATCATCAAAAGATTAGTCATGATATCGTTGAAACGGTGCTTAC AGGTAATAATCATGATGTTACGGAAATTATCGAAGCTGCCCAAGTAC TAGCAGATGCTAAAGCGAGCTCTACATTTAAAGATGATATTGAAGCT TTAACACGAGTTCAAAGAATTGCTACAAAGAATGAAGAAAGTGGAGA ACTTAATGTAGATCCACAATTATTTAATAATGCTTCTGAAGGCGAACT TTTTGATCAAATTATTAAAATTGAAGCTGCAAATAATTTGACAATGAG CCAACTATTTGCTAAATTATGCGAGTTGACTCCTGCGATTAGCAAGTA CTTTGACGCAACGATGGTCATGGACAAAGACGAAAATATTAAGTGTA ATCGTTTGAATATGATGAGTCGGTTAGCTAATTTAATTCTAAAAATTG GGGATCTAACTAACGTACTTGTAAAATAA |
| 75 | DP9 Glutamine synthetase | ATGGCAAAGAAAAATTATTCGCAAGCAGATATTCGTCAGATGGCAAA GGATGAAAATGTACGTTTTCTCCGATTAATGTTTACAGATCTTTTTGG AATAATTAAGAACGTTGAAGTACCAATTAGTCAATTGGACAAACTAT TAGATAATAAATTGATGTTTGATGGTTCCTCAATTGACGGGTTTGTTC GGATTGAAGAAAGTGACATGTATTTATACCCAGATCTTTCTACTTGGA TGGTTTTCCCATGGGGAAGCGAACATGGCAAGGTGGCTCGCATTATTT GTGAAGTATACTCAAATGATCGTAAACCATTCGTGGGTGATCCACGT AACAATTTAATTCGAGTACTCCAAGAGATGAAGGATGCAGGATTTAC TGATTTTAATATCGGACCTGAACCTGAGTTTTTCTTGTTGAAATTAGA TGAAAATGGTAAACCAACCACTAATTTAAATGATAAAGGTAGTTACT TTGATTTAGCTCCTGTTGATTTAGGTGAAAACTGCCGTCGTGATATTG TTTTGGAACTTGAAAATATGGGCTTTGATGTTGAAGCTTCTCATCATG AAGTTGCTCCAGGACAACACGAAATTGACTTTAAATACGCCGATGCT TTGACCGCTGCCGATAACATTCAAACCTTTAAGTTGGTTGTTAAGACA GTTGCCCGTAAATATAACCTGCATGCTACATTTATGCCTAAACCTATG GATGGAATCAATGGTTCAGGGATGCATTTAAACATGTCACTTTTCAAT AAGGAAGGCAATGCTTTCTATGACGAAAAGGGTGACTTACAACTTTC |

-continued

Sequence Listing

| Seq ID No. | Description | Sequence |
|---|---|---|
| | | TCAAAATGCTTACTGGTTCCTTGGTGGACTATTGAAGCATGCTCGTAG TTATACGGCCGTATGTAACCCAATTGTTAACTCGTACAAACGTTTAGT TCCTGGATATGAAGCTCCAGTATACGTTGCTTGGTCAGGTTCAAATCG TTCACCACTTATTCGCGTTCCTTCAAGTAAGGGACTCTCAACTCGTTTT GAAGTTCGAAGCGTCGATCCAGCTGCTAACCCATACTTAGCAATTGC ATCAGTATTGGAAGCAGGCTTAGATGGCATTAGAAACAAGATTGAAC CAGAAGATTCCGTTGATCGTAATATCTATCGAATGAACATTCAAGAA CGTAATGAAGAGCATATTACAGATCTACCTTCAACATTACACAATGCT TTGAAGGAATTCCAAAATGATGATGTAATGCGTAAGGCATTAGGAGA TCACATTTTCCAAAGCTTCCTCGAAGCTAAGAAGTTAGAATGGGCTTC TTACCGTCAAGAAGTGACACAATGGGAACGTGATCAATATCTCGAAA TGTTCTAG |
| 76 | DP9 DNA gyrase subunit B | TTGGCAGACGAAAAAGAAACGAAAGCAGAATTAGCCAGAGAATATG ATGCGAGTCAAATTCAGGTTTTAGAGGGGCTCGAAGCAGTTCGTAAA CGCCCAGGAATGTATATTGGGTCGACTAGTTCTCAAGGACTACACCAT TTGGTTTGGGAAATTATTGATAATGGTATTGATGAAGCTCTTGCAGGA TTTGCAGACAAAATTGATGTGATCGTTGAAAAAGACAATAGTATTAC CGTCACTGATAATGGACGTGGGATTCCGGTTGATATCCAAAAGAAAA CTGGAAAACCAGCTTTAGAAACAGTCTTTACGGTCCTACATGCCGGA GGTAAATTCGGCGGTGGCGGTTATAAAGTTTCTGGAGGATTGCATGG TGTGGGCGCATCCGTTGTAAATGCGTTATCAACGGAATTAGATGCGC GCGTCATGAAGGACGGTAAAATCTATTACATTGATTTTGCGCTAGGA AAAGTAAAAACACCGATGAAAACGATTGGTGATACTGAACATCCTGA CGATCATGGAACTATTGTTCATTTCGTTCCAGATCCAGATATTTTCCA AGAAACTACCACATACGACATTAATATCTTAAAAACACGAATTCGTG AATTAGCCTTTTTGAACAAAGGTCTACGGATTACTTTGAAGGATATGC GTCCTGAAAAGCCAACTGAAGACGACTTCTTGTATGAAGGTGGGATT CGCCACTACGTTGAATATCTAAACGAAGGCAAAGAAGTAATTTTCCC TGAACCTATCTATGTTGAAGGGGTTACAAAAGGTATCACTGTTGAAGT AGCTATGCAATATATCGAAGGTTATCAAAGTAAATTGTTAACTTTTAC TAACAATATTCATACTTACGAAGGCGGTACCCACGAAGAAGGTTTCA AACGTGCTTTAACACGAGTTATTAACGATTACGCTAAAAACAACAAT ATTTTAAAAGAAAATGATGATAAATTGTCTGGTGATGATGTTCGAGA AGGTTTGACGGCAGTAGTCAGCGTTAAGCATCCTGATCCTCAATTCGA AGGACAAACGAAAACAAAATTGGGTAACTCAGATGCTCGGACAGCTG TTAACGAAGTGTTTGCTGAAACTTTCAATAAATTCTTATTGGAAAATC CTAAGGTTGCACGTCAAATTGTTGATAAGGGAATCTTGGCAGCAAAA GCAAGAGTCGCCGCTAAACGAGCTCGTGAAGTTACGCGTAAGAAGAG TGGCCTAGAACTCAATAATCTTCCTGGTAAATTAGCTGATAATACTTC TAAGGATCCTTCAATTAGTGAATTATTCATTGTCGAGGGTGATTCTGC CGGTGGTAGTGCTAAGTCGGGACGTTCGCGTCTCACACAAGCTATTTT GCCAATTCGTGGGAAGATTTTGAACGTTGAAAAAGCCACTTTGGATC GGGTTTTGGCCAATGAAGAAATTCGTTCACTCTTTACAGCGCTCGGAA CTGGATTTGGTGAGGACTTTGATGTAAGTAAAGCCAACTATCATAAAT TGATTATCATGACCGATGCCGATGTCGATGGTGCTCATATTCGGACAC TATTATTGACGCTGTTCTATCGTTACATGCGTCCAATGATTGATGCAG GATTTGTTTACATTGCTCAACCACCGCTCTACCAAGTACGTCAAGGTA AGATGATTCAATATATCGATTCTGATGAAGAATTAGAAACAGTACTT GGACAATTGTCACCATCACCAAAACCTGTAATTCAACGTTATAAAGG TCTTGGTGAAATGGATGCTGAGCAACTTTGGGAAACAACCATGAATC CAGAAAATCGACGCTTGTTACGAGTTTCAGCCGAAGATGCTGATGCT GCAAGTGGTGATTTTGAAATGTTGATGGGTGACAAGGTTGAACCACG TCGTAAATTCATTGAAGAGAACGCTGTGTTTGTTAAAAACTTGGATAT CTAA |
| 77 | DP9 Leucine--tRNA ligase | ATGGCTTATAATCATAAAGATATCGAACAGAAGTGGCAGCAATTCTG GAGCGACAATGAGACTTTTAAGACGGTCGAAGATGCAGACAAACCCA AATATTATGCATTAGACATGTTCCCTTATCCATCAGGTCAAGGACTCC ATGTGGGCCATCCTGAAGGATATACAGCAACAGATATTATGTCACGA ATGAAACGGATGCAAGGTTACAAAGTACTTCATCCAATGGGATGGGA TGCTTTTGGTCTTCCAGCAGAACAATATGCGATGAAGACGGGTAACA ATCCGCGTGATTTTACAGCTAAGAATATTCAAAACTTTAAGCGTCAAA TCCAATCACTTGGTTTTTCTTATGACTGGTCGCGAGAAGTTAATACAA CTGATCCAGCTTACTACAAGTGGACTCAATGGATTTTTGAGCAACTCT ACAAGAAGGGCTTAGCTTATGAAAAAGAAACGCTGGTAAACTGGGCT CCTGATTTAATGGGTGGAACGGTAGTTGCTAACGAAGAAGTTGTGGA TGGTAAGACAGAACGTGGTGGGTTCCCCGTTTATCGTAAACCAATGA AACAATGGATTCTTAAAATTACAGCTTACGCCGACCGTTTGATTGACG ATTTGGACCTGGTAGATTGGCCCGATAGTATTAAAGAAATGCAAAAA AACTGGATTGGTCGTTCAGTGGGGGCTAGCGTCTTCTTTAATGTTGAA GATAGCGAAAAACAAATTGAAGTATTTACAACGCGTCCAGATACATT ATTTGGCGCAACATACTTGGTAATTTCACCAGAACATGACCTCGTTGA |

-continued

Sequence Listing

| Seq ID No. | Description | Sequence |
| --- | --- | --- |
| | | CCAAATTACAACTCCAGAAAGTAAAGCTGCCGTTGAAGAATACAAGA<br>AAGCTGTTGCAACTAAATCAGATCTTGAACGGACGGATTTGAGTAAA<br>GATAAGACGGGAGTCTTTACGGGAGCATACGCGGTTAACCCTGTTAA<br>TGGTAAGAAAATTCCAGTTTGGATTAGTGATTACGTATTGGCTTCATA<br>CGGAACTGGAGCAGTGATGGCTGTTCCTGCTCATGATGGCCGTGACT<br>ACGAATTTGCTAAGAAATTCAAGATAGATATGGTGCCAGTTTATGAA<br>GGTGGCAATCTTGAAGATGGAGTATTGGACAGCGAAGGCGGGCTAAT<br>TAACTCTGGATTCCTAGATGGGATGGATAAGCAGACGGCTATTGATA<br>CCATGATTAGCTGGTTGGAAGAACATGGAGTTGGTCATAAGAAGGTT<br>AACTATCGTCTTCGTGACTGGGTCTTCTCTCGCCAACGCTACTGGGGT<br>GAACCAATCCCTGTAATTCATTGGGAAGATGGAGAAACAACTTTGAT<br>TCCTGAAGATGAATTGCCATTGAGACTCCCGGCTGCAACTGACATTCG<br>TCCTTCCGGTACCGGAGAAAGCCCATTAGCTAACCTAGATGATTGGGT<br>AAACGTAGTTGATGAAAATGGTCGTAAGGGTCGCCGGGAAACTAATA<br>CAATGCCACAATGGGCGGGTAGTTCATGGTACTTCCTCCGTTACGTTG<br>ATCCTAAGAATGATCAAAAGATTGCTGACGAAGATTTACTTAAAGAA<br>TGGTTACCAGTCGACTTATATGTTGGTGGAGCTGAACATGCGGTACTT<br>CATTTACTTTATGCACGTTTCTGGCACAAAGTTTTATATGATCTAGGA<br>GTTGTACCAACTAAGGAACCATTCCAAAAATTGGTCAACCAAGGGAT<br>GATTCTCGGTAGCAATCATGAGAAGATGTCTAAGTCAAAAGGGAACG<br>TGGTTAATCCAGATGATATTGTTGAGCGCTTTGGAGCGGATACTTTAC<br>GATTATACGAAATGTTCATGGGACCTCTGACAGAATCAGTCGCCTGG<br>AGTGAAGATGGGCTTAACGGAAGTCGTAAGTGGATTGACCGCGTCTG<br>GCGCTTGATGATTGACGACGAAAACCAATTGCGTGATCATATTGTTAC<br>TGAAAATGATGGCAGTTTGGATATGATTTATAACCAAACTGTTAAGA<br>AGGTAACTGATGATTATGAAAACATGCGCTTTAACACGGCTATTTCAC<br>AAATGATGGTCTTTGTTAATGAAGCATACAAGGCTGATAAACTTCCA<br>GCAGTATATATGGAAGGATTAGTTAAGATGTTAGCTCCAATTATTCCG<br>CACGTTGCTGAAGAACTTTGGAGTTTGCTAGGTCACGAAGGTGGTATT<br>TCATACGCTGAATGGCCAACATATGATGAAAGTAAGTTAGTAGAAGC<br>TACAGTTCAAGTCATTCTACAAGTTAATGGTAAAGTTCGGAGTAAAAT<br>TACCGTTGACAAGGATATCGCCAAAGAAGAACTTGAAAAATTAGCGT<br>TAGCTGATGCTAAGATTCAACAATGGACGGCAGATAAGACTGTTCGT<br>AAGGTAATTGTTATTCCTAACAAGATTGTTAATATCGTAGTAGGCTAA |
| 78 | DP9 Glucose-6-phosphate isomerase | ATGGCACATATTTCATTTGACAGTTCTAATGTTGCAGATTTTGTACAT<br>GAAAACGAACTTGCAGAAATCCAACCACTTGTTACAGCTGCTGATCA<br>GATTTTACGTGATGGCTCTGGCGCTGGTAGTGATTTCCGTGGATGGAT<br>CGATTTACCATCAAATTATGATAAGGACGAATTTGCCCGTATCAAGA<br>AAGCCGCTGATAAGATCCGCAATGACTCAGAAGTATTCGTTGCTATC<br>GGTATTGGTGGTTCATATTTGGGTGCTCGTGCAGCCATTGATTTCTTG<br>AACAACACTTTCTACAATCTTCTTACTAAAGAACAACGTAATGGTGCT<br>CCTCAAGTAATCTTCGCTGGTAACTCAATTAGTTCAACTTACCTTGCT<br>GACGTATTGAACTTAATCGGGGACCGTGACTTCTCAATTAACGTAATT<br>TCTAAGTCAGGTACAACTACAGAACCAGCTATTGCATTCCGTGTTCTT<br>AAAGAAAAACTAATCAAGAAGTACGGTGAAGAAGAAGCTAAGAAAC<br>GTATCTATGCAACAACTGACCGTGCTAAAGGCGCCCTAAAGACAGAA<br>GCTGATGCAGAAAACTATGAAGAATTCGTAGTTCCTGATGACATTGG<br>TGGTCGTTTCTCTGTTCTTTCAGCTGTTGGTTTATTACCAATCGCGGTT<br>GCCGGTGGCGATATTGACCAATTGATGAAGGGTGCTGAAGATGCAAG<br>CAACGAATACAAGGATGCTGATGTTACAAAGAACGAAGCATACAAGT<br>ACGCTGCTTTACGTAACATCCTTTATCGTAAGGGCTACACAACAGAAC<br>TTCTTGAAAACTACGAACCAACACTTCAATACTTCGGCGAATGGTGG<br>AAGCAATTGATGGGTGAATCAGAAGGTAAAGATCAAAAGGGTATCTA<br>CCCATCTTCTGCTAACTTCTCAACTGACTTACATTCACTAGGACAATA<br>CATCCAAGAAGGTCGTCGCAATTTAATGGAAACAGTTATCAATGTTG<br>AAAAGCCTAACCATGACATCGACATTCCTAAGGCTGACCAAGACCTT<br>GATGGATTACGTTATCTCGAAGGTCGCACAATGGACGAAGTTAACAA<br>GAAAGCTTACCAAGGTGTAACTCTTGCTCATAACGACGGTGGTGTTCC<br>AGTTATGACGGTTAACATTCCTGATCAAACAGCTTACACATTAGGCTA<br>TATGATTTACTTCTTCGAAGCAGCTGTTGCTGTATCTGGTTACTTGAAC<br>GGAATTAATCCATTCAACCAACCAGGTGTTGAAGCATACAAGTCAAA<br>TATGTTTGCATTACTTGGTAAACCAGGTTATGAAGATAAGACAGCTGA<br>ATTAAACGCTCGTCTATAA |
| 79 | DP9 Phosphoglucomutase | ATGAGTTGGGAAGATTCTGTCAAAGAATGGCAAGATTATGCAGATTT<br>AGATTTTAATTTAAAAAAAGAATTAGCAACTTTAGCTGAAGATAAAG<br>ATGCTTTAAAAGAAGCCTTTTATGCTCCAATGGAATTTGGTACAGCAG<br>GAATGCGTGGCGTAATGGGCCCTGGTATCAACCGGATGAATATCTAT<br>ACGGTTCGTCAAGCAACAGAAGGTTTAGCTAATTTTATGGATACCTTA<br>GATTTTACTGATAAGAAACGGGGAGTGGCGATCAGTTTTGATTCCCGC<br>TATCACTCACAAGAGTTTGCTTTAGCAGCAGCTGGTGTTTTAGGTAAG<br>CATGGTATTCCAAGTTTTGTTTTTGATAGTATGCGTCCCACTCCAGAA |

-continued

Sequence Listing

| Seq ID No. | Description | Sequence |
|---|---|---|
| | | TTATCATATACAGTACGTGAGTTAAACACTTATGCTGGAATCATGATT<br>ACTGCTAGTCATAATCCTAAACAATATAATGGATATAAGATTTATGGT<br>CCTGATGGCGGACAAATGCCACCAATGGAATCTGATAAGATTACAGA<br>ATATATTCGCCAAGTAACTGACATCTTTGGTGTTGAAGCTCTTACTCA<br>AAGTGAATTAAGAGCTAAGGGCTTAATGACCATTATTGGTGAAGACA<br>TTGACCTCAAGTATCTTGAGGAAGTTAAGACGGTATCAATTAATCATG<br>AACTAATCCAGCGCTTTGGTGCAGACATGAAGTTGATCTACTCACCAT<br>TACATGGTACTGGAAAAGTAGTTGGTGGACGTGCGTTAGAAAATGCT<br>GGTTTTAAGGATTACACTATGGTCCCTGAACAAGCAATTGCTGACCCA<br>GAATTTATTACAACGCCATTCCCTAACCCAGAATTCCCACAAACTTTT<br>GATTTGGCTATTGAATTAGGTAAAAAGCAAGATGCTGACCTTTTGATT<br>GCCACTGATCCGGATGCCGATCGTTTGGGAGCTGCCGTTCGTTTACCA<br>AATGGTGACTACAAATTATTGACAGGGAACCAAATTGCAGCCTTGAT<br>GTTAGAATACATCTTAACTGCGCATGATGCAGCAGGTGACTTGCCAG<br>GTAACGCAGCTGCCGTTAAGTCAATTGTTTCTAGTGAACTAGCAACCA<br>GAATTGCCGAAGCCCATCATGTAGAAATGATTAACGTTCTAACTGGG<br>TTTAAGTACATTGCTGACCAAATTAAACATTACGAAGAAAATGGCGA<br>CCATACCTTTATGTTTGGTTTCGAAGAAAGTTATGGCTATCTTGTTCG<br>GCCATTTGTTCGCGATAAAGATGCCATCCAAGGAATTGTCCTATTGGC<br>TGAAATTGCTGCTTATTATCGTAGTAAGGGGCAAACCTTATATGACGG<br>TCTTCAAAACTTATTTACTACTTACGGATATCATGAAGAAAAGACCAT<br>TTCAAAAGATTTCCCTGGAGTTGACGGTAAAGAAAAAATGGCTGCCA<br>TTATGGAAAAGGTTCGTGAAGAACGCCCAAGTCAATTTGATCAGTAC<br>AAGGTATTAGAAACTGAAGACTTCTTAGCTCAAACTAAGTATGAAGC<br>AGATGGATCTACCCAAGCTATCAAATTACCAAAAGCGGATGTTTTGA<br>AATTTACATTAGATGATGGTACTTGGATTGCAATTCGTCCTTCTGGAA<br>CAGAACCAAAAATTAAATTCTATATTGGTACAGTTGGCGAAGATGAA<br>AAAGATGCTTTGAATAAGATTGATGTTTTTGAAACAGCTATTAATGAA<br>CTTATAAAATAA |
| 80 | DP9 2-oxoglutarate carboxylase small subunit | ATGCACCGTATTTTAATTGCCAACCGAGGCGAAATTGCGACCCGAATT<br>ATTCGGGCAACGCATGAACTCGGAAAAACAGCTGTAGCAATTTATGC<br>TAAAGCGGATGAATTTTCTATGCATCGTTTTAAAGCAGATGAAGCTTA<br>CCAAGTTGGTGAAGATAGTGATCCAATTGGAGCATATTTAAATATTG<br>ATGACATTATTCGTATTGCAAAAGAAAATAATATTGATGCAATTCACC<br>CCGGCTATGGATTTTTGTCGGAAAATGCTGTATTTGCGCGAGCAGTTG<br>AAGCAGCTGGGATTAAGTTCATTGGACCTCGACCCGAATTACTAGAA<br>ATGTTTGGTGATAAATTACAAGCTAAAAATGCAGCCATTAAGGCCGG<br>TGTACCAACTATTCCGGGAACGGAAAAACCAGTTAAAGATGTCGATG<br>ACGCGCTAAATTTTGCAGAGCAATTTGGCTATCCTATATTTGTTAAGT<br>CAGCGGCAGGTGGCGGCGGAAAAGGGATGCGGATTGTACATCATCAA<br>CAAGAGATGCGCGAAGCATTTAAGATGGCTCAGTCAGAAGCTTCTTC<br>GTCTTTTGGTGACGATGAAATTTACTTAGAACGTTACTTAGTTGATCC<br>AATCCATATTGAGGTTCAAGTAGTTGCGGATGAACACGGTGAGATGG<br>TTCATTTGTATGAACGAAATTCATCGATTCAGCGACGCCATCAAAAAA<br>TCATTGAATTTGCTCCAGCAGTGGGAATTTCTGCCACCGTCCGTGATC<br>AAATAAGAAAAGCTGCTTTAAAATTATTGAAGTCGGTCAATTATAGT<br>AACGCTGCAACCATTGAGTTTTTGGTAGAAGGTAATCAATTTTACTTT<br>ATGGAAGTGAATCCACGAATTCAGGTTGAACATACAGTTACCGAAGA<br>AGTCACGGGAATCGATATTGTGCAAACCCAAATTAAGGTTGCTGAAG<br>GTCAAAGATTACACGAAGAAATCGGTGTTCCTCAACAAGCCCAAATT<br>GAAGCTGTGGGAGTGGCAATTCAAGCCCGAATTACCACTGAAGATCC<br>AATGAATAACTTTATTCCAGATGTCGGTAGAATCCAGACGTATCGTTC<br>ACCTGGTGGAACAGGTGTGAGATTGGATGCTGGAAATGCCTTTGCTG<br>GAGCCATTGTAACTCCGCATTATGATTCACTTCTGACCAAGGCAATTG<br>TCCATGCGCCAACCTTTGACGAAGCCTTGGTAAAGATGGATCGAGTG<br>CTCAATGAATTTGTAATTGCTGGGGTTAAAACTAATATTCCATTTTTA<br>AAGAAATTAATTCATCATCCTATTTTTAGATCGGAATTAGCTCCGACA<br>ACCTTTGTGGATGAGACACCAGAACTCTTTGATTTAAAAGCTGAAACT<br>CCGGTAGTTACTCAACTTTTGAGTTACATTGCTAATACTACTATCAAT<br>GGTTATCCAGGCTTAGAAAAGCAGAATCCAGTAGTGTTAACTCGGCC<br>AGTCCGTCCACATTTTGAAGCACAAGTACCGCATGAAAATGCGAAAC<br>AGATCTTGGATAGTAAGGGACCTGATGCCATGATCAATTGGCTGTTA<br>AAACAAAAGCAGGTCTTGCTAACCGATACGACCATGCGGGATGCCCA<br>TCAATCATTATTTGCTACGCGAATGCGGACCAAAGACATGGTAGAAA<br>TTGCCGATCAAGTCCAGAAAGGTCTGCCTAACCTATTTTCAGCTGAAG<br>TTTGGGGCGGTGCGACCTTTGATGTTGCTTATCGGTTCCTAGGTGAGG<br>ATCCATGGGAAAGACTCCAACAATTGCGGGCTAAAATGCCAAATACG<br>ATGCTCCAAATGCTTTTACGTGGGTCAAATGCAGTAGGGTATCAAAAT<br>TATCCAGACAACGCCATTGACGAATTTATTCGATTGGCTGCCAAAAAT<br>GGAATTGATGTTTTCCGAATCTTTGATTCTCTTAATTGGGTGCCACAG<br>CTTGAAGAATCTATCCAACGGGTGCGTGATAATGGAAAAGTGGCTGA<br>AGCAGCCATGGCATATACTGGCGATATTTTAGATACTAATCGTACTAA |

-continued

Sequence Listing

| Seq ID No. | Description | Sequence |
|---|---|---|
| | | ATATAATTTGAAATATTATGTGGATTTGGCTCAAGAACTCCAAGCAGC AGGTGCTCATATTATTGGAATCAAAGATATGTCAGGAATTTTAAAACC ACAAGCTGCTTATGCATTAATTTCAGAGTTAAAAAATCATCTGGATGT GCCAATTCATTTGCATACGCACGATACTACAGGCAACGGCATTTTCTT ATATTCTGAAGCAATACGAGCTGGAGTTGATGTGGTCGACGTTGCCA CTTCTGCGCTAGCGGGAACGACTTCTCAGCCTTCAATGCAGTCTCTTT ACTATGCGTTGTCTAATAACCAGCGCCAACCAGATTTAGATATTCAAA AAGCAGAAAAACTAGATGAATATTGGGGCGGAATTCGACCATATTAC GAAGGATTTGGCACCCAATTAAATGGACCACAAACTGAAATTTATCG AATTGAAATGCCTGGTGGACAGTATACCAACCTTCGCCAGCAAGCTA ACGCAGTCCATTTGGGTAAGCGTTGGGATGAGATTAAGGAAATGTAC GCAACCGTCAATCAAATGTTTGGCGATATTCCAAAGGTTACGCCTTCT TCTAAAGTAGTTGGCGATATGGCACTATTCATGGTCCAAAATGATTTG ACGCCTGAAATGGTAATGAACGATAAGGGACAATTAAGTTTTCCCGA ATCAGTGGTAAACTTTTTCCGTGGTGATTTAGGACAACCGGCGGGTGG TTTTCCAAAACAGCTCCAAAAGGTGATTCTAAAAGAGCAAGCCCCAT TGACAGTACGACCAGGAGCTTTAGCCGATCCAGTTGATTTTGATCAAG TTCGTAAACAGGCAACTAAGGTTTTAGGTCACCAAGCAAGTGATGAA GAAGTTATGTCGTTTATTATGTATCCAGATGTGATGACCGAATACATT CAACGTCAAAATGAATATGGTCCAGTACCATTATTAGATACTCCAATC TTTTTCCAAGGCATGCATATTGGCCAACGCATTGATTTACAATTGGGA CGCGGAAAATCGGTCATTATTGTCCTTCGAGAAATTAGTGAAGCAGA TGAGGCGGGCCAAAGGTCACTTTTCTTTGATATAAATGGACAAAGTG AAGAAGTGATTGTTTATGATGTTAATGCGCAGGTAACGAAAGTAAAG AAGATTAAAGCTGATCCGACTAAAGCCGAACAGATTGGCGCTACTAT GGCGGGCTCGGTCATTGAAGTCCAAGTAGAAGCGGGCCAAAAGGTCC AGCGAGGTGATAACTTAATTGTCACTGAGGCGATGAAAATGGAGACC GCGTTAAGAGCACCTTTCGACGCAACCATTAAGAAGATTTATGCTACC CCTGAAATGCAAATCGAGACGGGGGATTTATTGATTGAACTAGAAAA GGAGTAA |
| 81 | DP3 Glycine--tRNA ligase beta subunit | ATGTCAACATTTTTATTAGAAATTGGACTTGAAGAAATACCAGCTCAT TTGGTAACCAGTTCAGAGAATCAGTTAATTGAAAGAACTAAAAAGTT CTTATCAGAGCATCGTTTAACAGTAGGTGATATTAAACCATATTCAAC ACCGCGACGTCTGGCTGTCGTTTTGACAGATGTTGCTGAAACATCAGA AAGTTTAAGCGAAGAAAAGCGTGGACCATCTGTTGACCGTGCACAAG ACGAAAACGGTAATTGGACAAAGGCAGCATTAGGTTTTGCACGTGGT CAAGGTGCTAATCCTGAAGCATTTGAAATTAAAGATGGATATGTTTG GCTAACAAAACGTACTGCTGGTGTAGCCGCGAATGAAATTTTAGCTA AAATTGGTGATGAAGTTGTCGCCCAAATGAAATTTTCAACTTATATGA AGTGGGCTAATCACAGCTTTTTGTATGTTCGACCTATTCGTTGGCTCG TAGCACTTCTTGATAGTGAAGTCATTTCTTTCAACGTGTTAGATATTA CCACAGATCGTTTCACACGTGGTCATCGTTTTTTGTCTTCAGAACATG TTGAAATATCTTCTGCAGATAATTATGTAACGACTTTGCAGGGTGCTA ACGTGGTTGTTGATGCTACAGTGCGCAAAAAATGAAATTCGATCGCAG TTGAATGCAATTGCTGAAGCTAATGGTTGGGTTCTGCAACTTGAGACC GATGCGGCGCAAGATTTGTTGGAAGAAGTTAATAACATTGTTGAGTG GCCAACAGCGTTTGCTGGCAGTTTCGATGAGAAATATTTAGAAATAC CAGATGAAGTTTTGATTACATCAATGCGCGAACATCAGCGTTTCTTCT TTGTGACGAATGAAAAAGGACAATTATTGCCACACTTTTTGTCAATAA GAAATGGTAACCGTGAGCATCTAAACAACGTTATTGCTGGAAATGAA AAAGTATTGGTAGCAAGGTTAGAAGATGCCGAATTCTTCTATCATGA AGACCAAACCAAATCAATTTCTGATTACATGACTAAAGTTAAAAAGT TAGTCTTCCATGAAAAAATTGGTACGGTGTATGAACACATGCAACGC ACTGGTGCTTTGGCTTCAGCAATGGCGGTGGTTTTGAAGTTTGATGAA GTACAACAGGCTGATTTGACCCGTGCATCAGAAATTTATAAATTTGAT TTGATGACCGGTATGGTTGGTGAATTTGATGAACTTCAAGGCATTATG GGTGAGCATTATGCCAAGCTTTTTGGCGAAGATGATGCGGTTGCAAC AGCCATTCGAGAGCATTATATGCCAACTTCAGCTAATGGTGAGGTTGC GCAATCTGAAATTGGTGCTTTGTTGGCCGTTGCGGATAAACTTGATAG CATTGTGACGTTTTTTGCTGCTGGATTAATACCAAGTGGTTCTAATGA TCCTTATGGCTTACGACGTGCAGCTACTGGCATCGTGCGTACATTGGT GGATAAAAAATGGCATATTGATTTGCGGCCTTTGCTAGCTGATTTTGT GCAACAGCAAGGTAAGGTAACTGACACCGATTTAACGACATTTGTTG ATTTCATGTTGGATCGTGTTCGTAAATTATCGTTGGATGCTGGAATAC GTCAAGATATTGTCATTGCTGGATTAGGCAACGTTGATAGAGCTGATA TCGTATATATTAGTCAGCGAGTCGAAGTTTTGTCCCAACATAGTGGTG ATGGCAATTTCCGAGATGTAATTGAGGCACTGACTCGTGTGGATCGCT TAGCCGTAAAGCAAGTAACTAATGCAACGGTTGATCCTGCTAAGTTT GAAAATCAATCTGAAAAGGACCTATATCAAGCAACGTTAACGCTTGA TTTAAATACTTTGATGCATGACGGTGCAGAAAATCTCTACATGGCCTT AGCAAATTTGCAAAAACCAATTGCGGCTTATTTTGATGAAACCATGGT TAACGCTGAAGATGAATCTGTTAAAGATAATCGATATGCGCAGCTGA |

-continued

Sequence Listing

| Seq ID No. | Description | Sequence |
|---|---|---|
| | | ACGTCATACAACGACTAACCAACGGATTAGGAGATTTGACGCAAATC GTCATTAAGTAA |
| 82 | DP3 Glutamine synthetase | ATGGCTCGTAAAACATTTACCAAAGAAGAAATTAAACAAATTGTTGT TGATGAAAATGTAGAATTCATTCGTGTAACATTCACTGATGTCTTAGG TGCGATTAAAAACGTTGAAGTACCAACTTCTCAATTAGATAAGGTGCT TGACAACAATTTAATGTTTGACGGTTCATCAATCGAGGGATTTGTTCG TATCAATGAATCAGATATGTATCTTTACCCCGATTTATCAACATTTAT GATTTTCCCATGGGCAACGGATGGTCATGGTGGTAAAGTGGCCCGCTT GATTGCCGACATTTATACTGCTGATCGTGAGCCATTTGCTGGAGACCC CCGTCATGCGTTACGTTCGGTACTCGCTGACGCGCGTGAAGCTGGGTT TACGGCGTTTAATGTCGGGACAGAACCTGAATTTTTCTTGTTTAAACT TGATGAAAAAGGCAACCCAACCACAGAGTTAAACGACAAAGGTGGTT ATTTTGACCTAGCACCATTGGATATGGGTGAAAATGTTCGTCGTGAAA TTGTTTTGACTTTGGAAAAAATGGGCTTTGAAATTGAAGCTGCTCACC ACGAAGTTGCCGAAGGACAGCATGAAGTAGACTTTAAATACGCTTCA GCTCTTGAAGCCGCTGACAACATTCAGACGTTTAAGTTGGTTGTTAAA ACCATCGCACGCAAGAATGGTTACTATGCTACCTTTATGCCAAAGCCT GTTGCAGGTATTAACGGATCCGGTATGCACACAAACATGTCATTATTT ACAAAAGATGGTAACGCATTTGTTGATACATCGGATGAAATGGGCTT GTCAAAAACAGCATATAACTTCTTGGGTGGTATTTTAGAACATGCGAC TGCGTTTACAGCGCTTGCAAACCCAACAGTTAACTCATACAAGCGCTT GACACCAGGATTCGAAGCACCTGTTTATGTTGCATGGTCAGCATCAA ATCGTTCACCAATGGTTCGAGTTCCGGCCTCACGTGGTAATTCAACAC GTTTGGAACTTCGTTCAGTTGACCCAACAGCTAATCCTTATACTGCAT TGGCAGCCATTTTGGCTTCAGGACTGGATGGGATCAAGCGTGAATTA GAGCCTTTGGCCTCAGTTGATAAAAATATTTATTTGATGGATGAGGTC GAACGGGAAAAGGCAGGCATTACAGACTTACCAGATACTCTGTTGGC TGCAGTTCGTGAGTTGGCGGCTGATGATGTTGTTCGTTCAGCTATTGG AGAACATATTGCTGATAAGTTTATTGAAGCAAAGAAGATTGAATACA CATCATATCGTCAGTTTGTTTCTGAATGGGAAACAGATTCTTATCTTG AAAATTACTAA |
| 83 | DP3 DNA gyrase subunit B | GTGTTCGCAGATTATATCTGTTCACACGCTAATAATATGGCAGAGAAT ATCGAAAATGAAGCATTGGAGAACATTGATGGCATCGTAACCGATGA TACCGAAATCCGTCAAGCAAGCACCGTTCATGCAGCAGCAGGCGCTT ACAATGCTGATCAGATTCAAGTTTTGGAAGGATTGGAAGCTGTCCGC AAACGCCCTGGCATGTACATTGGTACGACCACAGCGCAAGGCTTGCA CCATTTGGTATGGGAAATTGTTGATAACGGGATTGATGAGGCATTAG CAGGGTTTGCGTCACATATTACGGTCACAATCGAAAAGGATAACTCA ATCACGGTAACCGATGACGGCCGTGGTATTCCTGTCGACATTCAAACT AAAACGGGTAAGCCAGCTCTTGAAACTGTCTTTACGGTATTACACGCC GGTGGTAAATTTGGCGGTGGCGGTTATAAAGTATCTGGTGGATTACA CGGTGTTGGAGCTTCTGTTGTCAATGCCTTGTCAACGGATTTGGACGT TAGAGTTGTTCGTGATAATACTGTTTATTACATGGACTTCAAAGTGGG ACGCGTCAACACACCGATGAAACAATTGACGGAAAAGCCCACTATTG AGCGTGGTACAATTGTTCATTTTAAGCCCGATGCAGATATTTTTCCGTG AAACAACAGTTTATAACTACAACACATTACTAACACGTGTGCGCGAA TTGGCCTTTTTGAATAAAGGTTTGCGCATTTCGATTACAGATAATCGA CCTGAAGAAGCTGTTTCTGAAAGCTTTCATTTTGAAGGTGGGATTAAA GAATACGTCAGCTATTTGAATAAGGACAAGACTGCTATTTTTCCCTGAA CCTGTTTACGTTGAGGGTGAAGAAAATGGCATTGTAGTGGAAGCTGC CTTACAGTACACTACCGATATTAAAGACAATCTGCGGACGTTTACTAA CAATATCAATACCTATGAAGGTGGGACGCACGAAACTGGCTTTAAAA CAGCCTTAACACGTGTAATCAATGATTACGCTCGTAAAAATGGTCAG CTCAAAGATAATGCAGAAAGTTTGACAGGGGAAGATGTGCGCGAAG GCATGACTGCTATCGTGTCAATCAAGCACCCAGATCCACAATTTGAA GGACAAACCAAAACTAAATTAGGTAACTCCGATGCACGTCAAGCAAC GGATCGGATGTTCTCAGAAACGTTCAGTCGTTTCATGATGGAAAATCC AGCAGTTGCCAAGCAAATTGTTGAAAAAGGTGTCTTAGCCCAAAAAG CACGATTGGCTGCCAAGCGTGCACGCGAAATGACACGCAAACAATCT GGTTTGGAAATTGGTAATTTGCCAGGTAAATTAGCTGATAATACCTCA AATGATCCTGAAATTTCAGAATTATTTATTGTTGAGGGTGATTCAGCC GGTGGTTCAGCTAAGCAAGGACGTAACCGTTTGACGCAAGCTATTTT GCCAATTCGAGGCAAAATTTTAAATGTTGGGAAAGCCTCATTGGATC GGGTGTTAGCCAACGAAGAAATTCGATCATTGTTTACAGCAATGGGA ACTGGATTTGGTGAGGACTTTAATGTTGAAAAAGCCAATTATCACAA AGTCATTATTATGACAGATGCCGATGTCGATGGCGCCCATATTCGAAC ACTATTGTTAACGCTATTTTATCGTTATATGCGACCACTTGTTGACGC AGGCTATATTTATATTGCGCAGCCACCGCTTTACGGTGTTGCCTTAGG CAATAATAAATCAATGACGTACATTGATTCTGATGAAGAACTTGAAG ACTATTTGTCACAATTGCCATCTAATATTAAACCAAAAGTTCAACGTT ATAAGGGACTAGGGGAAATGGATTACGATCAACTAGCAGATACAACC |

-continued

Sequence Listing

| Seq ID No. | Description | Sequence |
|---|---|---|
| | | ATGGATCCGCAGAATCGTCGTTTGCTACGTGTTGACCCAACTGATGCT<br>GAAGAAGCCGAAGCAGTTATTGATATGTTAATGGGTGGGGATGTACC<br>ACCACGTCGTAAGTTTATTGAAGACAATGCTGTCTTTGTTGAGAACTT<br>GGATATTTAA |
| 84 | DP3 Leucine--tRNA ligase | ATGATTTTCGTCAACGAAGCTTACAAAACCGATGCTGTGCCGAAAGC<br>GGCGGCGGAAAACTTCGTACAGATGCTGTCCCCACTGGCACCGCATT<br>TGGCAGAAGAACTGTGGGAACGACTTGGTCATACCGATACGATTACG<br>TATGAACCATGGCCAACGTACGATGAGGCTTGGACCATAGAATCCGA<br>AGTGGAAATCGTCGTGCAAGTGAACGGCAAAATCGTAGAACGCACGA<br>AAATTTCCAAAGACCTGGATCAAGCAGCGATGCAAGAACACAGCTTA<br>AGCCTGCCGAATGTTCAGCAGGCTGTGGCTGGGAAGACGATCCGCAA<br>AGTGATTGCGGTGCCAGGCAAGCTGGTGAATATCGTCGTTGGATAA |
| 85 | DP3 Glucose-6-phosphate isomerase | ATGGCACACATTACATTTGACACAAAGAACATTGAGAATTTTGTTGCA<br>CCATACGAATTGGACGAAATGCAACCATTAATTACGATGGCTGACCA<br>ACAATTGCGCAATCGTACGGGCGCTGGTGCAGAATATTCTGATTGGTT<br>GACTCTACCTACTGATTACGACAAGGAAGAATTTGCACGTATTCAAA<br>AGGCGGCGCAACAAATTCAATCTGATTCAAAGATTTTGGTTGTCATTG<br>GTATTGGTGGTTCATATTTGGGCGCGAAGATGGCGGTTGATTTCTTGA<br>ATCCAATGTTTAATAATGAATTGTCGGATGACCAACGTCAAGGTGTTA<br>AAATTTATTTTGCTGGTAACTCAACTTCTGCAGCTTACTTAAATGATTT<br>AGTTCGTGTCATTGGTGATCAAGACTTTTCTGTCAACGTTATCTCAAA<br>GTCTGGCACAACAACGGAACCATCAATCGCTTTCCGTGTGTTTAAACA<br>ATTGTTAGAGAAAAAGTATGGTTCTGATGCTGCTAAGAAGCGTATCT<br>ATGCCACAACAGATGCCAATCGTGGTGCTTTGCACGATGAAGCAGCG<br>GCTTCAGGTTATGAAACATTCACAATTCCTGATGGTGTCGGTGGTCGC<br>TTCTCTGTTTTGACAGCTGTTGGCTTGTTGCCAATTGCTGCTTCAGGCG<br>CTGATATCCAAAAATTGATGGACGGCGCTCGTGATGCGCAAAACGAA<br>TATACTGATTCTGATTTGAAAAAGAACGAGGCATATAAATATGCAGC<br>CGTTCGTCGTATTTTGTATGATAAGGGTTATACAACAGAATTGTTGAT<br>TAACTGGGAACCTTCAATGCAATATTTGTCAGAGTGGTGGAAGCAAT<br>TGATGGGCGAGTCTGAAGGTAAAAATCAAAAGGGTATCTATCCATCT<br>TCAGCTAACTTCTCAACCGACTTGCACTCACTTGGACAATATATTCAA<br>GAAGGACGCCGTGATTTGTTTGAGACGGTGGTTAAGTTAGACAATCC<br>TGTATCTAATTTGGACCTACCACATGAAGAAGGCAACAATGATGGTTT<br>GCAATATTTGGAAGGTATCACGATCGATGAAGTGAACACCAAAGCAT<br>CTCAAGGGGTTACTTTGGCTCACGTTGATGGTGGTGTGCCTAACTTGG<br>CTGTTCACTTGCCAGCACAAGATGCTTATTCACTCGGTTACATGATTT<br>ACTTCTTTGAAATGGCTGTTGGGGCGTCTGGTTATACGTTTGGTATTA<br>ACCCATTCAACCAACCGGGTGTCGAAGCCTATAAGACAGCTATGTTT<br>GCACTATTAGGTAAGCCTGGCTATGAGGAAGCGACAAAAGCATTCCG<br>TGCCCGCTTAGACAAATAA |
| 86 | DP3 Beta-phosphoglucomutase | ATGACTAAATTTTCAGATATTAAAGGTTTTGCCTTTGATTTAGATGGG<br>GTTATTGCTGATACGGCGCGTTTCCATGGTGAAGCTTGGCATCAAACA<br>GCTGATGAGGTTGGCACAACTTGGACACCAGAATTGGCTGAAGGTTT<br>GAAGGGCATTAGTCGTATGGCTTCCTTGCAAATGATTTTGGATGCTGG<br>GGATCATGCCGATGATTTTTCGCAAGCAGATAAAGAAGCATTAGCAG<br>AAAAGAAAAATCATAATTATCAACAACTTATTTCAACATTGACGGAA<br>GATGATATTTTGCCTGGCATGAAAGATTTTATTCAATCAGCCAAGGCA<br>GCCGGCTATACAATGTCGGTGGCATCAGCTTCTAAAAACGCACCAAT<br>GATTCTAGATCATTTGGGATTGACCAAGTATTTTGTCGGCATTGTTGA<br>TCCCGCCACTTTGACAAAGGGAAAACCTGATCCTGAAATCTTCGTTCG<br>TGCTGCGGAAGTCTTACATTTAAATCCAGAAAATGTTATTGGATTGGA<br>AGATTCAGCTGCTGGTATTGTGTCAATCAATGGCGCAGGTGAGACAT<br>CACTAGCCATTGGTAACGCAGATGTTTTGTCAGGAGCGGACTTGAATT<br>TTGCGTCTACTTCAGAAGTGACCTTAGCAAATATTGAAGCTAAAATGC<br>AATAG |
| 87 | DP3 2-oxoglutarate carboxylase small subunit | ATGTTTAAAAAAGTGCTTGTTGCTAATCGTGGTGAAATTGCGGTTCGC<br>ATCATTCGAACGCTCAAAGAAATGGGGATTGCTTCAGTCGCTATTTAC<br>TCGACAGCCGATAAAGATAGTTTACACGTACAAATCGCTGACGAAGC<br>GATTGCTGTGGGGGGACCGAAACCTAAAGATTCATACTTAAATATGA<br>AAAATATTTTAAGTGCAGCCCTGCTGTCGGGAGCAGAGGCAATTCAT<br>CCAGGATATGGCTTTTTAGCTGAAAATACATTGTTTGCTGAAATGGTT<br>GGCGAAGTTGGTATTAAATGGATTGGGCCTAGGCCAGAAACAATTGA<br>GTTAATGGGTAACAAAGCTAACGCACGTGAAGAAATGCGGCGTGCCG<br>GCGTACCAGTAATTCCAGGTTCAGAGGGATTTATCCGTGATTTTCATG<br>AAGCAAAAACGGTTGCTGATAAAATTGGCTATCCTTTGTTGCTAAAA<br>GCTGCCGCTGGTGGTGGTGGTAAAGGCATGCGTTTTGTTTACGGTGAG<br>GATGAGTTATCAGATAAATTTGATGATGCTCAAAACGAAGCGCGTGC<br>TTCGTTTGGCGATGATCACATGTATATTGAAAAAGTTATGTCACGTGT |

-continued

Sequence Listing

| Seq ID No. | Description | Sequence |
| --- | --- | --- |
| | | TCGCCACATTGAAATGCAAGTGTTTCGTGATGAGAATGGTCATGTTGT<br>TTACTTGCCAGAACGAAATTGCTCATTGCAACGCAATAATCAAAAGG<br>TGATTGAAGAATCACCAGCTACGGGTGTAACGCCTGAAATGCGTGCG<br>CATCTTGGCGAAATTGTTACTAAAGCCGCAAAAGCATTGGCGTATGA<br>AAATACTGGAACCATTGAATTTTTGCAAGATCGCGATGGTCATTTCTA<br>CTTTATGGAAATGAACACACGTATTCAAGTAGAACATCCAGTTTCTGA<br>AATGGTAACGGGATTAGATTTAATTAAGTTACAAATTCAAGTTGCTGC<br>AGGCTTAGATTTACCGGTGGTTCAAGATGACGTGATCGTTCAAGGCC<br>ACTCTATCGAAGTACGTTTGACGGCTGAGCAGCCAGAAAAACACTTT<br>GCACCTAGTGCTGGAACGATTGATTTTGTTTTTTTGCCAACTGGTGGA<br>CCGGGTGTTCGTATTGATTCAGCCTTATTTAATGGCGATAAAATTCAA<br>CCATTTTACGATTCTATGATTGGCAAATTAATTGTTAAGGCCGATGAT<br>CGTGAAACAGCCATGAGAAAGATTCAACGTGTGGTTGATGAAACTGT<br>TGTACGTGGTGTAGCAACGAGCCGTAATTTTCAAAAAGCTCTGTTAGC<br>TGATCCACAGGTTCAACGTGGCGAATTTGACACACGTTATTTGGAAAC<br>TGAATTTTTACCGAGATGGACACAAACATTGCCAGATAATCAATAA |
| 88 | DP1 Glutamine--tRNA ligase | ATGAGCAAGCCCACTGTCGACCCTACCTCGAATTCCAAGGCCGGACC<br>TGCCGTCCCGGTCAATTTCCTGCGCCCGATCATCCAGGCGGACCTGGA<br>TTCGGGCAAGCATACGCAGATCGTCACCCGCTTCCCGCCAGAGCCCA<br>ACGGCTACCTGCACATCGGTCATGCCAAGTCGATTTGTGTGAACTTCG<br>GCCTGGCTCAGGAGTTCGGTGGCGTTACGCACCTGCGTTTCGACGACA<br>CCAACCCGGCCAAGGAAGACCAGGAATACATCGACGCCATCGAAAG<br>CGACATCAAGTGGCTGGGCTTCGAATGGTCCGGTGAAGTGCGCTATG<br>CATCCAAGTATTTCGACCAGCTGTTCGACTGGGCCGTCGAGTTGATCA<br>AGGCCGGCAAGGCCTACGTTGACGACCTGACCCCCGAGCAAGCCAAG<br>GAATACCGTGGCAGCCTGACCGAGCCGGGCAAGAACAGCCCGTTCCG<br>CGACCGTTCGGTCGAAGAGAACCTCGACTGGTTCAACCGCATGCGCG<br>CCGGTGAGTTCCCGGACGGCGCCCGCGTGCTGCGCGCCAAGATCGAC<br>ATGGCCTCGCCGAACATGAACCTGCGCGACCCGATCATGTACCGCAT<br>TCGCCATGCCCATCACCACCAGACCGGTGACAAGTGGTGCATCTACC<br>CCAACTACGACTTCACCCACGGTCAGTCGGACGCCATCGAAGGCATC<br>ACCCACTCCATCTGCACCCTGGAGTTCGAAAGCCATCGCCCTCTGTAC<br>GAATGGTTCCTGGACAGCCTGCCGGTGCCGGCGCACCCGCGTCAGTA<br>CGAATTCAGCCGCCTGAACCTGAACTACACCATCACCAGCAAGCGCA<br>AGCTCAAGCAACTGGTCGATGAAAAGCACGTGCATGGCTGGGACGAC<br>CCGCGCATGTCGACGCTCTCGGGTTTCCGTCGTCGTGGCTACACCCCG<br>GCGTCGATCCGCAATTTCTGCGACATGGTCGGCACCAACCGTTCTGAC<br>GGTGTGGTCGATTACGGCATGCTTGAGTTCAGCATCCGTCAGGATCTG<br>GACGCGAACGCGCCGCGCGCCATGTGCGTGCTGCGTCCGTTGAAAGT<br>CGTGATCACCAACTACCCGGAAGACAAGGTCGACCACCTTGAGCTGC<br>CGCGTCACCCGCAGAAAGAAGAGCTGGGCGTGCGCAAGCTGCCGTTC<br>GCGCGCGAAATCTACATCGACCGTGACGACTTCATGGAAGAGCCGCC<br>GAAGGGTTACAAGCGCCTGGAGCCGAACGGCGAAGTGCGCCTGCGTG<br>GCAGCTACGTGATCCGCGCCGACGAAGCAATCAAGGACGCCGAAGGC<br>AACATCGTCGAACTGCGCTGCTCGTACGATCCGGAAACACTCGGCAA<br>GAACCCTGAAGGCCGTAAGGTCAAGGGCGTGATCCACTGGGTGCCGG<br>CCGCTGCCAGCATCGAGTGCGAAGTGCGTCTGTACGATCGTCTGTTCC<br>GATCGCCGAACCCGGAGAAGGCCGAAGACAGCGCCAGCTTCCTGGAC<br>AACATCAACCCTGACTCGCTGCAAGTGCTTACAGGTTGTCGTGCTGAG<br>CCATCGCTTGGCGACGCACAGCCGGAAGACCGTTTCCAGTTCGAGCG<br>CGAAGGTTACTTCTGCGCGGATATCAAGGACTCGAAACCCGGTGCTC<br>CGGTATTCAACCGTACCGTGACCTTGCGTGATTCGTGGGGCCAGTGA |
| 89 | DP1 DNA gyrase subunit B | ATGAGCGAAGAAAACACGTACGACTCGACCAGCATTAAAGTGCTGAA<br>AGGTTTGGATGCCGTACGCAAACGTCCCGGTATGTACATCGGCGACA<br>CCGATGATGGTAGCGGTCTGCACCACATGGTGTTCGAGGTGGTCGAC<br>AACTCCATCGACGAAGCTTTGGCCGGTCACTGCGACGACATCAGCAT<br>TATCATCCACCCGGATGAGTCCATCACGGTGCGCGACAACGGTCGCG<br>GCATTCCGGTCGATGTGCACAAAGAAGAAGGCGTTTCGGCGGCTGAG<br>GTCATCATGACCGTGCTGCACGCCGGCGGTAAGTTCGATGACAACTCT<br>TATAAAGTCTCCGGCGGTCTGCACGGTGTAGGTGTGTCGGTAGTGAA<br>CGCACTGTCCGAAGAGCTGATCCTGACCGTTCGCCGTAGCGGCAAGA<br>TTTGGGAGCAGACGTACGTCCATGGTGTGCCACAAGAGCCGATGAAA<br>ATCGTTGGCGACAGTGAATCCACGGGTACGCAGATCCACTTCAAGCC<br>ATCGGCTGAAACCTTCAAGAACATCCACTTTAGCTGGGACATCCTGGC<br>CAAGCGGATTCGCGAACTGTCCTTCCTCAACTCCGGTGTGGGTATCGT<br>CCTCAAGGACGAGCGCAGCGGCAAGGAAGAACTGTTCAAGTACGAA<br>GGCGGTCTGCGCGCGTTCGTTGAATACCTGAACACCAATAAGACCGC<br>GGTCAACCAGGTGTTCCACTTCAACATTCAGCGTGAAGACGGCATCG<br>GCGTGGAAATCGCCCTGCAGTGGAACGACAGCTTCAACGAGAACTTG<br>TTGTGCTTCACCAACAACATTCCACAGCGCGATGGCGGTACTCACTTG<br>GTGGGTTTCCGTTCCGCACTGACGCGTAACCTGAACACTTACATCGAA |

-continued

Sequence Listing

| Seq ID No. | Description | Sequence |
|---|---|---|
| | | GCCGAAGGCTTGGCCAAGAAGCACAAAGTCGCCACCACCGGTGACGA<br>TGCGCGTGAAGGCCTGACCGCGATTATCTCGGTGAAAGTGCCGGATC<br>CCAAGTTCAGCTCCCAGACCAAAGACAAGCTGGTTTCTTCCGAGGTG<br>AAGACCGCCGTGGAACAGGAGATGGGCAAGTACTTCTCCGACTTCCT<br>GCTGGAGAACCCGAACGAAGCCAAGCTGGTCGTCGGCAAGATGATCG<br>ACGCTGCACGTGCTCGCGAAGCGGCGCGTAAAGCCCGTGAGATGACC<br>CGTCGTAAAGGCGCGCTGGATATTGCTGGCTTGCCTGGCAAGTTGGCT<br>GACTGCCAGGAGAAGGACCCAGCGCTCTCCGAGCTATATCTTGTGGA<br>AGGTGACTCTGCTGGCGGTTCCGCCAAGCAGGGTCGTAACCGTCGCA<br>CCCAGGCGATCCTGCCGTTGAAAGGCAAGATTCTCAACGTAGAGAAG<br>GCCCGCTTCGACAAGATGATTTCCTCCCAGGAAGTCGGCACCTTGATT<br>ACGGCGTTGGGTTGCGGCATTGGCCGCGATGAGTACAACATCGACAA<br>GCTGCGCTACCACAACATCATCATCATGACCGATGCTGACGTCGACG<br>GTTCGCACATCCGTACCTTGCTGCTGACCTTCTTCTTCCGTCAGTTGCC<br>TGAGCTGATTGAGCGTGGCTACATCTATATCGCGCAGCCGCCGTTGTA<br>CAAAGTGAAAAAGGGCAAGCAAGAGCAGTACATCAAAGACGACGAC<br>GCCATGGAAGAGTACATGACGCAGTCGGCCCTGGAAGATGCAAGCCT<br>GCACTTGAACGACGAAGCACCGGGTATCTCCGGTGAGGCGTTGGAGC<br>GTCTGGTTAACGACTTCCGTATGGTGATGAAGACCCTCAAGCGTCTAT<br>CGCGTCTGTACCCTCAGGAACTGACCGAGCACTTCATCTACCTGCCGG<br>CCGTCAGTCTGGAGCAGTTGGGTGATCATGCAGCGATGCAAGAGTGG<br>CTGGCTCAGTACGAAGTACGCCTGCGCACTGTTGAGAAGTCTGGCCT<br>GGTGTACAAAGCCAGTCTGCGTGAAGACCGTGAACGTAACGTGTGGC<br>TGCCGGAGGTTGAGTTGATCTCCCACGGCCTGTCGAATTACGTCACCT<br>TCAACCGCGACTTCTTCGGCAGTAATGACTACAAGACGGTCGTGACC<br>CTCGGCGCGCAGTTGAGCACCTTGCTGGATGATGGTGCTTACATTCAA<br>CGTGGCGAGCGTAAGAAAGCGGTCAAGGAGTTCAAGGAAGCCTTGG<br>ACTGGCTGATGGCGGAAAGCACCAAGCGTCATACCATTCAGCGATAC<br>AAAGGTCTGGGCGAGATGAACCCTGATCAGTTGTGGGAAACCACCAT<br>GGATCCAGCACAGCGTCGCATGCTGCGCGTGACCATCGAAGACGCCA<br>TTGGCGCAGATCAGATCTTCAACACCCTGATGGGTGATGCGGTCGAA<br>CCTCGCCGTGACTTCATCGAGAGCAATGCCTTGGCGGTGTCCAACCTG<br>GACTTCTGA |
| 90 | DP1 Isoleucine--tRNA ligase | ATGACCGACTATAAAGCCACGCTAAACCTTCCGGACACCGCCTTCCC<br>AATGAAGGCCGGCCTGCCACAGCGCGAACCGCAGATCCTGCAGCGCT<br>GGGACAGTATTGGCCTGTACGGAAAGTTGCGCGAAATTGGCAAGGAT<br>CGTCCGAAGTTCGTCCTGCACGACGGCCCTCCTTATGCCAACGGCACG<br>ATTCACATCGGTCATGCGCTGAACAAAATTCTCAAGGACATGATCCTG<br>CGCTCGAAAACCCTGTCGGGTTTTGACGCGCCGTATGTCCCGGGCTGG<br>GACTGCCATGGCCTGCCGATCGAACACAAAGTCGAAGTGACCTACGG<br>CAAAAACCTGGGCGCGGATAAAACCCGCGAACTGTGCCGTGCCTACG<br>CCACTGAGCAGATCGAAGGGCAGAAGTCCGAATTCATCCGCCTGGGC<br>GTGCTGGGCGAGTGGGACAACCCGTACAAGACCATGAACTTCAAGAA<br>CGAGGCCGGTGAAATCCGTGCCTTGGCTGAAATCGTCAAAGGCGGTT<br>TTGTGTTCAAGGGCCTCAAGCCCGTGAACTGGTGCTTCGACTGCGGTT<br>CGGCCCTGGCTGAGGCGGAAGTCGAATACGAAGACAAGAAGTCCTCG<br>ACCATCGACGTGGCCTTCCCGATCGCCGACGACGCCAAGTTGGCCCA<br>GGCTTTCGGCCTGGCAAGCCTGAGCAAGCCGGCGGCCATCGTGATCT<br>GGACCACCACCCCGTGGACCATCCCGGCCAACCAGGCGCTGAACGTG<br>CACCCGGAATTCACCTACGCCCTGGTGGACGTCGGTGATCGCCTGCTG<br>GTGCTGGCCGAGGAAATGGTCGAGGCCTGTCTGGCGCGCTACGAACT<br>GCAAGGTTCGGTGATCGCCACCACCACCGGCTCCGCGCTGGAACTGA<br>TCAACTTCCGTCACCCGTTCTATGACCGCCTGTCGCCGGTTTACCTGG<br>CTGACTACGTCGAACTGGGTTCGGGTACGGGTGTGGTTCACTCCGCAC<br>CGGCCTACGGCGTTGACGACTTCGTGACCTGCAAAGCCTACGGTATG<br>GTCAACGATGACATCCTCAACCCGGTGCAGAGCAATGGTGTGTACGC<br>GCCATCGCTGGAGTTCTTCGGCGGCCAGTTCATCTTCAAGGCTAACGA<br>GCCGATCATCGACAAACTGCGTGAAGTCGGTGCGCTGCTGCACACCG<br>AAACCATCAAGCACAGCTACATGCACTGCTGGCGCCACAAAACCCCG<br>CTGATCTACCGCGCCACCGCGCAGTGGTTTATCGGCATGGACAAAGA<br>GCCGACCAGCGGCGACACCCTGCGTGTGCGCTCGCTCAAAGCCATCG<br>AAGACACCAAGTTCGTCCCGGCCTGGGGCCAGGCGCGCCTGCACTCG<br>ATGATCGCCAATCGTCCGGACTGGTGCATCTCCCGCCAGCGTAACTGG<br>GGCGTACCGATCCCGTTCTTCCTGAACAAGGAAAGCGGCGAGCTGCA<br>CCCACGCACCGTCGAGCTGATGGAAGCCGTGGCCTTGCGCGTTGAAC<br>AGGAAGGCATCGAAGCCTGGTTCAAGCTGGACGCCGCCGAGCTGCTG<br>GGCGACGAAGCGCCGCTGTACGACAAGAAGGCTCGGACCAACACCGT<br>GGCTGGTTCCACTCGTCGCTGCTGA |
| 91 | DP1 NADH-quinone oxidoreductase | ATGACTACAGGCAGTGCTCTGTACATCCCGCCTTATAAGGCAGACGA<br>CCAGGATGTGGTTGTCGAACTCAATAACCGTTTTGGCCCTGACGCCTT<br>TACCGCCCAGGCCACACGTACCGGCATGCCGGTGCTGTGGGTGGCGC |

-continued

| Sequence Listing | | |
|---|---|---|
| Seq ID No. | Description | Sequence |
| | subunit C/D | GCGCCAGGCTCGTCGAAGTCCTGACCTTCCTGCGCAACCTGCCCAAGC<br>CGTACGTCATGCTCTATGACCTGCATGGCGTGGACGAGCGTCTGCGG<br>ACCAAGCGCCAGGGCCTGCCGAGCGGCGCCGATTTCACCGTGTTCTA<br>TCACCTGCTGTCGATCGAACGTAACAGCGACGTGATGATCAAGGTCG<br>CCCTCTCCGAAAGCGACCTGAGCGTCCCGACCGTGACCGGCATCTGG<br>CCCAACGCCAGTTGGTACGAGCGTGAAGTCTGGGACATGTTCGGTAT<br>CGACTTCCCTGGCCACCCGCACCTGACGCGCATCATGATGCCGCCGA<br>CCTGGGAAGGTCACCCGCTGCGCAAGGACTTCCCTGCGCGCGCCACC<br>GAATTCGACCCGTTCAGCCTGAACCTCGCCAAGCAACAGCTTGAAGA<br>AGAGGCTGCACGCTTCCGGCCGGAAGACTGGGGCATGAAACGCTCCG<br>GCACCAACGAGGACTACATGTTCCTCAACCTGGGCCCGAACCACCCT<br>TCGGCGCACGGTGCCTTCCGTATCATCCTGCAACTGGACGGCGAAGA<br>AATCGTCGACTGCGTGCCGGACATCGGTTACCACCACCGTGGTGCCG<br>AGAAGATGGCCGAGCGCCAGTCGTGGCACAGCTTCATCCCGTACACC<br>GACCGTATCGACTACCTCGGCGGCGTGATGAACAATCTGCCGTACGT<br>GCTCTCGGTCGAGAAGCTGGCCGGTATCAAGGTGCCGGACCGCGTCG<br>ACACCATCCGCATCATGATGGCCGAGTTCTTCCGGATCACCAGCCACC<br>TGCTGTTCCTGGGTACCTACATCCAGGACGTCGGCGCCATGACCCCGG<br>TGTTCTTCACCTTCACCGACCGTCAGCGCGCCTACAAGGTCATCGAAG<br>CCATCACCGGCTTCCGCCTGCACCCGGCCTGGTACCGCATCGGCGGTG<br>TCGCGCACGACCTGCCAAATGGCTGGGAACGCCTGGTCAAGGAATTC<br>ATCGACTGGATGCCCAAGCGTCTGGACGAGTACCAGAAAGCCGCCCT<br>GGACAACAGCATCCTCAAGGGCCGGACCATTGGGGTCGCGGCCTACA<br>ACACCAAAGAGGCCCTGGAATGGGGCGTCACCGGTGCTGGCCTGCGT<br>TCCACCGGTTGCGATTTCGACCTGCGTAAAGCGCGCCCGTACTCCGGC<br>TACGAGAACTTCGAATTCGAAGTGCCGTTGGCGGCCAATGGCGATGC<br>CTACGACCGTTGCATCGTGCGCGTCGAAGAAATGCGCCAGAGCCTGA<br>AGATCATCGAGCAATGCATGCGCAACATCCGGCAGGCCCGTACAAGG<br>CGGACCACCCGCTGACCACGCCGCCGCCGAAAGAGCGCACGCTGCAA<br>CACATCGAAACCCTGATCACGCACTTCCTGCAGGTTTCGTGGGGCCCG<br>GTGATGCCGGCCAACGAATCCTTCCAGATGATCGAAGCGACCAAGGG<br>TATCAACAGTTATTACCTGACGAGCGATGGCGGCACCATGAGCTACC<br>GCACCCGGATTCGCACTCCAAGCTTCCCGCACCTGCAGCAGATCCCTT<br>CGGTGATCAAAGGTGAAATGGTCGCGGACTTGATTGCGTACCTGGGT<br>AGTATCGATTTCGTTATGGCCGACGTGGACCGCTAA |
| 92 | DP1 Protein RecA | ATGGACGACAACAAGAAGAAAGCCTTGGCTGCGGCCCTGGGTCAGAT<br>CGAACGTCAATTCGGCAAGGGTGCCGTAATGCGTATGGGCGATCACG<br>ACCGTCAGGCGATCCCGGCTATTTCCACTGGCTCTCTGGGTCTGGACA<br>TCGCACTCGGCATTGGCGGCCTGCCAAAAGGCCGTATCGTTGAAATCT<br>ACGGCCCTGAATCTTCCGGTAAAACCACCCTGACCCTGTCGGTGATTG<br>CCCAGGCGCAAAAAATGGGCGCCACTTGTGCGTTCGTCGATGCCGAG<br>CACGCTCTTGACCCTGAATACGCCGGCAAGCTGGGCGTCAACGTTGA<br>CGACCTGCTGGTTTCCCAACCGGACACCGGTGAGCAAGCCTTGGAAA<br>TCACCGACATGCTGGTGCGCTCCAACGCCATCGACGTGATCGTGGTCG<br>ACTCCGTGGCTGCCCTGGTGCCGAAAGCTGAAATCGAAGGCGAAATG<br>GGCGACATGCACGTGGGCCTGCAAGCCCGTCTGATGTCCCAGGCGCT<br>GCGTAAAATCACCGGTAACATCAAGAACGCCAACTGCCTGGTGATCT<br>TCATCAACCAGATCCGTATGAAGATTGGCGTGATGTTCGGCAGCCCG<br>GAAACCACCACCGGTGGTAACGCGTTGAAGTTCTACGCTTCGGTCCGT<br>CTGGATATCCGCCGTACTGGCGCGGTGAAGGAAGGCGACGAGGTGGT<br>GGGTAGCGAAACCCGCGTTAAAGTTGTGAAGAACAAGGTGGCCCCGC<br>CATTCCGTCAGGCTGAGTTCCAGATTCTCTACGGCAAGGGTATCTACC<br>TGAACGGCGAGATGATCGACCTGGGCGTACTGCACGGTTTCGTCGAG<br>AAGTCCGGTGCCTGGTATGCCTACAACGGCAGCAAGATCGGTCAGGG<br>CAAGGCCAACTCGGCCAAGTTCCTGGCGGACAACCCGGATATCGCTG<br>CCACGCTTGAGAAGCAGATTCGCGACAAGCTGCTGACCCCGGCACCA<br>GACGTGAAAGCTGCTGCCAACCGCGAGCCGGTTGAAGAAGTAGAAG<br>AAGTCGACACTGACATCTGA |
| 93 | DP1 RNA polymerase sigma factor RpoD | ATGGAAATCACCCGCAAGGCTCTGAAAAAGCACGGTCGCGGCAACAA<br>GCTGGCAATTGCCGAGCTGGTGGCCCTGGCTGAGCTGTTCATGCCAAT<br>CAAGCTGGTGCCGAAGCAATTTGAAGGCCTGGTTGAGCGTGTGCGCA<br>GTGCTCTTGAGCGTCTGCGTGCCCAAGAGCGCGCAATCATGCAGCTCT<br>GCGTACGTGATGCACGCATGCCGCGTGCCGACTTCCTGCGCCAGTTCC<br>CGGGCAACGAAGTGGATGAAAGCTGGACCGACGCACTGGCCAAAGG<br>CAAGGCGAAGTACGCCGAAGCCATTGGTCGCCTGCAGCCGGACATCA<br>TCCGTTGCCAGCAGAAGCTGACCGCGCTTCAAACCGAAACCGGTCTG<br>ACGATTGCTGAGATCAAGGACATCAACCGTCGCATGTCGATCGGTGA<br>GGCCAAGGCCCGCCGCGCGAAGAAAGAGATGGTTGAAGCGAACTTG<br>CGTCTGGTGATCTCCATCGCCAAGAAGTACACCAACCGTGGCCTGCA<br>ATTCCTCGATCTGATCCAGGAAGGCAACATCGGCTTGATGAAGGCTG<br>TGGACAAGTTCGAATACCGTCGCGGCTACAAGTTCTCGACTTATGCCA |

-continued

Sequence Listing

| Seq ID No. | Description | Sequence |
|---|---|---|
| | | CCTGGTGGATCCGTCAGGCGATCACTCGCTCGATCGCAGACCAGGCC<br>CGCACCATCCGTATTCCGGTGCACATGATCGAGACCATCAACAAGCT<br>CAACCGTATTTCCCGGCAGATGTTGCAGGAAATGGGTCGCGAACCGA<br>CGCCGGAAGAGCTGGGCGAACGCATGGAAATGCCTGAGGATAAAAT<br>CCGTAAGGTATTGAAGATCGCTAAAGAGCCGATCTCCATGGAAACGC<br>CGATTGGTGATGACGAAGACTCCCATCTGGGTGACTTCATCGAAGAC<br>TCGACCATGCAGTCGCCCATCGATGTGGCTACCGTTGAGAGCCTTAAA<br>GAAGCGACTCGCGACGTACTGTCCGGCCTCACTGCCCGTGAAGCCAA<br>GGTACTGCGCATGCGTTTCGGCATCGACATGAATACCGACCACACCCT<br>TGAGGAAGTCGGTAAGCAGTTTGACGTGACCCGTGAACGGATCCGTC<br>AGATCGAAGCCAAGGCACTGCGCAAGTTGCGCCACCCGACGCGAAGC<br>GAGCATCTACGCTCCTTCCTCGACGAGTGA |
| 94 | DP1 DNA-directed RNA polymerase subunit beta | ATGGCTTACTCATATACTGAGAAAAAACGTATCCGCAAGGACTTTAG<br>CAAGTTGCCGGACGTCATGGATGTCCCGTACCTTCTGGCTATCCAGCT<br>GGATTCGTATCGTGAATTCTTGCAAGCGGGAGCGACTAAAGATCAGT<br>TCCGCGACGTGGGCCTGCATGCGGCCTTCAAATCCGTTTTCCCGATCA<br>TCAGCTACTCCGGCAATGCTGCGCTGGAGTACGTGGGTTATCGCCTGG<br>GCGAACCGGCATTTGATGTCAAAGAATGCGTGTTGCGCGGTGTTACG<br>TACGCCGTACCTTTGCGGGTAAAAGTCCGTCTGATCATTTTCGACAAA<br>GAATCGTCGAACAAAGCGATCAAGGACATCAAAGAGCAAGAAGTCT<br>ACATGGGCGAAATCCCATTGATGACTGAAAACGGTACCTTCGTTATC<br>AACGGTACCGAGCGCGTTATCGTTTCCCAGCTGCACCGTTCCCCGGGC<br>GTGTTCTTCGACCACGACCGCGGCAAGACGCACAGCTCCGGTAAGCT<br>CCTGTACTCCGCGCGGATCATTCCGTACCGCGGCTCGTGGTTGGACTT<br>CGAGTTCGACCCGAAAGACTGCGTGTTCGTGCGTATCGACCGTCGTCG<br>TAAGCTGCCGGCCTCGGTACTGCTGCGCGCGCTCGGCTATACCACTGA<br>GCAAGTGCTTGATGCTTTCTACACCACCAACGTATTCAGCCTGAAGGA<br>TGAAACCCTCAGCCTGGAACTGATTGCTTCGCGTCTGCGTGGTGAAAT<br>TGCCGTCCTGGATATCCAGGATGAAAACGGCAAGGTCATCGTTGAAG<br>CTGGCCGCCGTATTACCGCGCGCCACATCAACCAGATCGAAAAAGCC<br>GGTATCAAGTCGCTGGACGTGCCGCTGGACTACGTCCTGGGTCGCAC<br>CACTGCCAAGGTCATCGTTCACCCGGCTACAGGCGAAATCCTGGCTG<br>AGTGCAACACCGAGCTGAACACCGAGATCCTGGCAAAAATCGCCAAG<br>GCCCAGGTTGTTCGCATCGAGACCCTGTACACCAACGACATCGACTG<br>CGGTCCGTTCATCTCCGACACGCTGAAGATCGACTCCACCAGCAACC<br>AATTGGAAGCGCTGGTCGAGATCTATCGCATGATGCGTCCTGGTGAG<br>CCACCGACCAAAGACGCTGCCGAGACCCTGTTCAACAACCTGTTCTTC<br>AGCCCTGAGCGCTATGACCTGTCTGCGGTCGGCCGGATGAAGTTCAA<br>CCGTCGTATCGGTCGTACCGAGATCGAAGGTTCGGGCGTGCTGTGCA<br>AGGAAGACATCGTCGCGGTACTGAAGACCTTGGTCGACATCCGTAAC<br>GGTAAAGGCATCGTCGATGACATCGACCACTTGGGTAACCGTCGTGT<br>TCGCTGCGTAGGCGAAATGGCCGAGAACCAGTTCCGCGTTGGCCTGG<br>TACGTGTTGAGCGTGCGGTCAAAGAGCGTCTGTCGATGGCTGAAAGC<br>GAAGGCCTGATGCCGCAAGATCTGATCAACGCCAAGCCAGTGGCTGC<br>GGCGGTGAAAGAGTTCTTCGGTTCCAGCCAGCTCTCGCAGTTCATGGA<br>CCAGAACAACCCGCTCTCCGAGATCACCCACAAGCGCCGTGTTTCCG<br>CACTGGGCCCGGGCGGTCTGACCCGTGAGCGTGCAGGCTTTGAAGTT<br>CGTGACGTACACCCAACGCACTACGGTCGTGTTTGCCCGATCGAAAC<br>GCCGGAAGGTCCGAACATCGGTCTGATCAACTCCCTTGCCGCTTATGC<br>ACGCACTAACCAGTACGGCTTCCTCGAGAGCCCGTACCGTGTAGTGA<br>AAGATGCACTGGTCACCGACGAGATCGTGTTCCTGTCCGCCATCGAA<br>GAAGCCGATCACGTGATCGCTCAGGCTTCGGCCACGATGAACGACAA<br>GAAAGTCCTGATCGACGAGCTGGTAGCTGTTCGTCACTTGAACGAGTT<br>CACCGTTAAGGCGCCGGAAGACGTCACCTTGATGGACGTTTCGCCGA<br>AGCAGGTAGTTTCGGTTGCAGCGTCGCTGATCCCGTTCCTGGAGCACG<br>ATGACGCCAACCGTGCGTTGATGGGTTCCAACATGCAGCGTCAAGCT<br>GTACCCACCCTGCGTGCCGACAAGCCGCTGGTAGGTACCGGCATGGA<br>GCGTAACGTAGCCCGTGACTCCGGCGTTTGCGTCGTGGCTCGTCGTGG<br>CGGCGTGATCGACTCTGTTGATGCCAGCCGTATCGTGGTTCGTGTTGC<br>CGATGACGAAGTTGAGACTGGCGAAGCCGGTGTCGACATCTACAACC<br>TGACCAAATACACCCGCTCGAACCAGAACACCTGCATCAACCAGCGC<br>CCGCTGGTGAGCAAGGGTGATCGCGTTCAGCGTAGCGACATCATGGC<br>CGACGGCCCGTCCACCGATATGGGTGAGCTGGCACTGGGTCAGAACA<br>TGCGCATCGCGTTCATGGCATGGAACGGCTTCAACTTCGAAGACTCCA<br>TCTGCCTGTCCGAGCGTGTTGTTCAAGAAGACCGCTTCACCACGATCC<br>ACATTCAGGAGCTGACCTGTGTGGCGCGTGACACCAAGCTTGGGCCA<br>GAGGAAATCACTGCAGACATCCCGAACGTGGGTGAAGCTGCACTGAA<br>CAAACTGGACGAAGCCGGTATCGTTTACGTAGGTGCTGAAGTTGGCG<br>CAGGCGACATCCTGGTTGGTAAGGTCACTCCGAAAGGCGAGACCCAA<br>CTGACTCCGGAAGAGAAGCTGTTGCGTGCCATCTTCGGTGAAAAAGC<br>CAGCGACGTTAAAGACACTTCCCTGCGCGTACCTACCGGTACCAAGG<br>GTACTGTCATCGACGTACAGGTCTTCACCCGTGACGGCGTTGAGCGTG |

-continued

Sequence Listing

| Seq ID No. | Description | Sequence |
|---|---|---|
| | | ATGCTCGTGCACTGTCCATCGAGAAGACTCAACTCGACGAGATCCGC<br>AAGGACCTGAACGAAGAGTTCCGTATCGTTGAAGGCGCGACCTTCGA<br>ACGTCTGCGTTCCGCTCTGGTAGGCCACAAGGCTGAAGGCGGCGCAG<br>GTCTGAAGAAAGGTCAGGACATCACCGACGAAATCCTCGACGGTCTT<br>GAGCACGGCCAGTGGTTCAAACTGCGCATGGCTGAAGACGCTCTGAA<br>CGAGCAGCTCGAGAAGGCCCAGGCCTATATCGTTGATCGCCGCCGTC<br>TGCTGGACGACAAGTTCGAAGACAAGAAGCGCAAACTGCAGCAGGG<br>CGATGACCTGGCTCCAGGCGTGCTGAAAATCGTCAAGGTTTACCTGG<br>CAATCCGTCGCCGCATTCAGCCGGGCGACAAGATGGCCGGTCGTCAC<br>GGTAACAAGGGTGTGGTCTCCGTGATCATGCCGGTTGAAGACATGCC<br>GCACGATGCCAATGGCACCCCGGTCGACGTCGTCCTCAACCCGTTGG<br>GCGTACCTTCGCGTATGAACGTTGGTCAGATCCTTGAAACCCACCTGG<br>GCCTCGCGGCCAAAGGTCTGGGCGAGAAGATCAACCGTATGATCGAA<br>GAGCAGCGCAAGGTCGCAGACCTGCGTAAGTTCCTGCACGAGATCTA<br>CAACGAGATCGGCGGTCGCAACGAAGAGCTGGACACCTTCTCCGACC<br>AGGAAATCCTGGATCTGGCGAAGAACCTGCGCGGCGGCGTTCCAATG<br>GCTACCCCGGTATTCGACGGTGCCAAGGAAAGCGAAATCAAGGCCAT<br>GCTGAAACTGGCAGACCTGCCGGAAAGTGGCCAGATGCAGCTGTTCG<br>ACGGCCGTACCGGCAACAAGTTTGAGCGCCCGGTTACTGTTGGCTAC<br>ATGTACATGCTGAAGCTGAACCACTTGGTAGACGACAAGATGCACGC<br>TCGTTCTACCGGTTCGTACAGCCTGGTTACCCAGCAGCCGCTGGGTGG<br>TAAGGCTCAGTTCGGTGGTCAGCGTTTCGGGGAGATGGAGGTCTGGG<br>CACTGGAAGCATACGGTGCTGCTTACACTCTGCAAGAAATGCTCACA<br>GTGAAGTCGGACGATGTGAACGGTCGGACCAAGATGTACAAAAACAT<br>CGTGGACGGCGATCACCGTATGGAGCCGGGCATGCCCGAGTCCTTCA<br>ACGTGTTGATCAAAGAAATTCGTTCCCTCGGCATCGATATCGATCTGG<br>AAACCGAATAA |
| 95 | DP22 Glutamine--tRNA ligase | ATGAGTGAGGCTGAAGCCCGCCCAACAAATTTTATCCGTCAGATTATT<br>GATGAAGATCTGGCGACCGGGAAACACAATACCGTTCATACCCGTTT<br>CCCGCCTGAGCCAAATGGCTATCTGCATATCGGTCATGCGAAATCTAT<br>CTGCCTGAACTTCGGCATTGCGCAAGACTATCAGGGGCAGTGCAACC<br>TGCGTTTTGACGATACCAACCCGGCAAAAGAAGACATCGAATTCGTT<br>GAGTCGATCAAACACGACGTCCAGTGGTTAGGTTTCGACTGGAGCGG<br>TGATATTCACTACTCTTCAGACTATTTTGATCAACTGCACGCTTATGC<br>GCTGGAACTGATCAACAAAGGTCTGGCGTACGTTGACGAACTGTCAC<br>CGGATCAGATCCGTGAATACCGCGGCTCGCTGACGTCTCCGGGCAAA<br>AACAGCCCGTACCGTGACCGTTCAGTGGAAGAGAACATCGCGCTGTT<br>TGAGAAAATGCGTAACGGTGAATTTGCCGAAGGCGCTGCCTGTCTGC<br>GTGCAAAAATCGATATGGCGTCGCCTTTCTTCGTGATGCGCGATCCGG<br>TTCTGTACCGTATTAAGTTTGCAGAACACCACCAGACCGGCAAAAAA<br>TGGTGCATCTATCCGATGTACGATTTCACCCACTGCATTTCCGATGCG<br>CTGGAAGGGATCACCCATTCGCTGTGTACGCTGGAATTCCAGGACAA<br>CCGCCGTCTGTACGACTGGGTTCTGGATAACATCTCCATTCCATGCCA<br>CCCGCGTCAGTACGAGTTCTCCCGTCTGAATCTCGAGTACTCCATCAT<br>GTCTAAGCGTAAGCTGAACCAGCTGGTGACCGAGAAGATTGTGGAAG<br>GCTGGGACGACCCGCGTATGCCGACTGTTTCAGGTCTGCGTCGTCGTG<br>GTTACACCGCCGCGTCTATCCGTGAATTCTGCCGTCGTATCGGCGTCA<br>CCAAGCAAGACAACAACGTCGAAATGATGGCGCTGGAATCCTGTATC<br>CGTGACGATCTGAACGAAAATGCACCGCGCGCCATGGCGGTGATCAA<br>CCCGGTTAAAGTGATCATTGAAAACTTTACCGGTGATGACGTGCAGA<br>GGGTGAAAATGCCGAACCACCCGAGCAAACCGGAAATGGGCACCCG<br>CGAAGTGCCATTTACCCGTGAGATTTATATCGATCAGGCAGATTTCCG<br>CGAAGAAGCGAACAAGCAATACAAGCGTCTGGTGCTCGGCAAAGAA<br>GTGCGTCTGCGCAATGCGTATGTGATCAAAGCAGAACGTATCGAGAA<br>AGATGCAGAAGGCAATATCACCACGATCTTCTGTTCTTACGATATCGA<br>TACACTGAGCAAAGATCCTGCCGATGGCCGCAAGGTGAAAGGCGTGA<br>TCCACTGGGTTTCGGCGTCAGAAGGCAAACCGGCGGAGTTCCGCCTG<br>TATGACCGTCTGTTCAGCGTCGCCAACCCGGGTCAGGCAGAAGATTTC<br>CTGACCACCATCAACCCGGAATCTCTGGTGATTTCCCACGGTTTCGTG<br>GAGCCATCACTGGTGGCTGCACAGGCTGAAATCAGCCTGCAGTTCGA<br>GCGTGAAGGTTACTTCTGCGCCGACAGCCGCTACTCAAGCGCTGAAC<br>ATCTGGTGTTTAACCGTACCGTTGGCCTGCGCGATACCTGGGAAAGCA<br>AACCCGTCGTGTAA |
| 96 | DP22 DNA gyrase subunit B | ATGTCGAATTCTTATGACTCCTCAAGTATCAAGGTATTAAAAGGGCTG<br>GACGCGGTGCGTAAGCGCCCCGGCATGTATATCGGCGATACCGATGA<br>CGGCACTGGTCTGCACCACATGGTATTCGAGGTTGTGGACAACGCTAT<br>CGACGAAGCCCTCGCGGGCCACTGTAAAGAGATTCAGGTCACGATCC<br>ATGCGGATAACTCTGTGTCCGTACAGGATGATGGTCGTGGCATTCCGA<br>CCGGTATTCATGAAGAAGAGGGCGTTTCTGCTGCTCAGGTCATCATGA<br>CCGTTCTTCACGCCGGCGGTAAATTTGACGATAACTCGTATAAAGTCT<br>CCGGCGGTCTGCATGGCGTGGGTGTTTCCGTCGTTAACGCCCTGTCAG |

-continued

Sequence Listing

| Seq ID No. | Description | Sequence |
|---|---|---|
| | | AAAAACTGGAACTGGTTATCCGCCGCGAAGGCAAAGTGCACACCCAG<br>ACTTACGTGCATGGCGAACCTCAGGATCCGCTGAAAGTGATTGGCGA<br>TACTGACGTGACCGGTACCACGGTACGTTTCTGGCCAAGCTTCAACAC<br>CTTCACCAATCACACTGAATTCGAGTATGACATTCTGGCGAAACGCCT<br>GCGTGAACTGTCATTCCTGAACTCCGGCGTGGCGATCCGCCTGCTGGA<br>TAAACGTGATGGTAAAAACGATCACTTCCATTATGAAGGCGGTATCA<br>AAGCTTTCGTGGAATATCTGAACAAAAACAAAACCCCAATCCATCCG<br>ACCGTATTCTATTTCTCCACGGTCAAAGATGACATTGGCGTTGAAGTG<br>GCGTTGCAGTGGAACGACGGTTTCCAGGAAAACATTTACTGCTTCACC<br>AACAACATTCCACAGCGCGATGGCGGGACTCACTTAGCCGGTTTCCG<br>TTCGGCAATGACCCGTACCCTGAACGCGTACATGGATAAAGAAGGCT<br>ACAGCAAGAAATCCAAAATCAGCGCCACCGGTGATGATGCCCGTGAA<br>GGCCTGATTGCTGTGGTGTCGGTGAAGGTGCCGGATCCTAAGTTCTCT<br>TCTCAGACCAAAGACAAACTGGTGTCTTCTGAAGTGAAAACAGCGGT<br>TGAAACGCTGATGAACGAGAAGCTGGTGGATTACCTGATGGAAAACC<br>CGTCAGACGCCAAAATCGTTGTCGGTAAAATCATCGACGCAGCGCGT<br>GCCCGTGAAGCAGCACGTAAAGCGCGTGAAATGACCCGCCGTAAAGG<br>CGCGCTGGATCTGGCTGGCTTGCCAGGCAAACTGGCGGACTGTCAGG<br>AACGCGATCCGGCACATTCCGAACTGTACTTAGTGGAAGGGGACTCA<br>GCGGGCGGCTCTGCAAAACAAGGCCGTAACCGTAAGAACCAGGCGAT<br>TCTGCCGTTGAAAGGTAAAATCCTCAACGTGGAGAAAGCGCGCTTCG<br>ACAAAATGCTCTCTTCTCAGGAAGTGGCAACGCTGATTACAGCACTC<br>GGTTGCGGCATTGGCCGTGACGAATACAACCCGGACAAACTGCGCTA<br>TCACAGCATCATCATCATGACCGATGCCGACGTCGATGGTTCGCACAT<br>CCGTACCCTGTTGCTGACATTCTTCTACCGTCAGATGCCTGAAATTGT<br>AGAACGTGGCCACGTGTTTATCGCCCAGCCGCCGTTGTACAAAGTGA<br>AAAAAGGCAAGCAGGAACAGTACATTAAAGATGACGAAGCGATGGA<br>TCAGTATCAGATTTCCATTGCGATGGACGGGGCAACGTTACACGCCA<br>ACGCTCATGCGCCAGCCCTGGCGGGTGAACCGCTGGAGAAACTGGTC<br>GCTGAACATCACAGCGTGCAGAAAATGATTGGCCGCATGGAACGTCG<br>TTATCCGCGTGCGCTGCTGAATAACCTGATCTATCAGCCGACCCTGCC<br>GGGTGCAGATCTGGCCGATCAGGCGAAAGTGCAGGCCTGGATGGAAT<br>CGCTGGTGGCGCGTCTCAACGAGAAAGAGCAGCACGGCAGTTCTTAC<br>AGCGCGATCGTGCGTGAAAACCGCGAACATCAGCTGTTCGAACCGGT<br>TCTGCGTATCCGCACCCACGGTGTTGATACCGATTACGATCTGGATGC<br>CGACTTCATCAAAGGCGGCGAATACCGCAAAATCTGTGCGCTGGGTG<br>AACAGCTGCGCGGCCTGATCGAAGAAGATGCCTTCATCGAACGTGGC<br>GAACGCCGTCAGCCCGTCACCAGCTTCGAACAGGCGCTGGAATGGCT<br>GGTGAAAGAGTCCCGTCGTGGTCTGTCGATTCAGCGATACAAAGGTC<br>TGGGTGAAATGAACCCTGAACAGCTGTGGGAAACCACCATGGATCCT<br>GAGCAACGTCGCATGTTACGTGTGACCGTGAAGGATGCCATCGCCGC<br>TGACCAGTTGTTCACGACGCTGATGGGCGATGCGGTTGAACCGCGCC<br>GCGCCTTTATCGAAGAGAACGCCCTGAAAGCCGCCAATATCGATATC<br>TGA |
| 97 | DP22 Isoleucine--tRNA ligase | ATGAGTGACTACAAGAACACCCTGAATTTGCCGGAAACAGGGTTCCC<br>GATGCGTGGCGATCTGGCCAAGCGTGAACCTGACATGCTGAAAAATT<br>GGTATGACCAGGATCTGTACGGGATTATTCGTGCTGCCAAGAAAGGC<br>AAAAAAACCTTTATTTTGCATGACGGCCCTCCGTATGCGAACGGCAG<br>CATTCATATTGGTCACTCAGTAAACAAAATTCTTAAAGACATGATTAT<br>CAAGTCCAAAGGACTTGCGGGCTTTGATGCGCCGTATGTGCCGGGCT<br>GGGATTGTCATGGTCTGCCGATCGAGCTGAAAGTCGAACAACTGATC<br>GGTAAGCCGGGCGAGAAAGTTACGGCGGCGGAATTCCGTGAAGCCTG<br>CCGTAAATATGCCGCAGAACAGGTTGAAGGCCAGAAGAAAGACTTCA<br>TCCGTCTGGGCGTGCTGGGCGACTGGGATCATCCGTACCTGACGATG<br>GATTTCAAAACCGAAGCCAACATCATCCGTGCGCTGGGCAAAATCAT<br>CGGTAACGGCCACCTGCATAAAGGCGCCAAGCCGGTGCACTGGTGTA<br>CAGATTGCGGTTCGTCGCTGGCCGAAGCCGAAGTCGAATATTACGAC<br>AAAGCCTCGCCTTCTATTGATGTGGCGTTCAACGCGACGGATGCCGCA<br>GCCGTGGCAGCGAAATTTGGCGTTACTGCCTTTAATGGCCCGATCTCG<br>CTGGTTATCTGGACCACAACACCGTGGACTATGCCCGCTAACCGCGCC<br>ATTTCACTGAATCCTGAGTTTGCTTATCAGCTGGTTCAGGTCGAAGGT<br>CAGTGTCTGATCCTGGCAACCGATCTGGTTGAAAGCGTCATGAAACG<br>TGCCGGTATTGCCGGATGGACCGTTCTGGGCGAGTGCAAAGGCGCAG<br>ACCTCGAACTGCTGCGCTTCAAACACCCGTTCCTCGGTTTCGACGTTC<br>CGGCGATCCTGGGCGATCACGTGACGCTCGATGCGGGTACCGGTGCC<br>GTGCATACCGCACCAGGCCACGGCCCTGACGACTTTGTTATCGGCCA<br>GAAATACGGTCTGGAAGTGGCGAATCCGGTAGGGCCGAACGGTTGCT<br>ACCTGCCGGGCACTTACCCGACGCTGGACGGTAAATTTGTCTTTAAAG<br>CCAACGACCTGATCGTTGAGTTGCTGCGTGAAAAAGGCGCATTGCTG<br>CACGTTGAGAAAATCACGCACAGCTATCCTTGCTGCTGGCGCCACAA<br>AACGCCAATCATCTTCCGCGCGACGCCGCAATGGTTCATCAGCATGG<br>ATCAGAAGGGCCTGCGTCAGCAGTCGCTGGAAGAGATCAAAGGCGTG |

-continued

Sequence Listing

| Seq ID No. | Description | Sequence |
|---|---|---|
| | | CAGTGGATCCCGGACTGGGGTCAGGCACGTATCGAAAACATGGTCGC<br>TAACCGTCCTGACTGGTGTATCTCCCGTCAGCGTACCTGGGGCGTGCC<br>GATGTCTCTGTTCGTTCACAAAGACACTGAGCAGCTGCATCCGCGCAG<br>CCTTGAGCTGATGGAAGAAGTGGCGAAACGTGTTGAGGTGGATGGCA<br>TTCAGGCGTGGTGGGATCTGAATCCGGAAGACATTCTGGGTGCAGAC<br>GCCGCAGATTACGTCAAAGTACCGGACACGCTGGACGTCTGGTTTGA<br>CTCCGGTTCAACGCATTCTTCCGTTGTGGATGTGCGTCCTGAGTTCAA<br>CGGGCATTCTCCTGATCTGTATCTGGAAGGTTCTGACCAGCATCGCGG<br>CTGGTTCATGTCTTCCCTGATGATTTCGACGGCAATGAAAGGCAAAGC<br>GCCTTACAAACAAGTGCTGACTCACGGTTTCACCGTGGATGGTCAGG<br>GCCGCAAAATGTCTAAATCCATCGGCAATACCATCGCGCCGCAAGAC<br>GTGATGAACAAGCTGGGTGGCGACATTCTGCGTCTGTGGGTCGCGTC<br>GACGGATTACACCGGCGAAATCGCCGTGTCCGACGAAATCCTCAAAC<br>GTGCTGCTGATTCTTACCGCCGTATCCGTAACACCGCGCGCTTCCTGC<br>TGGCGAACCTTAACGGTTTCGATCCGGCGCTGCACAGCGTGGCTCCG<br>GAAGACATGGTGGTGCTGGACCGCTGGGCGGTTGGCCGTGCGAAAGC<br>CGCTCAGGAAGAAATCATTGCTGCGTATGAAGCCTATGATTTCCATGG<br>CGTTGTTCAGCGTCTGATGCAGTTCTGCTCGATCGAAATGGGTTCCTT<br>CTATCTGGATATCATTAAAGATCGTCAGTACACCGCGAAAAGCGACA<br>GCGTTGCACGTCGCAGCTGTCAGACCGCGCTGTATCACATCAGTGAA<br>GCGCTGGTTCGCTGGATGGCACCGATCATGTCGTTCACAGCCGATGA<br>AATCTGGGCGGAACTGCCGGGAAGCCGTGAGAAATTCGTCTTCACCG<br>AAGAGTGGTACGACGGTCTGTTCGGTCTCGCAGGCAACGAATCCATG<br>AACGATGCGTTCTGGGATGAACTGCTGAAAGTGCGTGGCGAAGTGAA<br>CAAAGTGATCGAACAGGCGCGTGCGGATAAACGTCTGGGCGGTTCTC<br>TGGAAGCAGCGGTTACGCTGTTTGCTGATGATGCGCTGGCAACAGAC<br>CTGCGTTCTCTGGGCAATGAACTGCGCTTTGTGCTGCTGACGTCAGGG<br>GCGAAAGTTGCCGCACTGAGTGATGCAGATGACGCGGCTCAGTCGAG<br>TGAATTGCTGAAAGGCCTGAAGATTGGTCTGGCGAAAGCAGAAGGCG<br>ACAAGTGCCCGCGCTGCTGGCATTACACTACCGATTAA |
| 98 | DP22 NADH-quinone oxidoreductase subunit C/D | ATGACAGATTTGACGACGCAAGATTCCGCCCTGCCAGCATGGCATAC<br>CCGTGATCATCTCGATGATCCGGTTATCGGCGAATTGCGTAACCGTTT<br>TGGGCCAGAGGCCTTTACTGTCCAGGCAACCCGCACCGGAATTCCCG<br>TGGTGTGGTTCAAGCGTGAACAGTTACTGGAAGCGATTACCTTTTTAC<br>GAAAACAGCCAAAACCTTACGTCATGCTTTTCGATTTGCATGGCTTTG<br>ATGAGCGTTTACGTACACACCGCGACGGTTTACCGGCTGCGGATTTTT<br>CCGTTTTCTACCACCTGATCTCCGTCGAGCGTAACCGCGACATCATGA<br>TCAAAGTGGCGTTGTCAGAAAACGATCTTCATGTTCCGACGATCACCA<br>AAGTGTTCCCGAACGCTAACTGGTACGAACGCGAAACATGGGAAATG<br>TTCGGTATTACCTTCGACGGCCATCCGCACCTGACGCGCATCATGATG<br>CCGCAGACCTGGGAAGGGCATCCGCTGCGTAAAGACTATCCGGCGCG<br>CGCCACCGAGTTCGATCCTTATGAGCTGACTAAGCAAAAAGAAGAAC<br>TCGAGATGGAATCGCTGACCTTCAAGCCGGAAGACTGGGGCATGAAG<br>CGCGGTACCGATAACGAGGACTTTATGTTCCTCAACCTCGGTCCTAAC<br>CACCCGTCAGCGCATGGTGCATTCCGTATTATCCTGCAGCTGGATGGC<br>GAAGAGATTGTCGACTGCGTGCCTGACGTCGGTTACCACCACCGTGG<br>TGCGGAGAAAATGGGCGAACGCCAGTCATGGCACAGCTACATTCCGT<br>ATACTGACCGTATCGAATATCTCGGCGGTTGTGTTAACGAAATGCCTT<br>ACGTGCTGGCTGTTGAAAAACTCGCCGGTATCGTGACGCCGGATCGC<br>GTTAACACCATCCGTGTGATGCTGTCTGAACTGTTCCGTATCAACAGC<br>CATCTGCTGTACATCTCTACGTTTATTCAGGACGTGGGTGCGATGACG<br>CCGGTATTCTTCGCCTTTACCGATCGTCAGAAAATTTACGATCTGGTG<br>GAAGCGATCACCGGTTTCCGTATGCACCCGGCCTGGTTCCGTATCGGT<br>GGCGTAGCGCATGACCTGCCGAAAGGCTGGGACCGCCTGCTGCGTGA<br>ATTCCTTGACTGGATGCCAGCCCGTTTGGATTCCTACGTCAAAGCGGC<br>GCTGAGAAACACCATTCTGATTGGCCGTTCCAAAGGCGTGGCCGCGT<br>ATAACGCCGACGACGCACTGGCCTGGGGCACCACCGGTGCTGGCCTG<br>CGCGCAACGGGTATCCCGTTCGATGTGCGTAAATGGCGTCCGTATTCA<br>GGTTATGAAAACTTTGACTTTGAAGTGCCGACCGGTGATGGCGTCAGT<br>GACTGCTATTCCCGCGTGATGCTGAAAGTGGAAGAACTTCGTCAGAG<br>CCTGCGCATTCTGGAACAGTGCTACAAAAACATGCCGGAAGGCCCGT<br>TCAAGGCGGATCACCCGCTGACCACGCCGCCACCGAAAGAGCGCACG<br>CTGCAACACATCGAGACCCTGATCACGCACTTCCTGCAAGTGTCGTGG<br>GGGCCGGTCATGCCTGCACAAGAATCTTTCCAGATGGTTGAAGCAAC<br>CAAAGGGATCAACAGCTACTACCTGACCAGTGACGGCAGCACCATGA<br>GCTACCGCACCCGTGTCCGTACGCCGAGCTTCCCGCATTTGCAGCAGA<br>TCCCGTCCGTAATCCGTGGCAGCCTGGTATCCGACCTGATCGTGTATC<br>TGGGCAGTATCGATTTTGTAATGTCAGATGTGGACCGCTAA |
| 99 | DP22 Protein RecA | ATGGCTATTGATGAGAACAAGCAAAAAGCGTTAGCTGCAGCACTGGG<br>CCAGATTGAAAAGCAATTCGGTAAAGGCTCCATCATGCGTCTGGGTG<br>AAGATCGCTCCATGGACGTTGAAACGATCTCTACCGGCTCTTTGTCTC |

-continued

Sequence Listing

| Seq ID No. | Description | Sequence |
|---|---|---|
| | | TGGATATCGCGTTAGGTGCCGGCGGTTTGCCAATGGGCCGTATCGTTG<br>AGATCTATGGCCCGGAATCTTCCGGTAAAACAACGCTGACCTTGCAA<br>GTTATCGCGGCTGCACAGCGTGAAGGCAAAACCTGTGCGTTCATCGA<br>TGCAGAACACGCCCTGGACCCGATCTACGCTAAAAAACTGGGCGTGG<br>ATATCGATAACCTGCTGTGTTCTCAGCCAGATACCGGCGAACAGGCTC<br>TGGAAATCTGTGACGCGCTGACCCGTTCAGGCGCTGTTGACGTGATCA<br>TCGTTGACTCCGTTGCCGCACTGACACCGAAAGCGGAAATCGAAGGC<br>GAAATTGGTGACTCTCACATGGGCCTCGCGGCACGTATGATGAGCCA<br>GGCGATGCGTAAGCTGGCCGGTAACCTGAAAAACGCCAACACCTTGC<br>TGATCTTCATCAACCAGATCCGTATGAAAATTGGTGTGATGTTCGGTA<br>ACCCGGAAACCACCACCGGCGGTAACGCCCTGAAATTCTACGCTTCT<br>GTGCGTCTGGATATCCGCCGTATCGGCGCGATCAAAGAAGGCGATGT<br>GGTTGTCGGTAGCGAAACGCGTGTGAAAGTGGTGAAGAACAAAATCG<br>CTGCGCCATTTAAACAAGCTGAATTCCAGATCATGTACGGCGAAGGC<br>ATCAATATCAACGGCGAGCTGATTGATCTCGGCGTGAAGCACAAGCT<br>GATCGAAAAAGCCGGTGCATGGTATAGCTACAACGGTGAGAAGATTG<br>GTCAGGGTAAAGCGAACTCCTGCAACTTCCTGAAAGAAAACCCGAAA<br>GTGGCTGCCGAGCTGGATAAAAAACTGCGTGATATGCTGTTGAGCGG<br>TACCGGTGAACTGAGTGCTGCGACCACGGCTGAAGATGCTGACGACA<br>ACATGGAAACCAGCGAAGAGTTTTAA |
| 100 | DP22 RNA polymerase sigma factor RpoD | ATGGAGCAAAACCCGCAGTCACAGCTTAAGCTACTTGTCACCCGTGG<br>TAAGGAGCAAGGCTATCTGACCTATGCTGAGGTCAATGACCATCTGC<br>CGGAAGATATCGTCGATTCCGACCAGATCGAAGACATCATCCAGATG<br>ATTAACGACATGGGCATCCAGGTACTTGAAGAAGCACCGGACGCCGA<br>TGATTTGATGCTGGCCGAAAACCGCCCTGATACCGATGAAGACGCTG<br>CAGAAGCCGCGGCGCAGGTGCTTTCCAGCGTTGAATCCGAAATTGGC<br>CGTACCACCGACCCTGTGCGTATGTATATGCGCGAGATGGGTACCGTT<br>GAGTTGCTGACCCGTGAAGGCGAAATCGACATCGCCAAACGTATCGA<br>AGACGGTATCAATCAGGTCCAGTGCTCCGTTGCTGAATATCCTGAAGC<br>TATCACTTATTTGTTAGAGCAATATGACCGTGTGGAAGCAGGCGAAG<br>TACGTCTGTCTGACCTGATCACCGGTTTTGTTGACCCGAACGCCGAAG<br>AAGAAATCGCACCAACTGCGACTCACGTGGGTTCTGAACTGACCACT<br>GAAGAGCAGAATGATGACGACGAAGACGAAGATGAAGACGACGACG<br>CTGAAGACGACAACAGCATCGATCCGGAACTGGCTCGCCAGAAGTTC<br>ACCGAACTGCGTGAACAGCATGAAGCGACGCGTCTGGTCATCAAGAA<br>AAACGGCCGTAGTCACAAGAGCGCAGCAGAAGAAATCCTGAAGCTGT<br>CCGATGTGTTCAAACAGTTCCGTCTGGTGCCAAAACAGTTCGATTTCC<br>TGGTTAACAGCATGCGTTCCATGATGGATCGCGTTCGTGCTCAGGAAC<br>GTCTGATCATGAAAGTGTGCGTTGAACAGTGCAAAATGCCGAAGAAA<br>AACTTCGTCAATCTGTTCGCCGGTAACGAAACCAGCGATACCTGGTTT<br>GATGCCGCTCTGGCAATGGGTAAACCATGGTCCGAGAAGCTGAAAGA<br>AGTCACCGAAGACGTGCAACGCGGCCTGATGAAACTGCGTCAGATCG<br>AAGAAGAAACCGGCCTGACTATCGAACAGGTTAAAGACATCAACCGT<br>CGCATGTCGATCGGCGAAGCGAAAGCCCGTCGCGCGAAGAAAGAGA<br>TGGTTGAAGCAAACTTACGTCTGGTTATTTCTATCGCCAAGAAATACA<br>CCAACCGTGGTCTGCAGTTCCTTGACCTGATCCAGGAAGGTAACATCG<br>GCCTGATGAAAGCCGTTGATAAGTTTGAATATCGCCGTGGTTATAAGT<br>TCTCAACTTATGCGACCTGGTGGATCCGTCAGGCTATCACCCGCTCCA<br>TCGCCGACCAGGCGCGTACCATCCGTATCCCGGTACATATGATTGAG<br>ACGATCAACAAACTCAACCGTATCTCCCGTCAGATGCTGCAAGAGAT<br>GGGCCGCGAACCGACACCGGAAGAGCTGGCTGAGCGTATGTTGATGC<br>CGGAAGACAAAATCCGCAAAGTGCTGAAAATTGCCAAAGAGCCAATC<br>TCCATGGAAACGCCAATCGGCGACGATGAAGATTCGCATCTGGGCGA<br>TTTCATCGAGGATACCACCCTCGAGCTGCCACTGGATTCTGCGACGTC<br>TGAAAGCCTGCGTTCTGCAACGCATGACGTTCTGGCTGGCCTGACTGC<br>ACGTGAAGCGAAAGTTCTGCGTATGCGTTTCGGTATCGATATGAACA<br>CTGACCACACGCTGGAAGAAGTGGGCAAACAGTTCGACGTGACCCGT<br>GAGCGTATCCGTCAGATCGAAGCGAAAGCGTTGCGTAAACTGCGCCA<br>CCCGAGCCGCTCCGAAGTACTGCGCAGCTTCCTGGACGATTAA |
| 101 | DP22 DNA-directed RNA polymerase subunit beta | GTGAAAGACTTACTAAAGTTTCTGAAAGCGCAAACTAAGACCGAAGA<br>GTTTGATGCGATCAAAATTGCTCTGGCATCGCCAGACATGATCCGTTC<br>TTGGTCTTTTGGTGAAGTTAAGAAGCCAGAAACCATTAACTACCGTAC<br>GTTCAAACCAGAACGTGACGGCCTTTTCTGTGCCCGTATTTTCGGACC<br>AGTAAAAGACTACGAATGCCTGTGCGGTAAGTACAAGCGTTTAAAAC<br>ATCGCGGCGTGATCTGCGAGAAGTGCGGCGTTGAAGTGACCCAGACT<br>AAAGTACGCCGTGAGCGTATGGGCCACATCGAACTGGCTTCCCCGAC<br>TGCACACATCTGGTTCCTGAAATCGCTGCCATCGCGCATCGGTTTGCT<br>GCTGGATATGCCACTGCGTGACATCGAACGTGTTCTGTACTTCGAATC<br>CTATGTGGTTATCGAAGGCGGCATGACTAACCTCGAAAAACGCCAGA<br>TCCTGACTGAAGAGCAGTATCTGGATGCGTTGGAAGAGTTTGGTGAT<br>GAGTTCGACGCGAAGATGGGTGCGGAAGCTATTCAGGCCCTGTTGAA |

-continued

Sequence Listing

| Seq ID No. | Description | Sequence |
| --- | --- | --- |
| | | AAACATGGATCTGGAAGCAGAGTGCGAGCAACTGCGTGAAGAGTTGA<br>ACGAAACCAACTCCGAAACCAAACGTAAGAAGCTGACCAAGCGTATC<br>AAGCTGCTGGAAGCGTTCGTTCAGTCTGGTAACAAACCAGAGTGGAT<br>GATCCTGACTGTGCTGCCGGTACTGCCACCAGACTTGCGTCCATTGGT<br>TCCGTTGGACGGCGGCCGTTTCGCAACGTCGGATCTGAACGATCTGTA<br>TCGTCGCGTGATCAACCGTAACAACCGTCTGAAACGCCTGCTGGATCT<br>GGCTGCGCCAGACATCATCGTACGTAACGAAAAACGTATGCTGCAAG<br>AAGCGGTAGATGCTTTGCTGGATAACGGCCGTCGCGGTCGTGCTATC<br>ACCGGCTCTAACAAGCGTCCGCTGAAATCTCTGGCAGACATGATTAA<br>AGGTAAACAGGGTCGTTTCCGTCAGAACTTGCTGGGTAAACGTGTCG<br>ACTACTCTGGTCGTTCCGTTATCACCGTAGGTCCATACCTGCGTCTGC<br>ACCAGTGTGGTCTGCCGAAGAAAATGGCACTGGAACTGTTCAAACCG<br>TTCATCTACGGCAAGCTGGAACTGCGTGGCCTGGCCACCACCATCAA<br>AGCCGCGAAGAAAATGGTTGAGCGCGAAGAAGCTGTCGTTTGGGACA<br>TCCTGGACGAAGTTATCCGCGAACACCCGGTACTGCTGAACCGTGCA<br>CCAACCCTGCACCGTTTGGGTATCCAGGCGTTTGAACCGGTTCTGATC<br>GAAGGTAAAGCAATCCAGCTGCACCCGCTGGTTTGTGCGGCATATAA<br>CGCCGACTTCGATGGTGACCAGATGGCTGTTCACGTACCGTTGACGCT<br>GGAAGCCCAGCTGGAAGCGCGTGCGTTGATGATGTCTACCAACAACA<br>TCCTGTCACCTGCGAACGGCGAGCCAATCATCGTTCCTTCTCAGGACG<br>TTGTATTGGGTCTGTACTACATGACCCGTGACTGTGTTAACGCCAAAG<br>GCGAAGGCATGGTTCTGACCGGTCCTAAAGAAGCTGAGCGTATTTAC<br>CGCGCCGGTTTGGCCTCTCTGCATGCGCGTGTCAAAGTGCGTATTACA<br>GAAGAGATCAAAAATACCGAAGGCGAAGTTACGCACAAGACGTCGA<br>TTATCGACACGACAGTTGGTCGCGCCATCCTTTGGATGATCGTACCTA<br>AAGGTCTGCCGTTCTCTATCGTCAACCAGCCTCTGGGCAAAAAAGCTA<br>TCTCCAAAATGCTGAACACCTGTTACCGCATTTTGGGCCTGAAGCCGA<br>CCGTTATTTTTGCTGACCAGATCATGTACACCGGTTTTGCTTACGCTGC<br>CCGTTCAGGCGCGTCAGTAGGTATCGATGACATGGTAATCCCTGCGA<br>AGAAAGCAGAGATCATCGAAGAAGCAGAAACCGAAGTTGCTGAAAT<br>CCAGGAACAGTTCCAGTCTGGTCTGGTCACTGCTGGCGAACGCTATA<br>ACAAAGTGATCGACATCTGGGCTGCGGCCAACGAACGTGTTGCTAAG<br>GCAATGATGGAAAACTTGTCTGTTGAAGACGTCGTCAACCGTGACGG<br>TGTTGTTGAACAGCAGGTTTCCTTCAACAGTATCTTTATGATGGCCGA<br>CTCCGGTGCGCGTGGTTCTGCTGCACAGATTCGTCAGCTGGCCGGTAT<br>GCGTGGCCTGATGGCGAAACCAGATGGTTCCATCATTGAAACGCCAA<br>TCACCGCGAACTTCCGTGAAGGTCTGAACGTACTCCAGTACTTCATCT<br>CTACTCACGGTGCTCGTAAAGGTTTGGCGGATACCGCACTTAAAACG<br>GCTAACTCCGGTTATCTGACCCGTCGTCTGGTTGACGTCGCGCAGGAT<br>CTGGTTGTGACCGAAGACGACTGTGGGACTCACGAAGGCATCATGAT<br>GACTCCGGTCATCGAAGGTGGCGACGTTAAAGAACCACTGCGTGAGC<br>GTGTACTGGGTCGTGTGACTGCAGAAGATATCCTCAAGCCGGGTACG<br>GCGGATATCCTGGTTCCACGTAACACCCTGCTTCACGAGAAGACGTGT<br>GATCTGTTAGAAGAGAACTCAGTCGACAGCGTGAAAGTACGTTCAGT<br>CGTAAGTTGCGAAACCGACTTTGGTGTGTGTGCAAACTGCTACGGTCG<br>CGACCTGGCACGTGGTCACATCATCAACAAAGGTGAAGCGATCGGTG<br>TTATTGCAGCACAGTCCATCGGTGAGCCGGGTACCCAGCTGACGATG<br>CGTACGTTCCACATCGGTGGTGCGGCATCTCGTGCGGCAGCGGAATC<br>CAGCATCCAGGTTAAGAACACTGGTACCATTAAACTGAGCAACCACA<br>AGCACGTTAGCAACTCTAACGGCAAACTGGTGATCACTTCCCGTAAC<br>ACTGAGCTGAAATTGATCGACGAATTCGGTCGTACCAAAGAAAGCTA<br>TAAAGTGCCTTACGGTTCCGTGATGGGCAAAGGCGATGGCGCATCAG<br>TTAACGGCGGCGAAACCGTTGCTAACTGGGATCCGCACACCATGCCA<br>GTTATCAGTGAAGTGAGTGGTTTCATTCGCTTTGCCGATATGGTGGAT<br>ACTCAGACCATCACACGCCAGACCGACGACCTGACCGGTTTGTCTTCT<br>CTGGTTGTTCTGGACTCTGCAGAGCGTACCGGTAGCGGTAAAGACCT<br>GCGTCCGGCACTGAAAATCGTTGACGCTAAAGGCGACGACGTATTGA<br>TTCCAGGTACTGATATGCCTGCTCAATACTTCCTGCCAGGTAAAGCGA<br>TTGTTCAGCTGGAAGATGGTACTCAGATCCACTCTGGTGACACCCTGG<br>CGCGTATTCCTCAGGAATCCGGCGGTACCAAGGACATCACCGGTGGT<br>CTGCCACGCGTTGCTGACCTGTTCGAAGCACGTCGTCCGAAAGAGCCT<br>GCAATCCTTGCTGAAATCAGCGGGATCATCTCCTTCGGTAAAGAAAC<br>CAAAGGCAAACGTCGTCTGGTAATTTCTCCGTTAGATGGCAGCGATG<br>CTTACGAAGAAATGATCCCTAAATGGCGTCAGCTGAACGTGTTCGAA<br>GGCGAAGTTGTGGAACGTGGTGACGTCGTATCCGACGGCCCTGAGTC<br>TCCGCACGACATCTTGCGTTTACGTGGTGTTCACGCGGTTACCCGCTA<br>CATCACCAACGAAGTGCAGGAAGTTTACCGTCTGCAAGGCGTTAAGA<br>TTAACGATAAGCACATCGAAGTTATCGTTCGTCAGATGTTGCGTAAAG<br>GCACCATCGTTAGCGCTGGTGGCACTGACTTCCTGGAAGGCGAGCAG<br>GCAGAAATGTCTCGCGTTAAAATCGCTAACCGTAAGCTGGAAGCTGA<br>AGGCAAAATCACGGCAACATTCAGCCGTGACCTGCTCGGTATCACCA<br>AGGCATCCCTGGCGACCGAATCCTTCATCTCTGCAGCGTCGTTCCAGG<br>AAACCACGCGTGTTCTTACCGAAGCGGCTGTTGCCGGTAAACGTGAT |

-continued

Sequence Listing

| Seq ID No. | Description | Sequence |
|---|---|---|
| | | GAACTGCGTGGCCTGAAAGAGAACGTTATCGTTGGCCGTCTGATCCC<br>AGCCGGTACCGGTTACGCTTATCATCAGGATCGTGCACGCCGTAAAG<br>CACAAGGCGAAGTGCCAGTTGTACCGCAAGTCAGCGCGGATGAAGCA<br>ACGGCTAACCTGGCTGAACTGCTGAACGCAGGTTTCGGTAACAGCGA<br>CGATTAA |
| 102 | DP67 Glutamine--tRNA ligase | ATGAGTGAGGCTGAAGCCCGCCCAACTAACTTTATTCGTCAGATTATC<br>GACGAAGATCTGGCGAACGGTAAGCACAGTTCAGTGCACACCCGCTT<br>CCCGCCTGAGCCGAATGGCTATCTGCATATTGGCCATGCGAAATCAAT<br>CTGCCTGAACTTTGGTATCGCTCAGGATTATCAGGGGCAGTGTAACCT<br>GCGCTTTGATGACACTAACCCGGTGAAAGAAGATCTGGAGTTTGTTG<br>AATCAATCAAGCGTGATGTGCAGTGGCTGGGCTTTAAGTGGAGTGGT<br>GACGTACGCTACTCATCTGACTATTTCGAGCAACTGCACAATTATGCC<br>GTTGAGCTGATTAGTAAAGGGCTGGCGTACGTTGATGAACTGTCACC<br>GGAGCAGATCCGTGAATACCGTGGCAGCCTGACCTCAGCGGGTAAAA<br>ACAGCCCCTTCCGCGATCGCAGCGTGGACGAAAACCTTGCGCTCTTTG<br>CAAAAATGCGCGCGGGCGGCTTTGCCGAGGGCACCGCGTGTTTACGA<br>GCCAAAATTGATATGGCTTCCAACTTTATCGTTCTGCGCGATCCGGTG<br>ATCTACCGCATCAAATTTGCCGAACATCATCAGACCGGCAATAAGTG<br>GTGCATCTATCCGATGTATGACTTTACCCACTGCATCTCTGATGCGCT<br>GGAAGGCATTACTCACTCACTGTGTACGCTGGAATTCCAGGATAACC<br>GTCGCCTGTACGACTGGGTGCTGGATAACATCACCATTCCGGTTCATC<br>CGCGTCAGTATGAATTCTCTCGCCTGAATCTTGAATATGCCATCATGT<br>CCAAGCGTAAGTTGAGTCAGTTGGTGACCGAGAACGTGGTGGAAGGT<br>TGGGATGATCCCCGTATGCTGACTGTTTCGGGTTTGCGCCGCCGTGGC<br>TACACTGCGGAATCCATCCGTGAATTCTGCCGCCGCATTGGGGTGACC<br>AAGCAGGACAATATTGTTGAAATGGCCGCTCTGGAATCCTGTATCCGT<br>GACGACCTCAATGAGAATGCCCCGCGTGCCATGGCAGTGATGGATCC<br>GGTAAAAGTGGTGATAGAAAATCTGCCTGCGCATCACGATGAGGTGA<br>TCACCATGCCGAATCATCCGAGCAAGCCGGAAATGGGTACCCGCGAA<br>GTCCCGTTCAGTCGTGAGATCTACATCGATCGTGCTGACTTCCGTGAG<br>GAAGCAAACAAGCAGTACAAGCGGCTGGTGCTGGGCAAAGAAGTGC<br>GTCTGCGTAACGCTTATGTGATCAAAGCCGAGCGCGTGGCAAAGGAC<br>GATGAAGGCAACATTACCTGCCTGTTCTGTACCTGTGATGTGGATACT<br>CTGAGCAAGGATCCGGCCGACGGGCGTAAAGTGAAGGGCGTTATCCA<br>CTGGGTGTCAGCTGTTCATGCCCTTCCGGCAGAGTTCCGTCTGTACGA<br>TCGGCTGTTCAGCGTACCGAATCCGGGGGCGGCAGAAGACTTCCTGG<br>CCAGCATCAACCCGGAATCTCTGGTGATCCGTCAGGGCTTCGTGGAG<br>CCCGGGATGCAGCAGGCGGAGGCGTCAGCCCCGTATCAGTTTGAGCG<br>TGAAGGCTACTTCTGCGCTGACAGTGTCTACTCCAGTGCCAGCAATCT<br>GGTGTTCAACCGCACCGTTGGCCTGCGTGACACCTGGGCGAAAGTCG<br>GCGAGTAA |
| 103 | DP67 DNA gyrase subunit B | ATGTCGAATTCTTATGACTCCTCCAGTATCAAAGTTCTGAAAGGGCTC<br>GATGCTGTACGCAAACGCCCGGGTATGTATATCGGCGATACGGATGA<br>CGGTACCGGTCTGCATCACATGGTATTTGAGGTCGTGGATAACGCCAT<br>TGACGAAGCGCTCGCCGGTCACTGTTCCGATATTCTTGTCACTATTCA<br>TGCCGATAACTCTGTTTCCGTTGTGGATGATGGCCGTGGTATTCCGAC<br>CGGTATTCACGAAGAAGAAGGCATCTCAGCCGCTGAAGTGATCATGA<br>CCGTGCTGCACGCCGGCGGTAAGTTCGACGATAACTCTTATAAAGTCT<br>CCGGCGGCCTGCACGGCGTGGGCGTGTCAGTGGTGAACGCCCTGTCG<br>GAAAAACTGGAGCTGACCATTCGTCGCGAAGGGAAAGTTCACCAGCA<br>GACTTACGTCCACGGCGTGCCACAGGCCCCGTTGAGTGTGAGCGGTG<br>AAACTGACCTGACGGGAACGCGCGTGCGTTTCTGGCCCAGCCATCAG<br>ACGTTCACTAACGTCGTGGAGTTCGAGTACGAAATTTTGGCAAAGCG<br>CCTGCGTGAGCTGTCGTTCCTGAACTCCGGTGTATCAATCAAGCTGGA<br>AGATAAGCGCGACGGTAAAAGCGACCATTACCACTATGAAGGTGGTA<br>TCAAGGCGTTTGTTGAGTACCTCAACAAGAACAAAACCCCGATCCAC<br>CCGAATGTGTTCTATTTCTCAACCGAGAAAGACGGCATTGGTGTGGA<br>AGTGGCGCTGCAGTGGAACGATGGTTTCCAGGAAAATATCTACTGCT<br>TTACCAACAACATCCCACAGCGGGATGGGGGCACGCACCTCGTTGGT<br>TTCCGTACCGCGATGACCCGTACCCTGAATGCCTACATGGATAAAGA<br>AGGCTACAGCAAGAAAGCCAAAGTCAGCGCCACCGGTGACGACGCG<br>CGTGAAGGCCTGATTGCTGTGGTGTCGGTGAAAGTGCCGGATCCGAA<br>ATTCTCTTCACAGACCAAAGATAAACTGGTCTCTTCTGAAGTGAAAAC<br>CGCCGTTGAGCAGCAGATGAACGAGCTGCTGGCAGAATACCTGCTGG<br>AAAACCCGACCGATGCCAAAATCGTCGTCGGTAAAATCATTGATGCG<br>GCCCGCGCCCGTGAAGCGGCCCGTCGTGCACGTGAAATGACCCGCCG<br>TAAAGGCGCGCTGGATCTGGCAGGCCTGCCGGGCAAACTGGCGGACT<br>GCCAGGAGCGTGATCCGGCTCTGTCCGAAATTTACCTGGTGGAAGGG<br>GACTCTGCGGGCGGCTCTGCCAAGCAGGGACGTAACCGTAAAAACCA<br>GGCCATCCTGCCGCTGAAGGGTAAAATCCTCAACGTCGAGAAGGCGC<br>GCTTTGACAAGATGCTCGCGTCGCAGGAAGTCGCTACGCTGATCACC |

-continued

Sequence Listing

| Seq ID No. | Description | Sequence |
|---|---|---|
| | | GCGCTGGGCTGTGGTATCGGTCGTGATGAGTACAACCCCGACAAACT |
| | | GCGCTATCACAGCATCATTATCATGACCGATGCCGACGTGGATGGCTC |
| | | GCATATCCGTACCCTGCTGCTGACCTTCTTCTACCGTCAGATGCCAGA |
| | | AATCATTGAGCGTGGTCATGTCTATATTGCCCAGCCACCGCTGTACAA |
| | | GGTGAAAAAAGGCAAGCAGGAGCAGTATATTAAAGACGACGATGCG |
| | | ATGGATCAGTACCAGATCGCCATCGCGCTGGACGGTGCCACGCTGCA |
| | | TGCGAACGCCAGCGCCCCGGCCCTTGGCGGTAAGCCACTGGAAGATC |
| | | TGGTGTCTGAGTTCAACAGCACGCGCAAGATGATCAAGCGCATGGAG |
| | | CGCCGTTACCCGGTGGCCTTGCTGAATGCGCTGGTCTACAACCCGACC |
| | | CTGAGCGATTTGACCGCCGAAGCGCCGGTACAGAGCTGGATGGATGT |
| | | GCTGGTGAAGTATCTGAACGACAACGACCAGCACGGCAGCACCTACA |
| | | GCGGTCTGGTACGCGAAAATCTGGAGCTGCATATCTTTGAGCCGGTA |
| | | CTGCGTATCAAAACCCACGGCGTGGATACCGATTATCCGCTCGACAG |
| | | CGAGTTTATGCTCGGCGGCGAATACCGTAAGCTCTGCGCGCTGGGTG |
| | | AGAAGCTGCGTGGCCTGATCGAAGAAGACGCGTTCATCGAACGTGGT |
| | | GAGCGGCGTCAGCCGATTGCCAGCTTTGAGCAGGCGATGGAGTGGCT |
| | | GGTTAAAGAGTCACGCCGTGGCCTGACGGTTCAGCGTTATAAAGGTC |
| | | TGGGCGAGATGAACCCGGATCAGCTGTGGGAAACCACCATGGATCCG |
| | | GACAGCCGCCGTATGCTGCGCGTGACCATCAAAGATGCCGTGGCCGC |
| | | CGACCAGCTGTTCACCACCCTGATGGGGGATGCGGTAGAGCCCCGTC |
| | | GTGCCTTTATTGAAGAGAACGCCCTGCGCGCGGCAAACATCGATATC |
| | | TGA |
| 104 | DP67 Isoleucine--tRNA ligase | ATGAGTGACTATAAATCTACCCTGAATTTGCCGGAAACGGGGTTCCC |
| | | GATGCGTGGCGATCTGGCCAAACGCGAACCGGGTATGCTGCAACGTT |
| | | GGTATGATGACAAGCTGTACGGCATCATTCGCGAAGCCAAGAAAGGG |
| | | AAAAAAACCTTTATCCTGCACGATGGCCCTCCTTACGCCAACGGCAG |
| | | CATTCATATTGGTCACTCCGTTAACAAGATTCTGAAAGACATTATCGT |
| | | TAAGTCGAAAGGCATGGCGGGCTATGACTCGCCTTATGTACCGGGTT |
| | | GGGACTGCCACGGTCTGCCTATCGAGCATAAAGTTGAGCAGATGATC |
| | | GGTAAGCCGGGAGAGAAAGTCAGCGCCGCTGAGTTCCGTGCTGCCTG |
| | | CCGCAAATACGCTGCCGAGCAGGTGGAAGGGCAGAAAGCCGACTTTA |
| | | TCCGTCTGGGTGTGTTGGGTGACTGGGATCGTCCGTATCTGACAATGA |
| | | ACTTCCAGACCGAAGCCAATATTATCCGTGCGCTGGGTAAAATCATC |
| | | GGTAACGGGCACCTGCACAAAGGGGCCAAGCCGGTACACTGGTGCCT |
| | | GGACTGCCGTTCTGCCCTGGCTGAGGCGGAAGTGGAGTACTACGATA |
| | | AAACCTCTCCGTCTATCGATGTCATGTTCAATGCGACTGATAAAGAGG |
| | | GGGTACAGGCCAAATTTGCGGCAACGAATGTTGACGGCCCGATCTCG |
| | | CTGGTGATCTGGACTACCACGCCGTGGACCATGCCGGCTAACCGCGC |
| | | TATCTCACTGCATCCTGAATTCGACTACCAGCTGGTACAGATTGAAGG |
| | | CCGTGCTCTGATCCTCGCCAAAGAGATGGTTGAGAGCGTGATGCAGC |
| | | GCGTTGGTGTTGCCGCCTGGACCGTGCTGGGCGAAGCGAAAGGGGCA |
| | | GACCTGGAGCTGATGGGCTTCCAGCATCCGTTCCTCGACCATACCTCT |
| | | CCGGTTGTGCTGGGTGAGCATGTCACGCTGGAAGCCGGTACCGGTGC |
| | | GGTCCATACCGCACCAGGCCATGGCCCGGACGACTATGTTATCGGTC |
| | | AGAAATACGGTATCGAAGTGGCTAACCCGGTCGGCCCGGATGGCTGC |
| | | TACCTGCCGGGAACCTACCCGACGCTGGATGGTGTGAACGTCTTTAA |
| | | AGCCAACGATATGATCGTTGAACTGCTGCGTGAAAAGGGTGCTCTGC |
| | | TGCACGTTGAGAAACTGTTCCACAGCTATCCACACTGCTGGCGTCATA |
| | | AAACGCCCATCATCTTCCGCGCTACGCCACAGTGGTTTATCAGCATGG |
| | | ATCAGAAGGGCCTGCGTGCGCAGTCGCTGAAAGAGATCAAGGGCGTG |
| | | CAGTGGATCCCGGACTGGGGTCAGGCACGTATTGAATCGATGGTCGC |
| | | GAACCGTCCTGACTGGTGTATTTCCCGTCAGCGTACCTGGGGCGTGCC |
| | | GATGGCGCTGTTCGTCCATAAAGACACCGAACAGCTGCACCCGGATT |
| | | CGCTGGAGCTGATGGAGAAAGTGGCGAAGCGGGTTGAGCAGGACGG |
| | | CATTCAGGCATGGTGGGATCTTGATGCCCGCGACCTGATGGGCGCCG |
| | | ATGCTGACAACTACGTTAAAGTCCCGGATACCCTGGACGTCTGGTTTG |
| | | ACTCCGGTTCAACCAGCTACTCGGTCGTCGATGCCCGCCCTGAATTTG |
| | | ACGGCAATGCCCCTGACCTGTATCTGGAAGGATCGGATCAGCACCGC |
| | | GGCTGGTTTATGTCCTCACTGATGATCTCGACCGCGATGAAAGGCAA |
| | | AGCGCCTTACCGTCAGGTACTGACGCACGGCTTCACCGTCGATGGTCA |
| | | GGGCCGTAAGATGTCCAAGTCACTGGGCAATACTGTCAGCCCGCAGG |
| | | ATGTGATGAACAAACTGGGCGCCGATATTCTGCGCCTGTGGGTCGCCT |
| | | CTACGGACTACTCCGGTGAGATCGCCGTATCCGACGAGATCCTTAAA |
| | | CGCTCTGCCGACAGCTATCGCCGCATCCGTAACACCGCACGTTTCCTG |
| | | CTGGCAAACCTTGCCGGTTTTAATCCGGAAACCGATAGGGTGAAACC |
| | | GGAAGAGATGGTGGTGGATCGCTGGGCCGTTGGCCGTGCGCTGG |
| | | CGGCACAGAATGATATCGTAGCCTCGTATGAAGCTTATGACTTCCATG |
| | | AAGTCGTGCAGCGTCTGATGCAGTTCTGTTCGGTTGAGATGGGCTCCT |
| | | TCTACCTGGATATCATCAAGGATCGTCAGTACACCGCGAAGGCCGAT |
| | | GGCCTGGCGCGTCGCAGCTGTCAGACGGCGCTGTGGTATATCGTGGA |
| | | AGCGCTGGTGCGCTGGATGGCACCGATTATGTCCTTCACTGCCGATGA |
| | | AATCTGGGGTTACCTGCCGGGTAAACGCAGCCAGTATGTCTTTACCGA |

-continued

Sequence Listing

| Seq ID No. | Description | Sequence |
|---|---|---|
| | | AGAGTGGTTTGACGGGCTGTTCAGCCTGGAGGACAATCAGCCGATGA ACGACAGTTACTGGGCAGAACTGCTGAAAGTACGCGGTGAAGTCAAC AAGGTGATCGAGCAGGCCCGCGCTGATAAGCGGATTGGCGGGTCTCT GGAAGCCAGCGTGACGCTGTATGCTGACGCAGACCTGGCCGCGAAGC TGACCAGCCTGGGTGAGGAGCTGCGCTTTGTGTTGCTGACTTCCGGGG CGCAGGTTGCGGATTATGCGCAGGCCACCGCTGATGCACAGCAAAGC GAAGGGGTAAAAGGTCTGAAAATTGCCCTGAGCAAAGCGGAAGGCG AGAAGTGCCCGCGCTGCTGGCATTACACTAACGATATCGGCCAGAAT GCTGAACACGCTGACGTGTGCGGCCGTTGTGTCACTAACGTCGCGGG CAGCGGCGAACAGCGTAAGTTTGCATGA |
| 105 | DP67 NADH-quinone Goxidoreductase subunit C/D | GTGATCGGCGAGCTGCGTAATCGTTTTGGGCCTGATGCCTTTACAGTA CAAGCGACCCGTACCGGCGTGCCGGTGGTCTGGGTAAAACGTGAGCA GTTGCTTGAGATTATTGAGTTCCTGCGCAAGCTGCCTAAACCCTATGT GATGCTGTATGACCTGCATGGCATGGATGAGCGCCTGCGTACTCACC GTGCCGGTTTACCGGCGGCGGATTTTTCCGTTTTCTATCACTTCATCTC CATTGAACGTAACCGCGACATCATGCTCAAGGTGGCGTTGTCTGAAA ACGATTTGAATGTGCCCACCATCACCAAAATTTTCCCGAATGCCAACT GGTATGAGCGTGAAACCTGGGAGATGTTTGGTATCAATGTTGAAGGC CACCCGCACCTGACGCGCATTATGATGCCGCAGAGCTGGGAAGGGCA TCCGCTGCGCAAAGATTACCCTGCGCGTGCGACCGAGTTCGATCCGTT TGAACTGACCAAGCAGAAAGAAGATCTGGAGATGGAATCTCTGACCT TCAAGCCTGAAGACTGGGGCATGAAGCGTTCGACCAACAATGAGGAC TTCATGTTCCTCAACCTGGGCCCGAACCACCCTTCTGCGCACGGCGCG TTCCGTATCATCCTGCAACTGGACGGTGAAGAGATCGTCGACTGCGTG CCGGATATCGGATACCACCATCGTGGTGCCGAAAAAATGGGTGAACG CCAGTCCTGGCACAGCTACATTCCGTATACCGACCGTATTGAGTATCT CGGCGGCTGCGTAAACGAAATGCCGTACGTGCTGGCGGTAGAAAAGC TGGCTGGTATCAAAGTCCCTGAGCGCGTGGAAGTCATTCGCGTGATG CTATCAGAGCTGTTCCGTATAAACAGCCACCTGCTGTACATCTCTACG TTTATCCAGGACGTCGGTGCTATGTCCCCGGTGTTCTTTGCCTTTACTG ACCGCCAGAAAATTTACGACGTGGTAGAAGCCATTACCGGCTTCCGT ATGCATCCGGCCTGGTTCCGCATTGGTGGCGTGGCGCATGATCTGCCT AAAGGCTGGGAGCGCCTGCTGCGTGAGTTCCTGGATTGGATGCCTAA GCGTCTGAAAGCCTATGAGCAGACCGCACTGAAAAACTCCGTGCTTA TTGCCCGTTCCAAAGGGGTTTCTGCCTATAACATGGAAGAAGCACTG GCCTGGGGCACGACGGGGGCTGGCCTGCGTGGTACCGGTCTGGACTT TGATGTGCGTAAATGGCGTCCATATTCCGGTTATGAAAACTTCGATTT CGAAGTGCCAATCGGAGATGGCGTAAGCTGTGCTTACACCCGTGTCA TGCTGAAGATGGAAGAGATGCGCCAGAGTATGCGCATCCTGGAACAG TGCCTGAAGAACATGCCAGCAGGCCCGTTCAAGGCTGACCATCCGCT GACCACGCCGCCGCCGAAAGAGCGCACGCTGCAGCATATCGAAACCC TGATCACTCACTTCCTGCAGGTTTCGTGGGGCCCGGTAATGCCGGCAA ACGAATCCTTCCAGATGATTGAAGCGACCAAAGGGATCAACAGTTAC TACCTGACCAGTGATGGCAGCACGATGAGCTACCGCACCCGCGTGCG TACGCCGAGCTTCCCGCATTTGCAACAGATCCCATCGGTGATCAACGG CAGCCTGGTATCCGATCTGATCGTATACCTCGGTAGTATCGATTTTGT TATGTCAGACGTGGACCGCTAA |
| 106 | DP67 Protein RecA | ATGGCTATCGACGAAAACAAGCAAAAAGCACTGGCAGCAGCGCTGG GCCAGATTGAAAAGCAGTTTGGTAAAGGCTCCATCATGCGCCTGGGT GAAGACCGCACCATGGATGTGGAAACCATCTCAACCGGTTCTTTATC ACTGGATATCGCGCTGGGTGCCGGTGGTTTACCAATGGGCCGTATCGT TGAAATCTATGGCCCGGAGTCTTCCGGTAAAACCACCCTGACGCTGC AGGTTATCGCTTCTGCACAGCGTAAAGGGAAAACCTGTGCATTTATCG ATGCCGAGCATGCTCTGGACCCGGTCTACGCTAAAAAACTGGGCGTG GATATCGATAACTTGCTGTGTTCTCAGCCGGATACCGGTGAGCAGGC GCTGGAAATCTGTGATGCGCTGGCCCGTTCCGGTGCGGTTGACGTCAT CATCGTCGACTCCGTAGCGGCGTTGACACCAAAAGCAGAAATCGAAG GTGAAATCGGTGACTCTCATATGGGCCTTGCGGCACGTATGATGAGC CAGGCGATGCGTAAGCTGGCCGGTAACCTGAAGAACTCCGGTACGCT GCTGATCTTTATCAACCAGATCCGTATGAAAATTGGCGTGATGTTCGG TAACCCGGAAACCACTACCGGTGGTAACGCTCTGAAATTCTACGCTTC TGTCCGTCTGGATATTCGCCGCATCGGCGCGATCAAAGAGGGTGATG AAGTGGTGGGTAGCGAAACCCGCGTTAAAGTGGTGAAAAACAAAATC GCAGCACCGTTTAAACAGGCTGAGTTCCAGATCATGTACGGCGAAGG TATCAACGTTTACGGTGAGCTGGTCGACCTGGGCGTGAAGCACAAGC TGATCGAAAAAGCCGGTGCCTGGTACAGCTATAACGGTGACAAGATT GGTCAGGGTAAAGCCAACTCAGGTAACTTCCTGAAAGAGAACCCGGC TATCGCTAACGAAATCGAAGCAAAACTGCGTGAAATGCTGTTGAACA GCCCGGACGATAAGCCTGATTTTGTTCCGGCTCCGCATGAAGCCGATA GTGAAGTTAACGAAGATATCTAA |

-continued

Sequence Listing

| Seq ID No. | Description | Sequence |
|---|---|---|
| 107 | RNA polymerase sigma factor RpoD | ATGGAGCAAAACCCGCAGTCACAGCTTAAGCTACTTGTCACCCGTGG<br>TAAGGAGCAAGGCTATCTGACCTATGCCGAGGTCAATGACCATCTGC<br>CGGAAGATATCGTCGACTCCGATCAGATTGAAGACATCATTCAGATG<br>ATCAACGACATGGGCATTCAGGTTGTAGAAGAAGCGCCTGATGCCGA<br>TGATTTGATGCTGAATGAGAACAACAACGACACGGACGAAGACGCTG<br>CCGAAGCGGCTGCTCAGGTATTATCCAGCGTAGAATCTGAAATCGGA<br>CGTACCACCGACCCGGTGCGCATGTACATGCGCGAAATGGGGACGGT<br>TGAACTGCTGACGCGTGAAGGCGAGATCGATATCGCCAAACGCATCG<br>AAGAGGGTATCAACCAGGTACAGTGTTCCGTTGCTGAATATCCTGAA<br>GCGATTACTTACCTGCTTGAGCAATATGACCGTGTTGAAGCGGGCGA<br>AGCGCGCCTGTCGGATCTGATCACCGGTTTTGTCGACCCGAATGCCGA<br>AGCAGAGATCGCCCCTACTGCGACTCACGTGGGTTCAGAACTTTCCGC<br>TGAAGAGCGTGATGACGAAGAAGAAGACGAAGAGTCTGACGACGAC<br>AGCTCGGATGATGACAACAGCATCGATCCGGAACTGGCGCGGGAAAA<br>ATTCAACGACCTGCGCGTTCAGTACGAAACCACCCGTACCGTTATCAA<br>AGCGAAAAGCCGCAGCCACGCTGATGCCATCGCTGAGATCCAGAATC<br>TGTCCGACGTGTTCAAGCAGTTCCGCCTGGTGCCGAAGCAGTTCGACT<br>TCCTGGTGAACAGCATGCGCACCATGATGGATCGCGTCCGTACTCAG<br>GAACGCCTGATCCTCAAGCTGTGCGTAGAAATCTGTAAGATGCCGAA<br>GAAGAACTTCATTACCCTGTTCACCGGTAATGAAACCAGCGAAACCT<br>GGTTCAAAGCGGCACTGGCAATGAATAAGCCGTGGTCAGAGAAGCTG<br>AACGATGTGTCAGATGACGTACACCGTAGCCTGATGAAGCTGCAGCA<br>GATCGAAACGGAAACTGGCCTGACGATTGAACAGGTAAAAGACATCA<br>ACCGTCGTATGTCGATCGGCGAAGCGAAAGCGCGCCGTGCGAAGAAA<br>GAGATGGTTGAGGCTAACCTGCGTCTGGTTATCTCTATCGCCAAGAAG<br>TACACCAACCGTGGCCTGCAGTTCCTGGATCTGATTCAGGAAGGTAA<br>CATCGGTCTGATGAAAGCGGTGGATAAGTTTGAATATCGCCGTGGTT<br>ATAAGTTCTCGACTTATGCCACCTGGTGGATCCGTCAGGCGATCACCC<br>GTTCAATCGCTGACCAGGCGCGTACCATCCGTATTCCGGTGCACATGA<br>TTGAGACGATTAACAAGCTCAACCGTATTTCCCGCCAGATGCTGCAA<br>GAGATGGGCCGTGAGCCGACGCCGGAAGAGCTGGCCGAGCGTATGCT<br>GATGCCGGAAGATAAGATCCGTAAGGTGCTGAAAATTGCCAAAGAGC<br>CGATCTCTATGGAGACGCCGATTGGTGATGATGAAGATTCACATCTG<br>GGTGATTTTATCGAAGACACCACGCTGGAGCTGCCGCTGGACTCCGC<br>GACGTCAGAGAGCCTGCGTTCTGCCACGCACGACGTGCTGGCCGGTC<br>TGACCGCGCGTGAAGCCAAAGTACTGCGTATGCGTTTCGGTATCGAT<br>ATGAATACCGACCACACGCTGGAAGAAGTGGGCAAACAGTTCGACGT<br>AACGCGTGAGCGTATTCGTCAGATTGAGGCGAAAGCGCTGCGTAAGC<br>TGCGTCACCCAAGCCGCTCTGAAGTGCTGCGCAGCTTCCTCGACGATT<br>AA |
| 108 | DNA-directed RNA polymerase subunit beta | ATGGTTTACTCCTATACCGAGAAAAAACGTATTCGTAAGGATTTTGGA<br>AAGCGTCCACAAGTTCTGGACATTCCATATCTCCTTTCTATCCAGCTT<br>GACTCGTTCCAGAAGTTCATCGAGCAAGATCCGGAAGGTCAATATGG<br>TCTGGAAGCAGCATTCCGCTCCGTATTTCCAATCCAAAGCTATAGCGG<br>TAATTCTGAGCTGCAGTACGTCAGCTACCGTTTAGGCGAACCCGTCTT<br>TGATGTGAAAGAGTGTCAGATTCGTGGCGTCACGTATTCTGCTCCTCT<br>GCGCGTAAAACTGCGCCTGGTGATCTACGAGCGCGAAGCGCCGGAAG<br>GCACCGTTAAAGACATCAAAGAACAAGAAGTTTACATGGGCGAAATT<br>CCGCTCATGACGGATAACGGTACCTTTGTTATCAACGGTACTGAGCGC<br>GTTATCGTTTCTCAGCTCCACCGTAGTCCTGGTGTCTTCTTCGACAGCG<br>ATAAGGGTAAAACCCACTCGTCCGGTAAAGTGCTGTATAACGCACGT<br>ATCATCCCTTACCGTGGTTCATGGCTGGACTTCGAGTTCGACCCGAAA<br>GACAACCTGTTCGTCCGTATTGACCGTCGCCGTAAACTGCCAGCGACC<br>ATCATTCTGCGCGCGTTGAATTACACCACTGAACAGATCCTCGACCTG<br>TTCTTCGATAAAGTGGTTTACCAAATTCGCGACAACAAGCTGCAGATG<br>GAGCTTATTCCTGAGCGCCTGCGTGGTGAGACCGCTTCATTTGATATT<br>GAAGCGAACGGCACCGTTTACGTCGAAAAAGGCCGCCGTATTACTGC<br>GCGCCATATTCGCCAGCTTGAGAAAGATGCTGTTGCCCACATCGAAG<br>TGCCGGTTGAGTATATTGCCGGTAAAGTGGTCGCTAAAGACTACGTTG<br>ATGAGAGCACCGGTGAACTGCTGATCGCAGCGAACATGGAACTGTCA<br>CTGGATCTGCTGGCTAAACTCAGCCAGTCCGGTCACAAGCGCATTGA<br>AACCCTGTTCACCAACGATCTGGATCACGGTGCGTACATGTCTGAGAC<br>GGTACGTGTCGACCCAACCAGCGATCGCCTGAGCGCTCTGGTTGAGA<br>TCTACCGCATGATGCGTCCTGGTGAGCCACCAACGCGTGAAGCGGCT<br>GAAAACCTGTTTGAGAACCTGTTCTTCTCTGAAGACCGCTATGATCTG<br>TCTGCGGTTGGTCGTATGAAGTTCAACCGTTCTCTGCTGCGCGACGAG<br>ATCGAAGGTTCCGGTATCCTGAGCAAAGACGACATCATTCAGGTGAT<br>GAAGAAGCTCATCGGTATCCGTAACGGTATTGGCGAAGTGGATGATA<br>TCGACCACCTCGGCAACCGTCGTATCCGTTCCGTTGGCGAAATGGCTG<br>AAAACCAGTTCCGTGTTGGCCTTGTGCGCGTAGAGCGTGCGGTGAAA<br>GAGCGTCTGTCCCTGGGCGATCTGGATACCCTGATGCCACAGGACAT<br>GATCAACGCCAAGCCAATTTCTGCGGCAGTGAAAGAGTTCTTCGGCT |

-continued

Sequence Listing

| Seq ID No. | Description | Sequence |
|---|---|---|
| | | CCAGCCAGCTGTCACAGTTTATGGACCAGAACAACCCGTTGTCTGAG<br>ATCACGCATAAGCGTCGTATCTCTGCACTGGGTCCGGGCGGTCTGACG<br>CGTGAGCGTGCAGGCTTCGAAGTTCGAGACGTACACCCGACGCACTA<br>CGGTCGCGTATGTCCAATCGAAACGCCGGAAGGTCCAAACATCGGTC<br>TGATCAACTCCTTGTCTGTGTATGCACAGACCAATGAGTACGGTTTCC<br>TGGAAACCCCATACCGTCGCGTTCGCGAAGGCGTGGTGACCGACGAA<br>ATTCATTACCTCTCTGCTATTGAAGAGGGTAACTACGTTATCGCTCAG<br>GCAAACACCAATCTCGACGACGAAGGTCACTTCGTAGACGACCTGGT<br>CACCTGCCGTAGCAAAGGCGAATCGAGTCTCTTCAACCGCGATCAAG<br>TTGACTACATGGACGTTTCCACCCAGCAGGTGGTTTCCGTCGGTGCGT<br>CACTGATCCCGTTCCTGGAGCACGATGACGCCAACCGCGCATTGATG<br>GGTGCAAACATGCAACGTCAGGCGGTTCCTACTCTGCGTGCTGATAA<br>GCCGCTGGTAGGTACCGGTATGGAGCGTGCGGTTGCGGTTGACTCCG<br>GTGTTACTGCCGTAGCGAAACGTGGTGGTACCGTGCAGTACGTGGAT<br>GCATCCCGTATCGTTATTAAAGTTAACGAAGACGAAATGTATCCGGG<br>CGAAGCCGGTATCGACATTTACAACCTGACCAAATATACCCGTTCTAA<br>CCAGAACACCTGCATCAACCAGATGCCTTGCGTGAACCTGGGTGAGC<br>CAATCGAACGTGGTGATGTGCTGGCTGATGGCCCTTCAACCGATCTCG<br>GCGAACTGGCACTCGGTCAGAACATGCGCGTCGCGTTCATGCCGTGG<br>AACGGCTACAACTTCGAAGACTCCATTCTGGTCTCGGAGCGCGTTGTT<br>CAGGAAGATCGCTTCACCACTATCCACATTCAGGAACTGGCGTGTGT<br>GTCTCGTGACACCAAGCTGGGGCCAGAAGAGATCACCGCTGACATCC<br>CTAACGTGGGTGAAGCTGCGCTCTCTAAACTGGATGAGTCCGGTATC<br>GTGTATATCGGTGCGGAAGTGACCGGTGGGGACATTCTGGTTGGTAA<br>GGTAACACCTAAAGGTGAAACCCAGCTGACGCCAGAAGAGAAACTG<br>CTGCGTGCGATCTTCGGTGAAAAAGCGTCTGACGTTAAAGACTCTTCT<br>CTGCGCGTACCAAACGGTGTGTCAGGGACAATCATCGACGTTCAGGT<br>CTTTACCCGCGATGGCGTGGAAAAAGACAAGCGTGCGCTGGAAATCG<br>AAGAGATGCAGCTGAAGCAGGCGAAGAAAGACCTGTCTGAAGAATT<br>GCAGATCCTCGAAGCCGGCTTGTTCAGCCGTATTAACTACCTGCTGGT<br>TGCCGGCGGTGTTGAAGCGGAAAAACTGGAGAAGCTGCCACGTGAGC<br>GCTGGCTCGAACTGGGCCTGACCGACGAAGAGAAGCAAAATCAGCTG<br>GAACAGCTGGCCGAGCAGTACGACGAGCTGAAGCACGAGTTTGAGA<br>AAAAACTTGAAGCCAAGCGCCGTAAAATCACTCAGGGCGATGACCTG<br>GCACCTGGCGTGCTGAAAATCGTGAAAGTGTATCTGGCCGTTAAACG<br>TCAGATCCAGCCTGGTGACAAAATGGCAGGTCGTCACGGGAACAAAG<br>GTGTTATCTCCAAGATCAACCCGATCGAAGATATGCCATACGATGAG<br>TTCGGTACGCCGGTCGACATCGTACTGAACCCGCTGGGCGTTCCATCA<br>CGTATGAACATTGGTCAGATTCTTGAAACCCACCTGGGTATGGCTGCG<br>AAAGGCATTGGCGAGAAAATTAACGCTATGCTTAAGAAGCAGGAAG<br>AAGTGTCCAAGCTGCGTGAATTCATTCAGCGTGCTTACGATCTGGGCA<br>GCGATCTGCGTCAGAAAGTTGACCTGAACACCTTCACCGATGACGAA<br>GTGCTGCGCCTGGCAGAGAATCTGAAAAAAGGTATGCCAATTGCAAC<br>ACCAGTGTTTGACGGCGCGAAAGAGAGCGAAATCAAAGAGCTGTTAC<br>AGCTCGGCGGCCTGCCTTCTTCTGGCCAGATCACGCTGTTTGATGGTC<br>GTACCGGTGAGCAGTTCGAACGTCAGGTTACCGTTGGCTACATGTAC<br>ATGCTGAAGCTGAACCACCTGGTTGATGACAAAATGCATGCGCGTTC<br>TACCGGTTCTTACAGCCTCGTTACTCAGCAGCCGCTGGGTGGTAAGGC<br>GCAGTTCGGTGGTCAGCGCTTCGGTGAGATGGAAGTGTGGGCACTGG<br>AAGCATACGGTGCCGCGTATACCCTGCAGGAAATGCTGACCGTGAAG<br>TCTGATGACGTTAACGGCCGTACCAAGATGTATAAAAACATCGTTGA<br>CGGCAACCATCAGATGGAACCGGGCATGCCGGAATCTTTCAACGTAC<br>TGTTGAAAGAGATCCGCTCGCTGGGTATCAACATCGAGCTGGAAGAC<br>GAGTAA |
| 109 | DP68 Glutamine--tRNA ligase | ATGAGCAAGCCCACTGTCGACCCTACCTCGAATTCCAAGGCCGGACC<br>TGCCGTCCCGGTCAATTTCCTGCGCCCGATCATCCAGGCGGACCTGGA<br>TTCGGGCAAGCACACGCAGATCGTCACCCGCTTCCCGCCAGAGCCCA<br>ACGGCTACCTGCACATCGGTCACGCCAAGTCGATCTGTGTGAACTTCG<br>GCCTGGCCCAGGAGTTCGGTGGCGTCACGCACCTGCGTTTCGACGAC<br>ACCAACCCGGCCAAGGAAGACCAGGAATACATCGACGCCATCGAAA<br>GCGACATCAAGTGGCTGGGCTTCGAATGGTCCGGTGAAGTGCGCTAT<br>GCGTCCAAGTATTTCGACCAGTTGTTCGACTGGGCCGTCGAGCTGATC<br>AAGGCCGGCAAGGCCTACGTCGACGACCTGACCCCGGAGCAGGCCAA<br>GGAATACCGTGGCACGCTGACCGAGCCGGGCAAGAACAGCCCGTTCC<br>GTGACCGTTCGGTAGAAGAGAACCTCGACTGGTTCAACCGCATGCGC<br>GCCGGTGAGTTCCCGGACGGCGCCCGCGTGCTGCGCGCCAAGATCGA<br>CATGGCCTCGCCGAACATGAACCTGCGCGACCCGATCATGTACCGCA<br>TCCGCCACGCCCATCACCACCAGACCGGTGACAAGTGGTGCATCTAC<br>CCGAACTATGACTTCACCCACGGTCAGTCGGACGCCATCGAAGGCAT<br>CACCCACTCCATCTGCACCCTGGAGTTCGAAAGCCATCGCCCGCTGTA<br>TGAGTGGTTCCTCGACAGCCTGCCGGTTCCGGCGCACCCGCGTCAGTA<br>CGAGTTCAGCCGCCTGAACCTGAACTACACCATCACCAGCAAGCGCA |

-continued

Sequence Listing

| Seq ID No. | Description | Sequence |
|---|---|---|
| | | AGCTCAAGCAGTTGGTGGACGAAAAGCACGTGCATGGCTGGGATGAC CCGCGCATGTCCACCCTGTCGGGTTTCCGCCGTCGCGGCTACACCCCG GCGTCGATCCGCAGCTTCTGCGACATGGTCGGCACCAACCGCTCCGA CGGCGTGGTCGATTACGGCATGCTCGAGTTCAGCATCCGTCAGGACCT GGACGCCAACGCGCCGCGTGCCATGTGCGTATTGCGCCCGTTGAAAG TCGTGATCACCAACTATCCGGAAGACAAGGTCGACCACCTCGAACTG CCGCGTCACCCGCAGAAAGAAGAACTTGGCGTGCGCAAGCTGCCGTT CGCGCGTGAAATCTACATCGACCGTGATGACTTCATGGAAGAGCCGC CGAAAGGCTACAAGCGCCTGGAGCCTAACGGCGAAGTGCGCCTGCGC GGCAGCTACGTGATCCGTGCCGATGAAGCGATCAAGGACGCCGATGG CAACATCGTCGAACTGCGATGCTCCTACGACCCGGAAACCCTGGGCA AGAACCCTGAAGGCCGCAAGGTCAAAGGCGTCGTTCACTGGGTGCCG GCTGCTGCCAGCATCGAGTGCGAAGTGCGCCTGTACGATCGTCTGTTC CGTTCGCCGAACCCTGAGAAGGCTGAAGACAGCGCCAGCTTCCTGGA CAACATCAACCCTGACTCCCTGCAAGTTCTCACGGGTTGTCGTGCCGA GCCATCGCTTGGCGACGCACAGCCGGAAGACCGTTTCCAGTTCGAGC GCGAAGGTTACTTCTGCGCGGATATCAAGGACTCCAAACCTGGTCAT CCGGTCTTCAACCGTACCGTGACCTTGCGTGATTCGTGGGGCCAGTG |
| 110 | DP68 DNA gyrase subunit B | ATGAGCGAAGAAAACACGTACGACTCGACCAGCATTAAAGTGCTGAA AGGTTTGGATGCCGTACGCAAACGTCCCGGTATGTACATCGGCGACA CCGATGATGGTAGCGGTCTGCACCACATGGTGTTCGAGGTGGTCGAC AACTCCATCGACGAAGCTTTGGCCGGTCACTGCGACGACATCAGCAT TATCATCCACCCGGATGAGTCCATCACCGTGCGCGACAACGGTCGCG GTATTCCGGTCGATGTGCACAAAGAAGAAGGCGTATCGGCGGCAGAG GTCATCATGACCGTGCTTCACGCCGGCGGTAAGTTCGACGACAACTCC TATAAAGTTTCCGGCGGTTTGCACGGTGTAGGTGTGTCGGTGGTGAAC GCTCTGTCCGAAGAGCTTATCCTGACTGTTCGCCGTAGCGGCAAGATC TGGGAACAGACCTACGTGCATGGTGTTCCACAAGAACCGATGAAAAT CGTTGGCGACAGTGAATCCACCGGTACGCAGATCCACTTCAAGCCTTC GGCAGAAACCTTCAAGAATATCCACTTCAGTTGGGACATCCTGGCCA AGCGTATTCGTGAACTGTCGTTCCTTAACTCCGGTGTGGGTATCGTCC TCAAGGACGAGCGCAGCGGCAAGGAAGAGTTGTTCAAGTACGAAGG CGGCTTGCGTGCGTTCGTTGAGTACCTGAACACCAACAAGACTGCGG TCAACCAGGTGTTCCACTTCAACATCCAGCGTGAAGACGGTATCGGC GTTGAAATCGCCCTGCAGTGGAACGACAGCTTCAACGAGAACCTGTT GTGCTTCACCAACAACATTCCACAGCGCGACGGCGGTACTCACTTGGT GGGTTTCCGTTCCGCACTGACGCGTAACCTGAACACCTACATCGAAGC GGAAGGCTTGGCCAAGAAGCACAAAGTGGCCACTACCGGTGACGATG CGCGTGAAGGCCTGACGGCGATTATCTCGGTGAAAGTGCCGGATCCA AAGTTCAGCTCCCAGACCAAAGACAAGCTGGTGTCTTCCGAAGTGAA GACCGCAGTGGAACAGGAGATGGGCAAGTACTTCTCCGACTTCCTGC TGGAAAACCCGAACGAAGCCAAGTTGGTTGTCGGCAAGATGATCGAC GCGGCGCGTGCCCGTGAAGCGGCGCGTAAAGCCCGTGAGATGACCCG CCGTAAAGGCGCGTTGGATATCGCCGGCCTGCCGGGCAAACTGGCTG ACTGCCAGGAGAAGGACCCTGCCCTCTCCGAACTGTACCTGGTGGAA GGTGACTCTGCTGGCGGTTCCGCCAAGCAGGGTCGTAACCGTCGCAC CCAGGCTATCCTGCCGTTGAAGGGTAAGATCCTCAACGTCGAGAAGG CCCGCTTCGACAAGATGATTTCCTCTCAGGAAGTCGGCACCTTGATCA CGGCGTTGGGCTGCGGTATTGGCCGCGATGAGTACAACATCGACAAA CTGCGTTACCACAACATCATCATCATGACCGATGCTGACGTCGACGGT TCGCACATCCGTACCCTGCTGCTGACCTTCTTCTTCCGTCAGTTGCCGG AGCTGATCGAGCGTGGCTACATCTACATCGCTCAGCCGCCGTTGTACA AAGTGAAAAAGGGCAAGCAAGAGCAGTACATCAAAGACGACGACGC CATGGAAGAGTACATGACGCAGTCGGCCCTGGAAGATGCCAGCCTGC ACTTGAACGACGAAGCCCCGGGCATTTCCGGTGAGGCGCTGGAGCGT TTGGTTAACGACTTCCGCATGGTAATGAAGACCCTCAAGCGTCTGTCG CGCCTGTACCCTCAGGAGCTGACCGAGCACTTCATCTACCTGCCTTCC GTGAGCCTGGAGCAGTTGGGCGATCACGCCCACATGCAGAATTGGCT GGCTCAGTACGAAGTACGTCTGCGCACCGTCGAGAAGTCTGGCCTGG TTTACAAAGCCAGCTTGCGTGAAGACCGTGAACGTAACGTGTGGCTG CCGGAGGTTGAACTGATCTCCCACGGCCTGTCGAACTACGTCACCTTC AACCGCGACTTCTTCGGCAGCAACGACTACAAGACCGTGGTTACCCT CGGCGCGCAATTGAGCACCCTGTTGGACGACGGTGCTTACATCCAGC GTGGCGAGCGTAAGAAAGCGGTCAAGGAGTTCAAGGAAGCCCTGGA CTGGTTGATGGCTGAAAGCACCAAGCGCCACACCATCCAGCGATACA AAGGTCTGGGCGAGATGAACCCGGATCAACTGTGGGAAACCACCATG GATCCTGCTCAGCGTCGCATGCTACGCGTGACCATCGAAGACGCCATT GGCGCAGACCAGATCTTCAACACCCTGATGGGTGATGCGGTCGAGCC TCGCCGTGACTTCATCGAGAGCAACGCCTTGGCGGTGTCTAACCTGGA TTTCTGA |

-continued

Sequence Listing

| Seq ID No. | Description | Sequence |
|---|---|---|
| 111 | DP68 Isoleucine--tRNA ligase | ATGACCGACTATAAAGCCACGCTAAACCTTCCGGACACCGCCTTCCC<br>AATGAAGGCCGGCCTGCCACAGCGCGAACCGCAGATCCTGCAGCGCT<br>GGGACAGTATTGGCCTGTACGGAAAGTTGCGCGAAATTGGCAAGGAT<br>CGTCCGAAGTTCGTCCTGCACGACGGCCCTCCTTATGCCAACGGCACG<br>ATTCACATCGGTCATGCGCTGAACAAAATTCTCAAGGACATGATCCTG<br>CGTTCGAAAACCCTGTCGGGCTTCGACGCGCCTTATGTTCCGGGCTGG<br>GACTGCCACGGCCTGCCGATCGAACACAAAGTCGAAGTGACCTACGG<br>CAAGAACCTGGGCGCGGATAAAACCCGCGAACTGTGCCGTGCCTACG<br>CCACCGAGCAGATCGAAGGGCAGAAGTCCGAATTCATCCGCCTGGGC<br>GTGCTGGGCGAGTGGGACAACCCGTACAAGACCATGAACTTCAAGAA<br>CGAGGCCGGTGAAATCCGTGCCTTGGCTGAAATCGTCAAAGGCGGTT<br>TCGTGTTCAAGGGCCTCAAGCCCGTGAACTGGTGCTTCGACTGCGGTT<br>CGGCCCTGGCTGAAGCGGAAGTCGAGTACGAAGACAAGAAGTCCTCG<br>ACCATCGACGTGGCCTTCCCGATCGCCGACGACGACAAGCTGGCTCA<br>AGCCTTTGGCCTGTCCAGCCTGCCAAAGCCTGCAGCCATCGTGATCTG<br>GACCACCACCCCGTGGACCATCCCGGCCAACCAGGCGCTGAACGTGC<br>ACCCGGAATTCACCTACGCCCTGGTGGACGTCGGTGATCGCCTGCTGG<br>TGCTGGCTGAAGAAATGGTCGAGGCCTGCCTGGCGCGCTACGAGCTG<br>CAAGGTTCGGTCATCGCCACCACCACCGGCACTGCGCTGGAGCTGAT<br>CAATTTCCGTCACCCGTTCTATGACCGTCTGTCGCCGGTGTACCTGGC<br>TGACTACGTAGAGCTGGGTTCGGGTACTGGTGTGGTTCACTCCGCGCC<br>GGCCTACGGCGTTGATGACTTTGTGACCTGCAAAGCCTACGGCATGGT<br>CAACGATGACATCCTCAACCCGGTGCAGAGCAATGGCGTGTACGCGC<br>CGTCGCTGGAGTTCTTTGGCGGCCAGTTCATCTTCAAGGCCAACGAGC<br>CGATCATCGACAAACTGCGTGAAGTCGGTTCGCTGCTGCACACCGAA<br>ACCATCAAGCACAGCTACATGCACTGCTGGCGTCACAAGACCCCGCT<br>GATCTACCGCGCTACCGCGCAGTGGTTTATCGGCATGGACAAAGAGC<br>CGACCAGCGGCGACACCCTGCGTGTGCGCTCGCTCAAAGCGATCGAA<br>GAGACCAAGTTTGTCCCGGCCTGGGGCCAGGCGCGCCTGCACTCGAT<br>GATCGCCAACCGCCCGGACTGGTGCATCTCCCGCCAGCGCAACTGGG<br>GCGTGCCGATTCCGTTCTTCCTGAACAAGGAAAGCGGCGAGCTGCAC<br>CCACGTACCGTTGAACTGATGGAAGCAGTGGCGCTGCGCGTTGAGCA<br>GGAAGGCATCGAAGCCTGGTTCAAGCTGGACGCCGCCGAACTGCTGG<br>GCGACGAAGCGCCGCTGTACGACAAGATCAGCGACACCCTCGACGTG<br>TGGTTCGACTCGGGTACCACCCACTGGCACGTGCTGCGCGGTTCGCAC<br>CCGATGGGTCACGCCACCGGCCCGCGTGCCGACCTGTACCTGGAAGG<br>CTCGGACCAACACCGTGGCTGGTTCCACTCGTCGTTGCTGACCGGCTG<br>CGCCATCGACAACCACGCGCCGTACCGCGAACTGCTGACCCACGGCT<br>TCACCGTCGACGAGACGGGCCGCAAGATGTCCAAGTCGCTGAAAAAC<br>GTGATCGAGCCGAAAAAGATCAACGACACCCTGGGCGCCGATATCAT<br>GCGTCTGTGGGTCGCCTCGACCGATTACTCGGGCGAAATCGCCGTGTC<br>GGACCAGATCCTGGCCCGTAGCGCCGATGCCTACCGCCGTATCCGTA<br>ATACCGCACGCTTCCTGCTGTCGAACCTGACCGGTTTCAACCCGGCCA<br>CCGACATCCTGCCGGCCGAGGACATGCTCGCCCTGGACCGTTGGGCC<br>GTGGACCGTACGCTGTTGCTGCAGCGCGAGTTGCAGGAACACTACGG<br>CGAATACCGTTTCTGGAACGTGTACTCCAAGATCCACAACTTCTGCGT<br>GCAGGAGCTGGGTGGTTTCTACCTCGATATCATCAAGGACCGCCAGT<br>ACACCACCGGCGCCAACAGCAAGGCGCGCCGCTCGGCGCAGACCGC<br>GCTGTACCACATCTCTGAAGCGCTGGTGCGCTGGATCGCACCGATCCT<br>GGCCTTCACCGCTGACGAACTGTGGGAATACCTGCCGGGCGAGCGTA<br>ACGAATCGGTGATGCTCAACACCTGGTACGAAGGCCTGACCGAATTG<br>CCGGCCAACTTCGAACTGGGCCGCGAGTACTGGGAAGGCGTGATGGC<br>CGTCAAGGTTGCGGTGAACAAGGAGCTGGAAGTTCAGCGCGCGGCCA<br>AGGCCGTCGGTGGCAACCTGCAAGCCGAAGTCACCCTGTTTGCCGAG<br>GAAGGCCTGACCGCCGACCTGGCCAAGCTGAGCAACGAACTGCGCTT<br>CGTACTGATCACCTCGACCGCGAGCCTGGCACCGTTTGCCCAGGCACC<br>TGCGGACGCAGTGGCCACCGAAGTGCCGGGCCTCAAGCTCAAAGTGG<br>TCAAGTCGGCCTTTCCTAAGTGCGCCCGTTGCTGGCACTGCCGTGAAG<br>ACGTCGGCGTGAACCCAGAGCATCCGGAAATCTGCGGTCGTTGCGTC<br>GACAACATCAGCGGTGCTGGCGAGGTTCGCCACTATGCCTAA |
| 112 | DP68 NADH-quinone oxidoreductase subunit C/D | ATGACTACAGGCAGTGCTCTGTACATCCCGCCTTACAAGGCAGACGA<br>CCAGGATGTGGTTGTCGAACTCAATAACCGTTTTGGCCCTGACGCCTT<br>CACCGCCCAGGCCACACGCACCGGTATGCCGGTGCTGTGGGTGGCGC<br>GCGCCAAGCTCGTCGAAGTCCTGAGCTTCCTGCGCAACCTGCCCAAG<br>CCGTACGTCATGCTTTATGACCTGCATGGCGTGGACGAGCGTCTGCGC<br>ACCAAGCGTCAAGGTTTGCCGAGCGGTGCCGATTTCACCGTGTTCTAC<br>CACTTGATGTCGCTGGAACGTAACAGCGACGTGATGATCAAGGTCGC<br>GCTGTCCGAAAGCGACTTGAGCATCCCGACCGTCACCGGTATCTGGC<br>CGAATGCCAGCTGGTACGAGCGCGAAGTTTGGGACATGTTCGGTATC<br>GACTTCCCGGGCCACCCGCACCTGACGCGCATCATGATGCCGCCGAC<br>CTGGGAAGGTCACCCGCTGCGCAAGGACTTTCCTGCCCGCGCAACCG |

-continued

Sequence Listing

| Seq ID No. | Description | Sequence |
|---|---|---|
| | | AATTCGACCCGTTCAGCCTCAACCTCGCCAAGCAGCAGCTTGAAGAA<br>GAAGCTGCACGCTTCCGTCCGGAAGACTGGGGCATGAAACGCTCCGG<br>CACCAACGAGGACTACATGTTCCTCAACCTGGGCCCGAACCACCCTTC<br>GGCTCACGGTGCCTTCCGTATCATCCTGCAACTGGACGGCGAAGAAA<br>TCGTCGACTGTGTGCCGGACATCGGTTACCACCACCGTGGTGCCGAG<br>AAGATGGCCGAGCGCCAGTCCTGGCACAGCTTCATCCCGTACACCGA<br>CCGTATCGACTACCTCGGCGGCGTGATGAACAACCTGCCGTACGTGCT<br>GTCGGTCGAGAAGCTGGCCGGTATCAAGGTGCCGGACCGCGTCGACA<br>CCATCCGCATCATGATGGCCGAGTTCTTCCGCATCACCAGCCACCTGC<br>TGTTCCTGGGTACCTATATCCAGGACGTTGGCGCCATGACCCCGGTGT<br>TCTTCACCTTCACCGACCGTCAACGCGCCTACAAGGTGATCGAAGCCA<br>TCACCGGTTTCCGCCTGCACCCGGCCTGGTATCGCATCGGCGGCGTGG<br>CGCACGACCTGCCGAACGGCTGGGAGCGCCTGGTCAAGGAATTCATC<br>GACTGGATGCCCAAGCGTCTGGACGAGTACCAAAAGGCTGCGCTGGA<br>CAACAGCATCCTCAAGGGTCGTACCATCGGCGTCGCGCAGTACAACA<br>CCAAAGAAGCCCTGGAATGGGGCGTCACTGGTGCCGGCCTGCGTTCG<br>ACCGGCTGCGACTTCGACCTGCGTAAAGCACGGCCGTACTCGGGCTA<br>CGAGAACTTCGAGTTCGAAGTGCCGCTGGCCGCCAATGGCGATGCCT<br>ACGACCGGTGCATCGTGCGCGTTGAAGAAATGCGCCAGAGCCTGAAG<br>ATCATCGAGCAGTGCATGCGCAACATGCCGGCTGGCCCGTACAAGGC<br>GGATCATCCGCTGACCACACCGCCGCCGAAAGAGCGCACGCTGCAGC<br>ACATCGAAACCCTGATCACGCACTTCCTGCAAGTTTCGTGGGGCCCGG<br>TGATGCCGGCCAACGAATCCTTCCAGATGATCGAAGCGACCAAGGGT<br>ATCAACAGTTATTACCTGACGAGCGATGGCGGCACCATGAGCTACCG<br>CACCCGGATTCGTACCCCAAGCTTTGCCCACTTGCAGCAGATCCCTTC<br>GGTGATCAAAGGCGAGATGGTCGCGGACTTGATTGCGTACCTGGGTA<br>GTATCGATTTCGTTATGGCCGACGTGGACCGCTAA |
| 113 | DP68 Protein RecA | ATGGACGACAACAAGAAGAAAGCCTTGGCTGCGGCCCTGGGTCAGAT<br>CGAACGTCAATTCGGCAAGGGTGCCGTAATGCGTATGGGCGATCACG<br>ACCGTCAGGCGATCCCGGCTATTTCCACTGGCTCTCTGGGTCTGGACA<br>TCGCACTCGGCATTGGCGGCCTGCCAAAAGGCCGTATCGTTGAAATCT<br>ACGGTCCTGAATCTTCCGGTAAAACCACCCTGACCCTGTCGGTGATTG<br>CCCAGGCGCAAAAAATGGGCGCCACCTGTGCGTTCGTCGACGCCGAG<br>CACGCCCTGGACCCGGAATACGCCGGTAAGCTGGGCGTCAACGTTGA<br>CGACCTGCTGGTTTCCCAGCCGGACACCGGTGAGCAAGCCCTGGAAA<br>TCACCGACATGCTGGTGCGCTCCAACGCCATCGACGTGATCGTGGTCG<br>ACTCCGTGGCTGCCCTGGTACCGAAAGCTGAAATCGAAGGCGAAATG<br>GGCGACATGCACGTGGGCCTGCAAGCCCGCCTGATGTCCCAGGCGCT<br>GCGTAAAATTACCGGTAACATCAAGAACGCCAACTGCCTGGTGATCT<br>TCATCAACCAGATCCGTATGAAGATCGGCGTAATGTTCGGCAGCCCG<br>GAAACCACTACCGGTGGTAACGCGCTGAAGTTCTACGCTTCGGTCCGT<br>CTGGACATCCGCCGTACCGGCGCGGTGAAGGAAGGTGACGAAGTTGT<br>TGGTAGCGAAACTCGCGTTAAAGTCGTGAAGAACAAGGTCGCTCCGC<br>CTTTCCGTCAGGCAGAGTTCCAGATTCTCTACGGCAAGGGTATCTACC<br>TGAACGGCGAGATGATTGACCTGGGCGTACTGCACGGTTTCGTCGAG<br>AAGTCCGGTGCCTGGTATGCCTACAACGGCAGCAAGATCGGTCAGGG<br>CAAGGCCAACTCGGCCAAGTTCCTGGCAGACAACCCGGATATCGCTG<br>CCACGCTTGAGAAGCAGATTCGCGACAAGCTGCTGACCCCAGCGCCA<br>GACGTGAAAGCTGCCGCCAACCGCGAGCCGGTTGAAGAAGTGGAAG<br>AAGCTGACACTGATATCTGA |
| 114 | DP68 RNA polymerase sigma factor RpoD | ATGTCCGGAAAAGCGCAACAACAGTCTCGTATTAAAGAGTTGATCAC<br>CCTTGGTCGTGAGCAGAAATATCTGACTTACGCAGAGGTCAACGATC<br>ACCTGCCTGAGGATATTTCAGATCCTGAGCAGGTGGAAGACATCATC<br>CGCATGATTAATGACATGGGGATCCCCGTACACGAGAGTGCTCCGGA<br>TGCGGACGCCCTTATGTTGGCCGACTCCGATACCGACGAGGCAGCTG<br>CTGAAGAAGCGGCTGCTGCGCTGGCAGCGGTGGAGACCGACATCGGT<br>CGTACGACTGACCCTGTGCGCATGTATATGCGTGAAATGGGTACCGTC<br>GAGCTGCTGACACGTGAAGGCGAAATCGAAATCGCCAAACGTATTGA<br>AGAGGGTATCCGTGAAGTGATGGGCGCAATCGCGCACTTCCCTGGCA<br>CGGTTGACCACATTCTCTCCGAGTACACTCGCGTCACCACCGAAGGTG<br>GCCGCCTGTCTGACGTTCTGAGCGGCTACATCGACCCGGACGACGGC<br>ATTGCGCCGCCTGCCGCCGAAGTACCGCCGCCCGTCGATGCGAAAGC<br>CGCGAAGGCTGACGACGACACCGAAGACGACGATGCTGAAGCCAGC<br>AGCGACGACGAAGATGAAGTTGAAAGCGGCCCGGACCCGATCATCGC<br>AGCCCAGCGTTTCGGTGCGGTTTCCGATCAAATGGAAATCACCCGCA<br>AGGCCCTGAAAAAGCACGGTCGCTCCAACAAGCTGGCGATTGCCGAG<br>CTGGTGGCCCTGGCTGAGCTGTTCATGCCGATCAAGCTGGTACCGAA<br>GCAATTCGAAGGCTTGGTTGAGCGTGTTCGCAGTGCCCTTGAACGTCT<br>GCGTGCGCAAGAACGCGCAATCATGCAGCTGTGTGTACGTGATGCAC<br>GTATGCCGCGGGCTGACTTCCTGCGCCAGTTCCCGGGCAACGAAGTA<br>GACGAAAGCTGGACCGACGCACTGGCCAAAGGCAAGGCGAAATACG |

-continued

Sequence Listing

| Seq ID No. | Description | Sequence |
|---|---|---|
| | | CCGAAGCCATTGGTCGCCTGCAGCCGGACATCATCCGTTGCCAGCAG<br>AAGCTGACCGCGCTTGAGACCGAAACCGGTCTGACGATTGCTGAAAT<br>CAAAGACATCAACCGTCGCATGTCGATCGGTGAGGCCAAGGCCCGCC<br>GCGCGAAGAAAGAGATGGTTGAAGCGAACTTGCGTCTGGTGATCTCG<br>ATCGCCAAGAAGTACACCAACCGTGGTCTGCAATTCCTCGATCTGATC<br>CAGGAAGGCAACATCGGCTTGATGAAGGCGGTGGACAAGTTCGAATA<br>CCGTCGCGGCTACAAGTTCTCGACTTATGCCACCTGGTGGATCCGTCA<br>GGCGATCACTCGCTCGATCGCCGACCAGGCTCGCACCATCCGTATTCC<br>GGTGCACATGATCGAGACGATCAACAAGCTCAACCGTATTTCCCGGC<br>AGATGTTGCAGGAAATGGGTCGCGAACCGACCCCGGAAGAGCTGGGC<br>GAACGCATGGAAATGCCTGAGGATAAAATCCGCAAGGTATTGAAGAT<br>CGCTAAAGAGCCGATCTCCATGGAAACGCCGATTGGTGATGACGAAG<br>ACTCCCACCTGGGTGACTTCATCGAAGACTCGACCATGCAGTCGCCA<br>ATCGATGTCGCCACTGTTGAGAGCCTTAAAGAAGCGACTCGCGACGT<br>ACTGTCCGGCCTCACTGCCCGTGAAGCCAAGGTACTGCGCATGCGTTT<br>CGGCATCGACATGAATACCGACCACACCCTTGAGGAAGTCGGTAAGC<br>AGTTTGACGTGACCCGCGAGCGGATCCGTCAGATCGAAGCCAAGGCG<br>CTGCGCAAGTTGCGCCACCCGACGCGAAGCGAGCATCTGCGCTCCTT<br>CCTCGACGAGTGA |
| 115 | DP68 DNA-directed RNA polymerase subunit beta | ATGGCTTACTCATATACTGAGAAAAAACGTATCCGCAAGGACTTTAG<br>CAAGTTGCCGGACGTCATGGATGTCCCGTACCTTCTGGCTATCCAGCT<br>GGATTCGTATCGTGAATTCTTGCAGGCGGGAGCGACCAAAGATCAGT<br>TCCGCGACGTGGGCCTGCATGCGGCCTTCAAATCCGTTTTCCCGATCA<br>TCAGCTACTCCGGCAATGCTGCGCTGGAGTACGTGGGTTATCGCCTGG<br>GCGAACCGGCATTTGATGTCAAAGAATGCGTGTTGCGCGGTGTTACG<br>TACGCCGTACCTTTGCGGGTAAAAGTCCGCCTGATCATTTTCGACAAA<br>GAATCGTCGAACAAAGCGATCAAGGACATCAAAGAGCAAGAAGTCT<br>ACATGGGCGAAATCCCACTGATGACTGAAAACGGTACCTTCGTAATC<br>AACGGTACCGAGCGTGTTATTGTTTCCCAGCTGCACCGTTCCCCGGGC<br>GTGTTCTTCGACCACGACCGCGGCAAGACGCACAGCTCCGGTAAACT<br>CCTGTACTCCGCGCGGATCATTCCGTACCGCGGTTCGTGGTTGGACTT<br>CGAGTTCGACCCGAAAGACTGCGTGTTCGTGCGTATCGACCGTCGTCG<br>CAAGCTGCCGGCCTCGGTACTGCTGCGCGCGCTCGGTTACACCACTGA<br>GCAGGTGCTGGACGCTTTCTACACCACCAACGTATTCAGCCTGAAGG<br>ATGAAACCCTCAGCCTGGAGCTGATTGCTTCGCGTCTGCGTGGTGAAA<br>TTGCCGTTCTGGACATTCAGGACGAAAACGGCAAAGTGATCGTTGAA<br>GCGGGTCGTCGTATTACTGCGCGCCACATCAACCAGATCGAAAAAGC<br>CGGCATCAAGTCGCTGGAAGTGCCTCTGGACTACGTCCTGGGTCGCA<br>CCACCGCCAAGGTTATCGTTCACCCGGCTACAGGCGAAATCCTGGCT<br>GAGTGCAACACCGAGCTGAACACCGAAATCCTGGCAAAAATCGCCAA<br>GGCCCAGGTTGTTCGCATCGAGACCCTGTACACCAACGACATCGACT<br>GCGGTCCGTTCATCTCCGACACACTGAAGATCGACTCCACCAGCAAC<br>CAATTGGAAGCGCTGGTCGAGATCTATCGCATGATGCGTCCTGGTGA<br>GCCACCGACCAAAGACGCTGCCGAGACCCTGTTCAACAACCTGTTCTT<br>CAGCCCTGAGCGTTATGACCTGTCTGCGGTCGGCCGGATGAAGTTCA<br>ACCGTCGTATCGGTCGTACCGAGATCGAAGGTTCGGGCGTGCTGTGC<br>AAGGAAGATATCGTCGCGGTACTGAAGACTCTGGTCGACATCCGTAA<br>CGGTAAAGGCATCGTCGATGACATCGACCACCTGGGTAACCGTCGTG<br>TTCGCTGCGTAGGCGAAATGGCCGAAAACCAGTTCCGCGTTGGCCTT<br>GTGCGTGTTGAACGTGCGGTCAAAGAGCGTCTGTCGATGGCTGAAAG<br>CGAAGGCCTGATGCCGCAAGACCTGATCAACGCCAAGCCAGTGGCTG<br>CGGCAGTGAAAGAGTTCTTCGGTTCCAGCCAGCTTTCCCAGTTCATGG<br>ACCAGAACAACCCGCTCTCCGAGATCACCCACAAGCGCCGTGTTTCT<br>GCACTGGGCCCGGGCGGTCTGACCCGTGAGCGTGCTGGCTTTGAAGT<br>TCGTGACGTACACCCGACGCACTACGGTCGTGTTTGCCCGATCGAAAC<br>GCCGGAAGGTCCGAACATCGGTCTGATCAACTCCCTGGCCGCTTATGC<br>GCGCACCAACCAGTACGGCTTCCTCGAGAGCCCGTACCGCGTGGTGA<br>AAGACGCTCTGGTCACCGACGAGATCGTATTCCTGTCCGCCATCGAA<br>GAAGCTGATCACGTGATCGCTCAGGCTTCGGCCACGATGAACGACAA<br>GAAAGTCCTGATCGACGAGCTGGTAGCTGTTCGTCACTTGAACGAGTT<br>CACCGTCAAGGCGCCGGAAGACGTCACCTTGATGGACGTTTCGCCGA<br>AGCAGGTAGTTTCGGTTGCAGCGTCGCTGATCCCGTTCCTGGAACACG<br>ATGACGCCAACCGTGCGTTGATGGGTTCCAACATGCAGCGTCAAGCT<br>GTACCAACCCTGCGCGCTGACAAGCCGCTGGTAGGTACCGGCATGGA<br>GCGTAACGTAGCCCGTGACTCCGGCGTTTGCGTCGTAGCCCGTCGTGG<br>CGGCGTGATCGACTCCGTTGATGCCAGCCGTATCGTGGTTCGTGTTGC<br>CGATGATGAAGTTGAAACTGGCGAAGCCGGTGTCGACATCTACAACC<br>TGACCAAATACACCCGCTCGAACCAGAACACCTGCATCAACCAGCGT<br>CCGCTGGTGAGCAAGGGTGACCGCGTTCAGCGTAGCGACATCATGGC<br>CGACGGCCCGTCCACTGACATGGGTGAACTGGCTCTGGGTCAGAACA<br>TGCGCATCGCGTTCATGGCATGGAACGGCTTCAACTTCGAAGACTCCA<br>TCTGCCTGTCCGAGCGTGTTGTTCAAGAAGACCGTTTCACCACGATCC |

-continued

Sequence Listing

| Seq ID No. | Description | Sequence |
|---|---|---|
| | | ACATTCAGGAACTGACCTGTGTGGCACGTGATACCAAGCTTGGGCCA<br>GAGGAAATCACTGCAGACATCCCGAACGTGGGTGAAGCTGCACTGAA<br>CAAGCTGGACGAAGCCGGTATCGTTTACGTAGGTGCTGAAGTTGGCG<br>CAGGCGACATCCTGGTAGGTAAGGTCACTCCGAAAGGCGAGACCCAA<br>CTGACTCCGGAAGAGAAGCTGCTGCGTGCCATCTTCGGTGAAAAAGC<br>CAGCGACGTTAAAGACACCTCCCTGCGTGTACCTACCGGTACCAAGG<br>GTACTGTTATCGACGTACAGGTCTTCACCCGTGACGGCGTTGAGCGTG<br>ATGCTCGTGCACTGTCCATCGAGAAGACTCAACTCGACGAGATCCGC<br>AAGGACCTGAACGAAGAGTTCCGTATCGTTGAAGGCGCGACCTTCGA<br>ACGTCTGCGTTCCGCTCTGGTAGGCCACAAGGCTGAAGGCGGCGCAG<br>GTCTGAAGAAAGGTCAGGACATCACCGACGAAGTACTCGACGGTCTT<br>GAGCACGGCCAGTGGTTCAAACTGCGCATGGCTGAAGATGCTCTGAA<br>CGAGCAGCTCGAGAAGGCCCAGGCCTACATCGTTGATCGCCGTCGTC<br>TGCTGGACGACAAGTTCGAAGACAAGAAGCGCAAACTGCAGCAGGG<br>CGATGACCTGGCTCCAGGCGTGCTGAAAATCGTCAAGGTTTACCTGG<br>CAATCCGTCGCCGCATCCAGCCGGGCGACAAGATGGCCGGTCGTCAC<br>GGTAACAAAGGTGTGGTCTCCGTGATCATGCCGGTTGAAGACATGCC<br>GCACGATGCCAATGGCACCCCGGTCGACGTCGTCCTCAACCCGTTGG<br>GCGTACCTTCGCGTATGAACGTTGGTCAGATCCTCGAAACCCACCTGG<br>GCCTCGCGGCCAAAGGTCTGGGCGAGAAGATCAACCGTATGATCGAA<br>GAGCAGCGCAAGGTTGCTGACCTGCGTAAGTTCCTGCACGAGATCTA<br>CAACGAGATCGGCGGTCGCAACGAAGAGCTGGACACCTTCTCCGACC<br>AGGAAATCCTGGACTTGGCGAAGAACCTGCGCGGCGGCGTTCCAATG<br>GCTACCCCGGTGTTCGACGGTGCCAAGGAAAGCGAAATCAAGGCCAT<br>GCTGAAACTGGCAGACCTGCCGGAAAGCGGCCAGATGCAGCTGTTCG<br>ACGGCCGTACCGGCAACAAGTTTGAGCGCCCGGTTACTGTTGGCTAC<br>ATGTACATGCTGAAGCTGAACCACTTGGTAGACGACAAGATGCACGC<br>TCGTTCTACCGGTTCGTACAGCCTGGTTACCCAGCAGCCGCTGGGTGG<br>TAAGGCTCAGTTCGGTGGTCAGCGTTTCGGGGAGATGGAGGTCTGGG<br>CACTGGAAGCATACGGTGCTGCATACACTCTGCAAGAAATGCTCACA<br>GTGAAGTCGGACGATGTGAACGGTCGGACCAAGATGTACAAAAACAT<br>CGTGGACGGCGATCACCGTATGGAGCCGGGCATGCCCGAGTCCTTCA<br>ACGTGTTGATCAAAGAAATTCGTTCCCTCGGCATCGATATCGATCTGG<br>AAACCGAATAA |
| 116 | DP69 Glutamine--tRNA ligase | GTGCGCGAGGACCTGGCCAGCGGAAAGCACCAGGCGATCAAGACCC<br>GCTTCCCGCCGGAGCCGAACGGCTACCTGCACATCGGCCACGCCAAG<br>TCGATCTGCCTGAACTTCGGCATCGCCGGTGAGTTCAGCGGCGTCTGC<br>AACCTGCGTTTCGACGACACCAATCCGGCCAAGGAAGACCCGGAGTA<br>CGTGGCCGCGATCCAGGACGACGTGCGCTGGCTGGGCTTTGAATGGA<br>ACGAGCTGCGCCACGCCTCGGACTACTTCCAGACCTATTACCTGGCCG<br>CCGAGAAGCTGATCGAACAGGGCAAGGCCTACGTCTGCGACCTGTCG<br>GCCGAGGAAGTGCGCGCCTACCGCGGCACCCTGACCGAGCCGGGCCG<br>CCCGTCGCCGTGGCGTGACCGCAGCGTCGAGGAGAACCTCGACCTGT<br>TCCGCCGCATGCGTGCCGGTGAATTCCCCGATGGCGCGCGCACCGTG<br>CGCGCCAAGATCGACATGGCCAGCGGCAACATCAACCTGCGTGATCC<br>GGCGCTGTACCGCATCAAGCACGTCGAGCACCAGAACACCGGCAACG<br>CGTGGCCGATCTACCCGATGTACGACTTCGCCCATGCGCTGGGCGATT<br>CGATCGAGGGCATCACCCACTCGCTGTGCACGCTGGAATTCGAAGAC<br>CACCGCCCGCTGTACGACTGGTGCGTGGACAACGTCGACTTCGCCCA<br>CGATGACGCGCTGACCCAGCCGCTGGTCGACGCCGGCCTGCCGCGCG<br>AAGCGGCCAAACCGCGCCAGATCGAGTTCTCGCGCCTGAACATCAAC<br>TACACGGTGATGAGCAAGCGCAAGCTGATGGCGCTGGTCACCGAACA<br>GCTGGTGGACGGCTGGGAAGACCCGCGCATGCCGACCCTGCAGGGCC<br>TGCGTCGCCGTGGCTACACCCCGGCAGCGATGCGCCTGTTCGCCGAG<br>CGCGTGGGCATCAGCAAGCAGAATTCGCTGATCGATTTCAGCGTGCT<br>GGAAGGCGCGCTGCGCGAAGACCTGGACAGCGCCGCACCGCGCCGC<br>ATGGCCGTGGTCGACCCGGTCAAGCTGGTGCTGACCAACCTGGCCGA<br>AGGCCACGAAGAGCAGCTGACCTTCAGCAACCACCCGAAGGACGAG<br>AGCTTCGGTACCCGCGAAGTGCCGTTCGCACGTGAAGTGTGGATCGA<br>CCGCGAGGACTTCGCCGAAGTGCCGCCGAAGGGCTGGAAGCGCCTGG<br>TTCCCGGTGGTGAAGTGCGCCTGCGCGGCGCCGGCATCATCCGCTGC<br>GACGACGTGATCAAGGATGCCGACGGCACCATCACCGAGCTGCGCGG<br>CTGGCTGGATCCGGAATCGCGCCCGGGCATGGAAGGCGCCAACCGCA<br>AGGTCAAGGGCACCATCCACTGGGTCAGCGCGGTGCACGGTGTGCCG<br>GCCGAGATCCGCCTGTATGACCGCCTGTTCTCGGTGCCGAACCCGGAC<br>GATGAATCGGAAGGCAAGACCTACCGCGACTACCTCAATCCGGACTC<br>GCGCCGCACCGTCACCGGCTATGTCGAGCCGGCGGCTGCCAGCGCTG<br>CGCCGGAACAGTCGTTCCAGTTCGAGCGCACCGGCTACTTCGTTGCCG<br>ACCGCCGCGACCACACCGAAGCCAAGCCGGTGTTCAACCGCAGCGTG<br>ACCCTGCGCGACACCTGGTCGGCCTGA |

-continued

Sequence Listing

| Seq ID No. | Description | Sequence |
|---|---|---|
| 117 | DP69 DNA gyrase subunit B | ATGACCGACGAACAGAACACCCCGGCAAACAACGGCAACTACGACG<br>CCAACAGCATTACGGCCCTGGAAGGCCTGGAGGCTGTCCGCAAGCGC<br>CCAGGCATGTACATCGGCGACGTCCATGACGGCACCGGCCTGCATCA<br>CATGGTGTTCGAGGTCGTCGACAACTCAATCGACGAAGCCCTCGCCG<br>GCCATGCCGACCACGTCTCGGTGACGATCCATGCCGATGGCTCGGTA<br>GGCGTGTCCGACAACGGTCGCGGCATCCCGACGGGCAAGCACGAGCA<br>GATGAGCAAGAAGCTCGACCGCGATGTGTCTGCAGCCGAAGTGGTGA<br>TGACGGTCCTGCACGCAGGCGGCAAGTTCGACGACAACAGCTACAAG<br>GTTTCCGGCGGCCTGCACGGCGTGGGCGTCAGCGTGGTCAACGCGCT<br>GTCGCAGAAGCTGGTCCTGGATATCTACCAGGGTGGCTTCCACTACCA<br>GCAGGAGTACGCCGACGGCGCAGCACTGCATCCGCTGAAGCAGATCG<br>GCCCCAGCACCAAGCGCGGGACCACCCTGCGCTTCTGGCCCTCGGTA<br>AAGGCTTTCCACGACAACGTGGAATTCCACTACGACATCCTGGCCCG<br>GCGCCTGCGCGAACTGTCCTTCCTCAATTCCGGCGTCAAGATCGTGCT<br>GGTGGACGAGCGTGGTGATGGCCGCCGCGACGACTTCCATTACGAGG<br>GCGGCATCCGCAGCTTCGTGGAGCATCTGGCGCAGTTGAAGACGCCG<br>TTGCACCCGAACGTGATCTCGGTGACCGGCGAATCCAATGGCATCAC<br>CGTGGAAGTGGCGCTGCAGTGGACCGACTCCTACCAGGAGACGATGT<br>ACTGCTTCACCAACAACATTCCGCAGAAGGACGGCGGTACCCACCTG<br>GCCGGCTTCCGTGGCGCATTGACCCGCGTGCTCAACAACTACATCGA<br>GCAGAACGGCATCGCCAAGCAGGCCAAGATCAACCTGACCGGCGATG<br>ACATGCGCGAAGGCATGATCGCGGTGCTGTCGGTGAAGGTGCCGGAT<br>CCCAGCTTCTCCAGCCAGACCAAGGAAAAGCTGGTCAGCTCGGATGT<br>GCGCCCGGCCGTGGAAAGCGCGTTCGGCCAGCGCCTGGAAGAGTTCC<br>TGCAGGAAAACCCGAACGAAGCCAAGGCCATCGCCGGCAAGATCGTC<br>GACGCTGCCCGTGCCCGCGAAGCGGCGCGCAAGGCCCGCGACCTGAC<br>CCGCCGCAAGGGTGCGCTGGATATCGCCGGCCTGCCGGGCAAGCTGG<br>CCGACTGCCAGGAAAAGGATCCGGCGCTGTCCGAACTGTTCATCGTC<br>GAGGGTGACTCGGCAGGTGGTTCGGCCAAGCAGGGTCGCAACCGCAA<br>GAACCAGGCGGTGCTGCCGCTGCGCGGCAAGATCCTCAACGTGGAAC<br>GTGCGCGCTTCGACCGCATGCTGGCGTCCGACCAGGTGGGTACGCTG<br>ATCACCGCGCTGGGTACCGGCATCGGTCGTGACGAGTACAACCCGGA<br>CAAGCTGCGGTACCACAAGATCATCATCATGACCGACGCCGACGTCG<br>ACGGCGCGCACATCCGCACCCTGCTGCTGACGTTCTTCTACCGTCAGA<br>TGCCGGAGCTGATCGAGCGCGGTTATGTCTATATCGGCCTGCCGCCGT<br>TGTACAAGATCAAGCAGGGCAAGCAGGAGCTGTACCTGAAGGACGA<br>CCCGGCGCTGGACAGCTATCTGGCCAGCAGCGCGGTGGAGAACGCTG<br>GGCTGGTGCCGGCCAGCGGCGAGCCGCCGATCGACGGCGTGGCACTG<br>GAAAAGCTGCTGCTCGCCTACGCTGCCGCGCAGGACACGATCAACCG<br>CAATACCCACCGCTACGACCGCAACCTGCTCGAAGCGCTGGTCGACT<br>TCATGCCGCTGGAGCTGGAAAACCTGCGCACTGCAGGTCCTGGCGAA<br>GGTCTGGACGCGTTGGCCAAGCACCTCAACCAGGGCAACCTCGGCAG<br>CGCCCGCTTCACCCTGGAACTGCAGGAACCCAACGAGCAGCGTCCGG<br>CGGCCGTACTGGTGACCCGCAGCCACATGGGCGAACAGCACATCCAG<br>GTGCTGCCGCTGTCCGCGCTGGAAAGCGGCGAACTGCGCGGCATCCA<br>TCAGGCAGCGCAGCTGCTGCACGGTCTGGTCCGCGAAGGCGCGGTCA<br>TCACCCGTGGCGCCAAGTCGATCGAGATCGACTCGTTCGCACAGGCC<br>CGCAACTGGCTGTTGGACGAAGCCAAGCGCGGCCGGCAGATCCAGCG<br>ATTCAAGGGTCTGGGCGAAATGAATCCGGAACAGCTGTGGGATACCA<br>CCGTCAATCCCGATACCCGTCGCCTGCTGCAGGTGCGCATCGAAGAC<br>GCGGTGGCCGCTGACCAGATCTTCAGCACCCTGATGGGTGATGTGGT<br>CGAACCGCGTCGTGACTTCATCGAAGACAACGCGTTGAAGGTCGCCA<br>ACCTGGATATCTGA |
| 118 | DP69 Isoleucine--tRNA ligase | GTGAGCCAGGACTACAAGACCACCCTCAACCTGCCGGCCACCGAATT<br>CCCGATGCGCGGCGACCTGCCCAAGCGCGAGCCGGGCATTCTGGCGC<br>GCTGGGAAGAGCAGGGGCTCTACCAGCAGCTGCGCGACAACGCCGCC<br>GGCCGCCCGCTGTTCGTGCTGCATGACGGCCCGCCGTACGCCAATGC<br>GCGCATCCACCTGGGCCATGCGGTCAACAAGATCCTCAAGGACATCA<br>TCGTCAAGTCGCGCTACCTGGCCGGCTTCGATGCGCCCTACGTGCCGG<br>GCTGGGACTGCCATGGCCTGCCGATCGAAATCGCGGTGGAAAAGAAG<br>TGGGGCAAGGTCGGGGTGAAGCTCGATGCGGTCGAGTTCCGGCAGAA<br>GTGCCGCGAGTTCGCCGAAGAACAGATCGACATCCAGCGTGCCGACT<br>TCAAGCGCCTGGGCGTCACCGGCGACTGGGACAACCCGTACAAGACC<br>CTAAGCTTCGATTTCGAGGCCAACGAGATCCGTGCGCTGTCCAAGATC<br>GTGGCCAACGGCCATCTGCTGCGTGGCGCCAAGCCGGTCTACTGGTG<br>CTTCGACTGCGGCTCGGCACTGGCCGAGGCCGAGATCGAGTACCACG<br>AGAAGACCTCGCCGGCGATCGACGTGGCCTACACCGCGCGTGATCCG<br>CAGGCGGTGGCGCAGGCGTTCGGCGTCAGCCTGCCGGCCGATGTCGA<br>AGTGGCGGTGCCGATCTGGACCACCACTCCGTGGACGCTGCCGGCTT<br>CGCTGGCGGTGTCGCTGGGCGCGGACATCCGCTACGTGCTGGCCGAA<br>GGCCCGGCGCACAACGGCAAGCGCCGTTGGCTGGTGCTGGCTGCTGC |

-continued

Sequence Listing

| Seq ID No. | Description | Sequence |
| --- | --- | --- |
| | | GCTGGCCGAACGGTCGCTGCAGCGCTACGGCGTGGACGCGGTGGTGC<br>TGCACGGTGAAGCCGAAGGTTCGGCGCTGGAAAACCAGCTGCTGGCG<br>CACCCGTTCTACCCGGAGCGCGAGATCCCCGTGCTCAACGGCGAACA<br>CGTGTCCGACGAGGACGGTACCGGTGCGGTGCACACTGCCCCCGGCC<br>ACGGCCAGGAAGACTACGTGGTCAGCCAGAAGTACGGCCTGCTGGAG<br>AAGTACAACGCCGGCCAGATCAATCCGGTCGACGGTGCGGGCGTGTA<br>CCTGGCGTCCACCCCGCCCGCCGGTGACCTGGTGCTGGCCGGTACCC<br>ACATCTGGAAGGCGCAGCAGCCGATCATCGAAGTGCTGGCCGCCAGC<br>GGCGCGCTGCTCAAGGCCGTGGAGATCGTGCACAGTTATCCGCATTG<br>TTGGCGCCACAAGAAGACCCCGCTGGTGTTCCGCGCCACCCCGCAGT<br>GGTTCATTTCGATGGACAAGGCCAACCTGCGCAACGATGCGCTGGCC<br>GCGATCGATACCGTCGGCTGGTTCCCGAGCTGGGGCAAGGCGCGCAT<br>CCAAAGCATGATCGACGGCCGCCCGGACTGGACCATCTCGCGCCAGC<br>GCACCTGGGGCGTGCCGATCGCGCTGTTCACCCACCGCCAGACCGGC<br>GAGATCCACCCGCGTTCGGTGGAGCTGATGCAGCAGGTGGCCGACCG<br>CGTTGAAGCCGAAGGCATCGACGTGTGGTACTCGCTGGATGCGGCTG<br>AACTGCTGGGCGCTGAAGCGGCCGACTACGAGAAGGTCACCGACATC<br>CTCGATGTCTGGTTCGATTCCGGCGTGACCCACGAAGCCGTGCTGGCT<br>GCCCGTGGCTTCGGCAAGCCGGCCGATCTGTACCTGGAAGGTTCGGA<br>CCAGCATCGCGGCTGGTTCCAGTCCTCGCTGCTGACCGGCGTGGCCAT<br>CGACAAGCGCGCGCCGTACAAGCAGTGCCTCACCCACGGTTTCACCG<br>TGGACGAGCACGGCCGCAAGATGTCCAAGTCGCTGGGCAACGGCATC<br>GAACCGCAGGAAATCATGAACAAGCTGGGCGCGGACATCCTGCGCCT<br>GTGGATCGCCTCGGCCGACTACAGCAACGAGATGTCGCTGTCGCAGG<br>AAATCCTCAAGCGCACCGCCGACGCCTACCGCCGCCTGCGCAACACC<br>GCCCGCTTCCTGCTGGGCAACCTGGACGGTTTCGATCCGGCCCAGCAC<br>CTGCGCCCGCTCAACGAGATGGTCGCGCTGGACCGCTGGATCGTGCA<br>TCGCGCCTGGGAGCTGCAGGAGAAGATCAAGGCGGCGTATGACAACT<br>ACGACATGGCCGAGATCGTGCAGTTGCTGCTGAACTTCTGCAGCGTG<br>GACCTGGGCTCGCTGTACCTGGACGTGACCAAGGATCGCCTGTATAC<br>GATGCCGACCGATTCGGATGGTCGTCGTTCGGCGCAGAGCGCGATGT<br>ACCACATCGCCGAAGCGTTCACCCGCTGGGTGGCGCCGATCCTGACC<br>TTCACCGCCGACGAGCTGTGGGGCTACCTGCCGGGCGATCGTGCCGG<br>CCACGTGCTGTTCACTACCTGGTACGAGGGCCTGGCACCGCTGCCGAC<br>CGATGCACAGCTCAACGCTGCCGACTTCGATCAGCTGCTGGCCGTGC<br>GCGAGCAGGTGGCCAAGGTGCTGGAGCCGATGCGCGCCAATGGTGCG<br>ATCGGTGCCGCGCTGGAAGCGGAGATCACCATCGCCGCCAGCGAAGA<br>GCAGGCCGCGCGCTGGCAGCCGCTGGCCGATGAACTGCGTTTCCTGTT<br>CATCAGTGGTGACGTGCAGGTGCGTCCGGCGACCACCGACGAGGTGT<br>TCGTCAGCGCGCAGCCGACGCAGAAGTCCAAGTGCGTGCGCTGCTGG<br>CACCACCGTGCCGACGTTGGCAGCAATGCCGACCACCCGGAACTGTG<br>CGGCCGCTGCGTGACCAACATCGCCGGTGCCGGCGAAGCGCGGAGCT<br>GGTTCTGA |
| 119 | DP69 Glycine--tRNA ligase beta subunit | ATGAGCCACTTGTCTCCCCTGCTGATTGAACTGGGCACCGAAGAGTTG<br>CCGGTCAAGGCGCTGCCGGGCCTGGCCCAGGCCTTCTTCGACGGTGTT<br>GTCGATGGCCTGCGCAAGCGCGGCGTCGAACTGGAGCTGGGCGATGC<br>CCGCCCGCTGTCGACCCCGCGCCGCCTGGCCGTGCTGCTGCCGGGCGT<br>TGGCCTGGAACAGCCGGAACAACACAGCGAAGTGCTGGGCCCGTACC<br>TGAACATCGCGCTGGACGCCGAAGGCCAGCCGACCAAGGCGCTGCAG<br>GGTTTCGCGGCCAAGGCCGGGATCGACTGGACCGCGCTGGAGAAGAC<br>CACCGACAACAAGGGTGAGCGCTTCGTGCACCGTGCGGTGACTCCGG<br>GCGCGCGCACCGCTGCGCTGCTGCCGGAGATCCTGCGCGAGGCCATC<br>GCCGGCATGCCGATTCCCAAGCCGATGCGCTGGGGCGACCACAGCTG<br>GGGCTTCGCCCGCCCGGTGCACTGGCTGGTGCTGCTGCATGGCGGCG<br>ACGTGGTCGAGGCCGAACTGTTTGGCCTGAAGGCCGACCGCATGAGC<br>CGCGGCCACCGCTTCCTGCACGACAAGACCGTGTGGCTGACCCAGCC<br>GCAGGACTATGTCGAATCGCTGCGCGCCGCCTTCGTGCTGGTCGATCC<br>GGCCGAGCGCCGCCGGCGCATCGTTGCCGAAGTGGAAGCCGCTGCCG<br>CCACCGCCGGTGGCAGCGCACGCATCACCGAGGACAACCTGGAGCAG<br>GTGGTGAACCTGGTCGAGTGGCCGGCGGCAGTGTTGTGCAGCTTCGA<br>GCGCGCGTTCCTGGCGGTACCGCAGGAAGCGCTGATCGAGACGATGG<br>AGATCAACCAGAAGTTCTTCCCGGTGCTGGATGACGGCGGCAAGCTG<br>ACCGAGAAGTTCATCGGCATCGCCAACATCGAGTCCAAGGACGTGGC<br>CGAAGTGGCCAAGGGCTACGAGCGCGTGATCCGCCCGCGCTTCGCCG<br>ATGCCAAGTTCTTCTTCGACGAAGACCTGAAGCAGGGCCTGCAGGCG<br>ATGGGCGAGGGCCTGAAGACGGTGACCTACCAGGCCAAGCTGGGCA<br>GCGTGGCCGACAAGGTCGCGCGCGTGGCGGCGCTGGCCGAGGTGATC<br>GCTGCGCAGGTGGGGGCCGACCCGGTGCTGGCCAAGCGTGCCGCGCA<br>GCTGGCCAAGAACGACCTGCAGTCGCGCATGGTCAATGAGTTCCCGG<br>AACTGCAGGGCATCGCTGGCCGCCACTACGCGGTGGCCGGTGGCGAG<br>TCGCCGGAGGTGGCGCTGGCCATCGACGAGGCCTACCAGCCGCGCTT<br>CGGTGGCGATGACATCGCGCTGTCGCCGCTGGGCAAGGTGCTGGCGA |

-continued

Sequence Listing

| Seq ID No. | Description | Sequence |
| --- | --- | --- |
| | | TCGCCGAGCGTGTGGACACGCTGGCCGGCGGTTTCGCCGCGGGCCTG AAGCCGACCGGCAACAAGGACCCGTTCGCCCTGCGCCGCAACGCGCT GGGCCTGGCCCGCACGATTATCGAAAGTGGCTTCGAGCTGGACCTGC GCGCGCTGCTGGCCAGCGCCAATGCCGGGCTGACCGTGCGCAACGTG CAGGCCGACGTGGCTGAGCTGTACGACTTCATCCTCGACCGCCTGAA GGGCTACTACAGCGACAAGGGCGTGCCGGCCAGCCACTTCAATGCGG TGGCTGAGCTGAAGCCGGTCTCGCTGTACGATTTCGACCGTCGCCTGG ACGCCATCGGTATCTTCGCGGCGCTGCCGGAGGCCGAGGCGCTGGCA GCGGCCAACAAGCGCATCCGCAACATCCTGCGCAAGGCCGAAGGCGA TATTCCGGGCCAGATCGATGCGGCCCTGTTGCAGGAAGATGCCGAGC GCGCGCTGGCGGAAGCCGTGACTGCAGCCATCGACGACACCGGCGCC AGCCTGCACCAGAAGGACTACGTGGCCGTGCTGGCGCGCCTGGCCCG CCTGCGTCCGCAGGTCGATGCGTTCTTCGATGGGGTGATGGTCAATGC CGAGGATCCGGCACTGCGCGGCAACCGCCTGGCGCTGCTGACGATGC TGGGCGAGCGCTTGGGCAAGGTCGCGGCGATCGAGCATCTGTCGAGC TGA |
| 120 | DP69 Glutamine synthetase | ATGTCCGTGGAAACCGTAGAGAAGCTGATCAAGGACAACCAGATCGA GTTCGTCGATCTGCGCTTCGTCGACATGCGTGGTGTCGAACAGCATGT GACCTTCCCGGTCAGCATCGTCGAGCCGTCGCTGTTTGAAGAAGGCA AGATGTTCGATGGCAGCTCGATCGCCGGCTGGAAGGGCATCAACGAG TCGGACATGGTGCTGCTGCCGGACACCGCCAGCGCCTACGTCGACCC GTTCTACGCCGATCCGACCATCGTGATCAGCTGCGACATCCTCGACCC GGCCACCATGCAGCCGTATGGCCGTTGCCCGCGCGGCATCGCCAAGC GCGCCGAGTCCTACCTGAAGTCCTCGGGCATCGCCGAAACCGCGTTCT TCGGCCCGGAGCCGGAGTTCTTCATCTTCGACTCGGTGCGTTTCGCCA ATGAAATGGGCAACACCTTCTTCAAGGTCGACTCGGAAGAAGCGGCG TGGAACAGCGGCGCCAAGTACGACGGCGCCAACAGCGGCTACCGTCC GGGCGTGAAGGGCGGTTATTTCCCCGTTCCGCCGACCGACACCCTGC ACGACCTGCGTGCGGAGATGTGCAAGACCCTGGAACAGGTCGGCATC GAAGTGGAAGTGCAGCACCACGAAGTGGCCACCGCCGGCCAGTGCG AGATCGGCACCAAGTTCAGCACCCTGGTGCAGAAGGCCGACGAACTG CTGCGGATGAAGTACGTCATCAAGAACGTCGCCCACCGCAACGGCAA GACCGTCACCTTCATGCCCAAGCCGATCGTCGGCGACAACGGCAGCG GCATGCACGTGCACCAGTCGCTGTCCAAGGGCGGCACCAACCTGTTC TCCGGTGACGGCTACGGTGGCCTGAGCCAGATGGCGCTGTGGTACAT CGGCGGCATCTTCAAGCATGCCAAGGCGATCAACGCCTTTGCCAACT CGGGTACCAACAGCTACAAGCGCCTGGTGCCGGGCTTCGAAGCCCCG GTGATGCTGGCCTACTCGGCGCGCAACCGTTCGGCCTCGTGCCGCATT CCGTGGGTGTCCAACCCGAAGGCGCGTCGCATTGAAATGCGCTTCCC CGATCCGATCCAGTCGGGCTACCTGACCTTCACCGCGCTGATGATGGC CGGCCTGGACGGCATCAAGAACCAGATCGACCCGGGCGCACCGAGCG ACAAGGATCTGTACGACCTGCCGCCGGAAGAAGAGAAGCTGATTCCG CAGGTCTGCTCCTCGCTGGACCAGGCCCTGGAAGCGCTGGACAAGGA CCGTGAGTTCCTCAAGGCCGGTGGCGTGATGAGCGATGACTTCATCG ACGGCTACATCGCGCTGAAGATGCAGGAAGTGACCAAGTTCCGCGCG GCGACCCACCCGCTGGAATACCAGTTGTACTACGCCAGCTGA |
| 121 | DP69 Glucose-6-phosphate isomerase | ATGACAACGAACAACGGATTCGACTCGCTGCATTCCCACGCCCAGCG CCTGAAGGGCGCAAGCATCCCCAGCCTGCTCGCCGCCGAACCCGGCC GCGTACAGGACCTGGCGCTGCGGGTCGGTCCGTTGTATGTCAACTTCG CCCGGCAGAAATACGATGCCGCGGCGTTGCAGGCGCTGTTGGCGCTG GCTGCCGAACGTGATGTCGGCGGCGCCATCACGCGCCTGTTCCGTGG CGAGCAGGTCAATCTGACCGAAGGCCGCGCCGCACTGCACACCGCAC TGCGCGGCGACGTGGTCGATGCGCCGGTTGCCGCCGAGGCCTATGCC ACGGCCCGCGAAATCCGCCAGCGCATGGGCGTGCTGGTGCGCGCACT GGAAGACAGTGGCGTGACCGATGTGGTCAGTGTCGGCATCGGCGGTT CCGATCTCGGTCCGCGTCTGGTCGCCGACGCACTGCGTCCAGTCACTG GCGCTCGCCTGCGCGTGCATTTCGTGTCTAACGTGGACGGCGCTGCCA TGCAGCGCACGCTGGCCACGCTGGATCCGGCGAAGACCGCCGGCATC CTCATTTCCAAGACCTTCGGTACCCAGGAAACCCTGCTCAACGGCCAG ATCCTGCACGATTGGCTGGGTGGCAGCGAGCGCCTGTACGCGGTCAG CGCCAATCCGGAACGCGCCGCCAAGGCCTTCGCCATCGCCGCCGAGC GCGTGCTGCCGATGTGGGACTGGGTAGGGGGGCGCTATTCGCTGTGG TCGGCCGTCGGTTTCCCGATCGCACTGGCCATCGGCTTCGAGCGTTTC GAGCAGTTGCTGGAAGGCGCCGCGCAGATGGATGCGCATGCGCTGGA CGCGCCGCTGGAGCGCAACCTGCCGGTGCTGCACGGCCTGACCGACA TCTGGAACCGCAATCTGCTGGGCTCTGCCACGCATGCGGTGATGACCT ACGACCAGCGCTTGGCGCTGCTGCCGGCCTACCTGCAGCAGCTGGTG ATGGAAAGCCTGGGCAAGCGCGTGCAGCGCGATGGCCAGCCGGTCAC CACCGACACCGTGCCGGTGTGGTGGGGCGGTGCCGGCACCGATGTGC AGCACAGCTTCTTCCAGGCCCTGCACCAGGGCACCAGCATCATTCCG GCCGATTTCATCGGCTGCGTGCACAACGACGATCCGTATACGGTCAA |

-continued

Sequence Listing

| Seq ID No. | Description | Sequence |
|---|---|---|
| | | CCACCAGGCGTTGATGGCCAACCTGCTGGCGCAGACCGAAGCGCTGG<br>CCAACGGCCAGGGCAGTGACGATCCGCACCGCGATTATCCGGGTGGC<br>CGCCCGAGCACGATGATCCTGCTCGACGCGCTCACCCCGCAGGCGCT<br>GGGCGCCTTGATCGCGATGTACGAACACGCCGTGTACGTGCAGTCGG<br>TGATCTGGAACATCAACGCCTTCGACCAGTTCGGTGTCGAGCTGGGC<br>AAGCAGCTGGCCAGTGGCCTGCTGCCCGCTCTGCAGGGTGAGGATGT<br>CGAGGTCAACGACCCGCTGACCCGTGAGCTGCTGGCCCAGCTGAAGG<br>GCTGA |
| 122 | DP69 Leucine--tRNA ligase | ATGACCAGCGTCGAACCCAACGTTTACGATCCGCAGCAGGTTGAATC<br>CGCCGCCCAGAAGTACTGGGACGCTACCCGTGCCTTCGAGGTCGATG<br>AAGCCTCGGACAAGCCGAAGTACTACTGCCTGTCGATGCTTCCGTATC<br>CGTCCGGTGCGCTGCACATGGGCCACGTGCGCAATTACACGATCGGC<br>GACGTGATCAGCCGCTACAAGCGCATGACCGGCCACAACGTGCTGCA<br>GCCGATGGGCTGGGACGCGTTTGGCCTGCCGGCGGAAAACGCTGCGA<br>TCAAGAACAAGACCGCGCCGGCCGCCTGGACCTACAAGAACATCGAC<br>CACATGCGCAGCCAGCTGCAGTCGCTGGGCTATGCCATCGACTGGTC<br>GCGCGAGTTCGCCACCTGCCGCCCGGACTATTACGTCCACGAGCAGC<br>GCATGTTCACCCGCCTGATGCGCAAGGGCCTGGCCTACCGCCGCAAC<br>GCGGTGGTGAACTGGGACCCGGTCGACCAGACCGTGCTGGCCAACGA<br>GCAGGTCATCGACGGCCGTGGCTGGCGCTCCGGCGCGCTTGTGGAAA<br>AGCGCGAGATCCCGCAGTGGTTCCTGCGCATCACCGACTACGCCCAG<br>GAACTGCTGGACGGCCTGGATGAGCTGGACGGCTGGCCGGAGTCGGT<br>CAAGACCATGCAGCGCAACTGGATCGGCCGCTCCGAAGGGCTGGAAA<br>TCCAGTTCGACGTGCGCGACGTCGATGGTGCCGCACTGGATCCGCTGC<br>GCGTGTTCACCACCCGCCCGGACACCGTGATGGGCGTGACTTTCGTGT<br>CGATCGCGGCCGAACATCCGCTGGCGCTGCATGCCGCGAAGAACAAC<br>CCGGAACTGGCTGCGCTGCTGTCGGAAATGAAGCAGGGCGGCGTGTC<br>CGAGGCCGAGCTGGAGACCCAGGAAAAGCGCGGCATGGATACCGGC<br>CTGCGCGCCGTGCATCCGGTTACCGGTGCCCAGGTGCCGGTGTGGGTC<br>GCCAACTTCGTGCTGATGGGCTACGGCACTGGCGCGGTGATGGCCGT<br>ACCGGGCCACGACCAGCGCGACAATGAATTCGCCAACAAGTACAACC<br>TGCCGATCCGCCAGGTCATCGCGCTGAAGTCGCTGCGCAAGGACGAA<br>GGCGCCTACGACGCGACGCGCTGGCAGGACTGGTACGGCGACAAGAC<br>CCGCGAGACCGAACTGGTCAACTCCGAAGAGTTCGACGGCCTGGACT<br>TCCAGGGCGCTTTCGAGGCGCTGGCCGAACGGTTCGAGCGCAAGGCC<br>CAGGGACAGCGCCGGGTGAACTACCGCCTGCGCGACTGGGGCGTGAG<br>CCGCCAGCGCTACTGGGGCTGCCCGATTCCGGTGATCTACTGCGACA<br>AGTGTGGCGCGGTACCGGTGCCGGAAGACCAGCTGCCGGTGGTGCTG<br>CCGGAAGACGTGGCGTTCGCCGGTACCGGTTCGCCGATCAAGACCGA<br>TCCGGAATGGCGCAAGACCACCTGCCCGGACTGCGGCGGTGCGGCCG<br>AGCGTGAGACCGACACCTTCGACACCTTCATGGAGTCGAGCTGGTAC<br>TACGCCCGCTACACCTCGCCGGGCGCCCGCGATGCGGTCGACAAGCG<br>CGGCAACTACTGGCTGCCGGTGGACCAGTACATCGGTGGCATCGAAC<br>ACGCGATCCTGCACCTGATGTATTTCCGCTTCTACCACAAGCTGCTGC<br>GCGACGCGCGGATGGTGGACAGCAACGAACCCGCGCGGAACCTGCTG<br>TGCCAGGGCATGGTGATCGCTGAGACCTACTACCGCCCGAACCCGGA<br>CGGCTCGAAGGACTGGATCAACCCGGCCGATGTGGAAGTGCAGCGCG<br>ACGAGCGCGGCCGCATCACCGGCGCCACCCTGATCGCCGACGGTCAG<br>CCGGTGGTGGTCGGTGGTACCGAGAAGATGTCCAAGTCGAAGAACAA<br>CGGCGTGGACCCGCAGGCGATGGTCGGCAAGTACGGCGCCGATACCG<br>TGCGCCTGTTCTCGATGTTCGCTGCACCGCCGGAACAGTCGCTGGAAT<br>GGAACGAAGCCGGCGTGGACGGCATGGCCCGCTTCCTGCGCCGCCTG<br>TGGGCACAGGTGCAGAAGCACGCTGCCGAGGGTGCCGCACCGGCGCT<br>CGACGCGGCCGCGCTGGATGCCGGCCAGAAGGCCCTGCGCCGCAAGA<br>CCCACGAGACCATCGGCAAGGTCGGCGACGACTACGGCCGCCGCCAC<br>AGCTTCAACACCGCCATTGCCGCGGTGATGGAGCTGATGAACGCGCT<br>GGCCAAGTTCGAGGACGGCAGTGAACAGGGGCGCGCCGTGCGCCAG<br>GAAGCACTGCAGGCCATCGTGCTGCTGCTCAACCCGATCACCCCGCA<br>TGCCAGCCACGCCCTGTGGCAGGTACTGGGCCATGGCGAAACGCTGC<br>TGGAAGATCAGCCGTTCCCGCAGGCCGACAGCAGTGCGCTGGTGCGC<br>GATGCGCTGACTTTGGCCGTGCAGGTCAATGGCAAGCTGCGTGGCAC<br>CATCGAGGTCGCCGCCGATGCCGCGCGCGAGCAGATCGAAGCGCTGG<br>CCCTGGCCGAGCCGAACGCGGCCAAGTTCCTGGAAGGCCTGACGGTG<br>CGCAAGATCATCATCGTTCCCGGCAAGATCGTGAACATCGTCGCTGCC<br>TGA |
| 123 | DP70 Glycine--tRNA ligase beta subunit | ATGTCTAAACATACAGTATTGTTCGAATTGGGCTGTGAAGAACTTCCA<br>CCTAAAAGCCTCAAAAAATTACGTGATGCACTGCATGCTGAAACGGT<br>AAAAGGCTTAAAAGATGCAGGCTTAGCATTCGACTCAATCGAAGCTT<br>ATGCAGCACCGCGTCGTTTGGCACTTAAAATTGTGAATATCGATGGCG<br>CTCAGCCTGATACACAAAAACGCTTTGACGGCCCTGCAAAAGAAGCG<br>GCTTATGATGCTGAAGGCAAACCAAGCAAAGCATTAGAAGGCTTTAT |

-continued

Sequence Listing

| Seq ID No. | Description | Sequence |
|---|---|---|
| | | GCGTGGTCAAGGCATCACTGCGGATCAAGTCACCACGTTCCAAGCGG GTAAAGTTGAAAAGGTTTGCTATTTAAAAGATGTTAAAGGTCAAAGC CTTGAGGTTTTACTGCCACAAATTCTACAAGCAGCTTTGGACAATCTT CCAATTGCAAAACGTATGCGTTCAGCGGCAAGCCGTACTGAATTCGT GCGTCCTGTAAAATGGGTGGTGTTGCTCAAAGACAATGATGTGATTG CAGCCACTATTCAAGATCACAAAGCAGGCAATGTGACTTATGGTCAT CGTTTCCATGCCCCTGAAGCGATTACTTTGGCTCATGCAGATGAATAT CTTGCCAAGTTAAAAGCGGCTTATGTGGTTGCTGACTTTGCAGAACGC CAAGCCATCATTGACCAACAAGTCAAAGCGTTGGCTGATGAAGTTAA TGCGATTGCGATTGTACCAAGCGACCTGCGTGATGAAGTGACCGCAT TGGTGGAATGGCCTGTTGCGCTACGTGCCAGCTTTGAGGAGCGTTTCC TTGCTGTACCGCAAGAAGCTTTGATTACCACGATGCAAGACAACCAA AAATACTTCTGTTTGGTGAATAGTGATAACAAGCTACAGCCTTATTTC ATTACTGTTTCAAATATTGAGTCTAAAGATCCGATTCAAATTATTGAA GGCAATGAAAAAGTGGTTCGTCCACGTTTGTCGGATGCTGAATTCTTC TTCTTGCAAGATCAAAAGCAACCACTAGCTTCTCGTAAAGAAAAACT GGCTAACATGGTGTTCCAAGCACAATTGGGTACGCTGTGGGATAAGT CACAACGTATTGCAAAATTGGCTGTGGCTTTATCGAACATCACGGGTG CAACTGCGGCTGATGCTGAAAAAGCAGCATTGCTGGCAAAATGTGAC TTAACCTCTGAATTGGTGGGTGAATTCCCTGAACTTCAAGGCATTGCG GGAACCTATTACGCACGCATTGAAGGTGAAAACCATGAAGTGGCTGA AGCTTTAGGCGAACAGTATTTACCTAAATTTGCAGGCGATGTTTTACC GCAAACAAAAACAGGCACAACCATTGCCCTTGCCGACCGTTTAGACA CGCTCACGGGTATTTTTGGTATTGGTCAAGCACCTACAGGTTCTAAAG ATCCGTTTGCATTACGTCGTTCTGCAATCGGTATTTTACGTTTGGTGAC TGAAAACAATCTTGATGTGTCGATTGAAGATTTAATCCAGCTGGCATT AAACGCTTATGGCGATGTTGTAGCGGATCATGCGAAGACTTTAGCGG ATGCTGTTGCATTCCTTGAAGGTCGTTACCGTGCCAAGTATGAAGACC AAGGCGTTGCAGTTGATGTGATTCAAGCGGTTCAAGCATTATCACCA AAATCACCTTTAGATTTTGATAAGCGTGTGACTGCGGTAAATCATTTC CGTGCATTGCCTGAAGCTGCTGCACTGGCTGCTGCAAATAAGCGTGTT GCCAACATTCTTGCCAAAGAAGCAGAACTAACAGGCGCAGTGGTTGA AGCAAACTTGGTTGAAGAGGCTGAAAAAGCATTATTCGCTGTACTTG CTAAAATTACGCCTGAAGTTGAACCATTATTTGCTGCCAAAGATTACA CCACTGCATTGTCTAAGCTTGCTGCTTTACGTGCGCCTGTGGATGCAT TCTTTGAAGGCGTCATGGTCATGGCAGATGATGCAGAATTGAAAGCC AACCGTTTACGTTTATTGGCTCAATTACGTGGTTTGTTTACAAGTGTTG CGGATATTTCGGTGTTGCAGCACTAA |
| 124 | DP70 DNA gyrase subunit B | ATGAGTTCAGAAGATCAAGCTGCTTCTCAAACAGAACAAACCAATGA AAAGGCTTATGATTCCTCTAGTATCAAAGTATTACGTGGCCTAGATGC TGTTCGTAAGCGTCCGGGTATGTATATTGGTGATACGGACGATGGTTC AGGTTTACATCACATGGTGTTTGAGGTGGTCGATAATGCGATTGATGA AGCCTTAGCGGGTCACTGTGATGAAATCTTAGTCACCATCCATGAAG ATGAGTCTGTAAGTGTTGCAGATAACGGTCGTGGGATTCCAACGGAT ATTCACCCTGAAGAAGGGGTATCTGCCGCTGAAGTGATTTTAACCATT TTGCATGCTGGCGGTAAGTTTGATGATAATAGCTATAAAGTTTCCGGT GGTTTACACGGGGTAGGTGTTTCTGTTGTAAATGCCTTGTCGAGTAAA TTATTACTAAATATTCGTCGTGCAGGAAAAGTATATGAACAGGAATA TCACCATGGTGATCCTGTCTATCCATTACGCGCGATTGGTGATACTGA AGAAACCGGTACCACCGTTCGTTTCTATCCGAGTGAATTAACCTTCTC TCAAACGATTTTTAATGTTGATATTTTAGCGCGTCGTTTGCGCGAACT TTCATTCTTAAATGCAGGGGTTCGTATTGTATTACGTGATGAACGTAT CAATGCTGAACATGTATTTGATTATGAAGGTGGTTTGTCTGAATTTGT AAAATATATCAATCAAGGTAAAACCCACTTGAATGAGATTTTTCATTT TACCAGTGAAGTTGTGGAAACAGGAATTACTGTTGAAGTAGCATTAC AGTGGAATGATACTTATCAAGAAAATGTCCGTTGCTTTACCAATAACA TCCCACAAAAAGATGGTGGTACGCATTTAGCCGGTTTCCGTGCCGCGT TAACACGGGGTTTAAACCAGTATCTTGATAGTGAAAATATTCTTAAGA AAGAAAAAGTTGCTGTCACAGGTGATGATGCCCGTGAAGGTTTAACG GCGATTGTTTCAGTGAAAGTGCCTGATCCAAAATTCTCATCACAAACC AAAGAAAAATTGGTTTCCAGTGAAGTGAAAACTGCTGTAGAGCAGGC GATGAACAAGTCTTTTTCTGAATATCTTTTAGAAAATCCACAAGCGGC TAAATCGATTGCCGGCAAAATTATTGATGCTGCACGTGCACGTGATGC TGCGCGTAAAGCACGTGAAATGACACGTCGTAAGAGTGCATTAGATA TTGCTGGTCTGCCTGGTAAACTGGCGGATTGCCAAGAAAAAGATCCA GCATTGTCTGAACTTTACTTGGTCGAAGGTGACTCGGCGGGCGGTTCT GCAAAACAGGGTCGTAACCGTAAGATGCAAGCTATTCTGCCGCTTAA AGGTAAAATCTTAAACGTAGAACGTGCACGTTTTGACAAAATGATTT CATCGCAAGAAGTGGGCACGCTGATTACTGCACTGGGCTGTGGTATT GGTCGTGAGGAATACAATCCTGATAAATTGCGTTATCACAAAATCATT ATCATGACCGATGCCGACGTCGATGGTTCGCACATTCGTACGCTCCTG TTGACCTTCTTCTTCCGTCAAATGCCAGAACTTGTGGAACGTGGTTAT |

-continued

Sequence Listing

| Seq ID No. | Description | Sequence |
|---|---|---|
| | | ATTTATATTGCACAGCCACCGTTGTATAAGTTGAAAAAAGGTAAGCA |
| | | AGAGCAATATCTTAAAGATAATGATGCTTTAGAAACCTATCTTATTTC |
| | | GAATGCCATTGATGAGCTTGAACTGCATATTAGTGCTGAGGCACCTGC |
| | | GATTCGTGGTGAATCTTTGGCTAAAGTGATTGCTGATTATCAAACCTC |
| | | ACAAAAAAGTTTAAATCGTTTAACGCTACGTTATCCTGCAAGCTTGCT |
| | | GGATGGTTTACTTGGTTTGGATGCATTTAAACTTGATCAAAATCATGA |
| | | TGAAGATTATGTAAAACAATGGTCTGAACAATTGCGTGCAGCAATTG |
| | | AACAACACCAACCAAGTTTGCGTCCTGAAATCACCTTAGAAGCTTTTG |
| | | AAAAAGAGCATGCAGATGGTGAGAAAGTGACGCATTATTGGCCACGT |
| | | GTAACGGTCTATGTACATAACTTGCCGCATCATTATTTACTTGATTCT |
| | | GGATTATTGGCTTCAAGTGAATACAAGCGTTTACTGCAAAATTCGAA |
| | | GAGTTGGTTCACATTGCTTGAAGATGGCGCTTATTTGCAAAAAGGTGA |
| | | GCGTAAAATTCATGTCGCCACTTTCCATCAAGTTTGGCAACATATTTT |
| | | ATCCGACTCGCGTCGTGGCATGATGATCCAGCGCTATAAAGGTTTGG |
| | | GTGAGATGAACGCGGAACAGCTTTGGGAAACCACCATGGATCCTGAA |
| | | AACCGTAACATGTTGCAAGTCACCATTAATGATGCGATTGAAGCGGA |
| | | TCGTATGTTCTCTTGTTTGATGGGAGATGATGTGGAACCACGTCGTGC |
| | | CTTCATTGAAGAAAATGCTTTAAATGCGGATATTGACGCTTAA |
| 125 | DP70 Leucine--tRNA ligase | ATGACTACTTCTCACATTGACCCTGAATATCAAGCGAGCGCGATTGAA |
| | | TCCACTGTCCAACAAGACTGGGAAACTCGCAAAGCCTTTAAAGTTGC |
| | | CGACACTGTAGAAGGTAAACATCGTTATATCCTCTCGATGTTCCCTTA |
| | | TCCAAGTGGCAAGCTGCATATGGGTCATGTGCGTAACTACACCATTG |
| | | GCGACGTGATTAGCCGTTTCCACCGTCTCAAAGGTGAAACTGTCCTAC |
| | | AACCGATGGGTTGGGATGCTTTTGGTCTGCCTGCGGAAAATGCAGCG |
| | | ATTGCACACCAAGTTGCCCCTGCAAAATGGACCTTTGAAAACATCGC |
| | | GTACATGCGTGACCAGTTAAAAAAATTGGGTCTGTCAGTCGATTGGG |
| | | ATCGTGAATTTGCGACCTGTACGCCAGAGTATTATCACTGGGAACAAT |
| | | GGTTATTTGTACAGCTGTATAAAAAAGGGCTGATTTATCGCAAACTTT |
| | | CAACGGTAAACTGGGATCCTGTCGATCAGACTGTACTTGCTAATGAA |
| | | CAAGTTGAAAATGGTCGTGGTTGGCGTTCGGGTGCATTGGTTGAAAA |
| | | ACGTGATATTCCAATGTATTACTTCCGTATTACCGATTATGCACAAGA |
| | | ATTATTAGACGATTTAGATTCGCTTAAAGATGGTTGGCCGCAACAAGT |
| | | CTTGACCATGCAACGCAACTGGATTGGTCGTTCACAAGGCATGGAAA |
| | | TCACCTTTCCATCTGCGAACCCTGAAATCTATGCAGATGATTTAACGG |
| | | TTTATACCACACGTGGTGACACCTTGATGGGCGTGACGTATGTTGCGG |
| | | TTGCCGCTGAACATCCAATGGCGCTTAAAGCGGCTGAAACAAATCCC |
| | | GAATTGGCTGCATTTATTGAAGAATGCCGTATGGGTTCAGTGGCTGAA |
| | | GCAGATCTTGCCACTGCCGAGAAAAAAGGCATGGCCACTGGTTTGTC |
| | | TGTGAAGCATCCTGTAACGGGTGAAGTGGTTCCAGTGTGGATTGCGA |
| | | ACTATGTATTGATGTCATACGGTTCAGGTGCGGTGATGGCAGTTCCAG |
| | | CACACGACGAACGTGATTTCGAATTTGCCAACAAATATGGTTTAACCC |
| | | TCCAGCAAGTGATTGATGCCAAAGGTGCAGACGATGCTGAATTTTCT |
| | | GCAACTGAATGGCAGGAATGGTATGGCTCGAAAGAAGGCAAACTGGT |
| | | TAATTCTGGCGAATTTGACGGTTTAGACTTCCAAGCTGCATTTGATGC |
| | | ATTCATTGCAAAATTAGAACCACAAAAACTGGCAAATACGAAAGTTC |
| | | AGTTCCGTCTACGTGACTGGGGTGTTTCGCGTCAGCGTTATTGGGGTT |
| | | GTCCAATTCCAATGATCAACTGTGAAACTTGTGGTCAAGTACCTGTAC |
| | | CTGAAGAACAACTTCCAGTAATTTTACCAACTGACGTGGTGCCAGAT |
| | | GGTTCAGGCAATCCGTTAAATAAAATGCCTGAATTTTATGAAACCCA |
| | | ATGTCCATGTTGTGGTGCAGGTGCACGCCGTGAAACCGATACTTTGGA |
| | | TACGTTCGTAGAGTCATCTTGGTACTATGCACGTTATGCATCTCCAGA |
| | | TTTCACTGGCGGTTTAGTTAAACCTGAAGCTGCAAAATCATGGCTACC |
| | | AGTCAACCAATATATTGGCGGTGTGGAACATGCAATTTTGCATTTATT |
| | | GTATGCCCGTTTCTTCCATAAATTGATGCGTGATGAAGGCGTCGTTGA |
| | | AGGCAATGAACCTTTCGCTAACTTACTGACTCAAGGTATGGTTTTAGC |
| | | TGATACCTTCTACCGTGAAGCCGAATCAGGTAAGAAAACATGGTTTA |
| | | ATCCTGCGGATATTGAATTAGAAAAAGACGAAAAAGGTCGTGTTCTT |
| | | TCTGCTAAATACACAGGTGATGGCCAAGAAGTTGTGGTTGGCGGTCA |
| | | AGAAAAAATGTCGAAATCGAAAAATAATGGCATCGACCCGCAATCGA |
| | | TTATTGATCAATACGGCGCAGATACTGCACGTGTATTTATGATGTTTG |
| | | CGGCCCCACCCGATCAATCGCTTGAATGGTCTGATGCCGGTGTGGAA |
| | | GGTGCAAACCGTTTCTTGAAACGTGTATGGCGTTTAACCACAGGTTTC |
| | | TTAGAAAAAGGCAACCATGCTGCTGTAATTGATGTTGCGAATTTGTCA |
| | | TCAGCGGCACAAGACTTACGTCGTAAAACCCACGAAACCATTCAAAA |
| | | AGTCGGTGATGACATTGAACGTCGTCATGCCTTCAATACTGCCATTGC |
| | | AGCGCAAATGGAATTATTGAATGCTTGCAATAAATTTGAAGCCAAAG |
| | | ATGATAATGACGTTGCGGTTGAACGCGATGCTATTGTTAGCTTACTCA |
| | | CTTTACTTGCACCATTTGCACCACATTTAAGTCAGACCCTATTGGCTC |
| | | AATTCGGTATTGAGTTAACTGAAACCTTGTTCCCTACTGTGGATGAGT |
| | | CTGCGCTAACCCGCAACACACAAACTATTGTGGTACAGGTCAATGGT |
| | | AAACTTCGTGGCAAGTTGGAAGTGTCTGTTGATCTCTCTAAAGAAGAT |

-continued

Sequence Listing

| Seq ID No. | Description | Sequence |
|---|---|---|
| | | ATTTTGGATCAAGCCAAAGCATTGCCTGAAGTACAACAATTCTTAACC<br>GGTCCAACCAAGAAAGAAATTGTGGTGCCGAATAAATTGGTCAATTT<br>GGTGGTTTAA |
| 126 | DP70 Glucose-6-phosphate isomerase | ATGAATAGTATTGAAAAATTTCCCTTGCATGATACGGATCTGATTCAG<br>GAAAAACTAAAAAGTTTTGCCCAACAAGAGCAAGAGATTAATTTAAA<br>TTATTTATTTAAAAAAAATAAAAAACGTTTTGATGAATATTCCGTTCA<br>TGCGGGTCAGTTATGTTTTGATTATAGTAAGCACCGTGTTGATGAGCG<br>TATTATTAACGAGCTTATTTGTTATGCGGAATCACAACATTTGGGTAA<br>CTGGATTCAGCGCTTATTTTCTTTAGAAAAAATTAATTACACTGAAAA<br>TCGCGCAGCGATGCATTGGGCTTTGCGTTTGCCGAAGCAAGATAGTA<br>CACATGCAGATTTGGCAGCGCAGGTACATAGTCAGCTTGATCGTATGT<br>ATCAATTGGTCGAGAAAATTCATCAGGGGCAGTATCGAGGAGCTACA<br>GGTGAGGTCATCCATGATGTGGTCAATATTGGTGTCGGTGGATCAGAT<br>CTTGGTCCTTTAATGGTGTCTCAAGCGCTGACTGATTTTAAAGTTCAA<br>ACGGCTCAAAAATTAAAAGTCCATTTTGTTTCGACGATGGATGGCAG<br>CCAACTTTCAGATCTTTTACATCAGTTTCGCCCAGAAACCACCTTGTTT<br>ATTATTTCATCCAAGTCTTTTGGCACCATTGATACGCTTTCCAATGCAC<br>AAACGGCAAAATGCTGGCTTGAGCAATCTTTAGGAACGTCGAAATCA<br>GTTCTAAGATGTCACTTTGTTGGTGTTTCAACCAAGCCCGATAAGATG<br>ACCGAGTGGGGAATCAGCACTGAAAATCAATTCTTATTGTGGGATTG<br>GGTCGGTGGGCGCTATTCACTATGGTCGTGTATTGGTTTGCCTATTGC<br>ATTAAGTATTGGGGTCGAGGGCTTTAAACAGTTGCTTGCTGGTGCTTA<br>TGAAATGGATCAGCATTTTCAGAACACACCACTTGAACAAAATATTC<br>CTGTGTTGATGGGTTTACTGGGAATATGGAATAACAACTTCCTGAATA<br>TTCAAACTCATGCGGTACTTCCTTATGATGGTCGGCTGAAATATTTTG<br>CGGCTTATTTACAGCAATTGGAAATGGAGTCGAATGGTAAGTCGATT<br>CAGCGTTCTGGTGAAAAAGTCGTATTAGATACCTGCCCAATTTTATGG<br>GGTGAAGTTGGACCAAATGCACAACATGCTTTTTATCAGCTGCTGCAT<br>CAAGGTACACATGCTGTGAGTTGTGACTTTATTGCACCTGTGAAACGC<br>TATAATGCCAATCAATTTACCTATGTTGAAAATGCAGAGGCTTTAGTT<br>GAACAACACCATTTAGCCTTATCGAATTGTTTGGCACAATCACGTCTA<br>TTGGCCTTTGGTAATCATGTTCTAGATCCGAAAGAAGTAGAAAGTTCA<br>CCGAAATATAAACAATATGCAGGCAACCAACCGACCACAACAATTTT<br>GTTAAAAGAGTTGAATCCGCGCAGTTTAGGTATGCTCATTGCGATGTA<br>TGAGCACAAGGTATTTGTGCAATCCGTGATGTGGAATATTAATCCATT<br>TGACCAATGGGGCGTAGAAAAAGGTAAAGAAATTGCCAATCAACTGT<br>TACCGATTCTCAATCAAGAGCAAGCTGATGTTTCTGATCTTGATTCTT<br>CAACGCAAGGTCTATTAAGAATTTTACTGGGAAAAGCTGATGGCTAA |
| 127 | DP70 NADH-quinone oxidoreductase subunit C/D | ATGGCTGAAACTGACATTGCTATGCCAGAATCAACGCCTGTTGATTCA<br>CGCCCAGCATTTGCAATTGTAGAAGAGCTCAAAGCCAAATTTGGTGA<br>GAACTTCTATGTGCAAGCGACTTTTGAAGATTTTCCAACGGTCTGGGT<br>TGAGCGCGCGCGCGTACAAGATGTTTTAATGTTCTTGCGTAAAGTATC<br>ACGTCCATACGTGATGCTGTTCGACTTGTCTGCGGTAGATGAGCGTTT<br>ACGTACCCACCGTGACGGTTTACCTGCATCAGACTTCACTGTGTTTTA<br>TCATTTGTTGTCGCTAGAGCGCAACAGTGATATTCGTATTAAAGTTGC<br>GTTGAGTGAGAGTGATCTCAATCTTCCAACCGCAACCAACATTTGGCC<br>AAATGCCAACTGGTACGAACGTGAAGCTTACGATATGTTCGGGATCA<br>ATTTCGAAGGGCATCCAATGCTCCGTCGTATTTTGTTGCCAACCTATT<br>GGGAAGGTCACCCACTGCGTAAAGAATATTCTGCACGTGCGACTGAA<br>TATACACCGTATATGCAGAACCAAGCGAAGCAGGATTTCGAGCAAGA<br>ACATTTACGTTTTGTTCCTGAAGATTGGGGTCTATCACGCGGTAATGC<br>CGATGAAGATTTCATGTTCTTGAACTTAGGTCCAAACCATCCATCTGC<br>GCACGGTGCATTCCGTATCATTTTGCAGTTGGACGGTGAAGAAGTGA<br>AAGACTGTGTGCCTGATATTGGCTATCACCACCGTGGTGTGGAAAAG<br>ATGGCTGAACGTCAAACTTGGCATTCATTCATTCCATATACCGACCGT<br>GTTGACTACTTGGGTGGTTGTGCGCAAAACATGCCTTATGTGATGGGT<br>GTGGAGCAAATGGCAGGAATTACTGTTCCTGACCGTGCACAATGTAT<br>CCGTGTCATGATGTCTGAATTATTCCGTATCAATAACCATTTATTGTTT<br>ATTGGTACTGCAATTCAAGATGCCGGCGGTATGACGCCAGTCTTCTAT<br>ATGTTTGCCGATCGTCAAAAGATCTATGATGCGATTGAAGCGATTACA<br>GGCTACCGTATGCATCCAGCATGGTTCCGTATTGGCGGGACTGCGCAC<br>GACCTTCCAAACAATTGGCAACATCTGATTCGTGAAATTCTCGAATGG<br>ATGCCGAAGCGTATGAATGAATACTATACAGCTGCACTACGCAACTC<br>AGTATTTATTGGTCGTACCCGTAATGTTGCACAATACGATGCAAAATC<br>TGCATTGGCTTGGGGTGTAACAGGTACAGGTCTACGCGCGACAGGGA<br>TTGATTTCGACGTGCGTAAATACCGTCCGTATAGCGGTTATGAAAACT<br>ACGACTTCGACGTGCCTTTAGAATACGAAGGCGATGCTTACGCTCGTG<br>TGATGGTTCACTTCCGTGAAATTGAAGAATCACTGAAAATTGTGAAG<br>CAGTGCTTGGATAACATGCCATCTGGTCCATATAAAGCGGATCATCCT<br>TTGGCTGTTCCACCACCAAAAGACAAGACATTACAAGATATTGAAAC<br>TTTGATTACGCACTTCTTGAGCGTGTCATGGGGTCCTGTGATGCCTGC |

-continued

| Sequence Listing | | |
|---|---|---|
| Seq ID No. | Description | Sequence |
| | | GGGTGAAGCGTCTGTAATGGCTGAAGTGGTAAAAGGTGCATCGAACT ACTACTTGACTTCAGACAAGTCAACCATGAGTTATCGTACCCGTATTC GTACACCAACTTTCACGCACTTACAGCAAATGCCTTCTGTGATTAATG GCAGTCTTGTATCTGACTTGATCATTTATTTAGCGACCATTGACGTCG TAATGGCTGACGTGGATCGCTAG |
| 128 | DP70 Protein RecA | ATGGATGATAATAAAAGTAAGGCGCTTAATGCTGCCCTAAGCCAGAT TGAAAAACAATTTGGTAAAAATACCGTAATGCGTCTTGGTGATAATA CCGTATTGGCCGTTGAAGCGGTCTCTACAGGTTCTTTAACACTAGACA TTGCACTTGGTATTGGTGGCTTACCAAAAGGTCGTATCGTTGAAATTT ACGGTCCTGAATCTTCTGGTAAAACCACAATGACATTGCAAGCGATT GCACAATGTCAAAAAGCCGGTGGTACTTGTGCTTTTATCGATGCAGA ACATGCACTCGATCCTCAGTATGCACGTAAGCTTGGTGTCGACCTTGA CAACCTGTTGGTTTCTCAACCAGACCACGGTGAACAAGCCCTTGAAAT TGCAGACATGTTAGTCCGCTCTGGTGCTATTGACATGATCGTTGTCGA TTCCGTGGCTGCACTGACACCTCGCGCTGAAATTGAAGGTGAAATGG GCGACTCACATATGGGCTTACAAGCACGTTTGATGAGTCAGGCATTA CGTAAAATTACTGGTAATGCAAAACGCTCAAACTGTATGGTGATCTTC ATTAACCAAATCCGTATGAAGATTGGTGTAATGTTTGGTAGCCCTGAA ACCACAACAGGTGGTAATGCACTCAAATTCTACGCTTCTGTACGTTTG GATATCCGTCGTATTGGTCAAGTGAAAGAAGGCGATGAAATTGTCGG TTCAGAAACCCGCGTTAAAGTCGTAAAAAATAAAATGGCACCTCCTT TTAAGGAAGCGTTATTCCAAATTTTATATGGCAAAGGTGTCAATCAAC TGGGTGAACTGGTTGATCTTGCTGTTGCGCAAGAACTGGTACAAAAA GCAGGTGCTTGGTATTCATATCAAGGCAATAAAATTGGTCAAGGTAA AAACAACGTGATCCGCCATTTAGAGGAAAATCCTCAAATTGCACAAG AACTTGATCGCCTGATTCGTGAAAAATTGTTGACACCAACGACCACG CCTATTGAAGAAAAAGATGAAGTAGAACCAGACTTTCTAGATGCTTA A |
| 129 | DP70 RNA polymerase sigma factor RpoD | ATGAGCGATATGACTTCCCCTACTTCGCAAGTAGCGGCTCTGATTAGC CGAGGCAAAGAGCAAGGTTACTTAACTTACGCTGAGGTTAACGATCA TCTCCCAGACTCGATCACGGAAAGCGAACAGATTGAAGACATTATTC AAATGCTTCAAGATGTCGGCATTCCAGTGCATGAACGTGCGCCTGAA TCTGATGACACCATGTTCGACGGTAACAATGCAGAAGCAACCGATGA AGTCGCTGAAGAAGAAGCGGCAGCTGTTCTTGCTTCAGTTGAAAGCG AACCTGGTCGTACCACCGATCCAGTACGTATGTACATGCGTGAAATG GGAACGGTTGAACTATTAACGCGTGAAGGCGAAATTAGCATTGCAAA ACGCATTGAAGAAGGTATTCGTGACGTTCTTCATTCGATTGCGTACTG GCCAAATGCAGTTGAAGTTGTATTAAAAGAATATAGCGATGTTGCTG AAGGCGAACGTCGTCTTGCTGATATTTTATCTGGTTATTTAGACCCAG AATCTGACGAAGAAATTCCAGAAGTTTTAGAAGAAGAAGCTGAAATT GTTGAAGATGATGAAGCGACGACTAAAACCACTAAAGATGTAAAATT GGACGATGACGAAGAAGAAGAATCTGAAAGTGATGATGATTCTGAA GGTGAGTCTGGTCCAGATCCAGAAATTGCACGTGTTCGTTTCACTGAA TTAGAAGATGCGTGGAAAGTAACCAAAGCCACCATTGAAAAGCATGG CCGTAACAGCAAACAAGCAGATGAAGCGCTTGAAGCTCTTGCAACTG TGTTTATGATGTTCAAATTTACACCACGTTTATTTGAAATCATTTCAGA AATGATTCGTGGCACGCATGAACAAATTCGTACAGCAGAACGTGAAG TGATGCGTTACGCAGTTCGTCGTGGTCGTATGGACCGTACCCAATTCC GTACATCGTTCCCAGGCCAAGAGTCAAATCCAGCTTGGTTAGATGAA CAAATTGCTAAAGCACCTGCGGATCAAAAAGGTTATTTAGAAAAAGT ACGTCCAGATGTTGTTGCATTCCAGCAAAAGATTGCCGATATCGAAA AAGAATTGGGCTTAGATGTTAAAGACATCAAAGACATTTCTAAACGT ATGGCTGTGGGTGAAGCGAAAGCACGTCGCGCGAAAAAAGAAATGG TTGAAGCAAACTTACGTTTGGTGATTTCGATTGCGAAAAAATATACCA ACCGTGGTTTACAATTCCTTGACTTGATTCAAGAAGGTAACATCGGTT TGATGAAAGCCGTAGACAAGTTTGAATACCGTCGTGGTTATAAATTCT CGACTTATGCAACTTGGTGGATTCGTCAGGCGATTACCCGTTCGATTG CCGATCAAGCACGTACCATCCGTATTCCAGTACACATGATCGAAACC ATTAACAAGATCAACCGTGTATCTCGTCAACTTCTTCAAGAAATGGGC CGTGAGCCTACCCCTGAAGAATTAGGCGAACGTCTGGAAATGGACGA AGTTAAAGTACGTAAAGTGCTGAAAATTGCCAAAGAACCGATTTCGA TGGAAACACCGATTGGTGATGACGAAGATTCGCATCTTGGTGACTTC ATTGAAGATGGTAACATTACCTCTCCAATTGATGCCGCGACTTCTGAA GGCTTAAAAGAAGCAACACGTGAAGTGCTGGAAAACTTGACCGAACG TGAAGCGAAAGTCTTAAAAATGCGTTTTGGTATTGATATGCCAACCG ACCATACTTTAGAAGAAGTGGGTAAACAATTTGATGTAACACGTGAA CGTATTCGTCAGATTGAAGCCAAAGCTTTACGTAAATTACGTCACCCT TCTCGTTCTGAACACTTACGTTCATTCCTAGAAAATGACTAA |

-continued

Sequence Listing

| Seq ID No. | Description | Sequence |
|---|---|---|
| 130 | DP71 Glutamine--tRNA ligase | ATGAGTGAGGCTGAAGCCCGCCCAACAAATTTTATCCGTCAGATTATT GATGAAGATCTGGCGACCGGGAAACACAATACCGTTCACACCCGTTT CCCGCCTGAGCCTAATGGCTATTTGCATATCGGCCATGCGAAGTCTAT CTGCCTGAATTTCGGCATTGCGCAAGACTACCAGGGTCAGTGCAATCT GCGTTTTGACGATACTAACCCGGCAAAAGAAGACATCGAATTCGTTG AGTCGATCAAATACGACGTCCAGTGGCTGGGCTTCGACTGGAGCGGT GATATTCACTACTCCTCAGACTATTTCGATCAACTGCACGCATACGCG CTGGAGCTAATCAACAAAGGTCTGGCGTACGTTGACGAACTGTCTCC CGATCAAATTCGCGAATACCGTGGTTCGCTGACCGCACCGGGCAAAA ACAGCCCGTATCGCGATCGCAGCGTGGAAGAAAATATCGCGCTGTTT GAAAAAATGCGTAACGGTGAATTCGCCGAAGGTGCCGCTTGCCTGCG TGCCAAAATCGATATGGCGTCGCCATTCTTCGTGATGCGCGATCCGGT CATCTACCGTATTAAGTTTGCCGAACATCATCAGACTGGCACAAAATG GTGCATCTACCCGATGTACGATTTCACTCACTGCATTTCCGATGCGCT GGAAGGGATCACCCATTCACTGTGTACGCTGGAATTCCAGGACAACC GCCGTCTGTACGACTGGGTACTGGATAACATCACTATTCCATGCCATC CGCGTCAGTATGAGTTCTCCCGTCTGAATCTTGAATACTCCATCATGT CCAAGCGTAAGCTGAACCTGCTGGTGACGGATAAGATTGTAGAAGGT TGGGACGATCCGCGTATGCCGACGGTTTCCGGTCTGCGTCGCCGTGGT TATACCGCCGCGTCTATCCGCGAATTCTGCCGTCGTATCGGCGTGACC AAGCAGGACAACAACGTTGAAATGATGGCGCTGGAATCCTGTATTCG TGACGATCTGAACGAAAACGCACCGCGCGCCATGGCCGTTATTAACC CGGTTAAAGTTGTCATTGAGAACTTCACCGGTGATGACGTGCAAATG GTGAAAATGCCGAATCATCCGAGCAAACCGGAAATGGGCACCCGCGA AGTGCCGTTCACCCGTGAGATTTACATCGATCAGGCTGATTTCCGCGA AGAAGCGAACAAACAGTACAAACGTCTGGTGCTGGGCAAAGAAGTTC GCCTGCGCAATGCGTATGTGATCAAAGCGGAACACATCGAGAAAGAC GCGGAAGGGAATATCACCACCATCTTCTGTTCTTACGATATCGATACG CTGAGCAAAGATCCCGCTGATGGCCGTAAGGTGAAAGGCGTGATTCA CTGGGTTTCTGCTTCTGAAGGTAAACCGGCAGAATTTCGCCTGTATGA CCGTCTGTTCAGTGTTGCGAACCCTGGCCAGGCTGAAGATTTCCTGAC CACCATCAACCCGGAATCTCTGGTGATTGCTCAGGGCTTCGTTGAGCC GTCTCTGGTCGCTGCTCAGGCAGAAGTCAGTGTGCAGTTCGAACGTG AAGGTTACTTCTGTGCCGACAGCCGCTATTCAAGTGCTGAGCATCTGG TGTTCAACCGCACCGTCGGCCTTCGCGACACCTGGGAAAGCAAACCC GTCGCCTGA |
| 131 | DP71 DNA gyrase subunit B | ATGTCGAATTCTTATGACTCCTCAAGTATCAAGGTATTAAAAGGGCTG GACGCGGTGCGTAAGCGCCCCGGCATGTATATCGGCGATACCGATGA CGGCACTGGTCTGCACCACATGGTATTCGAGGTTGTGGACAACGCTAT CGACGAAGCCCTCGCGGGCCACTGTAAAGAGATTCAGGTCACGATCC ATGCGGATAACTCTGTTTCCGTACAGGATGATGGTCGTGGTATTCCTA CCGGCATTCACGAAGAAGAGGGCGTTTCTGCTGCTCAGGTCATCATG ACCGTACTTCATGCCGGCGGTAAATTTGACGATAACTCGTACAAAGTC TCCGGCGGTCTGCATGGCGTGGGTGTTTCCGTCGTTAACGCCCTGTCG GAAAAACTGGAGCTGGTTATCCGCCGTGAAGGCAAAGTGCACACCCA GACTTACGTCCACGGTGAGCCGCAGGATCCGCTGAAAGTGGTTGGCG ATACCGAGGCGACCGGTACGACCGTGCGCTTCTGGCCAAGCTACGCC ACCTTCACCAATCAAACAGAATTCGAGTATGACATTCTGGCGAAACG CCTCCGTGAGCTGTCATTCCTGAACTCTGGTGTGGCGATCCGCCTGCT CGACAAACGCGATGGCAAGAACGATCACTTCCATTATGAAGGCGGTA TCAAAGCTTTCGTGGAATACCTGAACAAAAACAAAACCCCAATCCAC CCAACCGTGTTCTATTTCTCCACCGTGAAAGACGATATCGGTGTGGAA GTGGCGTTGCAGTGGAATGATGGTTTCCAGGAAAATATTTACTGCTTT ACCAACAATATCCCTCAGCGCGACGGCGGCACCCATCTGGTAGGCTT CCGTTCTGCGATGACCCGTACGCTTAACGCGTATATGGATAAAGAAG GCTACAGCAAGAAATCCAAAATCAGCGCCACCGGTGATGATGCCCGT GAAGGCCTGATCGCCGTGGTTTCGGTAAAAGTGCCGGATCCTAAGTT CTCCTCTCAGACCAAAGACAAACTGGTTTCTTCCGAAGTGAAGACCG CCGTTGAGTCTCTGATGAACGAGAAGCTGGTTGATTATCTGATGGAA AACCCGGCCGACGCGAAAATCGTTGTCGGTAAAATCATCGATGCAGC CCGTGCGCGTGAAGCCGCGCGTAAAGCACGTGAAATGACCCGTCGTA AAGGCGCGCTCGATCTGGCCGGTCTGCCAGGCAAACTGGCTGACTGT CAGGAACGCGACCCGGCACATTCCGAACTGTACTTAGTGGAAGGGGA CTCAGCGGGCGGCTCTGCAAAACAAGGCCGTAACCGTAAGAACCAGG CGATTCTGCCGTTGAAAGGGAAAATCCTCAACGTTGAGAAAGCGCGC TTCGACAAAATGCTCTCTTCTCAGGAAGTGGCGACGCTGATTACCGCG CTCGGTTGCGGTATCGGCCGTGACGAATACAACCCGGATAAACTGCG TTATCACAGCATCATCATCATGACCGATGCCGACGTCGATGGTTCGCA CATCCGTACCCTGTTACTGACATTCTTCTACCGTCAGATGCCTGAAAT TGTAGAGCGTGGCCACGTGTTTATCGCGCAGCCTCCGCTGTACAAAGT GAAAAAAGGCAAACAGGAACAGTACATTAAAGATGATGAAGCGATG |

-continued

Sequence Listing

| Seq ID No. | Description | Sequence |
|---|---|---|
| | | GATCAGTATCAAATCTCTATCGCGATGGACGGGGCAACGTTACACGC CAACGCCCATGCACCAGCACTGGCGGGCGAACCGCTGGAGAAACTGG TGGCTGAACATCACAGCGTGCAGAAAATGATTGGCCGTATGGAACGT CGTTATCCGCGTGCGCTGCTGAATAATCTGGTCTATCAGCCAACGCTG GCGGGTGCTGAACTTGCCGACGAAGCGAAAGTGAAGGAATGGATTGA AACGCTGGTGTCTCGTCTGAACGAGAAAGAGCAGCACGGCAGCAGCT ACAGTGCGATCGTGCGCGAAAATCTTGAACACCAGCTGTTCGAGCCA ATCCTGCGCATTCGTACTCACGGTGTGGATACCGACTACGATCTCGAT GCAGACTTCATTCAGGGCGGCGAATACCGCAAAATCTGTACCCTGGG TGAAAAACTGCGCGGCCTGATCGAAGAAGATGCTTACATCGAACGTG GCGAACGCCGTCAGCCAGTGACCAGCTTCGAGCAGGCGCTGGAATGG CTGGTGAAAGAGTCGCGTCGCGGTCTGTCGATTCAGCGTTATAAAGG TCTGGGTGAAATGAACCCTGAGCAATTGTGGGAAACCACGATGGATC CGACACAACGCCGCATGCTGCGCGTGACGGTGAAAGATGCTATCGCG GCGGACCAGCTGTTCACCACGCTGATGGGCGATGCGGTTGAACCGCG CCGCGCCTTCATCGAAGAGAACGCCCTTAAAGCTGCCAATATCGATA TCTGA |
| 132 | DP71 Isoleucine--tRNA ligase | ATGAGTGACTACAAGAACACCCTGAATTTGCCGGAAACAGGGTTCCC GATGCGTGGCGATCTGGCCAAGCGTGAACCTGACATGCTGAAGAATT GGTATGACCAGGATCTGTACGGGATTATTCGTGCTGCCAAGAAAGGC AAGAAAACCTTTATCTTGCATGACGGCCCTCCGTATGCGAACGGCAG CATTCATATTGGTCACTCAGTAAACAAAATTCTTAAAGACATGATCGT TAAGTCCAAAGGACTGGCGGGCTTTGATGCGCCGTATGTTCCGGGCT GGGATTGTCATGGTCTGCCGATTGAACTGAAAGTTGAACAGCTGATC GGTAAGCCGGGCGAAAAAGTCACGGCGGCGGAATTCCGTGAAGCCTG CCGCAAGTACGCTGCTGAACAGGTTGAAGGTCAGAAGAAAGACTTCA TCCGTCTGGGCGTGCTCGGTGACTGGGATCATCCGTACCTGACCATGG ACTTCAAAACAGAAGCCAACATCATTCGTGCCCTGGGTAAAATCATC GGCAACGGTCACCTGCATAAAGGTGCGAAACCTGTTCACTGGTGTAC CGATTGCGGATCTTCACTGGCTGAAGCCGAAGTCGAATATTACGACA AAGTGTCTCCGTCTATCGACGTGACGTTTAATGCGACGGATGCCGCCG CTGTTGCTGCGAAATTCGGTGCCACTGCTTTCAATGGCCCGGTTTCTC TGGTCATCTGGACCACCACCCCGTGGACCATGCCAGCTAACCGCGCG ATTTCACTCAACGCTGAGTTCTCTTATCAGCTGGTGCAGATTGAAGGT CAGTGCCTGATCCTGGCTACCGATCTGGTAGAAAGCGTGATGAATCG CGCCGGTATCGCTGAGTGGACTGTGCTGGGCGAATGTAAAGGTGCGG ATCTTGAATTGCTTCGATTCCAGCATCCGTTCCTCGGTTTCGATGTTCC GGCGATCCTCGGCGATCACGTTACTCTCGATGCCGGTACCGGTGCTGT ACATACCGCACCTGGCCACGGTCCTGATGACTTTGTCATTGGCCAGAA ATACGGTCTGGAAGTCGCAAACCCGGTTGGACCGAACGGCTGCTACC TGCCGGGCACTTATCCGACGCTGGATGGCAAATTCGTCTTTAAAGCGA ATGATCTGATCGTTGAATTGCTGCGTGAGAAGGGCGCACTGCTGCAC GTTGAGAAAATGAACCACAGCTATCCGTGCTGCTGGCGTCACAAAAC GCCGATCATCTTCCGCGCTACGCCACAATGGTTCATCAGCATGGATCA GAAAGGTTTGCGTCAGAAGTCTCTGGAAGAGATCAAAGGCGTGCAGT GGATCCCTGACTGGGGTCAGGCGCGTATCGAAAACATGGTCGCTAAC CGTCCTGACTGGTGTATCTCCCGCCAGCGTACGTGGGGCGTACCGATG TCTCTGTTCGTGCATAAAGATACCGAACAGCTTCATCCGCGCAGCCTT GAGCTGATGGAAGAAGTGGCAAAACGCGTGGAAGCCGATGGCATTC AGGCATGGTGGGATCTGAACCCTGAAGAGATTTTGGGTGCAGACGCT GCCGATTACGTCAAAGTGCCGGATACGCTGGACGTCTGGTTTGACTCC GGTTCCACGCACTCCTCCGTTGTGGATGTGCGCCCTGAGTTCAACGGT CATTCACCGGATCTGTATCTGGAAGGTTCTGACCAGCATCGCGGCTGG TTCATGTCTTCTCTGATGATTTCTACGGCGATGAAAGGCAAAGCGCCT TACAAACAAGTACTGACTCACGGTTTCACCGTCGATGGTCAGGGCCG TAAAATGTCTAAATCCATCGGTAACACCATCGCGCCTCAGGATGTGAT GAATAAGCTGGGTGGCGACATCCTGCGTTTGTGGGTGGCATCTACGG ATTACACCGGCGAAATCGCCGTGTCCGACGAAATCCTCAAACGTGCT GCCGATTCTTATCGCCGTATCCGTAACACCGCGCGCTTCCTGCTGGCG AACCTTAACGGTTTCGATCCGGCGCTGCACAGCGTGGCACCGGAAGA GATGGTTGTGCTGGATCGCTGGGCGGTTGGCCGCGCGAAAGCTGCAC AAGACGAGATCATTGCTGCGTACGAAGCCTATGATTTCCACGGCGTT GTTCAGCGTCTGATGCAGTTCTGCTCGATCGAAATGGGTTCGTTCTAT CTGGATATCATTAAAGATCGCCAGTACACCGCGAAGAGCGACAGCGT TGCGCGCCGCAGCTGCCAGACCGCGCTGTATCACATCTGCGAAGCAC TGGTTCGCTGGATGGCGCCAATCATGTCCTTCACTGCCGATGAAATCT GGGCTGAACTGCCAGGTCATCGCGAGAAGTTCGTCTTTACTGAAGAA TGGTACGACGGTCTGTTTGGCCTGATCGGTAACGAATCCATGAACGAT GCGTTCTGGGATGAGCTGCTGAAAGTGCGTGGTGAAGTGAACAAAGT GATCGAACAGGCGCGTGCTGATAAACGTCTGGGCGGTTCTCTGGAAG CAGCCGTGACCTTATATGCAGACGACGCGCTGGCAACAGACCTGCGT TCTCTGGGTAACGAACTGCGCTTTGTGCTCCTGACTTCCGGTGCGAAA |

-continued

Sequence Listing

| Seq ID No. | Description | Sequence |
|---|---|---|
| | | GTCGCCGCGCTGTCTGAAGCTGATGACTCAGCGCAGGCCAGCGAATT<br>GTTGAAAGGACTGAAAATTGGTCTGGCGAAAGCAGAAGGCGAGAAG<br>TGCCCGCGCTGCTGGCATTTCACCACTGATATCGGCCAGAATGCGGA<br>ACACAGTGACATCTGTGGCCGTTGTGTGACTAACATTGCCGGTGACG<br>GCGAAGAGCGTAAGTTTGCATAA |
| 133 | DP71 NADH-quinone oxidoreductase subunit C/D | ATGTCAGAACTTACTCATATTAATGCTTCCGGCGACGCCCACATGGTG<br>GATGTCTCCGGTAAAGACGACACCGTTCGTGAAGCCCGTGCCGAAGC<br>CTTTGTTGAAATGGCCGAAAGCACGCTGGCGATGATCATCGGCGGTA<br>ATCACCATAAGGGTGACGTGTTCGCGACCGCGCGGATTGCCGGTATT<br>CAGGCAGCGAAGAAAACCTGGGATCTGATCCCGCTGTGTCATCCGCT<br>GTTGCTGACCAAGGTGGAAGTGAATCTTGAAGCGCAGCCAGAATTTA<br>ATCGTGTACGTATTGAATCCCGCTGCCGCCTGAGCGGTAAAACCGGC<br>GTCGAGATGGAAGCGCTGACCTTCAAGCCTGAAGACTGGGGAATGAA<br>GCGCGGCACCGAAAACGAGGACTTCATGTTCCTCAACCTCGGACCTA<br>ACCATCCGTCTGCGCACGGTGCGTTCCGCATCATCCTGCAGCTTGATG<br>GCGAAGAAATTGTCGACTGTGTACCGGACGTCGGTTACCACCACCGT<br>GGTGCTGAGAAGATGGGCGAGCGCCAGTCATGGCACAGCTACATTCC<br>ATACACGGACCGTATCGAATACCTCGGCGGTTGCGTTAACGAGATGC<br>CATACGTACTGGCTGTTGAAAAACTGGCGGGTATCGTCGTGCCGGAT<br>CGCGTTAACACCATCCGCGTGATGCTGTCTGAACTGTTCCGTATCAAC<br>AGCCACCTGCTGTACATCTCTACGTTTATTCAGGACGTGGGCGCGATG<br>ACGCCAGTGTTCTTCGCCTTTACCGATCGTCAGAAAATTTACGATCTG<br>GTGGAAGCGATCACCGGTTTCCGTATGCACCCGGCCTGGTTCCGTATT<br>GGTGGCGTTGCACACGACCTGCCGAAAGGCTGGGAGCGTCTGCTGCG<br>TGAATTCCTTGACTGGATGCCAGCCCGTCTGGATTCCTACGTCAAGGC<br>AGCGCTGAAAAACACCATTCTGATTGGACGTTCCAAAGGCGTAGCAG<br>CATACAACGCCGATGATGCGCTGGCGTGGGGCACCACCGGTGCTGGC<br>CTGCGTGCGACCGGGATCGACTTCGATGTCCGCAAATGGCGTCCATAT<br>TCAGGTTACGAAAACTTCGATTTTGAAGTGCCGGTCGGCGATGGCGTC<br>AGTGATTGCTATTCCCGCGTGATGCTAAAAGTGGAAGAGCTTCGTCA<br>GAGCCTGCGCATTCTGGAACAGTGCTACAAAAACATGCCGGAAGGCC<br>CGTTCAAGGCGGATCACCCGCTGACCACGCCGCCACCGAAAGAGCGT<br>ACGCTGCAACACATCGAAACCCTGATCACTCACTTCCTGCAAGTGTCG<br>TGGGGTCCGATCATGCCTGCGCAAGAATCTTTCCAGATGGTTGAAGCC<br>ACCAAAGGGATCAACAGCTACTACCTGACCAGTGACGGCAGCACCAT<br>GAGCTACCGCACGCGCGTCCGTACGCCAAGCTTCCCGCATTTGCAGC<br>AGATCCCGTCCGTAATCCGTGGCAGCCTGGTATCCGACCTGATCGTGT<br>ATCTGGGCAGTATCGATTTTGTAATGTCAGATGTGGACCGCTAA |
| 134 | DP71 Protein RecA | ATGGCTATTGATGAGAACAAGCAAAAAGCGTTAGCTGCAGCACTGGG<br>CCAGATTGAAAAGCAATTCGGTAAAGGCTCCATCATGCGTCTGGGTG<br>AAGATCGCTCTATGGACGTGGAAACGATCTCTACCGGCTCTTTGTCTC<br>TGGATATCGCGTTAGGCGCCGGTGGTTTGCCGATGGGCCGTATCGTTG<br>AGATTTATGGCCCGGAATCCTCCGGTAAAACTACGCTGACCCTTCAGG<br>TTATTGCTGCCGCACAGCGCGAAGGCAAAACCTGTGCGTTCATCGAT<br>GCGGAACATGCACTTGACCCTATCTACGCGAAGAAATTGGGCGTAGA<br>TATCGACAACCTGTTGTGTTCTCAGCCGGATACCGGCGAACAGGCTCT<br>GGAAATCTGTGACGCGCTGACCCGTTCAGGCGCGGTCGACGTTATCA<br>TCGTCGACTCCGTTGCTGCACTGACGCCAAAAGCAGAAATCGAAGGC<br>GAAATCGGTGACTCTCACATGGGCCTTGCGGCACGTATGATGAGCCA<br>GGCAATGCGTAAGCTTGCCGGTAACCTGAAAAACGCCAACACCTTGC<br>TGATCTTCATCAACCAGATCCGTATGAAAATCGGTGTGATGTTCGGTA<br>ACCCGGAAACCACCACCGGTGGTAACGCCCTGAAATTCTACGCCTCT<br>GTGCGTCTGGATATCCGCCGCATCGGCGCTATCAAAGAAGGCGACGT<br>GGTGATCGGCAGTGAAACGCGCGTGAAAGTTGTGAAGAACAAAATCG<br>CTGCGCCTTTCAAACAGGCTGAATTCCAGATCCTATACGGCGAAGGC<br>ATCAACATTAACGGCGAGCTGATCGATTTGGGCGTTAAGCACAAACT<br>GGTCGAAAAAGCCGGTGCATGGTACAGCTACAACGGCGAGAAGATTG<br>GTCAGGGTAAATCTAACTCCTGCAACTATCTGAAAGAAAACCCGAAA<br>ATCGCTGCTGAACTGGATAAAAAACTGCGTGATATGTTGTTGAGTGG<br>CACTGGTGAACTGGCCGCTGCAACCACAGCAGAACTTGCAGACGACG<br>ATATGGAAACCAGCGAAGAGTTTTAA |
| 135 | DP71 RNA polymerase sigma factor RpoD | GGTAAGGAGCAAGGCTATCTGACCTTTGCTGAGGTCAATGACCATCT<br>GCCGGAAGATATCGTCGACTCCGACCAGATCGAAGACATCATCCAGA<br>TGATTAACGACATGGGCATCCAGGTTCTTGAAGAAGCGCCGGACGCC<br>GATGATTTGATGCTGGCCGAAAACCGCCCTGATACCGATGAAGATGC<br>TGCAGAAGCAGCGGCTCAGGTGCTTTCCAGCGTTGAATCTGAAATTG<br>GCCGTACCACCGACCCTGTGCGTATGTATATGCGCGAAATGGGTACC<br>GTTGAGCTCCTGACCCGTGAAGGCGAAATCGACATCGCCAAACGTAT<br>CGAAGACGGTATCAATCAGGTCCAGTGCTCCGTTGCTGAATATCCTGA<br>AGCTATCACCTATTTGTTAGAGCAATATGACCGTGTTGAAGCAGGCG |

-continued

Sequence Listing

| Seq ID No. | Description | Sequence |
|---|---|---|
| | | AAGCACGTCTGTCTGATTTGATCACCGGTTTTGTTGATCCGAACGCCG<br>AAGAAGAAATCGCGCCGACTGCGACTCACGTGGGTTCTGAACTGACC<br>ACTGAAGAGCAAAATGATACCGACGACGATGAAGAAGACGACGACG<br>ATGCTGAAGACGACAACAGCATCGACCCGGAACTGGCGCGTCAGAAG<br>TTCACCGATCTGCGTGAGCAACATGAAGCGACCCGTGCCGTCATCAA<br>GAAAAATGGCCGTAGCCACAAAAGCGCCGCAGAAGAAATTCTGAAG<br>CTGTCCGATGTGTTTAAACAGTTCCGTCTGGTACCAAAACAGTTCGAT<br>TTCCTGGTGAACAGCATGCGCTCCATGATGGATCGCGTCCGTACTCAG<br>GAACGTCTGATCATGAAAGTGTGCGTTGAACAGTGCAAAATGCCGAA<br>GAAAAACTTCGTCAATCTGTTCGCCGGTAACGAAACCAGCAGTACCT<br>GGTTTGATGCTGCTCTGGCAATGGGTAAACCATGGTCTGAGAAGCTG<br>AAAGAAGTGACCGAAGACGTGCAGCGCGGCCTGATGAAACTGCGCC<br>AAATCGAAGAAGAAACTGGCCTGACTATCGAACAGGTAAAAGACATT<br>AACCGTCGCATGTCGATCGGCGAAGCGAAAGCACGCCGCGCGAAGA<br>AAGAGATGGTTGAAGCGAACTTACGTCTGGTTATCTCTATCGCGAAG<br>AAATACACCAACCGTGGCTTGCAGTTCCTTGACCTGATTCAGGAAGGT<br>AACATCGGCCTGATGAAAGCCGTTGATAAGTTTGAATATCGCCGTGG<br>TTATAAGTTCTCTACTTATGCGACCTGGTGGATCCGTCAGGCTATCAC<br>CCGCTCCATCGCCGACCAGGCACGTACCATCCGTATTCCGGTGCATAT<br>GATTGAGACCATCAACAAACTCAACCGTATTTCGCGCCAGATGTTGC<br>AGGAGATGGGCCGTGAGCCGACGCCGGAAGAGCTGGCTGAACGCAT<br>GCTGATGCCGGAAGACAAGATCCGTAAAGTGCTGAAAATTGCTAAAG<br>AGCCAATCTCCATGGAAACGCCAATCGGCGACGATGAAGATTCGCAT<br>CTGGGTGATTTCATCGAGGATACTACCCTCGAGCTGCCGCTGGATTCT<br>GCGACCTCTGAAAGCCTGCGTTCTGCAACGCACGACGTTCTGGCTGGC<br>CTGACCGCACGTGAAGCGAAAGTTCTGCGTATGCGTTTCGGTATCGAT<br>ATGAACACTGACCACACTCTGGAAGAAGTGGGCAAACAGTTCGACGT<br>AACCCGTGAACGTATCCGTCAGATCGAAGCCAAAGCGTTGCGTAAAC<br>TACGCCACCCAAGCCGCTCCGAAGTGCTGCGCAGCTTCCTCGACGACT<br>AG |
| 136 | DP71 DNA-directed RNA polymerase subunit beta | ATGGACCAGAACAACCCGTTGTCTGAGATCACGCACAAACGTCGTAT<br>CTCTGCACTGGGCCCGGGCGGTTTGACCCGTGAACGTGCTGGCTTTGA<br>AGTTCGAGACGTACACCCGACGCACTACGGTCGCGTATGTCCAATCG<br>AAACGCCAGAAGGTCCAAACATCGGTCTGATCAACTCATTATCTGTCT<br>ATGCACAGACAAATGAGTATGGTTTCCTGGAAACCCCTTACCGCCGT<br>GTGCGTGAAGGTATGGTTACCGATGAAATTAACTACCTGTCTGCCATC<br>GAAGAAGGCAACTTTGTTATCGCTCAGGCGAACTCCAACCTGGATGA<br>CGAAGGCCACTTCCTGGAAGATTTAGTCACTTGTCGTAGCAAAGGCG<br>AATCAAGCCTGTTCAGCCGCGACCAGGTTGACTACATGGACGTTTCTA<br>CCCAGCAGATCGTATCCGTTGGTGCTTCACTGATTCCATTCCTGGAAC<br>ACGATGACGCCAACCGTGCATTGATGGGTGCGAACATGCAACGTCAG<br>GCAGTTCCTACTCTGCGTGCTGATAAGCCGCTGGTAGGTACTGGTATG<br>GAACGTGCTGTTGCGGTTGACTCCGGTGTTACTGCCGTTGCCAAACGT<br>GGTGGTACTGTTCAGTACGTAGATGCATCCCGTATCGTTATTCGTGTT<br>AACGAAGAAGAGATGAATCCAGGCGAAGCAGGTATCGACATTTATAA<br>CCTGACTAAGTACACCCGTTCTAACCAGAACACCTGCATCAACCAGA<br>TGCCGTGTGTGAATCTGGGCGAGCCAATCGAGCGCGGCGACGTGCTG<br>GCAGATGGTCCGTCAACAGATCTGGGCGAACTGGCACTGGGTCAGAA<br>CATGCGTGTCGCGTTCATGCCTTGGAACGGTTACAACTTCGAAGACTC<br>CATCTTGGTCTCCGAACGTGTTGTGCAGGAAGATCGCTTCACGACCAT<br>CCATATCCAGGAACTGGCATGTGTGTCCCGTGACACAAAGTTAGGGC<br>CTGAAGAGATCACTGCTGATATCCCTAACGTGGGTGAAGCTGCGCTCT<br>CCAAACTGGATGAGTCCGGTATTGTGTATATCGGTGCTGAAGTGACC<br>GGTGGTGACATTCTGGTCGGTAAAGTTACGCCTAAAGGCGAAACCCA<br>GCTGACTCCAGAAGAGAAACTGCTGCGTGCGATCTTCGGTGAGAAAG<br>CGTCTGACGTTAAAGATTCTTCTCTGCGTGTACCAAACGGCGTTTCCG<br>GTACGATTATTGACGTGCAAGTCTTTACCCGCGATGGCGTGGAAAAA<br>GATAAGCGTGCGTTAGAAATCGAAGAAATGCAGCTGAAACAGGCTAA<br>GAAAGACCTGACTGAAGAGCTGCAAATTCTGGAAGCTGGTCTGTTTG<br>CACGTATCCAGTCCGCGCTGGTTGCTGGCGGTGTTGAAGCCGATAAG<br>CTGGGCAAATTGCCACGCGATCGTTGGCTTGAACTGTCACTGACTGAC<br>GAAGACAAACAGAATCAGTTGGAACAGCTTGCTGAACAGTACGACGA<br>ACTGAAATCCGAGTTTGAGAAAAAACTCGAAGCTAAACGTCGTAAAA<br>TCACTCAGGGCGATGACCTAGCACCAGGTGTGCTGAAAATCGTTAAA<br>GTGTACCTGGCCGTTAAACGTCAGATCCAACCTGGTGACAAAATGGC<br>AGGCCGCCACGGTAACAAAGGTGTTATCTCCAAGATCAACCCGATCG<br>AAGATATGCCTTACGATGAAAACGGGACTCCTGTTGACATCGTACTG<br>AACCCGCTGGGCGTTCCATCACGTATGAACATTGGTCAGATTTTAGAA<br>ACCCACCTGGGTATGGCCGCGAAAGGTATTGGTGAAAAAATCAATGC<br>CATGCTTAAGAAACATGAAGAAGTTTCTAAGCTGCGCGAGTTCATCC<br>AGCGTGCCTATGATCTGGGCGACGACGTACGTCAGAAAGTTGATCTG<br>ACCACCTTCACCGATGATGAAGTATTGCGTTTGGCTGAAAACCTGAA |

-continued

Sequence Listing

| Seq ID No. | Description | Sequence |
|---|---|---|
| | | AAAGGGTATGCCAATTGCAACACCAGTCTTCGACGGTGCGAAAGAGA<br>CAGAGATCAAGCAACTGCTTGAAATGGGCGGCGTCCCAACCTCTGGC<br>CAGATCACACTGTTTGACGGCCGTACCGGCGAGCAATTCGAGCGCCA<br>GGTTACCGTCGGCTACATGTACATGCTGAAACTGAACCACCTGGTTGA<br>CGATAAGATGCATGCGCGTTCTACCGGTTCTTACAGCCTTGTTACTCA<br>GCAGCCGCTGGGTGGTAAAGCTCAGTTCGGTGGTCAGCGCTTCGGTG<br>AGATGGAAGTGTGGGCACTGGAAGCATACGGTGCCGCTTATACCCTG<br>CAGGAAATGCTGACTGTTAAGTCCGATGACGTGAACGGCCGTACTAA<br>GATGTATAAAAACATCGTAGATGGCGATCACCGGATGGAACCAGGCA<br>TGCCGGAATCATTCAACGTACTGTTGAAAGAAATCCGCTCTCTGGGTA<br>TCAACATCGAGCTGGAAGACGAGTAA |
| 137 | DP72 16S rRNA | TTCGGAGAGTTTGATCCTGGCTCAGGACGAACGCTGGCGGCGTGCCT<br>AATACATGCAAGTCGAGCGGACAGAAGGGAGCTTGCTCCCGGATGTT<br>AGCGGCGGACGGGTGAGTAACACGTGGGTAACCTGCCTGTAAGACTG<br>GGATAACTCCGGGAAACCGGAGCTAATACCGGATAGTTCCTTGAACC<br>GCATGGTTCAAGGATGAAAGACGGTTTCGGCTGTCACTTACAGATGG<br>ACCCGCGGCGCATTAGCTAGTTGGTGGGGTAATGGCTCACCAAGGCG<br>ACGATGCGTAGCCGACCTGAGAGGGTGATCGGCCACACTGGGACTGA<br>GACACGGCCCAGACTCCTACGGGAGGCAGCAGTAGGGAATCTTCCGC<br>AATGGACGAAAGTCTGACGGAGCAACGCCGCGTGAGTGATGAAGGTT<br>TTCGGATCGTAAAGCTCTGTTGTTAGGGAAGAACAAGTGCGAGAGTA<br>ACTGCTCGCACCTTGACGGTACCTAACCAGAAAGCCACGGCTAACTA<br>CGTGCCAGCAGCCGCGGTAATACGTAGGTGGCAAGCGTTGTCCGGAA<br>TTATTGGGCGTAAAGGGCTCGCAGGCGGTTTCTTAAGTCTGATGTGAA<br>AGCCCCCGGCTCAACCGGGGAGGGTCATTGGAAACTGGGAAACTTGA<br>GTGCAGAAGAGGAGAGTGGAATTCCACGTGTAGCGGTGAAATGCGTA<br>GAGATGTGGAGGAACACCAGTGGCGAAGGCGACTCTCTGGTCTGTAA<br>CTGACGCTGAGGAGCGAAAGCGTGGGGAGCGAACAGGATTAGATAC<br>CCTGGTAGTCCACGCCGTAAACGATGAGTGCTAAGTGTTAGGGGGTT<br>TCCGCCCCTTAGTGCTGCAGCTAACGCATTAAGCACTCCGCCTGGGGA<br>GTACGGTCGCAAGACTGAAACTCAAAGGAATTGACGGGGGCCCGCAC<br>AAGCGGTGGAGCATGTGGTTTAATTCGAAGCAACGCGAAGAACCTTA<br>CCAGGTCTTGACATCCTCTGACAACCCTAGAGATAGGGCTTTCCCTTC<br>GGGGACAGAGTGACAGGTGGTGCATGGTTGTCGTCAGCTCGTGTCGT<br>GAGATGTTGGGTTAAGTCCCGCAACGAGCGCAACCCTTGATCTTAGTT<br>GCCAGCATTTAGTTGGGCACTCTAAGGTGACTGCCGGTGACAAACCG<br>GAGGAAGGTGGGGATGACGTCAAATCATCATGCCCCTTATGACCTGG<br>GCTACACACGTGCTACAATGGACAGAACAAAGGGCTGCGAGACCGCA<br>AGGTTTAGCCAATCCCATAAATCTGTTCTCAGTTCGGATCGCAGTCTG<br>CAACTCGACTGCGTGAAGCTGGAATCGCTAGTAATCGCGGATCAGCA<br>TGCCGCGGTGAATACGTTCCCGGGCCTTGTACACACCGCCCGTCACAC<br>CACGAGAGTTTGCAACACCCGAAGTCGGTGAGGTAACCTTTATGGAG<br>CCAGCCGCCGAAGGTGGGGCAGATGATTGGGGTGAAGTCGTAACAAG<br>GTAGCCGTATCGGAAGGTGCGGCTGGATCACCTCCTTT |
| 138 | DP73 16S rRNA | AACGGAGAGTTTGATCCTGGCTCAGGACGAACGCTGGCGGCGTGCCT<br>AATACATGCAAGTCGAGCGGACAGAAGGGAGCTTGCTCCCGGACGTT<br>AGCGGCGGACGGGTGAGTAACACGTGGGCAACCTGCCCCTTAGACTG<br>GGATAACTCCGGGAAACCGGAGCTAATACCGGATAATCCCTTTCTCC<br>ACCTGGAGAGAGGGTGAAAGATGGCTTCGGCTATCACTAAGGGATGG<br>GCCCGCGGCGCATTAGCTAGTTGGTAAGGTAACGGCTTACCAAGGCG<br>ACGATGCGTAGCCGACCTGAGAGGGTGATCGGCCACACTGGGACTGA<br>GACACGGCCCAGACTCCTACGGGAGGCAGCAGTAGGGAATCTTCCGC<br>AATGGACGAAAGTCTGACGGAGCAACGCCGCGTGAGTGAGGAAGGC<br>CTTCGGGTCGTAAAGCTCTGTTGTGAGGGAAGAAGCGGTGCCGTTCG<br>AATAGGGCGGTACCTTGACGGTACCTCACCAGAAAGCCACGGCTAAC<br>TACGTGCCAGCAGCCGCGGTAATACGTAGGTGGCAAGCGTTGTCCGG<br>AATTATTGGGCGTAAAGCGCGCGCAGGCGGCTTCTTAAGTCTGATGT<br>GAAATCTCGGGGCTCAACCCCGAGCGGCCATTGGAAACTGGGGAGCT<br>TGAGTGCAGAAGAGGAGAGTGGAATTCCACGTGTAGCGGTGAAATGC<br>GTAGAGATGTGGAGGAACACCAGTGGCGAAGGCGACTCTCTGGTCTG<br>TAACTGACGCTGAGGCGCGAAAGCGTGGGGAGCAAACAGGATTAGA<br>TACCCTGGTAGTCCACGCCGTAAACGATGAGTGCTAGGTGTTAG |
| 139 | DP74 16S rRNA | GCCTAATACATGCAAGTCGTGCGGACCTTTTAAAAGCTTGCTTTTAAA<br>AGGTTAGCGGCGAACGGGTGAGTAACACGTGGGCAACCTGCCTGTAA<br>GATCGGGATAATGCCGGGAAACCGGGGCTAATACCGGATAGTTTTTT<br>CCTCCGCATGGAGGAAAAAGGAAAGACGGCTTCGGCTGTCACTTACA<br>GATGGGCCCGCGGCGCATTAGCTTGTTGGTGGGGTAACGGCTCACCA<br>AGGCAACGATGCGTAGCCGACCTGAGAGGGTGATCGGCCACATTGGG<br>ACTGAGACACGGCCCAAACTCCTACGGGAGGCAGCAGTAGGGAATCT<br>TCCGCAATGGACGAAAGTCTGACGGAGCAACGCCGCGTGAGTGAAGA |

-continued

Sequence Listing

| Seq ID No. | Description | Sequence |
|---|---|---|
| | | AGGCCTTCGGGTCGTAAAACTCTGTTGCCGGGGAAGAACAAGTGCCG TTCGAACAGGGCGGCGCCTTGACGGTACCCGGCCAGAAAGCCACGGC TAACTACGTGCCAGCAGCCGCGGTAATACGTAGGTGGCAAGCGTTGT CCGGAATTATTGGGCGTAAAGCGCGCGCAGGCGGCTTCTTAAGTCTG ATGTGAAATCTTGCGGCTCAACCGCAAGCGGTCATTGGAAACTGGGA GGCTTGAGTGCAGAAGAGGAGAGTGGAATTCCACGTGTAGCGGTGAA ATGCGTAGAGATGTGGAGGAACACCAGTGGCGAAGGCGGCTCTCTGG TCTGTAACTGACGCTGAGGCGCGAAAGCGTGGGGAGCAAACAGGATT AGATACCCTGGTAGTCCACGCCGTAAACGATGAGTGCTAAGTGTTAG AGGGTTTCCGCCCTTTAGTGCTGCAGCTAACGCATTAAGCACTCCGCC TGGGGAGTACGGCCGCAAGGCTGAAACTCAAAGGAATTGACGGGGG CCCGCACAAGCGGTGGAGCATGTGGTTTAATTCGAAGCAACGCGAAG AACCTTACCAGGTCTTGACATCCTCTGACCTCCCTGGAGACAGGGCCT TCCCCTTCGGGGGACAGAGTGACAGGTGGTGCATGGTTGTCGTCAGC TCGTGTCGTGAGATGTTGGGTTAAGTCCCGCAACGAGCGCAACCCTTG ACCTTAGTTGCCAGCATTCAG |
| 140 | DP75 16S rRNA | TGAAGAGTTTGATCATGGCTCAGATTGAACGCTGGCGGCAGGCCTAA CACATGCAAGTCGAGCGGTAGAGAGAAGCTTGCTTCTCTTGAGAGCG GCGGACGGGTGAGTAATGCCTAGGAATCTGCCTGGTAGTGGGGGATA ACGTTCGGAAACGGACGCTAATACCGCATACGTCCTACGGGAGAAAG CAGGGGACCTTCGGGCCTTGCGCTATCAGATGAGCCTAGGTCGGATT AGCTAGTTGGTGAGGTAATGGCTCACCAAGGCGACGATCCGTAACTG GTCTGAGAGGATGATCAGTCACACTGGAACTGAGACACGGTCCAGAC TCCTACGGGAGGCAGCAGTGGGGAATATTGGACAATGGGCGAAAGCC TGATCCAGCCATGCCGCGTGTGTGAAGAAGGTCTTCGGATTGTAAAG CACTTTAAGTTGGGAGGAAGGGTTGTAGATTAATACTCTGCAATTTTG ACGTTACCGACAGAATAAGCACCGGCTAACTCTGTGCCAGCAGCCGC GGTAATACAGAGGGTGCAAGCGTTAATCGGAATTACTGGGCGTAAAG CGCGCGTAGGTGGTTCGTTAAGTTGGATGTGAAAGCCCCGGGCTCAA CCTGGGAACTGCATTCAAAACTGACGAGCTAGAGTATGGTAGAGGGT GGTGGAATTTCCTGTGTAGCGGTGAAATGCGTAGATATAGGAAGGAA CACCAGTGGCGAAGGCGACCACCTGGACTGATACTGACACTGAGGTG CGAAAGCGTGGGGAGCAAACAGGATTAGATACCCTGGTAGTCCACGC CGTAAACGATGTCAACTAGCCGTTGGAATCCTTGAGATTTTAGTGGCG CAGCTAACGCATTAAGTTGACCGCCTGGGGAGTACGGCCGCAAGGTT AAAACTCAAATGAATTGACGGGGGCCCGCACAAGCGGTGGAGCATGT GGTTTAATTCGAAGCAACGCGAAGAACCTTACCAGGCCTTGACATCC AATGAACTTTCCAGAGATGGATGGGTGCCTTCGGGAACATTGAGACA GGTGCTGCATGGCTGTCGTCAGCTCGTGTCGTGAGATGTTGGGTTAAG TCCCGTAACGAGCGCAACCCTTGTCCTTAGTTACCAGCACGTTATGGT GGGCACTCTAAGGAGACTGCCGGTGACAAACCGGAGGAAGGTGGGG ATGACGTCAAGTCATCATGGCCCTTACGGCCTGGGCTACACACGTGCT ACAATGGTCGGTACAAAGGGTTGCCAAGCCGCGAGGTGGAGCTAATC CCATAAAACCGATCGTAGTCCGGATCGCAGTCTGCAACTCGACTGCG TGAAGTCGGAATCGCTAGTAATCGCGAATCAGAATGTCGCGGTGAAT ACGTTCCCGGGCCTTGTACACACCGCCCGTCACACCATGGGAGTGGG TTGCACCAGAACGGGAGGACGGTTACCACGGTGTGATTCATGACTGG GGTGAAGTCGTAACAAGGTAGCCGTAGGGGAACCTGCGGCTGGATCA CCTCCTT |
| 141 | DP76 16S rRNA | CTTGAGAGTTTGATCCTGGCTCAGAACGAACGCTGGCGGCAGGCTTA ACACATGCAAGTCGAGCGCCCCGCAAGGGGAGCGGCAGACGGGTGA GTAACGCGTGGGAATCTACCTTTTGCTACGGAACAACAGTTGGAAAC GACTGCTAATACCGTATGTGCCCTTCGGGGGAAAGATTTATCGGCAA AGGATGAGCCCGCGTTGGATTAGCTAGTTGGTGAGGTAAAGGCTCAC CAAGGCGACGATCCATAGCTGGTCTGAGAGGATGATCAGCCACACTG GGACTGAGACACGGCCCAGACTCCTACGGGAGGCAGCAGTGGGGAA TATTGGACAATGGGCGCAAGCCTGATCCAGCCATGCCGCGTGAGTGA TGAAGGCCCTAGGGTTGTAAAGCTCTTTCACCGGTGAAGATAATGAC GGTAACCGGAGAAGAAGCCCCGGCTAACTTCGTGCCAGCAGCCGCGG TAATACGAAGGGGGCTAGCGTTGTTCGGATTTACTGGGCGTAAAGCG CACGTAGGCGGATTTTTAAGTCAGGGGTGAAATCCCGGGGCTCAACC CCGGAACTGCCTTTGATACTGGAAGTCTTGAGTATGGTAGAGGTGAG TGGAATTCCGAGTGTAGAGGTGAAATTCGTAGATATTCGGAGGAACA CCAGTGGCGAAGGCGGCTCACTGGACCATTACTGACGCTGAGGTGCG AAAGCGTGGGGAGCAAACAGGATTAGATACCCTGGTAGTCCACGCCG TAAACGATGAATGTTAGCCGTCGGGGGGTTTACCTTTCGGTGGCGCA GCTAACGCATTAAACATTCCGCCTGGGGAGTACGGTCGCAAGATTAA AACTCAAAGGAATTGACGGGGGCCCGCACAAGCGGTGGAGCATGTG GTTTAATTCGAAGCAACGCGCAGAACCTTACCAGCCCTTGACATACC GGTCGCGGACACAGAGATGTGTCTTTCAGTTCGGCTGGACCGGATAC AGGTGCTGCATGGCTGTCGTCAGCTCGTGTCGTGAGATGTTGGGTTAA |

-continued

Sequence Listing

| Seq ID No. | Description | Sequence |
|---|---|---|
| | | GTCCCGCAACGAGCGCAACCCTCGCCTTTAGTTGCCAGCATTTAGTTG GGCACTCTAAAGGGACTGCCAGTGATAAGCTGGAGGAAGGTGGGGAT GACGTCAAGTCCTCATGGCCCTTACGGGCTGGGCTACACACGTGCTAC AATGGTGGTGACAGTGGGCAGCAAGCACGCGAGTGTGAGCTAATCTC CAAAAGCCATCTCAGTTCGGATTGCACTCTGCAACTCGAGTGCATGA AGTTGGAATCGCTAGTAATCGCGGATCAGCATGCCGCGGTGAATACG TTCCCGGGCCTTGTACACACCGCCCGTCACACCATGGGAGTTGGTTTT ACCCGAAGGCACTGTGCTAACCGCAAGGAGGCAGGTGACCACGGTAG GGTCAGCGACTGGGGTGAAGTCGTAACAAGGTAGCCGTAGGGGAACC TGCGGCTGGATCACCTCCTTT |
| 142 | DP77 16S rRNA | TCGGAGAGTTTGATCCTGGCTCAGGATGAACGCTGGCGGCGTGCCTA ATACATGCAAGTCGAGCGAACTGATTAGAAGCTTGCTTCTATGACGTT AGCGGCGGACGGGTGAGTAACACGTGGGCAACCTGCCTGTAAGACTG GGATAACTTCGGGAAACCGAAGCTAATACCGGATAGGATCTTCTCCT TCATGGGAGATGATTGAAAGATGGTTTCGGCTATCACTTACAGATGG GCCCGCGGTGCATTAGCTAGTTGGTGAGGTAACGGCTCACCAAGGCA ACGATGCATAGCCGACCTGAGAGGGTGATCGGCCACACTGGGACTGA GACACGGCCCAGACTCCTACGGGAGGCAGCAGTAGGGAATCTTCCGC AATGGACGAAAGTCTGACGGAGCAACGCCGCGTGAGTGATGAAGGCT TTCGGGTCGTAAAACTCTGTTGTTAGGGAAGAACAAGTACAAGAGTA ACTGCTTGTACCTTGACGGTACCTAACCAGAAAGCCACGGCTAACTA CGTGCCAGCAGCCGCGGTAATACGTAGGTGGCAAGCGTTATCCGGAA TTATTGGGCGTAAAGCGCGCGCAGGCGGTTTCTTAAGTCTGATGTGAA AGCCCACGGCTCAACCGTGGAGGGTCATTGGAAACTGGGGAACTTGA GTGCAGAAGAGAAAAGCGGAATTCCACGTGTAGCGGTGAAATGCGTA GAGATGTGGAGGAACACCAGTGGCGAAGGCGGCTTTTTGGTCTGTAA CTGACGCTGAGGCGCGAAAGCGTGGGGAGCAAACAGGATTAGATAC CCTGGTAGTCCACGCCGTAAACGATGAGTGCTAAGTGTTAGAGGGTT TCCGCCCTTTAGTGCTGCAGCTAACGCATTAAGCACTCCGCCTGGGGA GTACGGTCGCAAGACTGAAACTCAAAGGAATTGACGGGGGCCCGCAC AAGCGGTGGAGCATGTGGTTTAATTCGAAGCAACGCGAAGAACCTTA CCAGGTCTTGACATCCTCTGACAACTCTAGAGATAGAGCGTTCCCCTT CGGGGGACAGAGTGACAGGTGGTGCATGGTTGTCGTCAGCTCGTGTC GTGAGATGTTGGGTTAAGTCCCGCAACGAGCGCAACCCTTGATCTTA GTTGCCAGCATTCAGTTGGGCACTCTAAGGTGACTGCCGGTGACAAA CCGGAGGAAGGTGGGGATGACGTCAAATCATCATGCCCCTTATGACC TGGGCTACACACGTGCTACAATGGATGGTACAAAGGGCTGCAAGACC GCGAGGTCAAGCCAATCCCATAAAACCATTCTCAGTTCGGATTGTAG GCTGCAACTCGCCTACATGAAGCTGGAATCGCTAGTAATCGCGGATC AGCATGCCGCGGTGAATACGTTCCCGGGCCTTGTACACACCGCCCGTC ACACCACGAGAGTTTGTAACACCCGAAGTCGGTGGAGTAACCGTAAG GAGCTAGCCGCCTAAGGTGGGACAGATGATTGGGGTGAAGTCGTAAC AAGGTAGCCGTATCGGAAGGTGCGGCTGGATCACCTCCTTT |
| 143 | DP78 16S rRNA | TTGAAGAGTTTGATCATGGCTCAGATTGAACGCTGGCGGCAGGCCTA ACACATGCAAGTCGGACGGTAGCACAGAGAGCTTGCTCTTGGGTGAC GAGTGGCGGACGGGTGAGTAATGTCTGGGGATCTGCCCGATAGAGGG GGATAACCACTGGAAACGGTGGCTAATACCGCATAACGTCGCAAGAC CAAAGAGGGGGACCTTCGGGCCTCTCACTATCGGATGAACCCAGATG GGATTAGCTAGTAGGCGGGGTAATGGCCCACCTAGGCGACGATCCCT AGCTGGTCTGAGAGGATGACCAGCCACACTGGAACTGAGACACGGTC CAGACTCCTACGGGAGGCAGCAGTGGGGAATATTGCACAATGGGCGC AAGCCTGATGCAGCCATGCCGCGTGTATGAAGAAGGCCTTCGGGTTG TAAAGTACTTTCAGCGGGGAGGAAGGCGACGGGGTTAATAACCCTGT CGATTGACGTTACCCGCAGAAGAAGCACCGGCTAACTCCGTGCCAGC AGCCGCGGTAATACGGAGGGTGCAAGCGTTAATCGGAATTACTGGGC GTAAAGCGCACGCAGGCGGTCTGTTAAGTCAGATGTGAAATCCCCGG GCTTAACCTGGGAACTGCATTTGAAACTGGCAGGCTTGAGTCTTGTAG AGGGGGGTAGAATTCCAGGTGTAGCGGTGAAATGCGTAGAGATCTGG AGGAATACCGGTGGCGAAGGCGGCCCCCTGGACAAAGACTGACGCTC AGGTGCGAAAGCGTGGGGAGCAAACAGGATTAGATACCCTGGTAGTC CACGCCGTAAACGATGTCGACTTGGAGGTTGTTCCCTTGAGGAGTGG CTTCCGGAGCTAACGCGTTAAGTCGACCGCCTGGGGAGTACGGCCGC AAGGTTAAAACTCAAATGAATTGACGGGGGCCCGCACAAGCGGTGGA GCATGTGGTTTAATTCGATGCAACGCGAAGAACCTTACCTACTCTTGA CATCCAGCGAACTTAGCAGAGATGCTTTGGTGCCTTCGGGAACGCTG AGACAGGTGCTGCATGGCTGTCGTCAGCTCGTGTTGTGAAATGTTGGG TTAAGTCCCGCAACGAGCGCAACCCTTATCCTTTGTTGCCAGCGATTC GGTCGGGAACTCAAAGGAGACTGCCGGTGATAAACCGGAGGAAGGT GGGGATGACGTCAAGTCATCATGGCCCTTACGAGTAGGGCTACACAC GTGCTACAATGGCGCATACAAAGAGAAGCGACCTCGCGAGAGCAAG CGGACCTCACAAAGTGCGTCGTAGTCCGGATCGGAGTCTGCAACTCG |

-continued

Sequence Listing

| Seq ID No. | Description | Sequence |
|---|---|---|
| | | ACTCCGTGAAGTCGGAATCGCTAGTAATCGTGGATCAGAATGCCACG GTGAATACGTTCCCGGGCCTTGTACACACCGCCCGTCACACCATGGG AGTGGGTTGCAAAAGAAGTAGGTAGCTTAACCTTCGGGAGGGCGCTT ACCACTTTGTGATTCATGACTGGGGTGAAGTCGTAACAAGGTAACCG TAGGGGAACCTGCGGTTGGATCACCTCCTT |
| 144 | DP79 16S rRNA | TGAAGAGTTTGATCATGGCTCAGATTGAACGCTGGCGGCAGGCCTAA CACATGCAAGTCGAGCGGTAGAGAGAAGCTTGCTTCTCTTGAGAGCG GCGGACGGGTGAGTAATACCTAGGAATCTGCCTGATAGTGGGGGATA ACGTTCGGAAACGGACGCTAATACCGCATACGTCCTACGGGAGAAAG CAGGGGACCTTCGGGCCTTGCGCTATCAGATGAGCCTAGGTCGGATT AGCTAGTTGGTGAGGTAATGGCTCACCAAGGCTACGATCCGTAACTG GTCTGAGAGGATGATCAGTCACACTGGAACTGAGACACGGTCCAGAC TCCTACGGGAGGCAGCAGTGGGGAATATTGGACAATGGGCGAAAGCC TGATCCAGCCATGCCGCGTGTGTGAAGAAGGTCTTCGGATTGTAAAG CACTTTAAGTTGGGAGGAAGGGCAGTTACCTAATACGTGACTGTCTTG ACGTTACCGACAGAATAAGCACCGGCTAACTCTGTGCCAGCAGCCGC GGTAATACAGAGGGTGCAAGCGTTAATCGGAATTACTGGGCGTAAAG CGCGCGTAGGTGGTTTGTTAAGTTGAATGTGAAATCCCCGGGCTCAAC CTGGGAACTGCATCCAAAACTGGCAAGCTAGAGTATGGTAGAGGGTA GTGGAATTTCCTGTGTAGCGGTGAAATGCGTAGATATAGGAAGGAAC ACCAGTGGCGAAGGCGACTACCTGGACTGATACTGACACTGAGGTGC GAAAGCGTGGGGAGCAAACAGGATTAGATACCCTGGTAGTCCACGCC GTAAACGATGTCAACTAGCCGTTGGGAGTCTTGAACTCTTAGTGGCGC AGCTAACGCATTAAGTTGACCGCCTGGGGAGTACGGCCGCAAGGTTA AAACTCAAATGAATTGACGGGGGCCCGCACAAGCGGTGGAGCATGTG GTTTAATTCGAAGCAACGCGAAGAACCTTACCAGGCCTTGACATCCA ATGAACTTTCTAGAGATAGATTGGTGCCTTCGGGAACATTGAGACAG GTGCTGCATGGCTGTCGTCAGCTCGTGTCGTGAGATGTTGGGTTAAGT CCCGTAACGAGCGCAACCCTTGTCCTTAGTTACCAGCACGTAATGGTG GGCACTCTAAGGAGACTGCCGGTGACAAACCGGAGGAAGGTGGGGA TGACGTCAAGTCATCATGGCCCTTACGGCCTGGGCTACACACGTGCTA CAATGGTCGGTACAAAGGGTTGCCAAGCCGCGAGGTGGAGCTAATCC CATAAAACCGATCGTAGTCCGGATCGCAGTCTGCAACTCGACTGCGT GAAGTCGGAATCGCTAGTAATCGTGAATCAGAATGTCACGGTGAATA CGTTCCCGGGCCTTGTACACACCGCCCGTCACACCATGGGAGTGGGTT GCACCAGAAGTAGCTAGTCTAACCTTCGGGAGGACGGTTACCACGGT GTGATTCATGACTGGGGTGAAGTCGTAACAAGGTAGCCGTAGGGGAA CCTGCGGCTGGATCACCTCCTT |
| 145 | DP80 16S rRNA | CTTGAGAGTTTGATCCTGGCTCAGAGCGAACGCTGGCGGCAGGCTTA ACACATGCAAGTCGAGCGGGCACCTTCGGGTGTCAGCGGCAGACGGG TGAGTAACACGTGGGAACGTACCCTTCGGTTCGGAATAACGCTGGGA AACTAGCGCTAATACCGGATACGCCCTTTTGGGGAAAGGTTTACTGCC GAAGGATCGGCCCGCGTCTGATTAGCTAGTTGGTGGGGTAACGGCCT ACCAAGGCGACGATCAGTAGCTGGTCTGAGAGGATGATCAGCCACAC TGGGACTGAGACACGGCCCAGACTCCTACGGGAGGCAGCAGTGGGG AATATTGGACAATGGGCGCAAGCCTGATCCAGCCATGCCGCGTGAGT GATGAAGGCCTTAGGGTTGTAAAGCTCTTTTGTCCGGGACGATAATG ACGGTACCGGAAGAATAAGCCCCGGCTAACTTCGTGCCAGCAGCCGC GGTAATACGAAGGGGGCTAGCGTTGCTCGGAATCACTGGGCGTAAAG GGCGCGTAGGCGGCCATTCAAGTCGGGGGTGAAAGCCTGTGGCTCAA CCACAGAATTGCCTTCGATACTGTTTGGCTTGAGTTTGGTAGAGGTTG GTGGAACTGCGAGTGTAGAGGTGAAATTCGTAGATATTCGCAAGAAC ACCAGTGGCGAAGGCGGCCAACTGGACCAATACTGACGCTGAGGCGC GAAAGCGTGGGGAGCAAACAGGATTAGATACCCTGGTAGTCCACGCC GTAAACGATGAATGCTAGCTGTTGGGGTGCTTGCACCTCAGTAGCGC AGCTAACGCTTTAAGCATTCCGCCTGGGGAGTACGGTCGCAAGATTA AAACTCAAAGGAATTGACGGGGGCCCGCACAAGCGGTGGAGCATGT GGTTTAATTCGAAGCAACGCGCAGAACCTTACCATCCCTTGACATGTC GTGCCATCCGGAGAGATCCGGGGTTCCCTTCGGGGACGCGAACACAG GTGCTGCATGGCTGTCGTCAGCTCGTGTCGTGAGATGTTGGGTTAAGT CCCGCAACGAGCGCAACCCACGTCCTTAGTTGCCATCATTTAGTTGGG CACTCTAGGGAGACTGCCGGTGATAAGCCGCGAGGAAGGTGTGGATG ACGTC |
| 146 | DP81 16S rRNA | AACGGAGAGTTTGATCCTGGCTCAGGACGAACGCTGGCGGCGTGCCT AATACATGCAAGTCGAGCGGACAGAAGGGAGCTTGCTCCCGGACGTT AGCGGCGGACGGGTGAGTAACACGTGGGCAACCTGCCCCTTAGACTG GGATAACTCCGGGAAACCGGAGCTAATACCGGATAATCCCTTTCTCC ACCTGGAGAGAGGGTGAAAGATGGCTTCGGCTATCACTAGGGGATGG GCCCGCGGCGCATTAGCTAGTTGGTAAGGTAACGGCTTACCAAGGCG ACGATGCGTAGCCGACCTGAGAGGGTGATCGGCCACACTGGGACTGA |

-continued

Sequence Listing

| Seq ID No. | Description | Sequence |
|---|---|---|
| | | GACACGGCCCAGACTCCTACGGGAGGCAGCAGTAGGGAATCTTCCGC AATGGACGAAAGTCTGACGGAGCAACGCCGCGTGAGTGAGGAAGGC TTTCGGGTCGTAAAGCTCTGTTGTGAGGGAAGAAGCGGTACCGTTCG AATAGGGCGGTACCTTGACGGTACCTCACCAGAAAGCCACGGCTAAC TACGTGCCAGCAGCCGCGGTAATACGTAGGTGGCAAGCGTTGTCCGG AATTATTGGGCGTAAAGCGCGCGCAGGCGGCTTCTTAAGTCTGATGT GAAATCTCGGGGCTCAACCCCGAGCGGCCATTGGAAACTGGGGAGCT TGAGTGCAGAAGAGGAGAGTGGAATTCCACGTGTAGCGGTGAAATGC GTAGAGATGTGGAGGAACACCAGTGGCGAAGGCGACTCTCTGGTCTG TAACTGACGCTGAGGCGCGAAAGCGTGGGGAGCAAACAGGATTAGA TACCCTGGTAGTCCACGCCGTAAACGATGAGTGCTAGGTGTTAGGGG TTTCGATGCCCGTAGTGCCGAAGTTAACACATTAAGCACTCCGCCTGG GGAGTACGGCCGCAAGGCTGAAACTCAAAGGAATTGACGGGGACCC GCACAAGCAGTGGAGCATGTGGTTTAATTCGAAGCAACGCGAAGAAC CTTACCAGGTCTTGACATCCTTTGACCACCCAAGAGATTGGGCTTCCC CTTCGGGGGCAAAGTGACAGGTGGTGCATGGTTGTCGTCAGCTCGTG TCGTGAGATGTTGGGTTAAGTCCCGCAACGAGCGCAACCCTTGATCTT AGTTGCCAGCATTGAGTTGGGCACTCTAAGGTGACTGCCGGTGACAA ACCGGAGGAAGGTGGGGATGACGTCAAATCATCATGCCCCTTATGAC CTGGGCTACACACGTGCTACAATGGATGGTACAAAGGGCAGCGAAAC CGCGAGGTGAAGCCAATCCCATAAAGCCATTCTCAGTTCGGATTGCA GGCTGCAACTCGCCTGCATGAAGCCGGAATTGCTAGTAATCGCGGAT CAGCATGCCGCGGTGAATACGTTCCCGGGTCTTGTACACACCGCCCGT CACACCACGAGAGTTTGTAACACCCGAAGTCGGTGAGGCAACCTTTT GGAGCCAGCCGCCTAAGGTGGGACAAATGATTGGGGTGAAGTCGTAA CAAGGTAGCCGTATCGGAAGGTGCGGCTGGATCACCTCCTTT |
| 147 | DP82 16S rRNA | AACGGAGAGTTTGATCCTGGCTCAGGACGAACGCTGGCGGCGTGCCT AATACATGCAAGTCGAGCGGACAGAAGGGAGCTTGCTCCCGGACGTT AGCGGCGGACGGGTGAGTAACACGTGGGCAACCTGCCCCTTAGACTG GGATAACTCCGGGAAACCGGAGCTAATACCGGATAATCCCTTTCTCC ACCTGGAGAGAGGGTGAAAGATGGCTTCGGCTATCACTAAGGGATGG GCCCGCGGCGCATTAGCTAGTTGGTAAGGTAACGGCTTACCAAGGCA ACGATGCGTAGCCGACCTGAGAGGGTGATCGGCCACACTGGGACTGA GACACGGCCCAGACTCCTACGGGAGGCAGCAGTAGGGAATCTTCCGC AATGGACGAAAGTCTGACGGAGCAACGCCGCGTGAGTGAGGAAGGC CTTCGGGTCGTAAAGCTCTGTTGTGAGGGAAGAAGCGGTACCGTTCG AATAGGGCGGTACCTTGACGGTACCTCACCAGAAAGCCACGGCTAAC TACGTGCCAGCAGCCGCGGTAATACGTAGGTGGCAAGCGTTGTCCGG AATTATTGGGCGTAAAGCGCGCGCAGGCGGCTTCTTAAGTCTGATGT GAAATCTCGGGGCTCAACCCCGAGCGGCCATTGGAAACTGGGGAGCT TGAGTGCAGAAGAGGAGAGTGGAATTCCACGTGTAGCGGTGAAATGC GTAGAGATGTGGAGGAACACCAGTGGCGAAGGCGACTCTCTGGTCTG TAACTGACGCTGAGGCGCGAAAGCGTGGGGAGCAAACAGGATTAGA TACCCTGGTAGTCCACGCCGTAAACGATGAGTGCTAGGTGTTAGGGG TTTCGATGCCCGTAGTGCCGAAGTTAACACATTAAGCACTCCGCCTGG GGAGTACGGCCGCAAGGCTGAAACTCAAAGGAATTGACGGGGACCC GCACAAGCAGTGGAGCATGTGGTTTAATTCGAAGCAACGCGAAGAAC CTTACCAGGTCTTGACATCCTTTGACCACCCAAGAGATTGGGCTTCCC CTTCGGGGGCAAAGTGACAGGTGGTGCATGGTTGTCGTCAGCTCGTG TCGTGAGATGTTGGGTTAAGTCCCGCAACGAGCGCAACCCTTGATCTT AGTTGCCAGCATTCAGTTGGGCACTCTAAGGTGACTGCCGGTGACAA ACCGGAGGAAGGTGGGGATGACGTCAAATCATCATGCCCCTTATGAC CTGGGCTACACACGTGCTACAATGGATGGTACAAAGGGCAGCGAAAC CGCGAGGTGAAGCCAATCCCATAAAGCCATTCTCAGTTCGGATTGCA GGCTGCAACTCGCCTGCATGAAGCCGGAATTGCTAGTAATCGCGGAT CAGCATGCCGCGGTGAATACGTTCCCGGGTCTTGTACACACCGCCCGT CACACCACGAGAGTTTGTAACACCCGAAGTCGGTGAGGCAACCTTTT GGAGCCAGCCGCCTAAGGTGGGACAAATGATTGGGGTGAAGTCGTAA CAAGGTAGCCGTATCGGAAGGTGCGGCTGGATCACCTCCTTT |
| 148 | DP83 16S rRNA | ACGGAGAGTTTGATCCTGGCTCAGGACGAACGCTGGCGGCGTGCCTA ATACATGCAAGTCGAGCGGAGTTTCAAGAAGCTTGCTTTTTGAAACTT AGCGGCGGACGGGTGAGTAACACGTGGGCAACCTGCCCCTTAGACTG GGATAACTCCGGGAAACCGGAGCTAATACCGGATAATCCCTTTCTCC ACCTGGAGAGAGGGTGAAAGATGGCTTCGGCTATCACTAAGGGATGG GCCCGCGGCGCATTAGCTAGTTGGTAAGGTAACGGCTTACCAAGGCA ACGATGCGTAGCCGACCTGAGAGGGTGATCGGCCACACTGGGACTGA GACACGGCCCAGACTCCTACGGGAGGCAGCAGTAGGGAATCTTCCGC AATGGACGAAAGTCTGACGGAGCAACGCCGCGTGAGTGAGGAAGGC CTTCGGGTCGTAAAGCTCTGTTGTGAGGGAAGAAGCGGTACCGTTCG AATAGGGCGGTACCTTGACGGTACCTCACCAGAAAGCCACGGCTAAC TACGTGCCAGCAGCCGCGGTAATACGTAGGTGGCAAGCGTTGTCCGG |

-continued

Sequence Listing

| Seq ID No. | Description | Sequence |
|---|---|---|
| | | AATTATTGGGCGTAAAGCGCGCGCAGGCGGCTTCTTAAGTCTGATGT GAAATCTCGGGGCTCAACCCCGAGCGGCCATTGGAAACTGGGGAGCT TGAGTGCAGAAGAGGAGAGTGGAATTCCACGTGTAGCGGTGAAATGC GTAGAGATGTGGAGGAACACCAGTGGCGAAGGCGACTCTCTGGTCTG TAACTGACGCTGAGGCGCGAAAGCGTGGGGAGCAAACAGGATTAGA TACCCTGGTAGTCCACGCCGTAAACGATGAGTGCTAGGTGTTAGGGG TTTCGATGCCCGTAGTGCCGAAGTTAACACATTAAGCACTCCGCCTGG GGAGTACGGCCGCAAGGCTGAAACTCAAAGGAATTGACGGGGACCC GCACAAGCAGTGGAGCATGTGGTTTAATTCGAAGCAACGCGAAGAAC CTTACCAGGTCTTGACATCCTTTGACCACCCAAGAGATTGGGCTTCCC CTTCGGGGGCAAAGTGACAGGTGGTGCATGGTTGTCGTCAGCTCGTG TCGTGAGATGTTGGGTTAAGTCCCGCAACGAGCGCAACCCTTGATCTT AGTTGCCAGCATTCAGTTGGGCACTCTAAGGTGACTGCCGGTGACAA ACCGGAGGAAGGTGGGGATGACGTCAAATCATCATGCCCCTTATGAC CTGGGCTACACACGTGCTACAATGGATGGTACAAAGGGCAGCGAAGC CGCGAGGTGAAGCCAATCCCATAAAGCCATTCTCAGTTCGGATTGCA GGCTGCAACTCGCCTGCATGAAGCCGGAATTGCTAGTAATCGCGGAT CAGCATGCCGCGGTGAATACGTTCCCGGGTCTTGTACACACCGCCCGT CACACCACGAGAGTTTGTAACACCCGAAGTCGGTGAGGCAACCTTTT GGAGCCAGCCGCCTAAGGTGGGACAAATGATTGGGGTGAAGTCGTAA CAAGGTAGCCGTATCGGAAGGTGCGGCTGGATCACCTCCTTT |
| 149 | DP84 16S rRNA | TACGGAGAGTTTGATCCTGGCTCAGGATGAACGCTGGCGGCGTGCTT AACACATGCAAGTCGAACGGTGAAGCCAAGCTTGCTTGGTGGATCAG TGGCGAACGGGTGAGTAACACGTGAGCAACCTGCCCTGGACTCTGGG ATAAGCGCTGGAAACGGCGTCTAATACTGGATATGAGCTCTCATCGC ATGGTGGGGGTTGGAAAGATTTTTTGGTCTGGGATGGGCTCGCGGCCT ATCAGCTTGTTGGTGAGGTAATGGCTCACCAAGGCGTCGACGGGTAG CCGGCCTGAGAGGGTGACCGGCCACACTGGGACTGAGACACGGCCCA GACTCCTACGGGAGGCAGCAGTGGGGAATATTGCACAATGGGCGAAA GCCTGATGCAGCAACGCCGCGTGAGGGATGACGGCCTTCGGGTTGTA AACCTCTTTTAGCAGGGAAGAAGCGAAAGTGACGGTACCTGCAGAAA AAGCGCCGGCTAACTACGTGCCAGCAGCCGCGGTAATACGTAGGGCG CAAGCGTTATCCGGAATTATTGGGCGTAAAGAGCTCGTAGGCGGTTT GTCGCGTCTGCTGTGAAATCCCGAGGCTCAACCTCGGGCCTGCAGTG GGTACGGGCAGACTAGAGTGCGGTAGGGGAGATTGGAATTCCTGGTG TAGCGGTGGAATGCGCAGATATCAGGAGGAACACCGATGGCGAAGG CAGATCTCTGGGCCGTAACTGACGCTGAGGAGCGAAAGGGTGGGGAG CAAACAGGCTTAGATACCCTGGTAGTCCACCCCGTAAACGTTGGGAA CTAGTTGTGGGGACCATTCCACGGTTTCCGTGACGCAGCTAACGCATT AAGTTCCCCGCCTGGGGAGTACGGCCGCAAGGCTAAAACTCAAAGGA ATTGACGGGGACCCGCACAAGCGGCGGAGCATGCGGATTAATTCGAT GCAACGCGAAGAACCTTACCAAGGCTTGACATACACCAGAACGGGCC AGAAATGGTCAACTCTTTGGACACTGGTGAACAGGTGGTGCATGGTT GTCGTCAGCTCGTGTCGTGAGATGTTGGGTTAAGTCCCGCAACGAGC GCAACCCTCGTTCTATGTTGCCAGCACGTAATGGTGGGAACTCATGGG ATACTGCCGGGGTCAACTCGGAGGAAGGTGGGGATGACGTCAAATCA TCATGCCCCTTATGTCTTGGGCTTCACGCATGCTACAATGGCCGGTAC AAAGGGCTGCAATACCGTGAGGTGGAGCGAATCCCAAAAAGCCGGTC CCAGTTCGGATTGAGGTCTGCAACTCGACCTCATGAAGTCGGAGTCG CTAGTAATCGCAGATCAGCAACGCTGCGGTGAATACGTTCCCGGGTC TTGTACACACCGCCCGTCAAGTCATGAAAGGAGCCGTCGAAGGTGGG ATCGGTAATTAGGACTAAGTCGTAACAAGGTAGCCGTACCGGAAGGT GCGGCTGGATCACCTCCTTT |
| 150 | DP85 16S rRNA | ACGGTCGGGGGCATCAGTATTCAGTCGTCAGAGGTGAAATTCTTGGA TTGACTGAAGACTAACTACTGCGAAAGCATTTGCCAAGGACGTTTTCA TTAATCAAGAACGAAAGTTAGGGGATCGAAGATGATCAGATACCGTC GTAGTCTTAACCATAAACTATGCCGACTAGAGATCGGGTGGTGCTTTT TGCGCACTCGGCATCTTACGAGAAATCAAAGTCTTTGGGTTCTGGGGG GAGTATGGTCGCAAGGCTGAAACTTAAAGGAATTGACGGAGGGGCAC CACCAGGAGTGGAGCCTGCGGCTTAATTTGACTCAACACGGGGAAAC TCACCAGGTCCAGACGTAATAAGGATTGACAAGTTAGAGACTTCTCTT GATCTTACGGGTGGTGGTGCATGGCCGTTTTTAGTCCTTGGAGTGATT TGTCTGCTTAATTGCGATAACGGACGAGACCTTAACCTGCTAAATAGG GCTGCGAGCATCTGCTCGTGGGCTCTTCTTAGAGGGACTATGGGTATC AAACCCATGGAAGTTTGAGGCAACAACAGGTCTGTGATGCCCTTAGA CGTTCTGGGCCGCACGCGCGCTACACTGACGGAGCCAGCAAGCATAA CCTTGGTCGAGAGGCCTGGGTAATCTCGTGAAACTCCGTCGTGCTGGG GATAGAGCATTGTAATTTTTGCTCTTCAACGAGGAATTCCTAGTAAGC GCAAGTCATCAGCTTGCGTTGATTACGTCCCTGCCCCTTGTACACACC GCCCGTCGCTACTACCGATTGAATGGCTTAGTGAGGCTTCAAGACCG GCGCGGCCTGCGGGGCAACTCGCGCGCTGCGCTGGGAATTTAGTCAA |

-continued

Sequence Listing

| Seq ID No. | Description | Sequence |
|---|---|---|
| | | ACTTGGTCATTTAGAGGTCGTAAAAGTCGTAACAAGGTTTCCGTAGGT<br>GAACCTGCGGAAGGATCATT |
| 151 | DP86 16S rRNA | CGATGCGTAGCCGACCTGAGAGGGTGATCGGCCACACTGGGACTGAG<br>ACACGGCCCAGACTCCTACGGGAGGCAGCAGTAGGGAATCTTCCGCA<br>ATGGACGAAAGTCTGACGGAGCAACGCCGCGTGAGTGATGAAGGTTT<br>TCGGATCGTAAAGCTCTGTTGTTAGGGAAGAACAAGTGCCGTTCAAA<br>TAGGGCGGCACCTTGACGGTACCTAACCAGAAAGCCACGGCTAACTA<br>CGTGCCAGCAGCCGCGGTAATACGTAGGTGGCAAGCGTTGTCCGGAA<br>TTATTGGGCGTAAAGGGCTCGCAGGCGGTTTCTTAAGTCTGATGTGAA<br>AGCCCCCGGCTCAACCGGGGAGGGTCATTGGAAACTGGGGAACTTGA<br>GTGCAGAAGAGGAGAGTGGAATTCCACGTGTAGCGGTGAAATGCGTA<br>GAGATGTGGAGGAACACCAGTGGCGAAGGCGACTCTCTGGTCTGTAA<br>CTGACGCTGAGGAGCGAAAGCGTGGGGAGCGAACAGGATTAGATAC<br>CCTGGTAGTCCACGCCGTAAACGATGAGTGCTAAGTGTTAGGGGGTT<br>TCCGCCCCTTAGTGCTGCAGCTAACGCATTAAGCACTCCGCCTGGGGA<br>GTACGGTCGCAAGACTGAAACTCAAAGGAATTGACGGGGGCCCGCAC<br>AAGCGGTGGAGCATGTGGTTTAATTCGAAGCAACGCGAAGAACCTTA<br>CCAGGTCTTGACATCCTCTGACAATCCTAGAGATAGGACGTCCCCTTC<br>GGGGGCAGAGTGACAGGTGGTGCATGGTTGTCGTCAGCTCGTGTCGT<br>GAGATGTTGGGTTAAGTCCCGCAACGAGCGCAACCCTTGATCTTAGTT<br>GCCAGCATTCAGTTGGGTGTTCTTTGAAAACT |
| 152 | DP87 16S rRNA | TTTGAGAGTTTGATCCTGGCTCAGGACGAACGCTGGCGGCGTGCCTA<br>ATACATGCAAGTCGAACGAACTCTGGTATTGATTGGTGCTTGCATCAT<br>GATTTACATTTGAGTGAGTGGCGAACTGGTGAGTAACACGTGGGAAA<br>CCTGCCCAGAAGCGGGGGATAACACCTGGAAACAGATGCTAATACCG<br>CATAACAACTTGGACCGCATGGTCCGAGCTTGAAAGATGGCTTCGGC<br>TATCACTTTTGGATGGTCCCGCGGCGTATTAGCTAGATGGTGGGGTAA<br>CGGCTCACCATGGCAATGATACGTAGCCGACCTGAGAGGGTAATCGG<br>CCACATTGGGACTGAGACACGGCCCAAACTCCTACGGGAGGCAGCAG<br>TAGGGAATCTTCCACAATGGACGAAAGTCTGATGGAGCAACGCCGCG<br>TGAGTGAAGAAGGGTTTCGGCTCGTAAAACTCTGTTGTTAAAGAAGA<br>ACATATCTGAGAGTAACTGTTCAGGTATTGACGGTATTTAACCAGAA<br>AGCCACGGCTAACTACGTGCCAGCAGCCGCGGTAATACGTAGGTGGC<br>AAGCGTTGTCCGGATTTATTGGGCGTAAAGCGAGCGCAGGCGGTTTTT<br>TAAGTCTGATGTGAAAGCCTTCGGCTCAACCGAAGAAGTGCATCGGA<br>AACTGGGAAACTTGAGTGCAGAAGAGGACAGTGGAACTCCATGTGTA<br>GCGGTGAAATGCGTAGATATATGGAAGAACACCAGTGGCGAAGGCG<br>GCTGTCTGGTCTGTAACTGACGCTGAGGCTCGAAAGTATGGGTAGCA<br>AACAGGATTAGATACCCTGGTAGTCCATACCGTAAACGATGAATGCT<br>AAGTGTTGGAGGGTTTCCGCCCTTCAGTGCTGCAGCTAACGCATTAAG<br>CATTCCGCCTGGGGAGTACGGCCGCAAGGCTGAAACTCAAAGGAATT<br>GACGGGGGCCCGCACAAGCGGTGGAGCATGTGGTTTAATTCGAAGCT<br>ACGCGAAGAACCTTACCAGGTCTTGACATACTATGCAAATCTAAGAG<br>ATTAGACGTTCCCTTCGGGGACATGGATACAGGTGGTGCATGGTTGTC<br>GTCAGCTCGTGTCGTGAGATGTTGGGTTAAGTCCCGCAACGAGCGCA<br>ACCCTTATTATCAGTTGCCAGCATTAAGTTGGGCACTCTGGTGAGACT<br>GCCGGTGACAAACCGGAGGAAGGTGGGGATGACGTCAAATCATCATG<br>CCCCTTATGACCTGGGCTACACACGTGCTACAATGGATGGTACAACG<br>AGTTGCGAACTCGCGAGAGTAAGCTAATCTCTTAAAGCCATTCTCAGT<br>TCGGATTGTAGGCTGCAACTCGCCTACATGAAGTCGGAATCGCTAGT<br>AATCGCGGATCAGCATGCCGCGGTGAATACGTTCCCGGGCCTTGTAC<br>ACACCGCCCGTCACACCATGAGAGTTTGTAACACCCAAAGTCGGTGG<br>GGTAACCTTTTAGGAACCAGCCGCCTAAGGTGGGACAGATGATTAGG<br>GTGAAGTCGTAACAAGGTAGCCGTAGGAGAACCTGCGGCTGGATCAC<br>CTCCTT |
| 153 | DP88 16S rRNA | TAGTGGGTTTGATCCTGGCTCAGGACGAACGCTGGCGGCGTGCCTAA<br>TACATGCAAGTCGAGCGGACAGATGGGAGCTTGCTCCCTGATGTTAG<br>CGGCGGACGGGTGAGTAACACGTGGGTAACCTGCCTGTAAGACTGGG<br>ATAACTCCGGGAAACCGGGGCTAATACCGGATGGTTGTCTGAACCGC<br>ATGGTTCAGACATAAAAGGTGGCTTCGGCTACCACTTACAGATGGAC<br>CCGCGGCGCATTAGCTAGTTGGTGAGGTAACGGCTCACCAAGGCGAC<br>GATGCGTAGCCGACCTGAGAGGGTGATCGGCCACACTGGGACTGAGA<br>CACGGCCCAGACTCCTACGGGAGGCAGCAGTAGGGAATCTTCCGCAA<br>TGGACGAAAGTCTGACGGAGCAACGCCGCGTGAGTGATGAAGGTTTT<br>CGGATCGTAAAGCTCTGTTGTTAGGGAAGAACAAGTGCCGTTCAAAT<br>AGGGCGGCACCTTGACGGTACCTAACCAGAAAGCCACGGCTAACTAC<br>GTGCCAGCAGCCGCGGTAATACGTAGGTGGCAAGCGTTGTCCGGAAT<br>TATTGGGCGTAAAGGGCTCGCAGGCGGTTTCTTAAGTCTGATGTGAA<br>AGCCCCCGGCTCAACCGGGGAGGGTCATTGGAAACTGGGGAACTTGA<br>GTGCAGAAGAGGAGAGTGGAATTCCACGTGTAGCGGTGAAATGCGTA |

-continued

Sequence Listing

| Seq ID No. | Description | Sequence |
|---|---|---|
| | | GAGATGTGGAGGAACACCAGTGGCGAAGGCGACTCTCTGGTCTGTAA CTGACGCTGAGGAGCGAAAGCGTGGGGAGCGAACAGGATTAGATAC CCTGGTAGTCCACGCCGTAAACGATGAGTGCTAAGTGTTAGGGGGTT TCCGCCCCTTAGTGCTGCAGCTAACGCATTAAGCACTCCGCCTGGGGA GTACGGTCGCAAGACTGAAACTCAAAGGAATTGACGGGGGCCCGCAC AAGCGGTGGAGCATGTGGTTTAATTCGAAGCAACGCGAAGAACCTTA CCAGGTCTTGACATCCTCTGACAATCCTAGAGATAGGACGTCCCCTTC GGGGGCAGAGTGACAGGTGGTGCATGGTTGTCGTCAGCTCGTGTCGT GAGATGTTGGGTTAAGTCCCGCAACGAGCGCAACCCTTGATCTTAGTT GCCAGCATTCAGTTGGGCACTCTAAGGTGACTGCCGGTGACAAACCG GAGGAAGGTGGGGATGACGTCAAATCATCATGCCCCTTATGACCTGG GCTACACACGTGCTACAATGGACAGAACAAAGGGCAGCGAAACCGC GAGGTTAAGCCAATCCCACAAATCTGTTCTCAGTTCGGATCGCAGTCT GCAACTCGACTGCGTGAAGCTGGAATCGCTAGTAATCGCGGATCAGC ATGCCGCGGTGAATACGTTCCCGGGCCTTGTACACACCGCCCGTCACA CCACGAGAGTTTGTAACACCCGAAGTCGGTGAGGTAACCTTTATGGA GCCAGCCGCCGAAGGTGGGACAGATGATTGGGGTGAAGTCGTAACAA GGTAGCCGTATCGGAAGGTGCGGCTGGATCACCTCCTTT |
| 154 | DP89 16S rRNA | GTAACGGCTCACCAAGGCAACGATGCGTAGCCGACCTGAGAGGGTGA TCGGCCACACTGGGACTGAGACACGGCCCAGACTCCTACGGGAGGCA GCAGTAGGGAATCTTCCGCAATGGACGAAAGTCTGACGGAGCAACGC CGCGTGAGTGATGAAGGTTTTCGGATCGTAAAGCTCTGTTGTTAGGGA AGAACAAGTACCGTTCGAATAGGGCGGTACCTTGACGGTACCTAACC AGAAAGCCACGGCTAACTACGTGCCAGCAGCCGCGGTAATACGTAGG TGGCAAGCGTTGTCCGGAATTATTGGGCGTAAAGGGCTCGCAGGCGG TTTCTTAAGTCTGATGTGAAAGCCCCCGGCTCAACCGGGGAGGGTCAT TGGAAACTGGGGAACTTGAGTGCAGAAGAGGAGAGTGGAATTCCAC GTGTAGCGGTGAAATGCGTAGAGATGTGGAGGAACACCAGTGGCGA AGGCGACTCTCTGGTCTGTAACTGACGCTGAGGAGCGAAAGCGTGGG GAGCGAACAGGATTAGATACCCTGGTAGTCCACGCCGTAAACGATGA GTGCTAAGTGTTAGGGGGTTTCCGCCCCTTAGTGCTGCAGCTAACGCA TTAAGCACTCCGCCTGGGGAGTACGGTCGCAAGACTGAAACTCAAAG GAATTGACGGGGGCCCGCACAAGCGGTGGAGCATGTGGTTTAATTCG AAGCAACGCGAAGAACCTTACCAGGTCTTGACATCCTCTGACAATCC TAGAGATAGGACGTCCCCTTCGGGGGCAGAGTGACAGGTGGTGCATG GTTGTCGTCAGCTCGTGTCGTGAGATGTTGGGTTAAGTCCCGCAACGA GCGCAACCCTTGATCTTAGTTGCCAGCATTCAGTTGGGCACTCTAAGG TGACTGCCGGTGACAAACCGGAGGAAGGTGGGGATGACGTCAAATCA TCATGCCCCTTATGACCTGGGCTACACACGTGCTACAATGGACAGAA CAAAGGGCAGCGAAACCGCGAGGTTAAGCCAATCCCACAAATCTGTT CTCAGTTCGGATCGCAGTCTGCAACTCGACTGCGTGAAGCTGGAATC GCTAGTAATCGCGGATCAGCATGCCGCGGTGAATACGTTCCCGGGCC TTGTACACACCGCCCGTCACACCACGAGAGTTTGTAACACCCGAAGT CGGTGAGGTAACCTTTTAGGAGCCAGCCGCCGAAGGTGGGACAGATG ATTGGGGTGAAGTCGTAACAAGGTAGCCGTATCGGAAGGTGCGGCTG GATCACCTCCTTT |
| 155 | DP90 16S rRNA | TTTGAGAGTTTGATCCTGGCTCAGGACGAACGCTGGCGGCGTGCCTA ATACATGCAAGTCGAACGAACTCTGGTATTGATTGGTGCTTGCATCAT GATTTACATTTGAGTGAGTGGCGAACTGGTGAGTAACACGTGGGAAA CCTGCCCAGAAGCGGGGGATAACACCTGGAAACAGATGCTAATACCG CATAACAACTTGGACCGCATGGTCCGAGCTTGAAAGATGGCTTCGGC TATCACTTTTGGATGGTCCCGCGGCGTATTAGCTAGATGGTGGGGTAA CGGCTCACCATGGCAATGATACGTAGCCGACCTGAGAGGGTAATCGG CCACATTGGGACTGAGACACGGCCCAAACTCCTACGGGAGGCAGCAG TAGGGAATCTTCCACAATGGACGAAAGTCTGATGGAGCAACGCCGCG TGAGTGAAGAAGGGTTTCGGCTCGTAAAACTCTGTTGTTAAAGAAGA ACATATCTGAGAGTAACTGTTCAGGTATTGACGGTATTTAACCAGAA AGCCACGGCTAACTACGTGCCAGCAGCCGCGGTAATACGTAGGTGGC AAGCGTTGTCCGGATTTATTGGGCGTAAAGCGAGCGCAGGCGGTTTTT TAAGTCTGATGTGAAAGCCTTCGGCTCAACCGAAGAAGTGCATCGGA AACTGGGAAACTTGAGTGCAGAAGAGGACAGTGGAACTCCATGTGTA GCGGTGAAATGCGTAGATATATGGAAGAACACCAGTGGCGAAGGCG GCTGTCTGGTCTGTAACTGACGCTGAGGCTCGAAAGTATGGGTAGCA AACAGGATTAGATACCCTGGTAGTCCATACCGTAAACGATGAATGCT AAGTGTTGGAGGGTTTCCGCCCTTCAGTGCTGCAGCTAACGCATTAAG CATTCCGCCTGGGGAGTACGGCCGCAAGGCTGAAACTCAAAGGAATT GACGGGGGCCCGCACAAGCGGTGGAGCATGTGGTTTAATTCGAAGCT ACGCGAAGAACCTTACCAGGTCTTGACATACTATGCAAATCTAAGAG ATTAGACGTTCCCTTCGGGGACATGGATACAGGTGGTGCATGGTTGTC GTCAGCTCGTGTCGTGAGATGTTGGGTTAAGTCCCGCAACGAGCGCA ACCCTTATTATCAGTTGCCAGCATTAAGTTGGGCACTCTGGTGAGACT |

-continued

| Seq ID No. | Description | Sequence |
|---|---|---|
| | | GCCGGTGACAAACCGGAGGAAGGTGGGGATGACGTCAAATCATCATG CCCCTTATGACCTGGGCTACACACGTGCTACAATGGATGGTACAACG AGTTGCGAACTCGCGAGAGTAAGCTAATCTCTTAAAGCCATTCTCAGT TCGGATTGTAGGCTGCAACTCGCCTACATGAAGTCGGAATCGCTAGT AATCGCGGATCAGCATGCCGCGGTGAATACGTTCCCGGGCCTTGTAC ACACCGCCCGTCACACCATGAGAGTTTGTAACACCCAAAGTCGGTGG GGTAACCTTTTAGGAACCAGCCGCCTAAGGTGGGACAGATGATTAGG GTGAAGTCGTAACAAGGTAGCCGTAGGAGAACCTGCGGCTGGATCAC CTCCTT |
| 156 | DP92 16S rRNA | CGATGCGTAGCCGACCTGAGAGGGTGATCGGCCACACTGGGACTGAG ACACGGCCCAGACTCCTACGGGAGGCAGCAGTAGGGAATCTTCCGCA ATGGACGAAAGTCTGACGGAGCAACGCCGCGTGAGTGATGAAGGTTT TCGGATCGTAAAGCTCTGTTGTTAGGGAAGAACAAGTACCGTTCGAA TAGGGCGGTACCTTGACGGTACCTAACCAGAAAGCCACGGCTAACTA CGTGCCAGCAGCCGCGGTAATACGTAGGTGGCAAGCGTTGTCCGGAA TTATTGGGCGTAAAGGGCTCGCAGGCGGTTTCTTAAGTCTGATGTGAA AGCCCCCGGCTCAACCGGGGAGGGTCATTGGAAACTGGGGAACTTGA GTGCAGAAGAGGAGAGTGGAATTCCACGTGTAGCGGTGAAATGCGTA GAGATGTGGAGGAACACCAGTGGCGAAGGCGACTCTCTGGTCTGTAA CTGACGCTGAGGAGCGAAAGCGTGGGGAGCGAACAGGATTAGATAC CCTGGTAGTCCACGCCGTAAACGATGAGTGCTAAGTGTTAGGGGGTT TCCGCCCCTTAGTGCTGCAGCTAACGCATTAAGCACTCCGCCTGGGGA GTACGGTCGCAAGACTGAAACTCAAAGGAATTGACGGGGGCCCGCAC AAGCGGTGGAGCATGTGGTTTAATTCGAAGCAACGCGAAGAACCTTA CCAGGTCTTGACATCCTCTGACAATCCTAGAGATAGGACGTCCCCTTC GGGGGCAGAGTGACAGGTGGTGCATGGTTGTCGTCAGCTCGTGTCGT GAGATGTTGGGTTAAGTCCCGCAACGAGCGCAACCCTTGATCTTAGTT GCCAGCATTCAGTTGGGCACTCTAAGGTGACTGCCGGTGACAAACCG GAGGAAGGTGGGGATGACGTCAAATCATCATGCCCCTTATGACCTGG GCTACACACGTGCTACAATGGACAGAACAAAGGGCAGCGAAACCGC GAGGTTAAGCCAATCCCACAAATCTGTTCTCAGTTCGGATCGCAGTCT GCAACTCGACTGCGTGAAGCTGGAATCGCTAGTAATCGCGGATCAGC ATGCCGCGGTGAATACGTTCCCGGGCCTTGTACACACCGCCCGTCACA CCACGAGAGTTTGTAACACCCGAAGTCGGTGAGGTAACCTTTTAGGA GCCAGCCGCCGAAGGTGGGACAGATGATTGGGGTGAAGTCGTAACAA GGTAGCCGTATCGGAAGGTGCGGCTGGATCACCTCCTTT |
| 157 | DP93 16S rRNA | ATTGAGAGTTTGATCCTGGCTCAGGATGAACGCTGGCGGCGTGCCTA ATACATGCAAGTCGAACGCACAGCGAAAGGTGCTTGCACCTTTCAAG TGAGTGGCGAACGGGTGAGTAACACGTGGACAACCTGCCTCAAGGCT GGGGATAACATTTGGAAACAGATGCTAATACCGAATAAAACTTAGTG TCGCATGACAAAAAGTTAAAAGGCGCTTCGGCGTCACCTAGAGATGG ATCCGCGGTGCATTAGTTAGTTGGTGGGGTAAAGGCCTACCAAGACA ATGATGCATAGCCGAGTTGAGAGACTGATCGGCCACATTGGGACTGA GACACGGCCCAAACTCCTACGGGAGGCTGCAGTAGGGAATCTTCCAC AATGGGCGAAAGCCTGATGGAGCAACGCCGCGTGTGTGATGAAGGCT TTCGGGTCGTAAAGCACTGTTGTATGGGAAGAACAGCTAGAATAGGA AATGATTTTAGTTTGACGGTACCATACCAGAAAGGGACGGCTAAATA CGTGCCAGCAGCCGCGGTAATACGTATGTCCCGAGCGTTATCCGGATT TATTGGGCGTAAAGCGAGCGCAGACGGTTTATTAAGTCTGATGTGAA AGCCCGGAGCTCAACTCCGGAATGGCATTGGAAACTGGTTAACTTGA GTGCAGTAGAGGTAAGTGGAACTCCATGTGTAGCGGTGGAATGCGTA GATATATGGAAGAACACCAGTGGCGAAGGCGGCTTACTGGACTGCAA CTGACGTTGAGGCTCGAAAGTGTGGGTAGCAAACAGGATTAGATACC CTGGTAGTCCACACCGTAAACGATGAACACTAGGTGTTAGGAGGTTT CCGCCTCTTAGTGCCGAAGCTAACGCATTAAGTGTTCCGCCTGGGGAG TACGACCGCAAGGTTGAAACTCAAAGGAATTGACGGGGACCCGCACA AGCGGTGGAGCATGTGGTTTAATTCGAAGCAACGCGAAGAACCTTAC CAGGTCTTGACATCCTTTGAAGCTTTTAGAGATAGAAGTGTTCTCTTC GGAGACAAAGTGACAGGTGGTGCATGGTCGTCGTCAGCTCGTGTCGT GAGATGTTGGGTTAAGTCCCGCAACGAGCGCAACCCTTATTGTTAGTT GCCAGCATTCAGATGGGCACTCTAGCGAGACTGCCGGTGACAAACCG GAGGAAGGCGGGGACGACGTCAGATCATCATGCCCCTTATGACCTGG GCTACACACGTGCTACAATGGCGTATACAACGAGTTGCCAACCCGCG AGGGTGAGCTAATCTCTTAAAGTACGTCTCAGTTCGGATTGTAGTCTG CAACTCGACTACATGAAGTCGGAATCGCTAGTAATCGCGGATCAGCA CGCCGCGGTGAATACGTTCCCGGGTCTTGTACACACCGCCCGTCACAC CATGGGAGTTTGTAATGCCCAAAGCCGGTGGCCTAACCTTTTAGGAA GGAGCCGTCTAAGGCAGGACAGATGACTGGGGTGAAGTCGTAACAA GGTAGCCGTAGGAGAACCTGCGGCTGGATCACCTCCTTT |

-continued

Sequence Listing

| Seq ID No. | Description | Sequence |
|---|---|---|
| 158 | DP94 16S rRNA | ATCTGCCCAGAAGCAGGGGATAACACTTGGAAACAGGTGCTAATACC GTATAACAACAAAATCCGCATGGATTTTGTTTGAAAGGTGGCTTCGGC TATCACTTCTGGATGATCCCGCGGCGTATTAGTTAGTTGGTGAGGTAA AGGCCCACCAAGACGATGATACGTAGCCGACCTGAGAGGGTAATCGG CCACATTGGGACTGAGACACGGCCCAAACTCCTACGGGAGGCAGCAG TAGGGAATCTTCCACAATGGACGAAAGTCTGATGGAGCAATGCCGCG TGAGTGAAGAAGGGTTTCGGCTCGTAAAACTCTGTTGTTAAAGAAGA ACACCTTTGAGAGTAACTGTTCAAGGGTTGACGGTATTTAACCAGAA AGCCACGGCTAACTACGTGCCAGCAGCCGCGGTAATACGTAGGTGGC AAGCGTTGTCCGGATTTATTGGGCGTAAAGCGAGCGCAGGCGGTTTTT TAAGTCTGATGTGAAAGCCTTCGGCTTAACCGGAGAAGTGCATCGGA AACTGGGAGACTTGAGTGCAGAAGAGGACAGTGGAACTCCATGTGTA GCGGTGGAATGCGTAGATATATGGAAGAACACCAGTGGCGAAGGCG GCTGTCTAGTCTGTAACTGACGCTGAGGCTCGAAAGCATGGGTAGCG AACAGGATTAGATACCCTGGTAGTCCATGCCGTAAACGATGAGTGCT AAGTGTTGGAGGGTTTCCGCCCTTCAGTGCTGCAGCTAACGCATTAAG CACTCCGCCTGGGGAGTACGACCGCAAGGTTGAAACTCAAAGGAATT GACGGGGGCCCGCACAAGCGGTGGAGCATGTGGTTTAATTCGAAGCT ACGCGAAGAACCTTACCAGGTCTTGACATCTTCTGCCAATCTTAGAGA TAAGACGTTCCCTTCGGGGACAGAATGACAGGTGGTGCATGGTTGTC GTCAGCTCGTGTCGTGAGATGTTGGGTTAAGTCCCGCAACGAGCGCA ACCCTTATTATCAGTTGCCAGCATTCAGTTGGGCACTCTGGTGAGACT GCCGGTGACAAACCGGAGGAAGGTGGGGATGACGTCAAATCATCATG CCCCTTATGACCTGGGCTACACACGTGCTACAATGGACGGTACAACG AGTTGCGAAGTCGTGAGGCTAAGCTAATCTCTTAAAGCCGTTCTCAGT TCGGATTGTAGGCTGCAACTCGCCTACATGAAGTTGGAATCGCTAGTA ATCGCGGATCAGCATGCCGCGGTGAATACGTTCCCGGGCCTTGTACA CACCGCCCGTCACACCATGAGAGTTTGTAACACCCAAAGCCGGTGAG ATAACCTTCGGGAGTCAGCCGTCTAAGGTGGGACAGATGATTAGGGT GAAGTCGTAACAAGGTAGCCGTAGGAGAACCTGCGGCTGGATCACCT CCTT |
| 159 | DP95 16S rRNA | TGCTAATACCGCATAGATCCAAGAACCGCATGGTTCTTGGCTGAAAG ATGGCGTAAGCTATCGCTTTTGGATGGACCCGCGGCGTATTAGCTAGT TGGTGAGGTAATGGCTCACCAAGGCGATGATACGTAGCCGAACTGAG AGGTTGATCGGCCACATTGGGACTGAGACACGGCCCAAACTCCTACG GGAGGCAGCAGTAGGGAATCTTCCACAATGGACGCAAGTCTGATGGA GCAACGCCGCGTGAGTGAAGAAGGCTTTCGGGTCGTAAAACTCTGTT GTTGGAGAAGAATGGTCGGCAGAGTAACTGTTGTCGGCGTGACGGTA TCCAACCAGAAAGCCACGGCTAACTACGTGCCAGCAGCCGCGGTAAT ACGTAGGTGGCAAGCGTTATCCGGATTTATTGGGCGTAAAGCGAGCG CAGGCGGTTTTTTAAGTCTGATGTGAAAGCCCTCGGCTTAACCGAGGA AGCGCATCGGAAACTGGGAAACTTGAGTGCAGAAGAGGACAGTGGA ACTCCATGTGTAGCGGTGAAATGCGTAGATATATGGAAGAACACCAG TGGCGAAGGCGGCTGTCTGGTCTGTAACTGACGCTGAGGCTCGAAAG CATGGGTAGCGAACAGGATTAGATACCCTGGTAGTCCATGCCGTAAA CGATGAATGCTAGGTGTTGGAGGGTTTCCGCCCTTCAGTGCCGCAGCT AACGCATTAAGCATTCCGCCTGGGGAGTACGACCGCAAGGTTGAAAC TCAAAGGAATTGACGGGGGCCCGCACAAGCGGTGGAGCATGTGGTTT AATTCGAAGCAACGCGAAGAACCTTACCAGGTCTTGACATCTTTTGAT CACCTGAGAGATCAGGTTTCCCCTTCGGGGGCAAAATGACAGGTGGT GCATGGTTGTCGTCAGCTCGTGTCGTGAGATGTTGGGTTAAGTCCCGC AACGAGCGCAACCCTTATGACTAGTTGCCAGCATTTAGTTGGGCACTC TAGTAAGACTGCCGGTGACAAACCGGAGGAAGGTGGGGATGACGTC AAATCATCATGCCCCTTATGACCTGGGCTACACACGTGCTACAATGGA TGGTACAACGAGTTGCGAGACCGCGAGGTCAAGCTAATCTCTTAAAG CCATTCTCAGTTCGGACTGTAGGCTGCAACTCGCCTACACGAAGTCGG AATCGCTAGTAATCGCGGATCAGCACGCCGCGGTGAATACGTTCCCG GGCCTTGTACACACCGCCCGTCACACCATGAGAGTTTGTAACACCCG AAGCCGGTGGCGTAACCCTTTTAGGGAGCGAGCCGTCTAAGGTGGGA CAAATGATTAGGGTGAAGTCGTAACAAGGTAGCCGTAGGAGAACCTG CGGCTGGATCACCTCCTTT |
| 160 | DP96 16S rRNA | ACACGGCCCAAACTCCTACGGGAGGCAGCAGTAGGGAATCTTCCACA ATGGACGCAAGTCTGATGGAGCAACGCCGCGTGAGTGAAGAAGGCTT TCGGGTCGTAAAACTCTGTTGTTGGAGAAGAATGGTCGGCAGAGTAA CTGTTGTCGGCGTGACGGTATCCAACCAGAAAGCCACGGCTAACTAC GTGCCAGCAGCCGCGGTAATACGTAGGTGGCAAGCGTTATCCGGATT TATTGGGCGTAAAGCGAGCGCAGGCGGTTTTTTAAGTCTGATGTGAA AGCCCTCGGCTTAACCGAGGAAGCGCATCGGAAACTGGGAAACTTGA GTGCAGAAGAGGACAGTGGAACTCCATGTGTAGCGGTGAAATGCGTA GATATATGGAAGAACACCAGTGGCGAAGGCGGCTGTCTGGTCTGTAA |

-continued

| Sequence Listing | | |
|---|---|---|
| Seq ID No. | Description | Sequence |
| | | CTGACGCTGAGGCTCGAAAGCATGGGTAGCGAACAGGATTAGATACC<br>CTGGTAGTCCATGCCGTAAACGATGAATGCTAGGTGTTGGAGGGTTTC<br>CGCCCTTCAGTGCCGCAGCTAACGCATTAAGCATTCCGCCTGGGGAGT<br>ACGACCGCAAGGTTGAAACTCAAAGGAATTGACGGGGGCCCGCACA<br>AGCGGTGGAGCATGTGGTTTAATTCGAAGCAACGCGAAGAACCTTAC<br>CAGGTCTTGACATCTTTTGATCACCTGAGAGATCAGGTTTCCCCTTCG<br>GGGGCAAAATGACAGGTGGTGCATGGTTGTCGTCAGCTCGTGTCGTG<br>AGATGTTGGGTTAAGTCCCGCAACGAGCGCAACCCTTATGACTAGTT<br>GCCAGCATTTAGTTGGGCACTCTAGTAAGACTGCCGGTGACAAACCG<br>GAGGAAGGTGGGGATGACGTCAAATCATCATGCCCCTTATGACCTGG<br>GCTACACACGTGCTACAATGGATGGTACAACGAGTTGCGAGACCGCG<br>AGGTCAAGCTAATCTCTTAAAGCCATTCTCAGTTCGGACTGTAGGCTG<br>CAACTCGCCTACACGAAGTCGGAATCGCTAGTAATCGCGGATCAGCA<br>CGCCGCGGTGAATACGTTCCCGGGCCTTGTACACACCGCCCGTCACAC<br>CATGAGAGTTTGTAACACCCGAAGCCGGTGGCGTAACCCTTTTAGGG<br>AGCGAGCCGTCTAAGGTGGGACAAATGATTAGGGTGAAGTCGTAACA<br>AGGTAGCCGTAGGAGAACCTGCGGCTGGATCACCTCCTTT |
| 161 | DP97 16S rRNA | AATGAGAGTTTGATCCTGGCTCAGGACGAACGCTGGCGGCGTGCCTA<br>ATACATGCAAGTCGAGCGATGATTAAAGATAGCTTGCTATTTTTATGA<br>AGAGCGGCGAACGGGTGAGTAACGCGTGGGAAATCTGCCGAGTAGC<br>GGGGGACAACGTTTGGAAACGAACGCTAATACCGCATAACAATGAGA<br>ATCGCATGATTCTTATTTAAAAGAAGCAATTGCTTCACTACTTGATGA<br>TCCCGCGTTGTATTAGCTAGTTGGTAGTGTAAAGGACTACCAAGGCG<br>ATGATACATAGCCGACCTGAGAGGGTGATCGGCCACACTGGGACTGA<br>GACACGGCCCAGACTCCTACGGGAGGCAGCAGTAGGGAATCTTCGGC<br>AATGGGGGCAACCCTGACCGAGCAACGCCGCGTGAGTGAAGAAGGTT<br>TTCGGATCGTAAAACTCTGTTGTTAGAGAAGAACGTTAAGTAGAGTG<br>GAAAATTACTTAAGTGACGGTATCTAACCAGAAAGGGACGGCTAACT<br>ACGTGCCAGCAGCCGCGGTAATACGTAGGTCCCAAGCGTTGTCCGGA<br>TTTATTGGGCGTAAAGCGAGCGCAGGTGGTTTCTTAAGTCTGATGTAA<br>AAGGCAGTGGCTCAACCATTGTGTGCATTGGAAACTGGGAGACTTGA<br>GTGCAGGAGAGGAGAGTGGAATTCCATGTGTAGCGGTGAAATGCGTA<br>GATATATGGAGGAACACCGGAGGCGAAAGCGGCTCTCTGGCCTGTAA<br>CTGACACTGAGGCTCGAAAGCGTGGGGAGCAAACAGGATTAGATACC<br>CTGGTAGTCCACGCCGTAAACGATGAGTGCTAGCTGTAGGGAGCTAT<br>AAGTTCTCTGTAGCGCAGCTAACGCATTAAGCACTCCGCCTGGGGAG<br>TACGACCGCAAGGTTGAAACTCAAAGGAATTGACGGGGGCCCGCACA<br>AGCGGTGGAGCATGTGGTTTAATTCGAAGCAACGCGAAGAACCTTAC<br>CAGGTCTTGACATACTCGTGATATCCTTAGAGATAAGGAGTTCCTTCG<br>GGACACGGGATACAGGTGGTGCATGGTTGTCGTCAGCTCGTGTCGTG<br>AGATGTTGGGTTAAGTCCCGCAACGAGCGCAACCCTTATTACTAGTTG<br>CCATCATTAAGTTGGGCACTCTAGTGAGACTGCCGGTGATAAACCGG<br>AGGAAGGTGGGGATGACGTCAAATCATCATGCCCCTTATGACCTGGG<br>CTACACACGTGCTACAATGGATGGTACAACGAGTCGCCAACCCGCGA<br>GGGTGCGCTAATCTCTTAAAACCATTCTCAGTTCGGATTGCAGGCTGC<br>AACTCGCCTGCATGAAGTCGGAATCGCTAGTAATCGCGGATCAGCAC<br>GCCGCGGTGAATACGTTCCCGGGCCTTGTACACACCGCCCGTCACACC<br>ACGGAAGTTGGGAGTACCCAAAGTAGGTTGCCTAACCGCAAGGAGGG<br>CGCTTCCTAAGGTAAGACCGATGACTGGGGTGAAGTCGTAACAAGGT<br>AGCCGTATCGGAAGGTGCGGCTGGATCACCTCCTTT |
| 162 | DP98 16S rRNA | AATGAGAGTTTGATCCTGGCTCAGGACGAACGCTGGCGGCGTGCCTA<br>ATACATGCAAGTCGAGCGATGATTAAAGATAGCTTGCTATTTTTATGA<br>AGAGCGGCGAACGGGTGAGTAACGCGTGGGAAATCTGCCGAGTAGC<br>GGGGGACAACGTTTGGAAACGAACGCTAATACCGCATAACAATGAGA<br>ATCGCATGATTCTTATTTAAAAGAAGCAATTGCTTCACTACTTGATGA<br>TCCCGCGTTGTATTAGCTAGTTGGTAGTGTAAAGGACTACCAAGGCG<br>ATGATACATAGCCGACCTGAGAGGGTGATCGGCCACACTGGGACTGA<br>GACACGGCCCAGACTCCTACGGGAGGCAGCAGTAGGGAATCTTCGGC<br>AATGGGGGCAACCCTGACCGAGCAACGCCGCGTGAGTGAAGAAGGTT<br>TTCGGATCGTAAAACTCTGTTGTTAGAGAAGAACGTTAAGTAGAGTG<br>GAAAATTACTTAAGTGACGGTATCTAACCAGAAAGGGACGGCTAACT<br>ACGTGCCAGCAGCCGCGGTAATACGTAGGTCCCAAGCGTTGTCCGGA<br>TTTATTGGGCGTAAAGCGAGCGCAGGTGGTTTCTTAAGTCTGATGTAA<br>AAGGCAGTGGCTCAACCATTGTGTGCATTGGAAACTGGGAGACTTGA<br>GTGCAGGAGAGGAGAGTGGAATTCCATGTGTAGCGGTGAAATGCGTA<br>GATATATGGAGGAACACCGGAGGCGAAAGCGGCTCTCTGGCCTGTAA<br>CTGACACTGAGGCTCGAAAGCGTGGGGAGCAAACAGGATTAGATACC<br>CTGGTAGTCCACGCCGTAAACGATGAGTGCTAGCTGTAGGGAGCTAT<br>AAGTTCTCTGTAGCGCAGCTAACGCATTAAGCACTCCGCCTGGGGAG<br>TACGACCGCAAGGTTGAAACTCAAAGGAATTGACGGGGGCCCGCACA<br>AGCGGTGGAGCATGTGGTTTAATTCGAAGCAACGCGAAGAACCTTAC |

-continued

Sequence Listing

| Seq ID No. | Description | Sequence |
|---|---|---|
| | | CAGGTCTTGACATACTCGTGATATCCTTAGAGATAAGGAGTTCCTTCG GGACACGGGATACAGGTGGTGCATGGTTGTCGTCAGCTCGTGTCGTG AGATGTTGGGTTAAGTCCCGCAACGAGCGCAACCCTTATTACTAGTTG CCATCATTAAGTTGGGCACTCTAGTGAGACTGCCGGTGATAAACCGG AGGAAGGTGGGGATGACGTCAAATCATCATGCCCCTTATGACCTGGG CTACACACGTGCTACAATGGATGGTACAACGAGTCGCCAACCCGCGA GGGTGCGCTAATCTCTTAAAACCATTCTCAGTTCGGATTGCAGGCTGC AACTCGCCTGCATGAAGTCGGAATCGCTAGTAATCGCGGATCAGCAC GCCGCGGTGAATACGTTCCCGGGCCTTGTACACACCGCCCGTCACACC ACGGAAGTTGGGAGTACCCAAAGTAGGTTGCCTAACCGCAAGGAGGG CGCTTCCTAAGGTAAGACCGATGACTGGGGTGAAGTCGTAACAAGGT AGCCGTATCGGAAGGTGCGGCTGGATCACCTCCTTT |
| 163 | DP100 16S rRNA | TTTGAGAGTTTGATCCTGGCTCAGGACGAACGCTGGCGGCGTGCCTA ATACATGCAAGTCGAACGAACTCTGGTATTGATTGGTGCTTGCATCAT GATTTACATTTGAGTGAGTGGCGAACTGGTGAGTAACACGTGGGAAA CCTGCCCAGAAGCGGGGGATAACACCTGGAAACAGATGCTAATACCG CATAACAACTTGGACCGCATGGTCCGAGCTTGAAAGATGGCTTCGGC TATCACTTTTGGATGGTCCCGCGGCGTATTAGCTAGATGGTGGGGTAA CGGCTCACCATGGCAATGATACGTAGCCGACCTGAGAGGGTAATCGG CCACATTGGGACTGAGACACGGCCCAAACTCCTACGGGAGGCAGCAG TAGGGAATCTTCCACAATGGACGAAAGTCTGATGGAGCAACGCCGCG TGAGTGAAGAAGGGTTTCGGCTCGTAAAACTCTGTTGTTAAAGAAGA ACATATCTGAGAGTAACTGTTCAGGTATTGACGGTATTTAACCAGAA AGCCACGGCTAACTACGTGCCAGCAGCCGCGGTAATACGTAGGTGGC AAGCGTTGTCCGGATTTATTGGGCGTAAAGCGAGCGCAGGCGGTTTTT TAAGTCTGATGTGAAAGCCTTCGGCTCAACCGAAGAAGTGCATCGGA AACTGGGAAACTTGAGTGCAGAAGAGGACAGTGGAACTCCATGTGTA GCGGTGAAATGCGTAGATATATGGAAGAACACCAGTGGCGAAGGCG GCTGTCTGGTCTGTAACTGACGCTGAGGCTCGAAAGTATGGGTAGCA AACAGGATTAGATACCCTGGTAGTCCATACCGTAAACGATGAATGCT AAGTGTTGGAGGGTTTCCGCCCTTCAGTGCTGCAGCTAACGCATTAAG CATTCCGCCTGGGGAGTACGGCCGCAAGGCTGAAACTCAAAGGAATT GACGGGGGCCCGCACAAGCGGTGGAGCATGTGGTTTAATTCGAAGCT ACGCGAAGAACCTTACCAGGTCTTGACATACTATGCAAATCTAAGAG ATTAGACGTTCCCTTCGGGGACATGGATACAGGTGGTGCATGGTTGTC GTCAGCTCGTGTCGTGAGATGTTGGGTTAAGTCCCGCAACGAGCGCA ACCCTTATTATCAGTTGCCAGCATTAAGTTGGGCACTCTGGTGAGACT GCCGGTGACAAACCGGAGGAAGGTGGGGATGACGTCAAATCATCATG CCCCTTATGACCTGGGCTACACACGTGCTACAATGG |
| 164 | DP101 16S rRNA | ATGAGAGTTTGATCTTGGCTCAGGATGAACGCTGGCGGCGTGCCTAA TACATGCAAGTCGAACGAACTTCCGTTAATTGATTATGACGTACTTGT ACTGATTGAGATTTTAACACGAAGTGAGTGGCGAACGGGTGAGTAAC ACGTGGGTAACCTGCCCAGAAGTAGGGGATAACACCTGGAAACAGAT GCTAATACCGTATAACAGAGAAAACCGCATGGTTTTCTTTTAAAAGAT GGCTCTGCTATCACTTCTGGATGGACCCGCGGCGTATTAGCTAGTTGG TGAGGCAAAGGCTCACCAAGGCAGTGATACGTAGCCGACCTGAGAGG GTAATCGGCCACATTGGGACTGAGACACGGCCCAGACTCCTACGGGA GGCAGCAGTAGGGAATCTTCCACAATGGACGCAAGTCTGATGGAGCA ACGCCGCGTGAGTGAAGAAGGGTTTCGGCTCGTAAAGCTCTGTTGTT AAAGAAGAACGTGGGTAAGAGTAACTGTTTACCCAGTGACGGTATTT AACCAGAAAGCCACGGCTAACTACGTGCCAGCAGCCGCGGTAATACG TAGGTGGCAAGCGTTATCCGGATTTATTGGGCGTAAAGCGAGCGCAG GCGGTCTTTTAAGTCTAATGTGAAAGCCTTCGGCTCAACCGAAGAAGT GCATTGGAAACTGGGAGACTTGAGTGCAGAAGAGGACAGTGGAACTC CATGTGTAGCGGTGAAATGCGTAGATATATGGAAGAACACCAGTGGC GAAGGCGGCTGTCTGGTCTGCAACTGACGCTGAGGCTCGAAAGCATG GGTAGCGAACAGGATTAGATACCCTGGTAGTCCATGCCGTAAACGAT GATTACTAAGTGTTGGAGGGTTTCCGCCCTTCAGTGCTGCAGCTAACG CATTAAGTAATCCGCCTGGGGAGTACGACCGCAAGGTTGAAACTCAA AGAATTGACGGGGGCCCGCACAAGCGGTGGAGCATGTGGTTTAATT CGAAGCTACGCGAAGAACCTTACCAGGTCTTGACATCTTCTGACAGTC TAAGAGATTAGAGGTTCCCTTCGGGGACAGAATGACAGGTGGTGCAT GGTTGTCGTCAGCTCGTGTCGTGAGATGTTGGGTTAAGTCCCGCAACG AGCGCAACCCTTATTACTAGTTGCCAGCATTAAGTTGGGCACTCTAGT GAGACTGCCGGTGACAAACCGGAGGAAGGTGGGGACGACGTCAAAT CATCATGCCCCTTATGACCTGGGCTACACACGTGCTACAATGGATGGT ACAACGAGTCGCGAGACCGCGAGGTTAAGCTAATCTCTTAAAACCAT TCTCAGTTCGGACTGTAGGCTGCAACTCGCCTACACGAAGTCGGAATC GCTAGTAATCGCGGATCAGCATGCCGCGGTGAATACGTTCCCGGGCC TTGTACACACCGCCCGTCACACCATGAGAGTTTGTAAC |

-continued

Sequence Listing

| Seq ID No. | Description | Sequence |
|---|---|---|
| 165 | DP101 ITS sequence | TCCGTAGGTGAACCTGCGGAAGGATCATTACTGTGATTTAGTACTACA CTGCGTGAGCGGAACGAAAACAACAACACCTAAAATGTGGAATATAG CATATAGTCGACAAGAGAAATCTACGAAAAACAAACAAAACTTTCAA CAACGGATCTCTTGGTTCTCGCATCGATGAAGAGCGCAGCGAAATGC GATACCTAGTGTGAATTGCAGCCATCGTGAATCATCGAGTTCTTGAAC GCACATTGCGCCCCTCGGCATTCCGGGGGGCATGCCTGTTTGAGCGTC GTTTCCATCTTGCGCGTGCGCAGAGTTGGGGGAGCGGAGCGGACGAC GTGTAAAGAGCGTCGGAGCTGCGACTCGCCTGAAAGGGAGCGAAGCT GGCCGAGCGAACTAGACTTTTTTTCAGGGACGCTTGGCGGCCGAGAG CGAGTGTTGCGAGACAACAAAAAGCTCGACCTCAAATCAGGTAGGAA TACCCGCTGAACTTAAGCATATCAATAAGCGGAGGAAAAGAAACCAA CAGGGATTGCCTCAGTAGCGGCGAGTGAAGCGGCAAGAGCTCAGATT TGAAATCGTGCTTTGCGGCACGAGTTGTAGATTGCAGGTTGGAGTCTG TGTGGAAGGCGGTGTCCAAGTCCCTTGGAACAGGGCGCCCAGGAGGG TGAGAGCCCCGTGGGATGCCGGCGGAAGCAGTGAGGCCCTTCTGACG AGTCGAGTTGTTTGGGAATGCAGCTCCAAGCGGGTGGTAAATTCCAT CTAAGGCTAAATACTGGCGAGAGACCGATAGCGAACAAGTACTGTGA AGGAAAGATGAAAAGCACTTTGAAAAGAGAGTGAAACAGCACGTGA AATTGTTGAAAGGGAAGGGTATTGCGCCCGACATGGGGATTGCGCAC CGCTGCCTCTCGTGGGCGGCGCTCTGGGCTTTCCCTGGGCCAGCATCG GTTCTTGCTGCAGGAGAAGGGGTTCTGGAACGTGGCTCTTCGGAGTGT TATAGCCAGGGCCAGATGCTGCGTGCGGGGACCGAGGACTGCGGCCG TGTAGGTCACGGATGCTGGCAGAACGGCGCAACACCGCCCGTCTTGA AACATGGACCAAGGAGTCTAACGTCTATGCGAGTGTTTGGGTGTGAA ACCCGTACGCGTAATGAAAGTGAACGTAGGTCGGACCCCCTGCCCTC GGGGAGGGGAGCACGATCGACCGATCCCGATGTTTATCGGAAGGATT TGAGTAGGAGCATAGCTGTTGGGACCCGAAAGATGGTGAACTATGCC TGAATAGGGTGAAGCCAGAGGAAACTCTGGTGGAGGCTCGTAGCGGT TCTGACGTGCAAATCGATCGTCGAATTTGGGTATAGGGGCGAAAGAC TAATCGAACCATCTAGTAGCTGGTTCCTGCCGAAGTTTCCCTCAGGA |

What is claimed is:

1. A medical food, the medical food comprising: a unit dosage form formulated for oral administration to a subject, the dosage form comprising a synthetic microbial consortium comprising at least five heterologous microbes comprising at least (1) a *Pseudomonas* species; (2) a *Leuconostoc mesenteroides* species; (3) a *Lactobacillus brevis* species, (4) a *Lactobacillus plantarum* species; and (5) a *Pichia kudriavzevii* species, wherein the synthetic microbial consortium comprises at least 1×10^7 of each of the at least five heterologous microbes, wherein each of the at least five heterologous microbes comprises a gene or gene pathway directed to biosynthesis of short chain fatty acid (SCFA) or metabolites thereof and wherein the synthetic microbial consortium produces an increased amount of SCFA when grown together relative to the summed amount of SCFA produced by an equivalent amount of each distinct microbe grown in isolation under the same conditions, and wherein the synthetic microbial consortium comprises genes involved in biosynthetic pathways for producing Vitamin K2.

2. The medical food of claim 1, wherein the at least five heterologous microbes comprise at least (1) a *Pseudomonas* species having a 16s rRNA sequence at least 99% similarity to Seq ID NO: 1; (2) a *Leuconostoc mesenteroides* species having a 16s rRNA sequence at least 99% similarity to Seq ID NO: 157; (3) a *Lactobacillus brevis* species having a 16s rRNA sequence at least 99% similarity to Seq ID NO: 158, (4) a *Lactobacillus plantarum* species having a 16s rRNA sequence at least 99% similarity to Seq ID NO: 163; and (5) a *Pichia* kudriavzevii species having a 16s rRNA sequence at least 99% similarity to Seq ID NO: 165.

3. The medical food of claim 1, further comprising an effective amount of a cryoprotectant, wherein the effective amount of the cryoprotectant extends survival of the five heterologous microbes after thawing the composition from a cryogenic temperature as compared to survival of the five heterologous microbes in an otherwise identical composition that lacks the effective amount of the cryoprotectant, assayed under identical conditions.

4. The medical food of claim 1, wherein the medical food formulation comprises a prebiotic polysaccharide.

5. The medical food of claim 1, wherein the synthetic microbial consortium is grown in vitro and SCFA production is measured by gas chromatography.

6. The medical food of claim 1, wherein, following administration to the subject, the genes involved in biosynthetic pathways for producing Vitamin K2 increase Vitamin K2 synthesis gene abundance of the subject's microbiome by between 3 to 6 weeks following administration, and wherein the increase is relative to administration of a placebo.

7. The medical food of claim 1, wherein the subject has osteopenia or osteoporosis.

8. The medical food of claim 1, wherein the subject is post-menopausal.

9. The medical food of claim 1, wherein, following administration to the subject, the synthetic microbial consortium improves a bone turnover marker or reduces in the subject one or more of loss of bone mineral density (BMD), obesity induced bone loss, or decrease in bone volume.

10. The medical food of claim 1, wherein, following administration to the subject, the synthetic microbial consortium improves in the subject at least one marker of osteoporosis or osteopenia selected from an elevated level of an inflammatory cytokine in the blood selected from the group consisting of: Tumor necrosis factor alpha (TNFα), Interleukin-17 (IL-17), Interleukin-4 (IL-4), Interferon gamma (IFNγ), and Receptor activator of nuclear factor kappa-B ligand (RANKL).

11. The medical food of claim 1, wherein, following administration to the subject, the synthetic microbial consortium improves in the subject at least one marker of osteoporosis or osteopenia selected from a resorption blood marker selected from a crosslinked C-telopeptide of type 1 collagen, or a bone formation blood marker selected from the group consisting of: osteocalcin, alkaline phosphatase, and N-terminal propeptide of type 1 collagen.

12. The medical food of claim 1, wherein the SCFA comprises acetate or isomers thereof.

13. The medical food of claim 1, wherein the gene or gene pathway comprises one or more enzymes selected from the group consisting of: acetolactate synthase I, acetate kinase, phosphate acetyltransferase, and pyruvate dehydrogenase.

14. The medical food of claim 1, wherein the medical food is capable of reducing loss of bone mineral density (BMD) when assayed using an ovariectomized (OVX) model of postmenopausal osteoporosis.

15. The medical food of claim 1, wherein, following administration of the medical food to the subject, the subject having osteopenia or osteoporosis, the unit dosage form of the medical food comprising at least 1×10ˆ7 of each of the at least five heterologous microbes is an effective amount to reduce loss of bone mineral density (BMD) in the subject as assessed by an ovariectomized (OVX) model of postmenopausal osteoporosis.

16. The medical food of claim 1, wherein the subject is human.

* * * * *